United States Patent
Araujo et al.

(10) Patent No.: US 11,858,940 B2
(45) Date of Patent: Jan. 2, 2024

(54) SELECTIVE MODULATORS OF MUTANT LRRK2 PROTEOLYSIS AND ASSOCIATED METHODS OF USE

(71) Applicant: Arvinas Operations, Inc., New Haven, CT (US)

(72) Inventors: Erika Araujo, Woodbridge, CT (US); Michael Berlin, Flemington, NJ (US); Steven M. Sparks, Guilford, CT (US); Jing Wang, Milford, CT (US); Wei Zhang, Madison, CT (US)

(73) Assignee: Arvinas Operations, Inc., New Haven, CT (US)

( * ) Notice: Subject to any disclaimer, the term of this patent is extended or adjusted under 35 U.S.C. 154(b) by 60 days.

(21) Appl. No.: 17/207,330

(22) Filed: Mar. 19, 2021

(65) Prior Publication Data
US 2022/0064168 A1 Mar. 3, 2022

Related U.S. Application Data

(60) Provisional application No. 62/992,951, filed on Mar. 21, 2020.

(51) Int. Cl.
*C07D 487/04* (2006.01)
*A61K 45/06* (2006.01)
*C07D 519/00* (2006.01)

(52) U.S. Cl.
CPC ............ *C07D 487/04* (2013.01); *A61K 45/06* (2013.01); *C07D 519/00* (2013.01)

(58) Field of Classification Search
CPC .. C07D 487/04; C07D 487/10; C07D 519/00; A61K 31/519; A61K 31/5377
See application file for complete search history.

(56) References Cited

U.S. PATENT DOCUMENTS

2016/0031905 A1* 2/2016 Hoflack .................. A61P 25/16
540/472

FOREIGN PATENT DOCUMENTS

| WO | WO 2014/134774 A1 | 9/2014 | |
|----|-------------------|--------|---|
| WO | WO 2014/134776 A1 | 9/2014 | |
| WO | WO 2018/148443 A1 | 8/2018 | |
| WO | WO 2019/199816 A1 | 10/2019 | |
| WO | WO 2019/222173 A1 | 11/2019 | |
| WO | WO-2019222173 A1 * | 11/2019 | .............. A61P 25/14 |
| WO | WO 2020/081682 A1 | 4/2020 | |
| WO | WO-2020081682 A1 * | 4/2020 | ........... A61K 47/545 |

OTHER PUBLICATIONS

International Search Report and Written Opinion dated Jun. 6, 2021, for PCT/US2021/023179.
International Search Report and Written Opinion dated Jun. 6, 2021, for PCT/US2021/023183.

* cited by examiner

*Primary Examiner* — Theodore R. Howell
*Assistant Examiner* — George W Kosturko
(74) *Attorney, Agent, or Firm* — McCarter & English, LLP; Michael J. DeGrazia; James M. Alburger

(57) ABSTRACT

Bifunctional compounds, which find utility as modulators of non-receptor Leucine-rich repeat kinase 2 (LRRK2), are described herein. In particular, the bifunctional compounds of the present disclosure contain on one end a moiety that binds to the cereblon E3 ubiquitin ligase and on the other end a moiety which binds LRRK2, such that the target protein is placed in proximity to the ubiquitin ligase to effect degradation (and inhibition) of target protein. The bifunctional compounds of the present disclosure exhibit a broad range of pharmacological activities associated with degradation/inhibition of target protein. Diseases or disorders that result from aberrant regulation of the target protein are treated or prevented with compounds and compositions of the present disclosure.

12 Claims, 1 Drawing Sheet

SELECTIVE MODULATORS OF MUTANT LRRK2 PROTEOLYSIS AND ASSOCIATED METHODS OF USE

CROSS-REFERENCE TO RELATED APPLICATIONS

The present disclosure claims benefit of and priority to U.S. Provisional Application No. 62/992,951, filed 21 Mar. 2020, titled SELECTIVE MODULATORS OF MUTANT LRRK2 PROTEOLYSIS AND ASSOCIATED METHODS OF USE, which is incorporated herein in by reference in its entirety for all purposes.

INCORPORATION BY REFERENCE

All cited references are hereby incorporated herein by reference in their entirety, including U.S. patent application Ser. No. 14/686,640, filed on Apr. 14, 2015, published as U.S. Patent Application Publication No. 2015/0291562; and U.S. patent application Ser. No. 14/792,414, filed on Jul. 6, 2015, published as U.S. Patent Application Publication No. 2016/0058872; and U.S. patent application Ser. No. 15/953, 108, filed on Apr. 13, 2018, published as U.S. Patent Application Publication No. 2018/0228907; and International Patent Application No. PCT/US2019/032163, filed May 5, 2019, published as International Patent Application Publication No. WO2019/222173A1.

FIELD OF THE INVENTION

The description provides hetero-bifunctional compounds comprising a target protein binding moiety and a E3 ubiquitin ligase binding moiety, and associated methods of use. The bifunctional compounds are useful as modulators of targeted ubiquitination of leucine-rich repeat kinase 2 (LRRK2), which is then degraded and/or inhibited.

BACKGROUND

Most small molecule drugs bind enzymes or receptors in tight and well-defined pockets. On the other hand, protein-protein interactions are notoriously difficult to target using small molecules due to their large contact surfaces and the shallow grooves or flat interfaces involved. E3 ubiquitin ligases (of which hundreds are known in humans) confer substrate specificity for ubiquitination, and therefore, are more attractive therapeutic targets than general proteasome inhibitors due to their specificity for certain protein substrates. The development of ligands of E3 ligases has proven challenging, in part because they must disrupt protein-protein interactions. However, recent developments have provided specific ligands which bind to these ligases. For example, since the discovery of nutlins, the first small molecule E3 ligase inhibitors, additional compounds have been reported that target E3 ligases.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubiquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Bifunctional compounds such as those described in U.S. Patent Application Publications 2015/0291562 and 2014/0356322 (incorporated herein by reference), function to recruit endogenous proteins to an E3 ubiquitin ligase for ubiquitination and subsequent degradation in the proteasome degradation pathway. In particular, the publications cited above describe bifunctional or proteolysis-targeting chimeric (PROTAC®) protein degrader compounds, which find utility as modulators of targeted ubiquitination of a variety of polypeptides and other proteins, which are then degraded and/or inhibited by the bifunctional compounds.

Feucine-rich repeat kinase 2 (FRRK2) is a member of the leucine-rich repeat kinase family and is a large multi-domain protein with an N-terminal armadillo domain, ankryin repeat region, a leucine-rich repeat (ERR) domain, a tandem Roco type GTPase domain, a kinase domain containing a DFG-like motif, and a C-terminal WD40 domain. The FRRK2 protein is 2527 amino acids and a molecular weight of 280 kDa. Catalytic activities of FRRK2 are associated with the kinase and GTPase domain, and FRRK2 is a heterodimer in its active form (Greggio E, et al: The Parkinson disease-associated leucine-rich repeat kinase 2 (FRRK2) is a dimer that undergoes intramolecular autophosphorylation. *J Biol Chem* 2008, 283:16906-16914). GTP binding is essential for kinase activity, and mutations that prevent GTP binding have been shown to ablate LRRK2 kinase activity (Ito G, et al: GTP binding is essential to the protein kinase activity of LRRK2, a causative gene product for familial Parkinson's disease. *Biochemistry* 2007, 46:1380-1388). The only validated physiological substrates (other than LRRK2 itself) are a subset of low-molecular weight G-proteins including Rab8a and Rab10, which are involved in regulation of vesicle trafficking and endosome function and trafficking on cytoskeletal networks (Steger M, et al: Phosphoproteomics reveals that Parkinson's disease kinase LRRK2 regulates a subset of Rab GTPases. *Elife* 2016, 5. e12813). Expression levels of LRRK2 are highest in immune cells (neutrophils, monocytes and B cells), lung and kidney, with lower levels in the brain where it is expressed in dopaminergic neurons of the substantia nigra (West A B, et al: Differential LRRK2 expression in the cortex, striatum, and substantia nigra in transgenic and nontransgenic rodents. *J Comp Neurol* 2014, 522:2465-2480).

There are several dominant gain-of-function pathogenic and characterized mutations to LRRK2, located either in the Roco domains (N1437H, R1441G/C/H, Y1699C), effecting GTP hydrolysis, or in the kinase domain (G2019S and I2020T). The G2019S is the most common LRRK2 mutation linked to Parkinson's disease (PD), which is a progressive neurodegenerative disorder characterized by resting tremors, rigidity, decreased movement (bradykinesia), and postural instability. The histological hallmarks of PD include neurodegeneration of the dopaminergic neurons in the substantia nigra pars *compacta* as well as intracellular inclusions called Lewy bodies and neurites consisting of the aggregated form of the alpha-synuclein protein. G2019S is associated with 1-2% of all PD patients and causes an increase in kinase activity of 2-fold in vitro (West A B, et al: Parkinson's diseaseassociated mutations in leucine-rich repeat kinase 2 augment kinase activity. *Proc Natl Acad Sci USA* 2005, 102: 16842-16847) and autophosphorylation at Ser1292 is increased 4-fold (Sheng Z, et air Ser1292 autophosphorylation is an indicator of LRRK2 kinase activity and contributes to the cellular effects of PD mutations. *Sci Transl Med* 2012, 4:164ra161). The G2019S and I2020T mutations lie within the DFG motif (DYGI in the case of LRRK2), common to all kinases, which controls catalytic activity. These mutations are thought to disrupt the inactive conformation and thus increase catalytic activity (Schmidt S H, et al: The dynamic switch mechanism that leads to activation of LRRK2 is embedded in the DFGpsi motif in the kinase domain. *Proc Natl Acad Sci USA* 2019, 116: 14979-14988). Several of the above Parkinson disease-associated mutations (R1441C/G, Y1699C and I2020T) suppress phosphorylation of FRRK2 at Ser910 and Ser935, which in turn reduces LRRK2 association with 14-3-3 proteins, thought to represent an inactive form of LRRK2 (Nichols J, et al: 14-3-3 binding to LRRK2 is disrupted by multiple Parkinson's disease associated mutations and regulates cytoplasmic localisation. *Biochem J* 2010, 430:393-404).

Furthermore, LRRK2 is linked to autosomal dominant inherited PD through a mutation within a region of chromosome 12, termed PARK8, which is linked to the LRRK2 gene (Lunayama M, et al: A new locus for Parkinson's disease (PARK8) maps to chromosome 12p11.2-q13.1. *Ann Neurol* 2002, 51:296-301; Zimprich A, et al.: Mutations in LRRK2 cause autosomal-dominant parkinsonism with pleomorphic pathology. *Neuron* 2004, 44:601-607; Paisan-Ruiz C, et al.: Cloning of the gene containing mutations that cause PARK8-linked Parkinson's disease. *Neuron* 2004, 44:595-600). LRRK2 was first described as having a link to autosomal dominant inherited Parkinson's disease in 1978, where it was traced to a family in Japan (Nukada H, et al: [A big family of paralysis agitans (author's transl)]. *Rinsho Shinkeigaku* 1978, 18:627-634). The most common pathogenic LRRK2 mutation (G2019S) occurs in 4-8% of familial and 1-3% of sporadic PD cases. In addition, the G2019S mutation is common among PD patients of select ancestry, with 30-40% of North African Berber and 14% of Jewish patients harboring the mutation.

LRRK2 kinase inhibitors have been proposed as having the potential to treat mutation-driven PD, where there is an increase in LRRK2 activity, such as G2019S, and idiopathic PD, where the activity of LRRK2 is increased (Chen J, et al: Leucine-rich repeat kinase 2 in Parkinson's disease: updated from pathogenesis to potential therapeutic target. *Eur Neurol* 2018, 79:256-265; Alessi D P et al: LRRK2 kinase in Parkinson's disease. Science 2018, 360:36-37; Di Maio R, et al: LRRK2 activation in idiopathic Parkinson's disease. *Sci Transl Med* 2018, 10). Several therapeutics are progressing into the clinic, including LRRK2 kinase inhibitors that will directly affect phosphorylation of downstream targets, and oligonucleotides (ASO's) directly infused into the CNS to block translation of LRRK2 protein, thereby reducing LRRK2 protein levels.

Lewy bodies are the main histological hallmark of PD. Lewy bodies are composed primarily of alpha-synuclein aggregates, and mutations in alpha-synuclein that increase this aggregation also increase the risk of developing PD (Meade R M, et al: Alpha-synuclein structure and Parkinson's disease lessons and emerging principles. *Mol Neurodegener* 2019, 14. 29-29). Depletion of LRRK2 with ASOs (Zhao H T, et al: LRRK2 antisense oligonucleotides ameliorate a-synuclein inclusion formation in a Parkinson's disease mouse model. Molecular therapy. *Nucleic acids* 2017, 8:508-519) and deletion of LRRK2 at a genomic level have been shown to reduce alpha-synuclein mediated pathology in mouse models of PD (Lin X, et al.: Leucine-rich repeat kinase 2 regulates the progression of neuropathology induced by Parkinson's-disease-related mutant alpha-synuclein. *Neuron* 2009, 64:807-827). Mutations increasing LRRK2 activity, such as G2019S, increase the aggregation of alpha-synuclein in neurons and mouse models of PD. This increase was reversed with LRRK2 kinase inhibitors (Volpicelli-Daley L A, et al. G2019S-LRRK2 Expression Augments α-Synuclein Sequestration into Inclusions in Neurons. *J Neurosci.* 2016 Jul. 13; 36(28):7415-27. doi: 10.1523/JNEUROSCI.3642-15.2016). There is some evidence to suggest that the G2019S mutant form of LRRK2 is resistant to inhibition by kinase inhibitors in the CNS, potentially reducing their disease modifying effect (Kelly K, et al. The G2019S mutation in LRRK2 imparts resiliency to kinase inhibition. *Exp Neurol.* 2018 November; 309:1-13). Even though most cases of PD also have Lewy bodies upon post-mortem examination, Lewy bodies are not present in a high number of LRRK2 G2019S mutation associated PD cases (Kalia E V, et al.: Clinical correlations with Lewy body pathology in LRRK2-related Parkinson disease. *JAMA neurol* 2015, 72:100-105). In addition to Lewy bodies being a common feature of PD, Tau pathology is also a major feature of LRRK2 mutation carriers at post-mortem (Henderson M X, et al.: Alzheimer's disease tau is a prominent pathology in LRRK2 Parkinson's disease. *Acta Neuropathol Commun* 2019, 7. 183-183). In one study, Tau pathology was observed in 100% of LRRK2 mutation carriers, thereby highlighting LRRK2 as an important target linking PD with Tau pathology in the context of PD, though the genetic causal link was not as strong between LRRK2 and primary tauopathies, such as supranuclear palsy (PSP) and corticobasal degeneration (CBD) (Ross O A, et al. (2006) Lrrk2 R1441 substitution and progressive supranuclear palsy. *Neuropathol Appl Neurobiol* 32(1):23-25; Sanchez-Contreras M, et al. (2017) Study of LRRK2 variation in tauopathy: progressive supranuclear palsy and corticobasal degeneration. *Mov Disord* 32(1): 115-123). A common variation at the LRRK2 locus as a genetic determinant of PSP survival was recently reported (Jabbari E, et al., Common variation at the LRRK2 locus is associated with survival in the primary tauopathy progressive supranuclear palsy. bioRxiv 2020.02.04.932335; doi: https://doi.org/10.1101/2020.02.04.932335). It has been reported that increased LRRK2 expression in PSP by expression quantitative trait loci (eQTL) analysis may result in a reactive microglia-induced proinflammatory state which drives ongoing accumulation of misfolded Tau protein and clinical disease progression. Functional variants of LRRK2 have also been linked to Crohn's Disease and leprosy type 1 inflammatory reactions (Hui K Y, et al. Functional variants in the LRRK2 gene confer shared effects on risk for Crohn's disease and Parkinson's disease. *Sci Transl Med.* 2018 Jan. 10; 10(423). pii: eaai7795. doi: 10.1126/scitranslmed.aai7795; Fava et al. Pleiotropic effects for Parkin and LRRK2 in leprosy type-1 reactions and Parkinson's disease. *Proc Natl Acad Sci USA.* 2019 Jul. 30; 116(31): 15616-15624. doi: 10.1073/pnas.1901805116. Epub 2019 Jul. 15).

LRRK2 is highly expressed in the immune system in neutrophils, monocytes and macrophages, as well as in brain microglia, and is a modulator of the intrinsic regulation of microglial activation and of lysosomal degradation processes (Ma et al. Genetic comorbidities in Parkinson's disease. *Hum Mol Genet.* 2014 Feb. 1; 23(3):831-41. doi: 10.1093/hmg/ddt465. Epub 2013 Sep. 20, which was reviewed in Schapansky et al. The complex relationships between microglia, alpha-synuclein, and LRRK2 in Parkinson's disease. *Neuroscience.* 2015 Aug. 27; 302:74-88. doi: 10.1016/j.neuroscience.2014.09.049. Epub 2014 Oct. 2).

Prolonged activation of these immune cells through PD disease processes or mutations in LRRK2 could increase neuroinflammation and lead to a greater risk of developing PD and/or Tau pathology. Treatment with anti-TNF agents reduces the risk of developing PD by 78% in patients with inflammatory bowel disorder (Peter I, et al.: Anti-tumor necrosis factor therapy and incidence of Parkinson disease among patients with inflammatory bowel disease. *JAMA Neurol* 2018), thereby demonstrating the strong linkage between inflammation and PD. In addition to PD, LRRK2 has been linked to other diseases such as cancer, leprosy, and Crohn's disease (Lewis P A, Manzoni C. LRRK2 and human disease: a complicated question or a question of complexes? (2012). *Sci Signal.* 5(207), pe2).

As such, a class of small molecules targeting LRRK2 are reported to be useful in the modulation of the LRRK2 protein, including LRRK2 protein having a G2019S mutation (International Patent Application Publication WO2019/222173A1, incorporated herein by reference).

An ongoing need exists in the art for effective treatments for LRRK2 related disease and discorders, e.g., idiopathic PD, LRRK2 mutation-associated PD (e.g., PD associated with one or more LRRK2 activating mutations), primary tauopathies (e.g., supranuclear palsy (PSP) or corticobasal degeneration (CBD)), lewy body dementia, Crohn's Disease, Leprosy (e.g., Leprosy with type 1 inflammatory reactions), and/or neuroinflammation.

SUMMARY

The present disclosure describes hetero-bifunctional compounds that function to selectively or preferentially recruit a mutated Leucine-rich repeat kinase 2 (LRRK2) to an E3 ubiquitin ligase as compared to wild type LRRK2, for targeted ubiquitination and subsequent proteasomal degradation, and methods of making and using the same. In particular, compounds as described herein preferentially bind to LRRK2 proteins comprising a G2019S mutation. In addition, the description provides methods of using an effective amount of a compound of the invention, as described herein, for the treatment or amelioration of a disease condition or one or more symptoms thereof, such as a neurodegenerative disease, e.g., Parkinson's disease, Parkinson disease with dementia, Parkinson's disease at risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, and Shy-Drager syndrome, among others.

As such, in one aspect the disclosure provides hetero-bifunctional compounds that comprise an E3 ubiquitin ligase binding moiety (i.e., a ligand for an E3 ubiquitin ligase (a "ULM" group)), and a protein targeting moiety that preferentially binds to a mutated form of LRRK2 having a G2019S mutation compared to lesser (or no) binding to wild-type LRRK2 such that the mutated LRRK2 protein is thereby preferentially placed in proximity to the ubiquitin ligase to effect ubiquitination and subsequent preferential degradation (and/or inhibition) of the mutated LRRK2 protein. In a preferred embodiment, the ULM (ubiquitin ligase binding moiety) is a cereblon E3 ubiquitin ligase binding moiety (CLM). For example, the structure of the bifunctional compound can be depicted as:

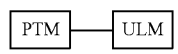

The respective positions of the PTM and ULM moieties (e.g., CLM), as well as their number as illustrated herein, is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as:

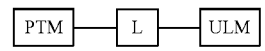

where PTM is a moiety that selectively or preferentially binds to an LRRK2 protein having at least one mutation that is a G2019S mutation compared to binding of the PTM to the wild-type LRRK2, L is a linker, e.g., a bond or a chemical linking group coupling PTM to ULM, and ULM is a cereblon E3 ubiquitin ligase binding moiety (CLM).

For example, the structure of the bifunctional compound can be depicted as:

wherein: PTM is a moiety that selectively or preferentially binds to an LRRK2 protein having at least one mutation that is a G2019S mutation compared to binding of the PTM to the wild-type LRRK2; "L" is a linker (e.g. a bond or a chemical linking group) coupling the PTM and CLM; and CLM is cereblon E3 ubiquitin ligase binding moiety that binds to cereblon.

In certain embodiments, the compounds as described herein comprise multiple independently selected ULMs, multiple PTMs, multiple chemical linkers or a combination thereof.

In any of the aspects or embodiments described herein, the PTM is a small molecule that selectively or preferentially binds to a LRRK2 protein having at least one mutation that is a G2019S mutation compared to the PTM binding to a wildtype LRRK2. In any of the aspects or embodiments described herein, the PTM is a small molecule capable of selectively binding the LRRK2 protein having at least one mutation that is a G2019S mutation, wherein selectivity towards the LRRK2 protein having at least one mutation that is a G2019S mutation is at least 1-60 times (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 times) compared to the wild-type LRRK2. In any of the aspects or embodiments described herein, the PTM is a small molecule that binds the LRRK2 protein having at least one mutation that is a G2019S mutation, wherein selectivity towards the LRRK2 protein having at least one mutation that is a G2019S mutation is at least 1-1000 times (e.g., 50, 100, 200, 300, 400, 500, 600, 700, 800, 900 times) compared to the wild-type LRRK2.

In an embodiment, the CLM comprises a chemical group derived from an imide, a thioimide, an amide, or a thioamide. In a particular embodiment, the chemical group is a phthalimido group, or an analog or derivative thereof. In a certain embodiment, the CLM is selected from thalidomide, lenalidomide, pomalidomide, analogs thereof, isosteres thereof, and derivatives thereof. Other contemplated CLMs are described in U.S. Patent Application Publication No. 2015/0291562, which is incorporated herein by reference in its entirety.

In certain embodiments, "L" is a bond. In additional embodiments, the linker "L" is a connector with a linear non-hydrogen atom number in the range of 1 to 20. The connector "L" can contain, but is not limited to one or more functional groups such as ether, amide, alkane, alkene, alkyne, ketone, hydroxyl, carboxylic acid, thioether, sulfoxide, and sulfone. The linker can contain aromatic, heteroaromatic, cyclic, bicyclic or tricyclic moieties. Substitution with halogen, such as Cl, F, Br and I can be included in the linker. In the case of fluorine substitution, single or multiple fluorines can be included.

In certain embodiments, CLM is a derivative of piperidine-2,6-dione, where piperidine-2,6-dione can be substituted at the 3-position, and the 3-substitution can be bicyclic hetero-aromatics with the linkage as C—N bond or C—C bond. Examples of CLM can be, but are not limited to, pomalidomide, lenalidomide and thalidomide and their analogs.

In an additional aspect, the description provides therapeutic compositions comprising an effective amount of a compound as described herein, or a salt form thereof, and a pharmaceutically acceptable carrier. The therapeutic compositions can be used to trigger targeted degradation and/or inhibition of a LRRK2 protein that has at least one mutation that is a G2019S mutation in a patient or subject in need thereof, for example, an animal such as a human, and can be used for treating or ameliorating one or more disease states, conditions, or symptoms causally related to the mutated LRRK2, which treatment is accomplished through preferential degradation of the mutated LRRK2 protein to control, stabilize or lower levels of protein of the mutated LRRK2 protein in a patient or subject. In certain embodiments, the therapeutic compositions as described herein may be used to effectuate the preferential degradation of mutated LRRK2 (e.g., G2019S) for the treatment or amelioration of a disease, disorder or symptom, such as, e.g., an infection, an inflammatory or immunological disorder, or cancer.

In yet another aspect, the present disclosure provides a method of ubiquitinating a mutant LRRK2 in a cell. In certain embodiments, the method comprises administering a hetero-bifunctional compound as described herein comprising a PTM that selectively or preferentially binds to a mutated LRRK2 as described herein, and a CLM, preferably linked together through a chemical linker moiety, as described herein, to effectuate selective or preferential degradation of the mutant LRRK2 protein. Though not wanting to be limited by theory, the inventors believe that, pursuant to the invention, poly-ubiquitination of the mutated LRRK2 protein will occur when it is placed in proximity to the E3 ubiquitin ligase via use of the hetero-bifunctional compound, thereby triggering subsequent selective or preferential degradation of the mutated LRRK2 protein via the proteasomal pathway, thereby controlling or reducing mutant LRRK2 protein levels in cells of the subject. The control or reduction in mutant LRRK2 protein levels afforded by the present disclosure provides treatment of a disease state, condition or at least one causally related symptom, as modulated through a lowering or stabilization of the amount of mutated LRRK2 protein in cells of the subject.

In still another aspect, the description provides methods for treating or ameliorating a disease, condition, or symptom thereof in a subject or a patient, e.g., an animal such as a human, comprising administering to a subject in need thereof a composition comprising an effective amount, e.g., a therapeutically effective amount, of a hetero-bifunctional compound as described herein or salt form thereof, and a pharmaceutically acceptable carrier, wherein the composition is effective for treating or ameliorating the disease or disorder or symptom thereof in the subject.

In another aspect, the description provides methods for identifying the effects of the selective or preferential degradation of a mutant LRRK2 protein according to the disclosure in a biological system using compounds according to the present disclosure.

In another aspect, the description provides processes and intermediates for making a hetero-bifunctional compound of the invention capable of targeted ubiquitination and selective or preferential degradation of a mutant LRRK2 protein according to the disclosure in a cell.

The preceding general areas of utility are given by way of example only and are not intended to be limiting on the scope of the present disclosure and appended claims. Additional objects and advantages associated with the compositions, methods, and processes of the present disclosure will be appreciated by one of ordinary skill in the art in light of the instant claims, description, and examples. For example, the various aspects and embodiments of the disclosure may be utilized in numerous combinations, all of which are expressly contemplated by the present description. These additional aspects and embodiments are expressly included within the scope of the present disclosure. The publications and other materials used herein to illuminate the background of the disclosure, and in particular cases, to provide additional details respecting the practice, are incorporated by reference.

BRIEF DESCRIPTION OF THE DRAWINGS

The accompanying drawings, which are incorporated into and form a part of the specification, illustrate several embodiments of the present disclosure and, together with the description, serve to explain the principles of the disclosure. The drawings are only for the purpose of illustrating embodiments of the disclosure and are not to be construed as limiting the disclosure. Further objects, features and advantages of the disclosure will become apparent from the following detailed description taken in conjunction with the accompanying figures showing illustrative embodiments of the disclosure.

FIG. 1A. Exemplary hetero-bifunctional protein degrading compounds comprise a protein targeting moiety (PTM; darkly shaded rectangle), a ubiquitin ligase binding moiety (ULM; lightly shaded triangle), and optionally a linker moiety (L; black line) coupling or tethering the PTM to the ULM. FIG. 1B Illustrates the functional use of the hetero-bifunctional protein degrading compounds (commercially known as PROTAC® brand compounds) as described herein. Briefly, the ULM (triangle) recognizes and binds to a specific E3 ubiquitin ligase, and the PTM (large rectangle) binds and recruits a target protein bringing it into close proximity to the E3 ubiquitin ligase. Typically, the E3 ubiquitin ligase is complexed with an E2 ubiquitin-conjugating protein (E2), and either alone or via the E2 protein catalyzes attachment of multiple ubiquitin molecules (black circles) to a lysine on the target protein via an isopeptide bond. The poly-ubiquitinated protein (far right) has thereby been targeted for degradation by the proteosomal machinery of the cell.

DETAILED DESCRIPTION

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, and other references mentioned herein are expressly incorporated by reference in their entirety.

Figure 1A:
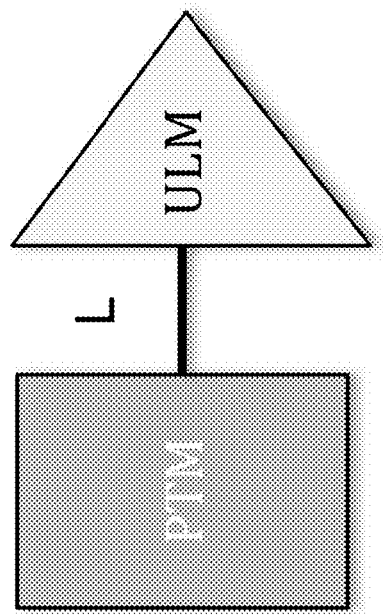
FIGS. 1A and 1B. Illustration of general principle for the functioning of hetero-bifunctional protein degrading compounds as described herein.
Figure 1B:
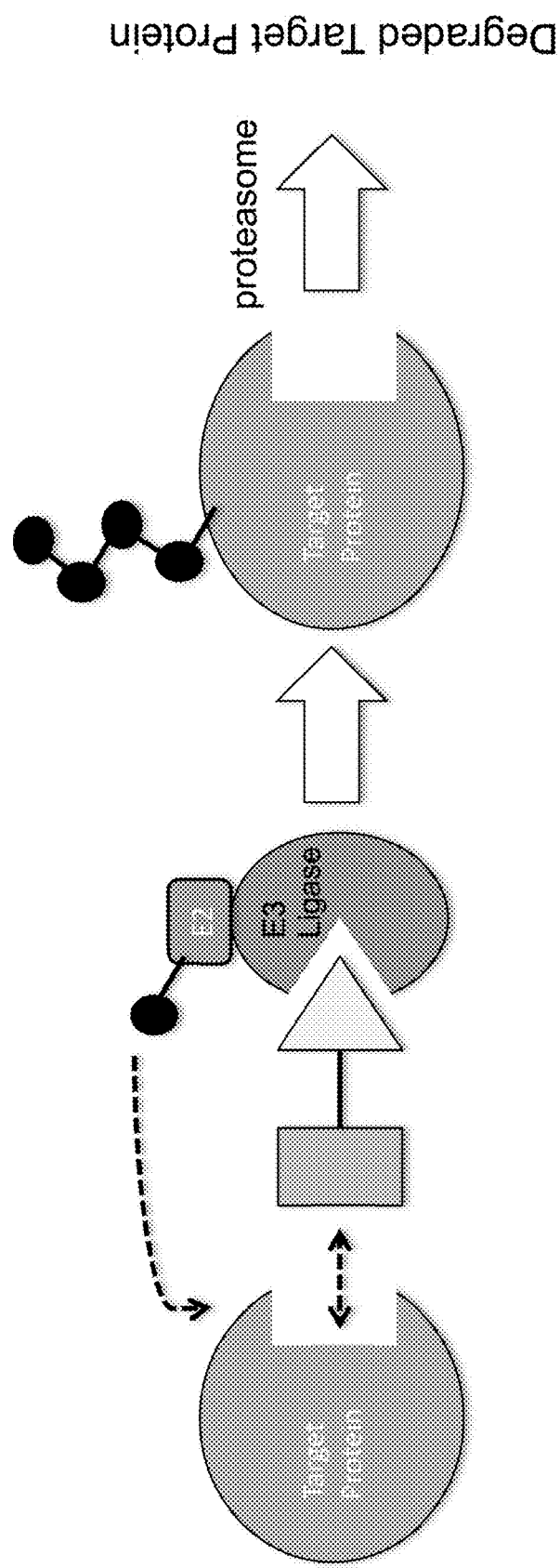

Presently described are compounds, compositions and methods that relate to the surprising and unexpected discovery that an E3 ubiquitin ligase (e.g., a cereblon E3 ubiquitin ligase) ubiquitinates the human LRRK2 protein once the E3 ubiquitin ligase and the LRRK2 protein are placed in proximity via a bifunctional compound that binds both the E3 ubiquitin ligase and the LRRK2 protein. Accordingly the present disclosure provides compounds and compositions comprising an E3 ubiquitin ligase binding moiety ("ULM") coupled by a bond or chemical linking group (L) to a protein targeting moiety ("PTM") that targets the LRRK2 protein, which results in the ubiquitination of the LRRK2 protein, and which leads to degradation of the LRRK2 protein by the proteasome (see FIG. 1).

In one aspect, the description provides compounds in which the PTM preferably binds the LRRK2 protein. The present disclosure also provides a library of compositions and the use thereof to produce targeted degradation of the LRRK2 protein in a cell.

In certain aspects, the present disclosure provides hetero-bifunctional compounds which comprise a ligand, e.g., a small molecule ligand (i.e., having a molecular weight of below 2,000, 1,000, 500, or 200 Daltons), which is capable of binding to an E3 ubiquitin ligase, such as cereblon. The compounds also comprise a small molecule moiety that is capable of binding to LRRK2 in such a way that the LRRK2 protein is placed in proximity to the ubiquitin ligase to effect ubiquitination and degradation (and/or inhibition) of the LRRK2 protein. "Small molecule" means, in addition to the above, that the molecule is non-peptidyl, that is, it is not considered a peptide, e.g., comprises fewer than 4, 3, or 2 amino acids. In accordance with the present description, each of the PTM, ULM and hetero-bifunctional molecule is a small molecule.

Unless otherwise defined, all technical and scientific terms used herein have the same meaning as commonly understood by one of ordinary skill in the art to which this disclosure belongs. The terminology used in the description is for describing particular embodiments only and is not intended to be limiting of the disclosure.

Where a range of values is provided, it is understood that each intervening value in the range, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either/or both of those included limits are also included in the disclosure.

The following terms are used to describe the present disclosure. In instances where a term is not specifically defined herein, that term is given an art-recognized meaning by those of ordinary skill applying that term in context to its use in describing the present disclosure.

The articles "a" and "an" as used herein and in the appended claims are used herein to refer to one or to more than one (i.e., to at least one) of the grammatical object of the article unless the context clearly indicates otherwise. By way of example, "an element" means one element or more than one element, unless otherwise indicated.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

It should also be understood that, in certain methods or processes described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time-varied administration (administration of one or more therapeutic agents at a time different from that of the administration of an additional therapeutic agent or agents), as long as the two or more therapeutic agents are present in the patient to some extent, preferably at effective amounts, at the same time. In certain preferred aspects, one or more of the hetero-bifunctional compounds described herein are coadministered with at least one additional bioactive agent, e.g., an anticancer agent. In particularly preferred aspects, the co-administration of such compounds results in synergistic activity and/or therapy such as, e.g., anticancer activity.

The term "compound", as used herein, unless otherwise indicated, refers to any specific hetero-bifunctional compound disclosed herein, pharmaceutically acceptable salts and solvates thereof, and deuterated forms of any of the aforementioned molecules, where applicable. Deuterated compounds contemplated are those in which one or more of the hydrogen atoms contained in the drug molecule have been replaced by deuterium. Such deuterated compounds preferably have one or more improved pharmacokinetic or pharmacodynamic properties (e.g., longer half-life) compared to the equivalent "undeuterated" compound.

The term "ubiquitin ligase" refers to a family of proteins that facilitate the transfer of one or more ubiquitins to a specific substrate protein. Addition of a chain of several ubiquitins (poly-ubiquitination) targets the substrate protein for degradation. For example, cereblon is an E3 ubiquitin ligase that alone, or in combination with an E2 ubiquitin-conjugating enzyme, can ultimately cause the attachment of a chain of four ubiquitins to a lysine residue on the target protein, thereby targeting the protein for degradation by the proteasome. The ubiquitin ligase is involved in poly-ubiquitination such that a first ubiquitin is attached to a lysine on the target protein; a second ubiquitin is attached to the first; a third is attached to the second, and a fourth is attached to the third. Such poly-ubiquitination marks proteins for degradation by the proteasome.

The term "patient" or "subject" is used throughout the specification to describe an animal, preferably a human or a domesticated animal, to whom treatment, including prophylactic treatment, with the compositions according to the present disclosure is provided. For treatment of those diseases, conditions or symptoms that are specific for a specific animal, such as a human patient, the term "patient" refers to that specific animal, including a domesticated animal such as a dog or cat, or a farm animal such as a horse, cow, sheep, etc. In general, in the present disclosure, the terms "patient" and "subject" refer to a human patient unless otherwise stated or implied from the context of the use of the term.

The terms "effective" and "therapeutically effective" are used to describe an amount of a compound or composition which, when used within the context of its intended use, and either in a single dose or, more preferably after multiple doses within the context of a treatment regimen, effects an intended result such as an improvement in a disease or condition, or amelioration or reduction in one or more symptoms associated with a disease or condition. The terms "effective" and "therapeutically effective" subsume all other "effective amount" or "effective concentration" terms, which are otherwise described or used in the present application.

Compounds and Compositions

In one aspect, the description provides hetero-bifunctional compounds comprising an E3 ubiquitin ligase binding moiety ("ULM") that is a cereblon E3 ubiquitin ligase binding moiety (a "CLM"), The CLM is covalently coupled to a protein targeting moiety (PTM) that binds to the protein, which coupling is either directly by a bond or via a chemical linking group (L) according to the structure:

PTM-L-CLM (A)

wherein L is the bond or chemical linking group, and PTM is a protein targeting moiety that binds to the protein LRRK2, where the PTM is a LRRK2 targeting moiety. The term CLM is inclusive of all cereblon binding moieties.

In any of the aspects or embodiments, the CLM demonstrates a half maximal inhibitory concentration ($IC_{50}$) for the E3 ubiquitin ligase (e.g., cereblon E3 ubiquitin ligase) of less than about 200 µM. The $IC_{50}$ can be determined according to any suitable method known in the art, e.g., a fluorescent polarization assay.

In certain embodiments, the hetero-bifunctional compounds described herein demonstrate an $IC_{50}$ or a half maximal degradation concentration ($DC_{50}$) of less than about 100, 50, 10, 1, 0.5, 0.1, 0.05, 0.01, 0.005, 0.001 mM, or less than about 100, 50, 10, 1, 0.5, 0.1, 0.05, 0.01, 0.005, 0.001 µM, or less than about 100, 50, 10, 1, 0.5, 0.1, 0.05, 0.01, 0.005, 0.001 nM, or less than about 100, 50, 10, 1, 0.5, 0.1, 0.05, 0.01, 0.005, 0.001 pM.

The term "alkyl" shall mean within its context a linear, branch-chained or cyclic fully saturated hydrocarbon radical, preferably a $C_1$-$C_{10}$, preferably a $C_1$-$C_6$, or more preferably a $C_1$-$C_3$ alkyl group, which may be optionally substituted with any suitable functional group or groups. Examples of alkyl groups are methyl, ethyl, n-butyl, sec-butyl, n-hexyl, n-heptyl, n-octyl, n-nonyl, n-decyl, isopropyl, 2-methylpropyl, cyclopropyl, cyclopropylmethyl, cyclobutyl, cyclopentyl, cyclopentylethyl, cyclohexylethyl and cyclohexyl, among others. In certain embodiments, the alkyl group is end-capped with a halogen group (At, Br, Cl, F, or I).

The term "Alkenyl" refers to linear, branch-chained or cyclic $C_2$-$C_{10}$ (preferably $C_2$-$C_6$) hydrocarbon radicals containing at least one C=C bond.

The term "Alkynyl" refers to linear, branch-chained or cyclic $C_2$-$C_{10}$ (preferably $C_2$-$C_6$) hydrocarbon radicals containing at least one C≡C bond.

The term "alkylene" when used, refers to a —$(CH_2)_n$— group (n is an integer generally from 0-6), which may be optionally substituted. When substituted, the alkylene group preferably is substituted on one or more of the methylene groups with a $C_1$-$C_6$ alkyl group (including a cyclopropyl group or a t-butyl group), but may also be substituted with one or more halo groups, preferably from 1 to 3 halo groups or one or two hydroxyl groups, O—($C_1$-$C_6$ alkyl) groups or amino acid sidechains as otherwise disclosed herein. In certain embodiments, an alkylene group may be substituted with a urethane or alkoxy group (or other suitable functional group) which may be further substituted with a polyethylene glycol chain (of from 1 to 10, preferably 1 to 6, or more preferably 1 to 4 ethylene glycol units) to which is substituted (preferably, but not exclusively on the distal end of the polyethylene glycol chain) an alkyl chain substituted with a single halogen group, preferably a chlorine group. In still other embodiments, the alkylene (e.g., methylene) group, may be substituted with an amino acid sidechain group such as a sidechain group of a natural or unnatural amino acid, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine.

The term "unsubstituted" shall mean substituted only with hydrogen atoms. A range of carbon atoms which includes $C_0$ means that carbon is absent and is replaced with H. Thus, a range of carbon atoms which is $C_0$-$C_6$ includes carbons atoms of 1, 2, 3, 4, 5 and 6 and for $C_0$, H stands in place of carbon.

The term "substituted" or "optionally substituted" shall mean independently (i.e., where more than one substituent occurs, each substituent is selected independent of another substituent) one or more substituents (independently up to five substituents, preferably up to three substituents, more preferably 1 or 2 substituents on a moiety in a compound according to the present disclosure and may include substituents which themselves may be further substituted) at a carbon (or nitrogen) position anywhere on a molecule within context, and includes as possible substituents hydroxyl, thiol, carboxyl, cyano (C≡N), nitro ($NO_2$), halogen (preferably, 1, 2 or 3 halogens, especially on an alkyl, especially a methyl group such as a trifluoromethyl), an alkyl group (preferably, $C_1$-$C_{10}$, more preferably, $C_1$-$C_6$), aryl (especially phenyl and substituted phenyl, for example benzyl or benzoyl), alkoxy group (preferably, $C_1$-$C_6$ alkyl or aryl, including phenyl and substituted phenyl), thioether (preferably, $C_1$-$C_6$ alkyl or aryl), acyl (preferably, $C_1$-$C_6$ acyl), ester or thioester (preferably, $C_1$-$C_6$ alkyl or aryl) including alkylene ester (such that attachment is on the alkylene group, rather than at the ester function which is preferably substituted with a $C_1$-$C_6$ alkyl or aryl group), halogen (preferably, F or Cl), amine (including a five- or six-membered cyclic alkylene amine, further including a $C_1$-$C_6$ alkyl amine or a $C_1$-$C_6$ dialkyl amine which alkyl groups may be substituted with one or two hydroxyl groups) or an optionally substituted —N($C_0$-$C_6$ alkyl)C(O)(O—$C_1$-$C_6$ alkyl) group (which may be optionally substituted with a polyethylene glycol chain to which is further bound an alkyl group containing a single halogen, preferably chlorine substituent), hydrazine, amido, which are preferably independently substituted with one or two $C_1$-$C_6$ alkyl groups (including a carboxamide which is optionally substituted with one or two $C_1$-$C_6$ alkyl groups), alkanol (preferably, $C_1$-$C_6$ alkyl or aryl), or alkanoic acid (preferably, $C_1$-$C_6$ alkyl or aryl). Substituents according to the present disclosure may include, for example —SiR$_1$R$_2$R$_3$ groups where each of R$_1$ and R$_2$ is as otherwise described herein and R$_3$ is H or a $C_1$-$C_6$ alkyl group, preferably R$_1$, R$_2$, R$_3$ together is a $C_1$-$C_3$ alkyl group (including an isopropyl or t-butyl group). Each of the above-described groups may be linked directly to the substituted moiety or alternatively, the substituent may be linked to the substituted moiety (preferably in the case of an aryl or heteroaryl moiety) through an optionally substituted —(CH$_2$)$_m$— or alternatively an optionally substituted —(OCH$_2$)$_m$—, —(OCH$_2$CH$_2$)$_m$— or —(CH$_2$CH$_2$O)$_m$— group, which may be substituted with any one or more of the above-described substituents. Alkylene groups —(CH$_2$)$_m$— or —(CH$_2$)$_n$— groups or other chains such as ethylene glycol chains, as identified above, may be substituted anywhere on the chain. Preferred substituents on alkylene groups include halogen or $C_1$-$C_6$ (preferably $C_1$-$C_3$) alkyl groups, which may be optionally substituted with one or two hydroxyl groups, one or two ether groups (O—$C_1$-$C_6$ groups), up to three halo groups (preferably F), or a side chain of an amino acid as otherwise described herein and optionally substituted amide (preferably carboxamide substituted as described above) or urethane groups (often with one or two $C_0$-$C_6$ alkyl substituents, which group(s) may be further substituted). In certain embodiments, the alkylene group (often a single methylene group) is substituted with one or two optionally substituted $C_1$-$C_6$ alkyl groups, preferably $C_1$-$C_4$ alkyl group, most often methyl or O-methyl groups or a sidechain of an amino acid as otherwise described herein. In the present disclosure, a moiety in a molecule may be optionally substituted with up to five substituents, preferably up to three substituents. Most often, in the present disclosure moieties which are substituted are substituted with one or two substituents.

The term "substituted" (each substituent being independent of any other substituent) shall also mean within its context of use $C_1$-$C_6$ alkyl, $C_1$-$C_6$ alkoxy, halogen, amido, carboxamido, sulfone, including sulfonamide, keto, carboxy, $C_1$-$C_6$ ester (oxyester or carbonylester), $C_1$-$C_6$ keto, urethane —O—C(O)—NR$_1$R$_2$ or —N(R$_1$)—C(O)—O—R$_1$, nitro, cyano and amine (especially including a $C_1$-$C_6$ alkylene-NR$_1$R$_2$, a mono- or di-$C_1$-$C_6$ alkyl substituted amines which may be optionally substituted with one or two hydroxyl groups). Each of these groups contain unless otherwise indicated, within context, between 1 and 6 carbon atoms. In certain embodiments, preferred substituents will include for example, —NH—, —NHC(O)—, —O—, =O, —(CH$_2$)$_m$— (here, m and n are in context, 1, 2, 3, 4, 5 or 6), —S—, —S(O)—, SO$_2$— or —NH—C(O)—NH—, —(CH$_2$)$_n$OH, —(CH$_2$)$_n$SH, —(CH$_2$)$_n$COOH, $C_1$-$C_6$ alkyl, —(CH$_2$)$_n$O—($C_1$-$C_6$ alkyl), —(CH$_2$)$_n$C(O)—($C_1$-$C_6$ alkyl), —(CH$_2$)$_n$OC(O)—($C_1$-$C_6$ alkyl), —(CH$_2$)$_n$C(O)O—($C_1$-$C_6$ alkyl), —(CH$_2$)$_n$NHC(O)—R$_1$, —(CH$_2$)$_n$C(O)—NR$_1$R$_2$, —(OCH$_2$)$_n$OH, —(CH$_2$O)$_n$COOH, $C_1$-$C_6$ alkyl, —(OCH$_2$)$_n$O—($C_1$-$C_6$ alkyl), —(CH$_2$O)$_n$C(O)—($C_1$-$C_6$ alkyl), —(OCH$_2$)$_n$NHC(O)—R$_1$, —(CH$_2$O)$_n$C(O)—NR$_1$R$_2$, —S(O)$_2$—R$_S$, —S(O)—R$_S$ (R$_S$ is $C_1$-$C_6$ alkyl or a —(CH$_2$)$_m$—NR$_1$R$_2$ group), NO$_2$, CN or halogen (F, Cl, Br, I, preferably F or Cl), depending on the context of the use of the substituent. R$_1$ and R$_2$ are each, within context, H or a $C_1$-$C_6$ alkyl group (which may be optionally substituted with one or two hydroxyl groups or up to three halogen groups, preferably fluorine). The term "substituted" shall also mean, within the chemical context of the compound defined and substituent used, an optionally substituted aryl or heteroaryl group or an optionally substituted heterocyclic group as otherwise described herein. Alkylene groups may also be substituted as otherwise disclosed herein, preferably with optionally substituted $C_1$-$C_6$ alkyl groups (methyl, ethyl or hydroxymethyl or hydroxyethyl is preferred, thus providing a chiral center), a sidechain of an amino acid group as otherwise described herein, an amido group as described hereinabove, or a urethane group O—C(O)—NR$_1$R$_2$ group where R$_1$ and R$_2$ are as otherwise described herein, although numerous other groups may also be used as substituents. Various optionally substituted moieties may be substituted with 3 or more substituents, preferably no more than 3 substituents and preferably with 1 or 2 substituents. It is noted that in instances where, in a compound at a particular position of the molecule substitution is required (principally, because of valency), but no substitution is indicated, then that substituent is construed or understood to be H, unless the context of the substitution suggests otherwise.

The term "aryl" or "aromatic", in context, refers to a substituted (as otherwise described herein) or unsubstituted monovalent aromatic radical (e.g., a 5-16 membered ring) having a single ring (e.g., benzene, phenyl, benzyl, or 5, 6, 7 or 8 membered ring) or condensed rings (e.g., naphthyl, anthracenyl, phenanthrenyl, 10-16 membered ring, etc.) and can be bound to the compound according to the present disclosure at any available stable position on the ring(s) or as otherwise indicated in the chemical structure presented. Other examples of aryl groups, in context, may include heterocyclic aromatic ring systems, "heteroaryl" groups having one or more nitrogen, oxygen, or sulfur atoms in the ring (moncyclic) such as imidazole, furyl, pyrrole, furanyl, thiene, thiazole, pyridine, pyrimidine, pyrazine, triazole, oxazole or fused ring systems such as indole, quinoline, indolizine, azaindolizine, benzofurazan, etc., among others, which may be optionally substituted as described above. Among the heteroaryl groups which may be mentioned include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, azaindolizine, purine, indazole, quinoline, dihydroquinoline, tetrahydroquinoline, isoquinoline, dihydroisoquinoline, tetrahydroisoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, pyrimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising 2 or more hetero atoms selected from among nitrogen, sulfur and oxygen, such as thiazole, thiadizole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "substituted aryl" refers to an aromatic carbocyclic group comprised of at least one aromatic ring or of multiple condensed rings at least one of which being aromatic, wherein the ring(s) are substituted with one or more substituents. For example, an aryl group can comprise a substituent(s) selected from: —(CH$_2$)$_n$OH, —(CH$_2$)$_n$—O—(C$_1$-C$_6$)alkyl, —(CH$_2$)$_n$—O—(CH$_2$)$_n$—(C$_1$-C$_6$)alkyl, —(CH$_2$)$_n$—C(O)(C$_0$-C$_6$) alkyl, —(CH$_2$)$_n$—C(O)O(C$_0$-C$_6$) alkyl, —(CH$_2$)$_n$—OC(O)(C$_0$-C$_6$)alkyl, amine, mono- or di-(C$_1$-C$_6$ alkyl) amine wherein the alkyl group on the amine is optionally substituted with 1 or 2 hydroxyl groups or up to three halo (preferably F, Cl) groups, OH, COOH, C$_1$-C$_6$ alkyl, preferably CH$_3$, CF$_3$, OMe, OCF$_3$, NO$_2$, or CN group (each of which may be substituted in ortho-, meta- and/or para-positions of the phenyl ring, preferably para-), an optionally substituted phenyl group (the phenyl group itself is preferably connected to a PTM group, including a ULM group, via a linker group), and/or at least one of F, Cl, OH, COOH, CH$_3$, CF$_3$, OMe, OCF$_3$, NO$_2$, or CN group (in ortho-, meta- and/or para-positions of the phenyl ring, preferably para-), a naphthyl group, which may be optionally substituted, an optionally substituted heteroaryl, preferably an optionally substituted isoxazole including a methyl substituted isoxazole, an optionally substituted oxazole including a methyl substituted oxazole, an optionally substituted thiazole including a methyl substituted thiazole, an optionally substituted isothiazole including a methyl substituted isothiazole, an optionally substituted pyrrole including a methyl substituted pyrrole, an optionally substituted imidazole including a methylimidazole, an optionally substituted benzimidazole or methoxybenzylimidazole, an optionally substituted oximidazole or methyloximidazole, an optionally substituted diazole group, including a methyldiazole group, an optionally substituted triazole group, including a methyl substituted triazole group, an optionally substituted pyridine group, including a halo- (preferably, F) or methyl substituted pyridine group or an oxapyridine group (where the pyridine group is linked to the phenyl group by an oxygen), an optionally substituted furan, an optionally substituted benzofuran, an optionally substituted dihydrobenzofuran, an optionally substituted indole, indolizine or azaindolizine (2, 3, or 4-azaindolizine), an optionally substituted quinoline, and combinations thereof.

"Carboxyl" denotes the group —C(O)OR, where R is hydrogen, alkyl, substituted alkyl, aryl, substituted aryl, heteroaryl or substituted heteroaryl, whereas these generic substituents have meanings which are identical with definitions of the corresponding groups defined herein.

The term "heteroaryl" or "hetaryl" can mean but is in no way limited to a 5-16 membered heteroaryl (e.g., 5, 6, 7 or 8 membered monocyclic ring or a 10-16 membered heteroaryl having multiple condensed rings), an optionally substituted quinoline (which may be attached to the pharmacophore or substituted on any carbon atom within the quinoline ring), an optionally substituted indole (including dihydroindole), an optionally substituted indolizine, an optionally substituted azaindolizine (2, 3 or 4-azaindolizine) an optionally substituted benzimidazole, benzodiazole, benzoxofuran, an optionally substituted imidazole, an optionally substituted isoxazole, an optionally substituted oxazole (preferably methyl substituted), an optionally substituted diazole, an optionally substituted triazole, a tetrazole, an optionally substituted benzofuran, an optionally substituted thiophene, an optionally substituted thiazole (preferably methyl and/or thiol substituted), an optionally substituted isothiazole, an optionally substituted triazole (preferably a 1,2,3-triazole substituted with a methyl group, a triisopropylsilyl group, an optionally substituted —(CH$_2$)$_m$—O—C$_1$-C$_6$ alkyl group or an optionally substituted —(CH$_2$)$_m$—

C(O)—O—C$_1$-C$_6$ alkyl group), an optionally substituted pyridine (2-, 3, or 4-pyridine) or a group according to the chemical structure:

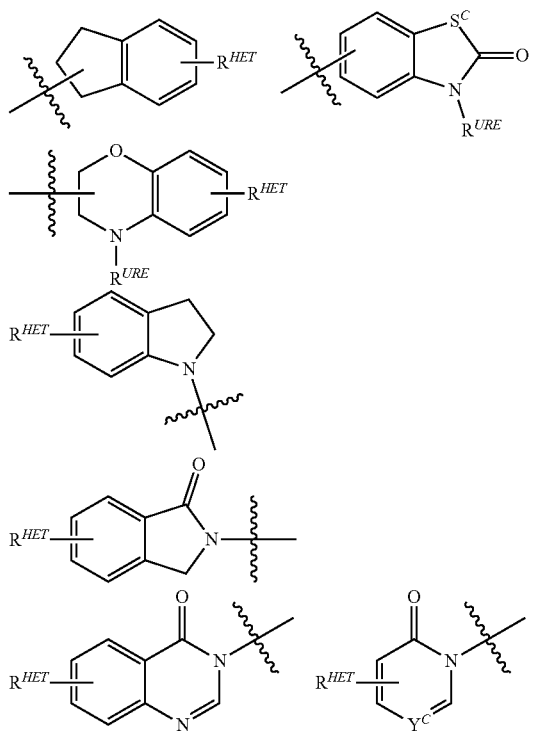

wherein:
S$^C$ is CHR$^{SS}$, NR$^{URE}$, or O;
R$^{HET}$ is H, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups) or an optionally substituted acetylenic group —C≡C—R$_a$ where R$_a$ is H or a C$_1$-C$_6$ alkyl group (preferably C$_1$-C$_3$ alkyl);
R$^{SS}$ is H, CN, NO$_2$, halo (preferably F or Cl), optionally substituted C$_1$-C$_6$ alkyl (preferably substituted with one or two hydroxyl groups or up to three halo groups), optionally substituted O—(C$_1$-C$_6$ alkyl) (preferably substituted with one or two hydroxyl groups or up to three halo groups) or an optionally substituted —C(O) (C$_1$-C$_6$ alkyl) (preferably substituted with one or two hydroxyl groups or up to three halo groups);
R$^{URE}$ is H, a C$_1$-C$_6$ alkyl (preferably H or C$_1$-C$_3$ alkyl) or a —C(O)(C$_1$-C$_6$ alkyl), each of which groups is optionally substituted with one or two hydroxyl groups or up to three halogen, preferably fluorine groups, or an optionally substituted heterocycle, for example piperidine, morpholine, pyrrolidine, tetrahydrofuran, tetrahydrothiophene, piperidine, piperazine, each of which is optionally substituted, and
Y$^C$ is N or C—R$^{YC}$, where R$^{YC}$ is H, OH, CN, NO$_2$, halo (preferably Cl or F), optionally substituted C$_1$-C$_6$ alkyl (preferably substituted with one or two hydroxyl groups or up to three halo groups (e.g. CF$_3$), optionally substituted O(C$_1$-C$_6$ alkyl) (preferably substituted with one or two hydroxyl groups or up to three halo groups)

or an optionally substituted acetylenic group —C≡C—$R_a$ where $R_a$ is H or a $C_1$-$C_6$ alkyl group (preferably $C_1$-$C_3$ alkyl).

The terms "aralkyl" and "heteroarylalkyl" refer to groups that comprise both aryl or, respectively, heteroaryl as well as alkyl and/or heteroalkyl and/or carbocyclic and/or heterocycloalkyl ring systems according to the above definitions.

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above.

The term "Heterocycle" refers to a cyclic group which contains at least one heteroatom, e.g., N, O or S, and may be aromatic (heteroaryl) or non-aromatic. Thus, the heteroaryl moieties are subsumed under the definition of heterocycle, depending on the context of its use. Exemplary heteroaryl groups are described hereinabove.

Exemplary heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, ethyleneurea, 1,3-dioxolane, 1,3-dioxane, 1,4-dioxane, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, pyridone, 2-pyrrolidone, pyridine, piperazinyl, N-methylpiperazinyl, piperidinyl, phthalimide, succinimide, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, tetrahydroquinoline, thiazolidinyl, thiazolyl, thienyl, tetrahydrothiophene, oxane, oxetanyl, oxathiolanyl, thiane among others.

Heterocyclic groups can be optionally substituted with a member selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxy, carboxyalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SOaryl, —SO— heteroaryl, —SO2-alkyl, —SO2-substituted alkyl, —SO2-aryl, oxo (=O), and —SO2-heteroaryl. Such heterocyclic groups can have a single ring or multiple condensed rings. Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxynitrogen containing heterocycles. The term "heterocyclic" also includes bicyclic groups in which any of the heterocyclic rings is fused to a benzene ring or a cyclohexane ring or another heterocyclic ring (for example, indolyl, quinolyl, isoquinolyl, tetrahydroquinolyl, and the like).

The term "cycloalkyl" can mean but is in no way limited to univalent groups derived from monocyclic or polycyclic alkyl groups or cycloalkanes, as defined herein, e.g., saturated monocyclic hydrocarbon groups having from three to twenty carbon atoms in the ring, including, but not limited to, cyclopropyl, cyclobutyl, cyclopentyl, cyclohexyl, cycloheptyl and the like. The term "substituted cycloalkyl" can mean but is in no way limited to a monocyclic or polycyclic alkyl group and being substituted by one or more substituents, for example, amino, halogen, alkyl, substituted alkyl, carbyloxy, carbylmercapto, aryl, nitro, mercapto or sulfo, whereas these generic substituent groups have meanings which are identical with definitions of the corresponding groups as defined in this legend.

"Heterocycloalkyl" refers to a monocyclic or polycyclic alkyl group in which at least one ring carbon atom of its cyclic structure being replaced with a heteroatom selected from the group consisting of N, O, S or P. "Substituted heterocycloalkyl" refers to a monocyclic or polycyclic alkyl group in which at least one ring carbon atom of its cyclic structure being replaced with a heteroatom selected from the group consisting of N, O, S or P and the group is containing one or more substituents selected from the group consisting of halogen, alkyl, substituted alkyl, carbyloxy, carbylmercapto, aryl, nitro, mercapto or sulfo, whereas these generic substituent group have meanings which are identical with definitions of the corresponding groups as defined in this legend.

The term "hydrocarbyl" shall mean a compound which contains carbon and hydrogen and which may be fully saturated, partially unsaturated or aromatic and includes aryl groups, alkyl groups, alkenyl groups and alkynyl groups.

The term "independently" is used herein to indicate that the variable, which is independently applied, varies independently from application to application.

The term "lower alkyl" refers to methyl, ethyl or propyl

The term "lower alkoxy" refers to methoxy, ethoxy or propoxy.

Exemplary CLMs

Neo-Imide Compounds

In any aspect or embodiment described herein, the description provides CLMs useful for binding and recruiting cereblon. In certain embodiments, the CLM is selected from the group consisting of chemical structures:

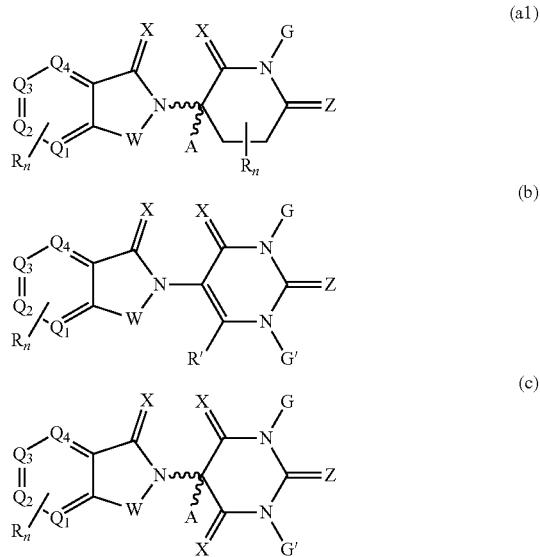

-continued

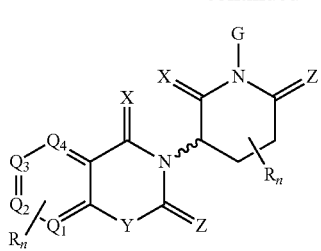
(d1)

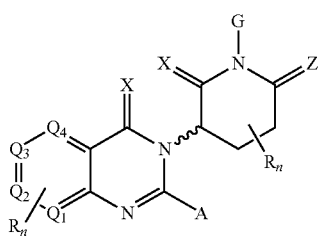
(e)

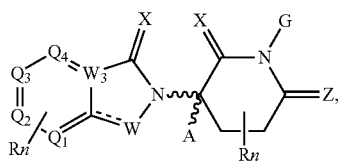
(a2)

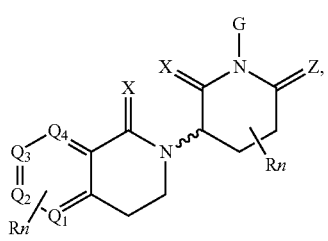
(d2)

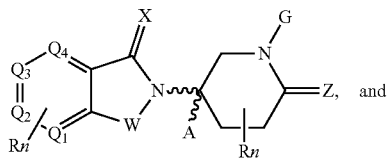
(a3)

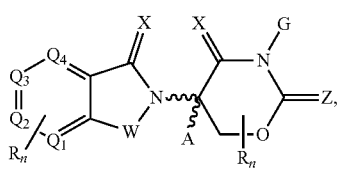
(a4)

wherein:
W of Formulas (a1) through (e) [e.g., (a1), (a2), (a3), (a4), (b), (c), (d1), (d2), and/or (e)] is independently selected from the group $CH_2$, O, CHR, C=O, $SO_2$, NH, N, optionally substituted cyclopropyl group, optionally substituted cyclobutyl group, and N-alkyl;

$W_3$ of Formulas (a1) through (e) is selected from C or N;

X of Formulas (a1) through (e) is independently selected from the group absent, O, S and $CH_2$;

Y of Formulas (a1) through (e) is independently selected from the group $CH_2$, —C=CR', NH, N-alkyl, N-aryl, N-heteroaryl, N-cycloalkyl, N-heterocyclyl, O, and S;

Z of Formulas (a1) through (e) is independently selected from the group absent, O, and S or $CH_2$ except that both X and Z cannot be $CH_2$ or absent;

G and G' of Formulas (a1) through (e) are independently selected from the group H, optionally substituted linear or branched alkyl, OH, R'OCOOR, R'OCONRR", $CH_2$-heterocyclyl optionally substituted with R', and benzyl optionally substituted with R';

Q1-Q4 of Formulas (a1) through (e) represent a carbon C or N substituted with a group independently selected from H, R, N or N-oxide;

A of Formulas (a1) through (e) is independently selected from the group H, optionally substituted linear or branched alkyl, cycloalkyl, Cl and F;

n of Formulas (a1) through (e) represent an integer from 1 to 10 (e.g., 1-4, 1, 2, 3, 4, 5, 6, 7, 8, 9, or 10);

R of Formulas (a1) through (e) comprises, but is not limited to: a bond, H, —C(=O)R' (e.g., a carboxy group), —CONR'R" (e.g., an amide group), —OR' (e.g., OH), —NR'R" (e.g., an amine group), —SR', —$SO_2$R', —$SO_2$NR'R", —CR'R"—, —CR'NR'R"—, (—CR'O)$_n$R", optionally substituted heterocyclyl, optionally substituted aryl, (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted heteroaryl, optionally substituted alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", OP(O)(OR')R", —OP(O)R'R", —Cl, —F, —Br, —I, —$CF_3$, —CN, —NR'$SO_2$NR'R", —NR'CONR'R", —CONR'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ and —$OCF_3$, wherein at least one W, X, Y, Z, G, G', R, R', R", Q1-Q4, or A is modified to be covalently joined to a PTM, a chemical linking group (L), a ULM, CLM, or combination thereof;

each of x, y, and z of Formulas (a1) through (e) are independently 0, 1, 2, 3, 4, 5, or 6;

R' and R" of Formulas (a1) through (e) are independently selected from a bond, H, optionally substituted linear or branched alkyl, optionally substituted cycloalkyl, optionally substituted aryl, optionally substituted heteroaryl, optionally substituted heterocyclic, —C(=O)R, optionally substituted heterocyclyl;

n' of Formulas (a1) through (e) is an integer from 1-10 (e.g. 1-4, 1, 2, 3, 4, 5, 6, 7, 8, 9, or 10);

⁓⁓⁓ represents a single bond or a double bond; and

〰 of Formulas (a1) through (e) represents a bond that may be stereospecific ((R) or (S)) or non-stereospecific.

In any aspect or embodiment described herein, the CLM comprises a chemical structure selected from the group consisting of:

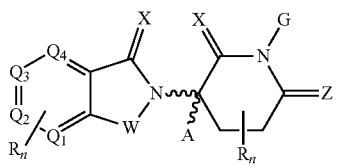
(a1)

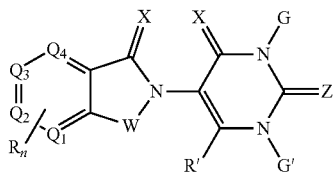
(b)

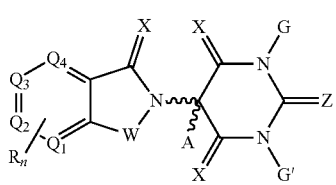
(c)

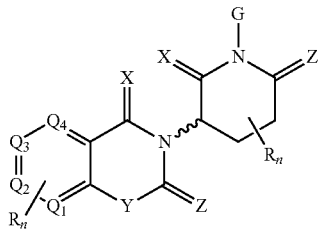
(d1)

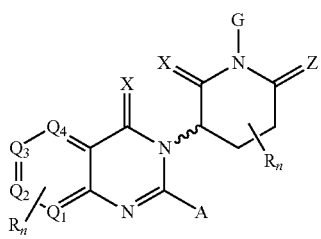
(e)

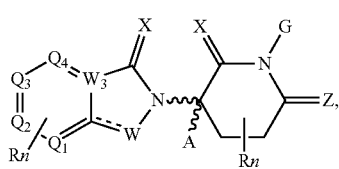
(a2)

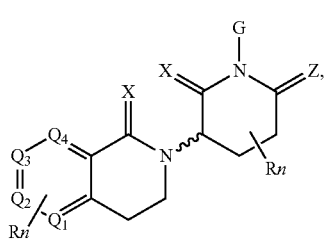
(d2)

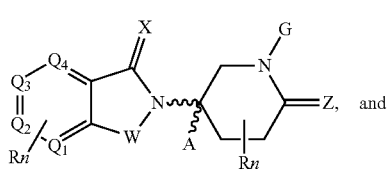
(a3)

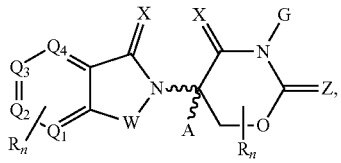
(a4)

-continued wherein:
W of Formulas (a1) through (e) [e.g., (a1), (a2), (a3), (a4), (b), (c), (d1), (d2), and/or (e)] is independently selected from the group $CH_2$, O, CHR, C=O, $SO_2$, NH, N, optionally substituted cyclopropyl group, optionally substituted cyclobutyl group, and N-alkyl;

$W_3$ of Formulas (a1) through (e) is selected from C or N;

X of Formulas (a1) through (e) is independently selected from the group O, S and $CH_2$;

Y of Formulas (a1) through (e) is independently selected from the group $CH_2$, —C=CR', NH, N-alkyl, N-aryl, N-hetaryl, N-cycloalkyl, N-heterocyclyl, O, and S;

Z of Formulas (a1) through (e) is independently selected from the group O, and S or CH2 except that both X and Z cannot be $CH_2$ or absent;

G and G' of Formulas (a1) through (e) are independently selected from the group H, optionally substituted linear or branched alkyl, OH, R'OCOOR, R'OCONRR", $CH_2$-heterocyclyl optionally substituted with R', and benzyl optionally substituted with R';

Q1-Q4 of Formulas (a1) through (e) represent a carbon C or N substituted with a group independently selected from H, R, N or N-oxide;

A of Formulas (a1) through (e) is independently selected from the group H, optionally substituted linear or branched alkyl, cycloalkyl, Cl and F;

n of Formulas (a1) through (e) represent an integer from 1 to 10 (e.g., 1-4, 1, 2, 3, 4, 5, 6, 7, 8, 9, or 10);

R of Formulas (a1) through (e) comprises, but is not limited to: a bond, H, —C(=O)R' (e.g., a carboxy group), —CONR'R" (e.g., an amide group), —OR' (e.g., OH), —NR'R" (e.g. an amine group), —SR', —SO2R', —SO2NR'R", —CR'R"—, —CR'NR'R"—, (—CR'O)$_n$R", optionally substituted aryl (e.g., an optionally substituted C5-C7 aryl), optionally substituted alkyl-aryl (e.g., an alkyl-aryl comprising at least one of an optionally substituted C1-C6 alkyl, an optionally substituted C5-C7 aryl, or combinations thereof), optionally substituted hetaryl, -optionally substituted linear or branched alkyl (e.g., a C1-C6 linear or branched alkyl optionally substituted with one or more halogen, cycloalkyl (e.g., a C3-C6 cycloalkyl), or aryl (e.g., C5-C7 aryl)), optionally substituted alkoxyl group (e.g., a methoxy, ethoxy, butoxy, propoxy, pentoxy, or hexoxy; wherein the alkoxyl may be substituted with one or more halogen, alkyl, haloalky, fluoroalkyl, cycloalkyl (e.g., a C3-C6 cycloalkyl), or aryl (e.g., C5-C7 aryl)), optionally substituted cycloalkyl, optionally substituted heterocyclyl, —P(O)(OR')R", —P(O)R'R", OP(O)(OR')R", —OP(O)R'R", —Cl, —F, —Br, —I, —CF3, —CN, —NR'SO2NR'R", —NR'CONR'R", —CONR'COR", —NR'C(=N—CN)NR'R", —C(=N—CN)NR'R", —NR'C(=N—CN)R", —NR'C(=C—NO2)NR'R", —SO2NR'COR", —NO2, —CO2R', —C(C=N—OR')R", —CR'=CR'R", —CCR', —S(C=O)(C=N—R')R", —SF5 and —OCF3, wherein at least one of W, X, Y, Z, G, G', R, R', R", Q1-Q4, or A is covalently joined (directly or indirectly, e.g., via a functional group or an atom, such as O, S, N) to a PTM, a chemical linking group (L), a ULM, CLM, or combination thereof;

each of x, y, and z of Formulas (a1) through (e) are independently 0, 1, 2, 3, 4, 5, or 6;

R' and R" of Formulas (a1) through (e) are independently selected from a bond, H, optionally substituted linear or branched alkyl, optionally substituted cycloalkyl, optionally substituted aryl, optionally substituted heteroaryl, optionally substituted heterocyclic, —C(=O)R, optionally substituted heterocyclyl;

n' of Formulas (a1) through (e) is an integer from 1-10 (e.g., 1-4, 1, 2, 3, 4, 5, 6, 7, 8, 9, or 10); and ⌇ of Formulas (a1) through (e) represents a bond that may be stereospecific ((R) or (S)) or non-stereospecific.

In any aspect or embodiment described herein, the CLM or ULM is selected from the structure of Formula (g):

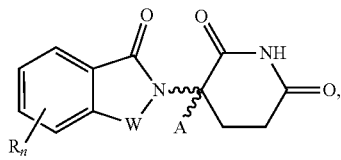

Formula (g)

wherein:

W of Formula (g) is independently selected from the group CH$_2$, O, C=O, NH, and N-alkyl;

A of Formula (g) is selected from a H, methyl, or optionally substituted linear or branched alkyl;

n is an integer from 1 to 4;

R of Formula (g) is independently selected from a bond, H, O, OH, N, NH, NH$_2$, Cl, —F, —Br, —I, methyl, optionally substituted linear or branched alkyl (e.g., optionally substituted linear or branched C1-C6 alkyl), optionally substituted linear or branched alkoxy (e.g., optionally substituted linear or branched C1-C6 alkoxy), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy), wherein at least one R or W is modified to be covalently joined to a PTM, a chemical linking group (L), a ULM, CLM, or combination thereof; and ⌇ of Formula (g) represents a bond that may be stereospecific ((R) or (S)) or non-stereo specific.

In any aspect or embodiment described herein, the CLM or ULM is selected from the group consisting of:

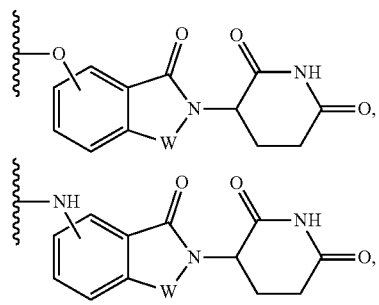

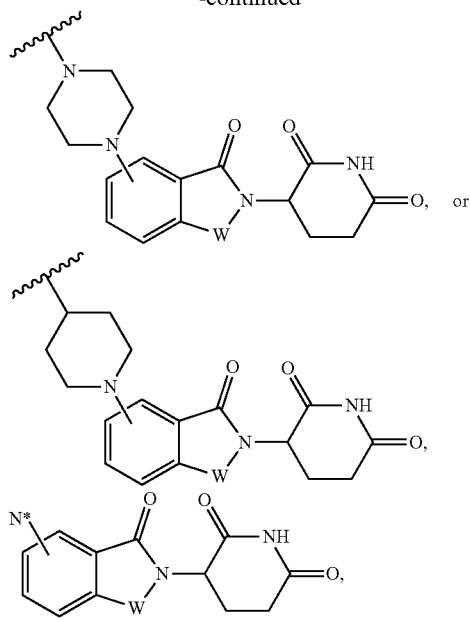

wherein:

W is C=O or CH$_2$;

N* is a nitrogen atom that is covalently linked to the PTM or linker, or that is shared with the PTM or linker (L) (e.g., a heteroatom shared with an optionally substituted heterocyclyl of the linker (L) or PTM); and ⌇— indicates the point of attachment of the CLM or ULM to the linker (L) or PTM.

In any aspect or embodiment described herein, R is selected from: H, O, OH, N, NH, NH$_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy).

In any aspect or embodiment described herein, at least one R (e.g. an R group selected from the following H, O, OH, N, NH, NH$_2$, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy) or W is modified to be covalently joined to a PTM, a chemical linker group (L), a ULM, a CLM, or a combination thereof In any aspect or embodiment described herein, the W, X, Y, Z, G, G', R, R', R", Q1-Q4, and A of Formulas (a) through (g) can independently be covalently coupled to a linker and/or a linker to which is attached one or more PTM, ULM, or CLM groups.

In any of the aspects or embodiments described herein, n is an integer from 1 to 4, and each R is independently selected functional groups or atoms, for example, O, OH, N, —Cl, —F, C1-C6 alkyl, C1-C6 alkoxy, -alkyl-aryl (e.g., an -alkyl-aryl comprising at least one of C1-C6 alkyl, C4-C7 aryl, or a combination thereof), aryl (e.g., C5-C7 aryl), amine, amide, or carboxy, on the aryl or heteroaryl of the CLM, and optionally, one of which is modified to be covalently joined to a PTM, a chemical linker group (L), a ULM, CLM or combination thereof.

More specifically, non-limiting examples of CLMs include those shown below as well as those "hybrid" molecules that arise from the combination of one or more of the different features shown in the molecules below wherein at least one R or W is modified to be covalently joined to a PTM, a chemical linking group (L), a ULM, CLM, or combination thereof.
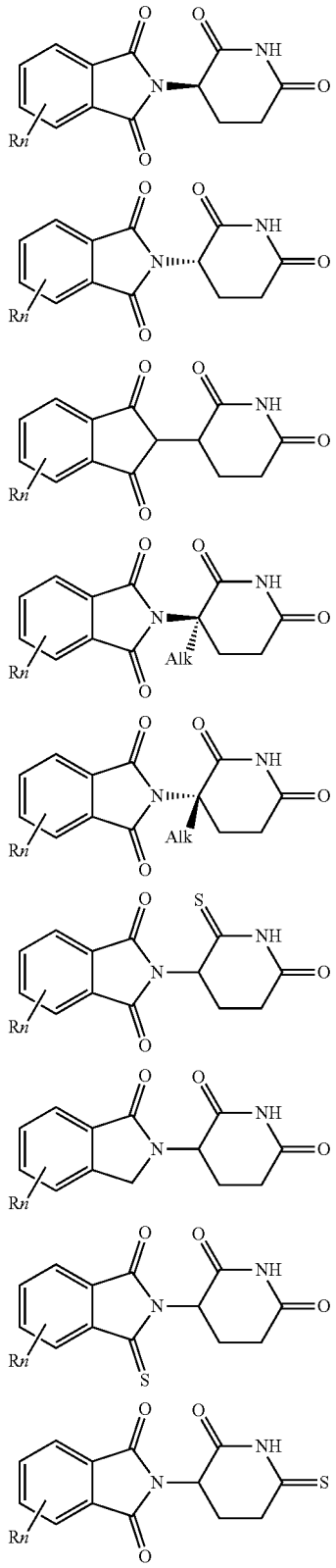
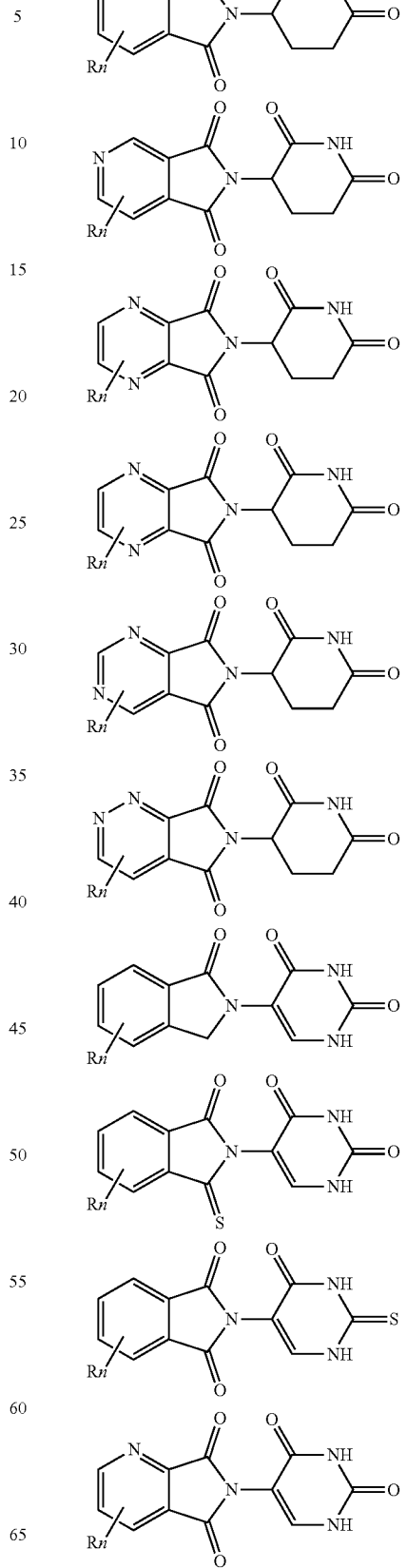

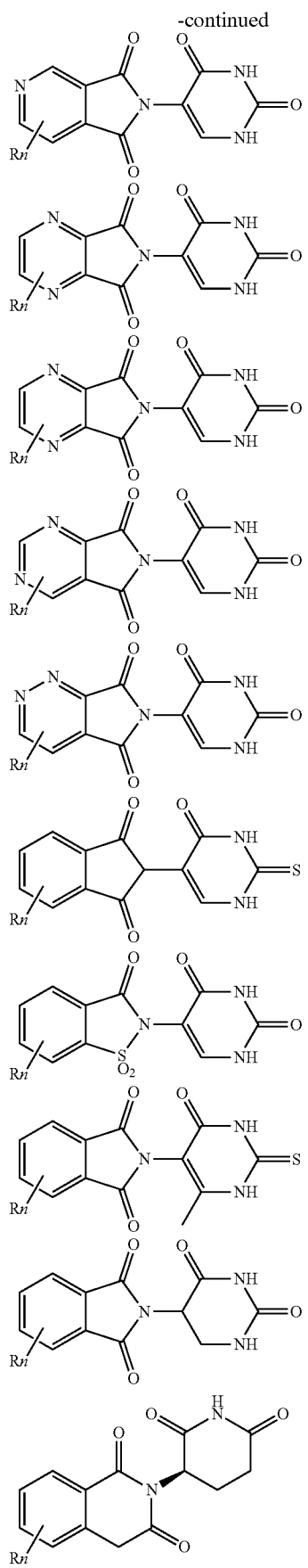
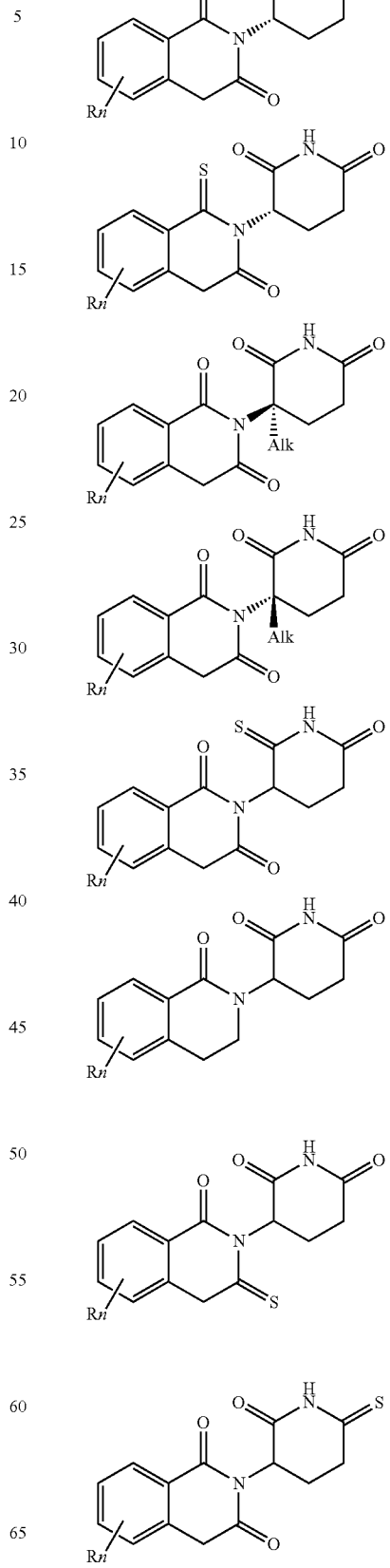

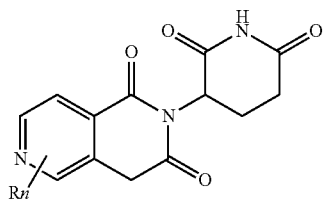
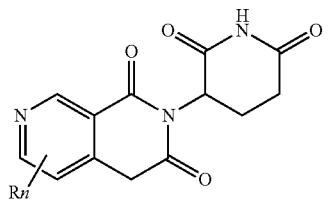
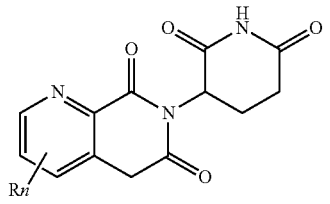
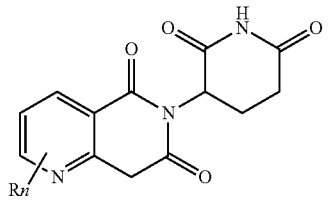
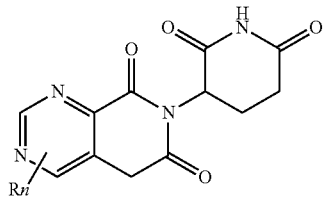
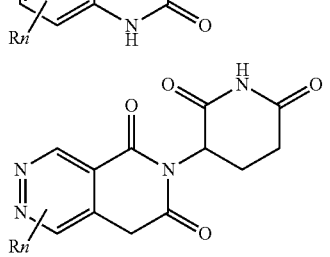
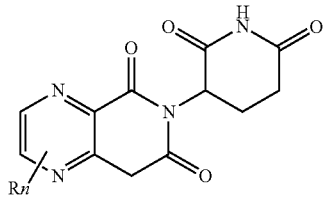
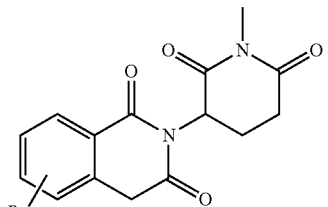
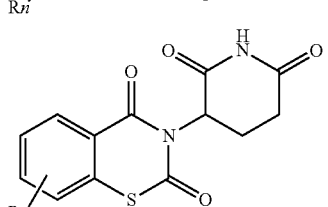
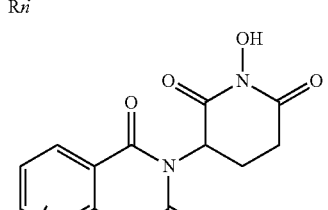
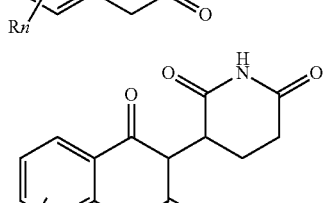
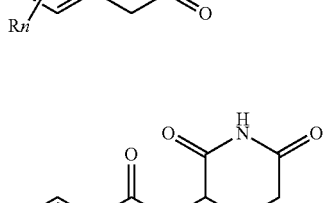

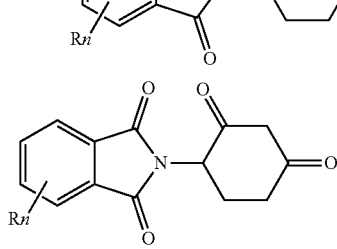

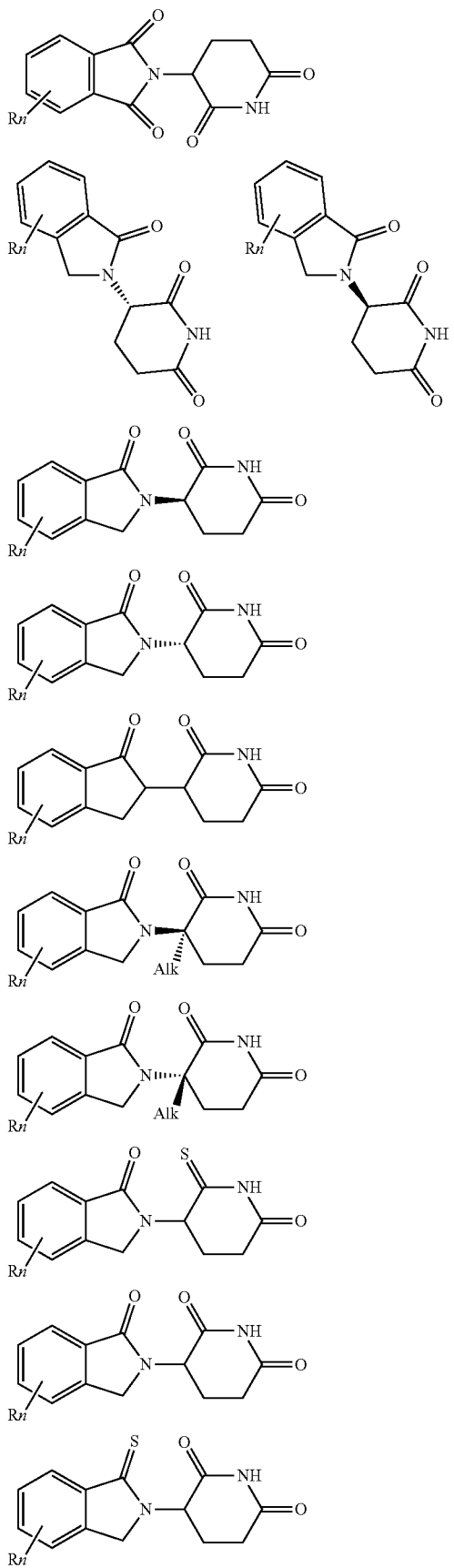
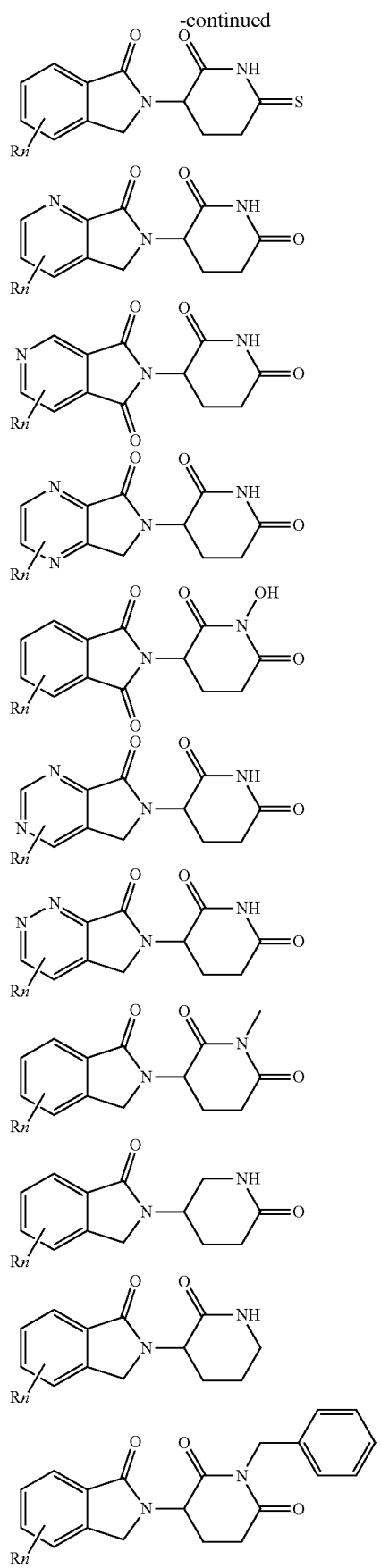

-continued
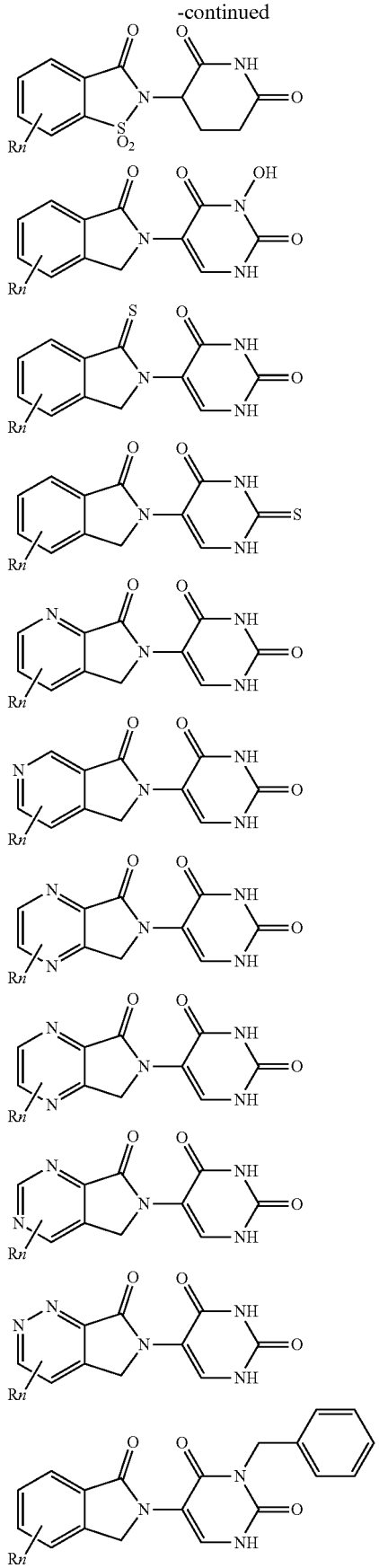
-continued
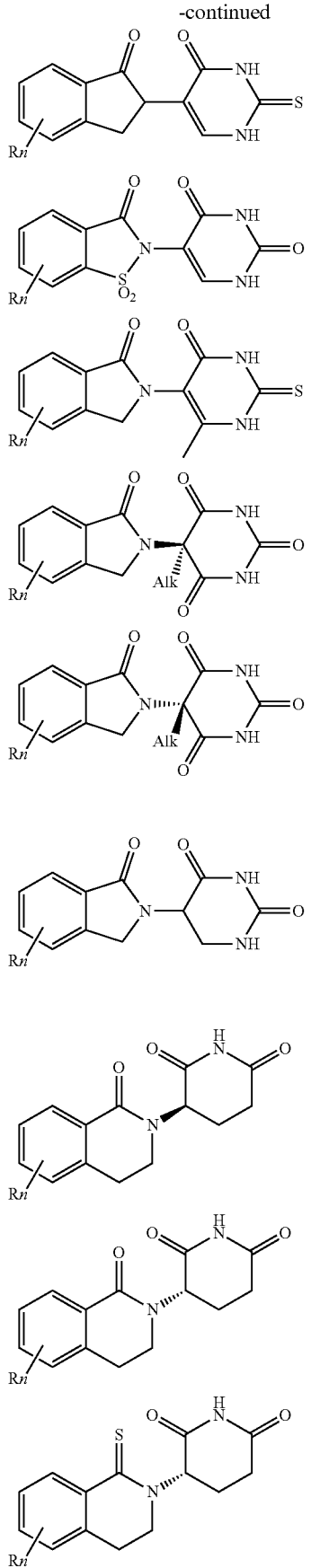

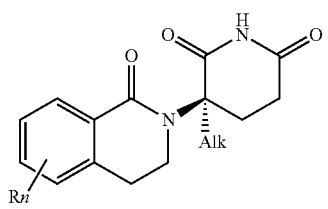
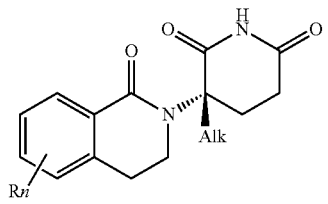
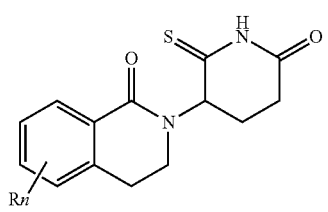
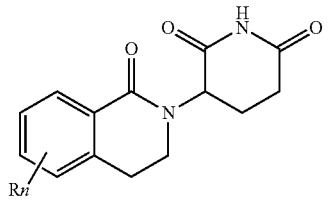
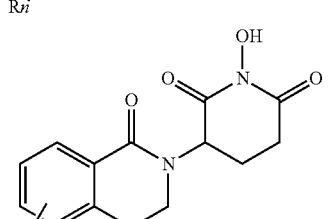
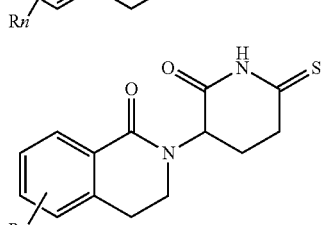
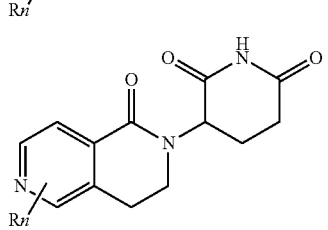
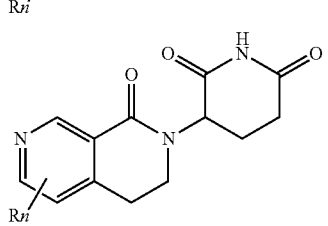
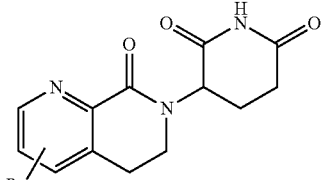
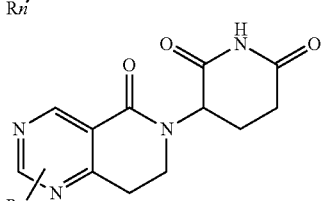
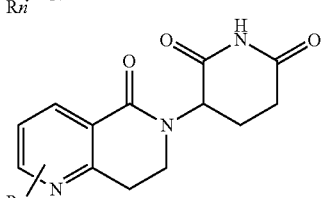
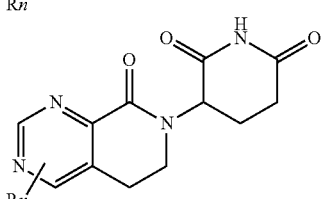
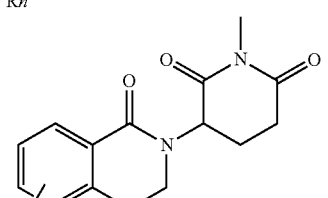
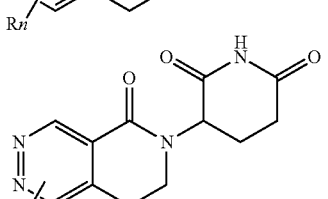
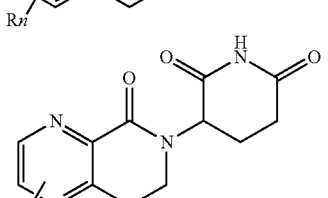
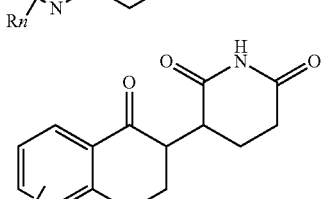
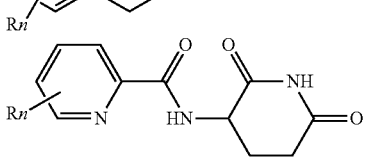

-continued
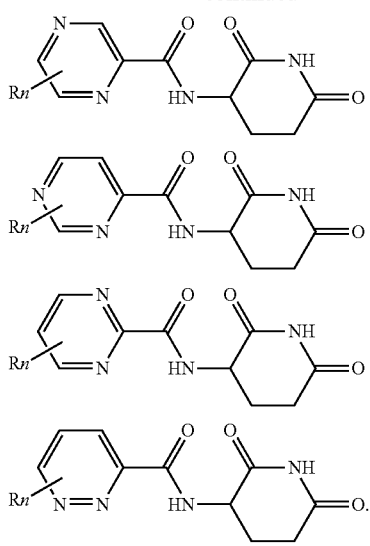
In any aspect or embodiment described herein, the CLM comprises a chemical structure selected from the group:
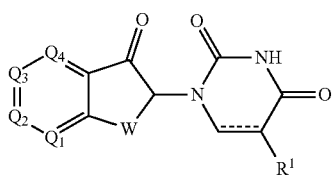
(h)
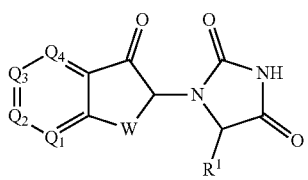
(i)
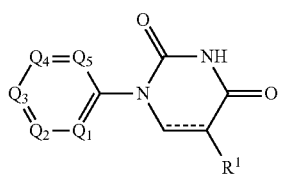
(j)
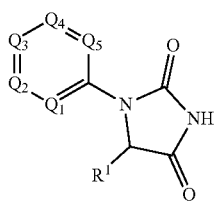
(k)
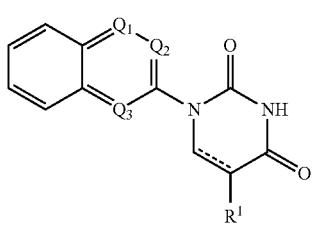
(l)
-continued
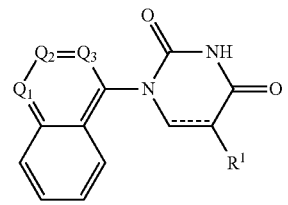
(m)
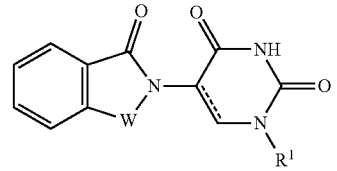
(n)
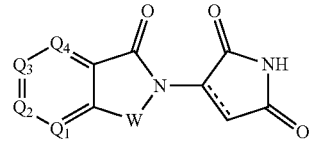
(o)
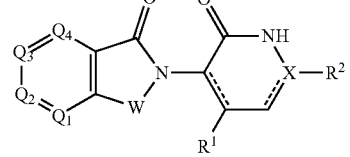
(p)
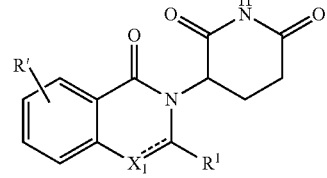
(q)
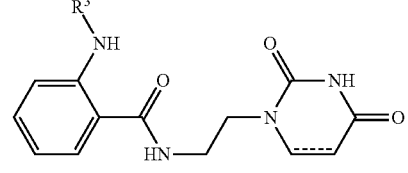
(r)
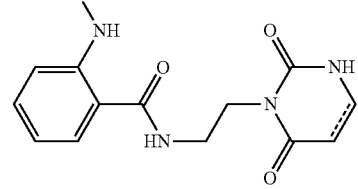
(s)
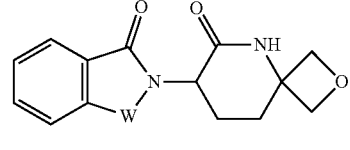
(t)
(u)

-continued
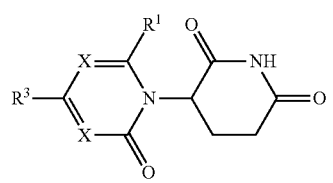 (v)
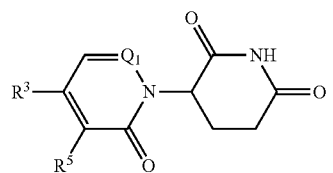 (w)
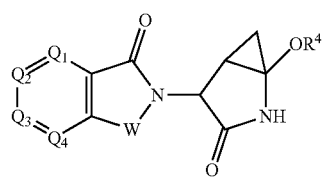 (x)
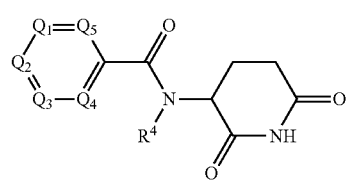 (y)
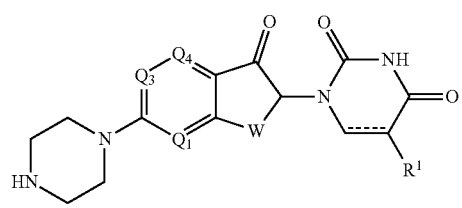 (z)
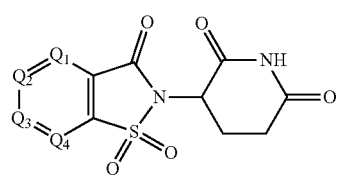 (aa)
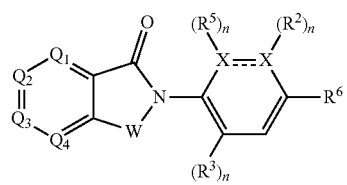 (ab)
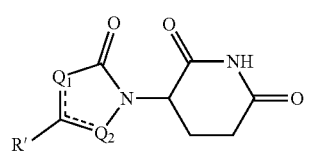 (ac)
-continued
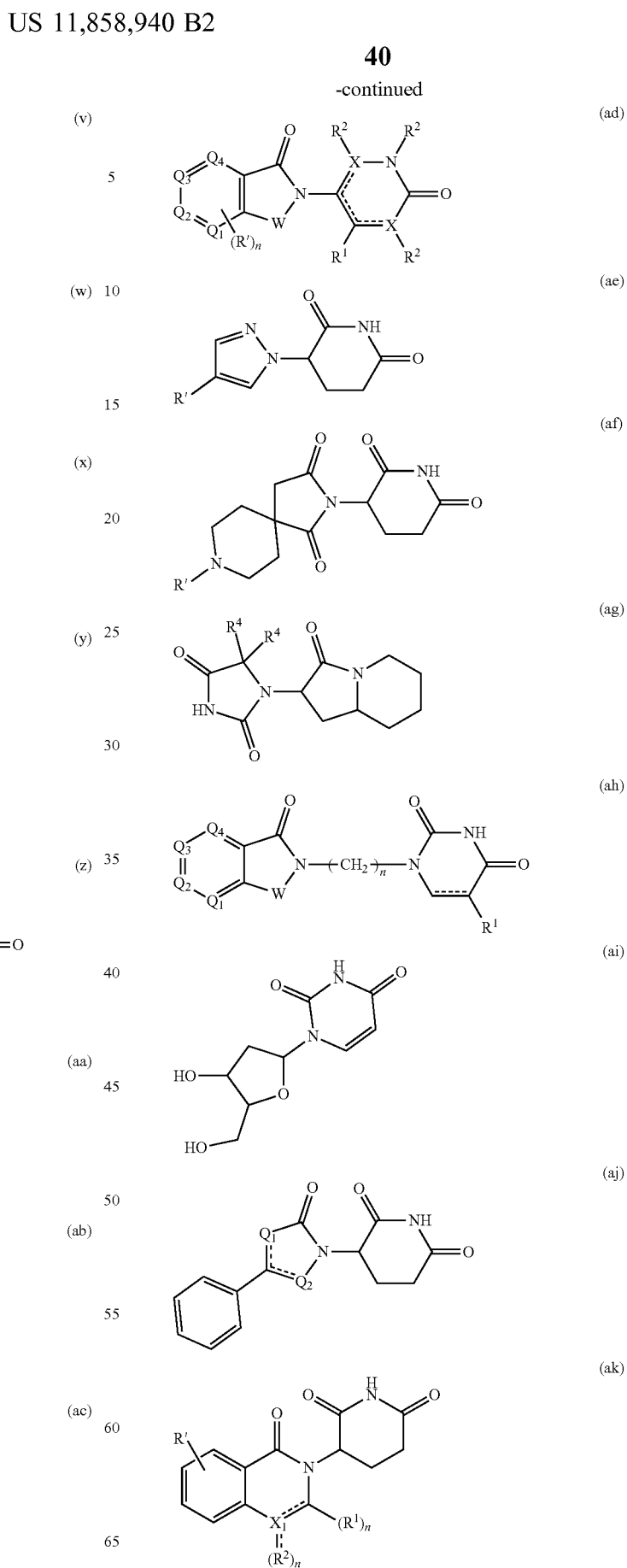

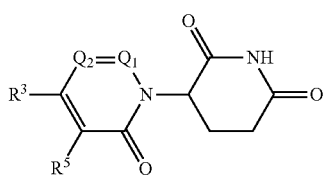

(al)

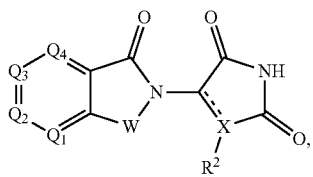

(am)

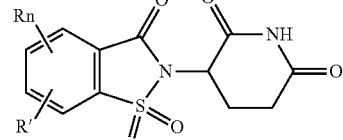

(an)

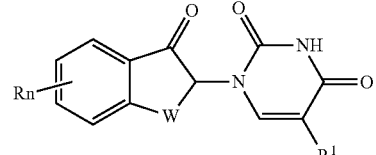

(ao)

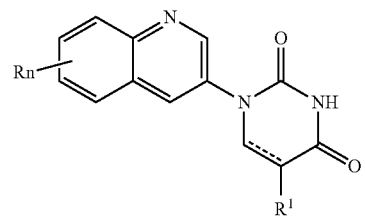

(ap)

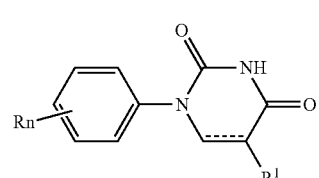

(aq)

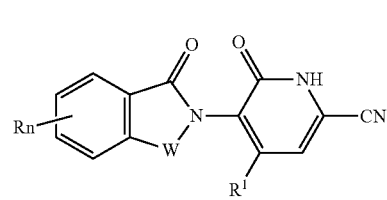

(ar)

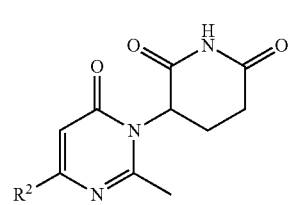

(as)

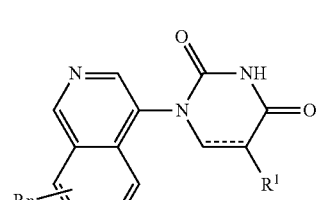

(at)

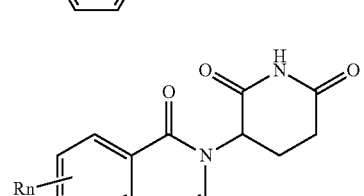

(au)

wherein:
- W is independently selected from $CH_2$, O, CHR, C=O, $SO_2$, NH, N, optionally substituted cyclopropyl group, optionally substituted cyclobutyl group, and N-alkyl (e.g., $CH_2$, CHR, C=O, $SO_2$, NH, and N-alkyl);
- $Q_1$, $Q_2$, $Q_3$, $Q_4$, $Q_5$ are each independently represent a carbon C or N substituted with a group independently selected from R', N or N-oxide;
- $R^1$ is selected from absent (i.e., a bond), H, OH, CN, C1-C3 alkyl, C=O;
- $R^2$ is selected from the group absent (i.e., a bond), H, OH, CN, C1-C3 alkyl, $CHF_2$, $CF_3$, CHO, $C(=O)NH_2$;
- $R^3$ is selected from a bond, H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), substituted alkoxy (e.g., substituted C1-C6 or C1-C3 alkoxyl);
- $R^4$ is selected from a bond, H, alkyl, substituted alkyl;
- $R^5$ and $R^6$ are each independently a bond, H, halogen, C(=O)R', CN, OH, $CF_3$;
- X is C, CH, C=O, or N;
- $X_1$ is C=O, N, CH, or $CH_2$;
- R' is selected from a bond, H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, $C(=O)OR^2$, optionally substituted phenyl;
- n is 0-4;
- ⫽ is a single or double bond; and
- the CLM is covalently joined to a PTM, a chemical linker group (L), a ULM, CLM or combination thereof.

In any aspect or embodiment described herein, the CLM is covalently joined to a PTM or a chemical linker group (L) via an R group (such as, R, $R^1$, $R^2$, $R^3$, $R^4$ or R'), W, X, or a Q group (such as, $Q_1$, $Q_2$, $Q_3$, $Q_4$, or $Q_5$).

In any aspect or embodiment described herein, the CLM is covalently joined to a PTM or a chemical linker group (L) via W, X, R, $R^1$, $R^2$, $R^3$, $R^4$, $R^5$, R', $Q_1$, $Q_2$, $Q_3$, $Q_4$, and $Q_5$.

In any aspect or embodiment described herein, the W, X, $R^1$, $R^2$, $R^3$, $R^4$, R', $Q_1$, $Q_2$, $Q_3$, $Q_4$, and $Q_5$ can independently be covalently coupled to a linker and/or a linker to which is attached to one or more PTM, ULM, CLM groups.

More specifically, non-limiting examples of CLMs include those shown below as well as "hybrid" molecules or compounds that arise from combining one or more features of the following compounds:

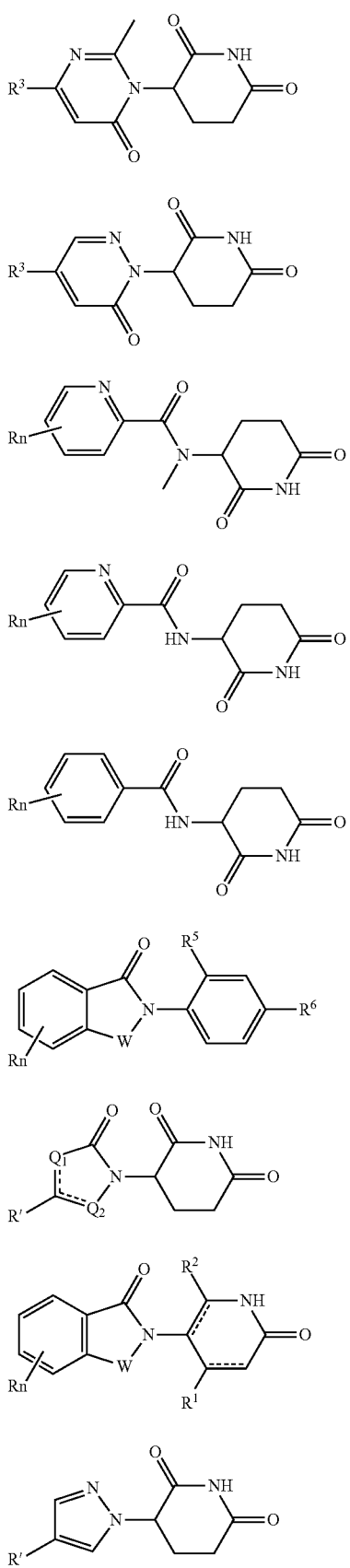
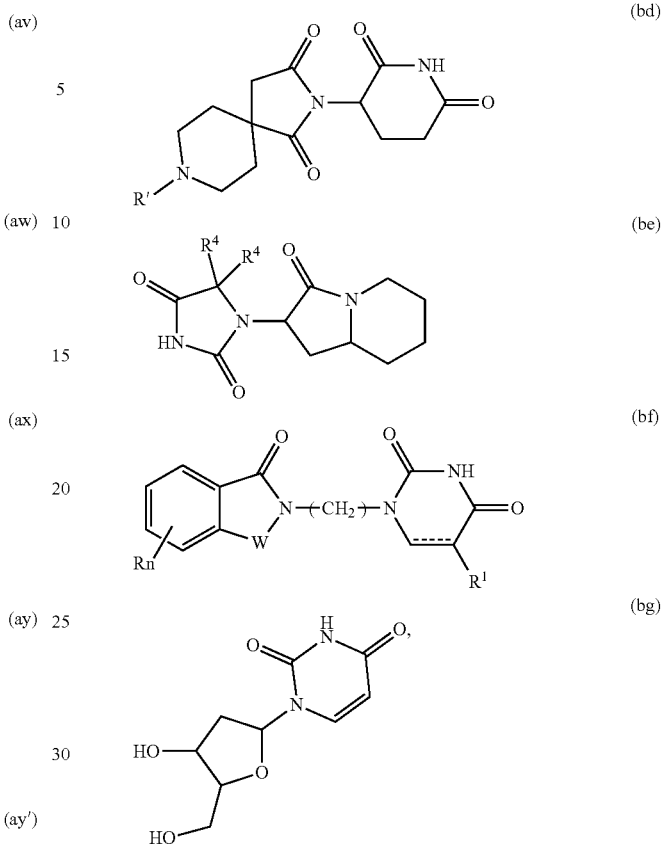

wherein:
W is independently selected from the group $CH_2$, CHR, C=O, $SO_2$, NH, and N-alkyl;
$R^1$ is selected from the group absent (i.e., a bond), H, CH, CN, C1-C3 alkyl;
$R^2$ is selected from a bond, H or a C1-C3 alkyl;
$R^3$ is selected from a bond, H, alkyl, substituted alkyl, alkoxy, substituted alkoxy;
$R^4$ is selected from a bond, methyl or ethyl;
$R^5$ is selected from a bond, H or halo;
$R^6$ is selected from a bond, H or halo;
n is an integer from 0-4;
R and R' are independently a bond, H, a functional group, or an atom (e.g., H, halogen (e.g., —Cl, —F), amine, C1-C3 alkyl, C1-C3 alkyl, C1-C3 alkoxyl, $NR^2R^3$, or C(=O)$OR^2$); or an attachment point for a PTM or a chemical linker group (L);
$Q_1$ and $Q_2$ are each independently C or N substituted with a group independently selected from H or C1-C3 alkyl;
⁓ is a single or double bond.

In any aspect or embodiment described herein, the W, $R^1$, $R^2$, $Q_1$, $Q_2$, $Q_3$, $Q_4$, R, and R' can independently be covalently coupled to a linker and/or a linker to which is attached one or more PTM groups.

In any aspect or embodiment described herein, the $R^1$, $R^2$, $Q_1$, $Q_2$, $Q_3$, $Q_4$, R, and R' can independently be covalently coupled to a linker and/or a linker to which is attached one or more PTM groups.

In any aspect or embodiment described herein, the $Q_1$, $Q_2$, $Q_3$, $Q_4$, R, and R' can independently be covalently coupled to a linker and/or a linker to which is attached one or more PTM groups.

In any aspect or embodiment described herein, R is modified to be covalently joined to the linker group (L), or a PTM, or combination thereof.
In any aspect or embodiment described herein, the CLM is selected from:
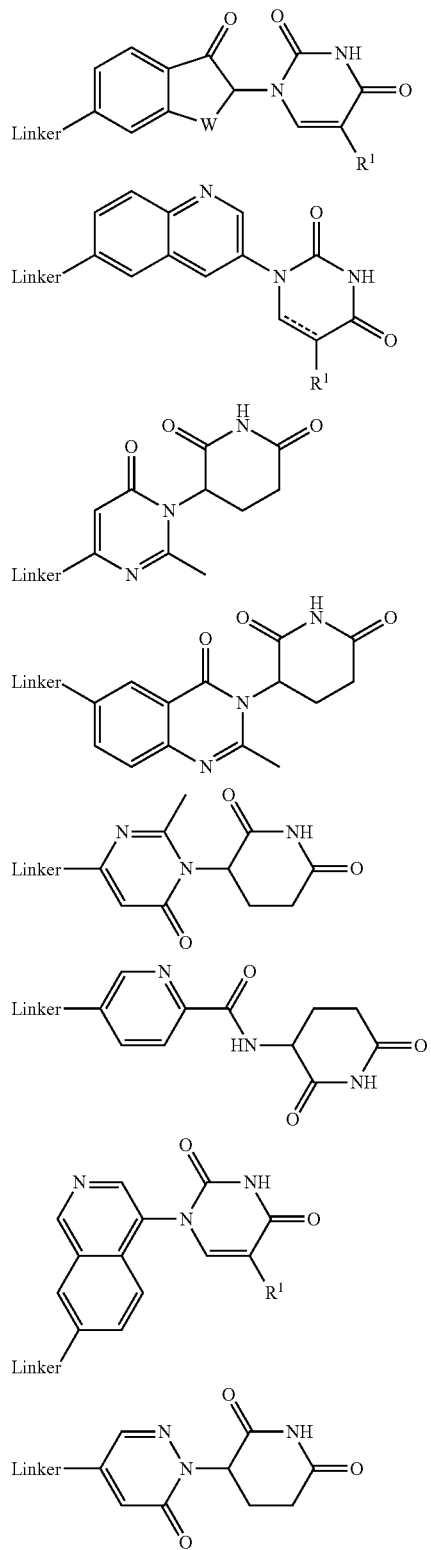
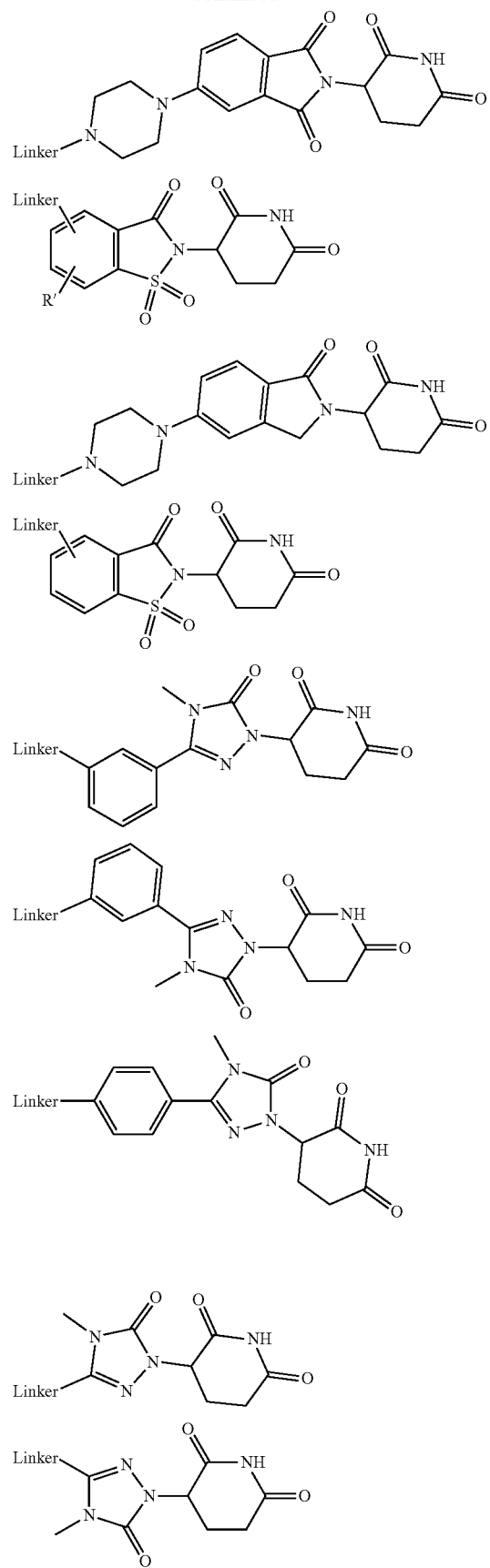

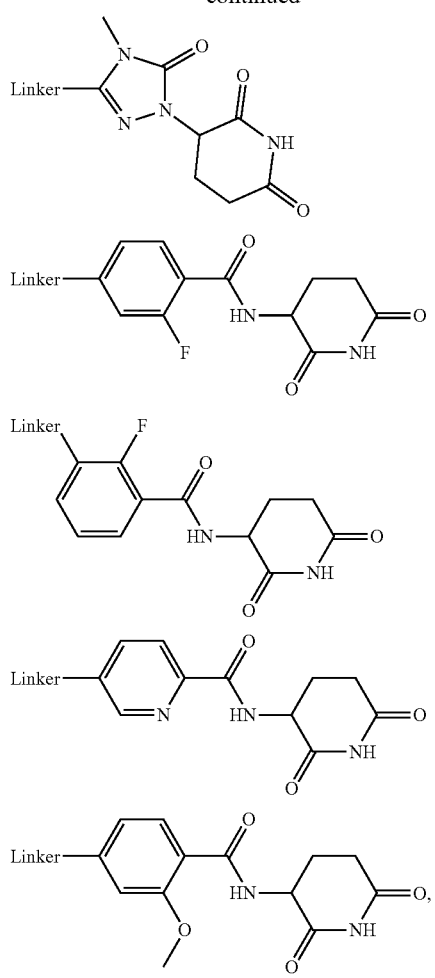
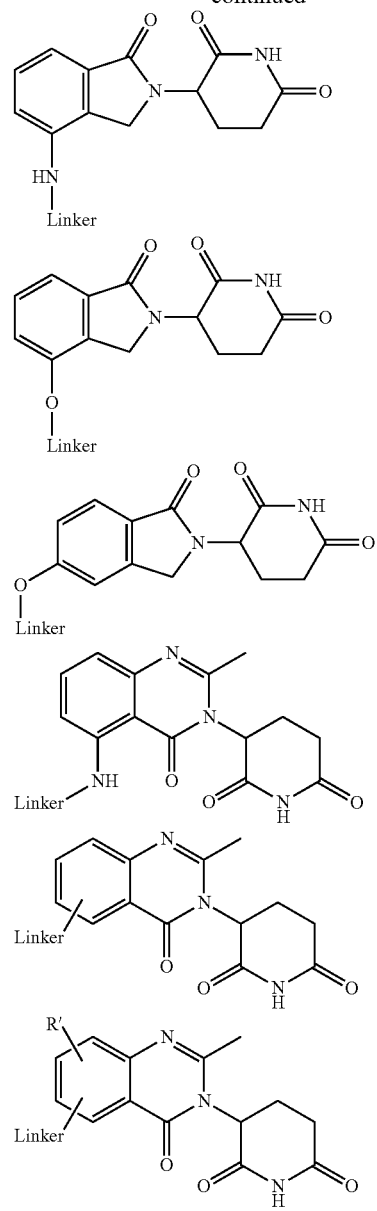
wherein R' is a halogen and $R^1$ is as described herein.
In any aspect or embodiment described herein, "CLM" can be an imide that binds to cereblon E3 ligase. These imides and linker attachment point can be, but not be limited to one of the following structures:
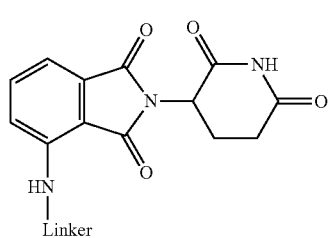
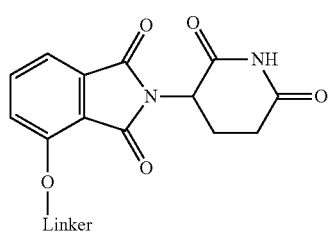
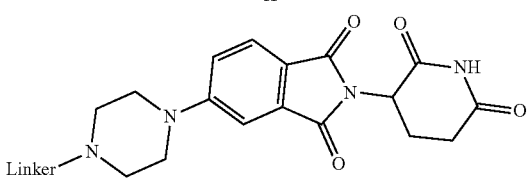
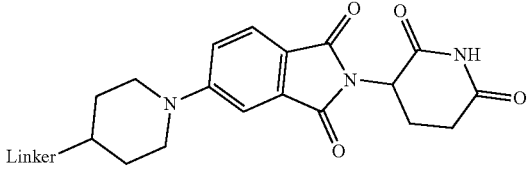
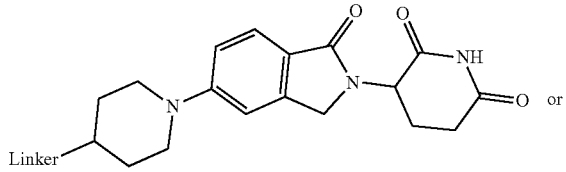

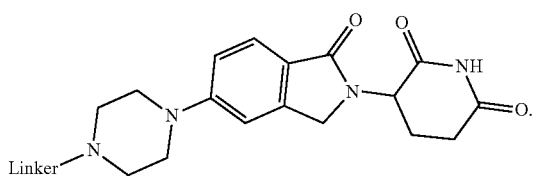
In any aspect or embodiment described herein, the ULM is selected from the group consisting of:
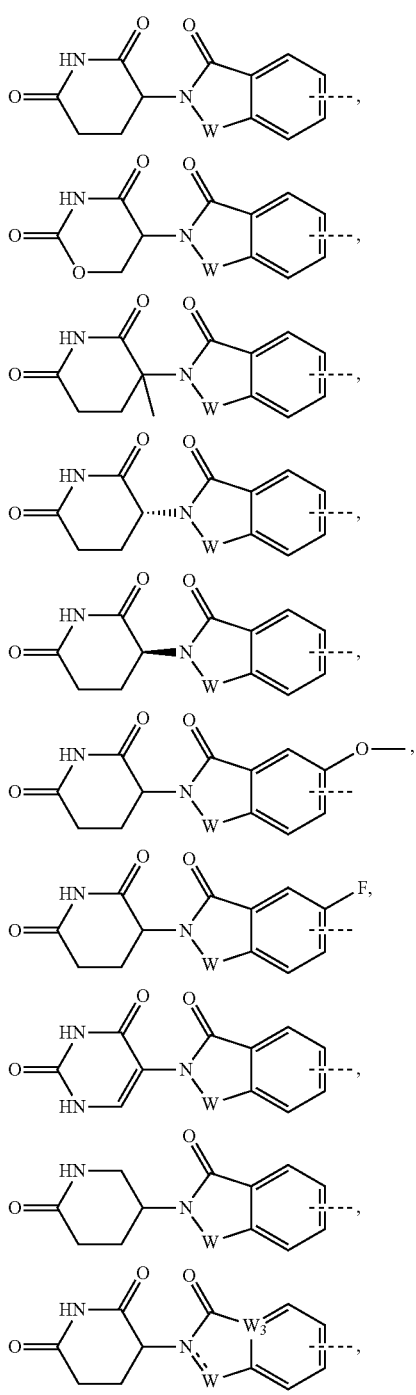
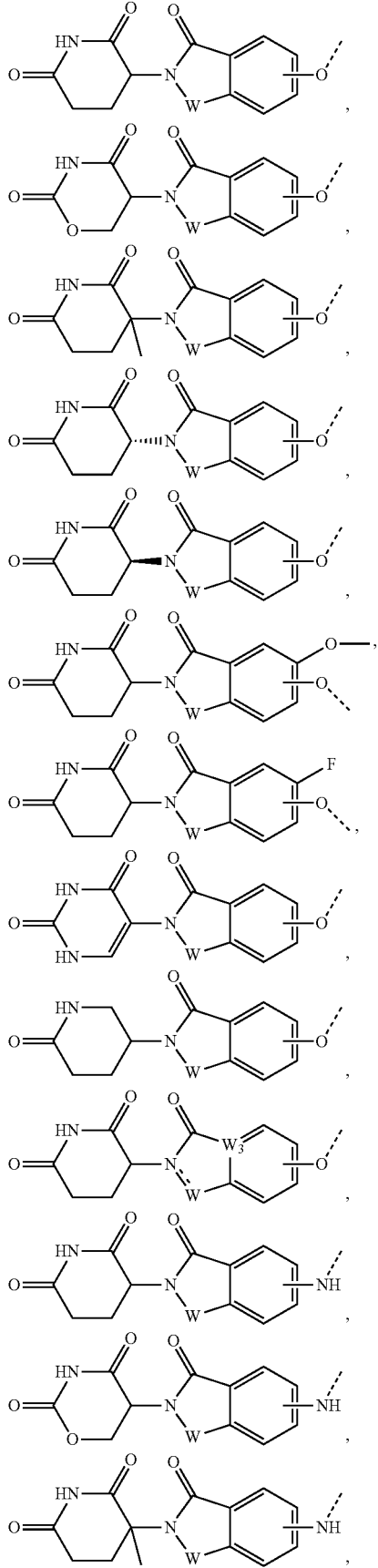

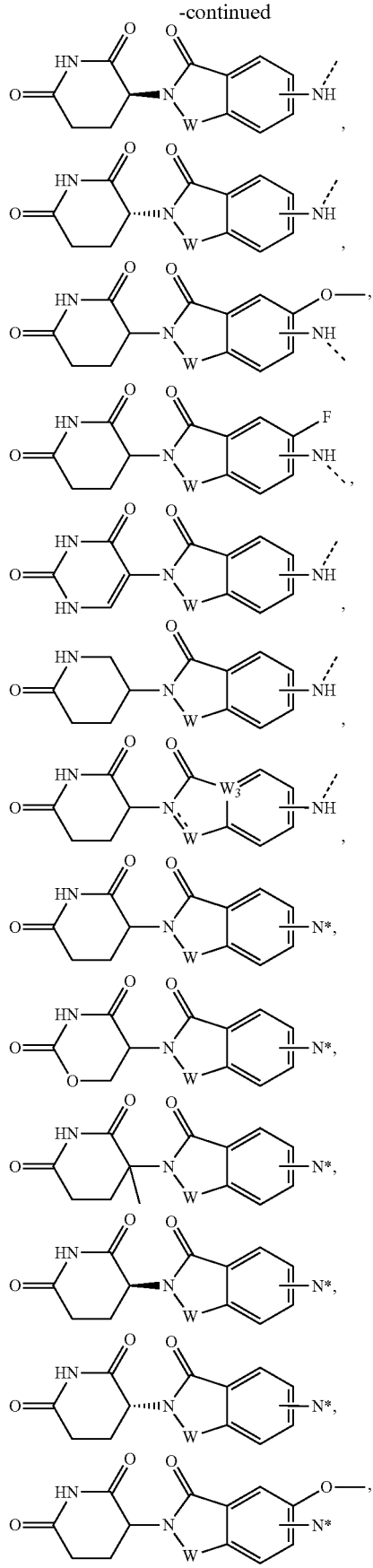
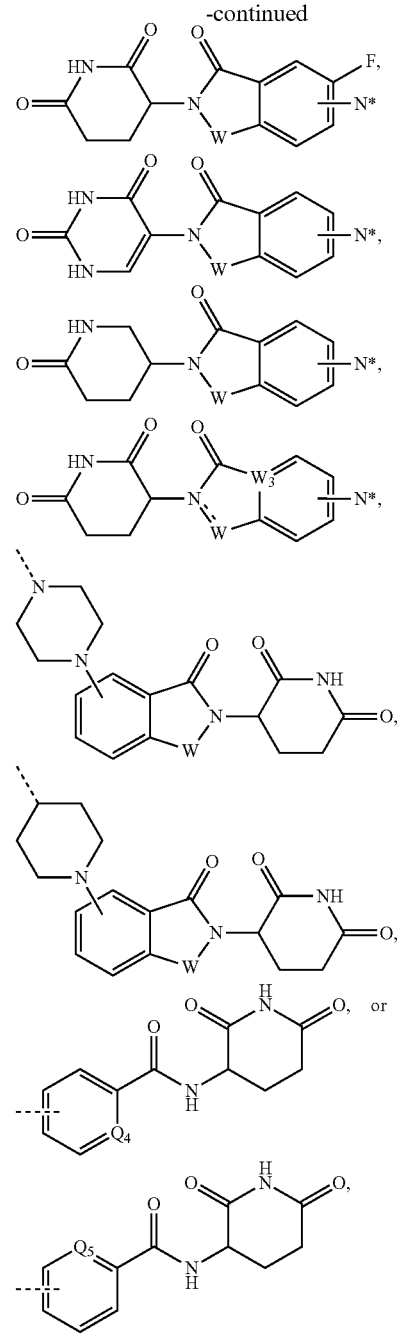
wherein:
- ⸺ of the CLM indicates the point of attachment with a linker group or a PTM; and
- N* is a nitrogen atom that is shared with the chemical linker group or PTM
In any aspect or embodiment described herein, the ULM is selected from the group consisting of:
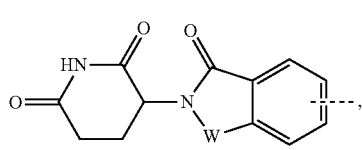

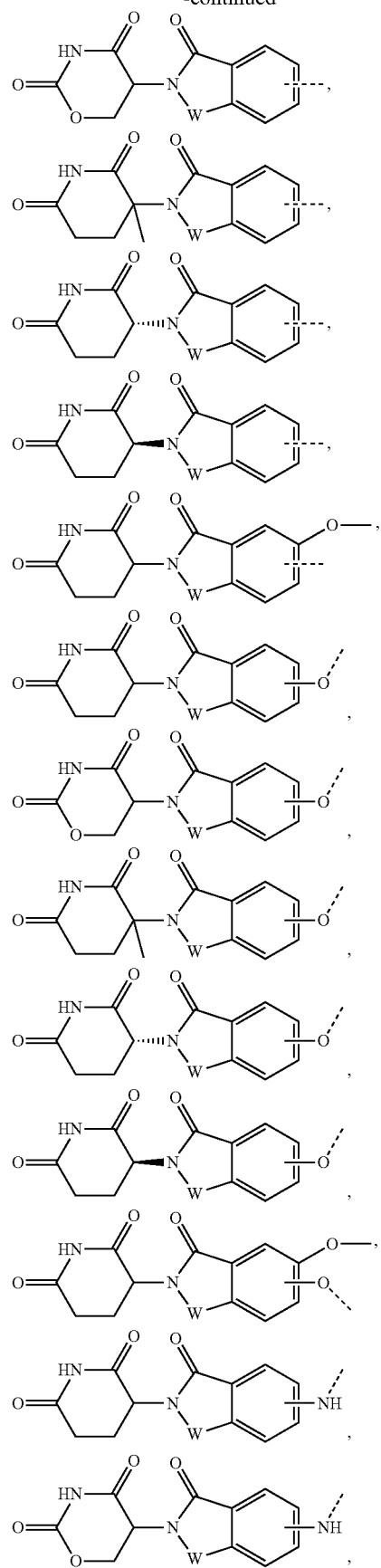
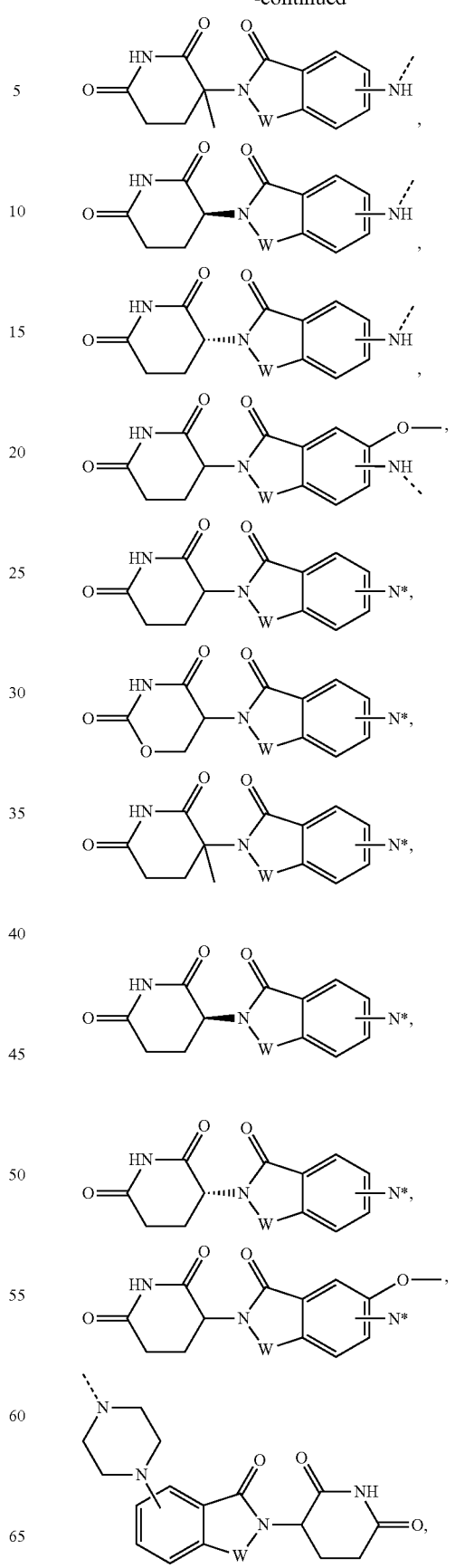

-continued

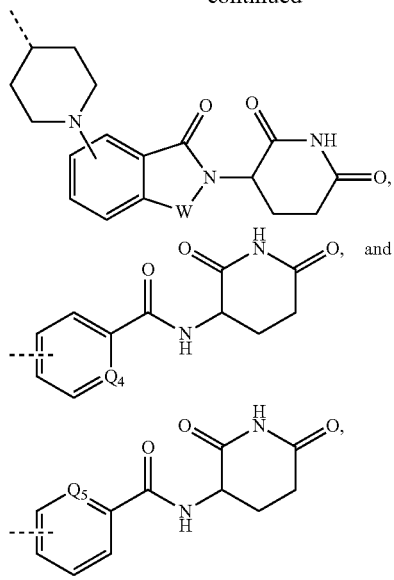

wherein:
- ⌇ of the ULM indicates the point of attachment with a linker group or a PTM;
- N* is a nitrogen atom that is shared with the chemical linker group or PTM; and
- W, Q4, and Q5 are each defined as described in any aspect or embodiment described herein.

Exemplary Tankers

In any aspect or embodiment described herein, the compounds as described herein include a PTM chemically linked to a ULM (e.g., CLM) via a chemical linker (L). In certain embodiments, the linker group L comprises one or more covalently connected structural units (e.g., $-A^L_1 \ldots (A^L)_q$- or $-(A^L)_q-$), wherein $A^L_1$ is a group coupled to PTM, and $(A^L)_q$ is a group coupled to ULM.

In any aspect or embodiment described herein, the linker (L) to a ULM (e.g., CLM) connection is a stable L-ULM connection. For example, in certain embodiments, when a linker (L) and a ULM are connected via a heteroatom (e.g., N, O, S), any additional heteroatom, if present, is separated by at least a carbon atom (e.g., —CH$_2$—), such as with an acetal or aminal group. By way of further example, in certain embodiments described herein, when a linker (L) and a ULM are connected via a heteroatom, the heteroatom is not part of an ester.

In any aspect or embodiment described herein, the linker group L is a bond or a chemical linker group represented by the formula $-(A^L)_q-$, wherein A is a chemical moiety and q is an integer from 1-100 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80), and wherein L is covalently bound to both the PTM and the ULM, and provides for binding of the PTM to the protein target and the ULM to an E3 ubiquitin ligase to effectuate target protein ubiquitination.

In any aspect or embodiment described herein, the linker group L is a bond or a chemical linker group represented by the formula $-(A^L)_q-$, wherein A is a chemical moiety and q is an integer from 6-30 (e.g., 1, 2, 3, 4, 5, 6, 7, 8, 9, 10, 11, 12, 13, 14, 15, 16, 17, 18, 19, 20, 21, 22, 23, 24, or 25), and wherein L is covalently bound to both the PTM and the ULM, and provides for binding of the PTM to the protein target and the ULM to an E3 ubiquitin ligase in sufficient proximity to result in target protein ubiquitination.

In any aspect or embodiment described herein, the linker group L is $-(A^L)_q-$, wherein:
- $(A^L)_q$ is a group which connects a ULM (e.g., CLM), to PTM;
- q of the linker is an integer greater than or equal to 1;
- each $A^L$ is independently selected from the group consisting of, a bond, $CR^{L1}R^{L2}$, O, S, SO, SO$_2$, NR$^{L3}$, SO$_2$NR$^{L3}$, SONR$^{L3}$, CONR$^{L3}$, NR$^{L3}$CONR$^{L4}$, NR$^{L3}$SO$_2$NR$^{L4}$, CO, CR$^{L1}$=CR$^{L2}$, C≡C, SiR$^{L1}$R$^{L2}$, P(O)R$^{L1}$, P(O)OR$^{L1}$, NR$^{L3}$C(=NCN)NR$^{L4}$, NR$^{L3}$C(=NCN), NR$^{L3}$C(=CNO$_2$)NR$^{L4}$, C$_{3-11}$cycloalkyl optionally substituted with 1-6 R$^{L1}$ and/or R$^{L2}$ groups, C$_{5-13}$ spirocycloalkyl optionally substituted with 1-9 R$^{L1}$ and/or R$^{L2}$ groups, C$_{3-11}$heterocyclyl optionally substituted with 1-6 R$^{L1}$ and/or R$^{L2}$ groups, C$_{5-13}$ spiroheterocyclyl optionally substituted with 1-8 R$^{L1}$ and/or R$^{L2}$ groups, aryl optionally substituted with 1-6 R$^{L1}$ and/or R$^{L2}$ groups, heteroaryl optionally substituted with 1-6 R$^{L1}$ and/or R$^{L2}$ groups, where R$^{L1}$ or R$^{L2}$, each independently are optionally linked to other groups to form cycloalkyl and/or heterocyclyl moiety, optionally substituted with 1-4 R$^{15}$ groups; and
- R$^{L1}$, R$^{L2}$, R$^{L3}$, R$^{L4}$ and R$^{L5}$ are, each independently, H, halo, C$_{1-8}$alkyl, OC$_{1-8}$alkyl, SC$_{1-8}$alkyl, NHC$_{1-8}$alkyl, N(C$_{1-8}$alkyl)$_2$, C$_{3-11}$cycloalkyl, aryl, heteroaryl, C$_{3-11}$heterocyclyl, OC$_{3-8}$cycloalkyl, SC$_{3-8}$cycloalkyl, NHC$_{3-8}$cycloalkyl, N(C$_{3-5}$cycloalkyl)$_2$, N(C$_{3-8}$cycloalkyl)(C$_{1-8}$alkyl), OH, NH$_2$, SH, SO$_2$C$_{1-8}$alkyl, P(O)(OC$_{1-8}$alkyl)(C$_{1-8}$alkyl), P(O)(OC$_{1-8}$alkyl)$_2$, CC—C$_{1-8}$alkyl, CCH, CH=CH(C$_{1-8}$alkyl), C(C$_{1-8}$alkyl)=CH(C$_{1-8}$alkyl), C(C$_{1-8}$alkyl)=C(C$_{1-8}$alkyl)$_2$, Si(OH)$_3$, Si(C$_{1-8}$alkyl)$_3$, Si(OH)(C$_{1-8}$alkyl)$_2$, COC$_{1-8}$alkyl, CO$_2$H, halogen, CN, CF$_3$, CHF$_2$, CH$_2$F, NO$_2$, SF$_5$, SO$_2$NHC$_{1-8}$alkyl, SO$_2$N(C$_{1-8}$alkyl)$_2$, SONHC$_{1-8}$alkyl, SON(C$_{1-8}$alkyl)$_2$, CONHC$_{1-8}$alkyl, CON(C$_{1-8}$alkyl)$_2$, N(C$_{1-8}$alkyl)CONH(C$_{1-8}$alkyl), N(C$_{1-8}$alkyl)CON(C$_{1-8}$alkyl)$_2$, NHCONH(C$_{1-8}$alkyl), NHCON(C$_{1-8}$alkyl)$_2$, NHCONH$_2$, N(C$_{1-8}$alkyl) SO$_2$NH(C$_{1-8}$alkyl), N(C$_{1-8}$alkyl) SO$_2$N(C$_{1-8}$alkyl)$_2$, NH SO$_2$NH(C$_{1-8}$alkyl), NH SO$_2$N(C$_{1-8}$alkyl)$_2$, NH SO$_2$NH$_2$.

In certain embodiments, q is an integer greater than or equal to 1.

In certain embodiments, e.g., where q of the linker is greater than 2, $(A^L)_q$ is a group which is $A^L_1$ and $(A^L)_q$ wherein the linker couples a PTM to a ULM.

In certain embodiments, e.g., where q of the linker is 2, $A^L_2$ is a group which is connected to $A^L_1$ and to a ULM.

In certain embodiments, e.g., where q of the linker is 1, the structure of the linker group L is $-A^L_1-$, and $A^L_1$ is a group which connects a ULM moiety to a PTM moiety.

In any aspect or embodiment described herein, the unit $A^L$ of linker (L) comprises a group represented by a general structure selected from the group consisting of:

—NR(CH$_2$)$_n$-(lower alkyl)-, —NR(CH$_2$)$_n$-(lower alkoxyl)-, —NR(CH$_2$)$_n$-(lower alkoxyl)-OCH$_2$—, —NR(CH$_2$)$_n$-(lower alkoxyl)-(lower alkyl)-OCH$_2$—, —NR(CH$_2$)$_n$-(cycloalkyl)-(lower alkyl)-OCH$_2$—, —NR(CH$_2$)$_n$-(heterocycloalkyl)-, —NR(CH$_2$CH$_2$O)$_n$-(lower alkyl)-O—CH$_2$—, —NR(CH$_2$CH$_2$O)$_n$-(heterocycloalkyl)-O—CH$_2$—, —NR(CH$_2$CH$_2$O)$_n$-Aryl-O—CH$_2$—, —NR(CH$_2$CH$_2$O)$_n$-(heteroaryl)-O—CH$_2$—, —NR(CH$_2$CH$_2$O)$_n$-(cyclo alkyl)-O-(heteroaryl)-O—CH$_2$—, —NR(CH$_2$CH$_2$O)$_n$-(cyclo alkyl)-O-Aryl-O—

CH$_2$—, —NR(CH$_2$CH$_2$O)$_n$-(lower alkyl)-NH-Aryl-O—CH$_2$—, —NR(CH$_2$CH$_2$O)$_n$-(lower alkyl)-O-Aryl-CH$_2$, —NR(CH$_2$CH$_2$O)$_n$-cycloalkyl-O-Aryl-, —NR(CH$_2$CH$_2$O)$_n$-cycloalkyl-O-(heteroaryl)l-, —NR(CH$_2$CH$_2$)$_n$-(cycloalkyl)-O-(heterocyclyl)-CH$_2$, —NR(CH$_2$CH$_2$)$_n$-(heterocyclyl)-(heterocyclyl)-CH$_2$, and —N(R1R2)-(heterocyclyl)-CH$_2$; where n of the linker can be 0 to 10;

R of the linker can be H, or lower alkyl; and

R1 and R2 of the linker can form a ring with the connecting N.

In any aspect or embodiment described herein, the linker (L) includes an optionally substituted $C_1$-$C_{50}$alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, Cn, $C_{45}$, $C_{46}$, $C_{47}$, $C_{48}$, $C_{49}$, or $C_{50}$ alkyl, and including all implied subranges, e.g., C1-C10, C1-C20; C2-C10, C2-20; C10-C20, C10-C50 etc.), wherein each carbon is optionally independently substituted or replaced with (1) a heteroatom selected from N, O, S, P, or Si atoms that has an appropriate number of hydrogens, substitutions, or both to complete valency, (2) an optionally substituted cycloalkyl or bicyclic cycloalkyl, (3) an optionally substituted heterocyloalkyl or bicyclic heterocyloalkyl, (4) an optionally substituted aryl or bicyclic aryl, or (5) optionally substituted heteroaryl or bicyclic heteroaryl. In any aspect or embodiment described herein, the linker (L) does not have heteroatom-heteroatom bonding (e.g., no heteroatoms are covalently linked or adjacently located).

In any aspect or embodiment described herein, the linker (L) includes an optionally substituted $C_1$-$C_{50}$ alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl), wherein:

each carbon is optionally independently substituted or replaced with $CR^{L1}R^{L2}$, O, S, SO, SO$_2$, $NR^{L3}$, SO$_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $SiR^{L1}R^{L2}$, $P(O)R^{L1}$, $P(O)OR^{L1}$, $NR^{L3}C(=NCN)NR^{L4}$, $NR^{L3}C(=NCN)$, $NR^{L3}C(=CNO_2)NR^{L4}$, $C_{3-11}$cycloalkyl optionally substituted with 1-6 $R^{L1}$ and/or $R^{L2}$ groups, $C_{5-13}$ spirocycloalkyl optionally substituted with 1-9 $R^{L1}$ and/or $R^{L2}$ groups, $C_{3-11}$ heterocyclyl optionally substituted with 1-6 $R^{L1}$ and/or $R^{L2}$ groups, $C_{5-13}$ spiroheterocyclyl optionally substituted with 1-8 $R^{L1}$ and/or $R^{L2}$ groups, aryl optionally substituted with 1-6 $R^{L1}$ and/or $R^{L2}$ groups, heteroaryl optionally substituted with 1-6 $R^{L1}$ and/or $R^{L2}$ groups, where $R^{L1}$ or $R^{L2}$, each independently are optionally linked to other groups to form a cycloalkyl and/or a heterocyclyl moiety, optionally substituted with 1-4 $R^{L5}$ groups; and $R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-5}$alkyl$)_2$, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, $N(C_{3-5}$cycloalkyl$)_2$, $N(C_{3-8}$cycloalkyl$)(C_{1-8}$alkyl$)$, OH, NH$_2$, SH, SO$_2C_{1-8}$alkyl, $P(O)(OC_{1-8}$alkyl$)(C_{1-8}$alkyl$)$, $P(O)(OC_{1-8}$alkyl$)_2$, CC—$C_{1-8}$alkyl, CCH, CH=CH($C_{1-8}$alkyl), $C(C_{1-8}$alkyl)=CH($C_{1-8}$alkyl), $C(C_{1-8}$alkyl)=C($C_{1-8}$alkyl)$_2$, Si(OH)$_3$, Si($C_{1-8}$alkyl)$_3$, Si(OH)($C_{1-8}$alkyl)$_2$, $COC_{1-8}$alkyl, CO$_2$H, halogen, CN, CF$_3$, CHF$_2$, CH$_2$F, NO$_2$, SF$_5$, SO$_2NHC_{1-8}$alkyl, SO$_2N(C_{1-8}$alkyl)$_2$, $SONHC_{1-8}$alkyl, SON($C_{1-8}$alkyl)$_2$, CONHC$_{1-8}$alkyl, CON($C_{1-8}$alkyl)$_2$, N($C_{1-8}$alkyl)CONH($C_{1-8}$alkyl), N($C_{1-8}$alkyl)CON($C_{1-8}$alkyl)$_2$, NHCONH($C_{1-8}$alkyl), NHCON($C_{1-8}$alkyl)$_2$, NHCONH$_2$, N($C_{1-8}$alkyl) SO$_2$NH($C_{1-8}$alkyl), N($C_{1-8}$alkyl) SO$_2$N($C_{1-8}$alkyl)$_2$, NH SO$_2$NH($C_{1-8}$alkyl), NH SO$_2$N($C_{1-8}$alkyl)$_2$, NH SO$_2$NH$_2$.

In any aspect or embodiment described herein, the linker group is optionally substituted an optionally substituted $C_1$-$C_{50}$alkyl (e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ alkyl, and including all implied subranges, e.g., C1-C10, C1-C20; C2-C10, C2-20; C10-C20, C10-C50 etc.), wherein each carbon atom optionally substituted or replaced with: a O, N, S, P or Si atom that has an appropriate number of hydrogens, substitutions (e.g., OH, halo, alkyl, methyl, ethyl, haloalkyl, hydroxyalkyl, alkoxy, methoxy, etc.), or both to complete valency; an optionally substituted aryl (e.g., an optionally substituted C5 or C6 aryl) or bicyclic aryl (e.g, an optionally substituted C5-C20 bicyclic heteroaryl); an optionally substituted heteroaryl (e.g., an optionally substituted C5 or C6 heteroaryl) or bicyclic heteroaryl (e.g., an optionally substituted heteroaryl or bicyclic heteroaryl having one or more heteroatoms selected from N, O, S, P, and Si that has an appropriate number of hydrogens, substitutions (e.g., OH, halo, alkyl, methyl, ethyl, haloalkyl, hydroxyalkyl, alkoxy, methoxy, etc.), or both to complete valency); an optionally substituted C1-C6 alkyl; an optionally substituted C1-C6 alkenyl; an optionally substituted C1-C6 alkynyl; an optionally substituted cycloalkyl (e.g., an optionally substituted C3-C7 cycloalkyl) or bicyclic cycloalkyl (e.g., an optionally substituted C5-C20 bicyclic cycloalkyl); or an optionally substituted heterocycloalkyl (e.g., an optionally substituted 3-, 4-, 5-, 6-, or 7-membered heterocyclic group) or bicyclicheteroalkyl (e.g., an optionally substituted heterocyclo alkyl bicyclicheteroalkyl having one or more heteroatoms selected from N, O, S, P, or Si atoms that has an appropriate number of hydrogens, substitutions (e.g., OH, halo, alkyl, methyl, ethyl, haloalkyl, hydroxyalkyl, alkoxy, methoxy, etc.), or both to complete valency). In any aspect or embodiment described herein, the optionally substituted alkyl linker is optionally substituted with one or more OH, halo, linear or branched C1-C6 alkyl (such as methyl or ethyl), linear or branched C1-C6 haloalkyl, linear or branched C1-C6 hydroxyalkyl, or linear or branched C1-C6 alkoxy (e.g., methoxy).

In any aspect or embodiment described herein, the linker (L) does not have heteroatom-heteroatom bonding (e.g., no heteroatoms are covalently linked or adjacently located).

In any aspect or embodiment described herein, the linker (L) includes about 1 to about 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50) alkylene glycol units that are optionally substituted, wherein carbon or oxygen may be substituted with a heteroatom selected from N, S, P, or Si atoms with an appropriate number of hydrogens to complete valency.

In any aspect or embodiment described herein, the L is selected from the group consisting of:

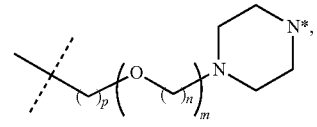

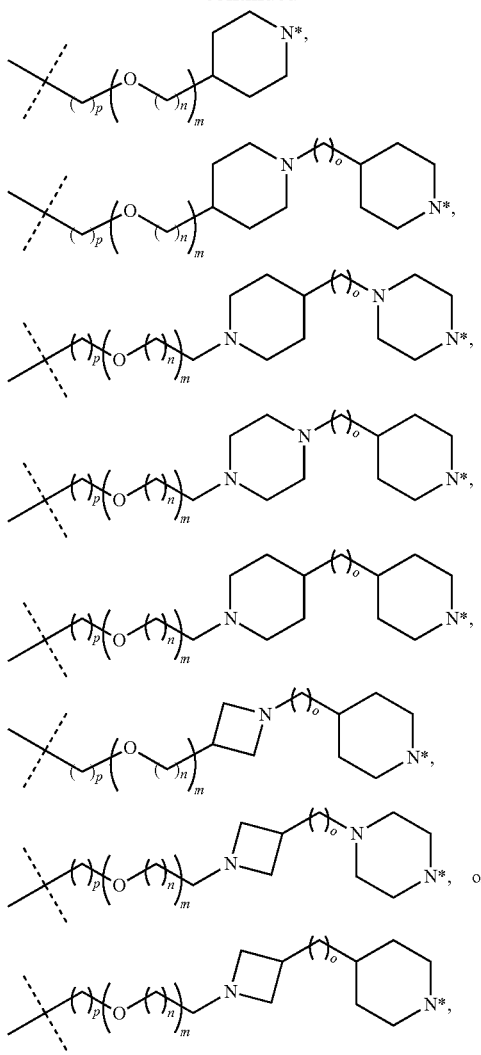

wherein:
  N* is a nitrogen atom that is covalently linked to the CLM or PTM, or that is shared with the CLM or PTM;
  each m, n, o, and p is independently 0, 1, 2, 3, 4, 5, 6, 7, 8, 9, 10, 11, 12, 13, 14, 15, 16, 17, 18, 19, or 20; and
  the chemical linker group is optionally substituted with 1, 2, 3, or 4 substitutions independently selected from a halogen (e.g., F or Cl) and a $C_{1-4}$ alkyl In any aspect or embodiment described herein, the until $A^L$ of the linker (L) comprises a structure selected from the group consisting of:

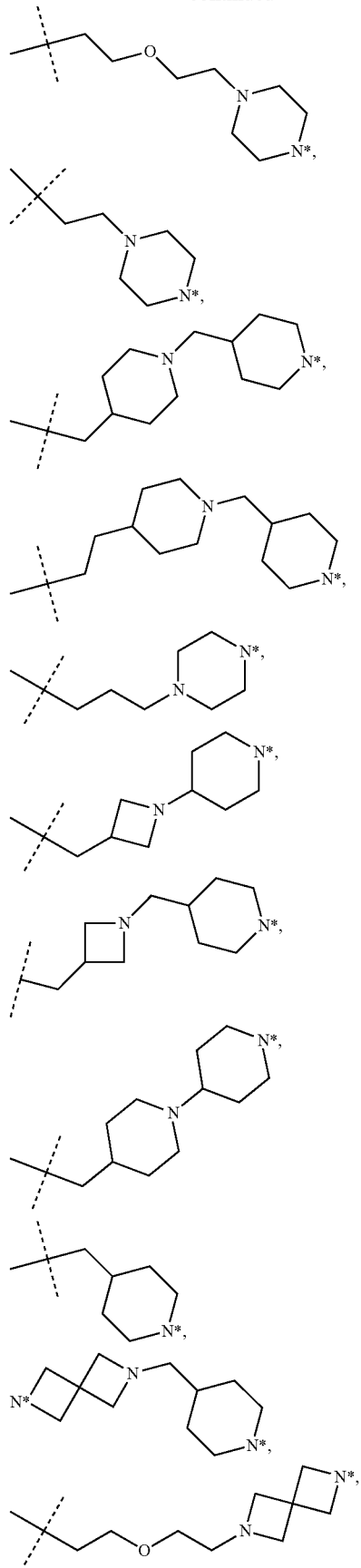

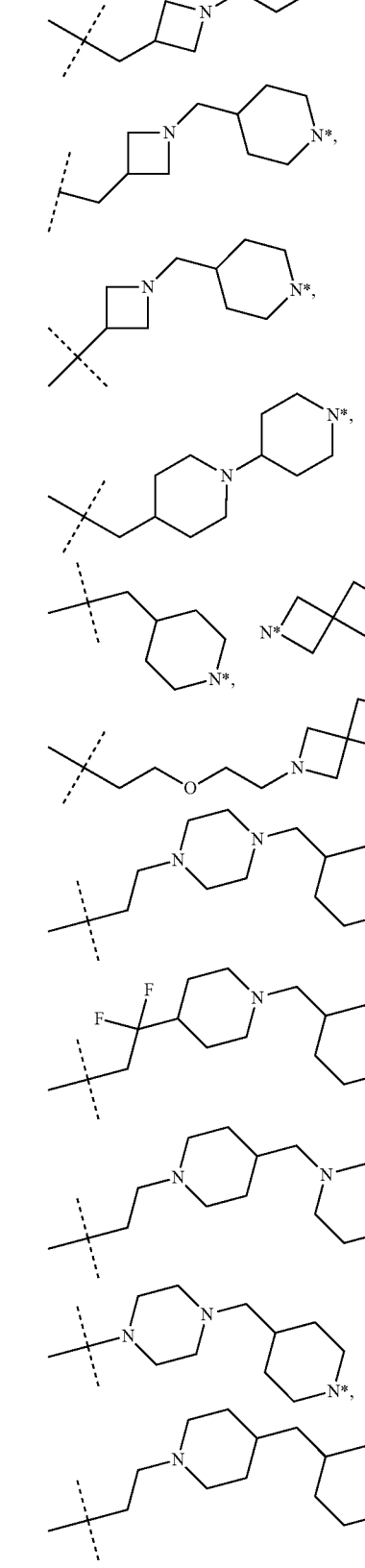
wherein N* is a nitrogen atom that is covalently linked to the ULM or PTM, or that is shared with the ULM or PTM.
In any aspect or embodiment described herein, the until $A^L$ of the linker (L) comprises a structure selected from the group consisting of:
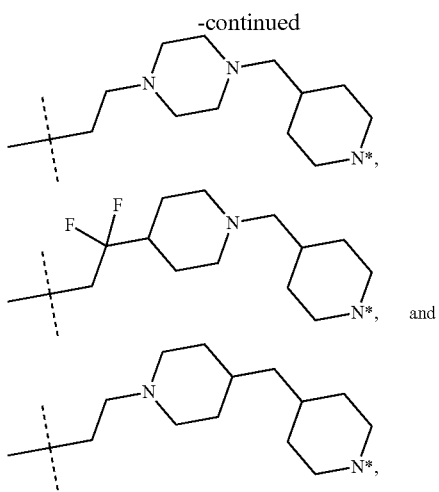

wherein N* is a nitrogen atom that is covalently linked to the ULM or PTM, or that is shared with the ULM or PTM.
In any aspect or embodiment described herein, the unit $A^L$ of the linker (L) comprises a structure selected from the group consisting of:
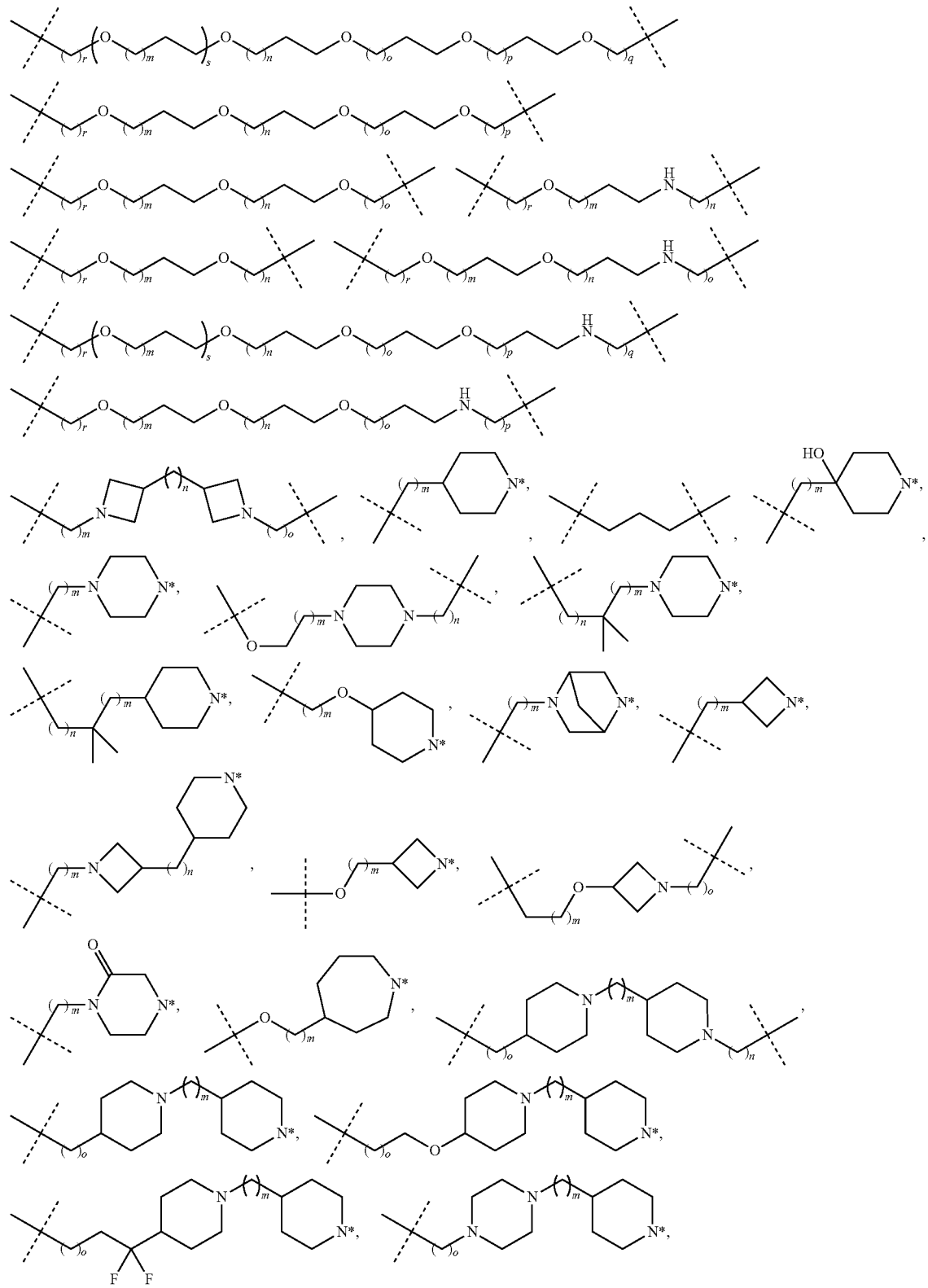

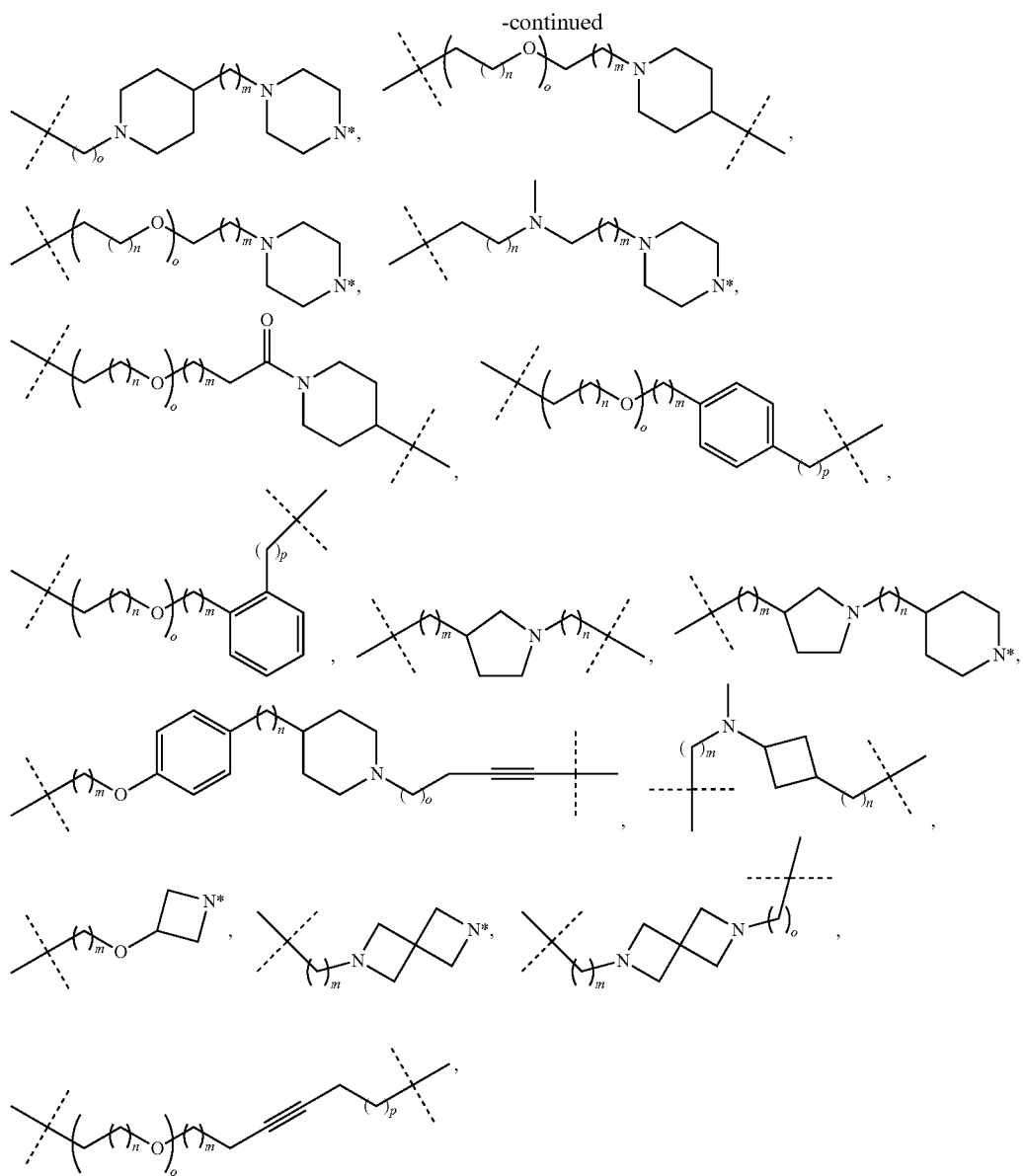
wherein:
N* is a nitrogen atom that is covalently linked to the ULM or PTM, or that is shared with the ULM or PTM; and
each m, n, o, p, q, and r is independently 0, 1, 2, 3, 4, 5, 6, 7, 8, 9, 10, 11, 12, 13, 14, 15, 16, 17, 18, 19, or 20.
In any aspect or embodiment described herein, the unit $A^L$ of the linker (L) is selected from:
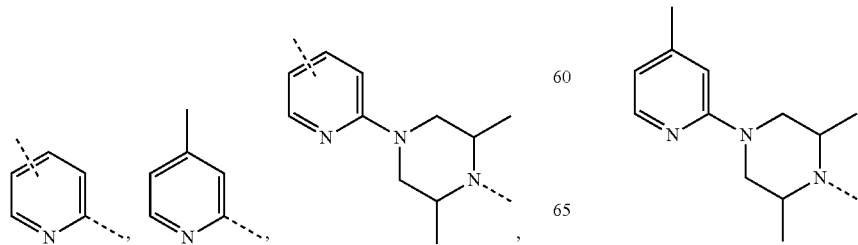

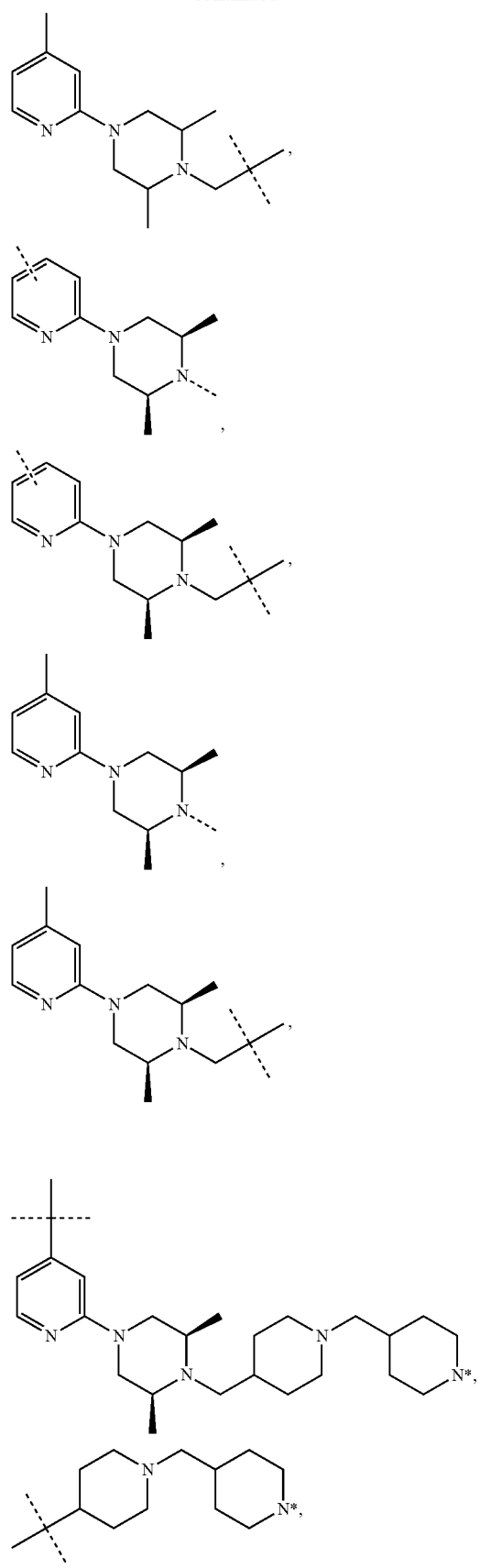
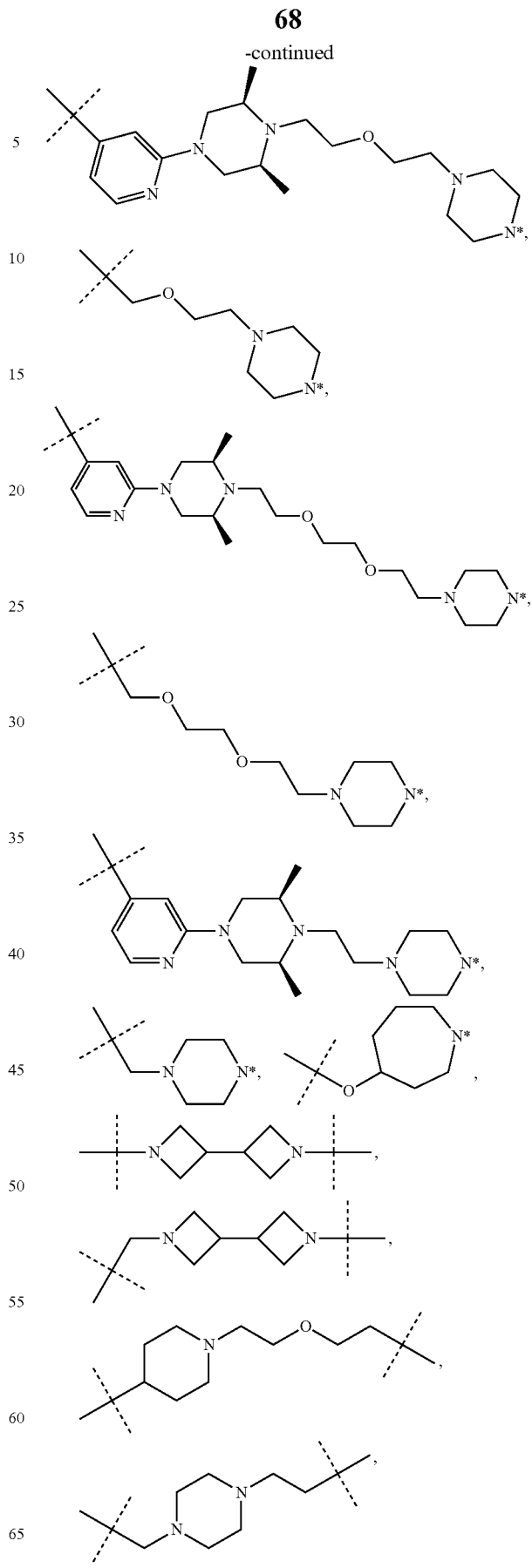

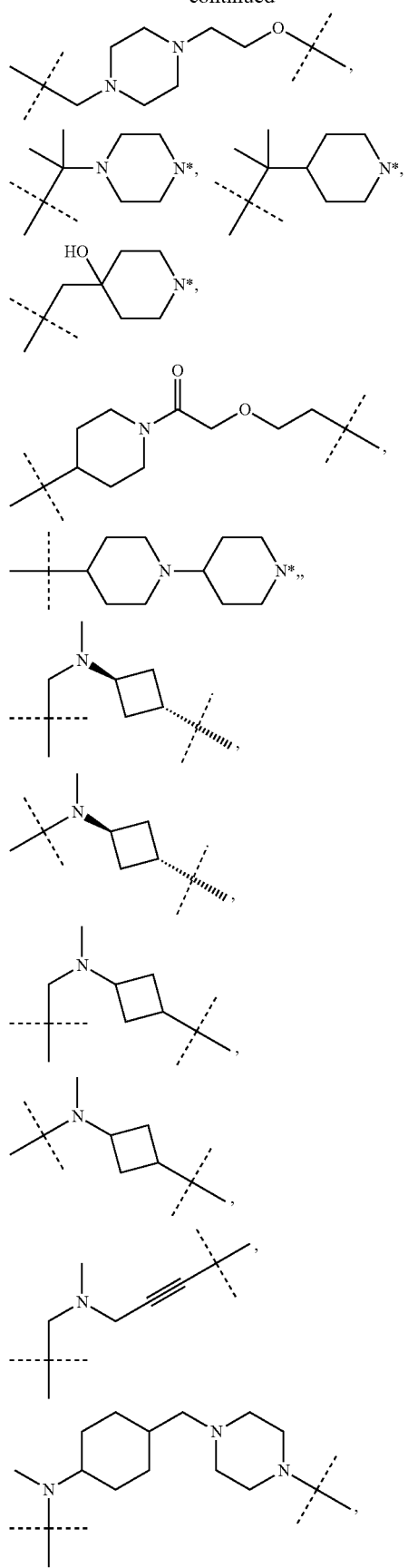
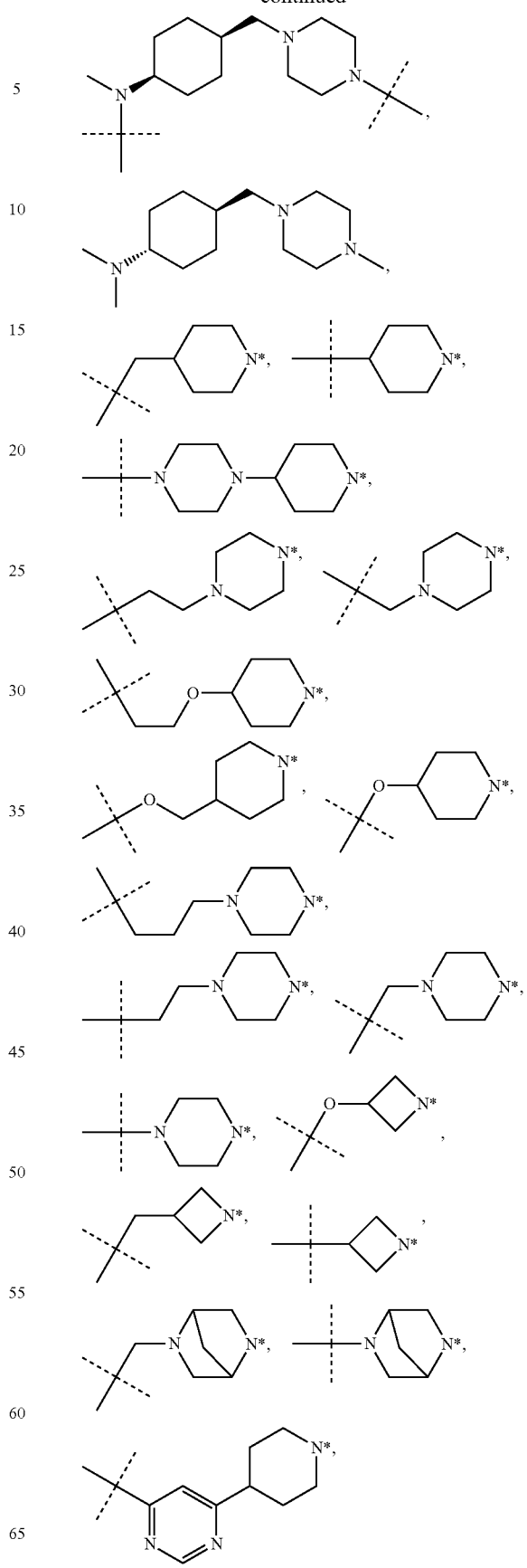

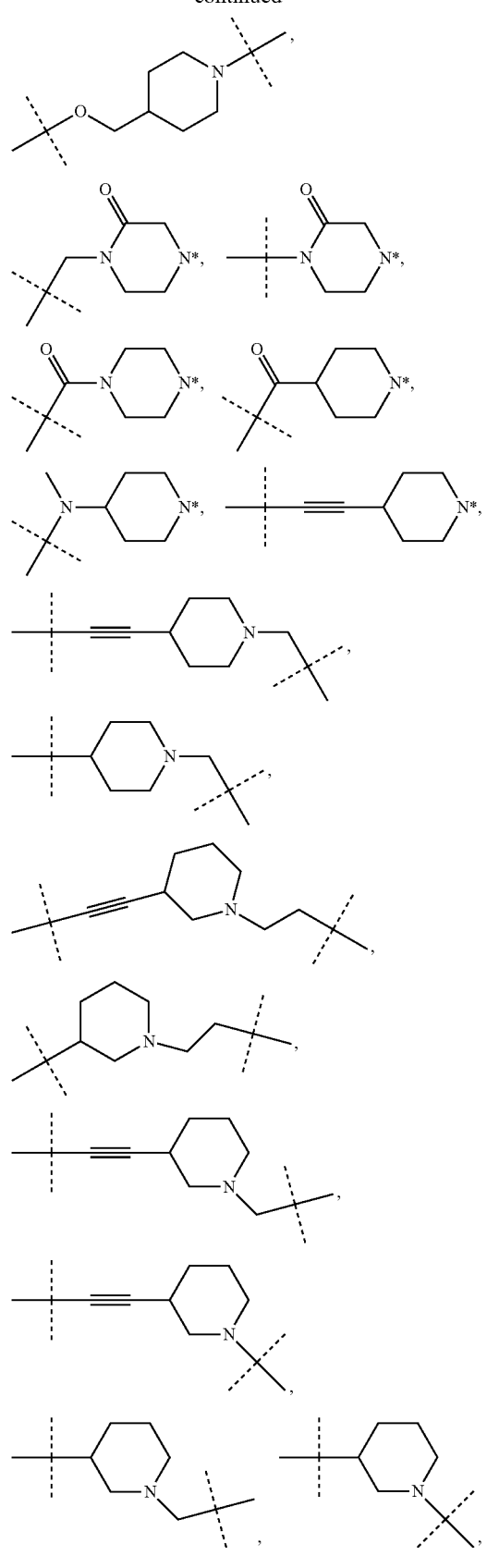
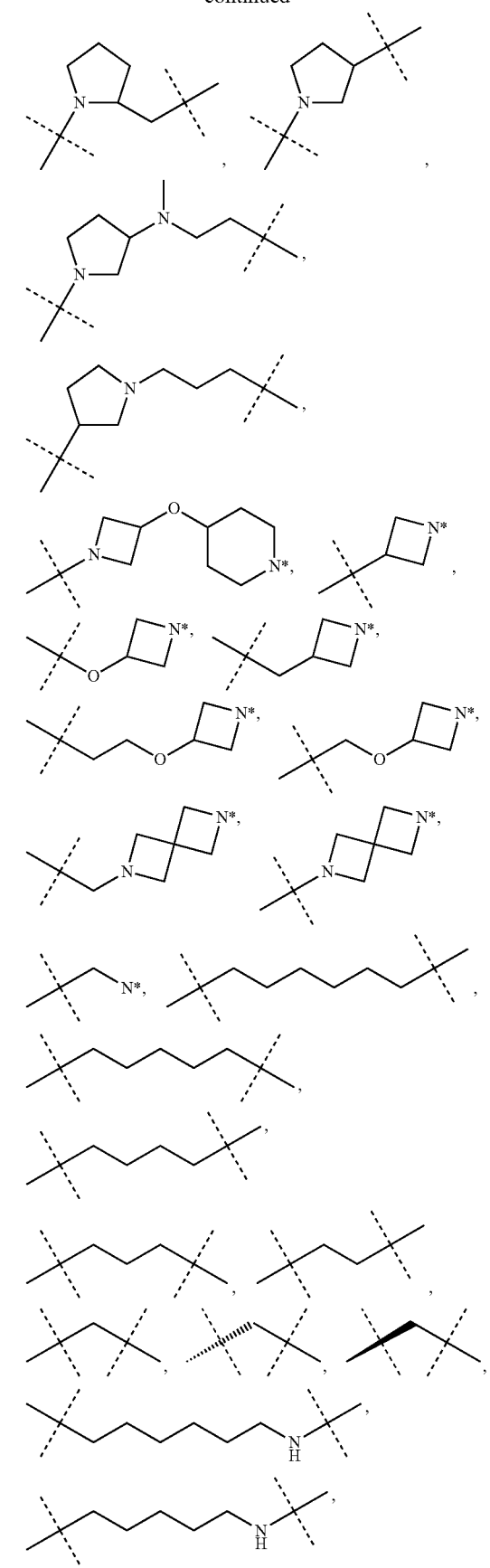

-continued
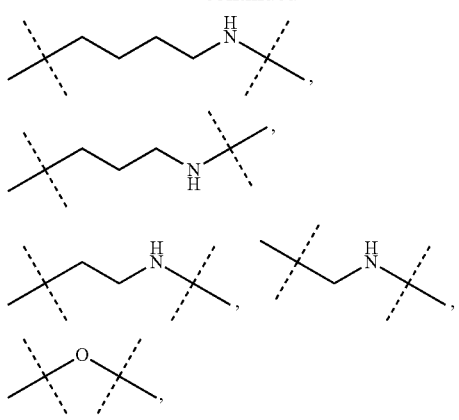
wherein dashed line or * indicates the site that is covalently linked to the ULM or PTM, or that is shared with the ULM or PTM.
In any aspect or embodiment described herein, the unit $A^L$ of the linker (L) is selected from:
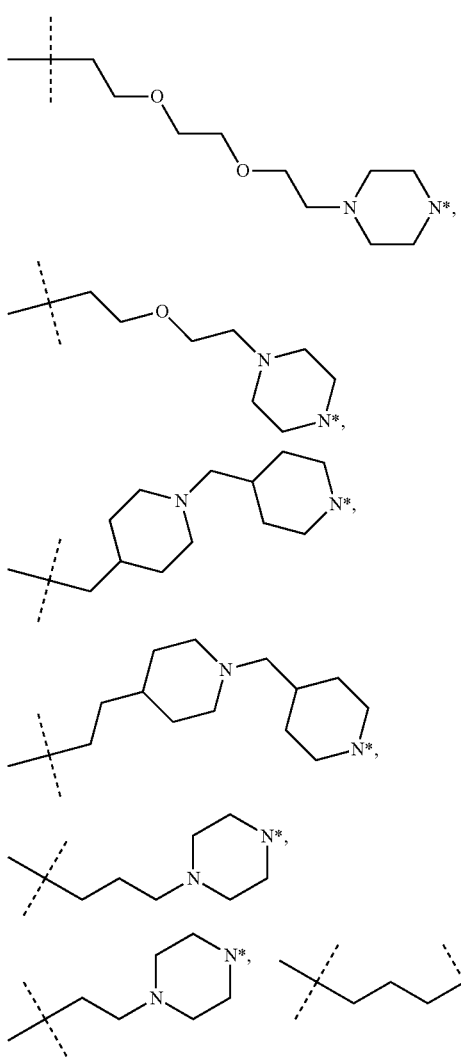
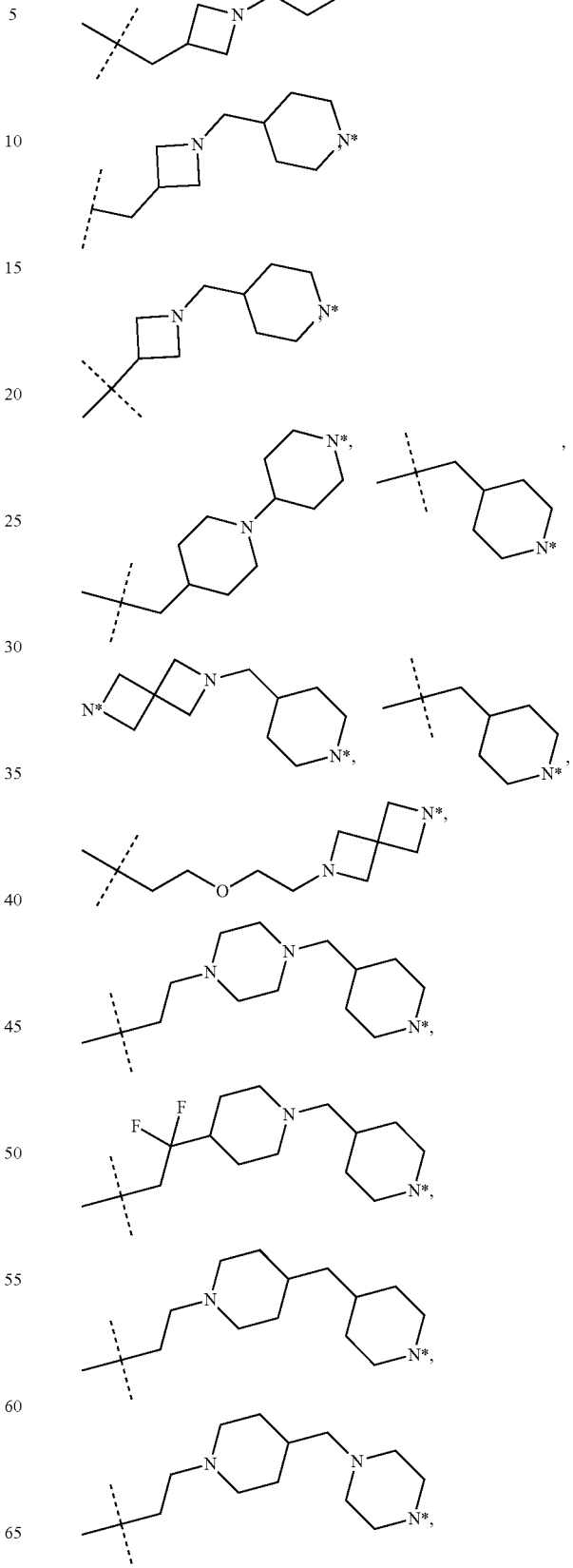

75
-continued
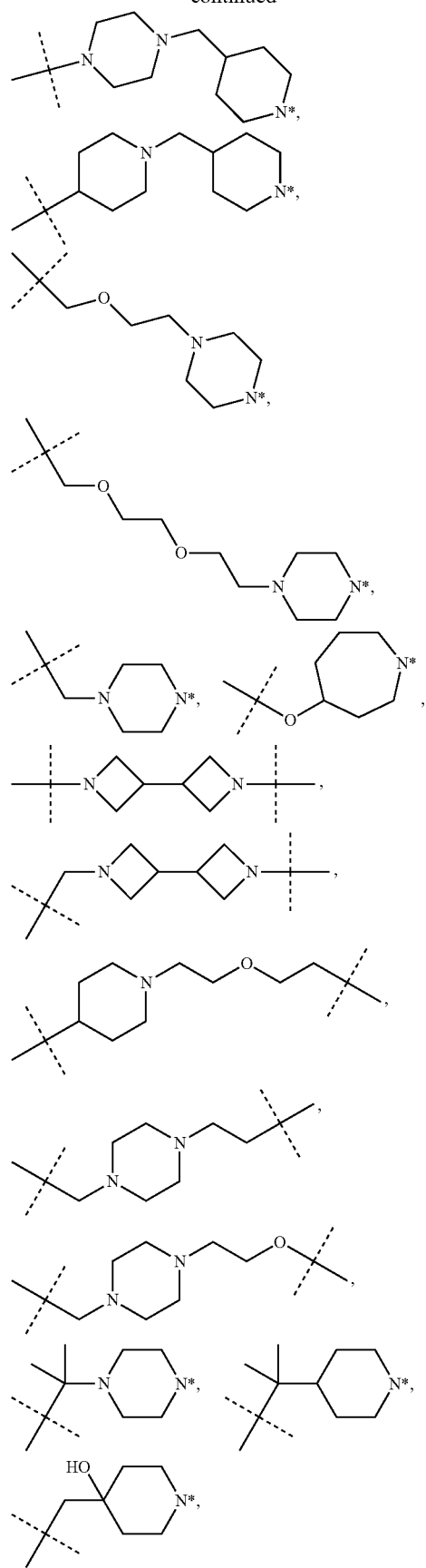
76
-continued
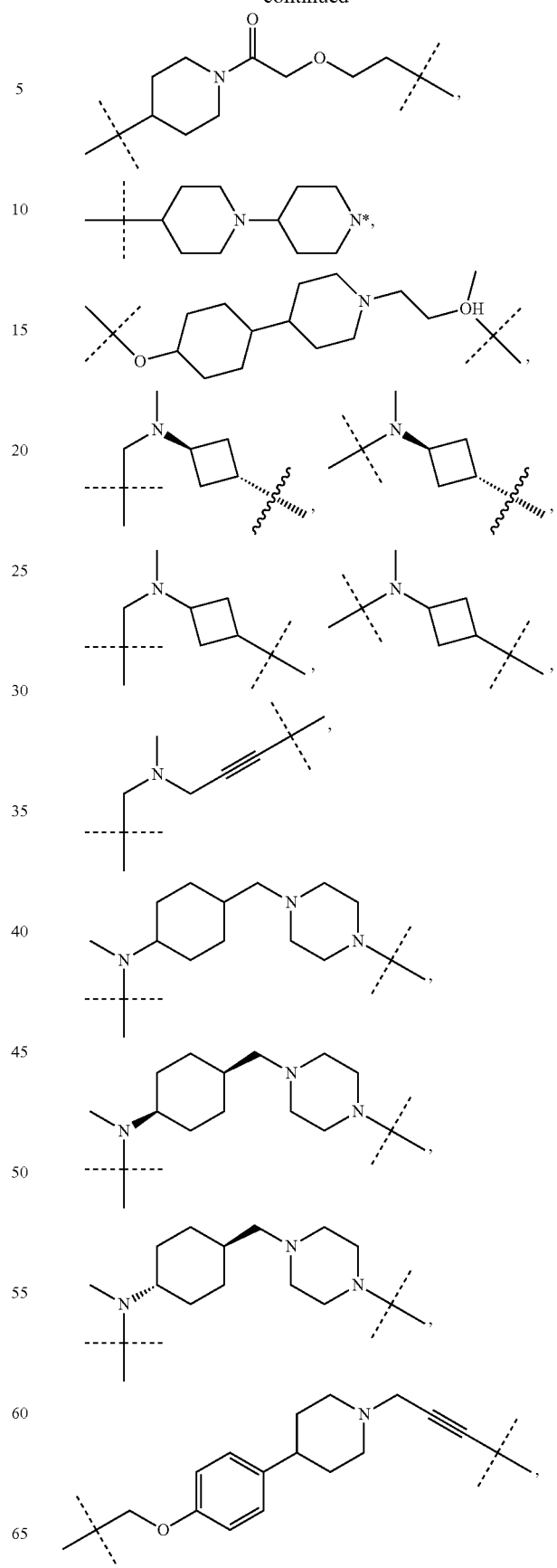

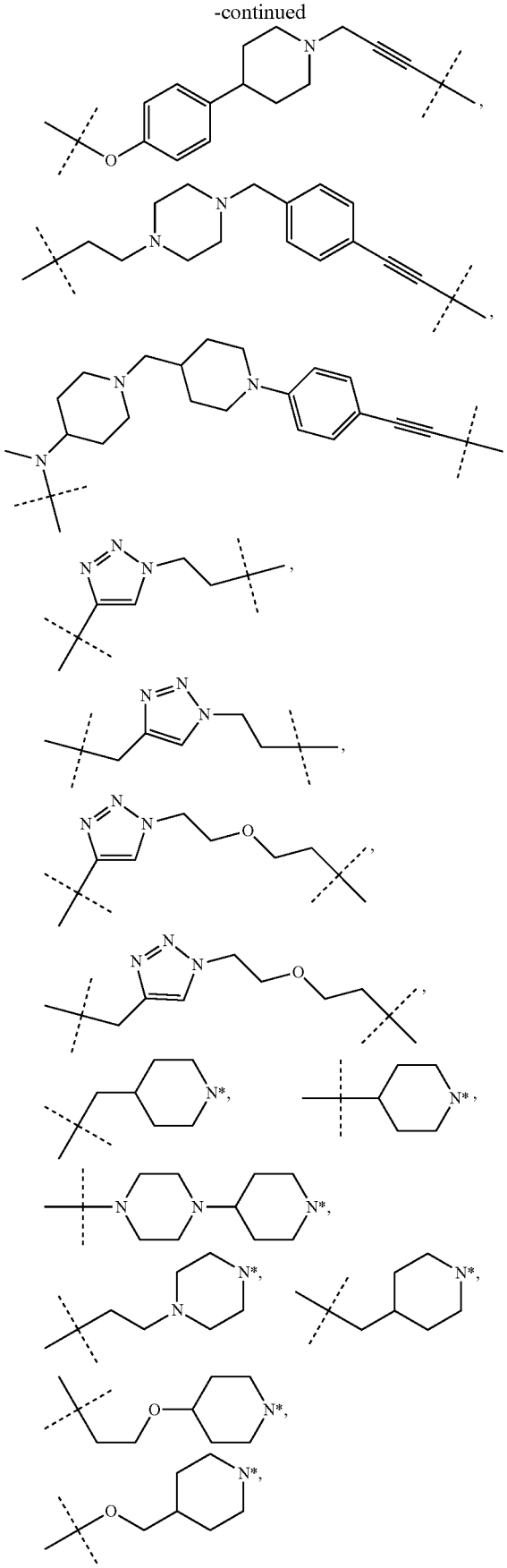
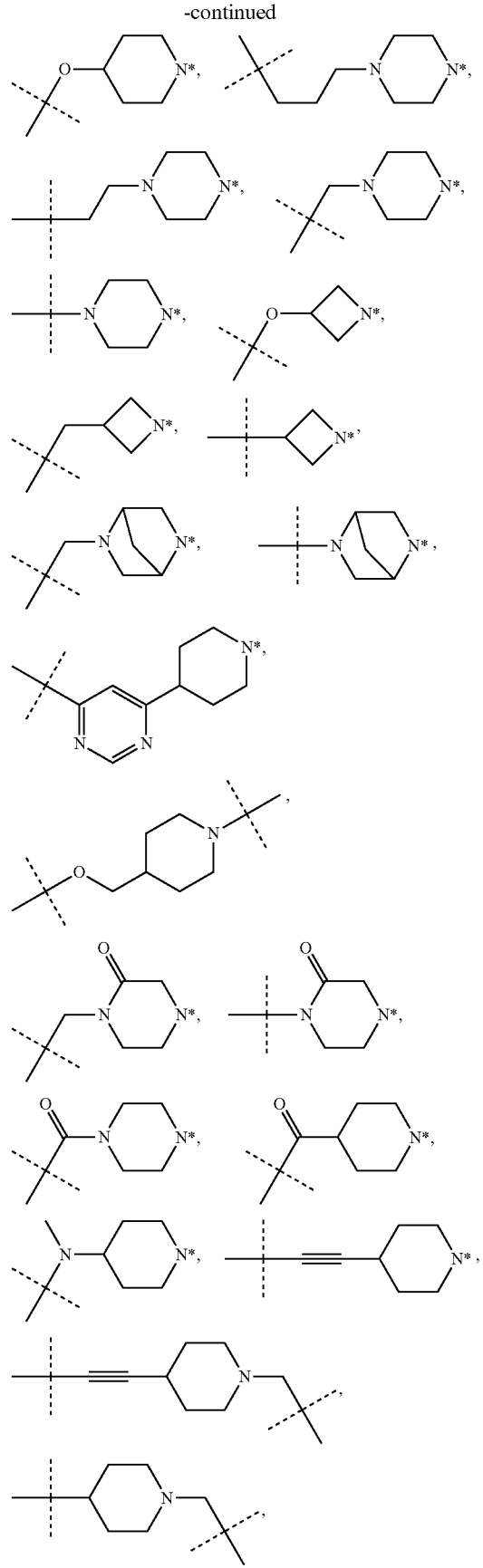

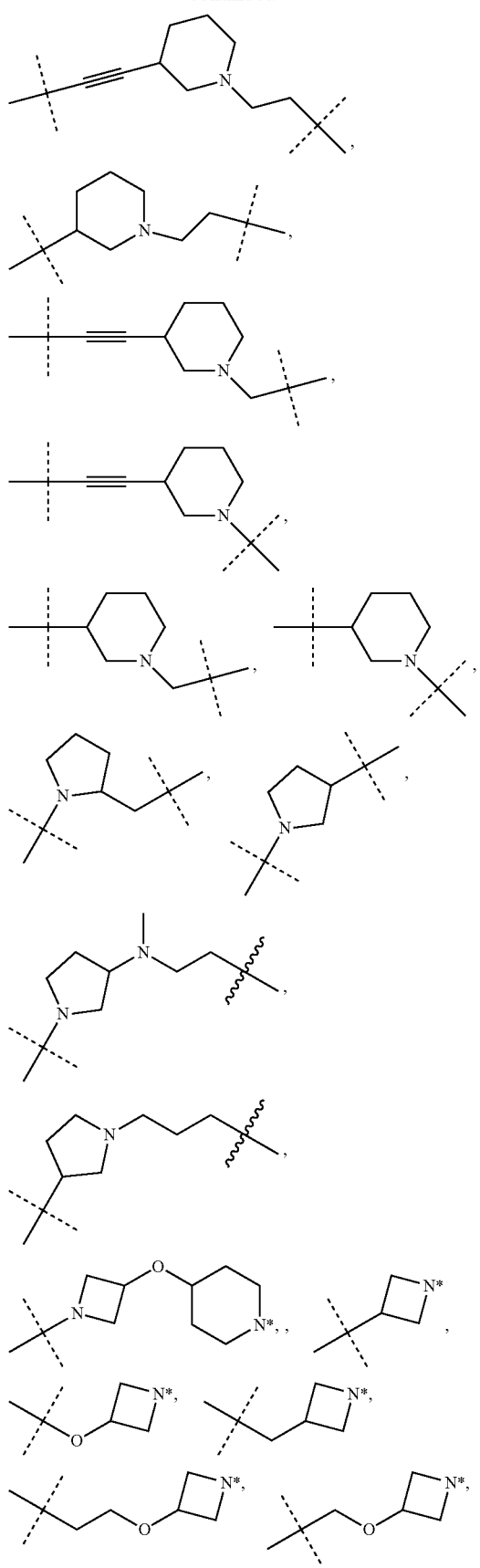
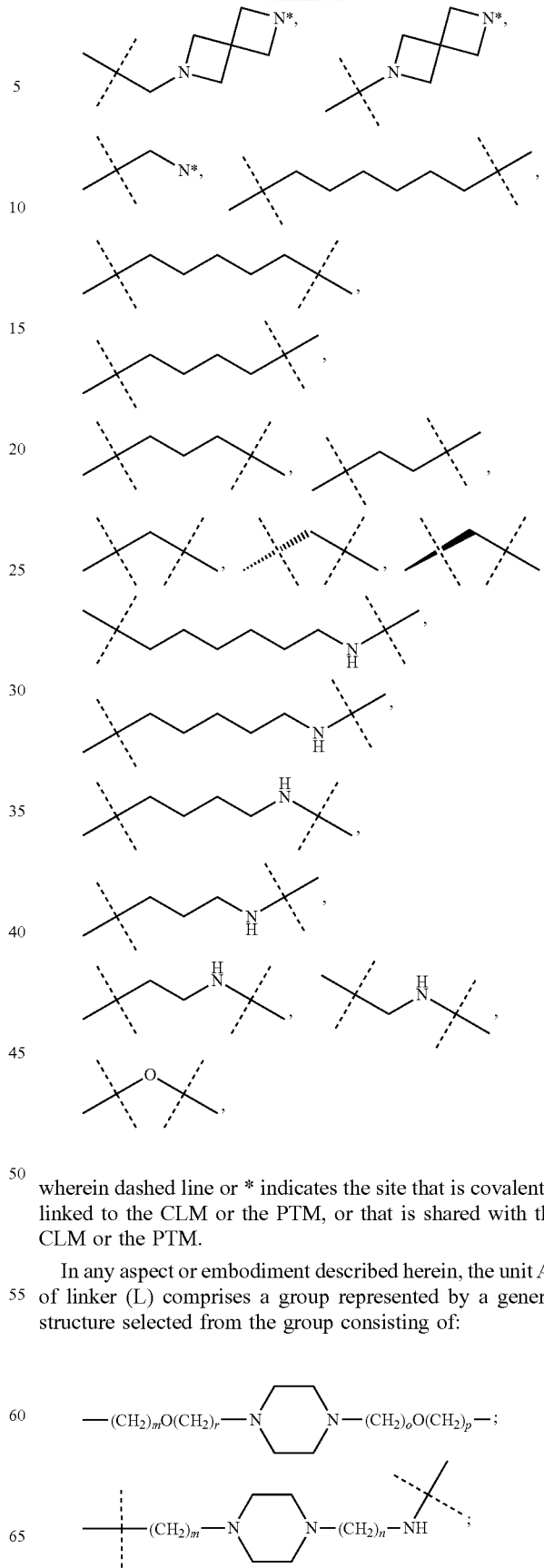
wherein dashed line or * indicates the site that is covalently linked to the CLM or the PTM, or that is shared with the CLM or the PTM.
In any aspect or embodiment described herein, the unit $A^L$ of linker (L) comprises a group represented by a general structure selected from the group consisting of:
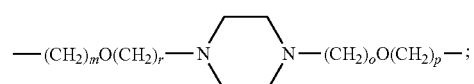
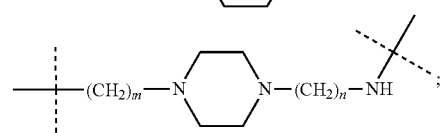

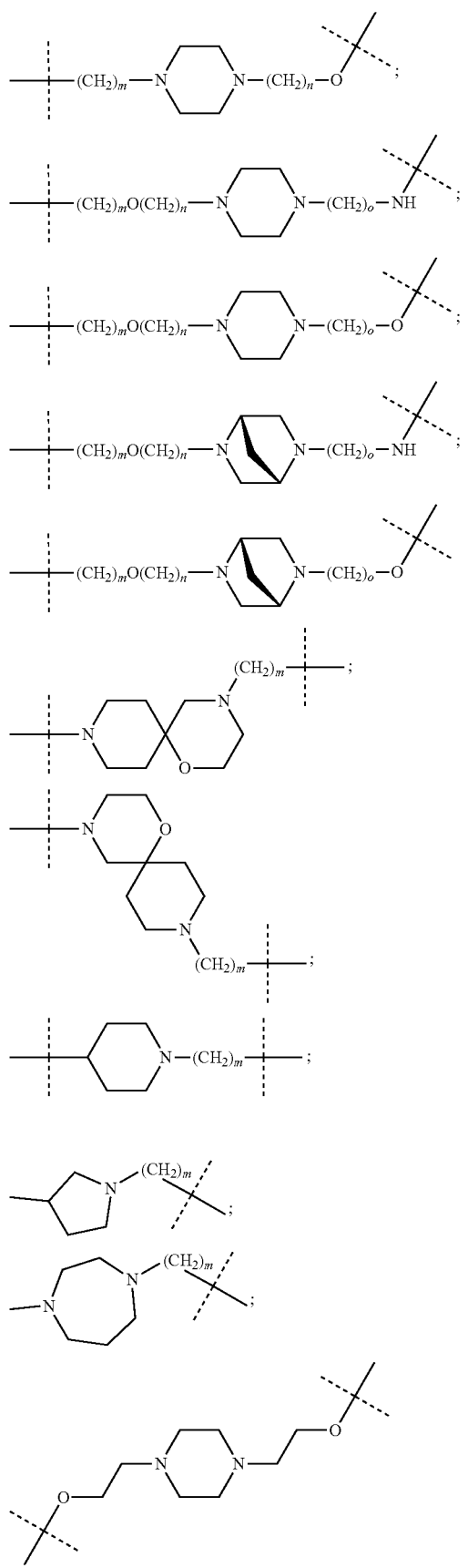
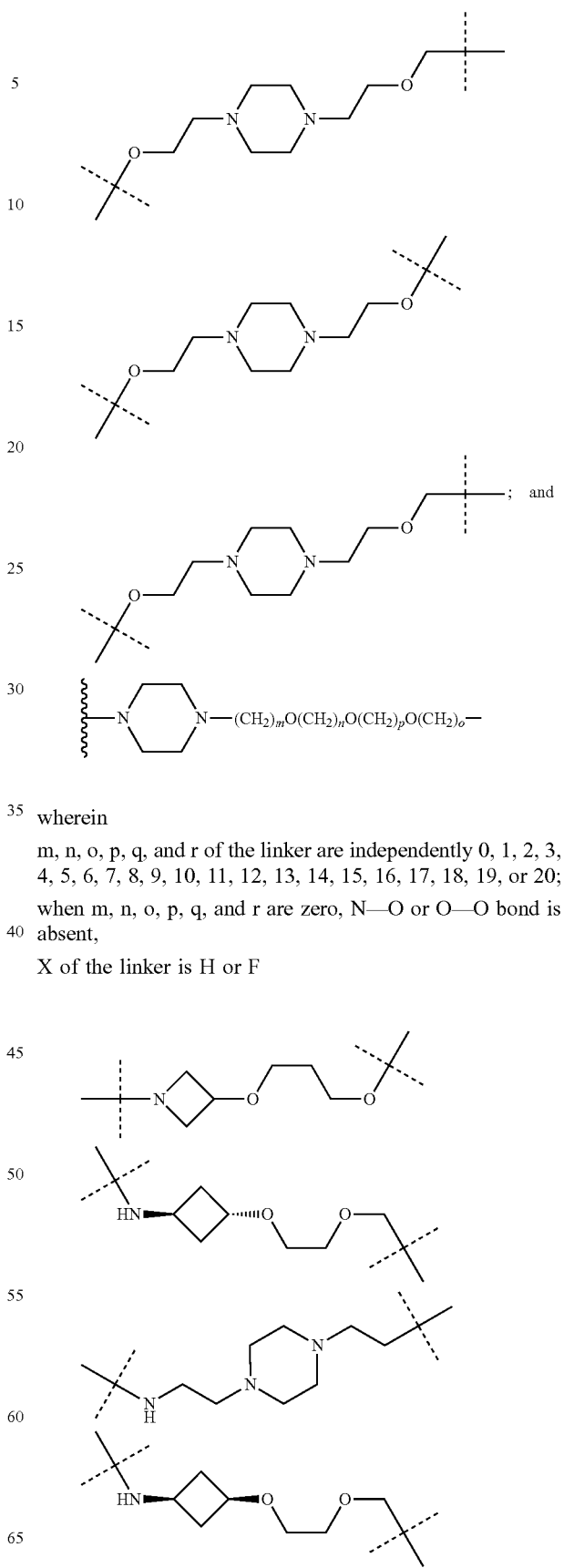
wherein
m, n, o, p, q, and r of the linker are independently 0, 1, 2, 3, 4, 5, 6, 7, 8, 9, 10, 11, 12, 13, 14, 15, 16, 17, 18, 19, or 20;
when m, n, o, p, q, and r are zero, N—O or O—O bond is absent,
X of the linker is H or F

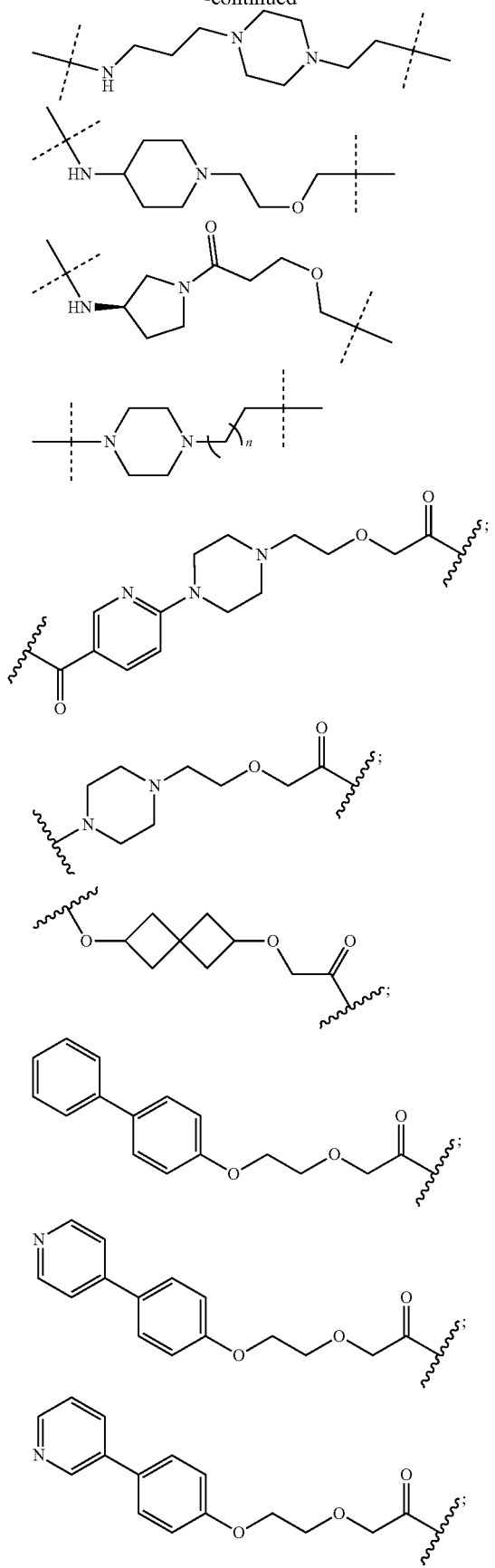
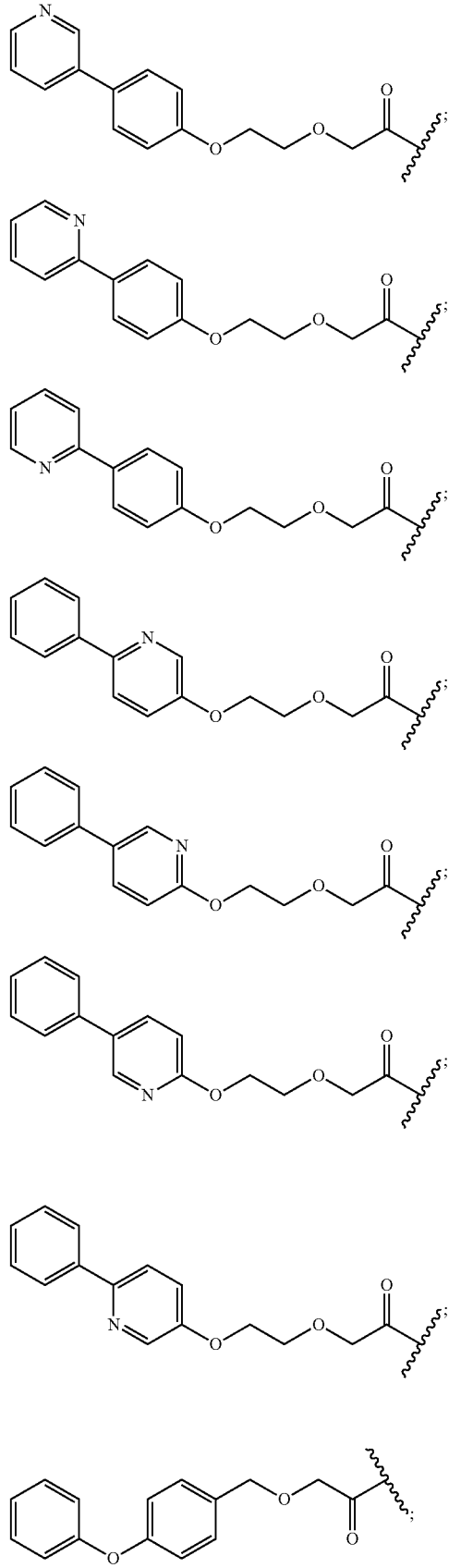

85
-continued
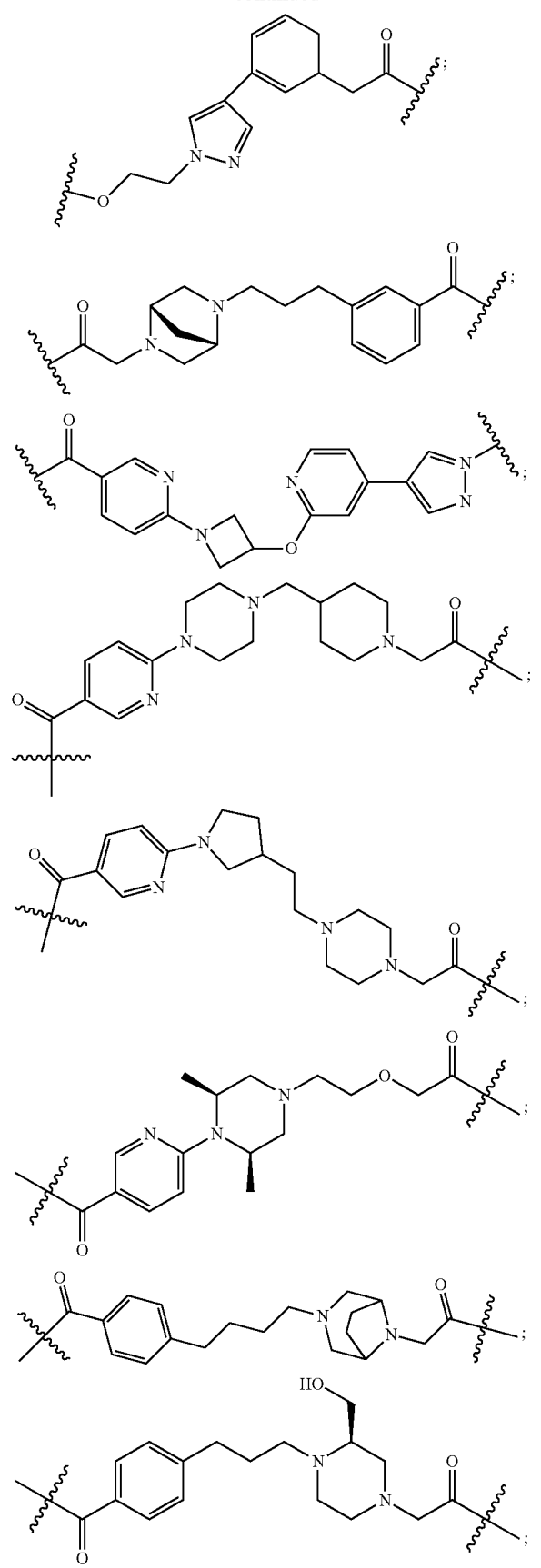
86
-continued
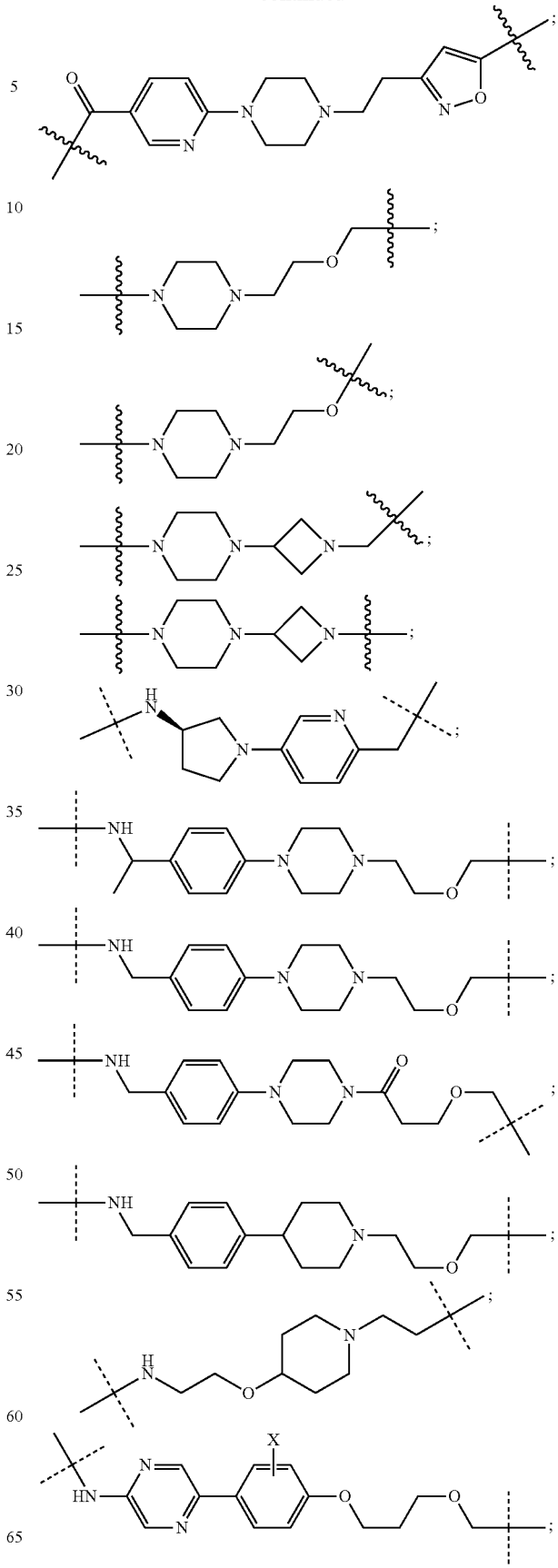

-continued
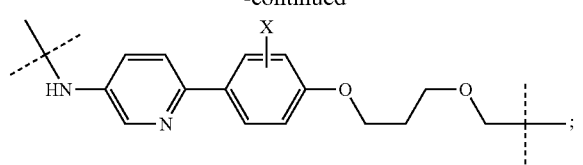
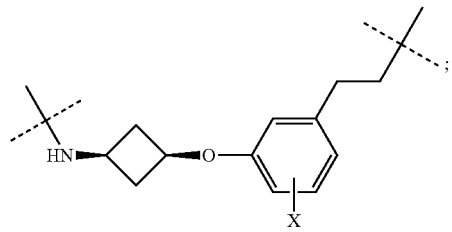
X = H, F
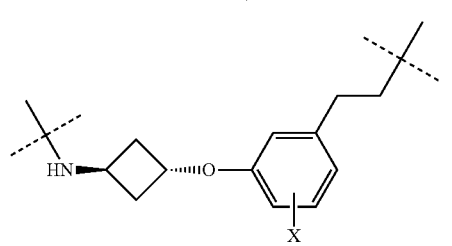
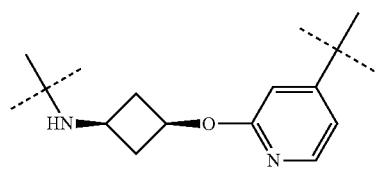
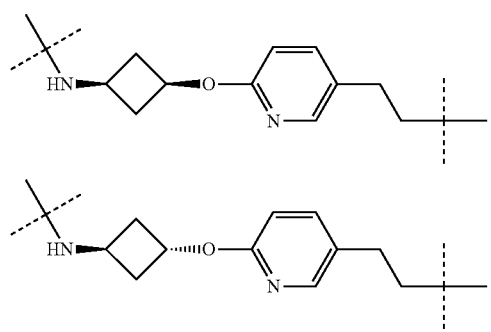
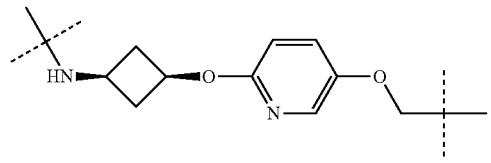
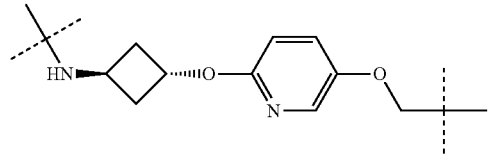
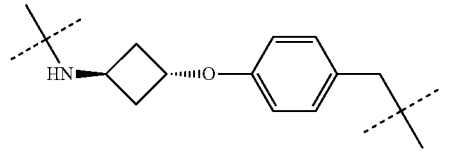
-continued
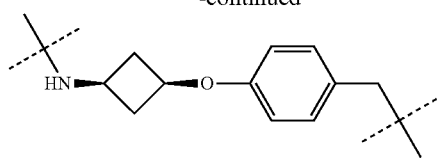
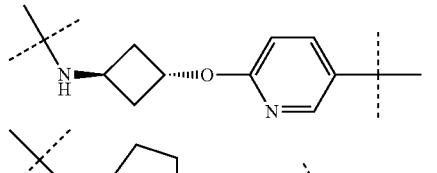
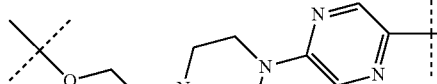
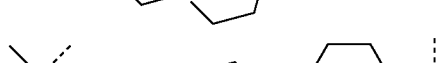
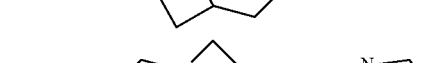
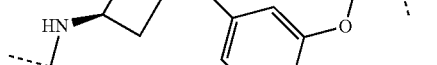
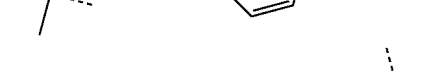
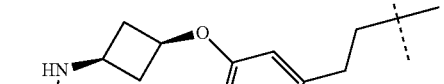

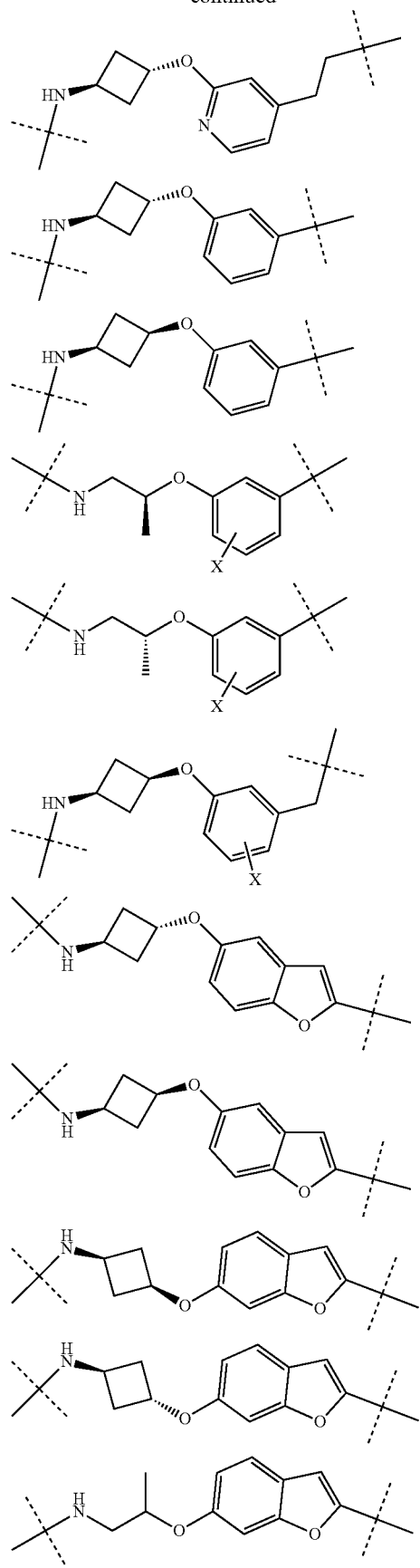
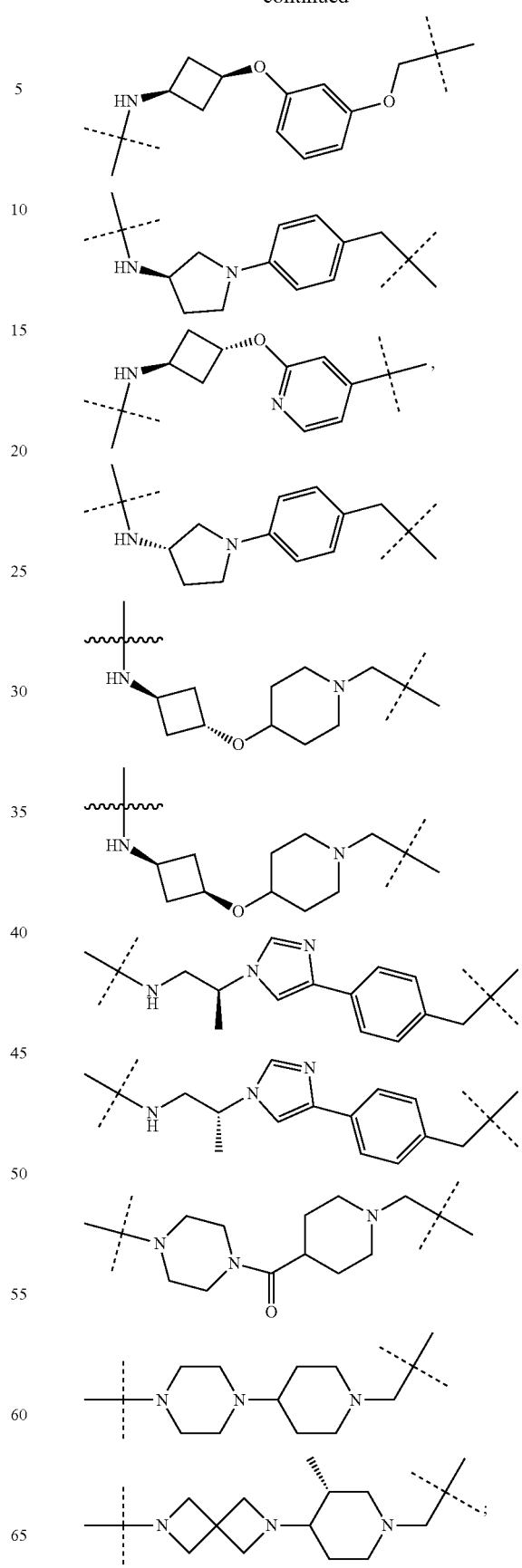

91
-continued
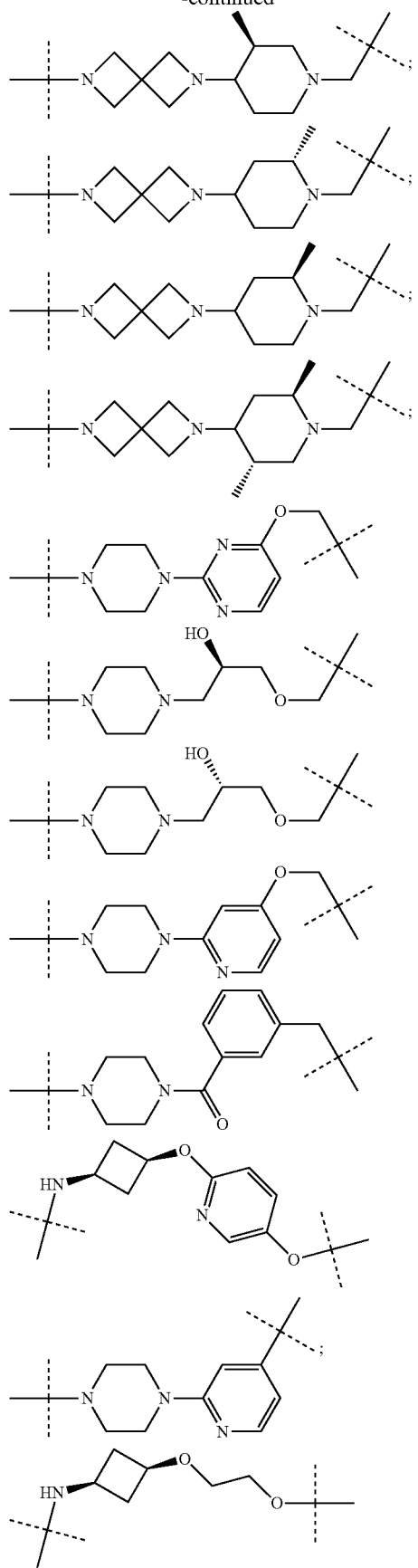
92
-continued
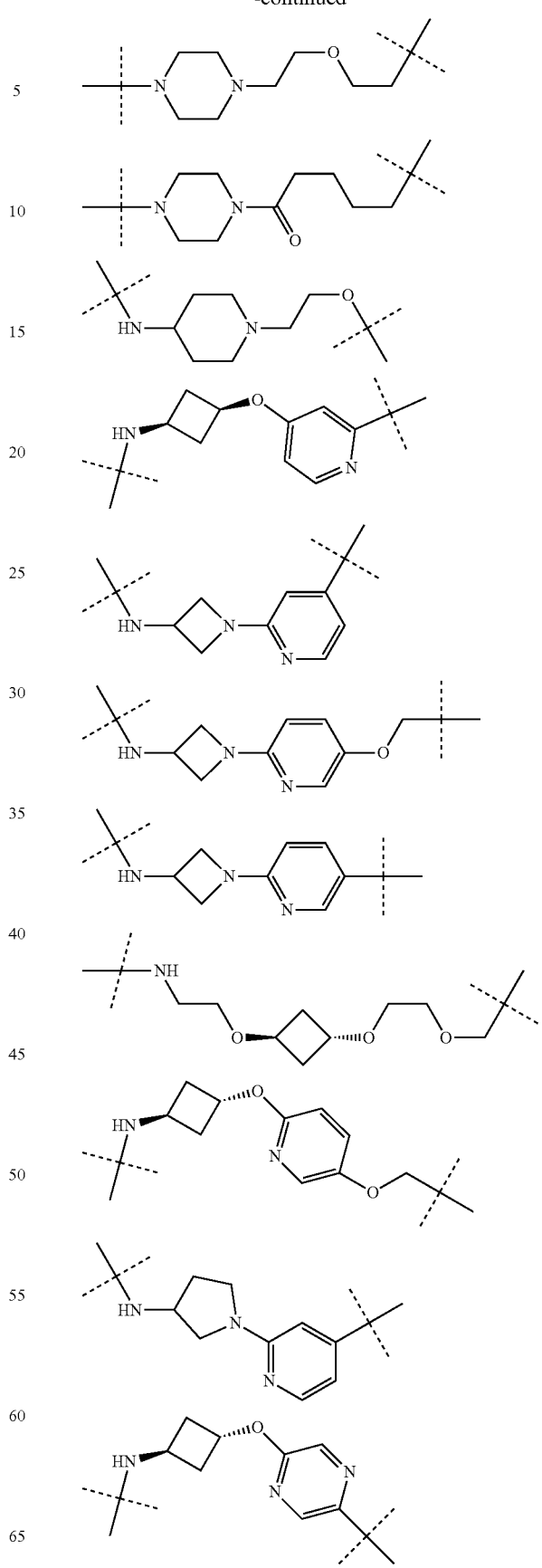

-continued
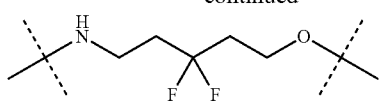
where each n and m of the linker can independently be 0, 1, 2, 3, 4, 5, or 6.
In any aspect or embodiment described herein, the unit $A^L$ of linker (L) is selected from the group consisting of:
-continued
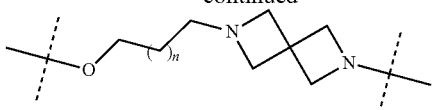
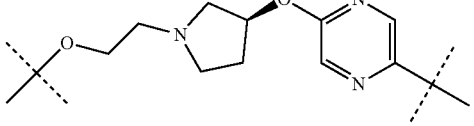
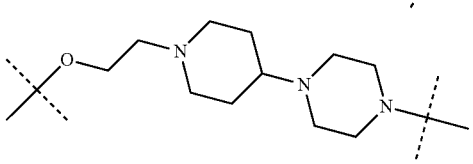
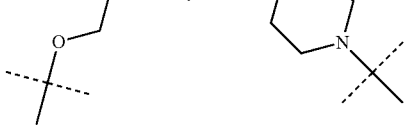
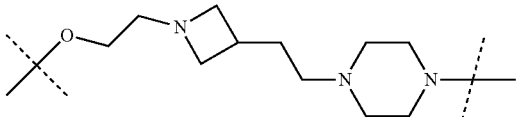
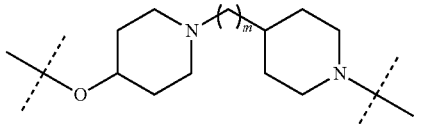
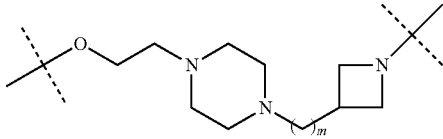
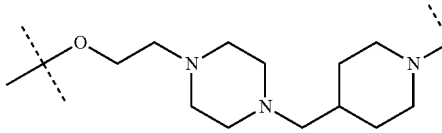
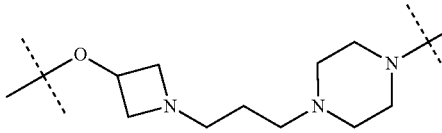
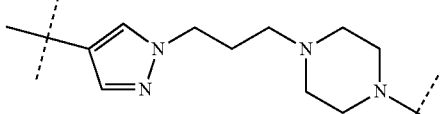
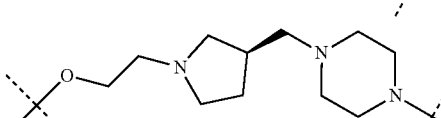
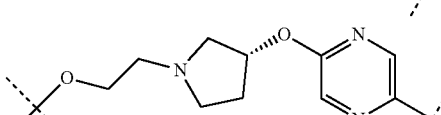

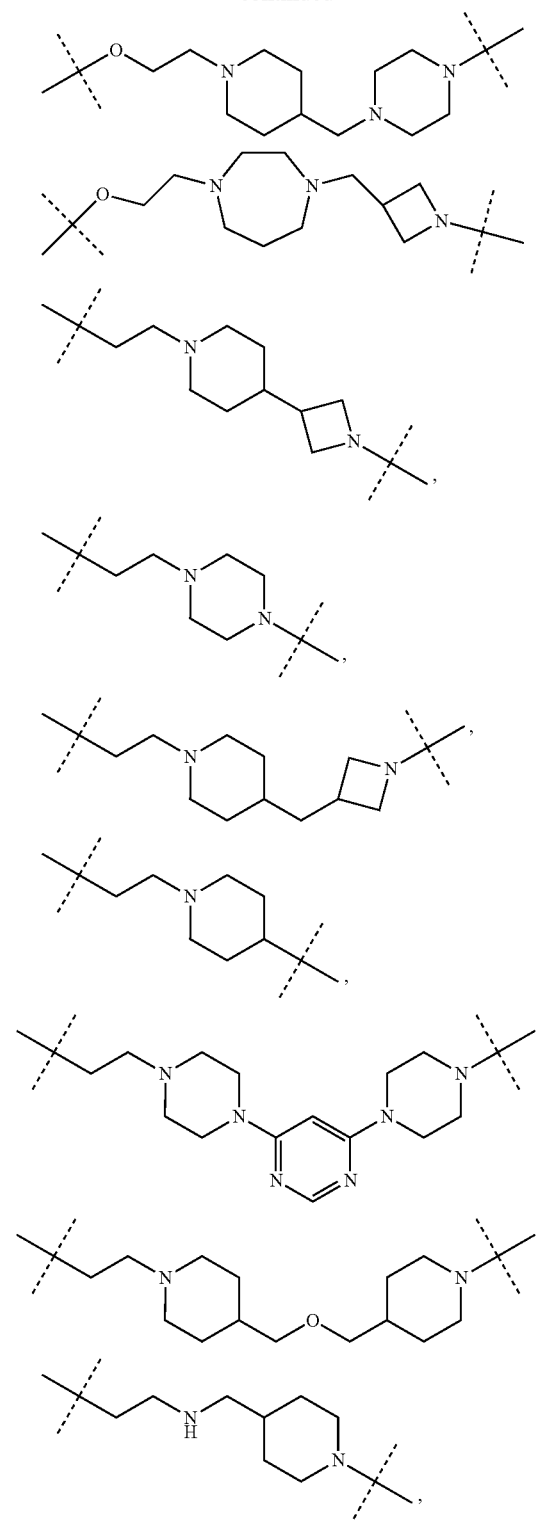
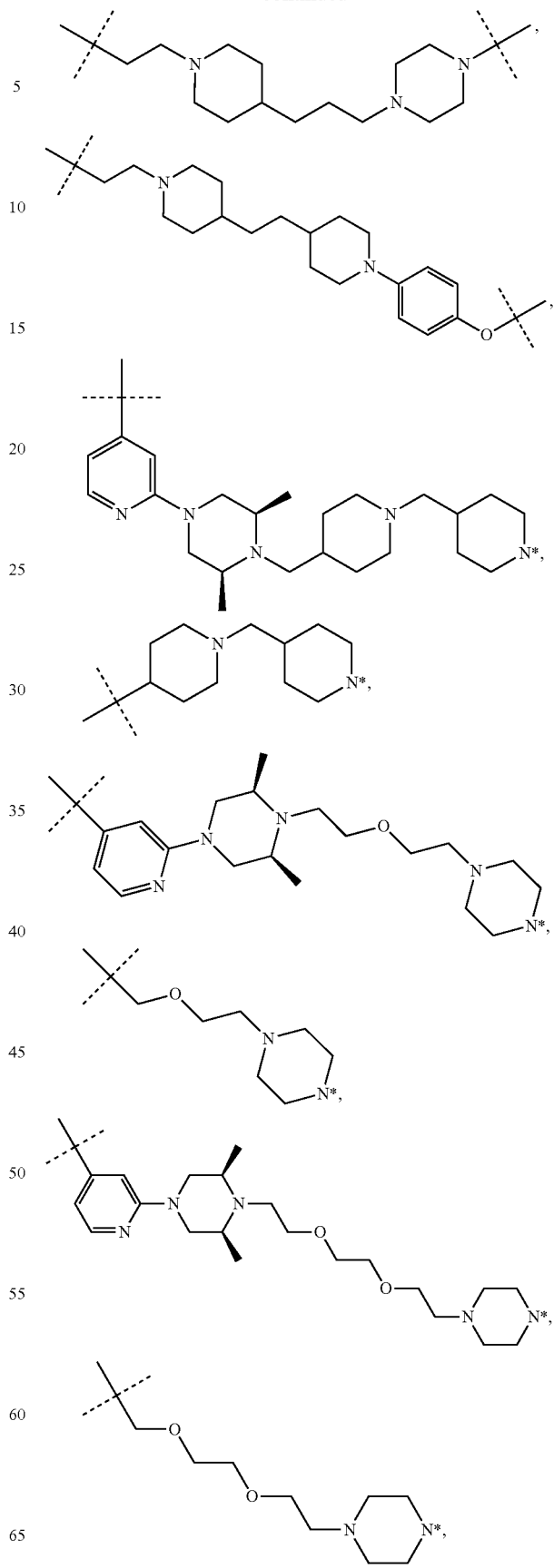

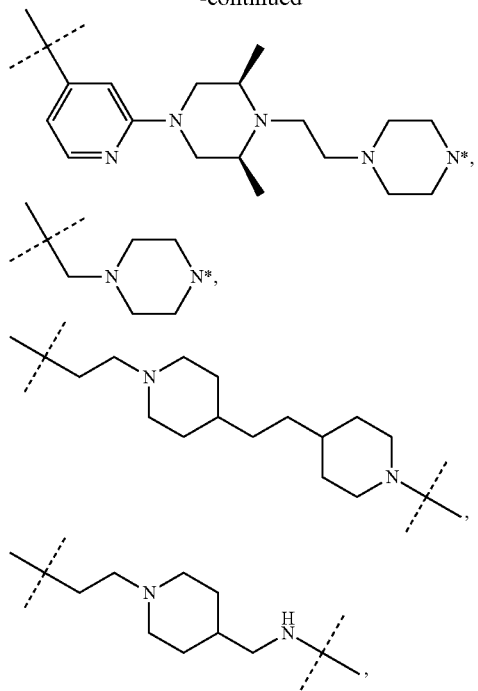
wherein each m and n is independently selected from 0, 1, 2, 3, 4, 5, or 6.
In any aspect or embodiment described herein, the unit $A^L$ of linker (L) is selected from the group consisting of:
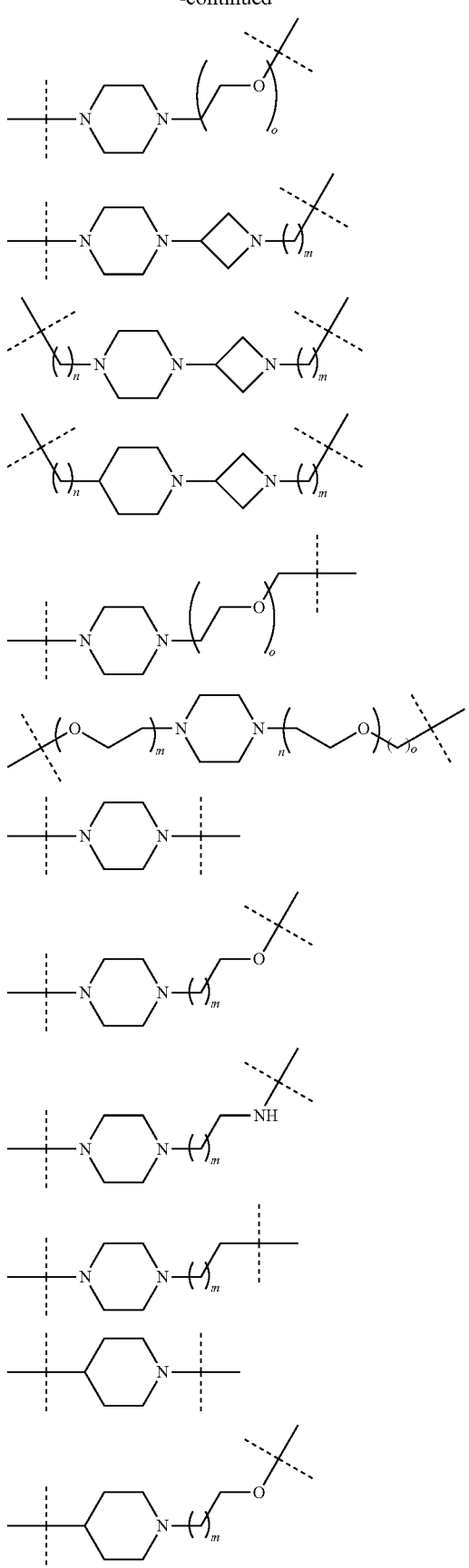

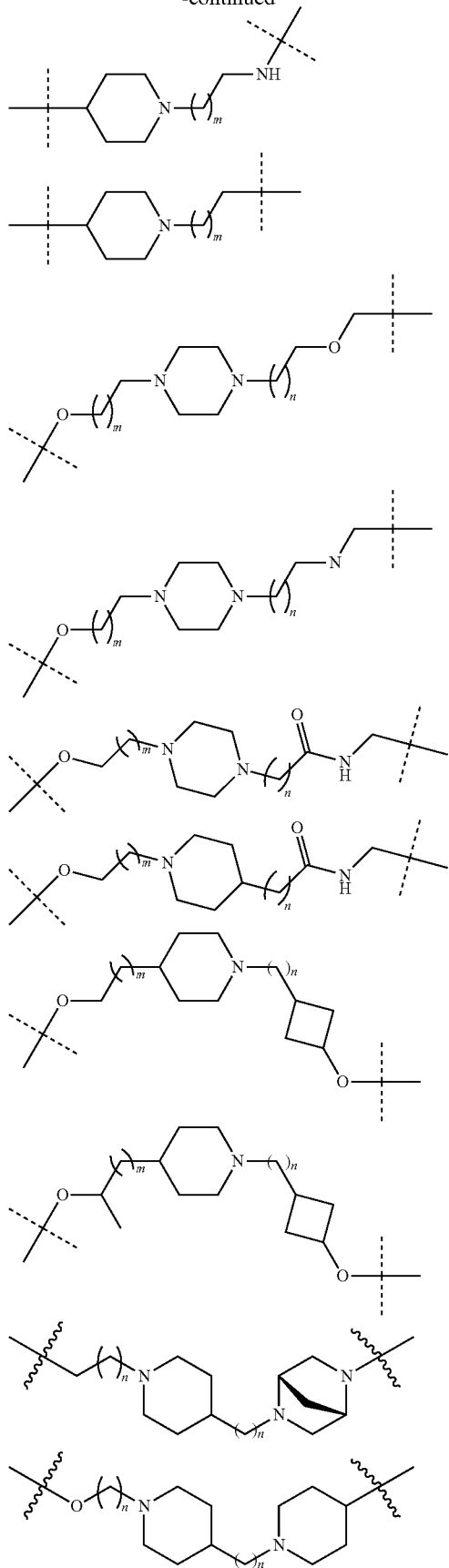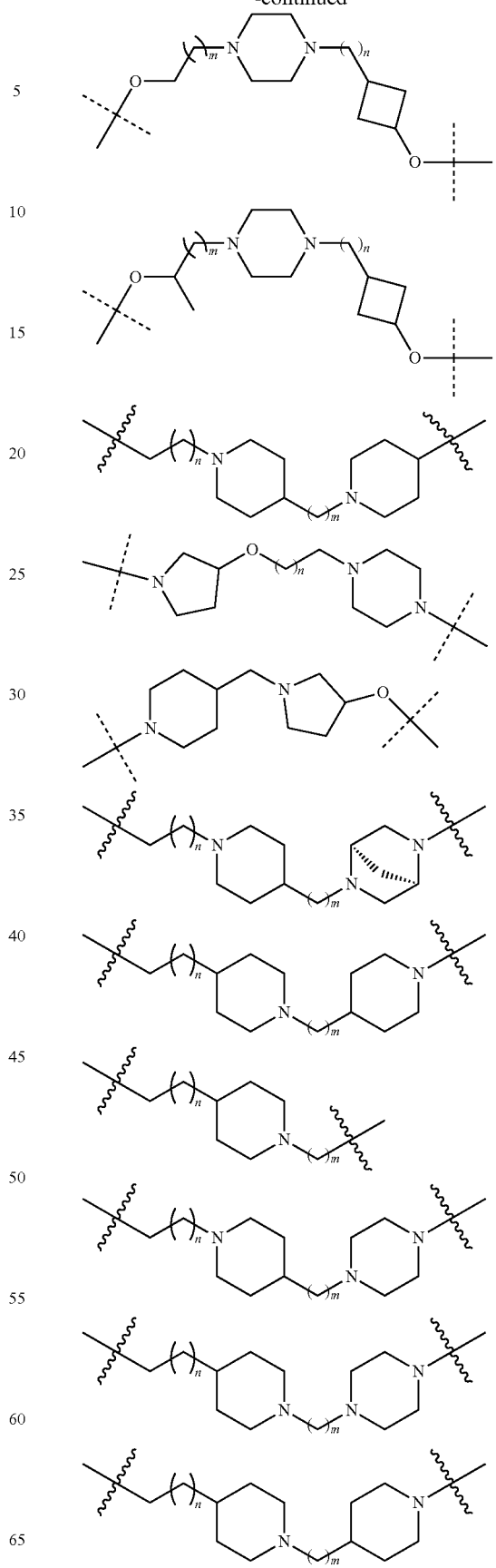

101
-continued
102
-continued
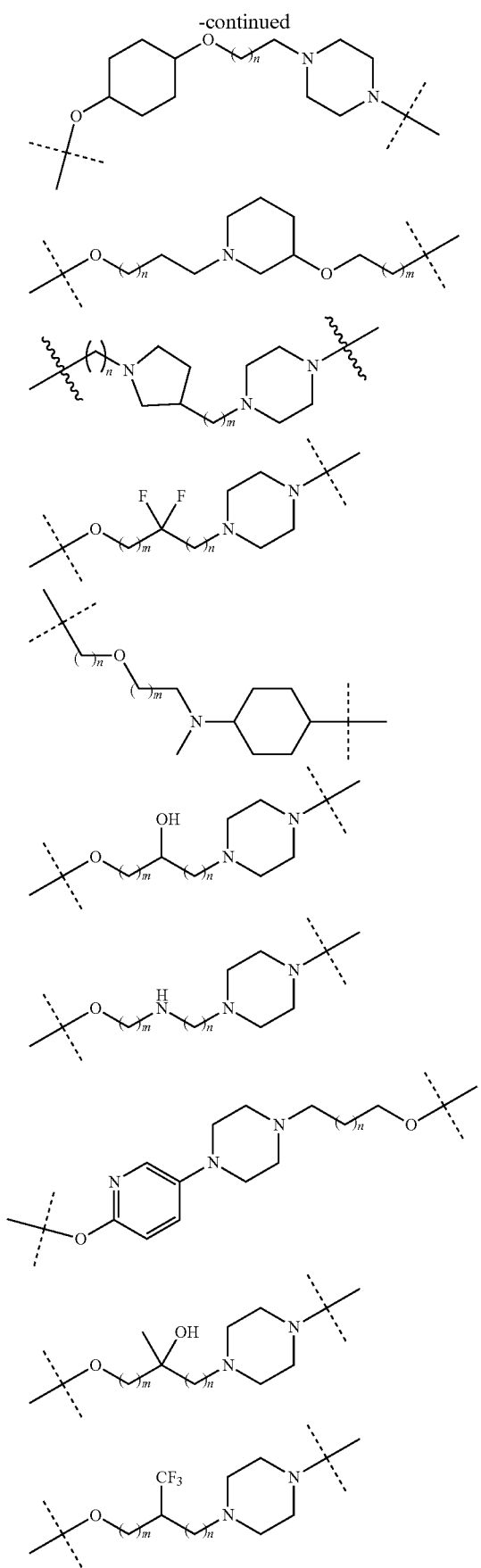
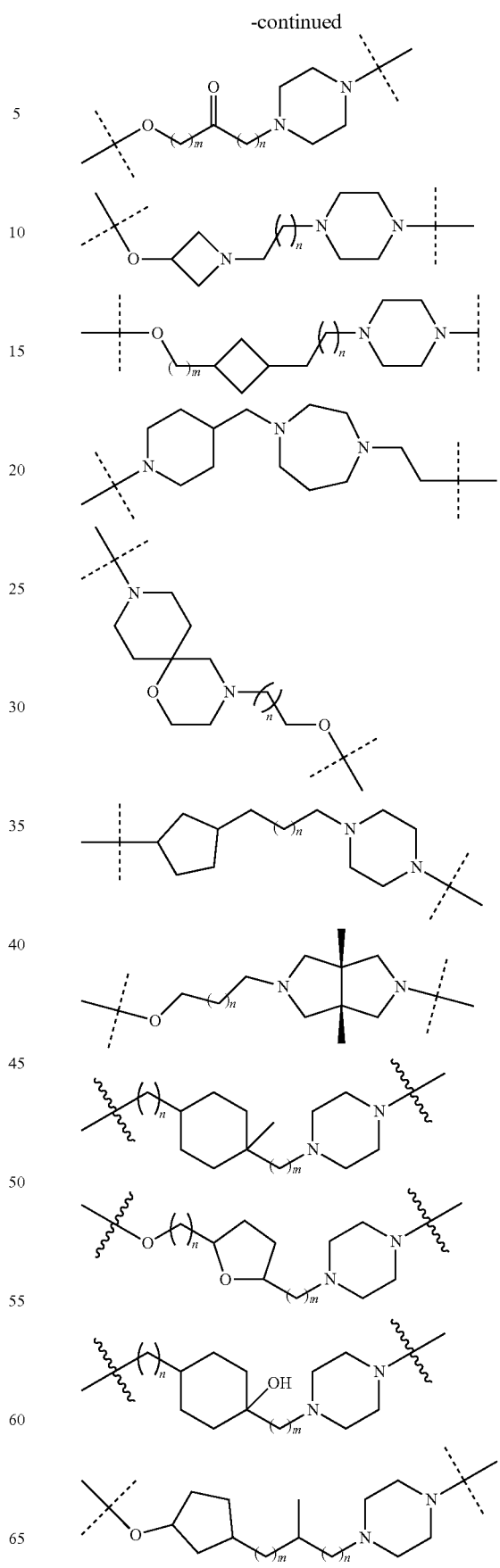

103
-continued
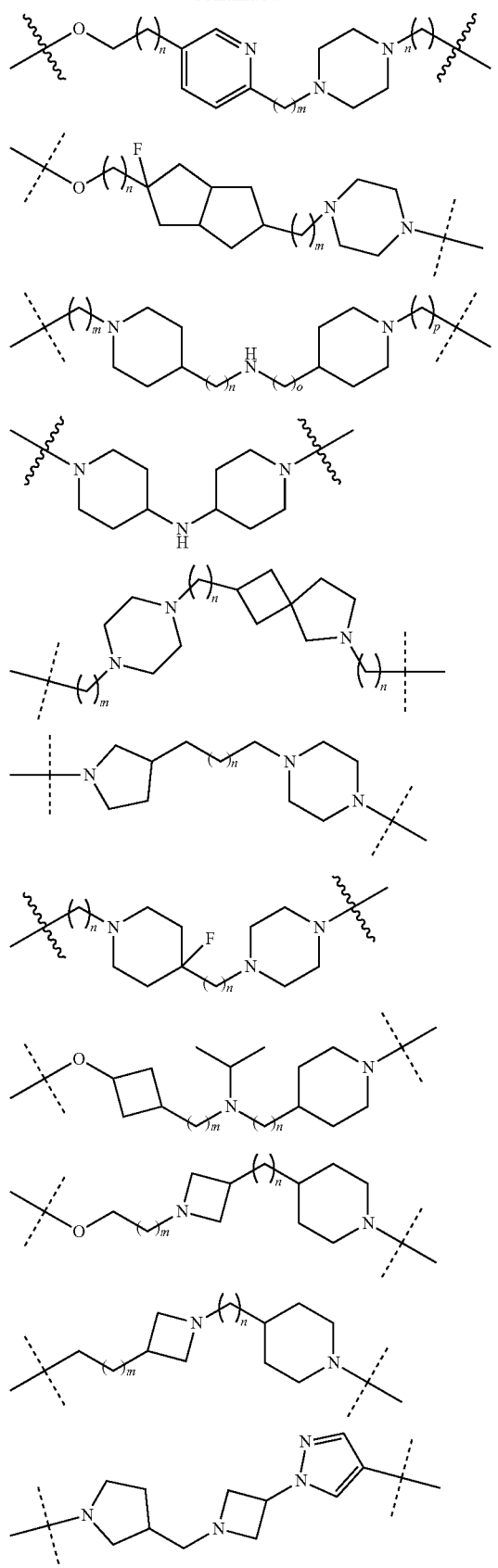
104
-continued
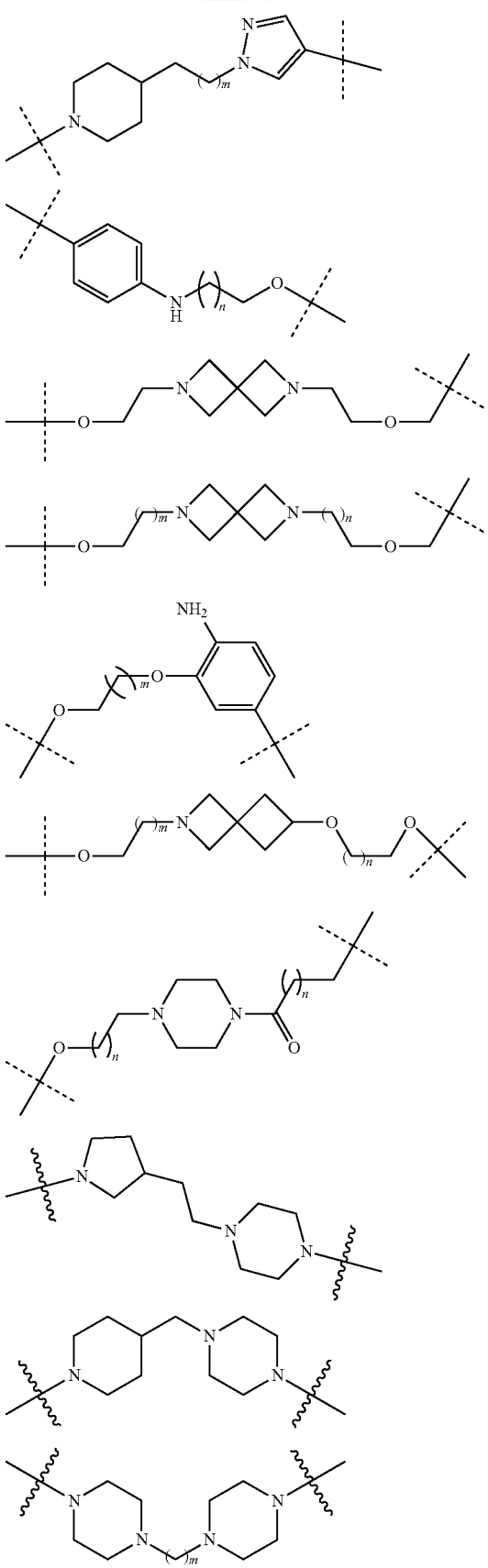

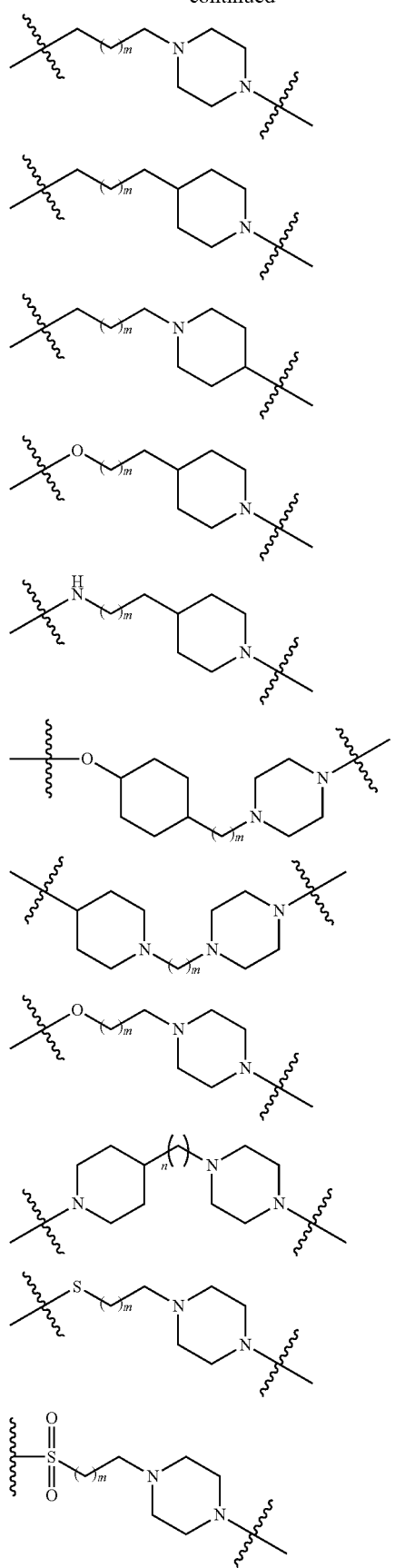
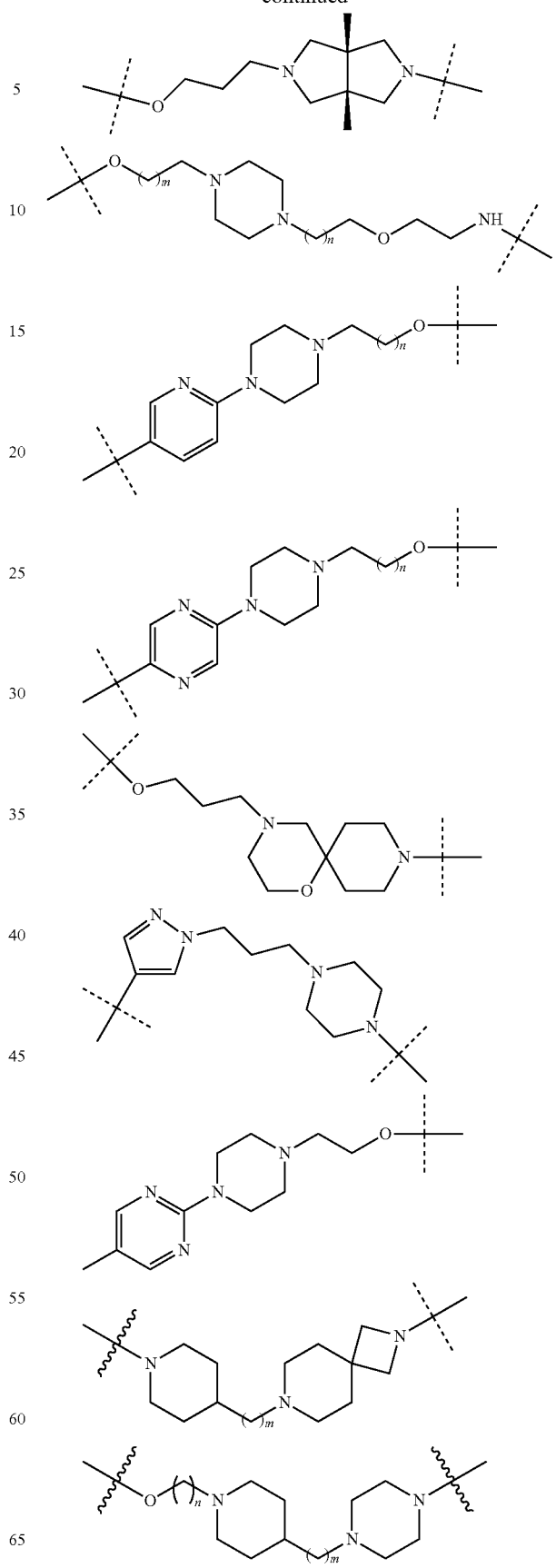

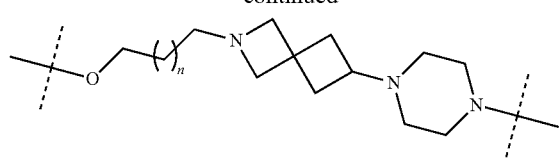
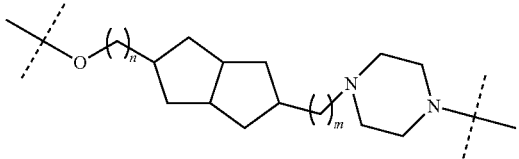
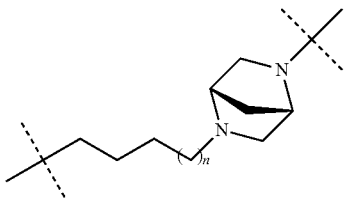
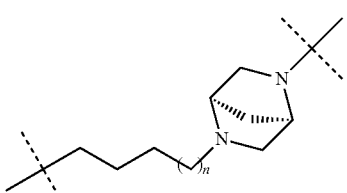
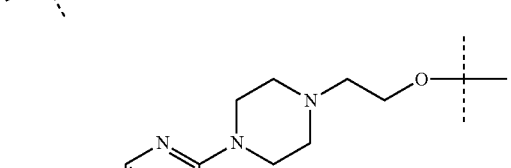
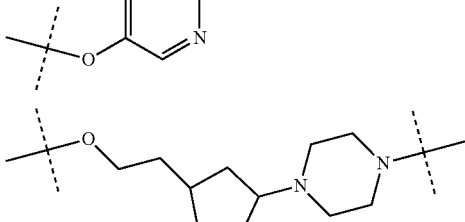
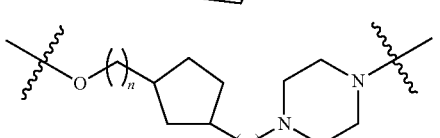
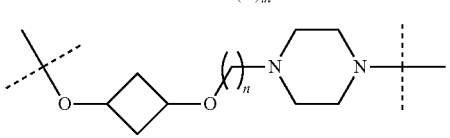
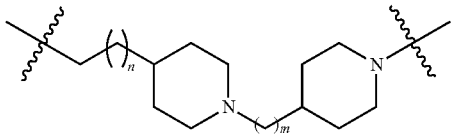
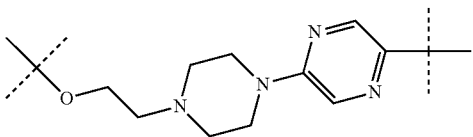
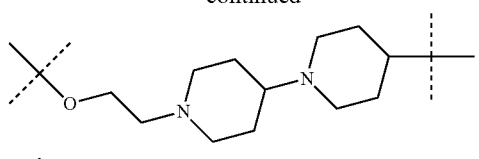
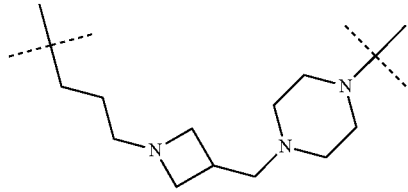
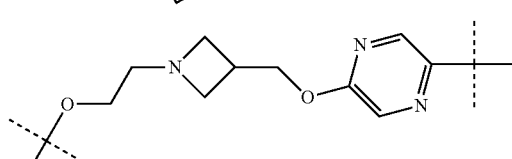
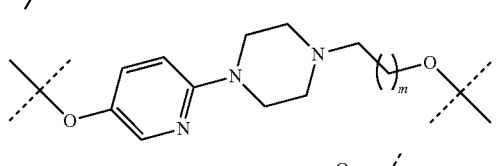
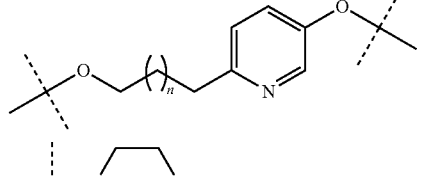
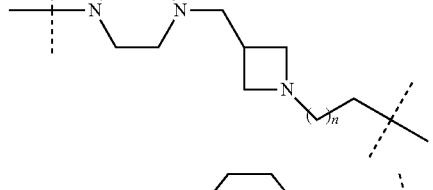
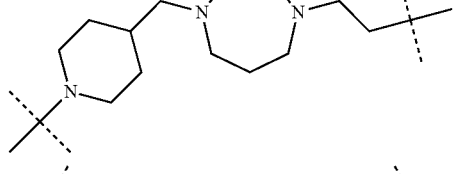
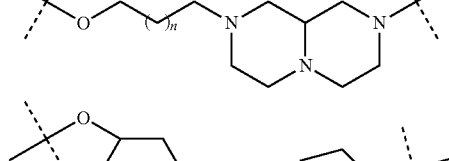
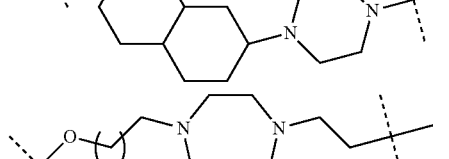
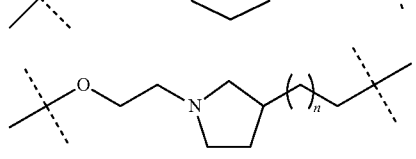

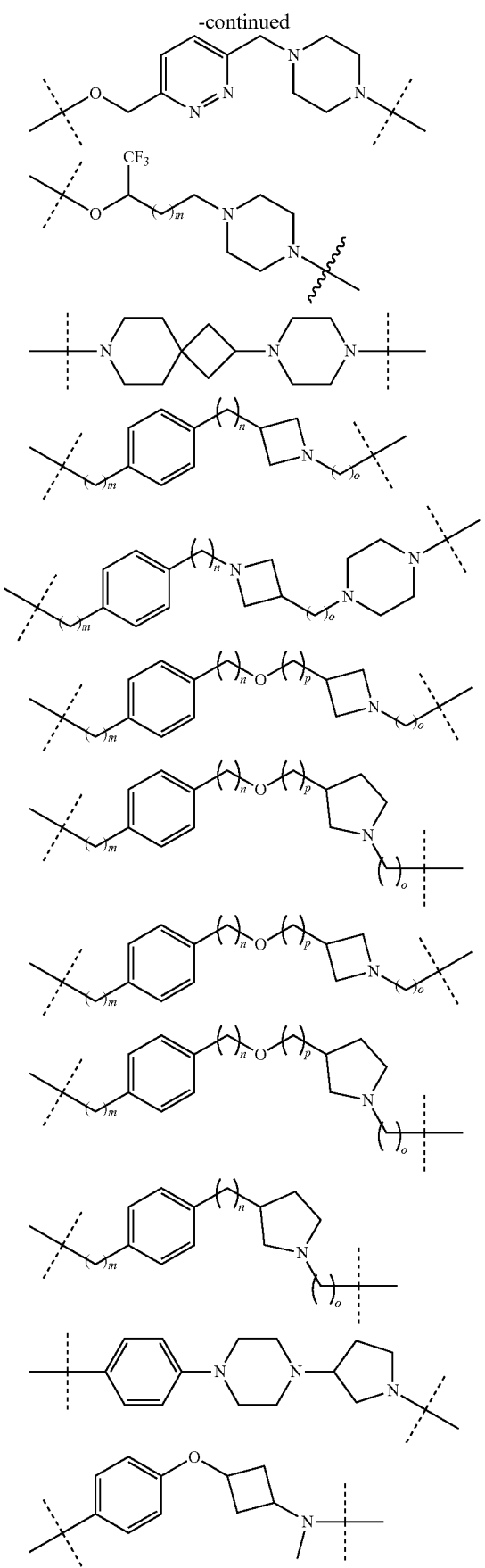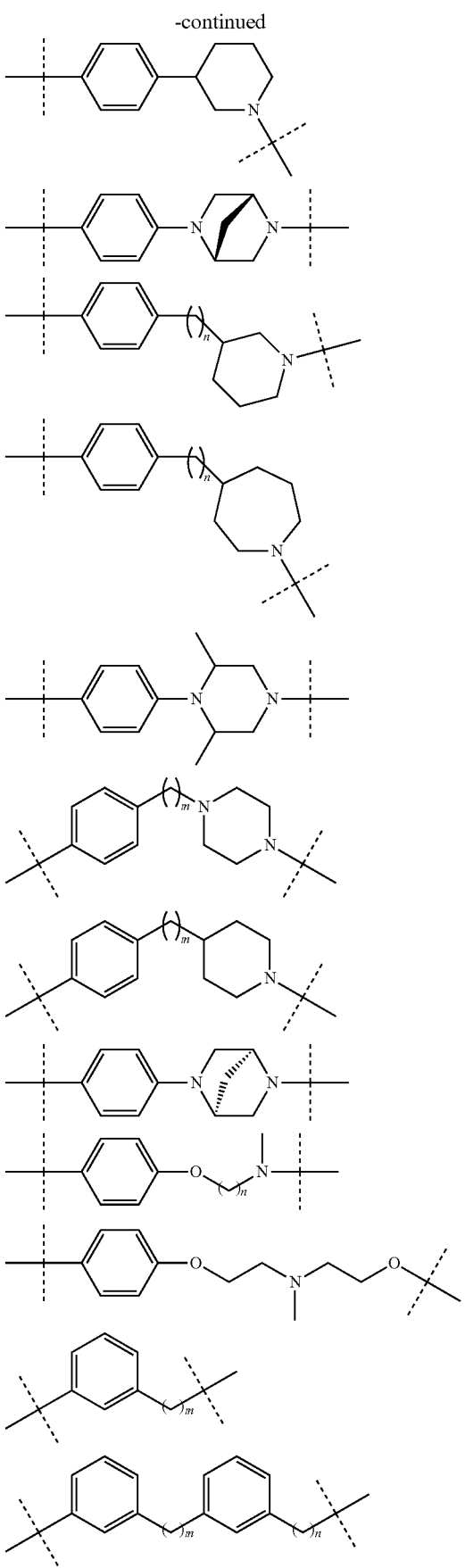

111 -continued
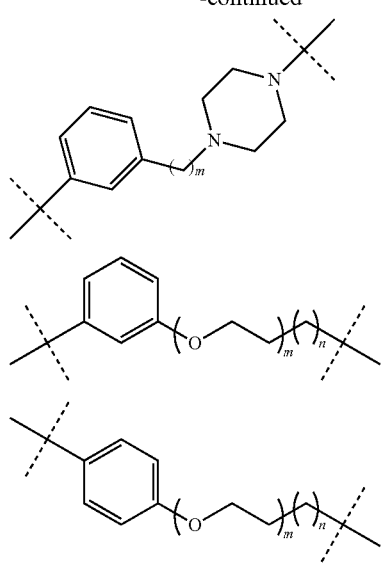
112 -continued
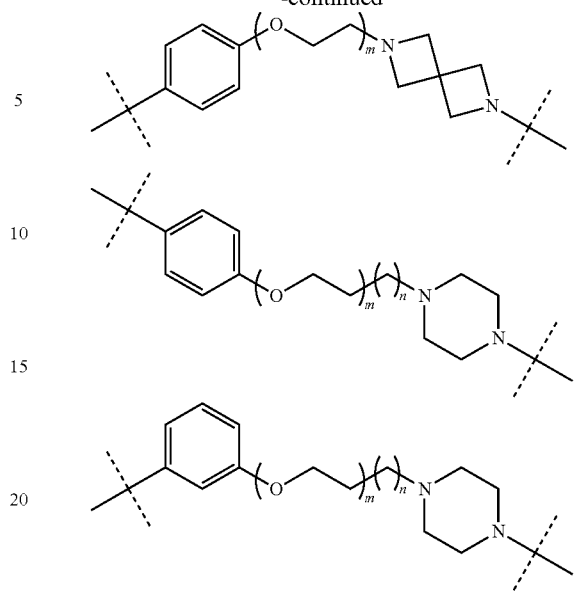
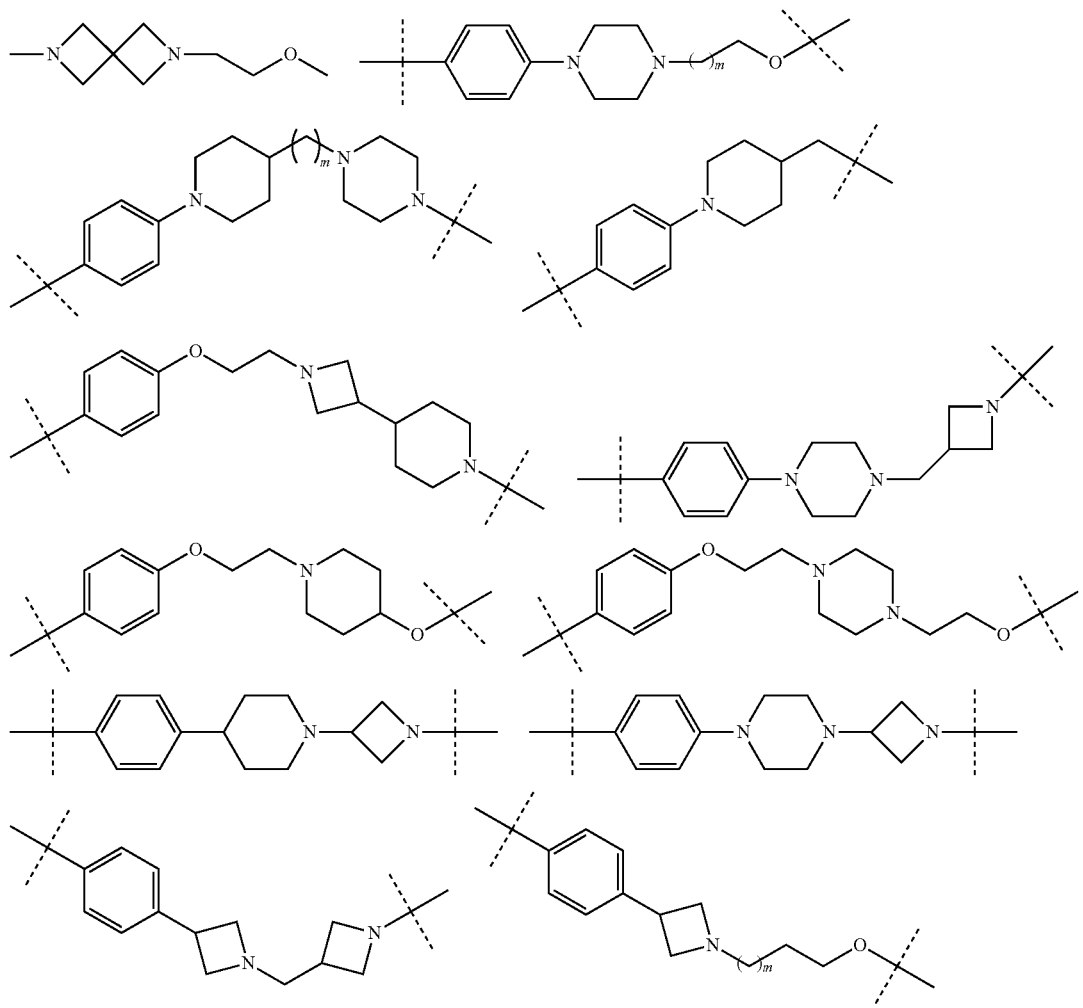

-continued
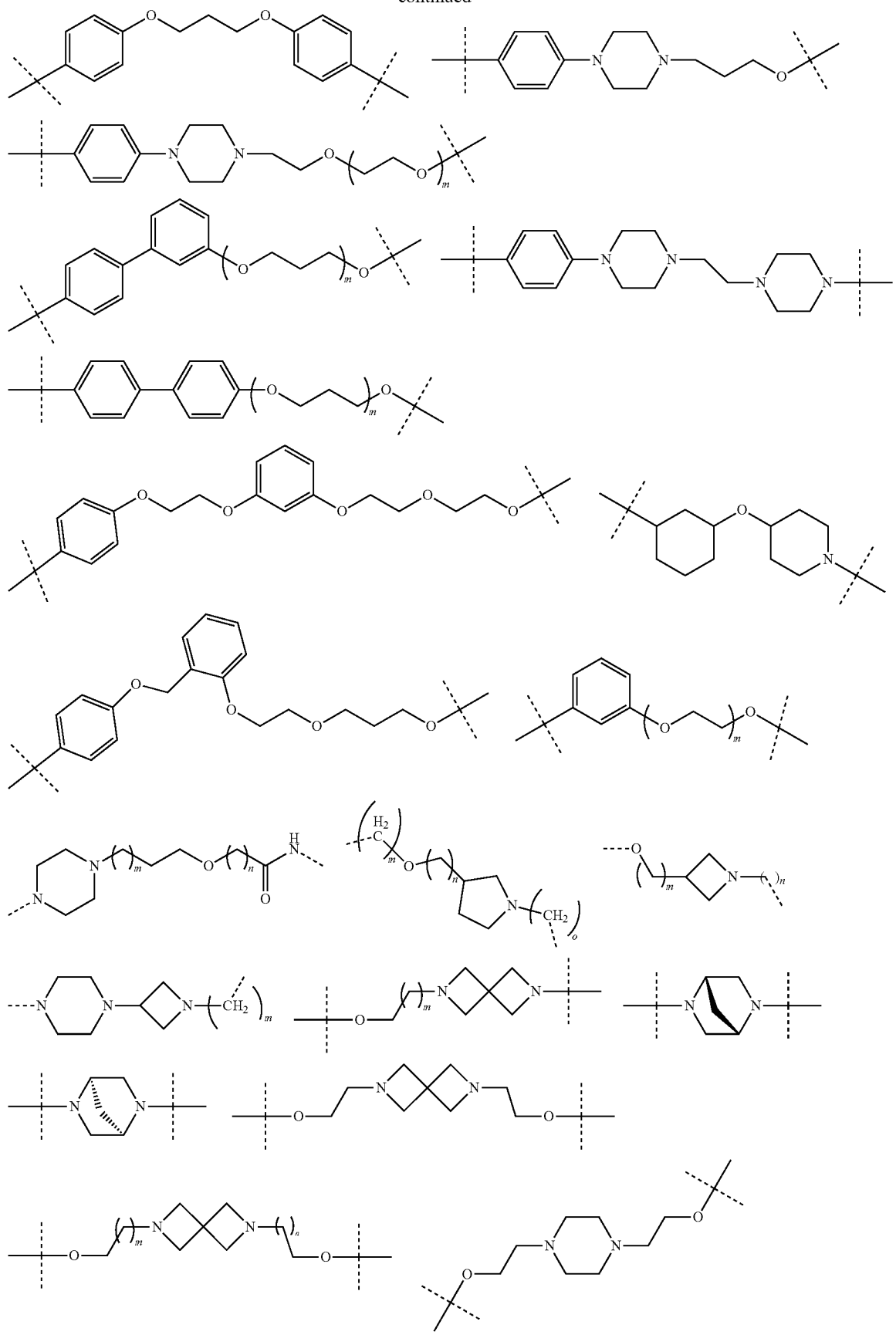

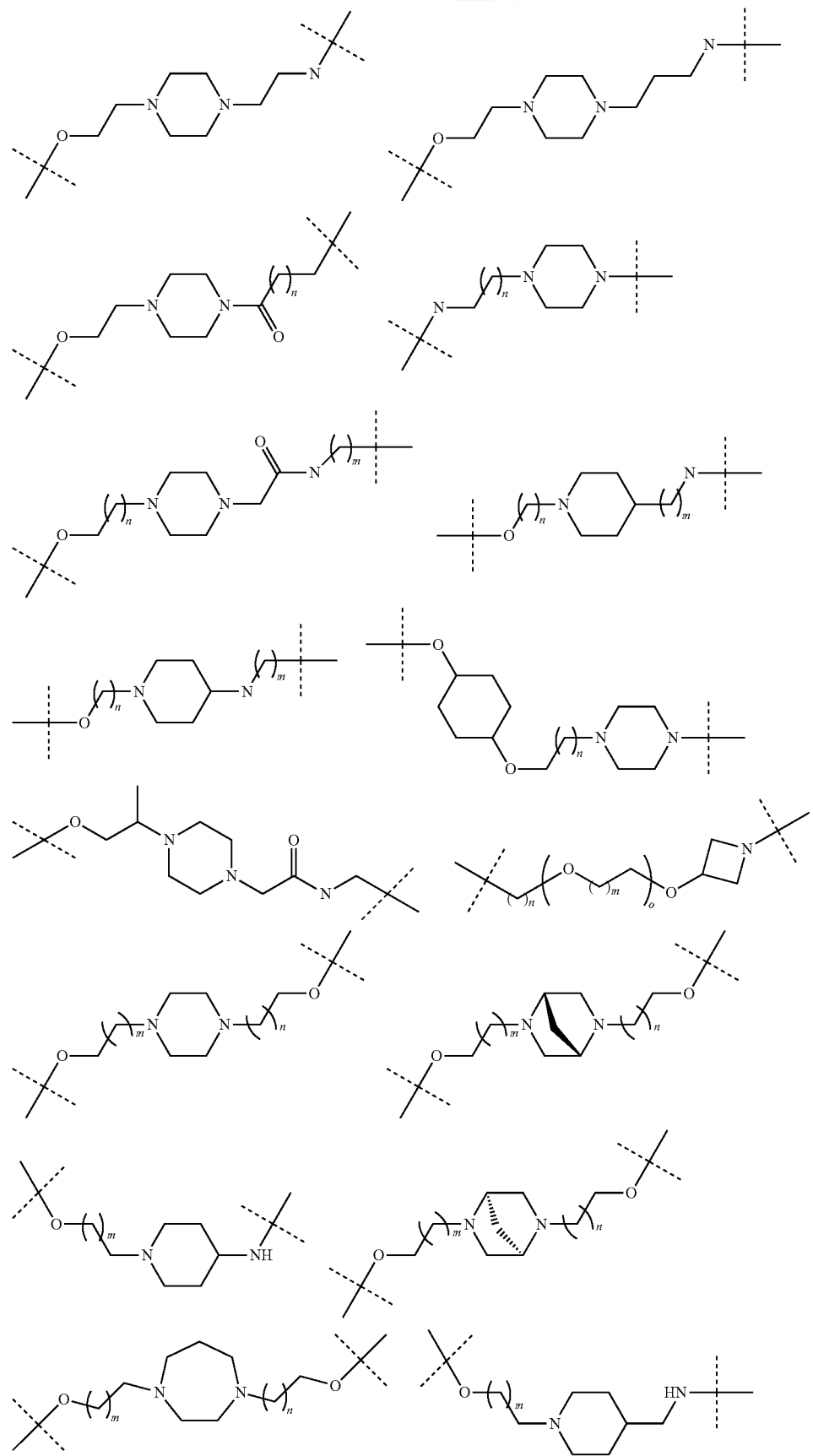

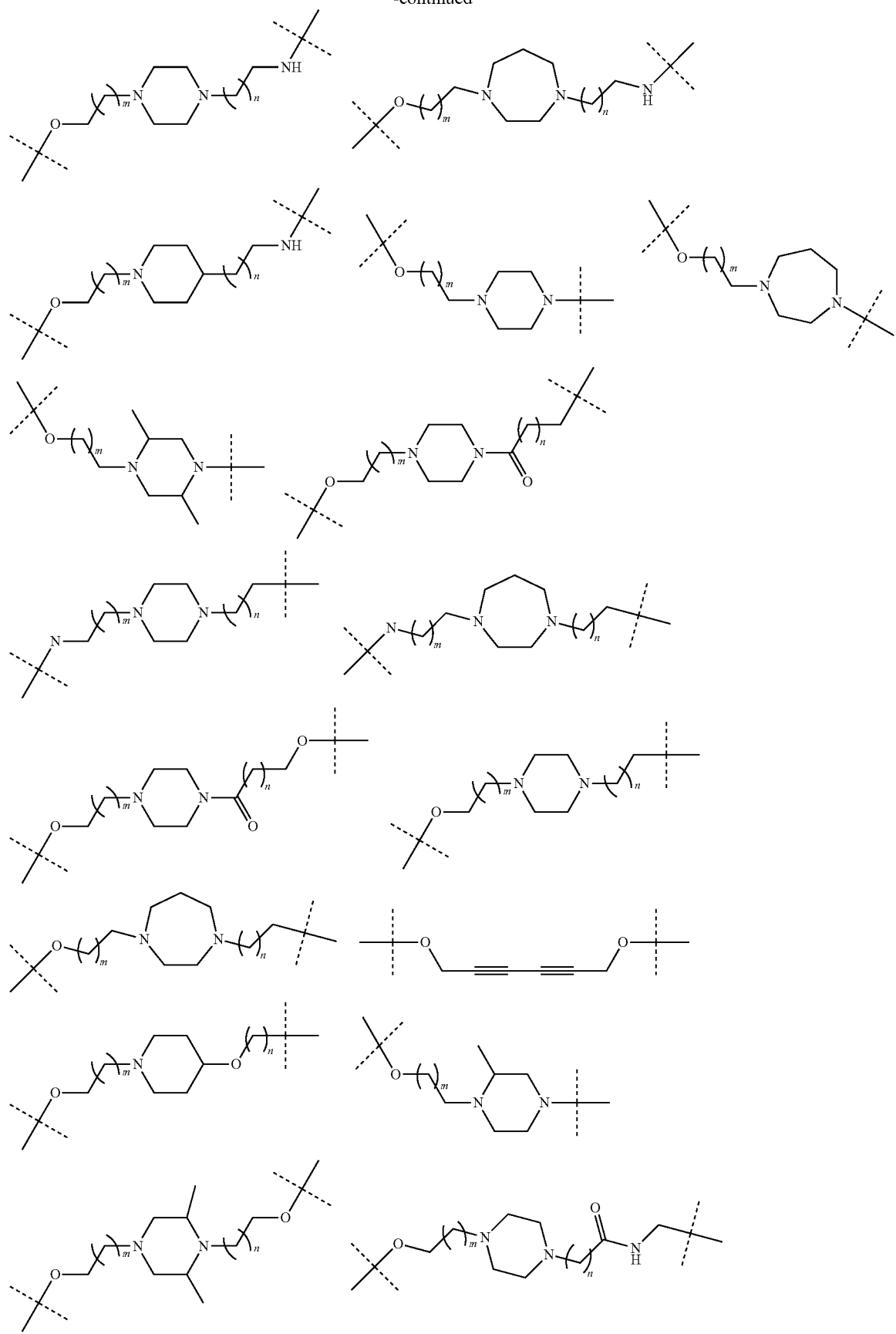

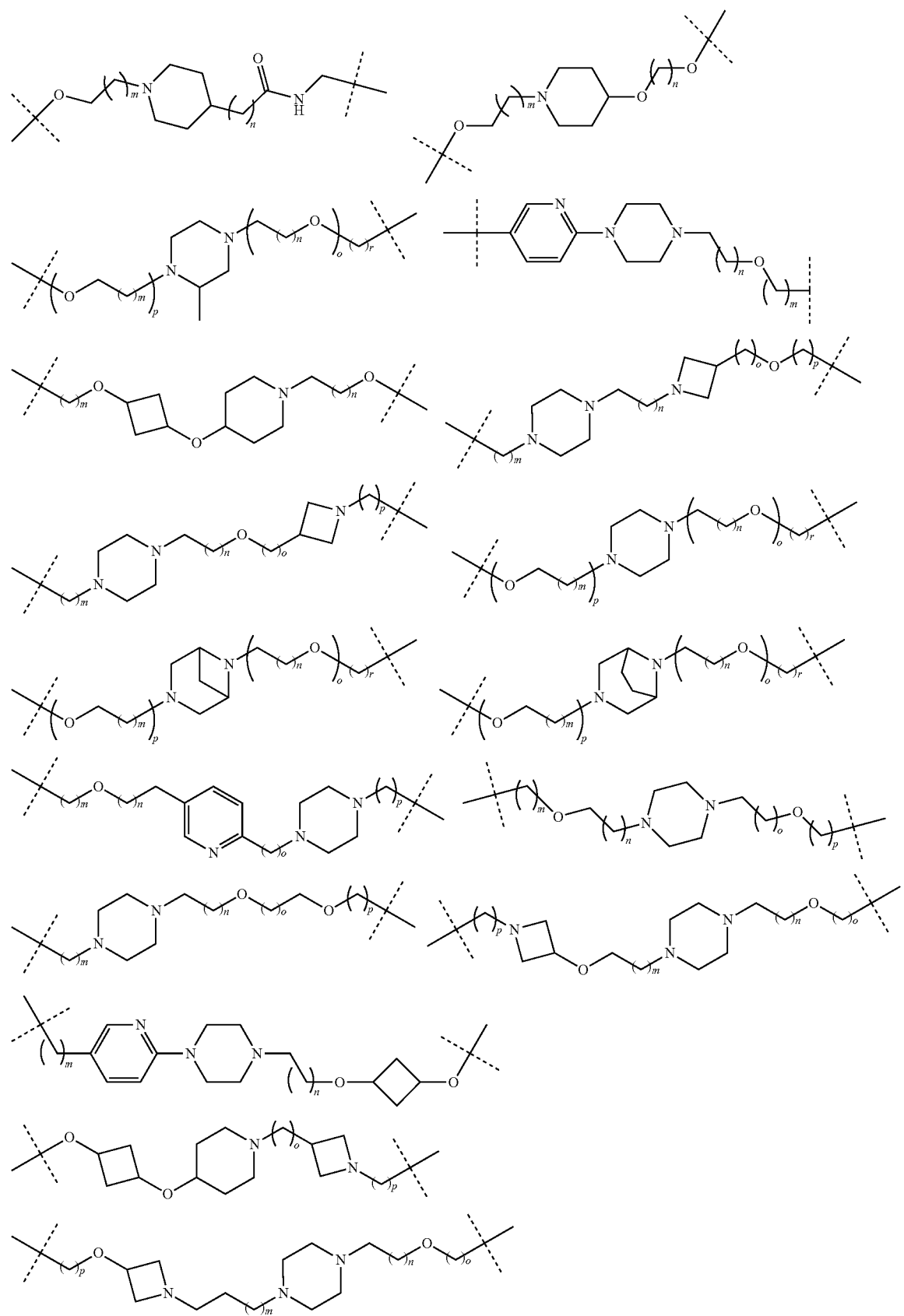

-continued
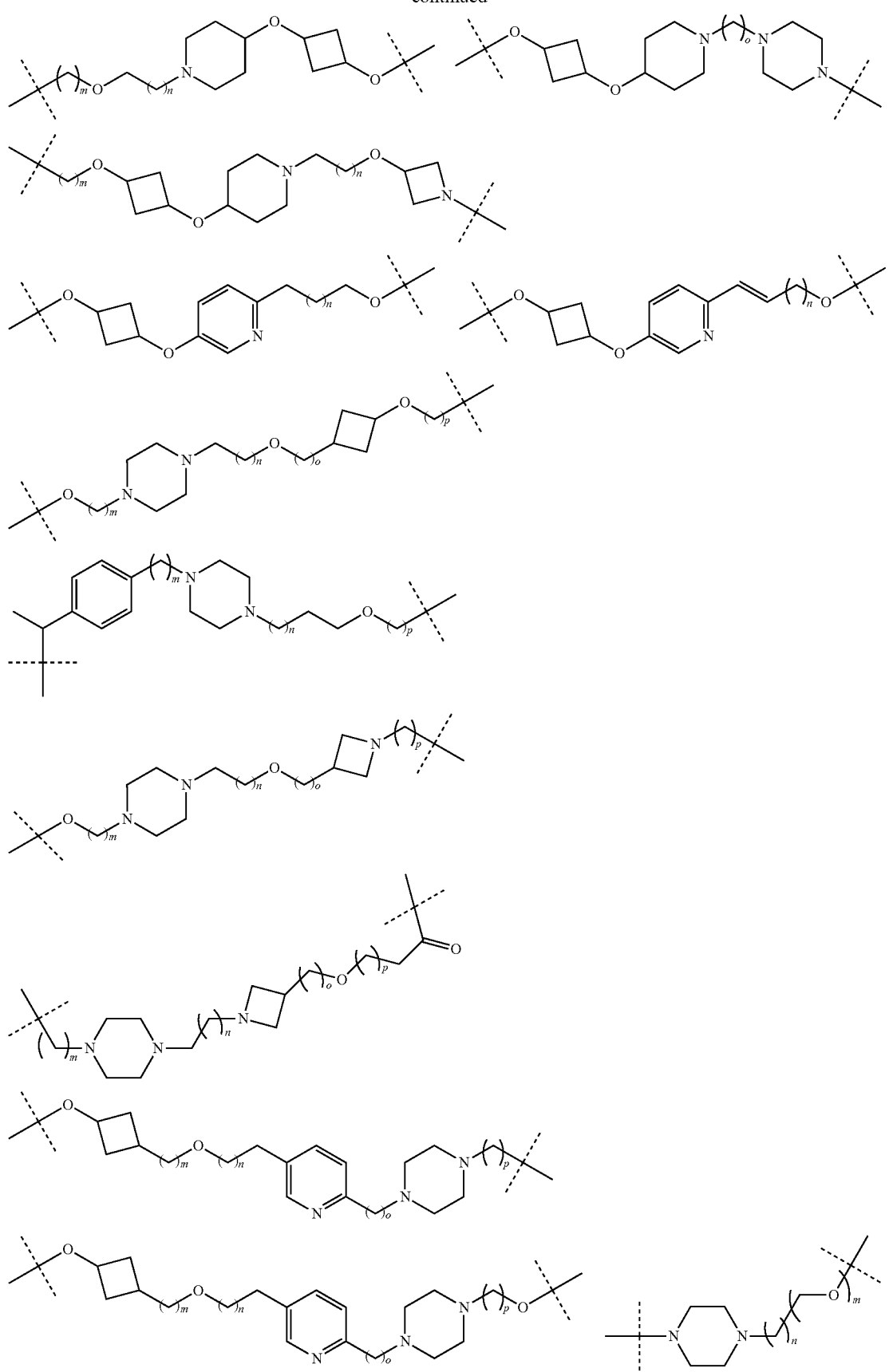

-continued
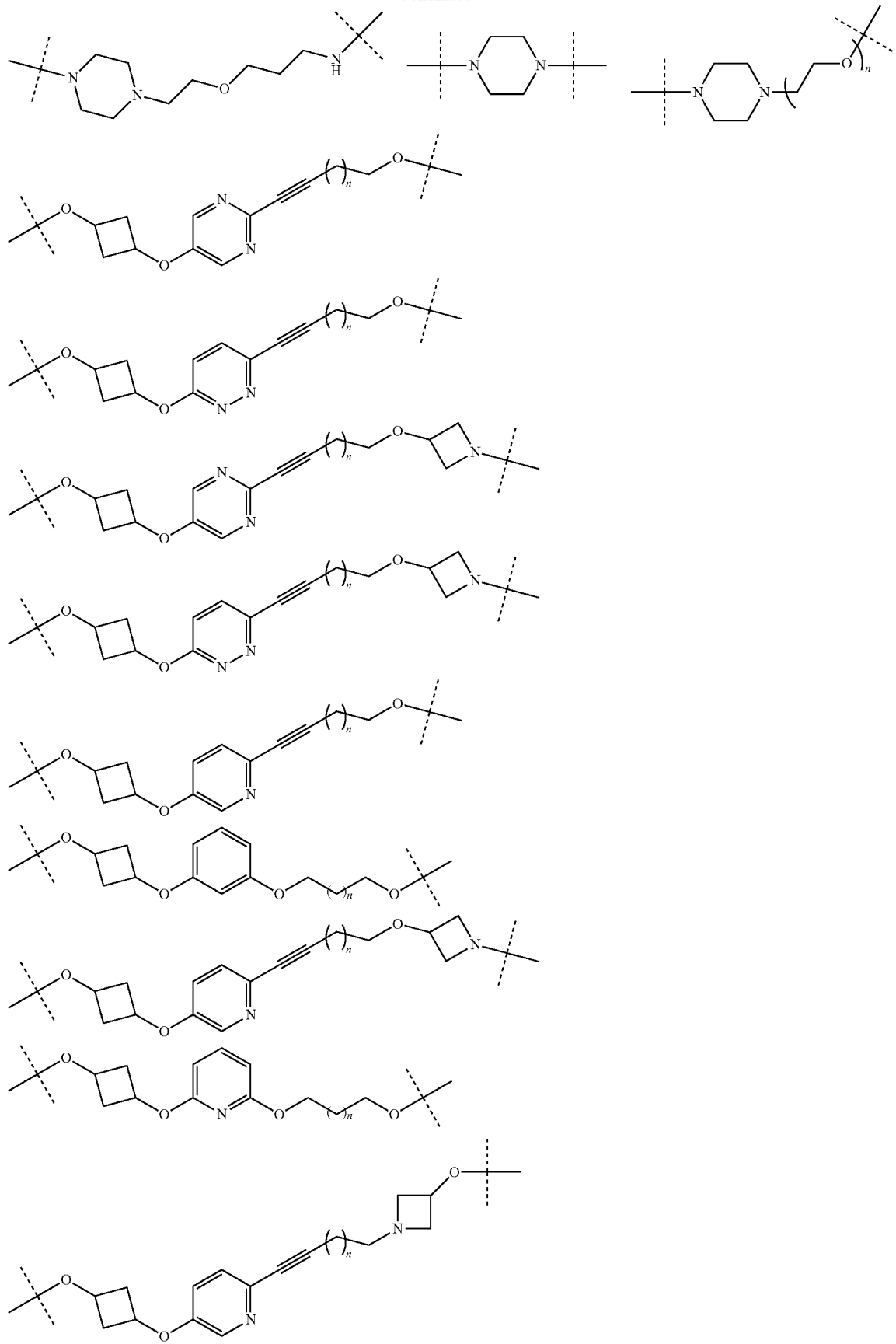

-continued
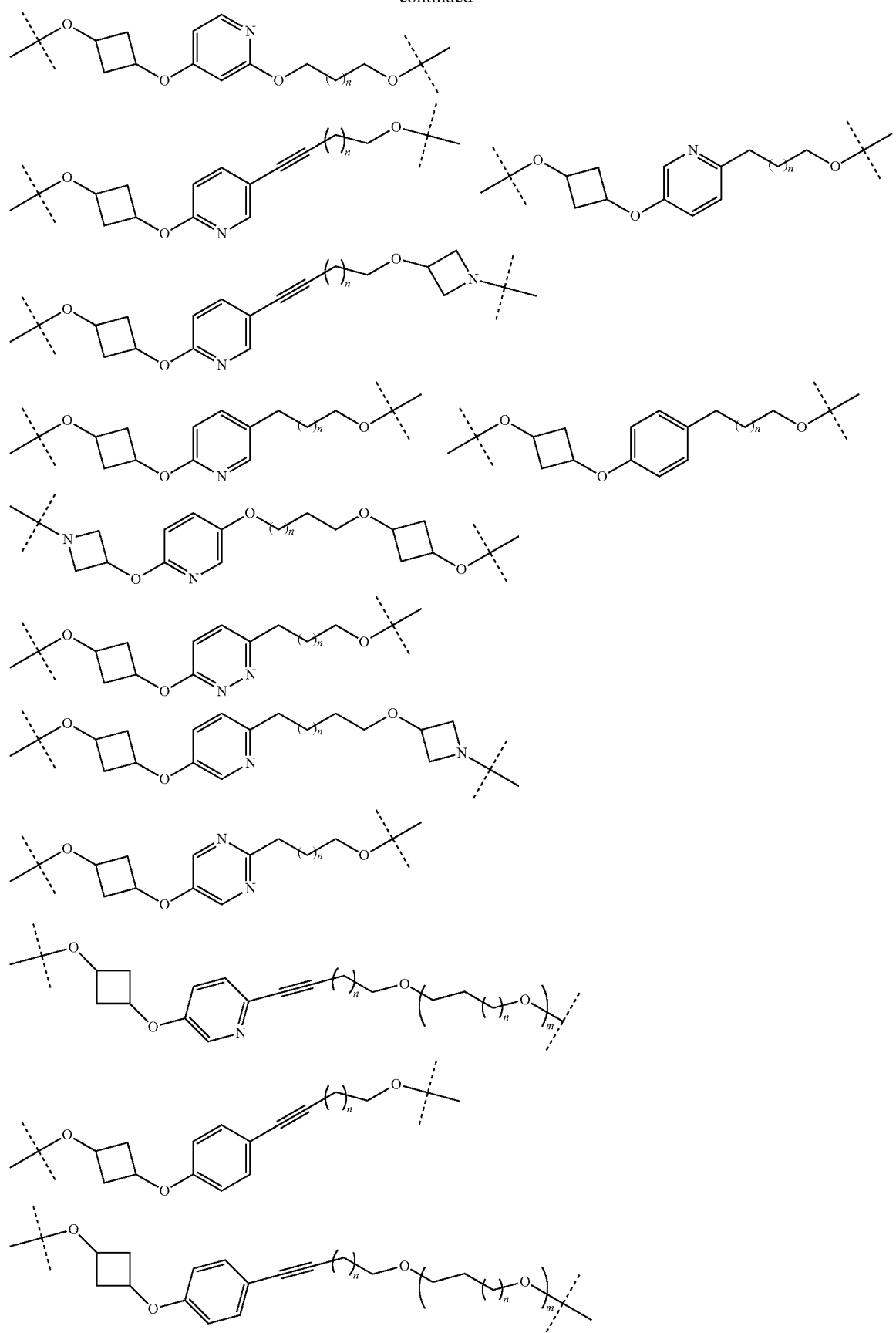

-continued
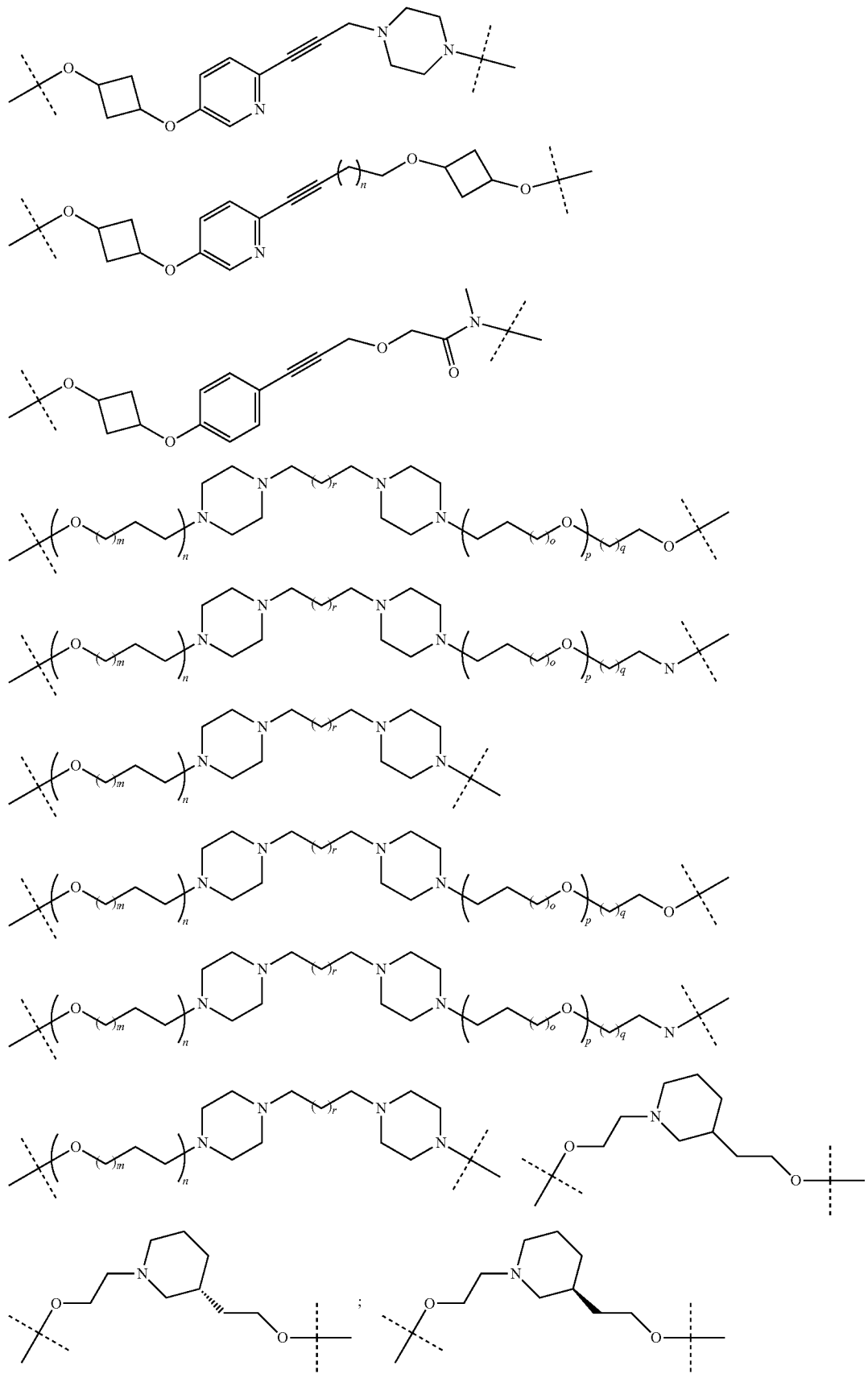

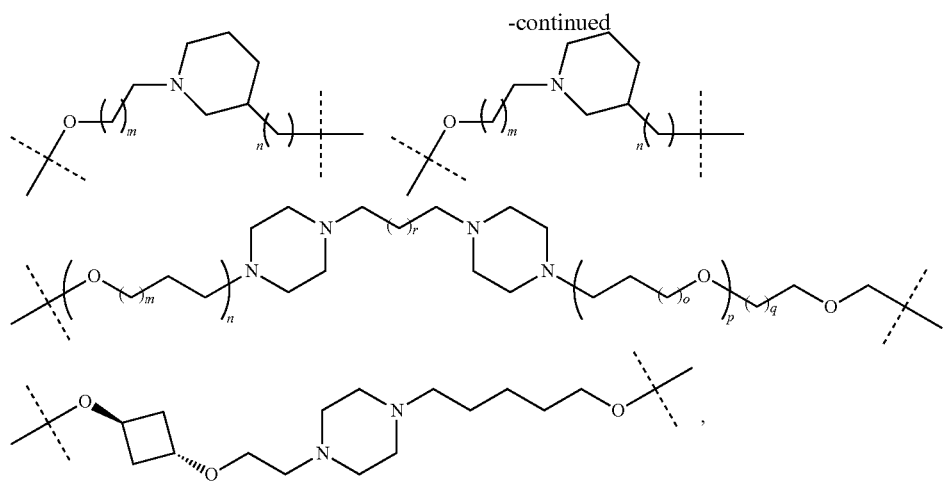
wherein each m, n, o, p, q, r, and s is independently 0, 1, 2, 3, 4, 5, 6, 7, 8, 9, 10, 11, 12, 13, 14, 15, 16, 17, 18, 19, or 20.
In any aspect or embodiment described herein, the unit $A^L$ of linker (L) is selected from the group consisting of:
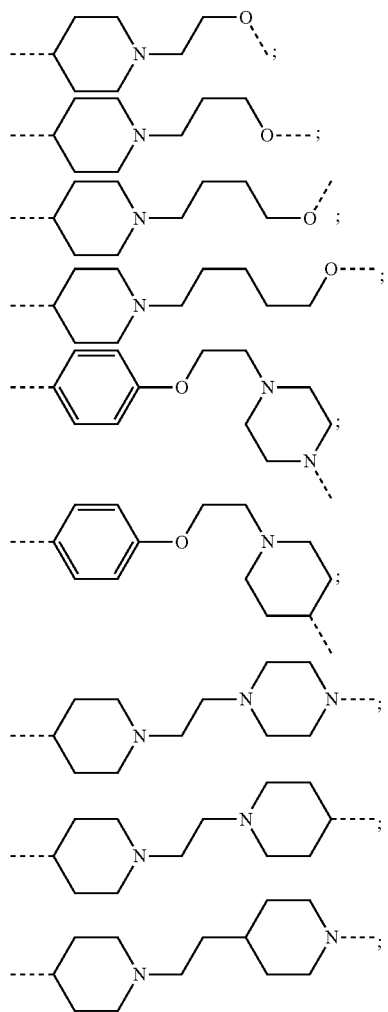
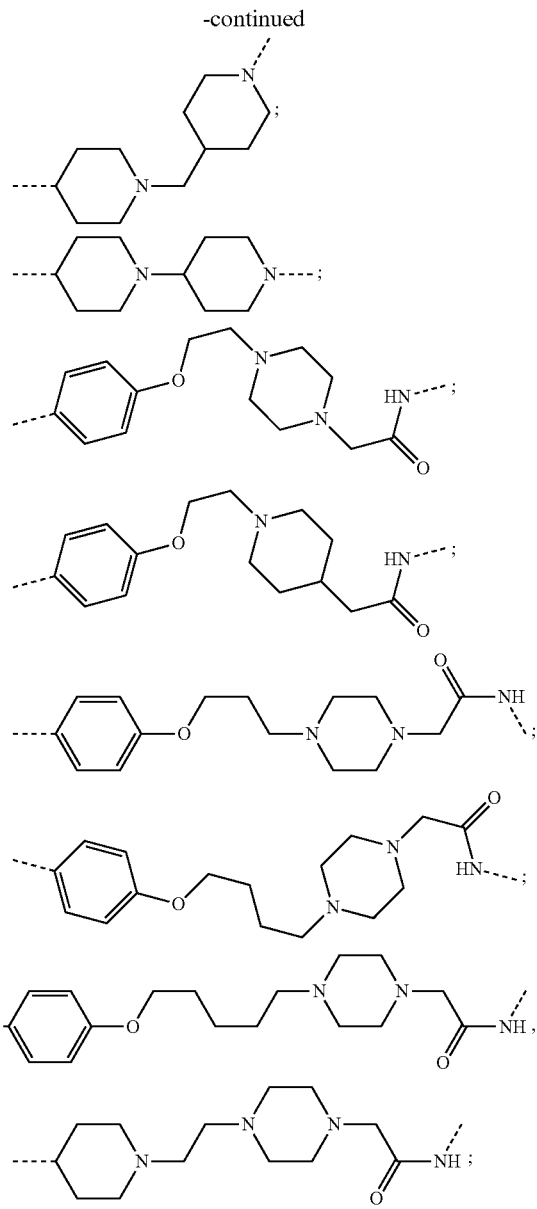

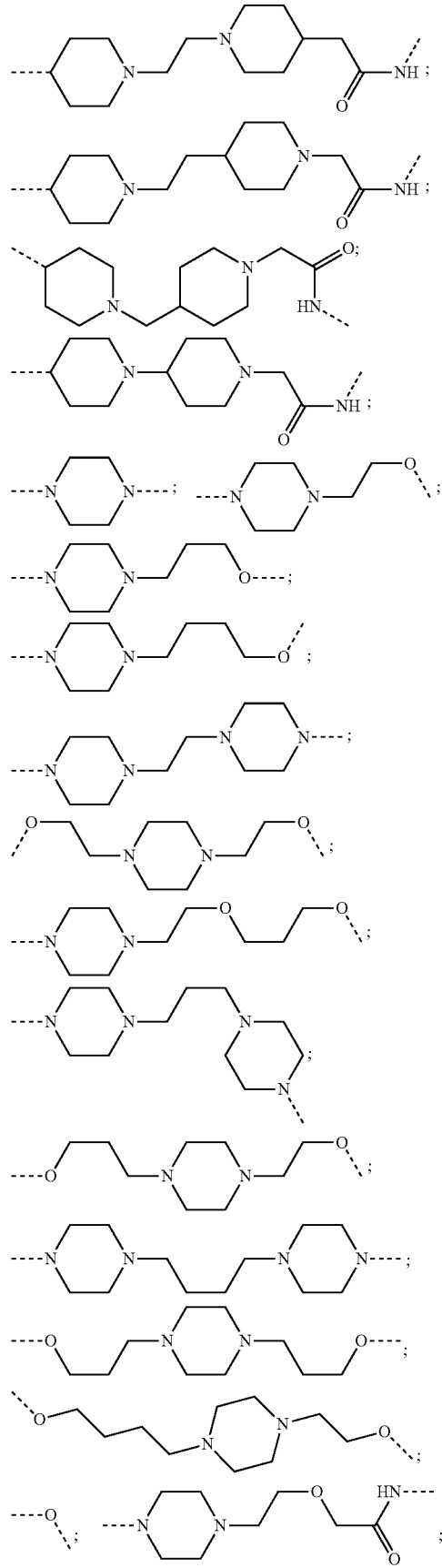
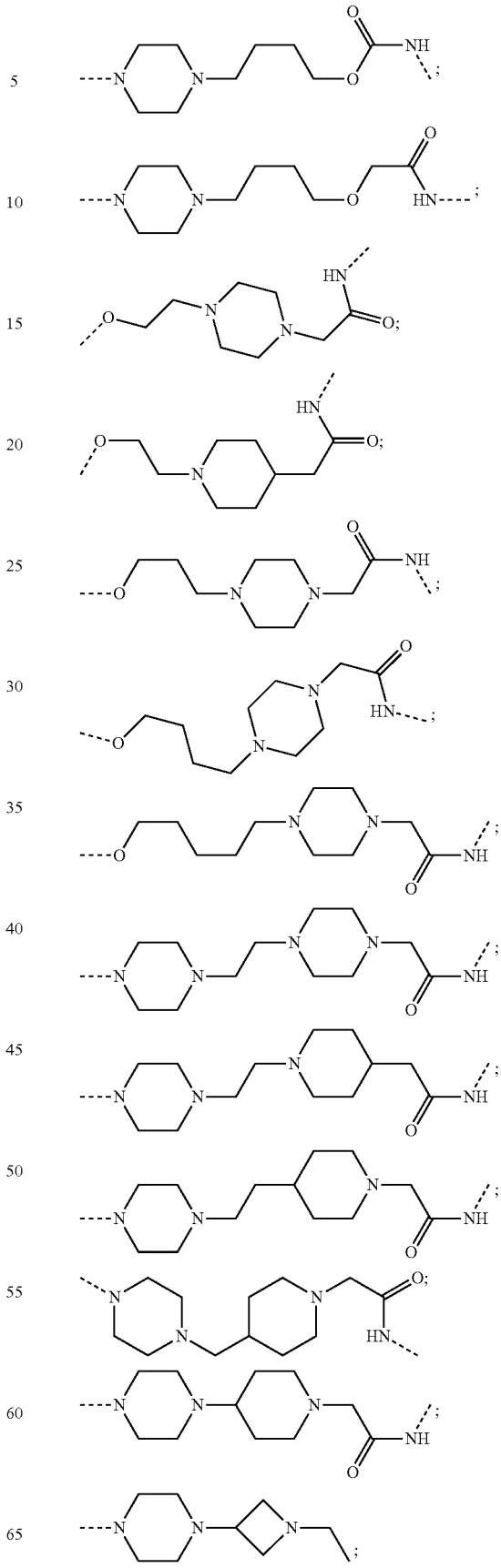

133
-continued
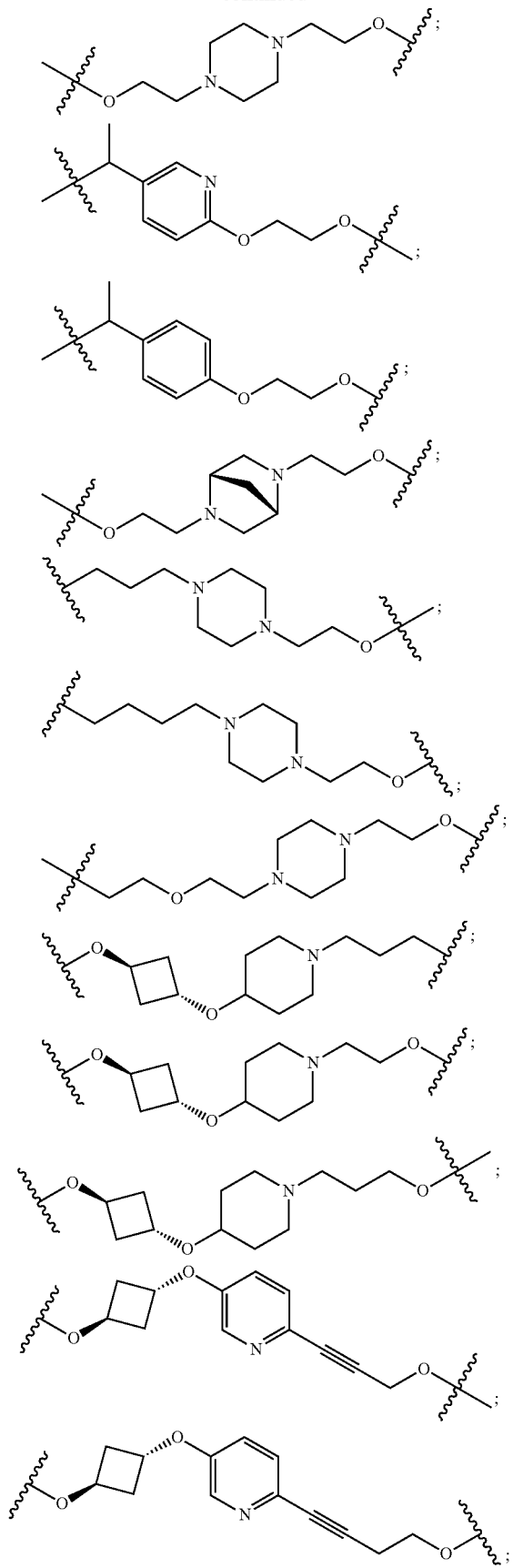
134
-continued
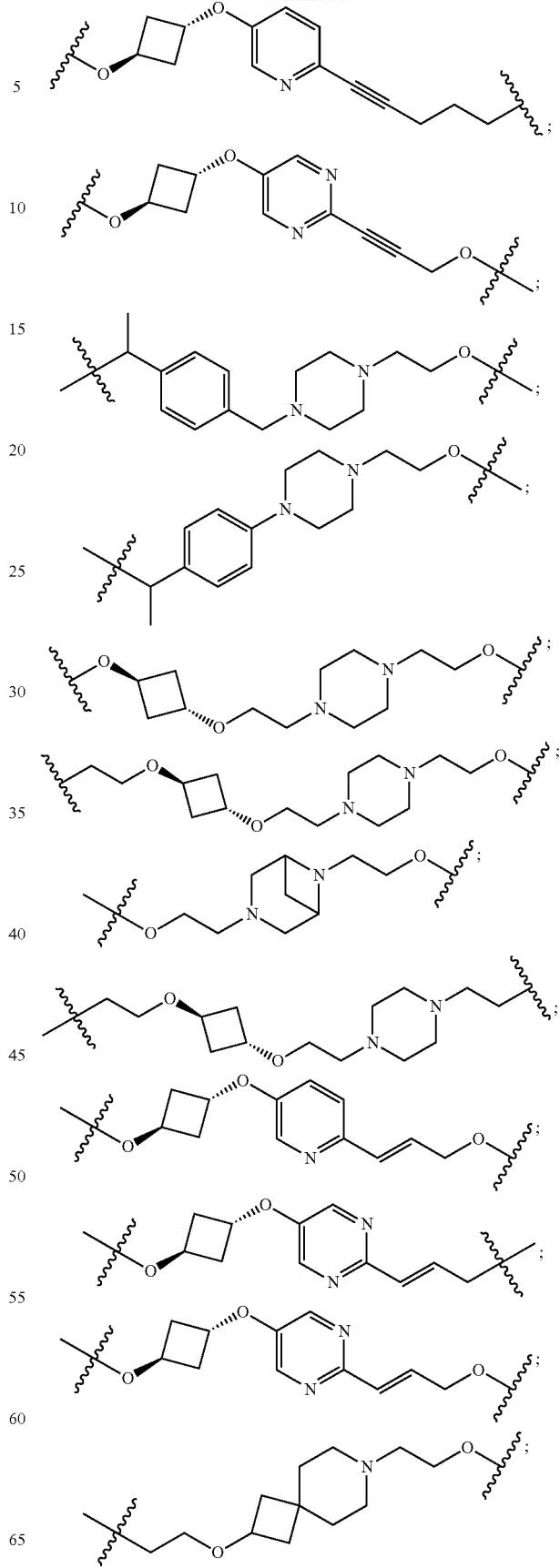

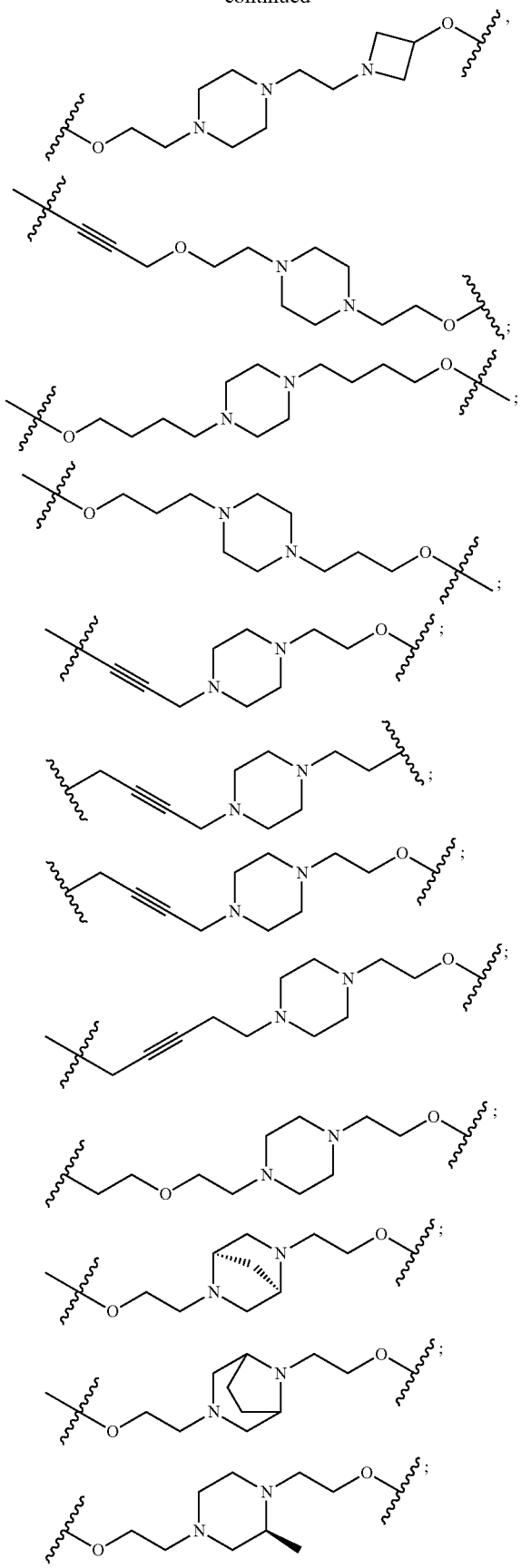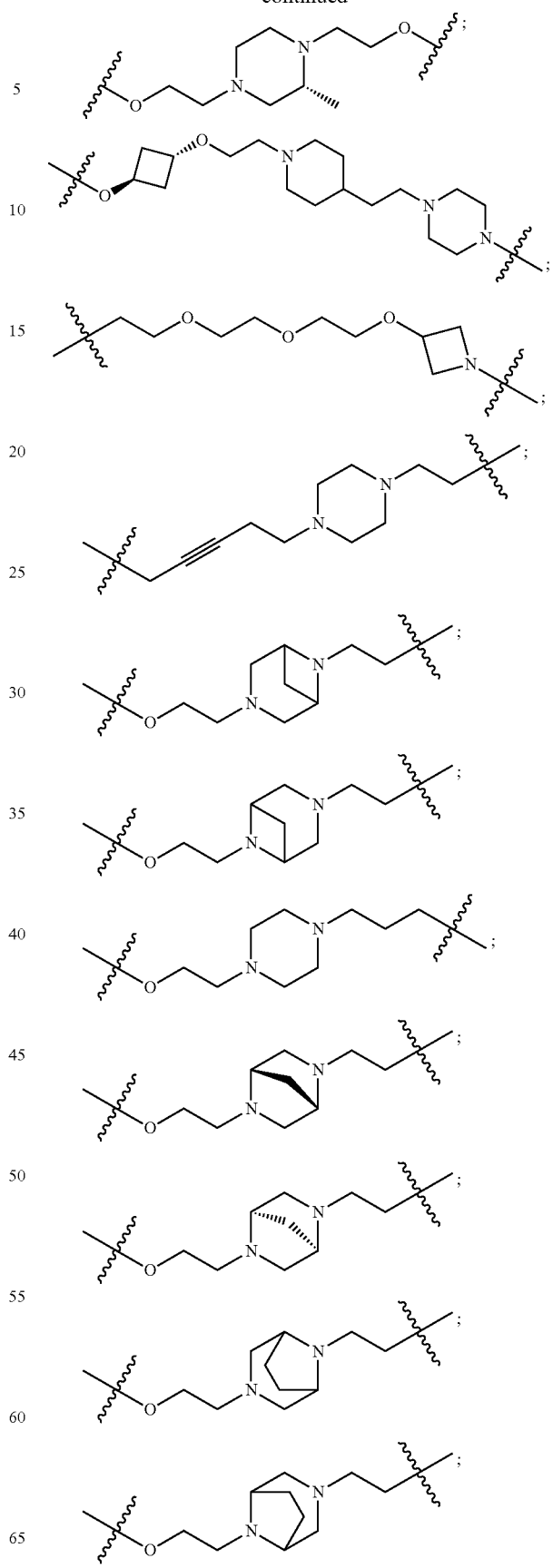

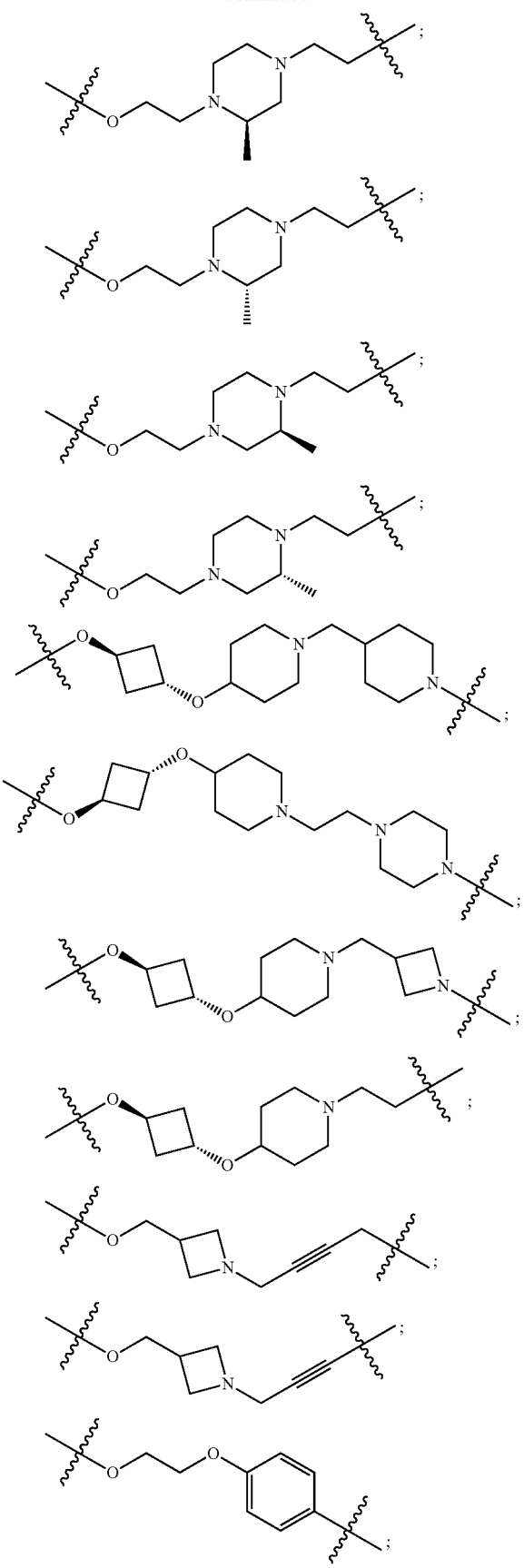
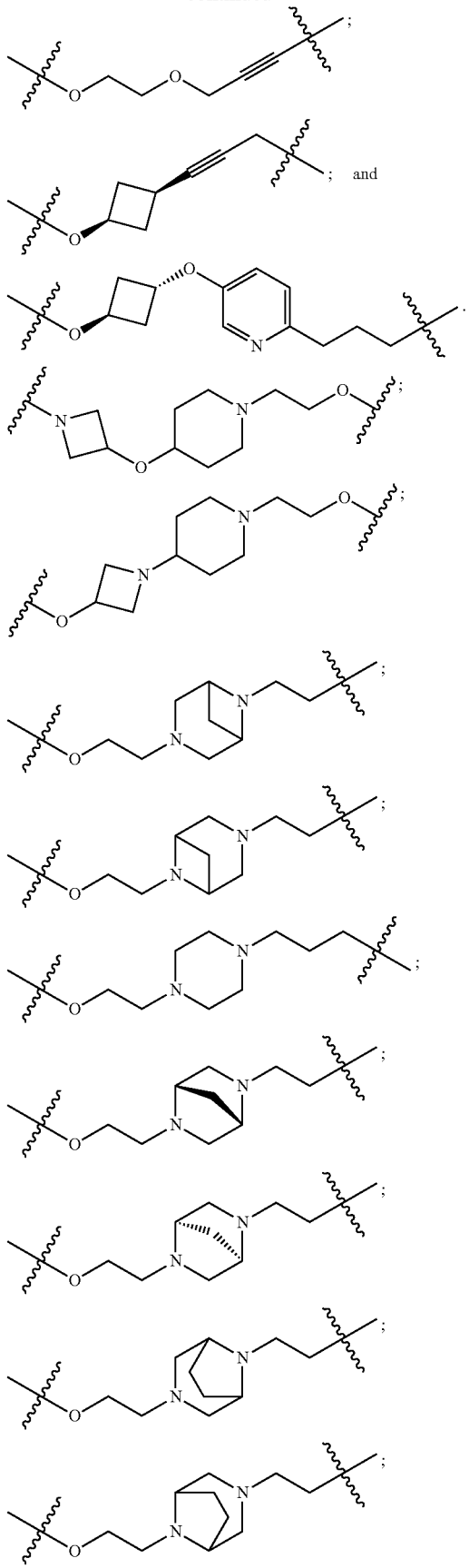

-continued

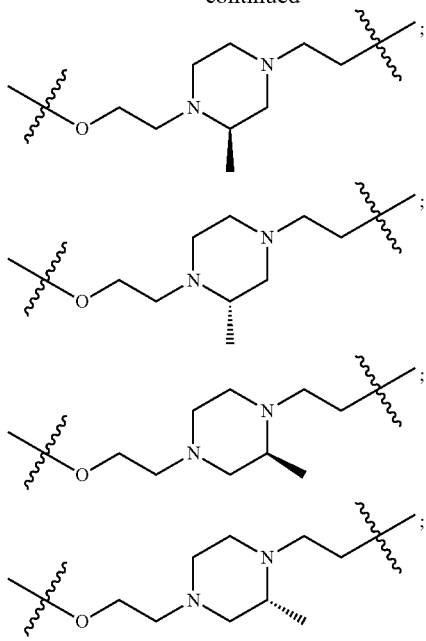

In any aspect or embodiment described herein, the linker (L) comprises a structure selected from the structure shown below:

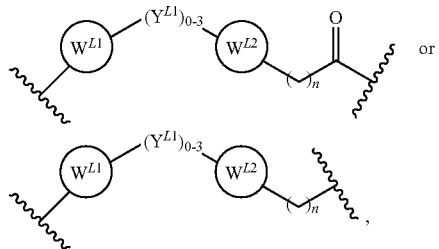

wherein:
W$^{L1}$ and W$^{L2}$ are each independently absent, a 4-8 membered ring with 0-4 heteroatoms, optionally substituted with R$^Q$, each R$^Q$ is independently a H, halo, OH, CN, CF$_3$, optionally substituted linear or branched C$_1$-C$_6$ alkyl, optionally substituted linear or branched C$_1$-C$_6$ alkoxy, or 2 R$^Q$ groups taken together with the atom they are attached to, form a 4-8 membered ring system containing 0-4 heteroatoms;
Y$^{L1}$ is each independently a bond, optionally substituted linear or branched C$_1$-C$_6$ alkyl and optionally one or more C atoms are replaced with O or NR$^{YL1}$, optionally substituted C$_1$-C$_6$ alkene and optionally one or more C atoms are replaced with O, optionally substituted C$_1$-C$_6$ alkyne, and optionally one or more C atoms are replaced with O, or optionally substituted linear or branched C$_1$-C$_6$ alkoxy;
R$^{YL1}$ is H, or optionally substituted linear or branched C$_{1-6}$ alkyl;
n is 0-10; and and indicates the attachment point to the PTM or ULM moieties.

In any aspect or embodiment described herein, the linker (L) comprises a structure selected from the structure shown below:

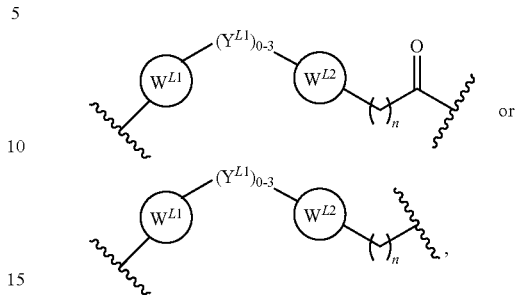

wherein:
W$^{L1}$ and W$^{L2}$ are each independently absent, piperazine, piperidine, morpholine, optionally substituted with R$^Q$, each R$^Q$ is independently a H, —Cl—, —F—, OH, CN, CF$_3$, optionally substituted linear or branched C$_1$-C$_6$ alkyl (e.g. methyl, ethyl), optionally substituted linear or branched C$_1$-C$_6$ alkoxy (e.g. methoxy, ethoxy);
Y$^{L1}$ is each independently a bond, optionally substituted linear or branched C$_1$-C$_6$ alkyl and optionally one or more C atoms are replaced with O or NR$^{YL1}$; optionally substituted C$_1$-C$_6$ alkene and optionally one or more C atoms are replaced with O, optionally substituted C$_1$-C$_6$ alkyne and optionally one or more C atoms are replaced with O, or optionally substituted linear or branched C$_1$-C$_6$ alkoxy;
R$^{YL1}$ is H, or optionally substituted linear or branched C$_{1-6}$ alkyl (e.g. methyl, ethyl);
n is 0-10; and and indicates the attachment point to the PTM or ULM moieties.

In any aspect or embodiment described herein, the linker (L) comprises a structure selected from the structure shown below:

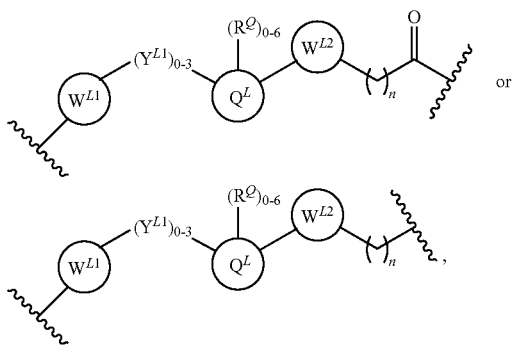

wherein:
W$^{L1}$ and W$^{L2}$ are each independently absent, aryl, heteroaryl, cyclic, heterocyclic, C$_{1-6}$ alkyl and optionally one or more C atoms are replaced with O or NR$^{YL1}$, C$_{1-6}$ alkene and optionally one or more C atoms are replaced with O, C$_{1-6}$ alkyne and optionally one or more C atoms are replaced with O, bicyclic, biaryl, biheteroaryl, or biheterocyclic, each optionally substituted with R$^Q$, each R$^Q$ is independently a H, halo, OH, CN, CF$_3$, hydroxyl, nitro, C≡CH, C$_{2-6}$ alkenyl, C$_{2-6}$ alkynyl, optionally substituted linear or branched $C_1$-$C_6$ alkyl, optionally substituted linear or branched $C_1$-$C_6$ alkoxy, optionally substituted $OC_{1-3}$alkyl (e.g., optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}R^{YL2}$, C=O, C=S, SO, $SO_2$, optionally substituted linear or branched $C_1$-$C_6$ alkyl and optionally one or more C atoms are replaced with O; optionally substituted linear or branched $C_1$-$C_6$ alkoxy;

$Q^L$ is a 3-6 membered alicyclic, bicyclic, or aromatic ring with 0-4 heteroatoms, optionally bridged, optionally substituted with 0-6 $R^Q$, each $R^Q$ is independently H, optionally substitute linear or branched $C_{1-6}$ alkyl (e.g., optionally substituted by 1 or more halo, $C_{1-6}$ alkoxyl), or 2 $R^Q$ groups taken together with the atom they are attached to, form a 3-8 membered ring system containing 0-2 heteroatoms;

$R^{YL1}$, $R^{YL2}$ are each independently H, OH, optionally substituted linear or branched $C_{1-6}$ alkyl (e.g., optionally substituted by 1 or more halo, $C_{1-6}$ alkoxyl), or $R^1$, $R^2$ together with the atom they are attached to, form a 3-8 membered ring system containing 0-2 heteroatoms;

n is 0-10; and

\ and ⌇ indicates the attachment point to the PTM or ULM moieties.

In any aspect or embodiment described herein, the linker (L) comprises a structure selected from the structure shown below:

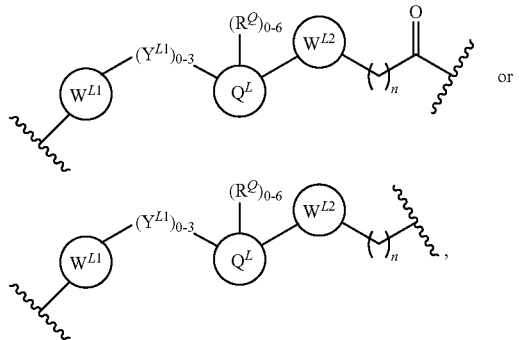

wherein:

$W^{L1}$ and $W^{L2}$ are each independently absent, cyclohexane, cyclopentane, piperazine, piperidine, morpholine, $C_{1-6}$ alkyl and optionally one or more C atoms are replaced with O or $NR^{YL1}$, $C_{1-6}$ alkene and optionally one or more C atoms are replaced with O, or $C_{1-6}$ alkyne and optionally one or more C atoms are replaced with O, each optionally substituted with $R^q$, each $R^Q$ is independently a H, Cl—, —F—, OH, CN, $CF_3$, hydroxyl, optionally substituted linear or branched $C_1$-$C_6$ alkyl (e.g. methyl, ethyl), optionally substituted linear or branched $C_1$-$C_6$ alkoxy;

$Y^{L1}$ is each independently a bond, $NR^{YL1}$, O, $CR^{YL1}R^{YL2}$, C=O, optionally substituted linear or branched $C_1$-$C_6$ alkyl and optionally one or more C atoms are replaced with O or $NR^{YL1}$, $C_{1-6}$ alkene and optionally one or more C atoms are replaced with O, $C_{1-6}$ alkyne and optionally one or more C atoms are replaced with O, or optionally substituted linear or branched $C_1$-$C_6$ alkoxy;

$Q^L$ is a 3-6 membered heterocyclic, heterobicyclic, or heteroaryl ring, optionally substituted with 0-6 $R^q$, each $R^Q$ is independently H, or optionally substituted linear or branched $C_{1-6}$ alkyl (e.g., methyl or ethyl, optionally substituted by 1 or more halo, $C_{1-6}$ alkoxyl);

$R^{YL1}$, $R^{YL2}$ are each independently H, optionally substituted linear or branched $C_{1-6}$ alkyl (e.g., optionally substituted by 1 or more halo, $C_{1-6}$ alkoxyl);

n is 0-10; and

\ and ⌇ indicates the attachment point to the PTM or ULM moieties.

Exemplary PTMs

The term "protein target moiety" or PTM is used to describe a small molecule which binds to LRRK2, and can be used to target the PTM for ubiquitination and degradation. The compositions described below exemplify members of LRRK2 binding moieties that can be used according to the present invention. These binding moieties are linked to the ubiquitin ligase binding moiety preferably through a chemical linking group in order to present the LRRK2 protein in proximity to the ubiquitin ligase for ubiquitination and subsequent degradation.

In certain contexts, the term "target protein" is used to refer to the LRRK2 protein, a member of the ROCO protein family, that serves as an upstream central integrator of multiple signaling pathways that are crucial for proper neuronal functioning, which is a target protein to be ubiquitinated and degraded.

The compositions described herein exemplify the use of some of the members of these types of small molecule target protein binding moieties.

In any aspect or embodiment described herein, the PTM is a small molecule that binds LRRK2. For example, in any aspect or embodiment described herein, the PTM is represented by the chemical structure PTM-I:

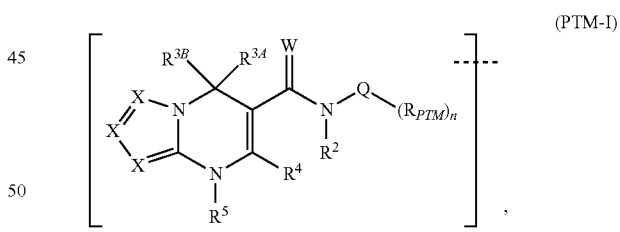

(PTM-I)

wherein:

X is CH or N;

W is O or S;

Q is selected from the group:

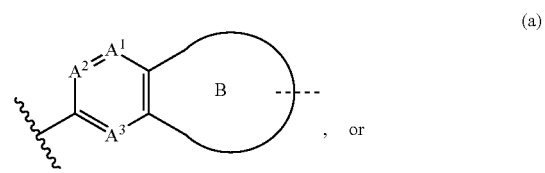

(a)

, or

143

-continued (b)

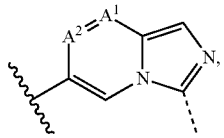

wherein:
- $A^1$, $A^2$, and $A^3$ are each independently selected from N and $CR^6$, wherein for (a) no more than two of $A^1$, $A^2$, and $A^3$ are simultaneously N, ring B is an optionally substituted C3-C8 aryl, optionally substituted C3-C8 heteroaryl, optionally substituted C3-C8 cycloalkyl, optionally substituted C3-C8 heterocycloalkyl, optionally substituted C3-C8 aryl, optionally substituted C3-C8 aryl, the  of Q indicates the point of attachment with the nitrogen, and the ⋰ of Q indicates an optional covalent attachment to $R_{PTM}$;
- $R^2$ is H or $C_{1-4}$ alkyl;
- $R^{3A}$ and $R^{3B}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^1$ are each optionally substituted with 1, 2, 3, 4, or 5 substituents independently selected from $Cy^2$, $Cy^2$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;
- or $R^{3A}$ and $R^{3B}$ together form a $C_{3-7}$ cycloalkyl or 4-10 membered heterocycloalkyl ring, each optionally substituted with 1, 2, 3, 4, or 5 substituents independently selected from $Cy^2$, $Cy^2$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;
- $R^4$ is H, $C_{1-4}$ alkyl, halo, $C_{1-4}$ haloalkyl, or CN;
- $R^5$ is H, $C_{1-6}$ alkyl, $C_{2-6}$ alkenyl, $C_{2-6}$ alkynyl, $C_{6-10}$ aryl, $C_{3-10}$ cycloalkyl, 5-14 membered heterocycloalkyl, $C_{6-10}$ aryl —$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^1$ are each optionally substituted with 1, 2, 3, 4, or 5 substituents independently selected from $Cy^3$, $Cy^3$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, or $S(O)_2NR^{c2}R^{d2}$;
- each $R^6$ is independently selected from H, halo, $C_{1-6}$ alkyl, $C_{1-6}$ haloalkyl, $C_{6-10}$ aryl, $C_{3-7}$ cycloalkyl, 5-6 membered heteroaryl, 4-7 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl, $C_{1-6}$ haloalkyl, $C_{6-10}$ aryl, $C_{3-7}$ cycloalkyl, 5-6 membered heteroaryl, 4-7 membered heterocycloalkyl of $R^6$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;
- each $Cy^1$ is independently selected from $C_{6-10}$ aryl, $C_{3-10}$ cycloalkyl, 5-14 membered heteroaryl, and 4-14 membered heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
- each $Cy^2$ is independently selected from $C_{6-10}$ aryl, $C_{3-10}$ cycloalkyl, 5-14 membered heteroaryl, and 4-14 membered heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, OC(O)R$^{b1}$, OC(O)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, C(=NR$^{e1}$)R$^{b1}$, C(=NR$^{e1}$)NR$^{c1}$R$^{d1}$, NR$^{c1}$C(=NR$^{e1}$)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$;

each Cy$^3$ is independently selected from C$_{6-10}$ aryl, C$_{3-10}$ cycloalkyl, 5-14 membered heteroaryl, and 4-14 membered heterocycloalkyl, each optionally substituted by 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-14 membered heteroaryl, 4-14 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, 4-10 membered heterocycloalkyl-C$_{1-4}$ alkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

each R$^a$, R$^b$, R$^c$, R$^d$, R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, and R$^{d3}$ is independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl, wherein said C$_{1-6}$ alkyl, C$_{2-6}$ alkenyl, C$_{2-6}$ alkynyl, C$_{6-10}$ aryl, C$_{3-7}$ cycloalkyl, 5-10 membered heteroaryl, 4-10 membered heterocycloalkyl, C$_{6-10}$ aryl-C$_{1-4}$ alkyl, C$_{3-7}$ cycloalkyl-C$_{1-4}$ alkyl, 5-10 membered heteroaryl-C$_{1-4}$ alkyl, and 4-10 membered heterocycloalkyl-C$_{1-4}$ alkyl of R$^a$, R$^b$, R$^c$, R$^d$, R$^{a1}$, R$^{b1}$, R$^{c1}$, R$^{d1}$, R$^{a2}$, R$^{b2}$, R$^{c2}$, R$^{d2}$, R$^a$R$^{b3}$, R$^{c3}$, or R$^{d3}$ is optionally substituted with 1, 2, 3, 4, or 5 substituents independently selected from halo, C1-4 alkyl, C1-4 haloalkyl, Ci-$_6$ haloalkyl, C2-6 alkenyl, C2-6 alkynyl, CN, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)NR$^{c4}$R$^{d4}$, NR$^{c4}$C(O)OR$^{a4}$, C(=NR$^{e4}$)NR$^{c4}$R$^{d4}$, NR$^{c4}$C(=NR$^{e4}$)NR$^{c4}$R$^{d4}$, S(O)R$^{b4}$, S(O)NR$^{c4}$R$^{d4}$, S(O)$_2$R$^{b4}$, NR$^{c4}$ S(O)$_2$R$^m$, NR$^{c4}$S(O)$_2$NR$^{c4}$R$^{d4}$, and S(O)$_2$NR$^{c4}$R$^{d4}$;

each R$^{a4}$, R$^{b4}$, R$^{c4}$, and R$^{d4}$ are independently selected from H, C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-6 membered heteroaryl, 4-7 membered heterocycloalkyl, wherein said C$_{1-6}$ alkyl, C$_{1-6}$ haloalkyl, C$_{2-6}$ alkenyl, C$_{2-6}$ alkynyl, C$_{6-10}$ aryl, C$_{3-7}$ cycloalkyl, 5-6 membered heteroaryl, and 4-7 membered heterocycloalkyl are each optionally substituted with 1, 2, or 3 substituents independently selected from OH, CN, amino, halo, C$_{1-6}$ alkyl, C$_{1-6}$ alkoxy, C$_{1-6}$ haloalkyl, and C$_{1-6}$ haloalkoxy;

each R$^e$, R$^{e1}$, R$^{e2}$, R$^{e3}$, and R$^{e4}$ is independently selected from H, C$_{1-4}$ alkyl, and CN;

R$_{PTM}$ is H; halogen (e.g., Cl or F); —CN; —OH; —NO$_2$; —NH$_2$; optionally substituted linear or branched alkyl (e.g., optionally substituted linear or branched C1-C6 alkyl or optionally substituted linear or branched C1-C4 alkyl or C1-C8 alkyl optionally substituted with OH); optionally substituted cycloalkyl (e.g., cyclopropyl, cyclobutyl, cyclopentyl, cyclohexyl); O-optionally substituted linear or branched C1-C4 alkyl; an optionally substituted C1-C4 alkynyl; an optionally substituted C1-C4 alkyne; optionally substituted linear or branched hydroxyalkyl (e.g., optionally substituted linear or branched C1-C7 hydroxy alkyl); optionally substituted alkylcycloalkyl (e.g., includes optionally substituted C1-C6 alkyl, optionally substituted C3-C10 cycloalkyl; or both); optionally substituted alkyl-aryl (e.g., includes an optionally substituted linear or branched C1-C6 alkyl, an optionally substituted 5-10 member heteroaryl, or both); optionally substituted alkyl-heteroaryl (e.g., includes an optionally substituted linear or branched C1-C6 alkyl, an optionally substituted 5-10 member heteroaryl, or both); optionally substituted alkyl-heteroaryl (e.g., includes a C1-C6 alkyl, an optionally substituted 5 or 6 member heteroaryl, optionally substituted with a C1-C4 alkyl; the heteroaryl is selected from oxazol-4-yl, 1,3,4-triazol-2-yl, and imidazole-1-yl; or combination thereof); optionally substituted —NH-alkyl-heteroaryl (e.g., an optionally substituted linear or branched C1-C5 alkyl, an optionally substituted 5-8 member heteroaryl, optionally substituted with a C1-C4 alkyl, N—CH$_2$-pyrazol-4-yl, or a combination thereof); optionally substituted alkoxy (e.g., an optionally substituted linear or branched C1-C6 alkyl or —OCH$_3$); optionally substituted O-heterocyclyl (e.g., includes an optionally substituted 3-12 or 4-7 member heterocyclyl; an optionally substituted heterocycloalkyl; an optionally substituted C$_{3-12}$ monocyclic or bicyclic heterocycloalkyl; optionally substituted with at least one OH, C1-C5 alkyl (such as a methyl), =O, NH$_2$, or a combination thereof; or a combination thereof); optionally substituted S-heterocyclyl (e.g., includes an optionally substituted 4-7 member heterocyclyl; an optionally substituted heterocycloalkyl; optionally substituted with at least one C1-C4 alkyl (such as a methyl), =O, or a combination thereof; or a combination thereof); optionally substituted

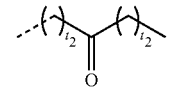

(e.g., optionally substituted with a linear or branched C1-C4 alkyl; —(CH$_2$)$_u$CO(CH$_2$)$_v$CH$_3$, —COCH$_3$, or —CH$_2$CH$_2$COCH$_3$, wherein each u and v is independently selected from 1, 2, 3, 4 or 5);

optionally substituted

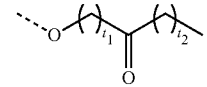

(e.g., optionally substituted with a linear or branched C1-C4 alkyl; —O(CH$_2$)$_u$CO(CH$_2$)$_v$CH$_3$, —O(CH$_2$)$_u$CH((CH$_2$)$_x$CH$_3$)(CH$_2$)$_w$CO(CH$_2$)$_v$CH$_3$, —O—CH$_2$COCH$_3$, —O—CH$_2$COCH$_2$CH$_3$, —O—CH(CH$_3$)COCH$_3$, —OCH$_2$COCH$_3$, or —OCH$_2$(CH$_3$)COCH$_3$, wherein each u, v, w, and * is independently selected from 1, 2, 3, 4 or 5); optionally substituted

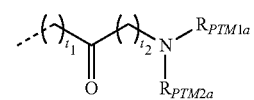

(e.g., optionally substituted with a linear or branched C1-C4 alkyl; —(CH$_2$)$_u$CO(CH$_2$)$_v$NR$_{PTM1a}$R$_{PTM2a}$, —CONR$_{PTM1a}$R$_{PTM2a}$, —CH$_2$CONR$_{PTM1a}$R$_{PTM2a}$, —CH$_2$CH$_2$CONR$_{PTM1a}$R$_{PTM2a}$, —CONHCH$_3$, or —CH$_2$CONHCH$_3$, wherein each u and v is independently selected from 1, 2, 3, 4 or 5); optionally substituted

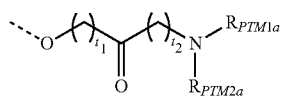

(e.g., optionally substituted with a linear or branched C1-C4 alkyl; —O(CH$_2$)$_u$CO(CH$_2$)$_v$NR$_{PTM1a}$R$_{PTM2a}$, —O(CH$_2$)$_u$CH((CH$_2$)$_x$CH$_3$)(CH$_2$)$_w$CO(CH$_2$)$_v$ NR$_{PTM1a}$R$_{PTM2a}$, —O—CH(CH$_3$)CONR$_{PTM1a}$R$_{PTM2a}$, —O—CH$_2$CONR$_{PTM1a}$R$_{PTM2a}$, or —OCH$_2$C(O)NHOCH$_3$, wherein each u, v, w, and x is independently selected from 1, 2, 3, 4 or 5); optionally substituted

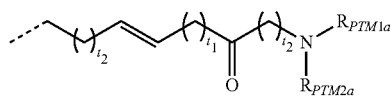

(e.g., optionally substituted with a linear or branched C1-C4 alkyl; —(CH$_2$)$_u$CHCH(CH$_2$)$_w$CO(CH$_2$)$_v$ NR$_{PTM1a}$R$_{PTM2a}$ or —CHCHCONR$_{PTM1a}$R$_{PTM2a}$, wherein each u, v, and w is independently selected from 1, 2, 3, 4 or 5); optionally substituted

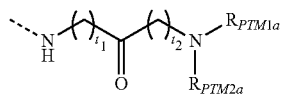

(e.g., optionally substituted with a linear or branched C1-C4 alkyl; —NH—(CH$_2$)$_u$CO(CH$_2$)$_v$ NR$_{PTM1a}$R$_{PTM2a}$ or —NH—CH$_2$CONR$_{PTM1a}$R$_{PTM2a}$, wherein each u and v is independently selected from 1, 2, 3, 4 or 5); fluoroalkoxy (e.g., a mono-, bi- and/or tri-fluoroalkoxy); optionally substituted monocyclic or bicyclic cycloalkyl (e.g., an optionally substituted 3-12 member cycloalkyl; optionally substituted with at least one of OH, =O, linear or branched C1-C6 alkyl (such as a methyl, ethyl, or butyl), or NH$_2$; or a combination thereof); optionally substituted hydroxycycloalkyl; optionally substituted aryl (e.g., an optionally substitute C5-C10 aryl, an optionally substituted 5-7 member aryl; optionally substituted with at least one halogen or C1-C3 alkyl (e.g., methyl or ethyl); or a combination thereof), optionally substituted heteroaryl (e.g., an optionally substituted 5-10 or member heteroaryl, an optionally substituted 5-7 member heteroaryl; an optionally substituted 5-member heteroaryl; optionally substituted with at least one halogen or C1-C3 alkyl (e.g., methyl or ethyl); or a combination thereof) optionally linked to Q via a C or N-atom of the heteroaryl (e.g., at least one of optionally linked to Q, optionally linked via an optionally substituted —(CH$_2$)$_u$O(CH$_2$)$_v$O(CH$_2$)$_x$—, or a combination thereof); optionally substituted monocyclic or bicyclic heterocyclyl (e.g., an optionally substituted 3-12 member heterocyclyl; an C3-C12 monocyclic or bicyclic heterocycloalkyl, azetidine1-yl, pyrrolidin-1-yl, piperidin-1yl, piperazin-1-yl, or morpholin-4-yl, or homopiperazin-1-yl, each optionally substituted with OH, a linear or branched C1-C5 alkyl (a methyl, ethyl, or butyl group) or NH$_2$) optionally linked to Q via a C or N atom of the heterocyclyl (e.g., at least one of optionally linked to Q, optionally linked via an optionally substituted —(CH$_2$)$_u$O(CH$_2$)$_v$O(CH$_2$)$_x$—, or both);

$t_1$ is selected from 1, 2, 3, 4, or 5;

each $t_2$ is independently is independently selected from 0, 1, 2, 3, 4, or 5;

R$_{PTM1a}$ and R$_{PTM2a}$ are independently H, optionally substituted C1-C4 alkyl (e.g., a CH$_3$ or CH$_2$CH$_3$), optionally substituted C1-C4 alkoxy (e.g., —OCH$_2$ or —CH$_2$CH$_3$), optionally substituted CH$_2$OCH$_3$ or R$_{PTM1a}$ and R$_{PTM2a}$ are joined together form an optionally substituted 3-10 member ring;

n is an integer from 0 to 10; and

--- of the PTM indicates the point of attachment with a chemical linker group or a ULM.

In any of the aspects or embodiments described herein, R$_{PTM}$ of PTM-I is modified to be covalently linked to a linker group (L) or a ULM (such as CLM). In any aspect or embodiment described herein, R$_{PTM}$ of PTM-I is modified to be covalently linked to a chemical linker group (L) or a ULM.

In any aspect or embodiment described herein, W of PTM-I is O.

In any aspect or embodiment described herein, Q of PTM-I is group (a) and ring B is selected from:

(a)

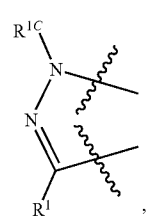

(b)

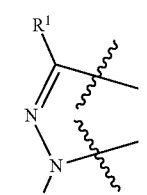

(c)

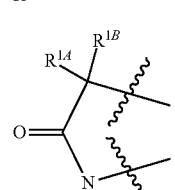

(d)

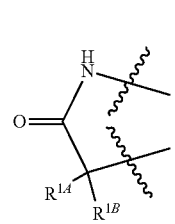

-continued (e) 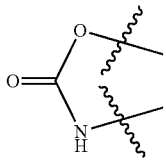

(f) 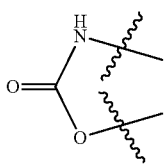

(g) 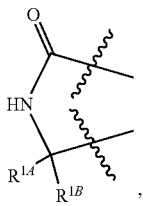

(h) 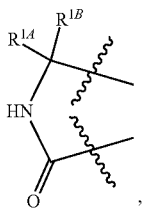

(i) 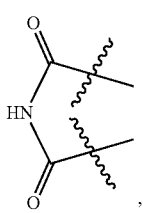

(j) 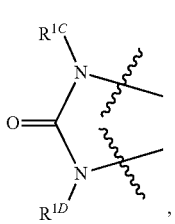

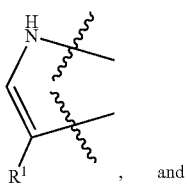, and

-continued (l) 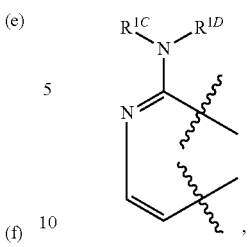

wherein
$R^1$, $R^{1A}$, $R^{1B}$, $R^{1C}$ and $R^{1D}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, and $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$, and $R_{PTM}$, wherein said $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, wherein one of $R^1$, $R^{1A}$, $R^{1B}$, $R^{1C}$, and $R^{1D}$ is optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
or $R^{1A}$ and $R^{1B}$ together form a $C_{3-7}$ cycloalkyl or 4-10 membered heterocycloalkyl ring, each optionally substituted with 1, 2, 3, 4, or 5 substituents independently selected from $Cy^1$, $Cy^1C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, $S(O)_2NR^cR^d$, and $R_{PTM}$, wherein ring B or a substituent of ring B is covalently coupled to at least one of $R_{PTM}$, a linking group (L) or a CLM.

In any aspect or embodiment described herein, Q if PTM-I is group (a) and ring B is selected from:

(k) 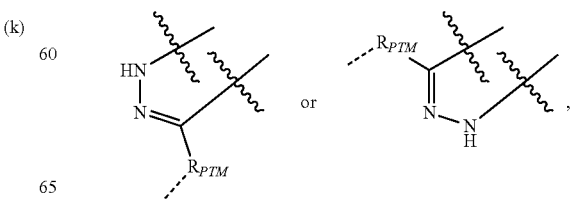

wherein $R_{PTM}$ is as described herein, and the ⸺ indicates a covalent attachment to a linking group (L) or CLM.

In any of the aspects or embodiments, the Q of PTM-I is covalently coupled to the linker (L) or CLM.

In any aspect or embodiment described herein, Q of PTM-I is group (a):

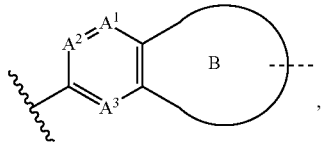

wherein $A^1$, $A^2$, and $A^3$ are $CR^6$; $R^6$ is independently selected from H, halo, $C_{1-6}$ alkyl, $C_{1-6}$ haloalkyl, $C_{6-10}$ aryl, $C_{3-7}$ cycloalkyl, 5-6 membered heteroaryl, 4-7 membered heterocycloalkyl, CN, and $NO_2$; ring B is a group as described herein, the ⸺ of Q indicates the point of attachment with the nitrogen, and the ⸺ of Q indicates the site of attachment to at least one of $R_{PTM}$, a chemical linking group (L) or CLM. In any of the aspects or embodiments, the Q of PTM-I is covalently coupled to a chemical linking group (L) or CLM.

In any aspect or embodiment described herein, Q of PTM-I is:

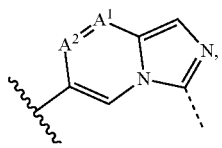

wherein $A^1$, $A^2$ and $A^3$ are defined in any aspect or embodiment described herein, the ⸺ of Q indicates the point of attachment with the nitrogen, and the ⸺ indicates the site of covalent attachment to at least one of $R_{PTM}$, a chemical linking group (L) or CLM. In any of the aspects or embodiments, the Q of PTM-I is covalently coupled to the linker (L) or CLM.

In any aspect or embodiment described herein, Q of PTM-I is:

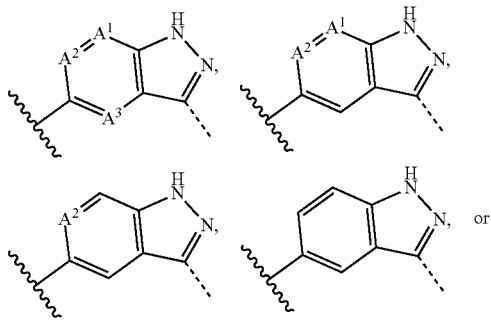

wherein $A^1$, $A^2$, and $A^3$ are defined in any aspect or embodiment described herein, the ⸺ of Q indicates the point of attachment with the nitrogen, and the ⸺ indicates the site of covalent attachment to at least one of $R_{PTM}$, a chemical linking group (L) or CLM. In any of the aspects or embodiments, the Q of PTM-I is covalently coupled to the linker (L) or CLM.

In any aspect or embodiment described herein, Q of PTM-I is:

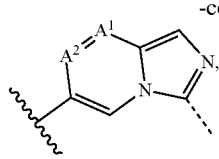

wherein $A^1$, $A^2$, and $A^3$ are defined in any aspect or embodiment described herein, the ⸺ of Q indicates the point of attachment with the nitrogen, and the ⸺ indicates the site of covalent attachment to at least one of $R_{PTM}$, a chemical linking group (L) or CLM. In any of the aspects or embodiments, the Q of PTM-I is covalently coupled to the linker (L) or CLM.

In any aspect or embodiment described herein, Q of PTM-I is:

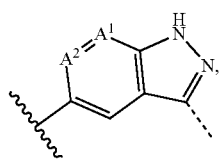

wherein:
  $A^1$ and $A^2$ are each $CR^6$;
  each $R^6$ is independently selected from H, halo, $C_{1-6}$ alkyl, $C_{1-6}$ haloalkyl, Ono aryl, $C_{3-7}$ cycloalkyl, 5-6 membered heteroaryl, 4-7 membered heterocycloalkyl, CN, and $NO_2$;

the ⸺ of Q indicates the point of attachment with the nitrogen; and the ⸺ indicates a covalent attachment to at least one of $R_{PTM}$, a chemical linking group (L) or CLM.

In any aspect or embodiment described herein, W PTM-I is O.

In any aspect or embodiment described herein, $R^2$ PTM-I is H.

In any aspect or embodiment described herein, $R^5$ of PTM-I is H or $C_{1-6}$ alkyl.

In any aspect or embodiment described herein, $R^{3A}$ and $R^{3B}$ of PTM-I are each independently selected from H, halo, and $C_{1-6}$ alkyl.

In any aspect or embodiment described herein, $R_{PTM}$ is selected from a bond, methyl, ethyl, propyl, butyl, pentyl, hexyl, H, O H, ethyl,

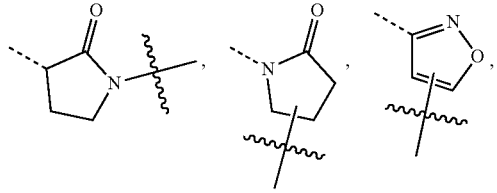

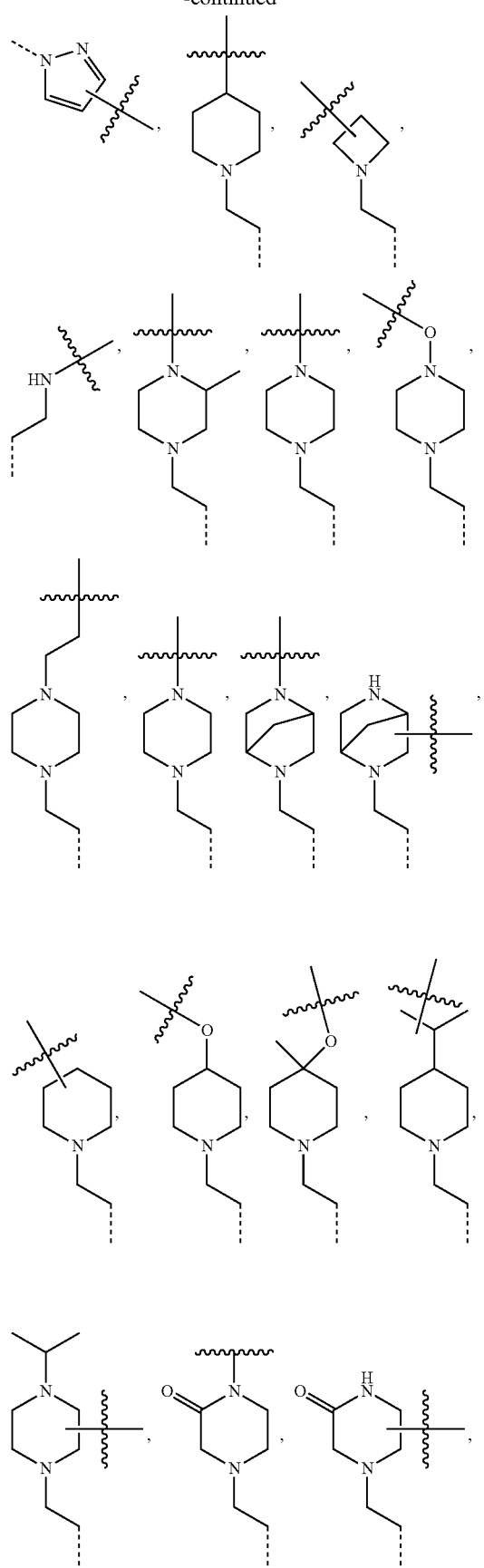
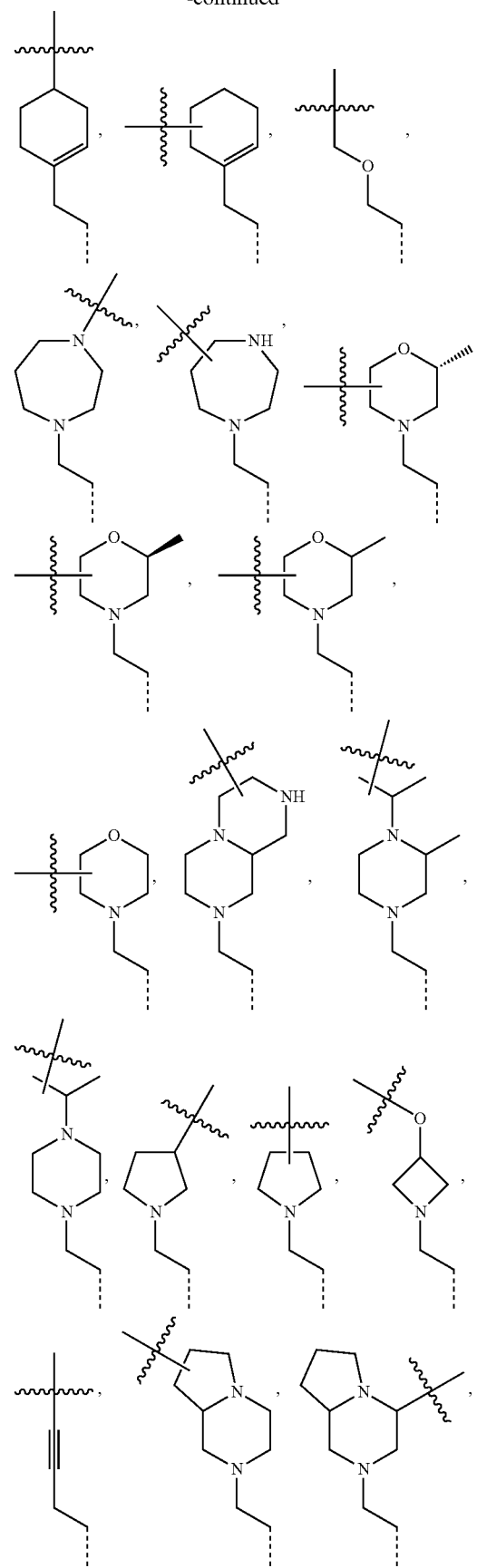

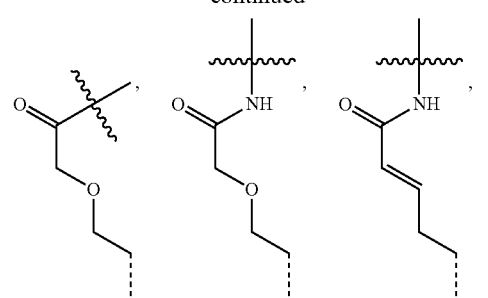
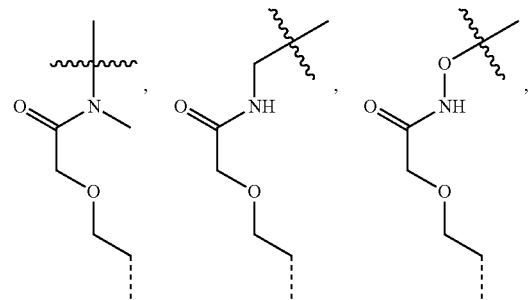
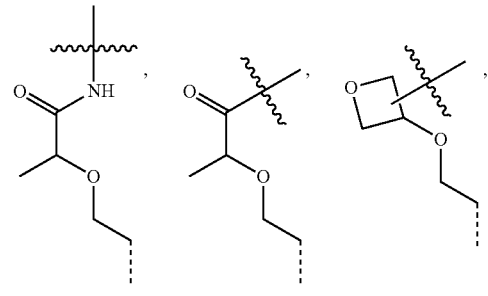
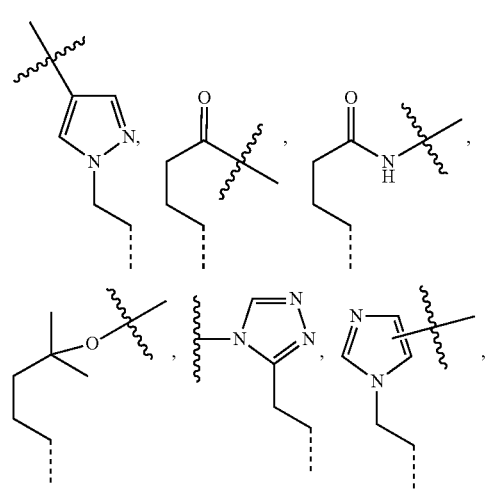
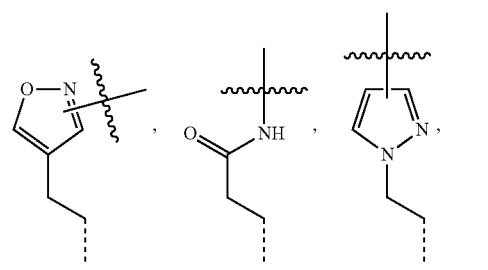
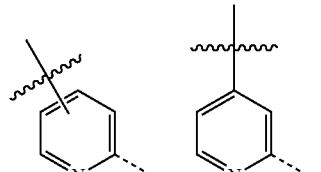
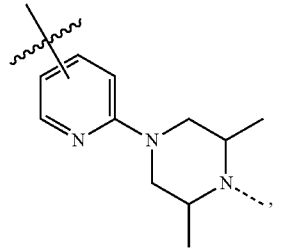
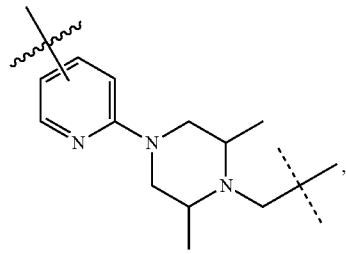
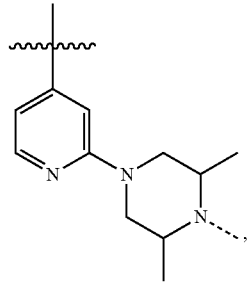
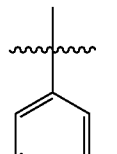
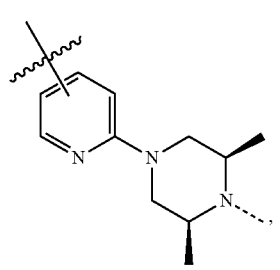

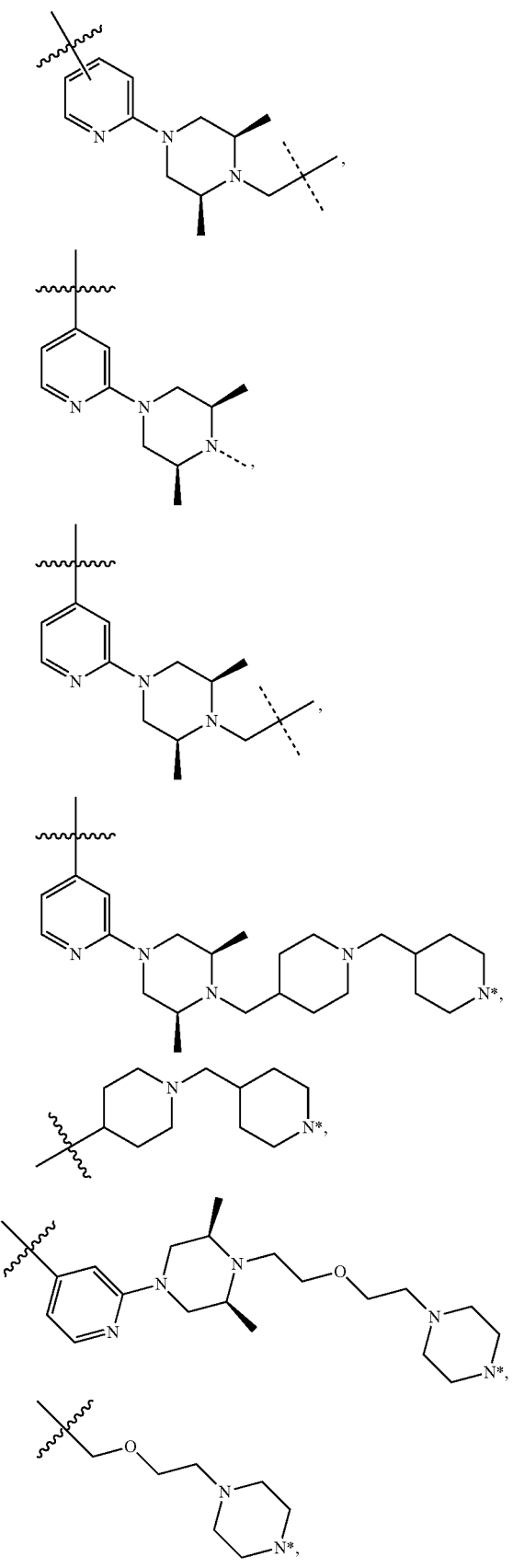
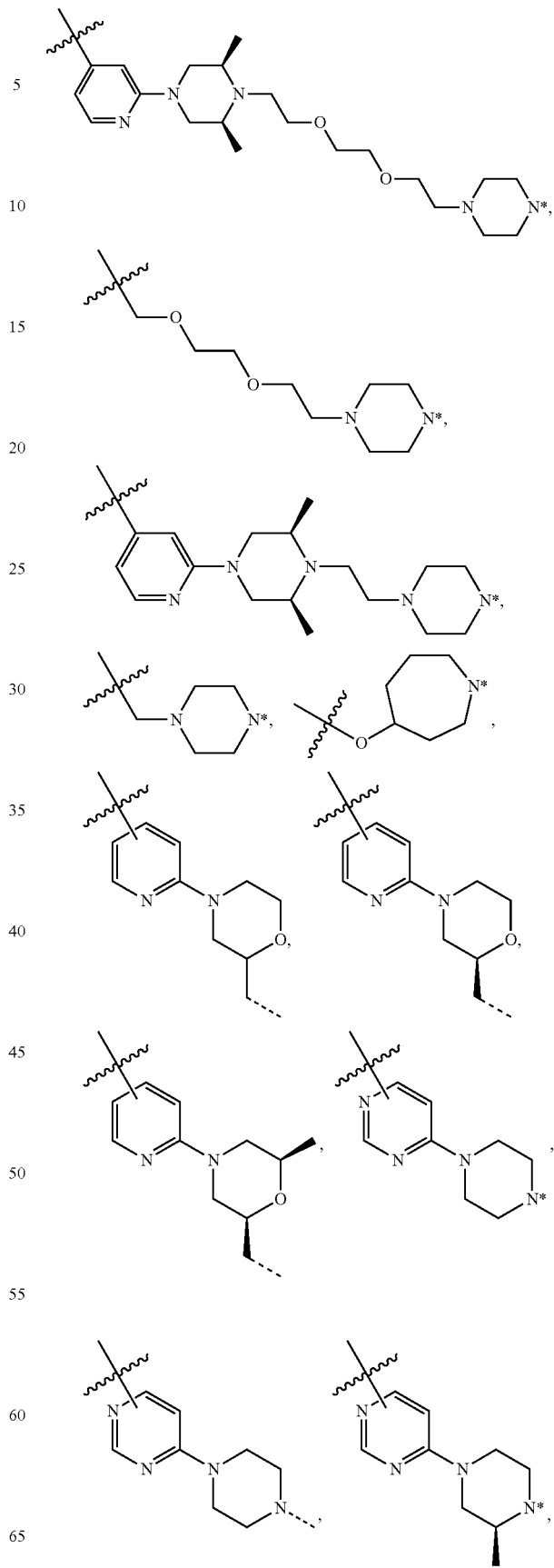

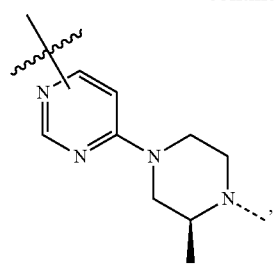
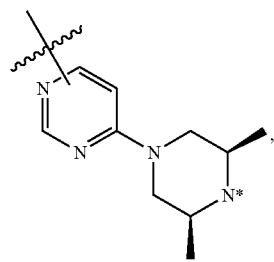
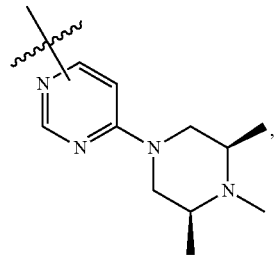
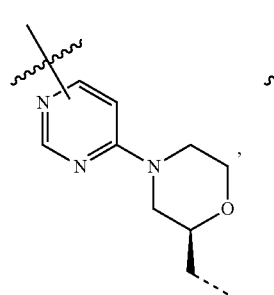
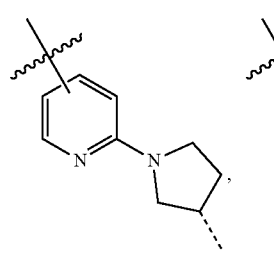
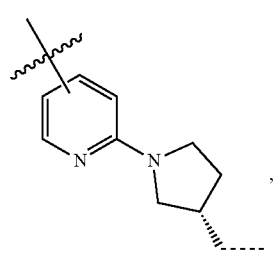
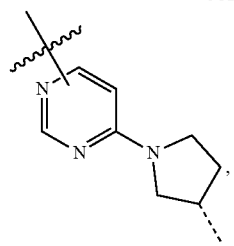
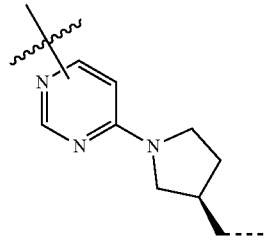
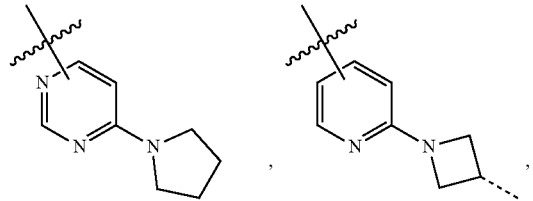
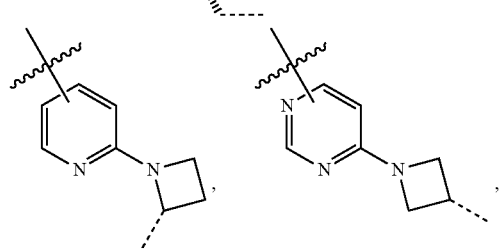
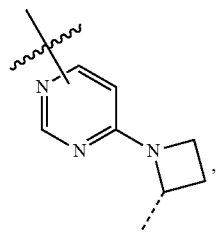
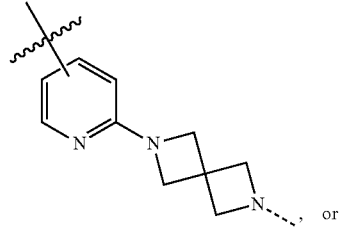, or
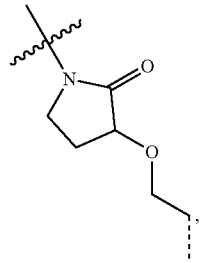

wherein ⁓ represents the site of attachment with PTM and the or ⤳ indicates the site of covalent attachment with a chemical linking group (L) or CLM.

In any of the aspects or embodiments, the $R_{PTM}$ is covalently coupled to the linker (L) or CLM.

In any aspect or embodiment described herein, the PTM-I is selected from the group consisting of:

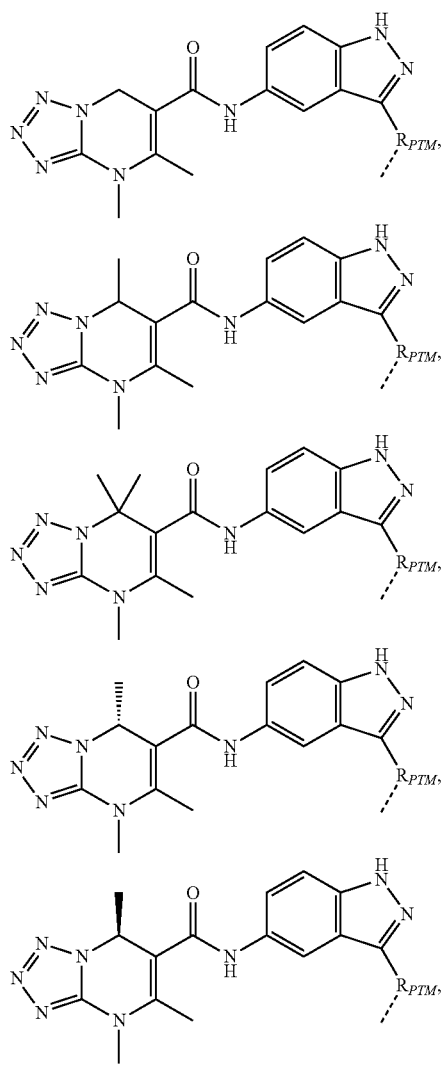

wherein $R_{PTM}$ is a bond, an atom or chemical group as described herein, and the ⤳ of the $R_{PTM}$ indicates the point of attachment of a chemical linking group (L) or a CLM.

In any aspect or embodiment described herein, $R_{PTM}$ is a 5-7 membered aryl or heteroaryl (e.g., a 6-membered aryl or heteroaryl), wherein:
- the heteroaryl has 1, 2, or 3 heteroatoms selected from O, N, and S; and
- the $R_{PTM}$ is optionally substituted with (a) $Cy^1$ or (b) a 3- to 10-membered cycloalkyl (e.g., 5- or 6-membered cycloalkyl), heterocycloalkyl (e.g., 5- or 6-membered heterocycloalkyl), spirocycloalky (e.g., 6- to 12-membered or 8- to 10-membered spirocycloalkyl), spiroheterocycloalkyl (e.g., 6- to 12-membered or 8- to 10-membered spiroheterocycloalkyl), bicyclic cycloalkyl (e.g., 6- to 10-membered bicyclic cycloalkyl), or bicyclic hetercycloalkyl (5- to 10-membered bicyclic heterocycloalkyl), wherein each of these is optionally substituted with 1, 2, 3, or 4 groups selected from the group consisting of H, $C_{1-3}$ alkyl, methyl, ethyl, and halogen.

In any aspect or embodiment described herein, $R_{PTM}$ is a 5-7 membered aryl or heteroaryl (e.g., a 6-membered aryl or heteroaryl), wherein:
- the heteroaryl has 1, 2, or 3 heteroatoms selected from O, N, and S; and
- the $R_{PTM}$ is optionally substituted with a 3- to 10-membered cycloalkyl (e.g., 5- or 6-membered cycloalkyl), heterocycloalkyl (e.g., 5- or 6-membered heterocycloalkyl), spirocycloalky (e.g., 6- to 12-membered spirocycloalkyl), spiroheterocycloalkyl (e.g., 6- to 12-membered spiroheterocycloalkyl), bicyclic cycloalkyl (e.g., 6- to 10-membered bicyclic cycloalkyl), or bicyclic hetercycloalkyl (5- to 10-membered bicyclic heterocycloalkyl), wherein each of these is optionally substituted with 1, 2, 3, or 4 groups selected from the group consisting of H, $C_{1-3}$ alkyl, methyl, ethyl, and halogen.

In any aspect or embodiment described herein $R_{PTM1a}$ or $R_{PTM2a}$ is selected from: a bond, methyl, ethyl, propyl, butyl, pentyl, hexyl, H, O H, ethyl,

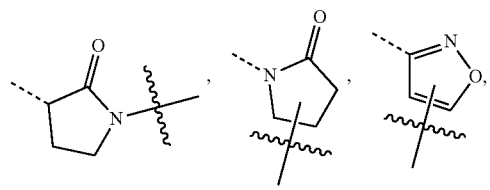

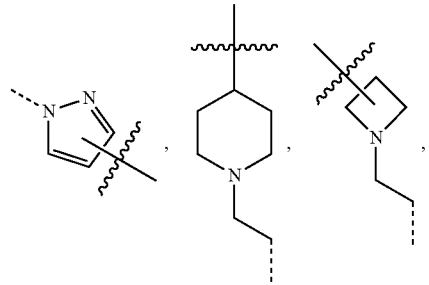

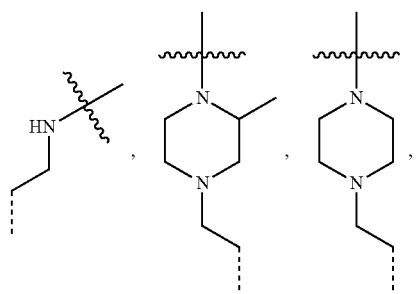

-continued
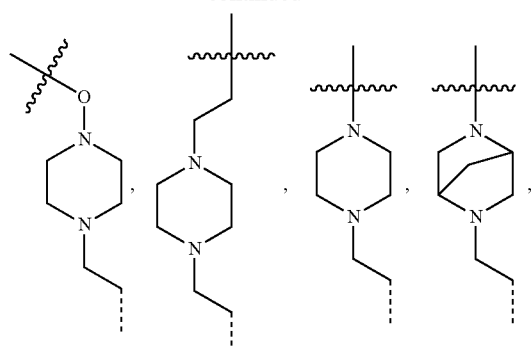
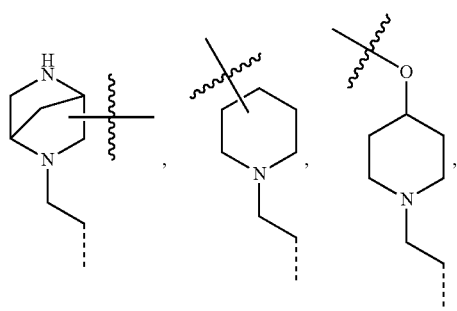
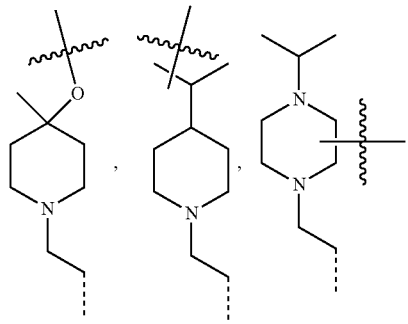
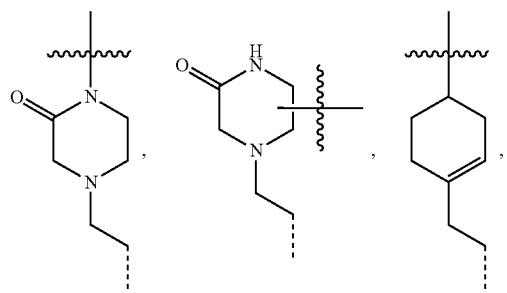
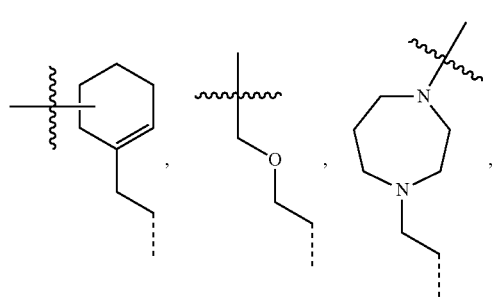
-continued
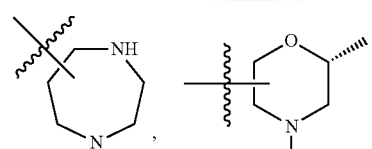
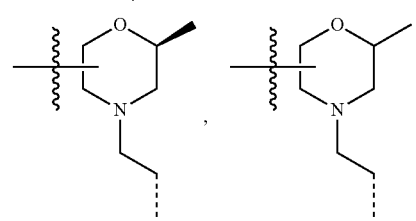
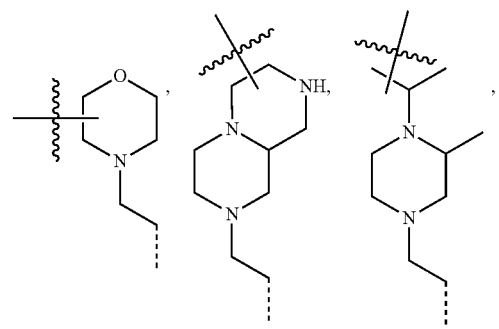
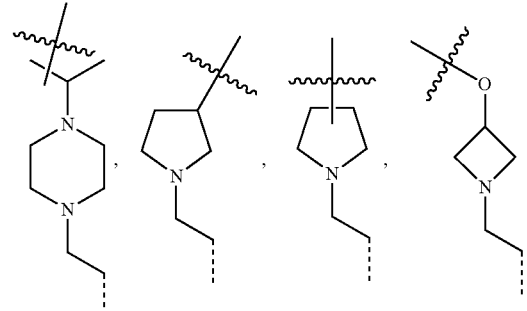
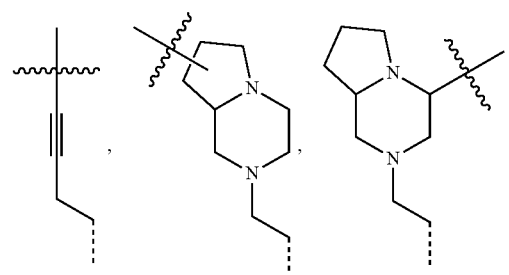
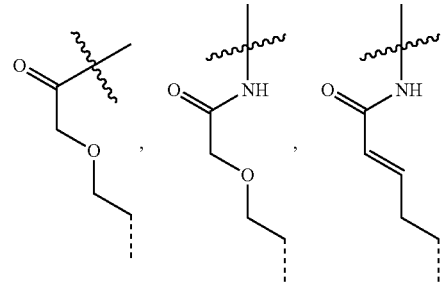

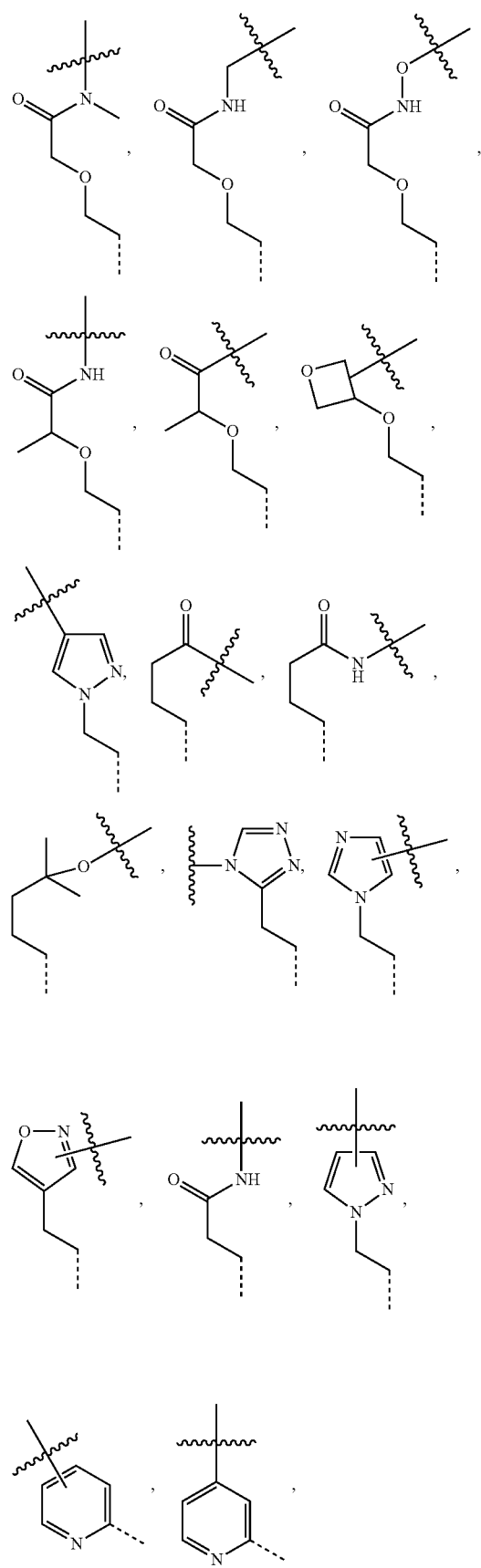
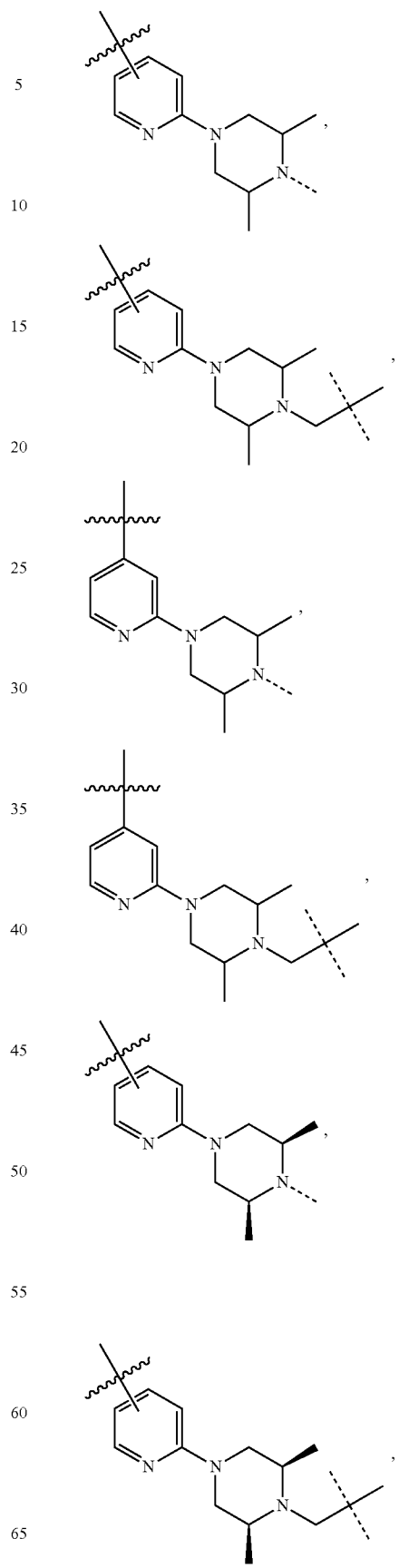

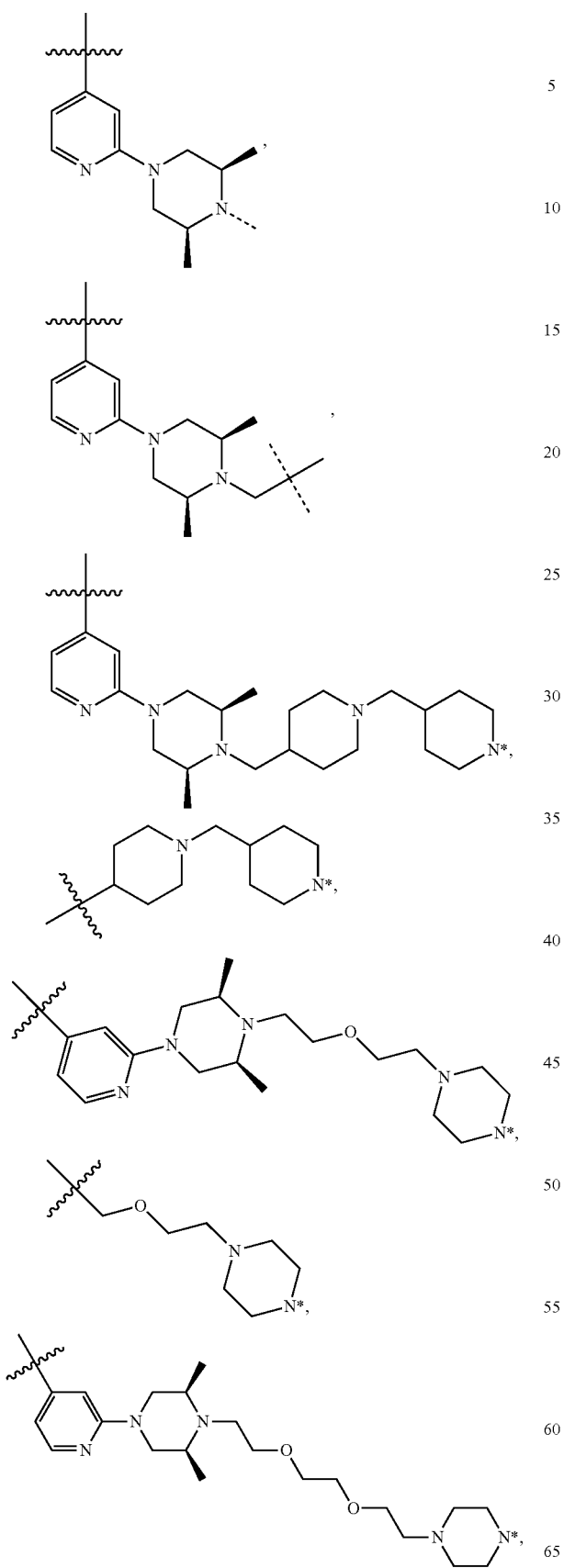
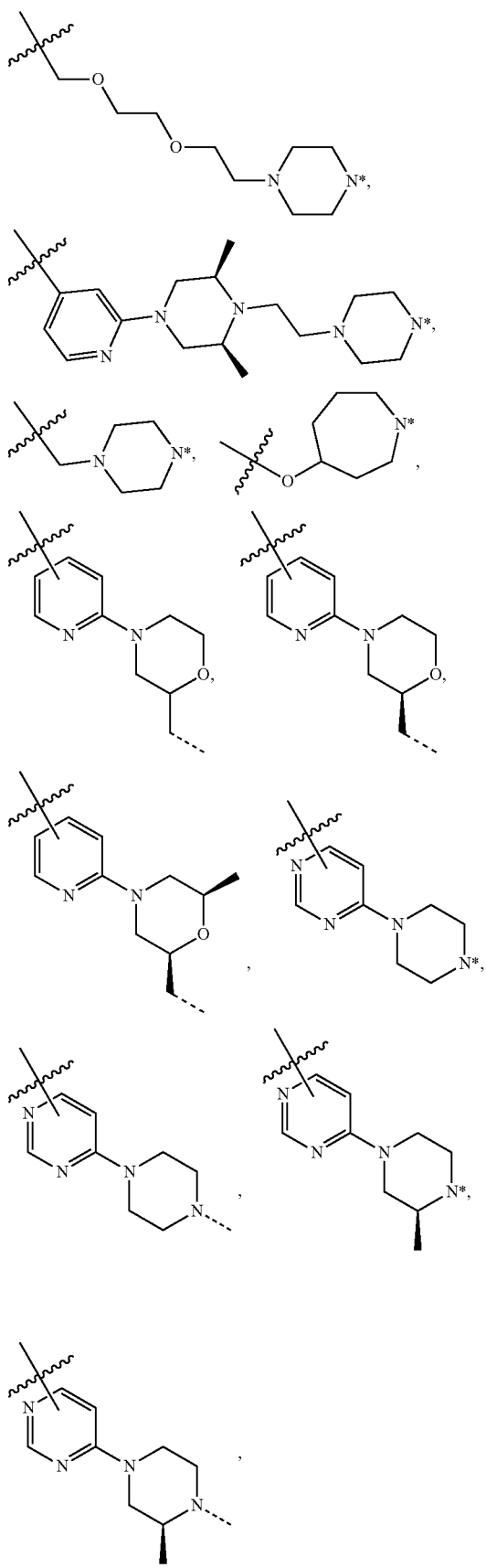

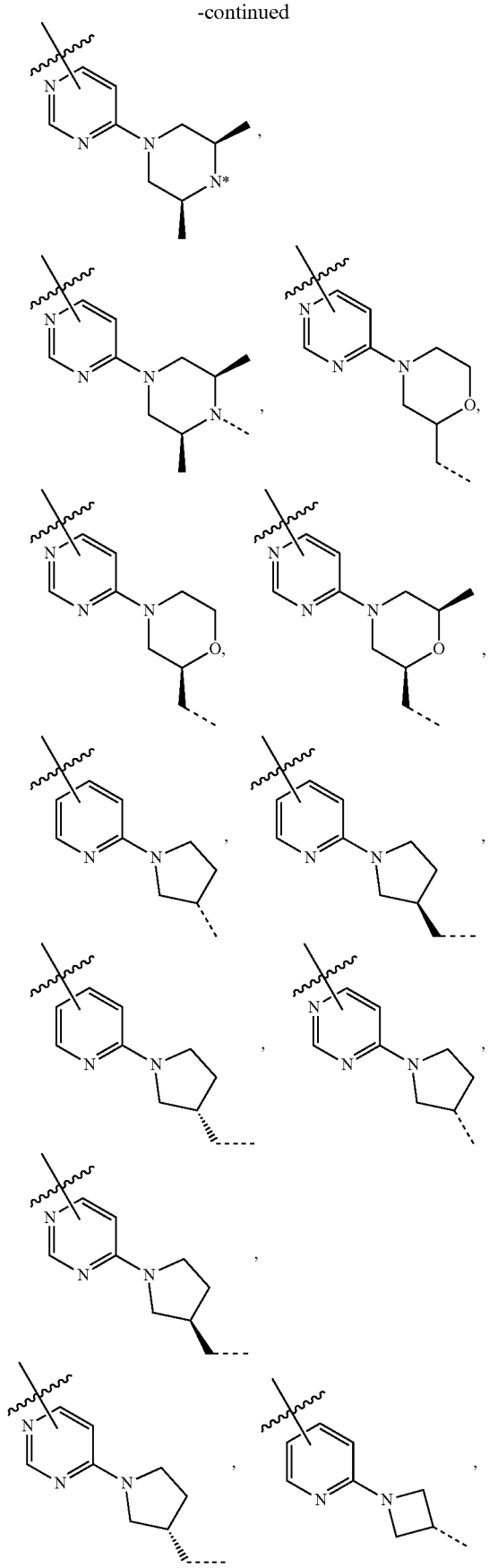
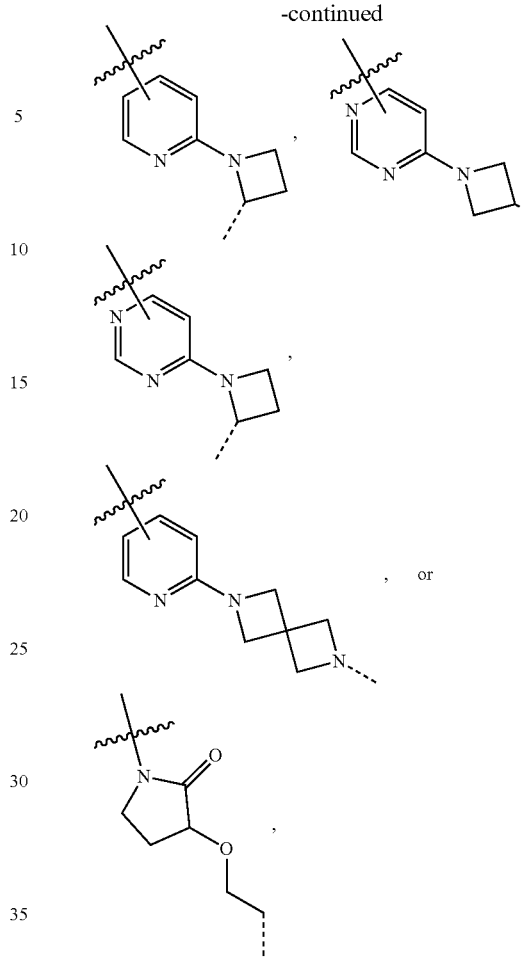

wherein ⌇ represents the site of attachment with PTM and the ⟋ or * indicates the site of covalent attachment with a chemical linking group (L) or CLM.

In any aspect or embodiment described herein, the $R_{PTM}$ or the corresponding location of any PTM described herein (e.g. PTM-I and derivatives thereof) is a linear or branched C1-C8 alkyl optionally substituted with OH.

In any aspect or embodiment described herein, the $R_{PTM}$ or the corresponding location of any PTM described herein (e.g. PTM-I derivatives thereof) is H, OH, CN, optionally substituted linear or branched C1-C4 alkyl, O-optionally substituted linear or branched C1-C4 alkyl, an optionally substituted C1-C4 alkynyl, an optionally substituted C1-C4 alkyne, an optionally substituted monocyclic or bicyclic C3-C12 heterocyclyl (e.g., an optionally substituted C3-C12 monocyclic or bicyclic heterocycloalkyl, such as an C3-C12 monocyclic or bicyclic heterocycloalkyl, azetidine1-yl, pyrrolidin-1-yl, piperidin-1yl, piperazin-1-yl, or morpholin-4-yl, or homopiperazin-1-yl, each optionally substituted with one or more of OH, a linear or branched C1-C5 alkyl or $NH_2$), or an optionally substituted —O—$C_{3-12}$ monocyclic or bicyclic heterocyclyl (e.g., an optionally substituted —O—$C_{3-12}$ monocyclic or bicyclic heterocycloalkyl, such as —O—$C_{3-12}$ monocyclic or bicyclic heterocycloalkyl optionally substituted with at least one OH, a linear or branched C1-C5 alkyl or $NH_2$), or an optionally substituted C3-C12 member ring (e.g., an optionally substituted C3-C12 non-aryl membered ring optionally substituted with one or more of OH, linear or branched C1-C5 alkyl, or NH$_2$), wherein when R$_{PTM}$ is a ring structure it is optionally covalently linked to Q$_{16}$ via a C or N of the R$_{PTM}$ ring.

In any aspect or embodiment described herein, the PTM is represented by the chemical structure:

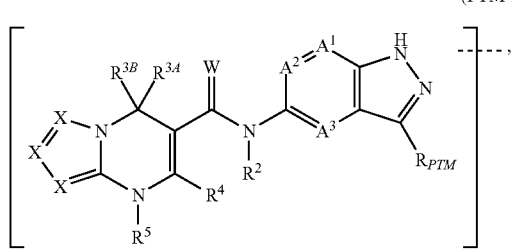

(PTM-IIa)

wherein X, A$^1$, A$^2$, A$^3$, R$^2$, R$^{3A}$, R$^{3B}$, R$^4$, R$^5$, and R$_{PTM}$ are defined as described in any aspect or embodiment herein, and the ⌇ indicates a covalent attachment to a chemical linking group (L) or CLM In any aspect or embodiment described herein, the PTM is represented by the chemical structure:

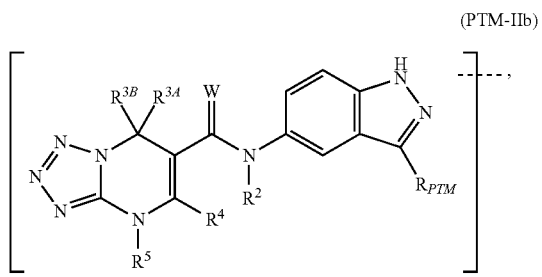

(PTM-IIb)

wherein R$^2$, R$^{3A}$, R$^{3B}$, R$^4$, R$^5$, and R$_{PTM}$ are defined as in any aspect or embodiment described herein, and the ⌇ indicates a covalent attachment to a chemical linking group (L) or CLM.

In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:

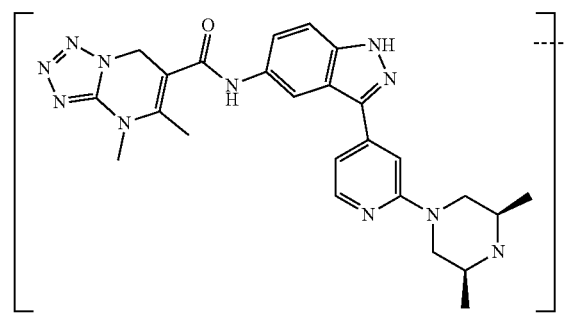

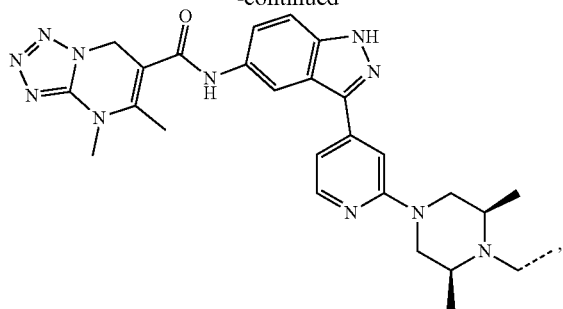

wherein the ⌇ indicates a covalent attachment of a chemical linking group (L) or CLM.

In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:

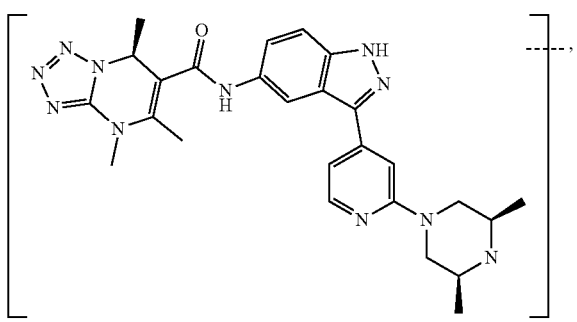
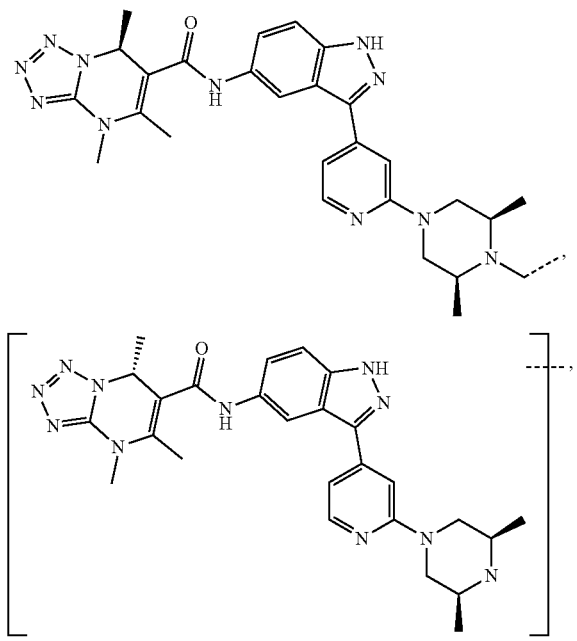
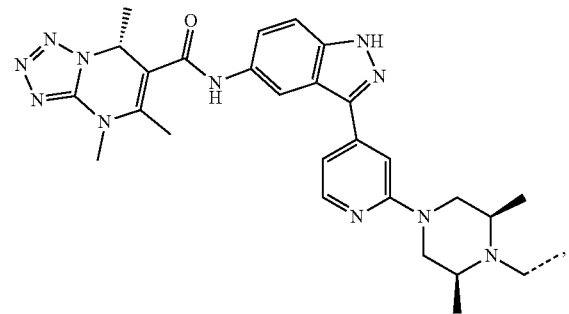
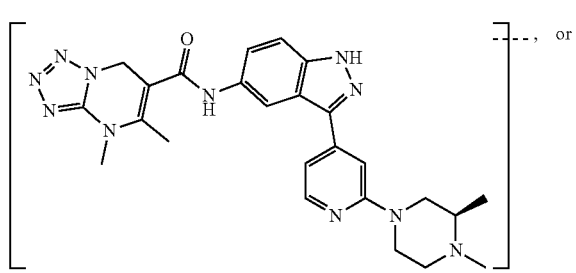
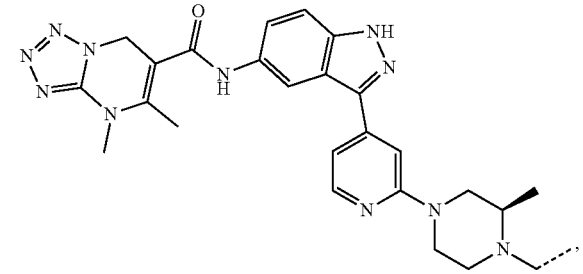
wherein the ⌇⌇⌇ indicates a covalent attachment of a chemical linking group (L) or CLM.
In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:
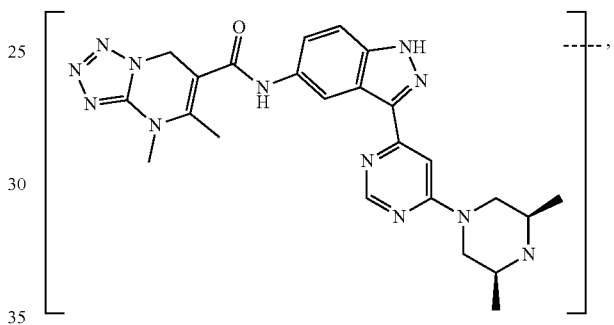
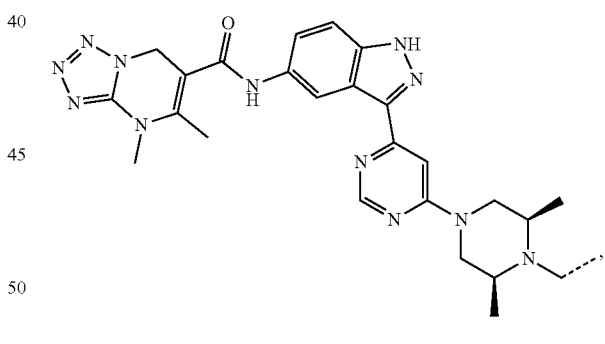
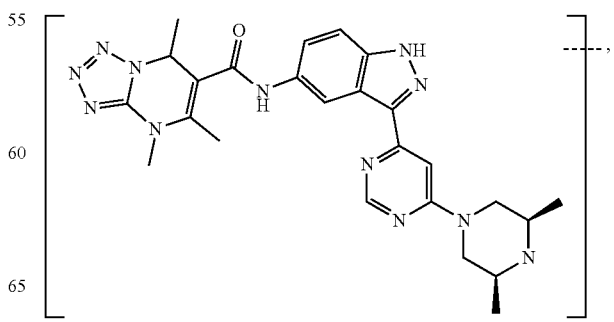

175
-continued

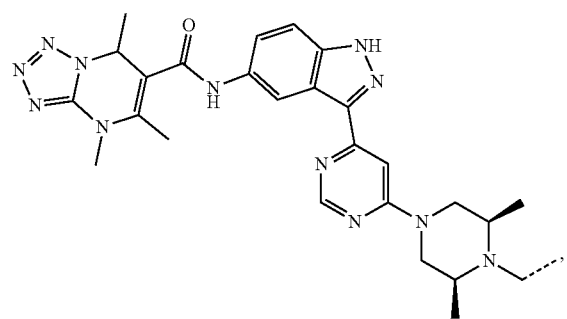

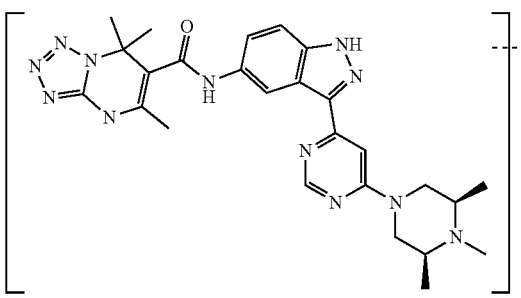
or

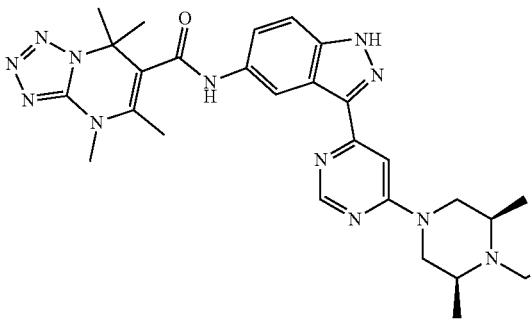

176
-continued

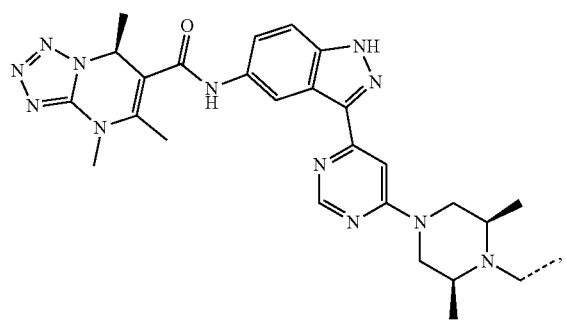

wherein the indicates a covalent attachment of a chemical linking group (L) or CLM.

In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:

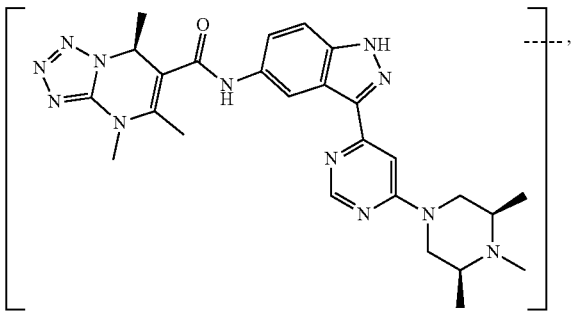

wherein the indicates a covalent attachment of a chemical linking group (L) or CLM.

In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:

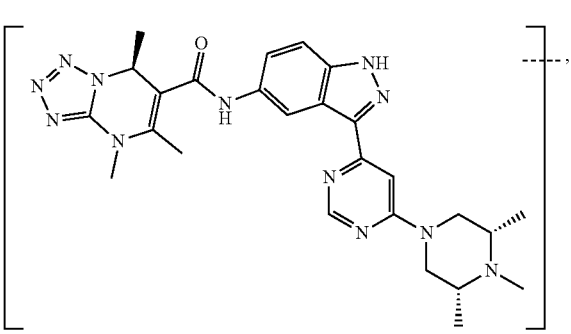

177
-continued
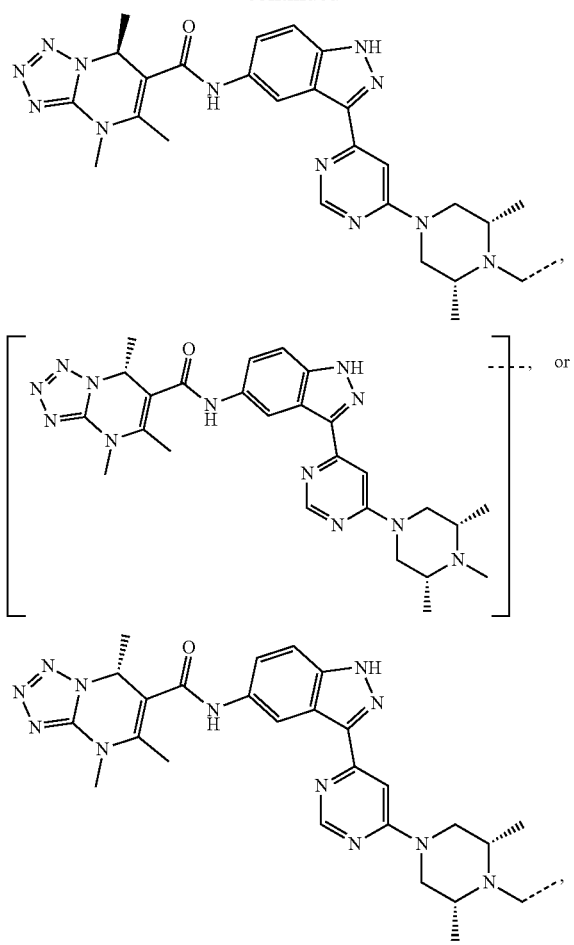
wherein the ⟋ indicates a covalent attachment of a chemical linking group (L) or CLM.
In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:
178
-continued
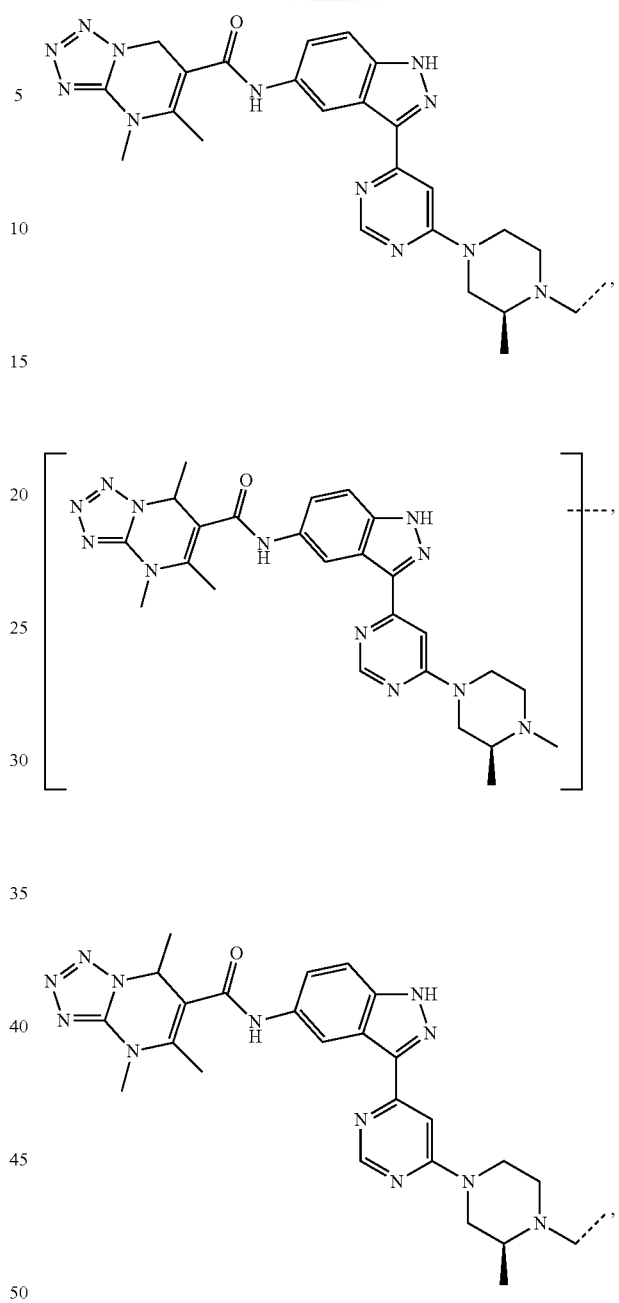
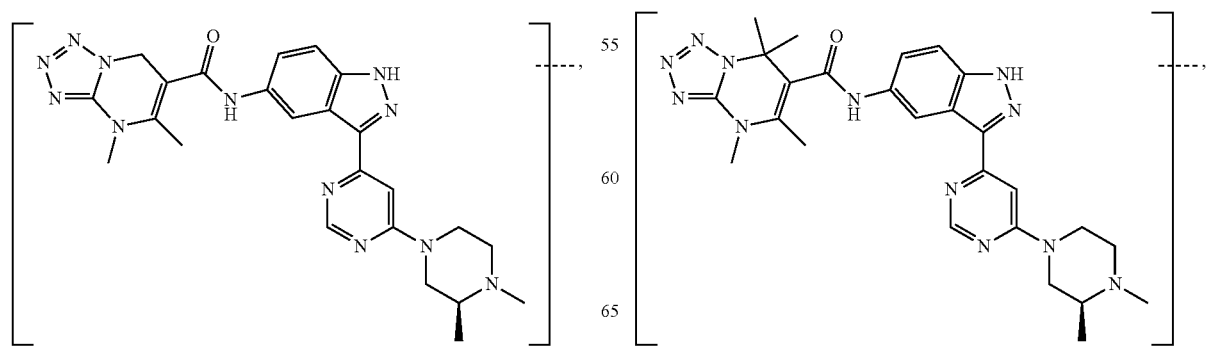

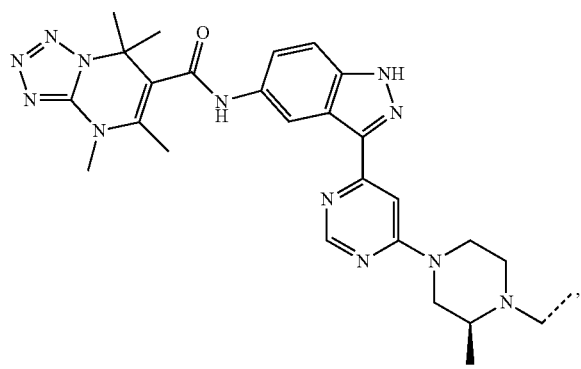
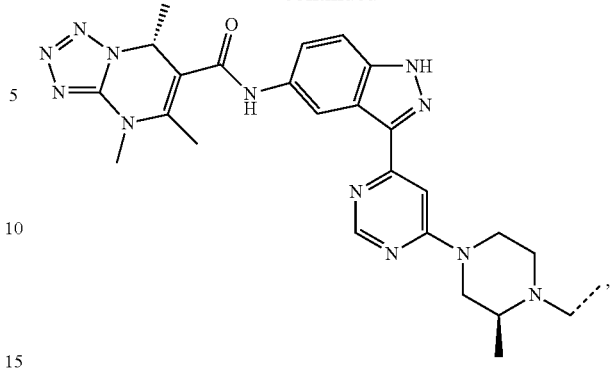
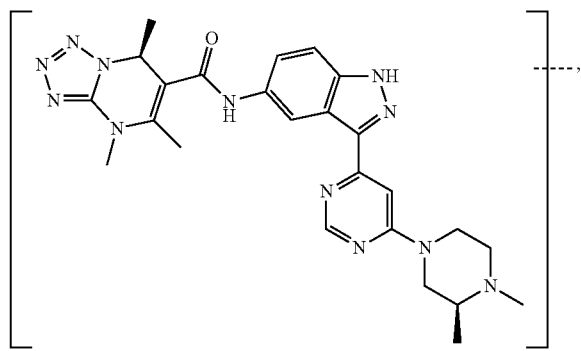
wherein the ⟋⟋ indicates a covalent attachment of a chemical linking group (L) or CLM.
In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:
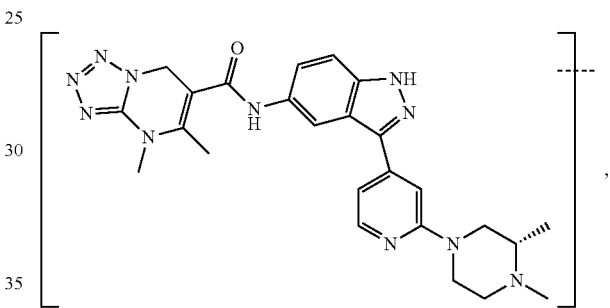
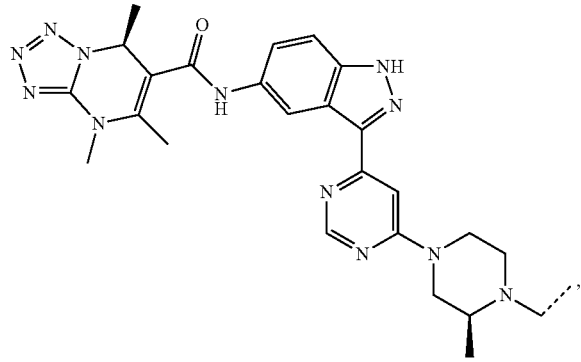
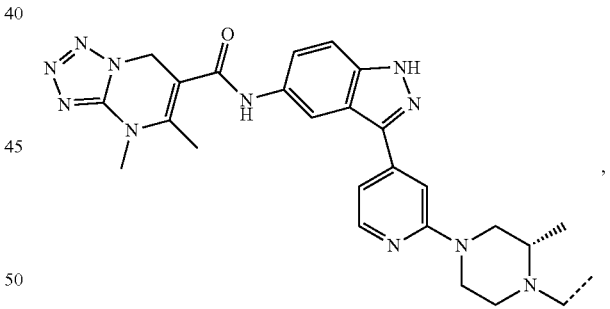
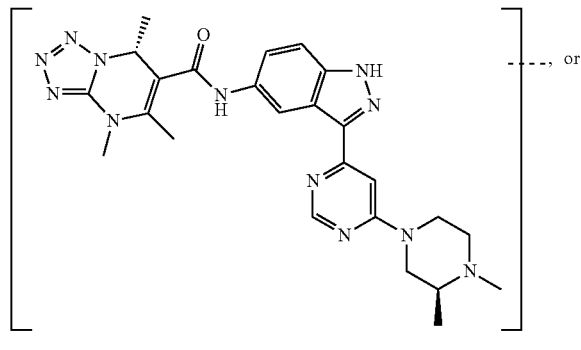
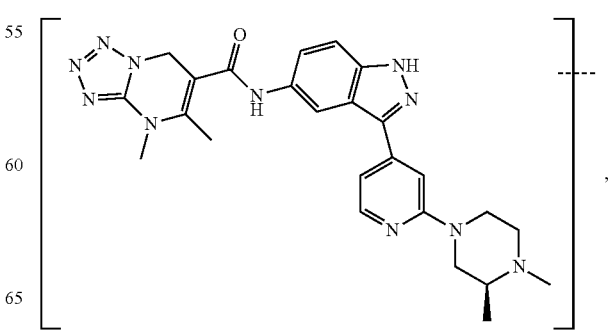

181
-continued
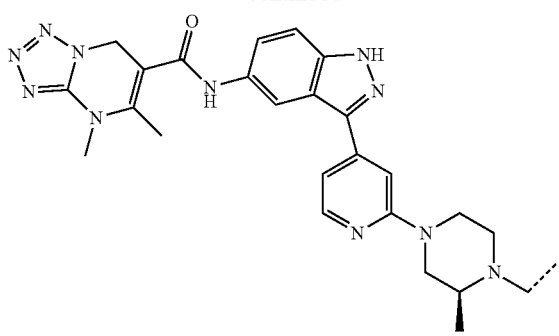
,
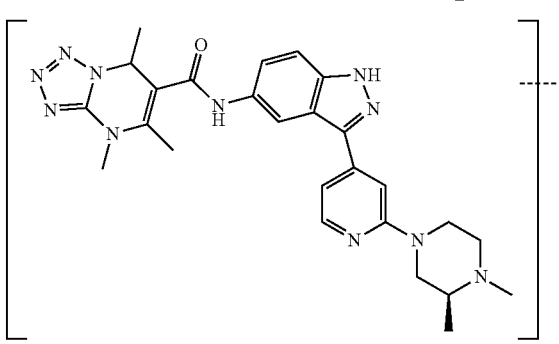
,
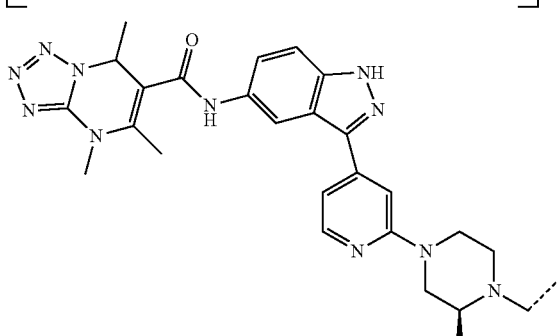
,
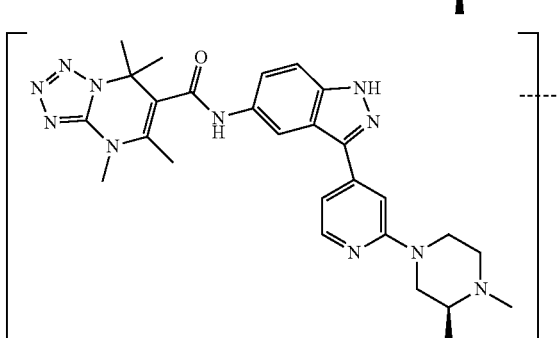
,
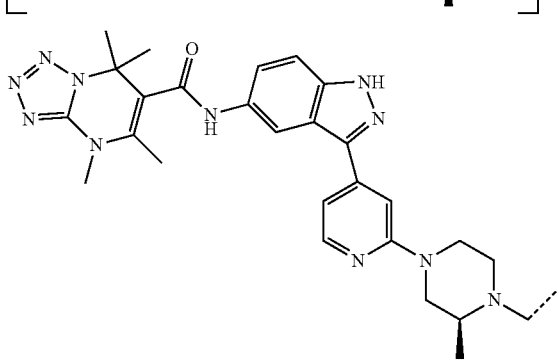
,
182
-continued
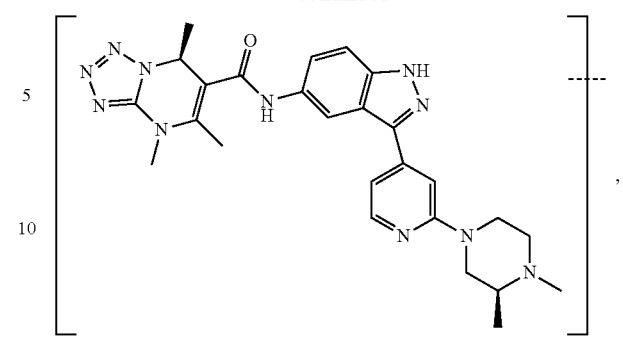
,
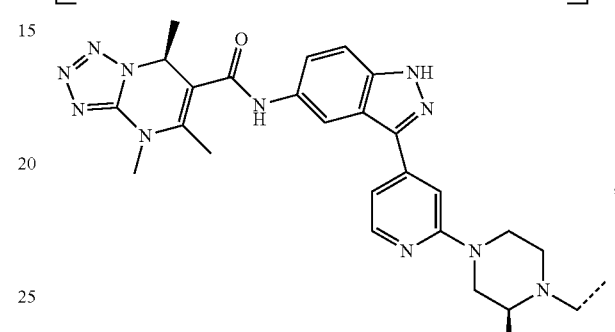
,
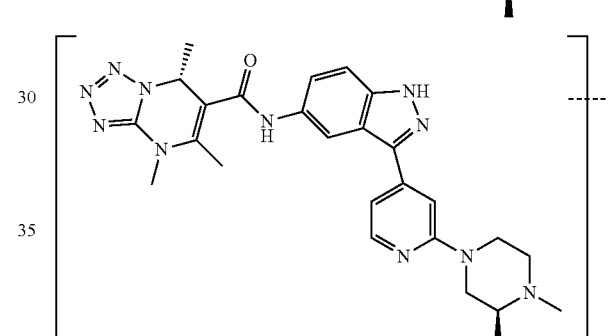
,
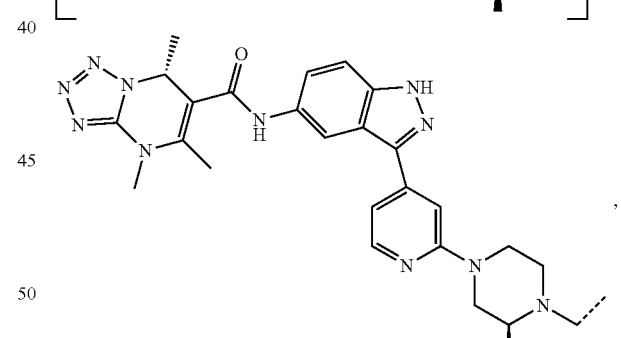
,
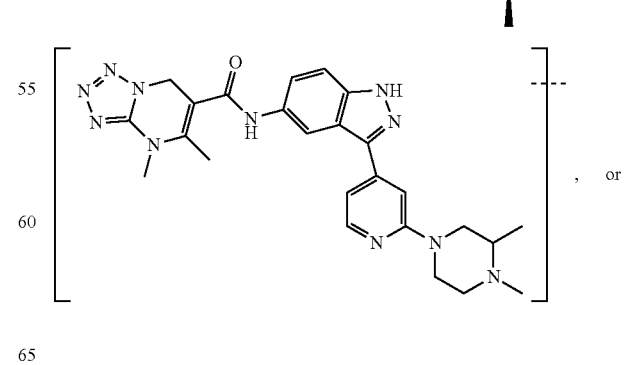
, or

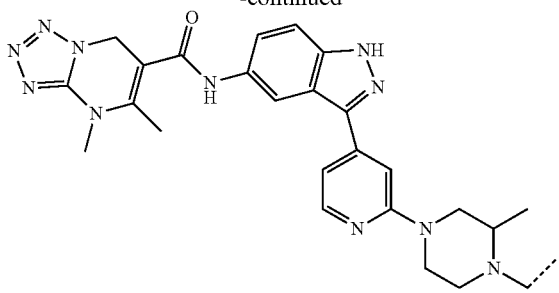
,
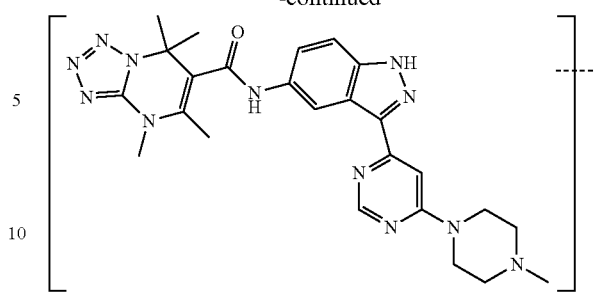
,
wherein the ⌇ indicates a covalent attachment of a chemical linking group (L) or CLM.
In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:
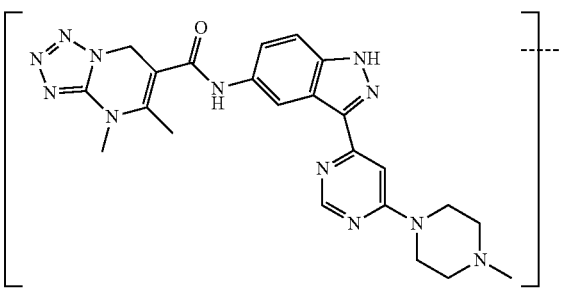
,
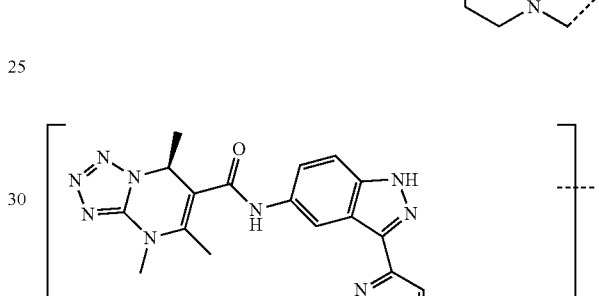
,
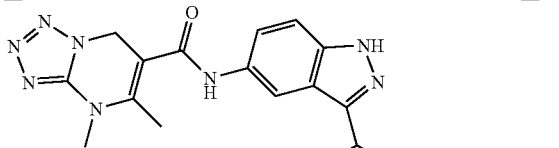
,
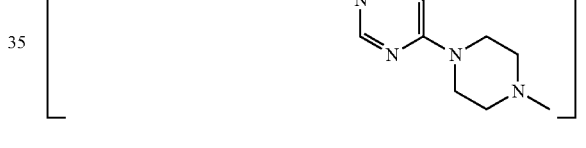
,
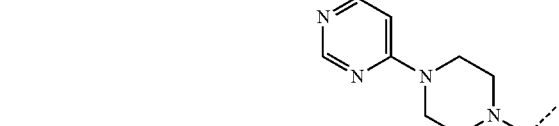
,
,
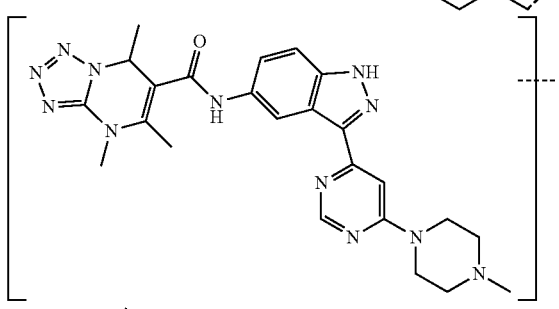
,
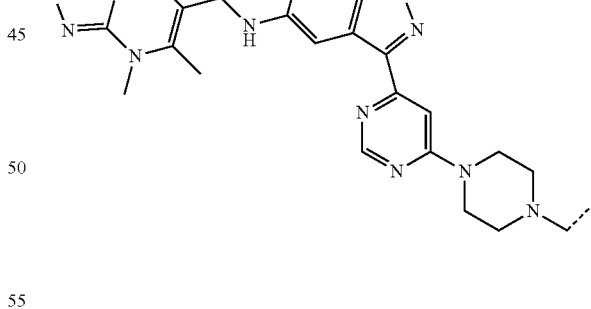
,
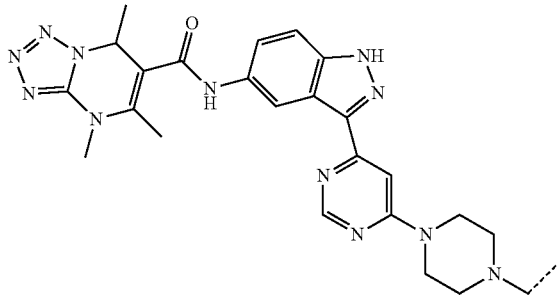
,
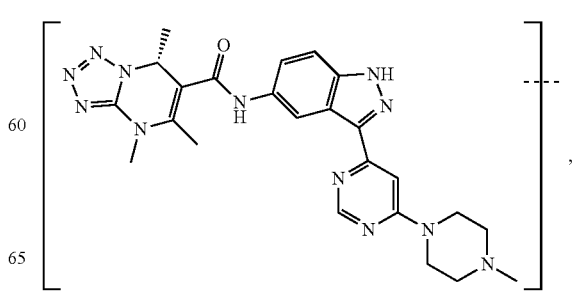
, or

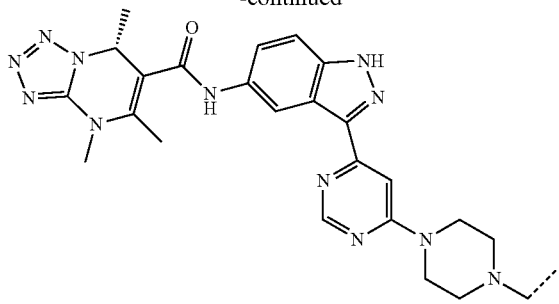
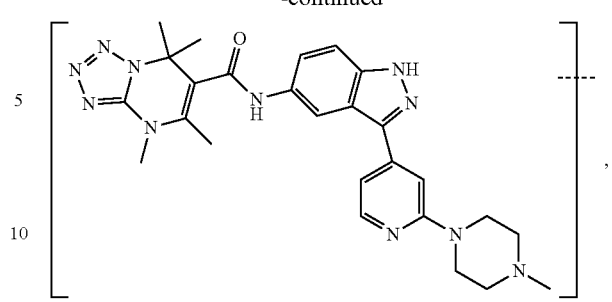
wherein the ⟋ indicates a covalent attachment of a chemical linking group (L) or CLM.
In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:
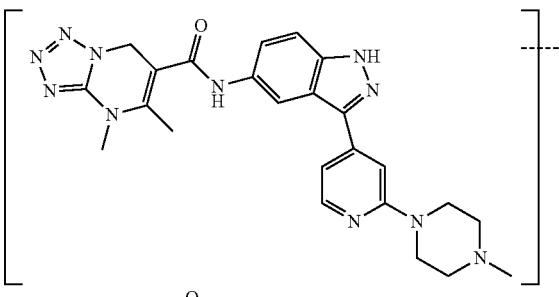
,
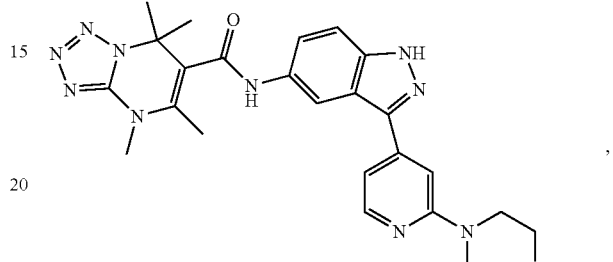
,
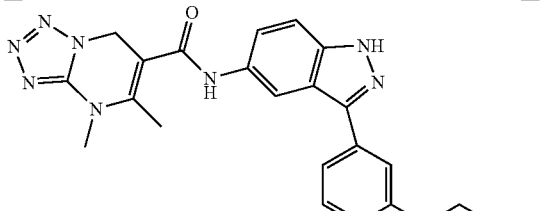
,
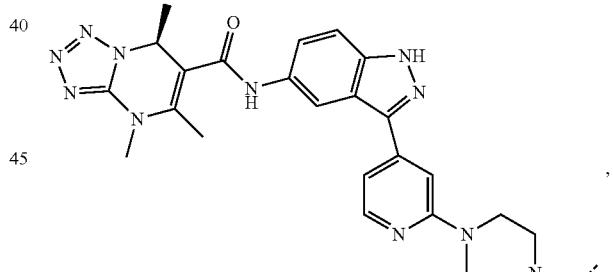
,
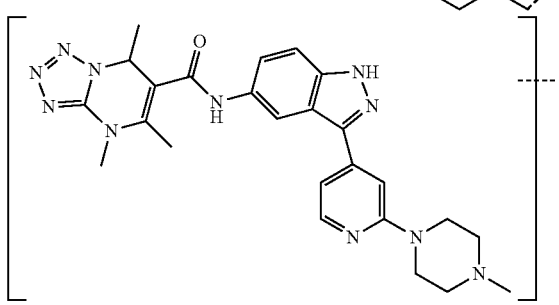
,
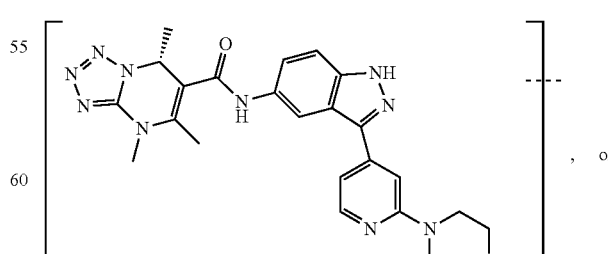
,
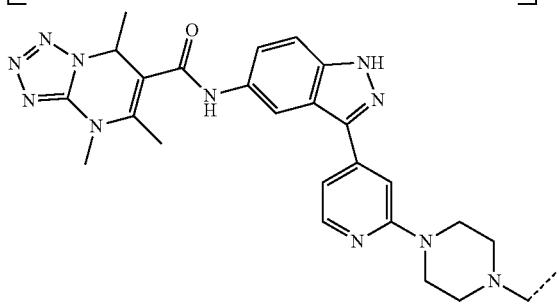
,
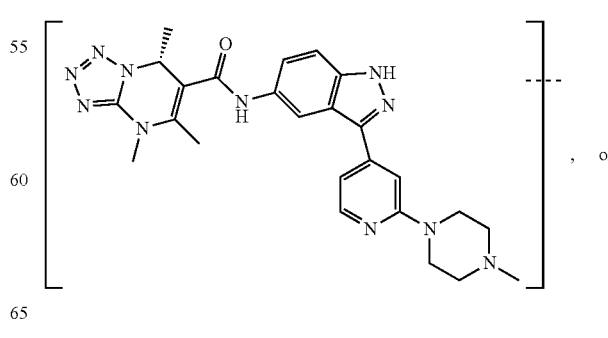
, or 187
-continued
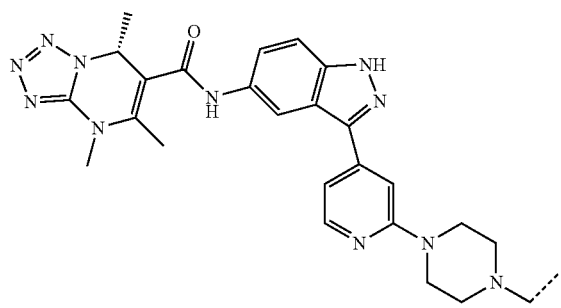
wherein the ⸺ indicates a covalent attachment of a chemical linking group (L) or CLM.
In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:
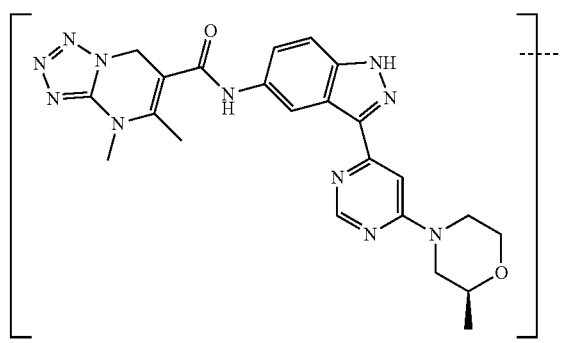
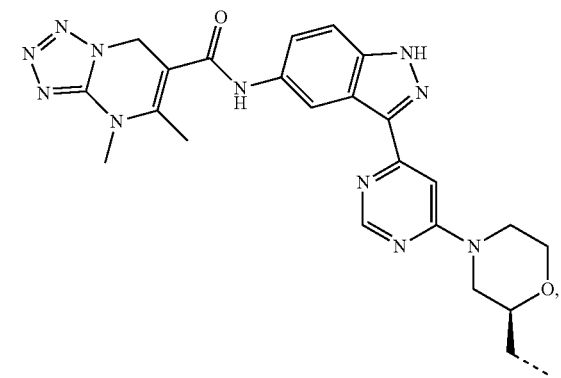
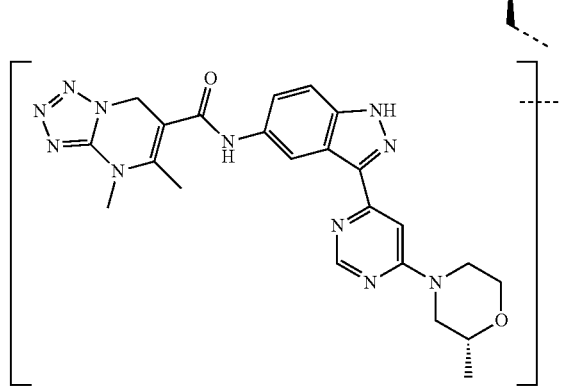
188
-continued
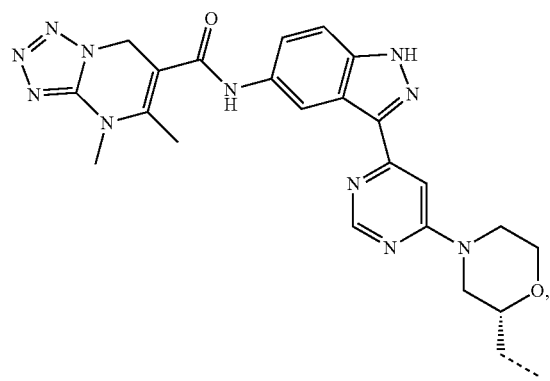
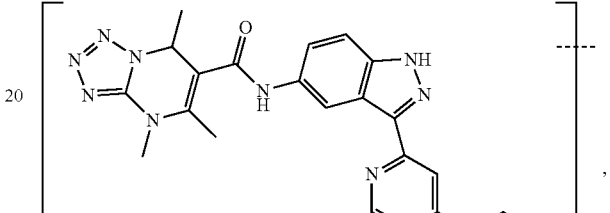
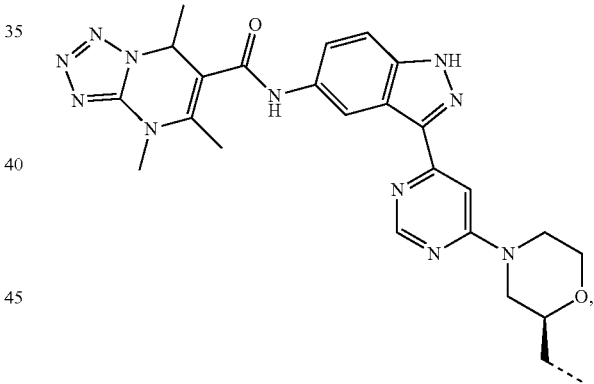
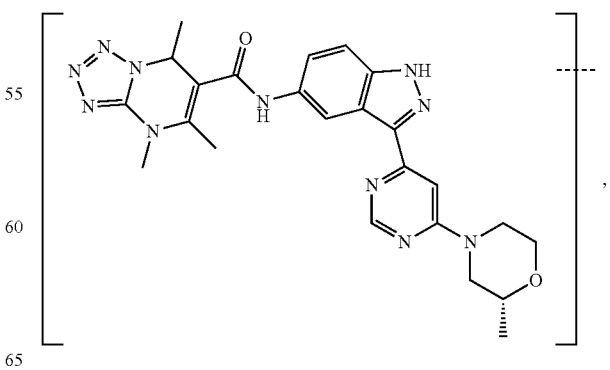

189
-continued
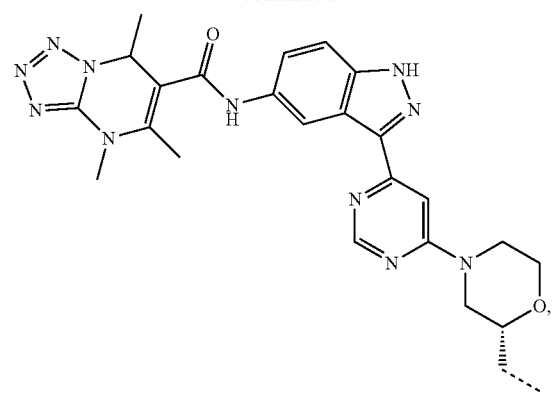
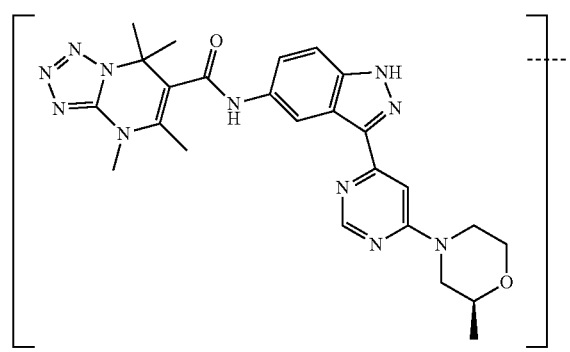
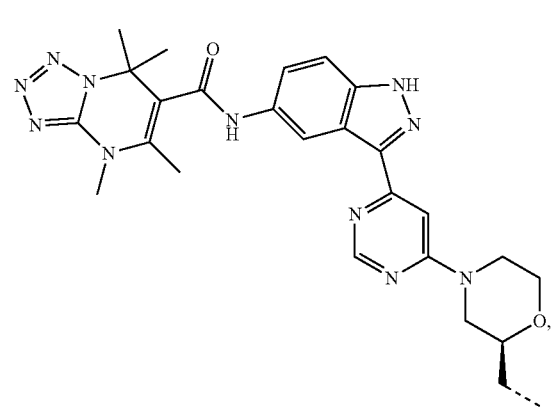
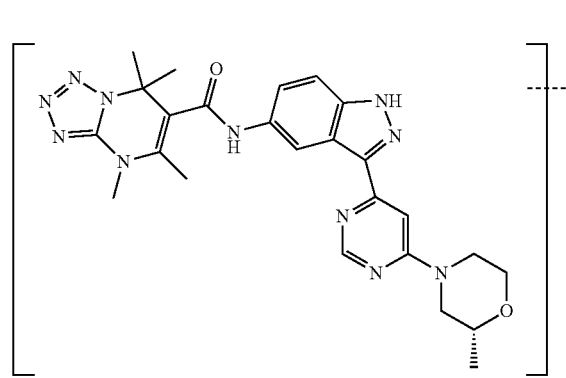
190
-continued
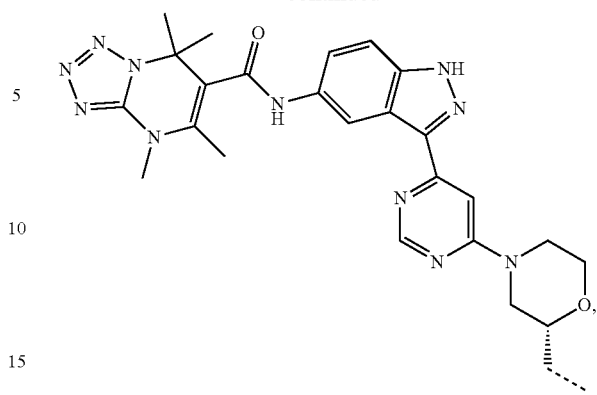
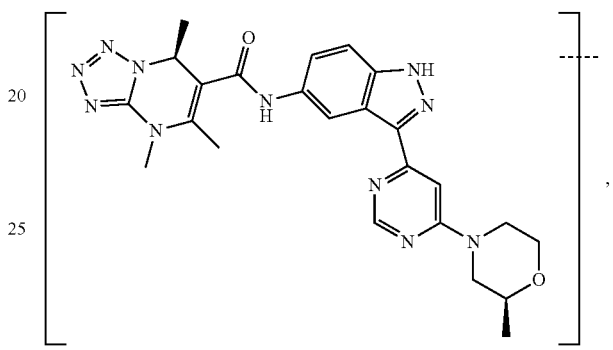
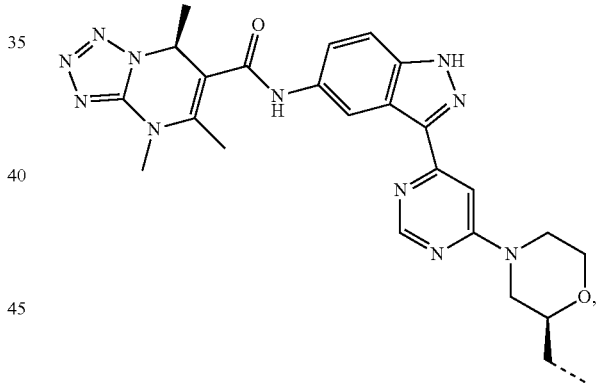
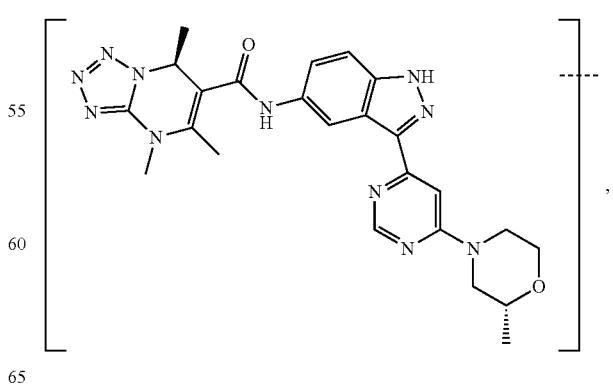

191
-continued
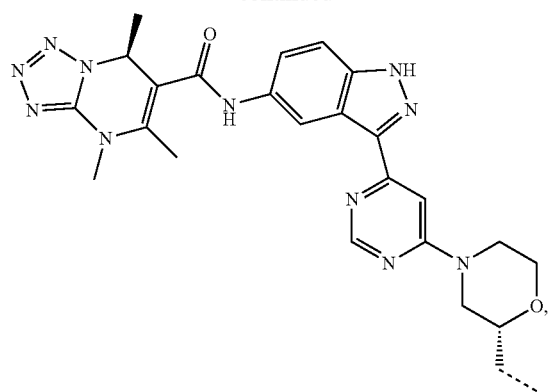
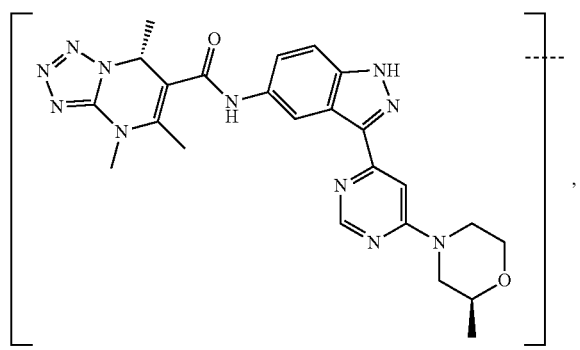
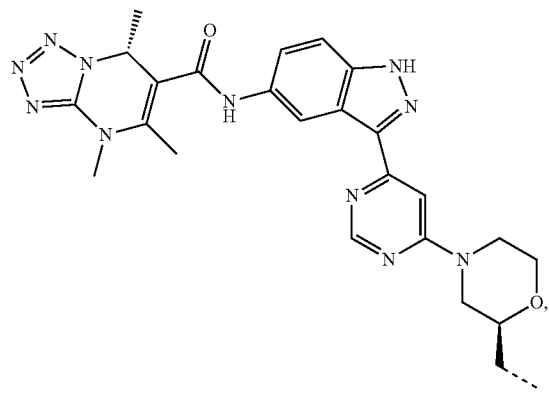
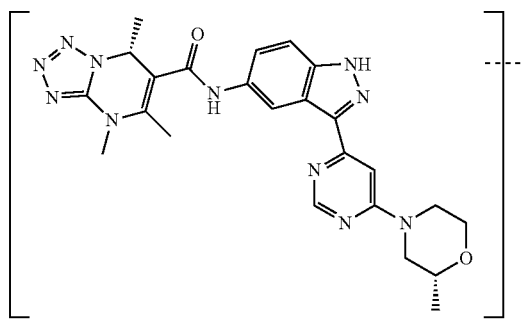
, or
192
-continued
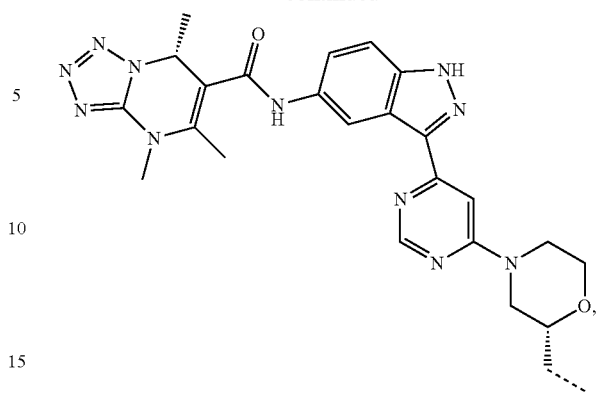
wherein the ⌇ indicates a covalent attachment of a chemical linking group (L) or CLM.
In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is represented by a chemical structure selected from:
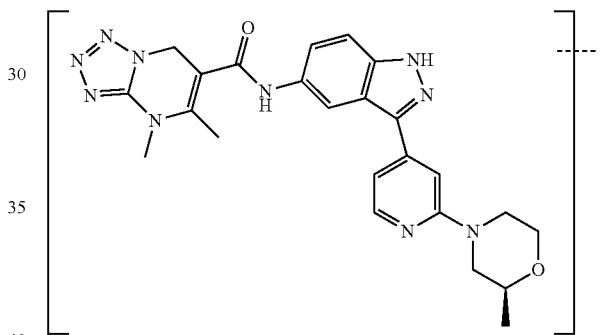
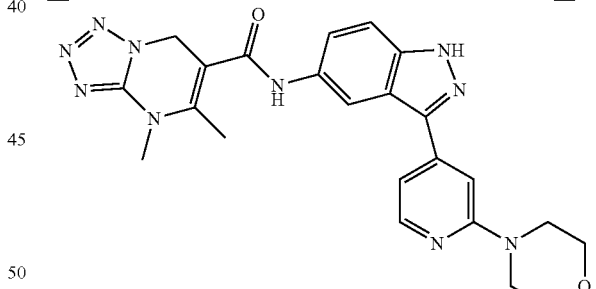
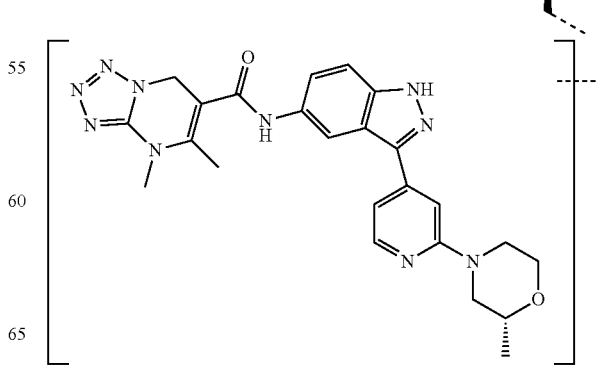

193
-continued
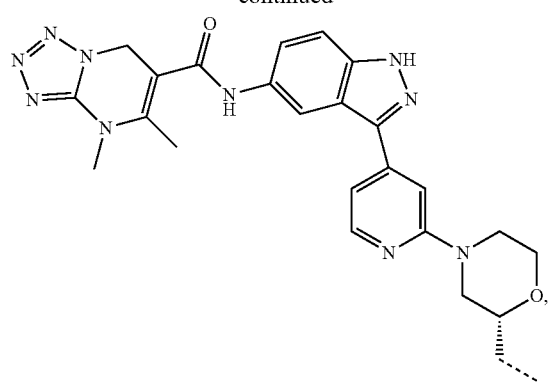
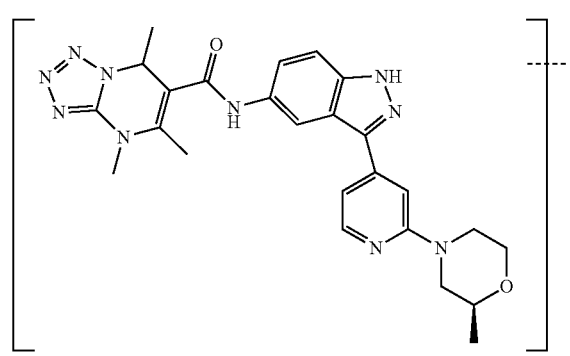
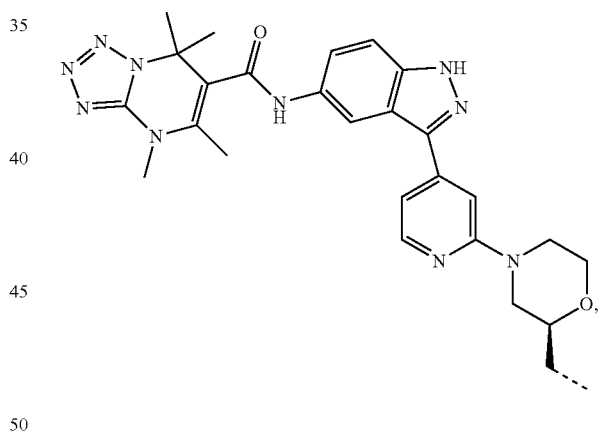
194
-continued
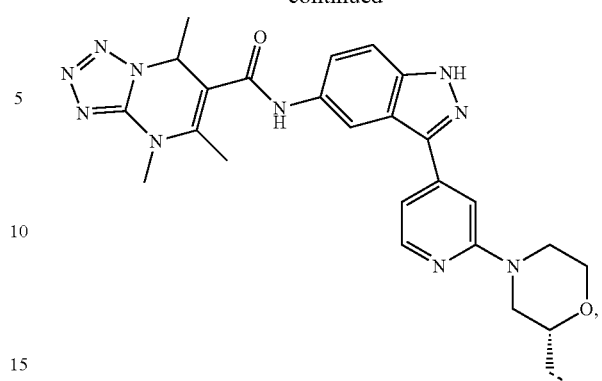
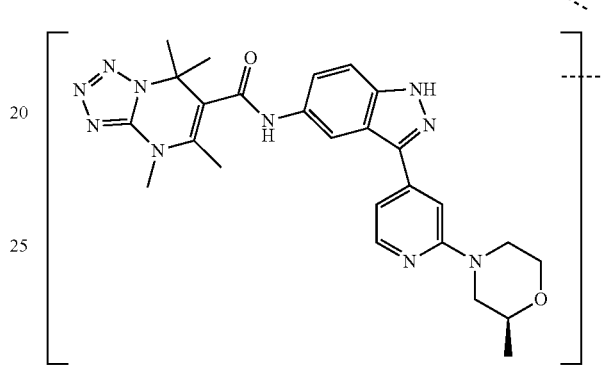
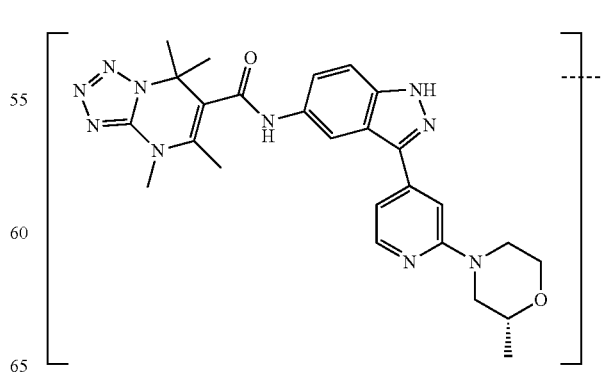

195
-continued
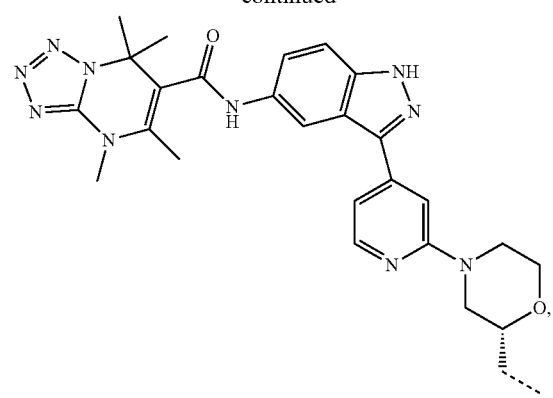
,
[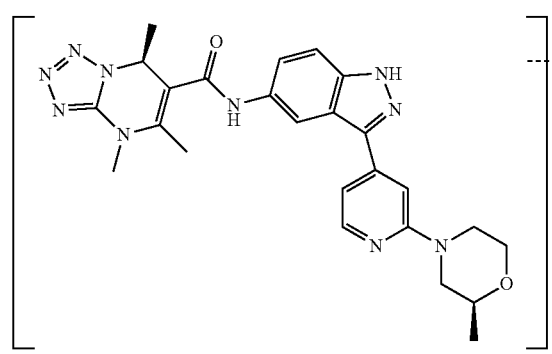]
,
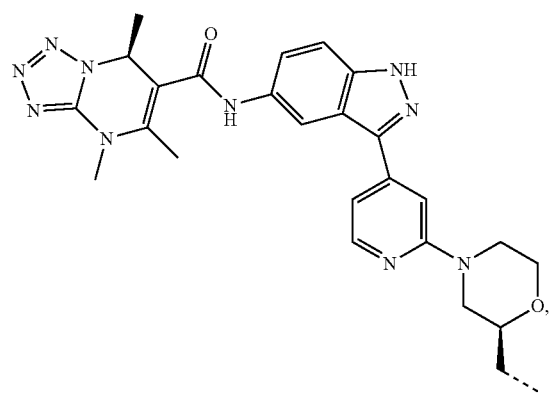
,
[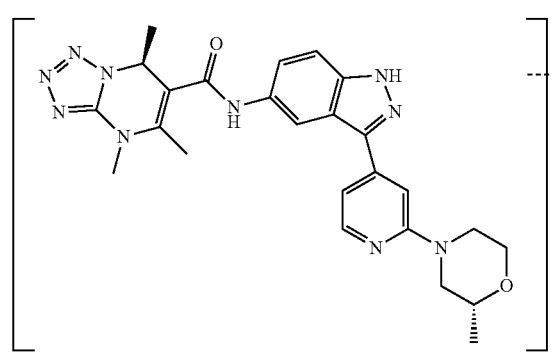]
,
196
-continued
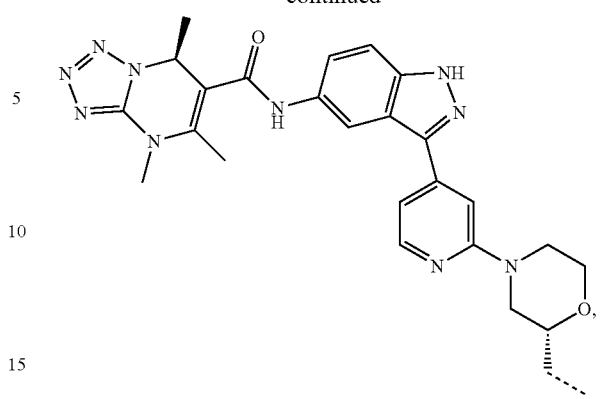
,
[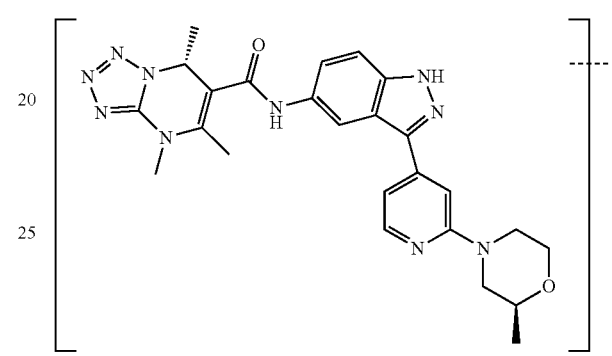]
,
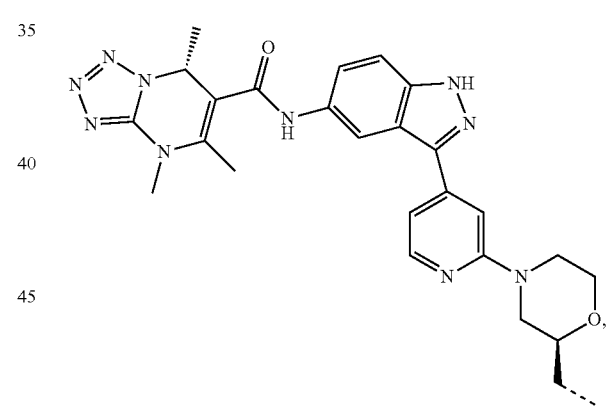
,
[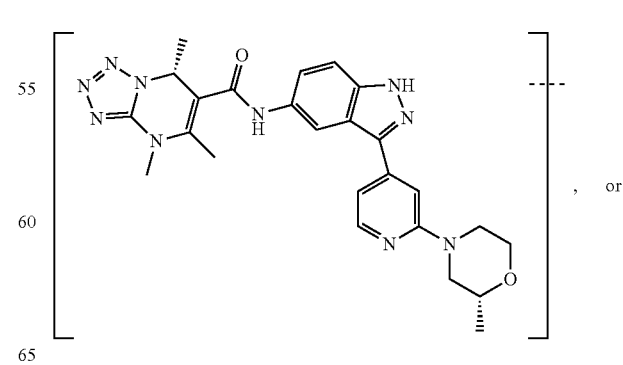] , or 197
-continued
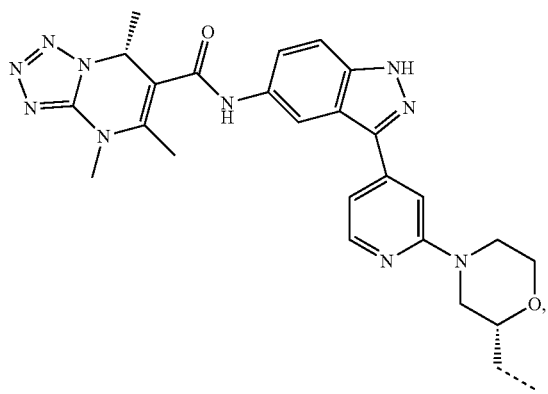
wherein the ⟋ indicates a covalent attachment of a chemical linking group (L) or CLM.
In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) is selected from:
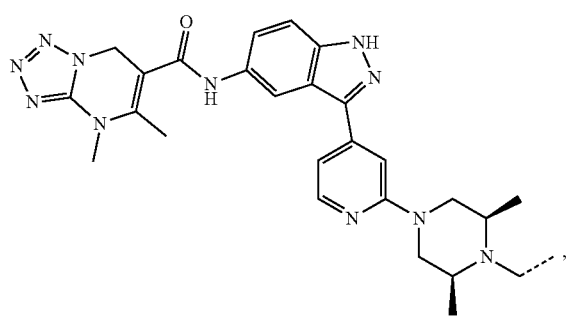
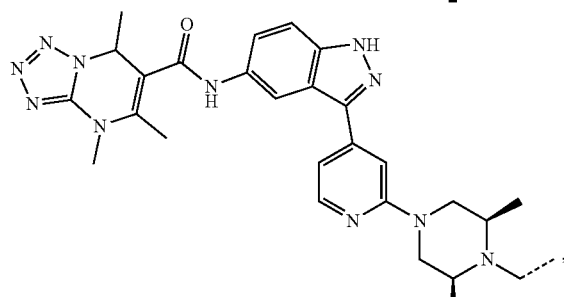
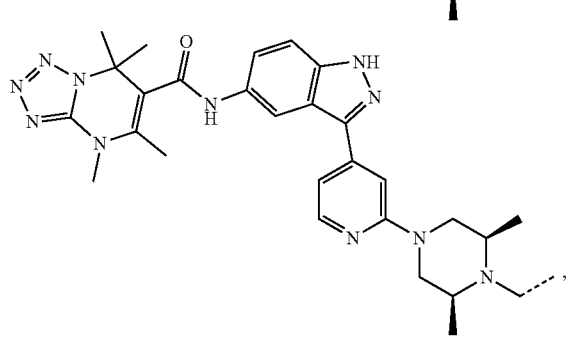
198
-continued
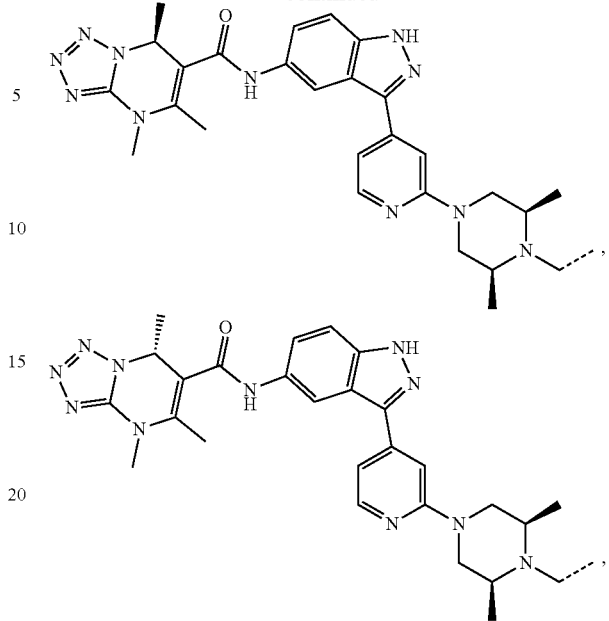
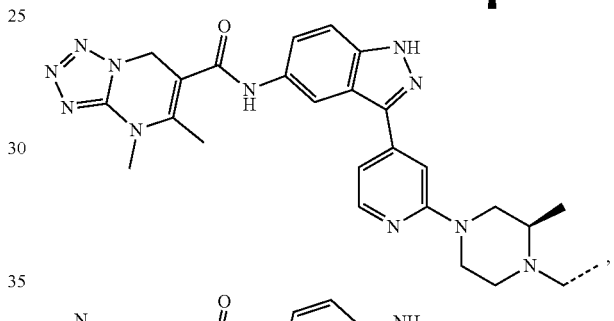
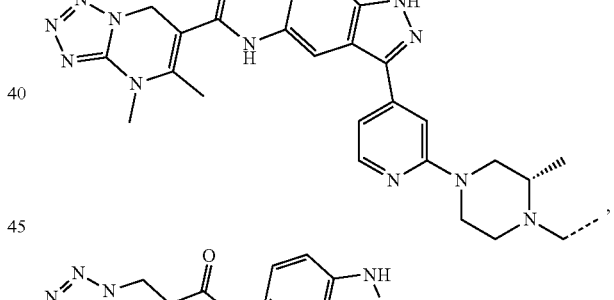
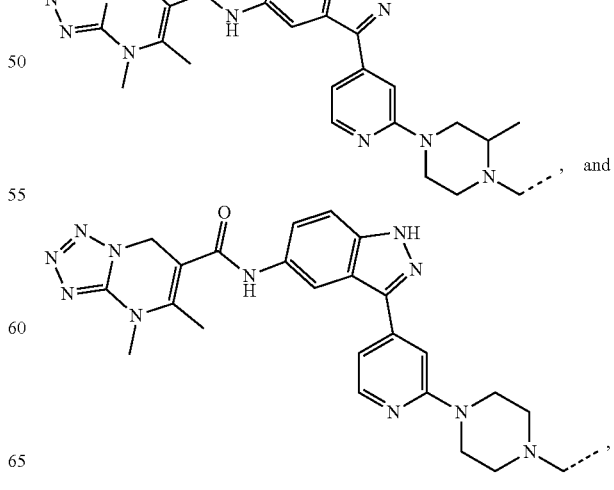

wherein the ⚏ of the PTM indicates the site of attachment of a chemical linking group (L) or a CLM.
In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) has the chemical structure:
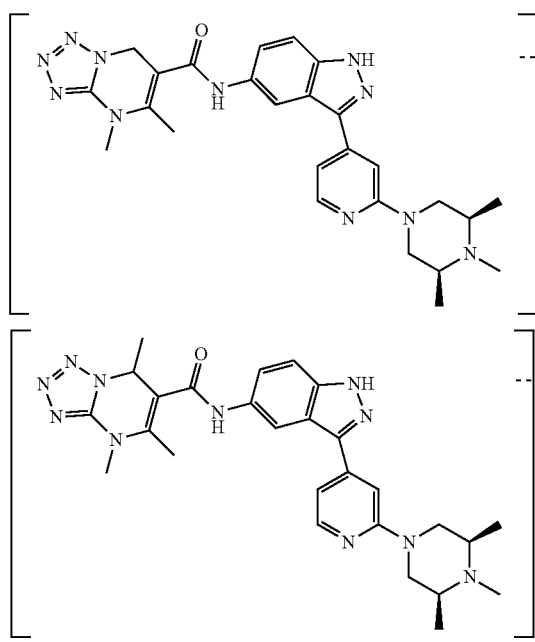
,

,

,
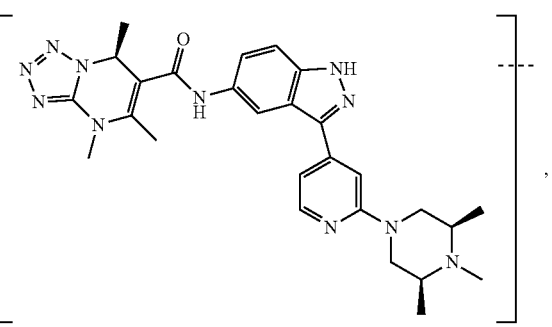
,

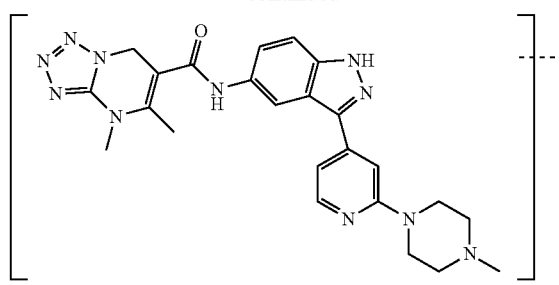
,
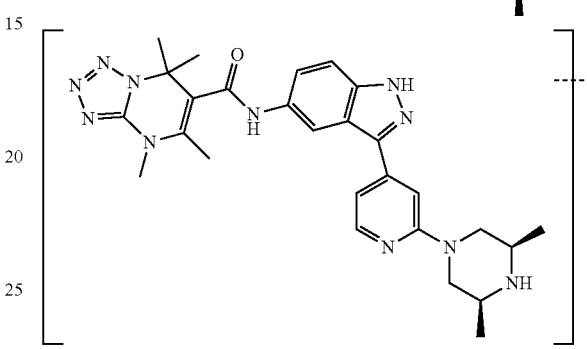
,
and wherein the ⟶ of the PTM indicates the covalent attachment of a chemical linking group or a CLM.
In any aspect or embodiment described herein, the PTM (for e.g. PTM-I, PTM-IIa, PTM-IIb, PTM-IIIa, or PTM-IIIb, or the PTM of Formulas IIIa-IIIh and IVa-IVh) has the chemical structure:
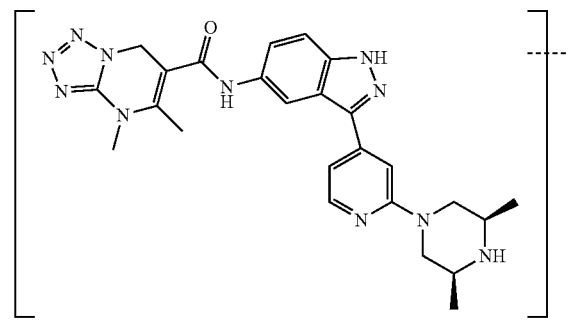
,
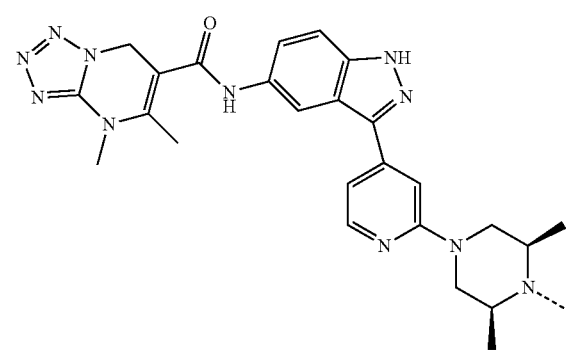
,
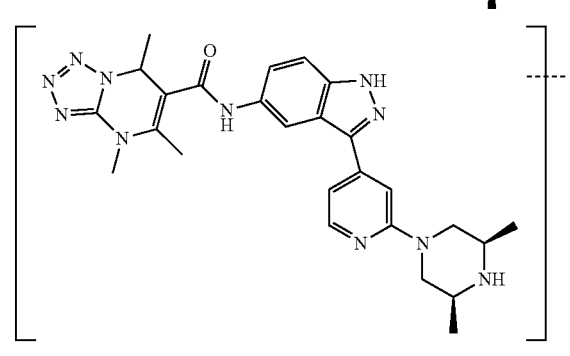
, 203
-continued
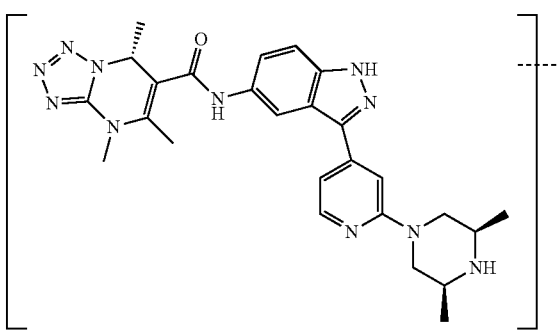,
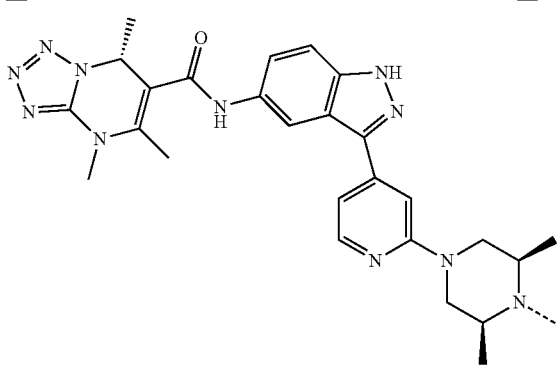,
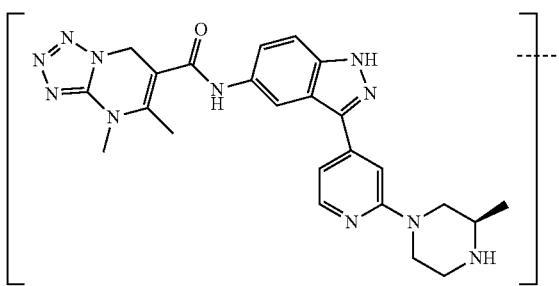,
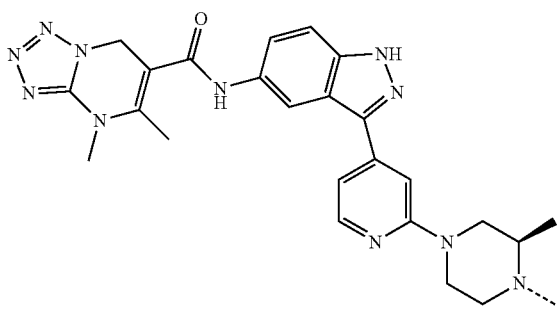,
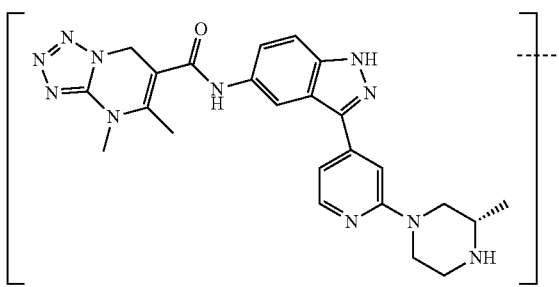,
204
-continued
,
,
,
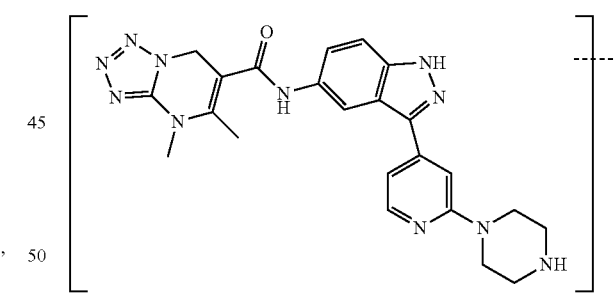,
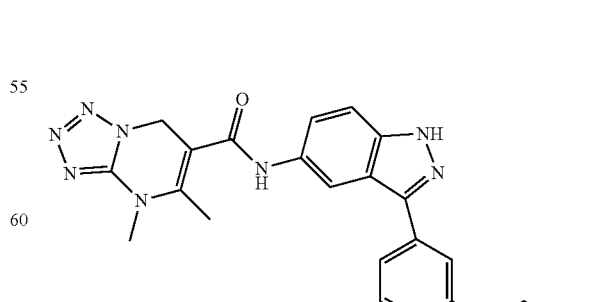

205
-continued
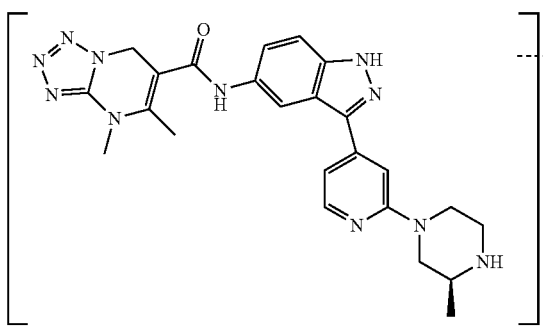
,
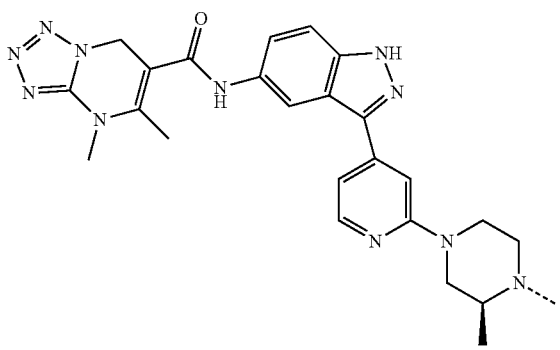
,
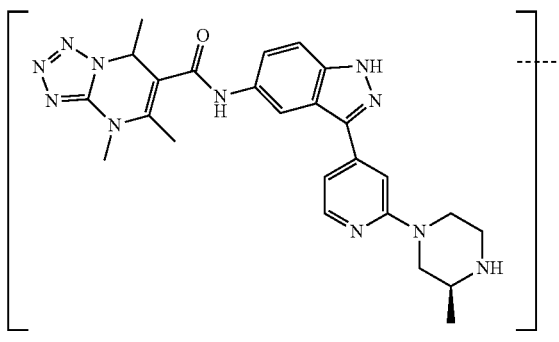
,
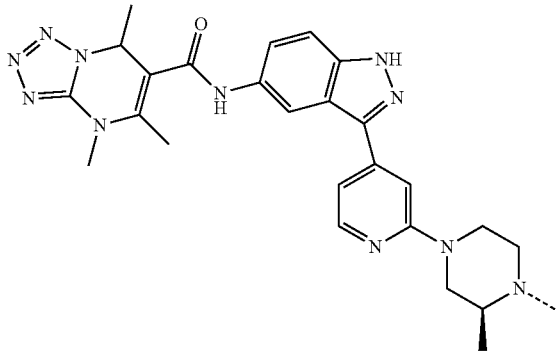
,
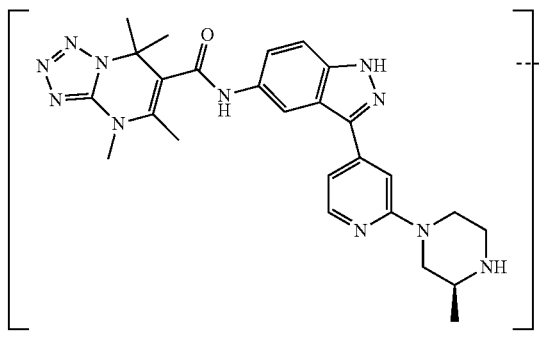
,
206
-continued
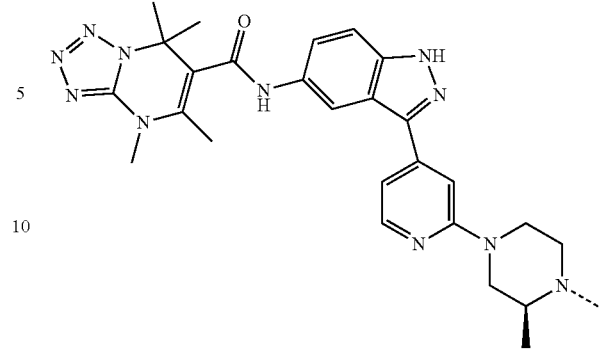
,
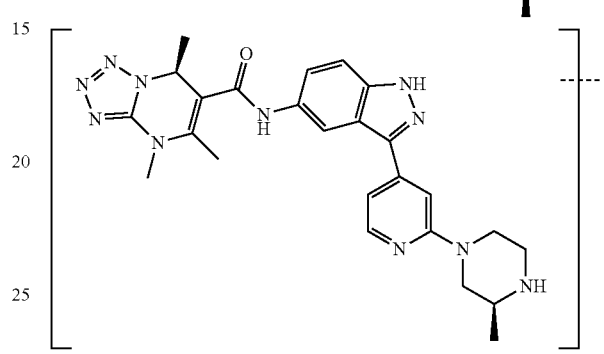
,
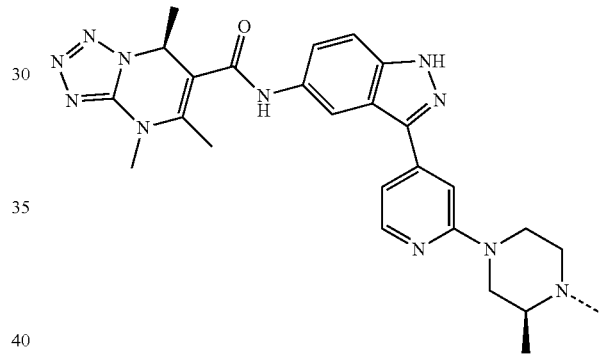
,
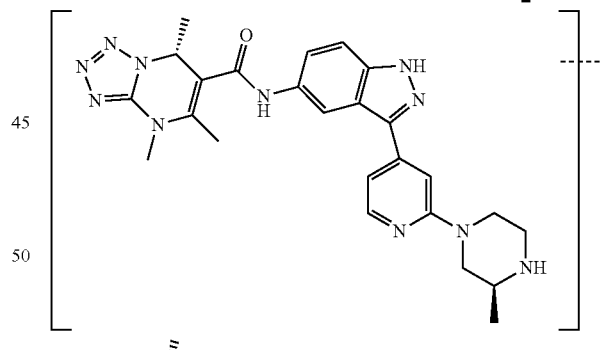
,
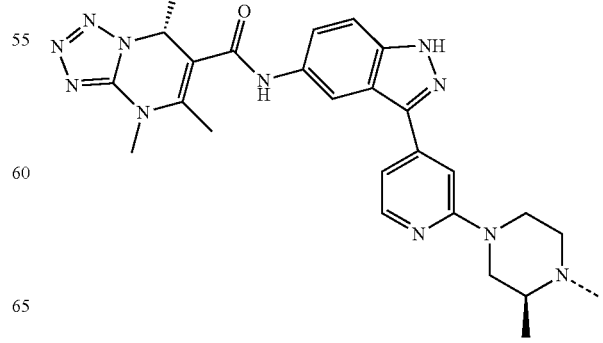
,

207
-continued
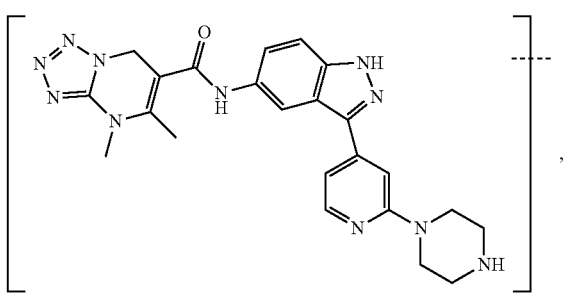
,
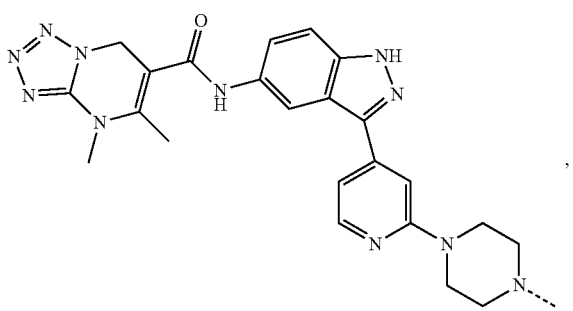
,
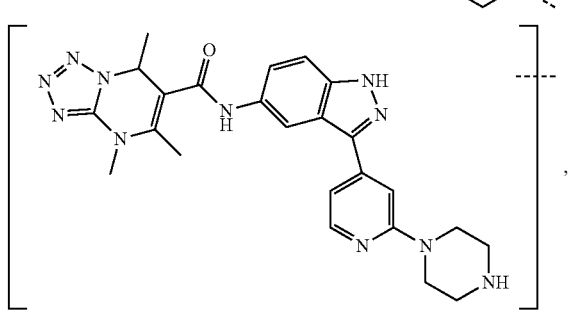
,
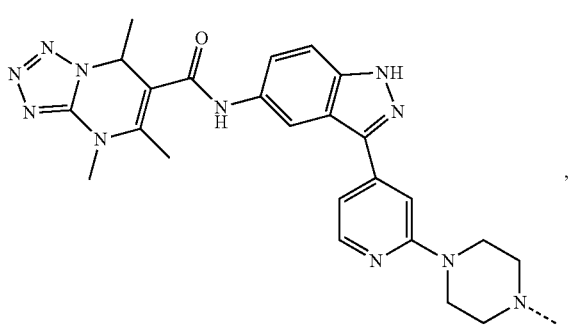
,
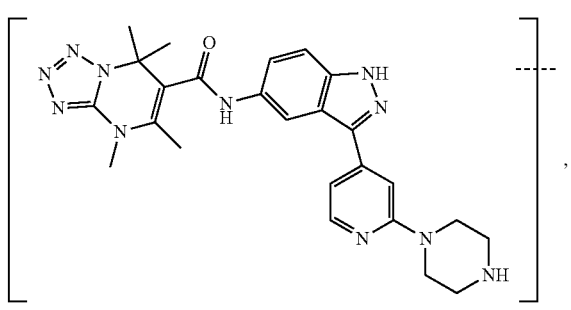
,
208
-continued
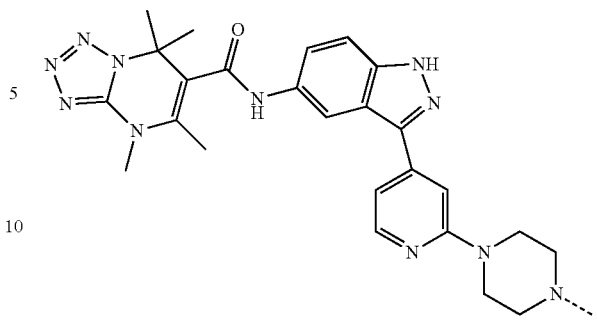
,
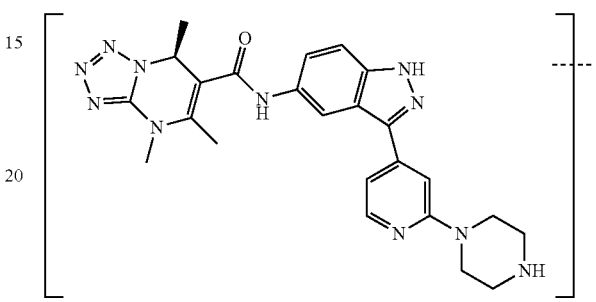
,
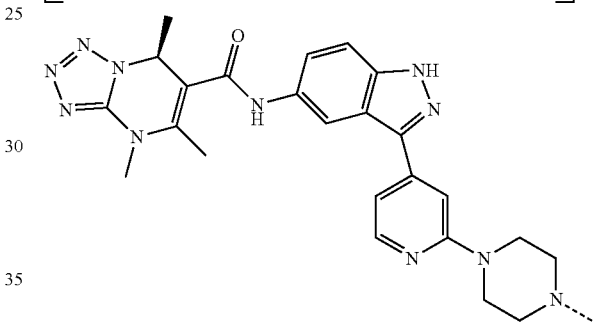
,
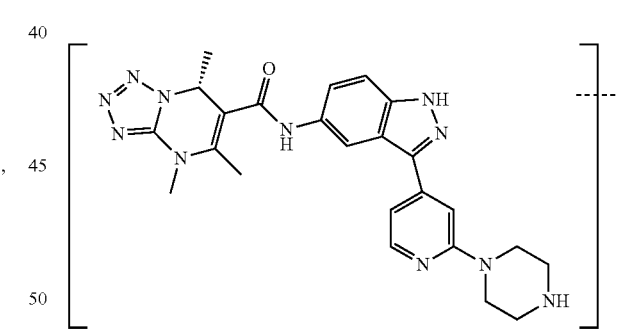
,
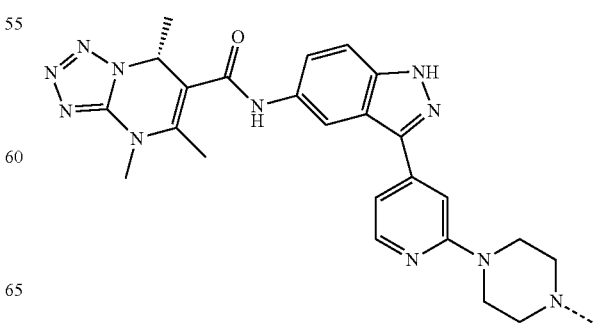
,

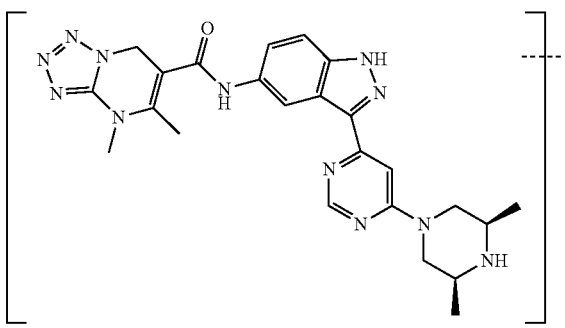,
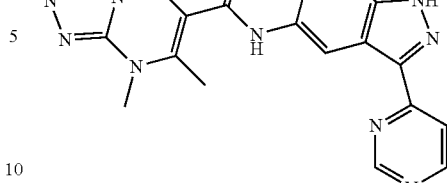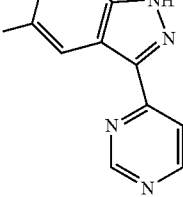,
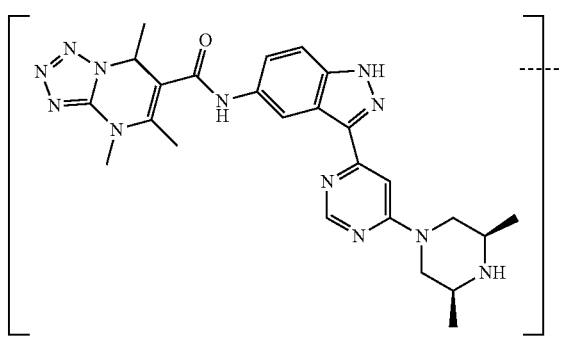,
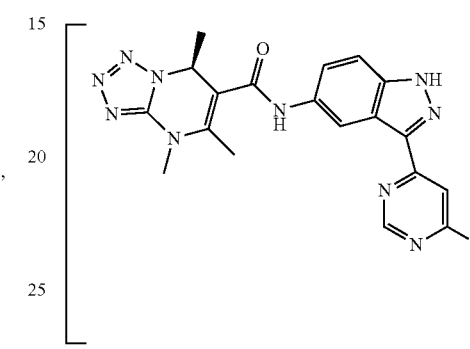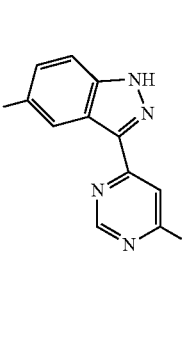,
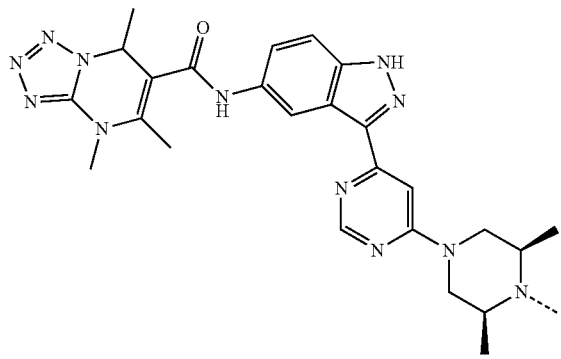,
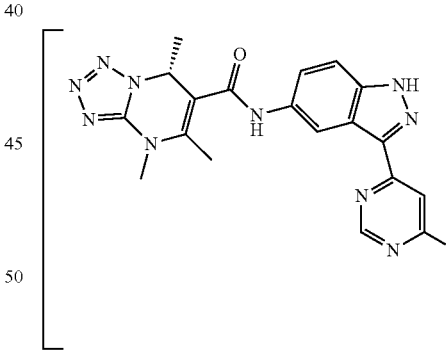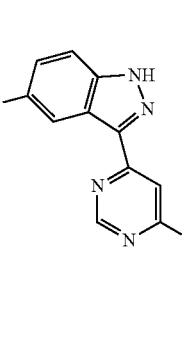,
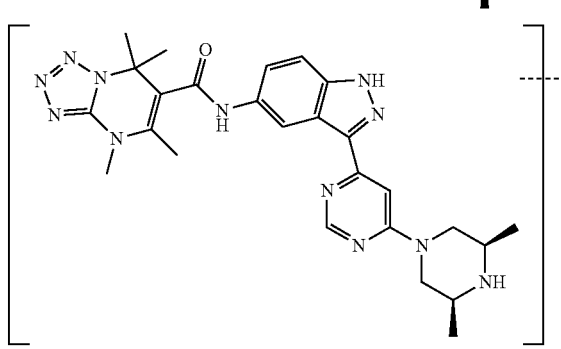,
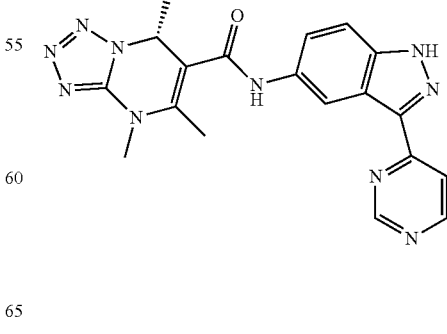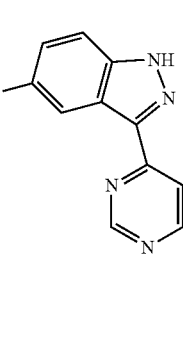, 211
-continued
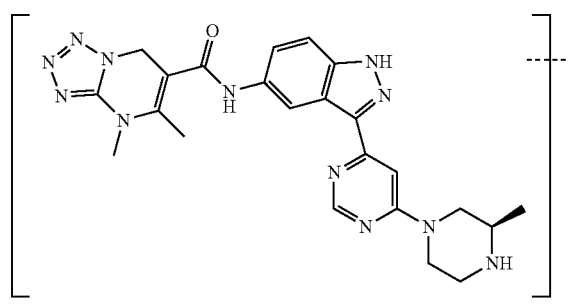
,
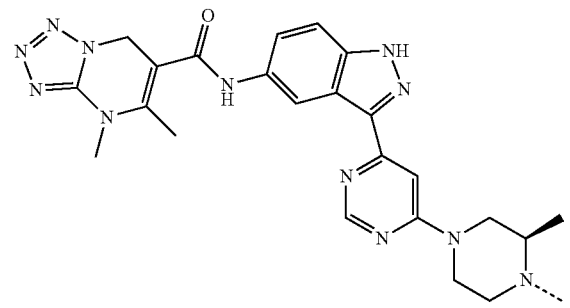
,
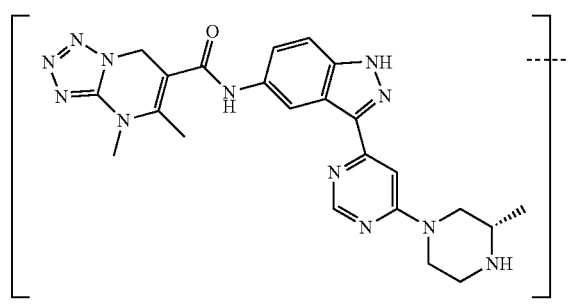
,
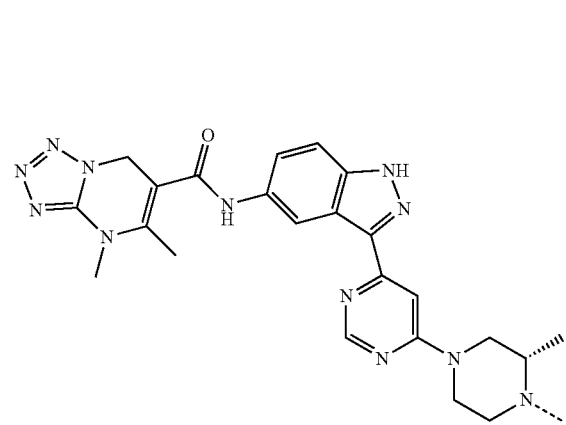
,
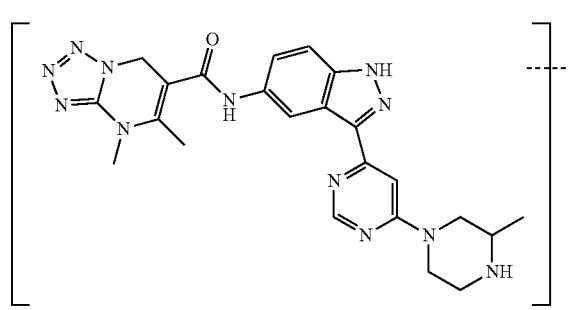
,
212
-continued

,

,

,
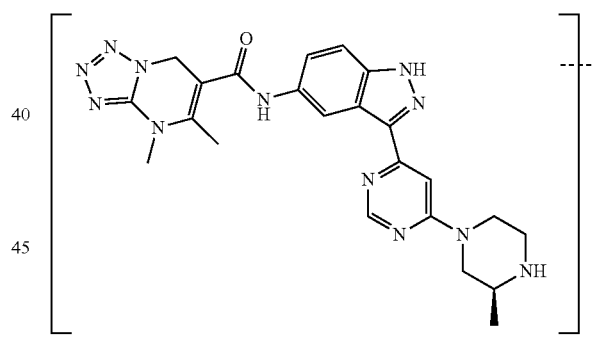
,
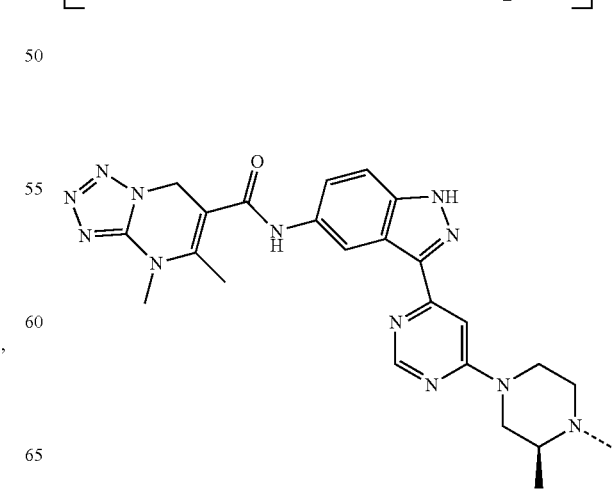
,

213
-continued
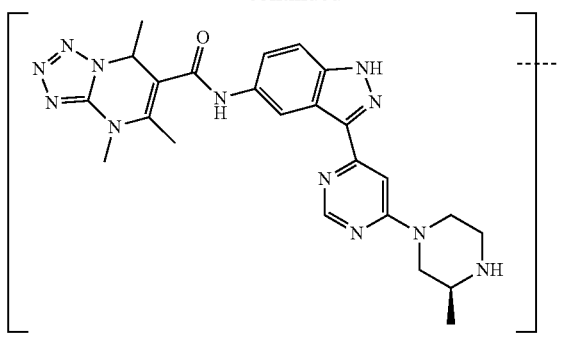,
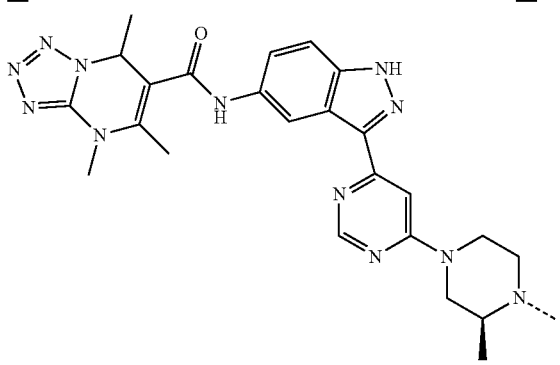,
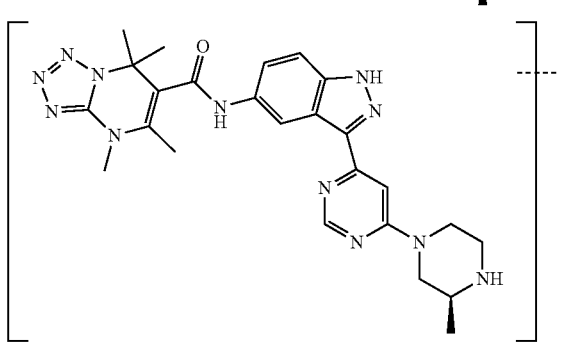,
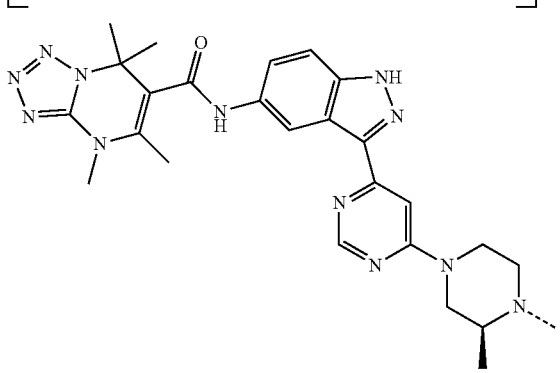,
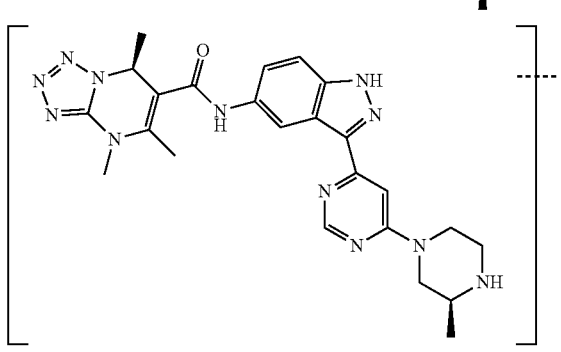,
214
-continued
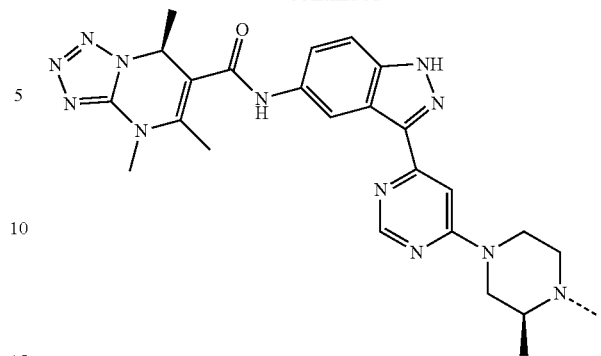,
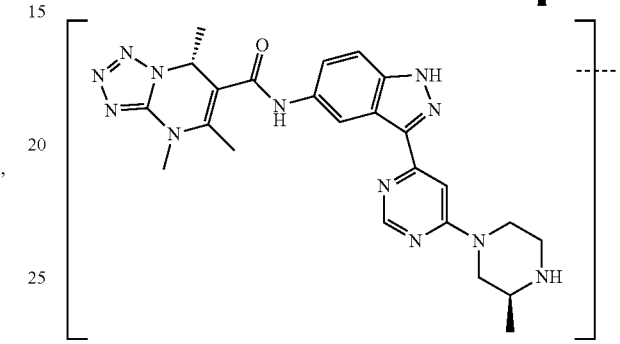,
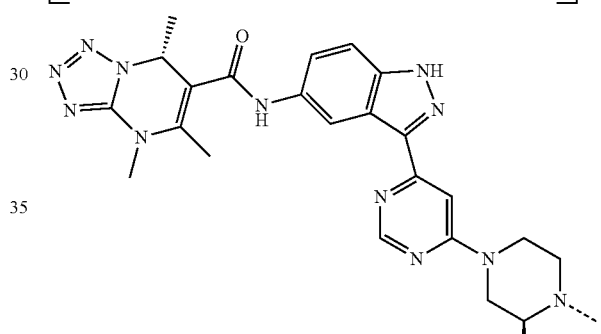,
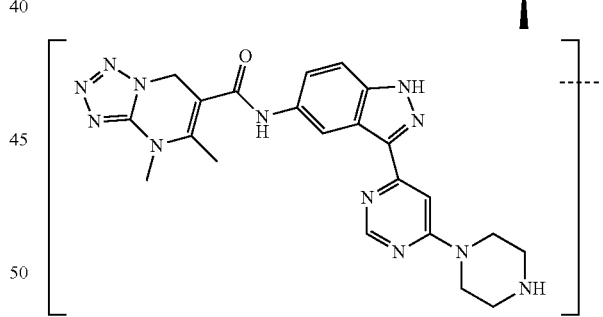,
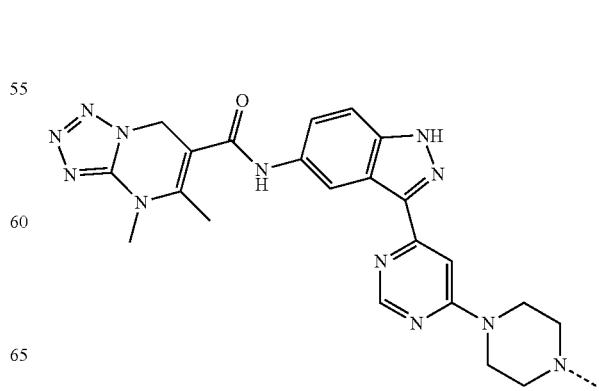,

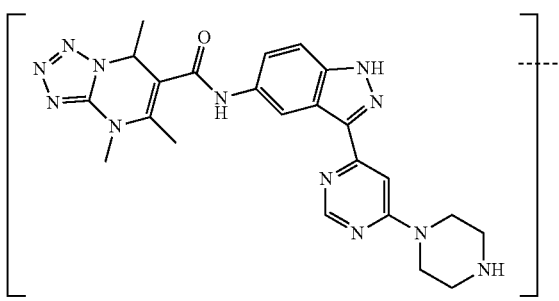,
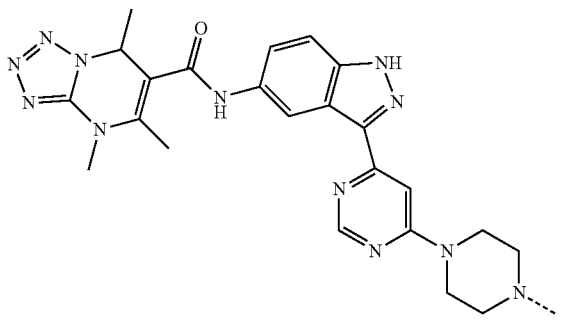,
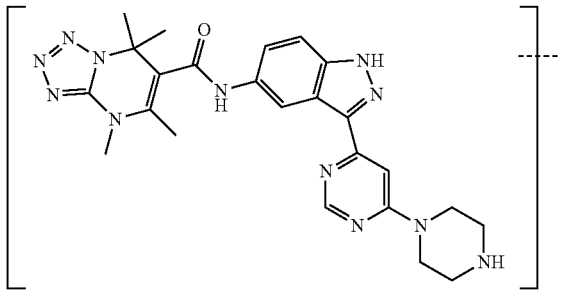,
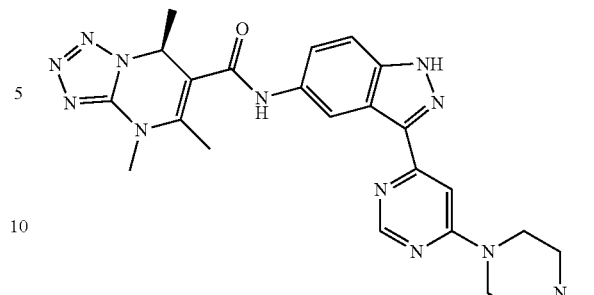,
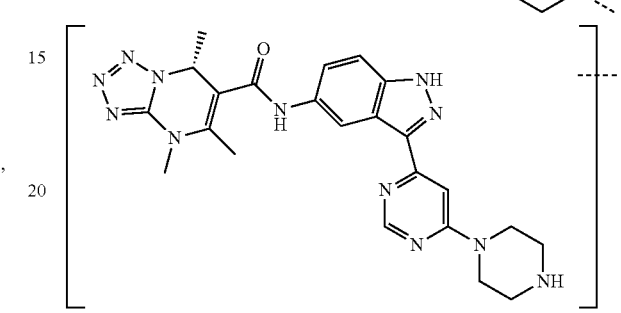,
,
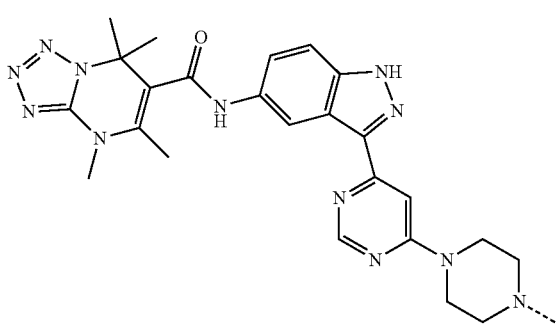,
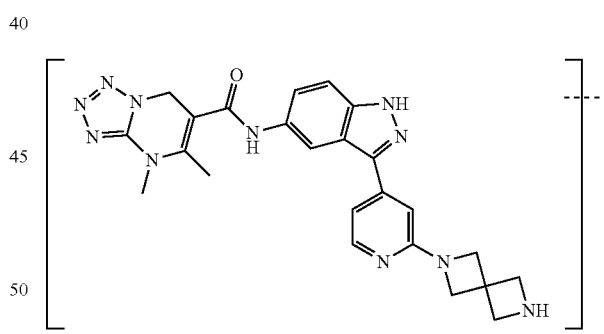,
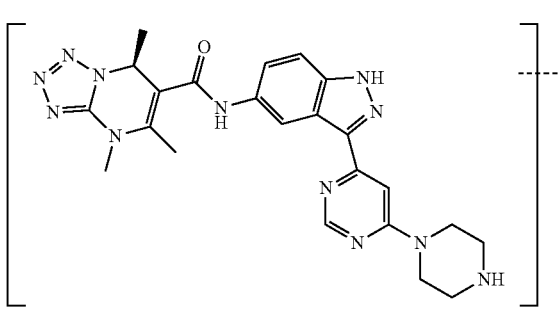,
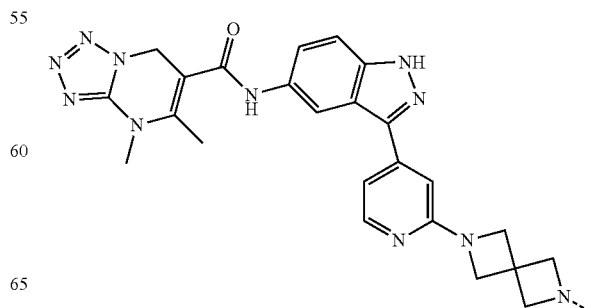,

217
-continued
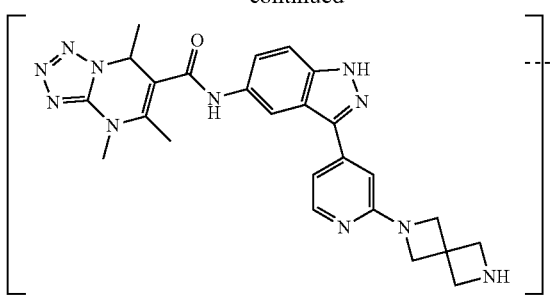
,
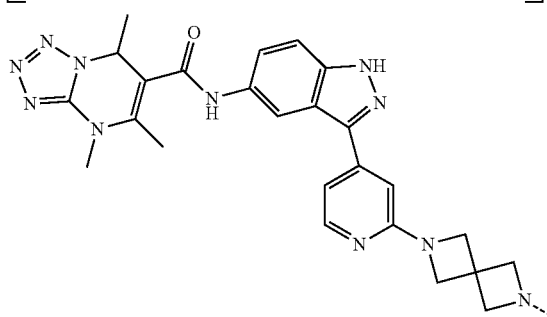
,
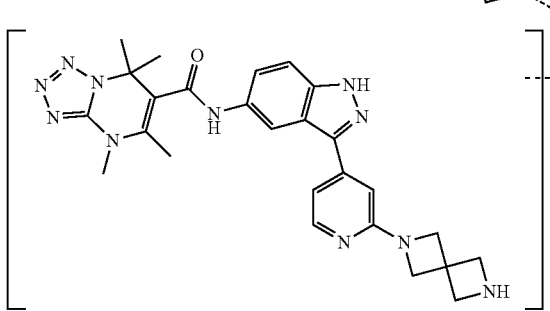
,
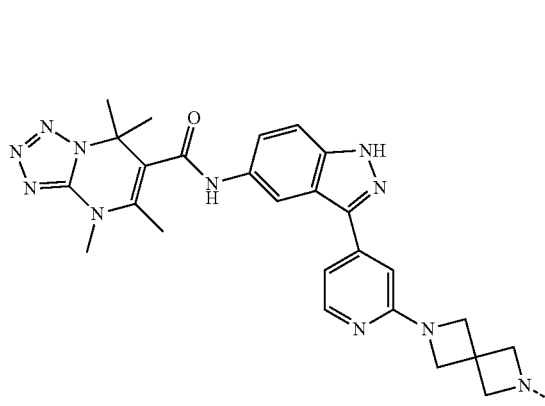
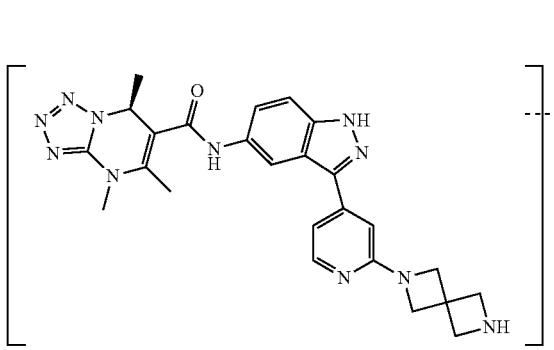
,
218
-continued
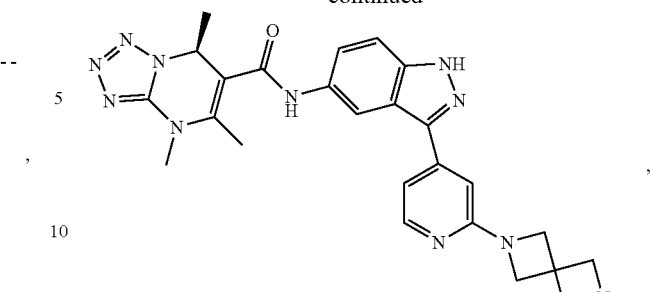
,
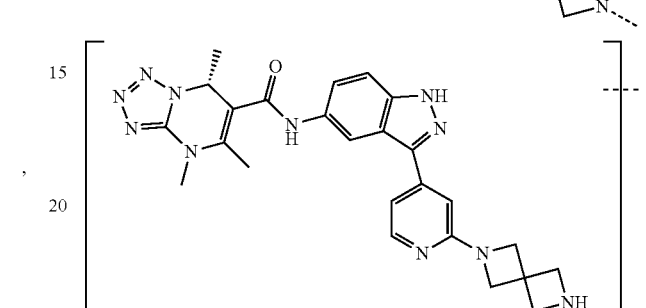
,
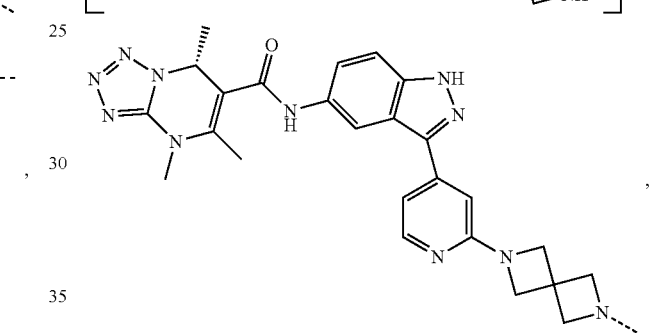
,
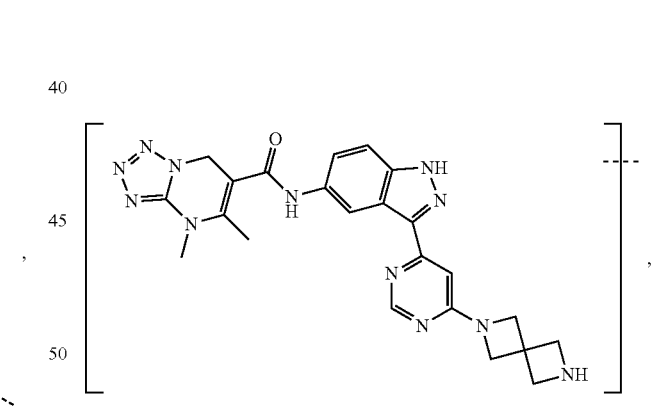
,
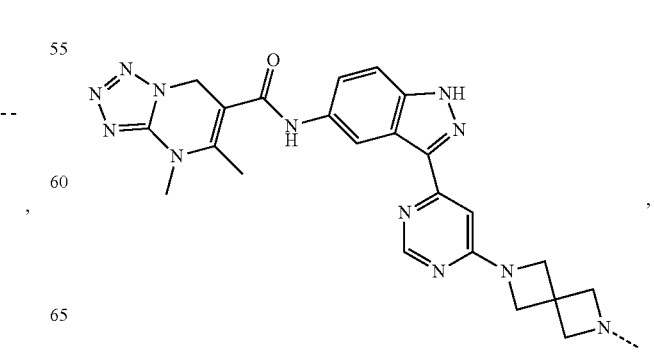
,

219
-continued
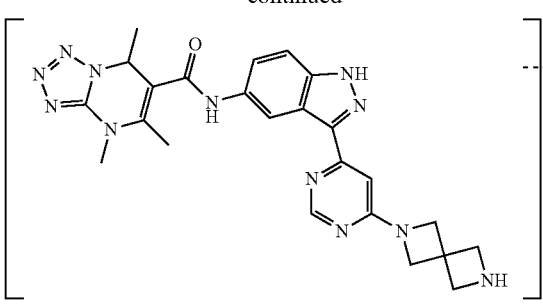
,
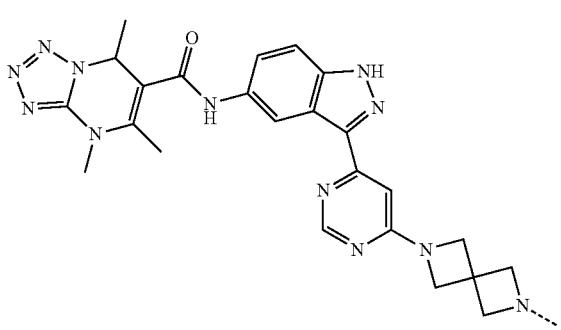
,
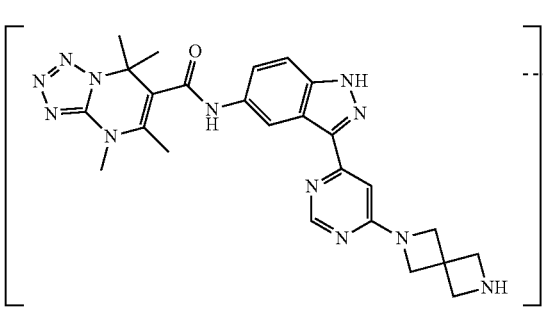
,
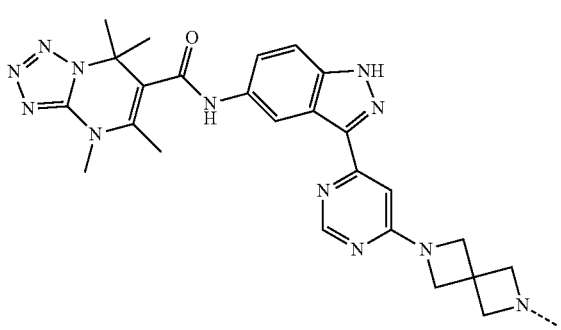
,
220
-continued
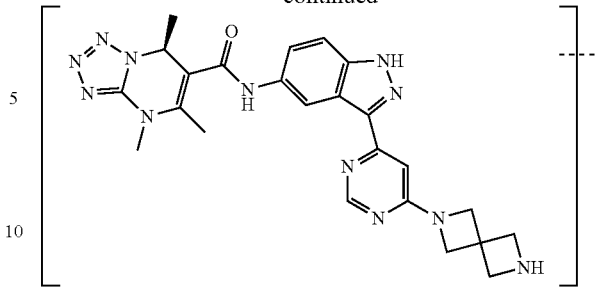
,
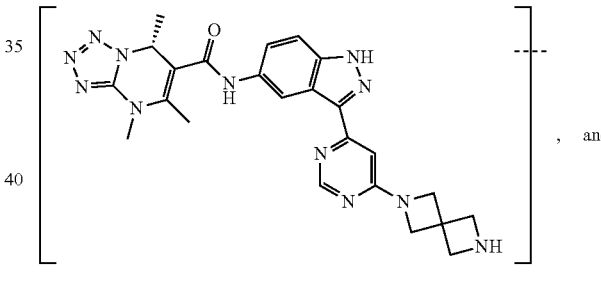
, and
wherein the ⌇⌇⌇ indicates a site of attachment of a linker or ULM, and wherein each PTM is coupled to at least one linker or ULM
In any aspect or embodiment described herein, the heterobifunctional compound is represented by the chemical structure:

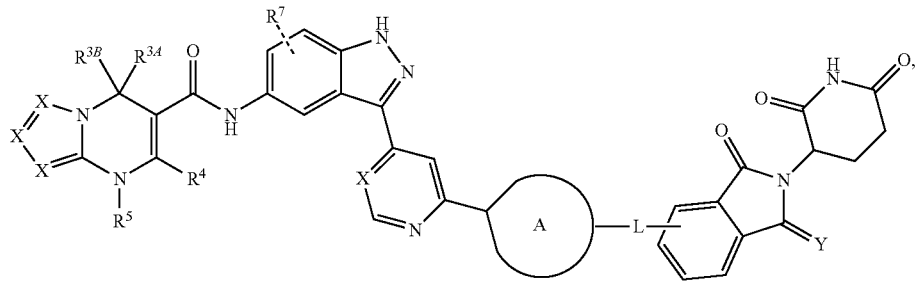

(Formula III)

wherein:
$R^{3A}$, $R^{3B}$, $R^4$ and $R^5$ are defined as described herein;
X is CH or N;
$R^7$ is H, C1-C6 alkyl, C1-C6 alkoxy, or halogen;
A is a 4-7 membered aryl, heteroaryl, cycloalkyl or heterocycloalkyl;
L is a chemical linker group optionally coupled to the phthalimido group via an oxygen, amine group or methyl group;
X is CH or N; and
Y is O or $H_2$ (i.e., absent).

In any aspect or embodiment described herein, the heterobifunctional compound is represented by the chemical structure:

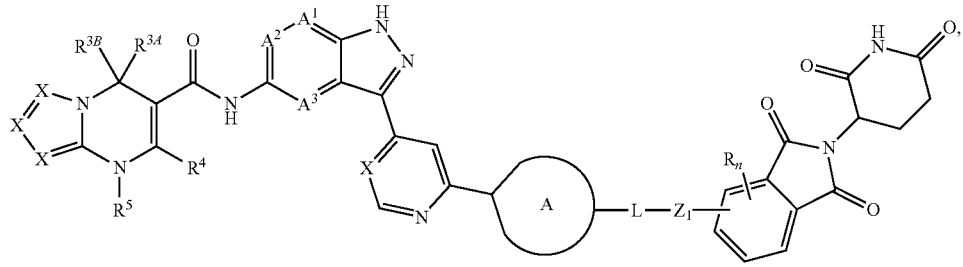

(Formula IIIa)

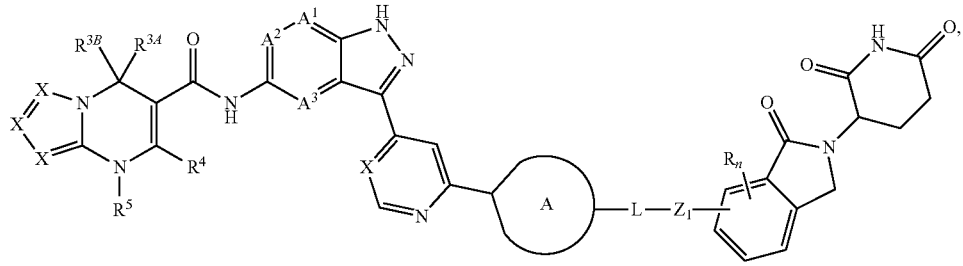

(Formula IIIb)

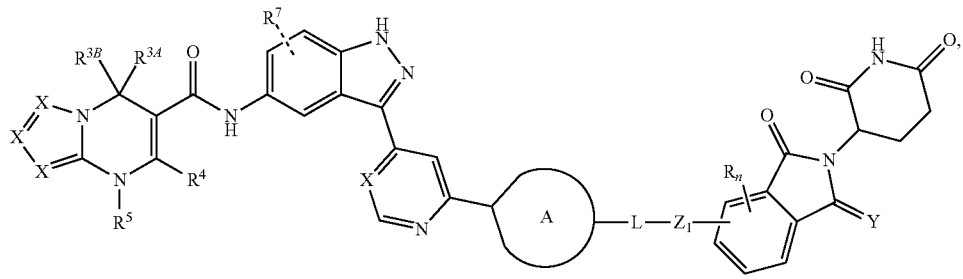

(Formula IIIc)

-continued (Formula IIId)
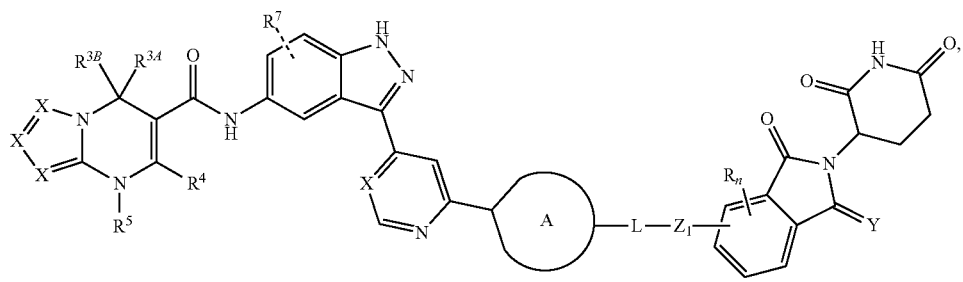

(Formula IIIe)
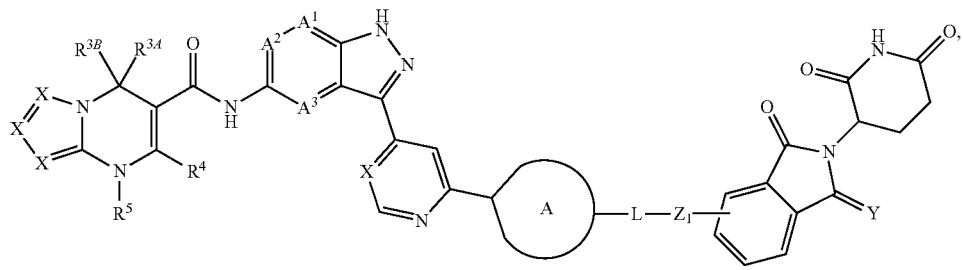

(Formula IIIf)
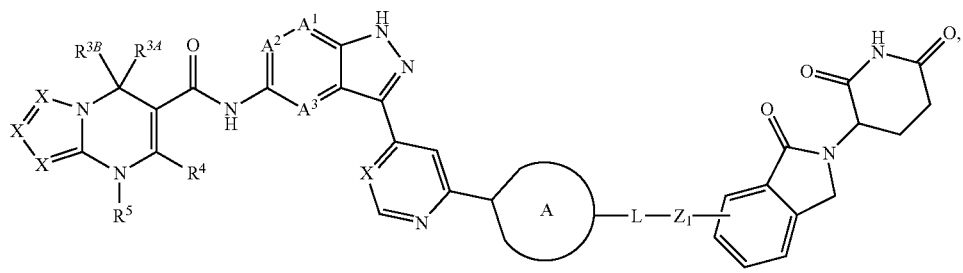

(Formula IIIg)
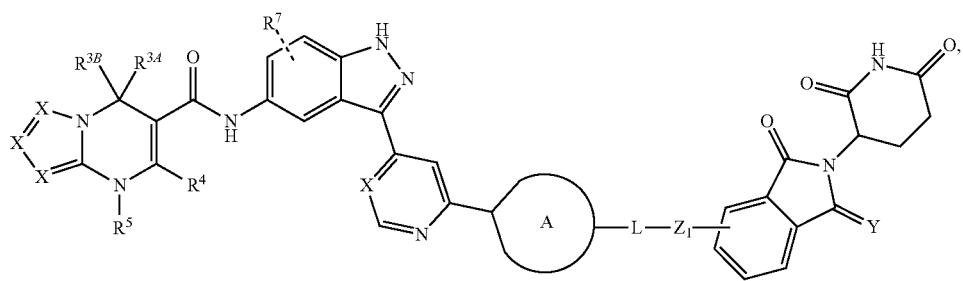

(Formula IIIh)
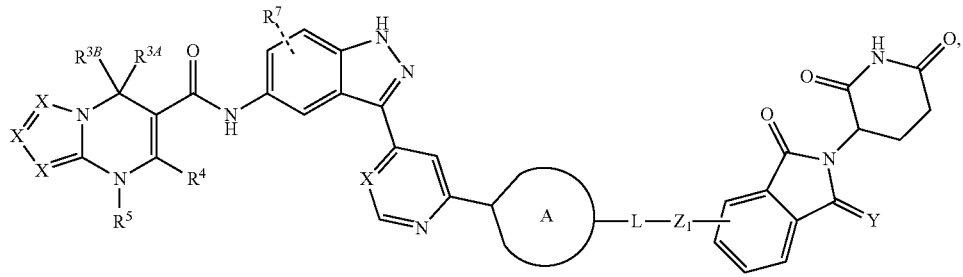

wherein:

$Z_1$ is an R group of a CLM as described in any aspect or embodiment described herein that is modified to be covalently linked to L, such a group selected from —C(=O)—, —CONR'—, —O—, —NR'—, a carbon shared with a cyclic group of L, or a nitrogen shared with a cyclic group of L;

n is an integer from 0 to 3 (e.g., 0, 1, 2, or 3);

R is selected from H, O, OH, N, NH, $NH_2$, Cl, —F, —Br, —I, methyl, optionally substituted linear or branched alkyl (e.g., optionally substituted linear or branched C1-C6 alkyl), optionally substituted linear or branched alkoxy (e.g., optionally substituted linear or branched C1-C6 alkoxy), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy;

L, $R^{3A}$, $R^{3B}$, $R^4$, and $R^5$ are defined as in any aspect or embodiment described herein;
each X is individually CH or N;
$R^7$ is H, C1-C6 alkyl, C1-C6 alkoxy, or halogen;
A is a 4-7 membered aryl, heteroaryl, cycloalkyl or heterocycloalkyl or a 6- to 12-membered (e.g., 8- to 10-membered) spirocycloalkyl or spiroheterocycloalkyl, each optionally substituted with 1, 2, 3, or 4 groups selected from the group consisting of H, $C_{1-3}$ alkyl, methyl, ethyl, and halogen;
X is CH or N;
$A^1$, $A^2$, and $A^3$ as defined in any aspect or embodiment described herein (e.g., $A^1$ and $A^3$ are individually N or CH, and $A^2$ is $CR^7$ or N); and
Y is O or $H_2$ (i.e., absent).

In any aspect or embodiment described herein, the heterobifunctional compound is represented by the chemical structure:

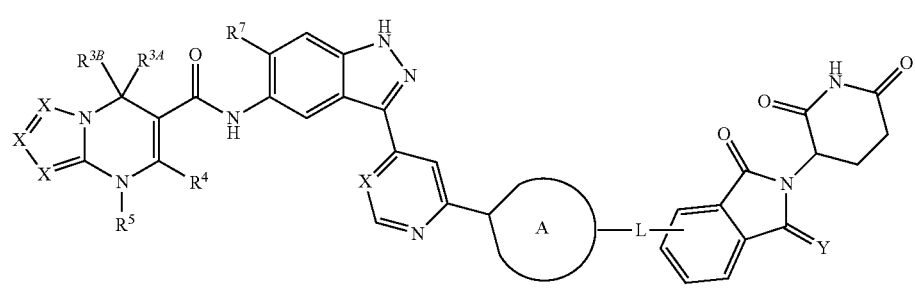

(PTM-IV)

wherein:
$R^{3A}$, $R^{3B}$, $R^4$, and $R^5$ are defined as described herein;
$R^7$ is H or halogen;
A is a 4-7 membered heterocycloalkyl;
L is a chemical linker group optionally coupled to the phthalimido group via an oxygen, amine group or methyl group;
X is CH or N; and
Y is O or $H_2$ (i.e., absent).

In any aspect or embodiment described herein, the heterobifunctional compound is represented by the chemical structure:

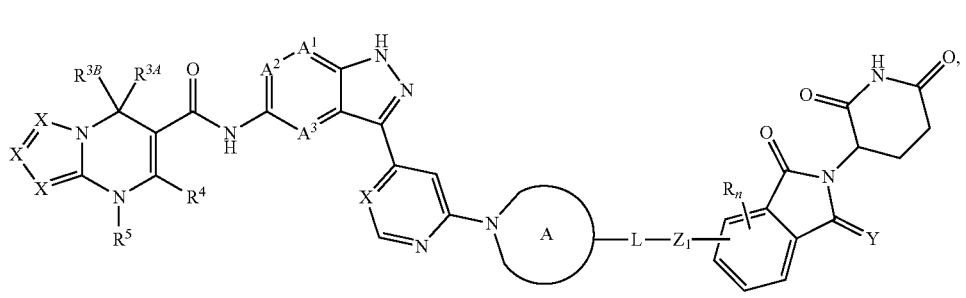

(Formula IVa)

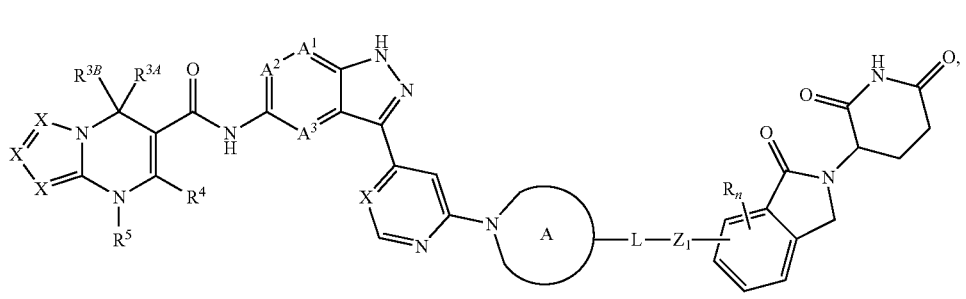

(Formula IVb)

-continued
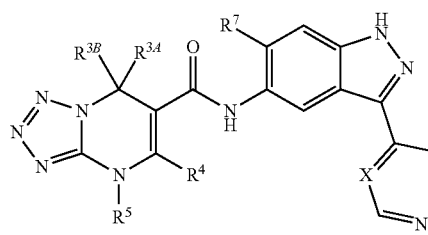 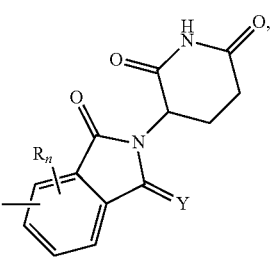
(Formula IVc)
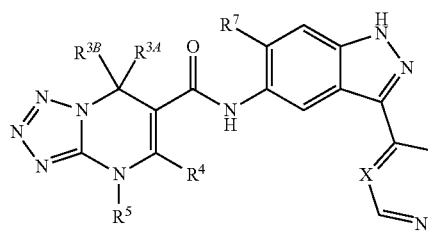 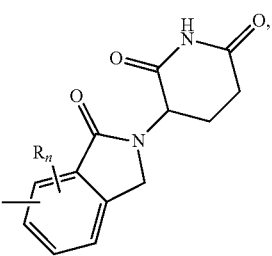
(Formula IVd)
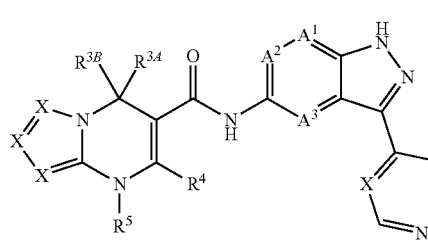 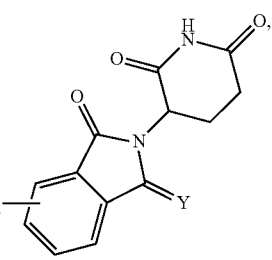
(Formula IVe)
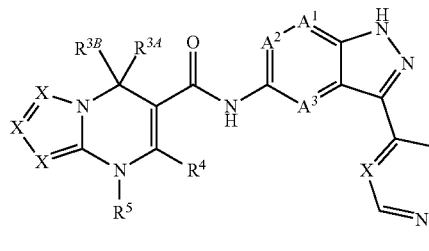 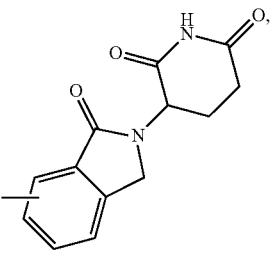
(Formula IVf)
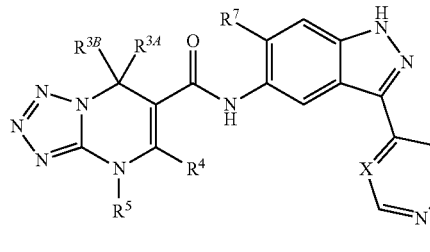 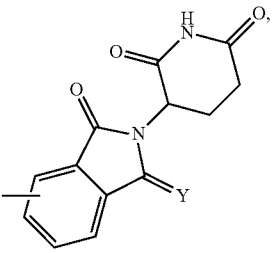
(Formula IVg)

(Formula IVh)

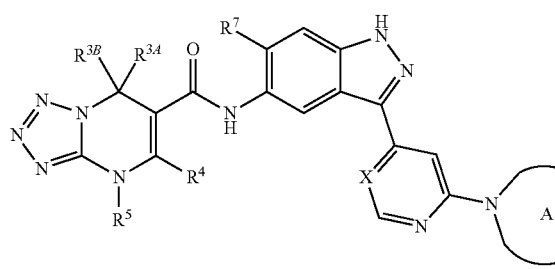

wherein:
- $Z_1$ is an R group of a CLM as described in any aspect or embodiment described herein that is modified to be covalently linked to L, such a group selected from —C(=O)—, —CONR'—, —O—, —NR'—, a carbon shared with a cyclic group of L, or a nitrogen shared with a cyclic group of L;
- n is an integer from 0 to 3 (e.g., 0, 1, 2, or 3);
- R is selected from H, O, OH, N, NH, NH$_2$, Cl, —F, —Br, —I, methyl, optionally substituted linear or branched alkyl (e.g., optionally substituted linear or branched C1-C6 alkyl), optionally substituted linear or branched alkoxy (e.g., optionally substituted linear or branched C1-C6 alkoxy), -alkyl-aryl (e.g., an -alkyl-aryl comprising at least one of C1-C6 alkyl, C4-C7 aryl, or a combination thereof), aryl (e.g., C5-C7 aryl), amine, amide, or carboxy;
- L, $R^{3A}$, $R^{3B}$, $R^4$, and $R^5$ are defined as in any aspect or embodiment described herein;
- $R^7$ is H or halogen;
- A is a 4-7 membered heterocycloalkyl or a 6- to 12-membered (e.g., 8- to 10-membered) spiroheterocycloalkyl, each optionally substituted with 1, 2, 3, or 4 groups selected from the group consisting of H, $C_{1-3}$ alkyl, methyl, ethyl, and halogen;
- each X is individually CH or N;
- $A^1$, $A^2$, and $A^3$ as defined in any aspect or embodiment described herein (e.g., $A^1$ and $A^3$ are individually N or CH, and $A^2$ is $CR^7$ or N); and
- Y is O or H$_2$ (i.e., absent).

In any aspect or embodiment described herein, the heterobifunctional compound has the chemical structure:

PTM-L-CLM, or a pharmaceutically acceptable salt or solvate thereof, wherein:
(a) the CLM is a small molecule E3 ubiquitin ligase binding moiety that binds a cereblon E3 ubiquitin ligase and is represented by the chemical structure:

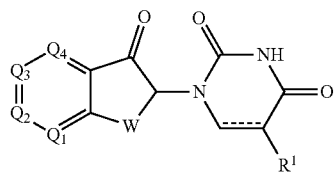 (h)

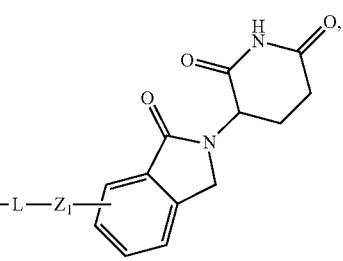

(i)

(j)

(k)

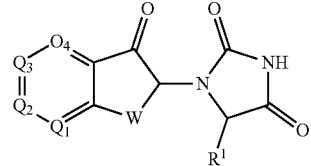 (l)

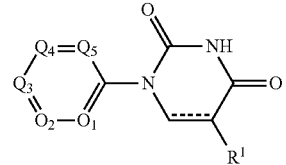 (m)

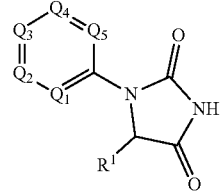 (n)

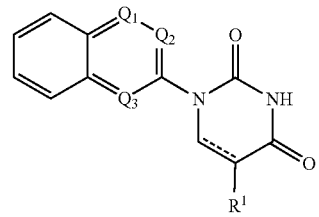

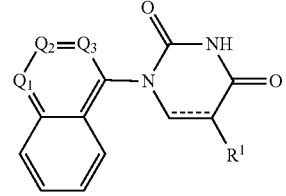

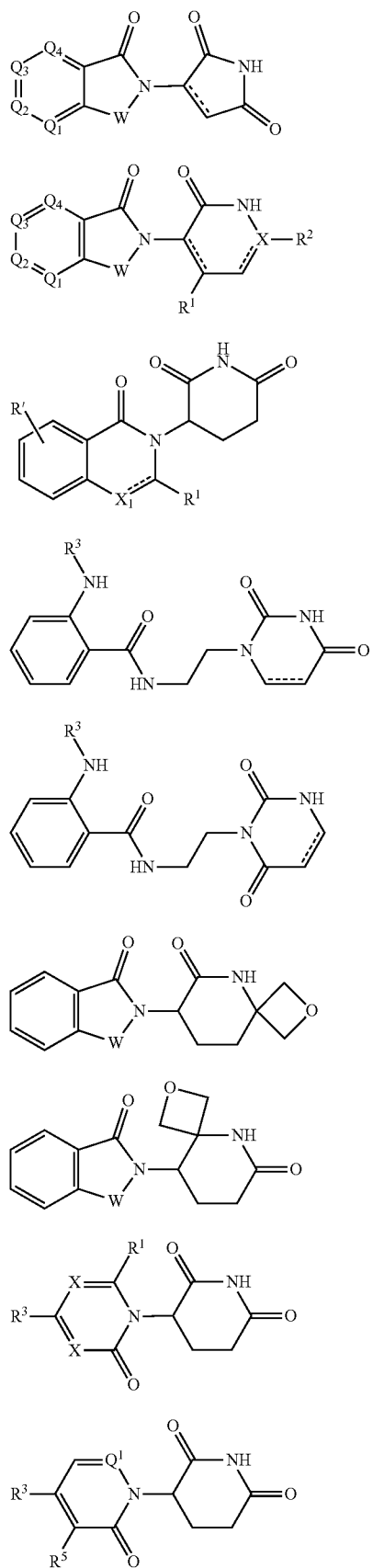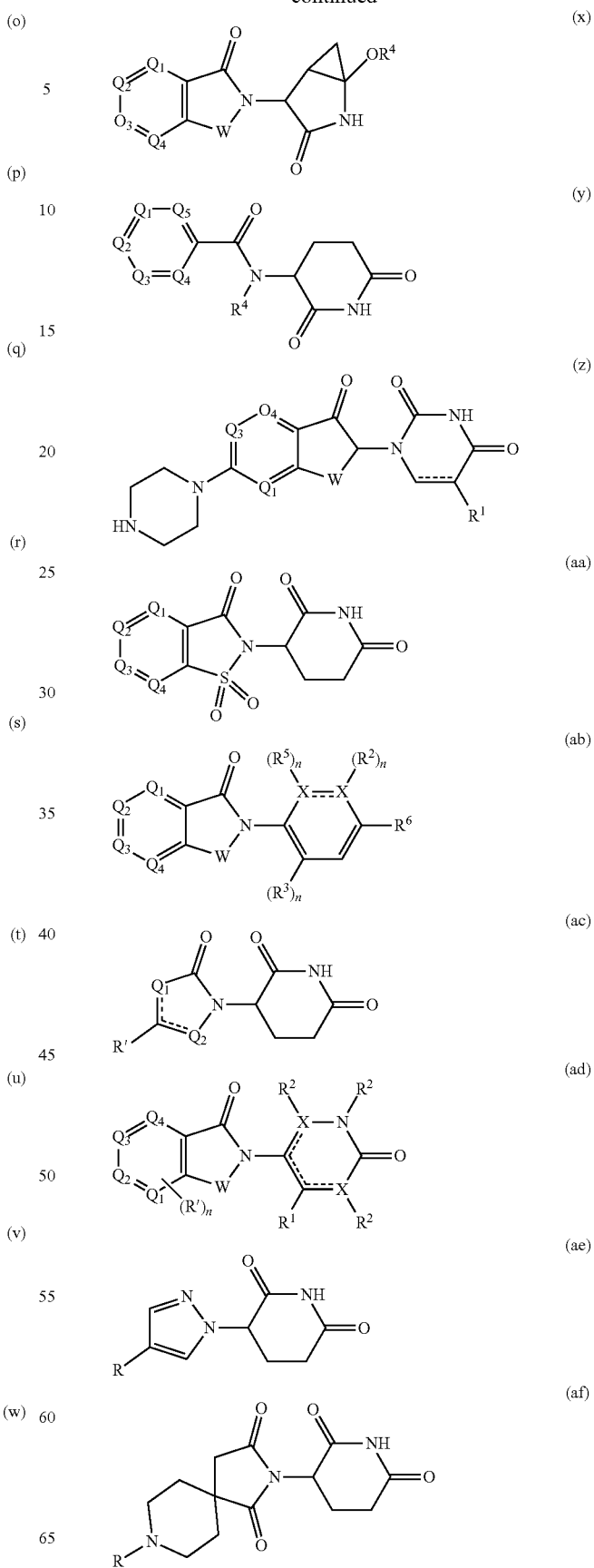

-continued (ag)
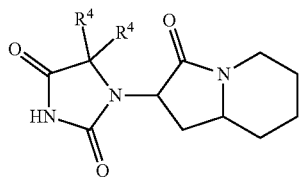

(ah)
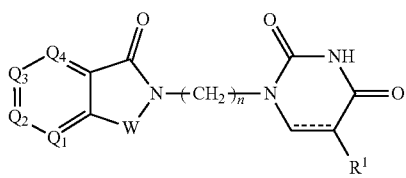

(ai)
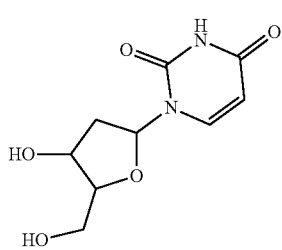

(aj)
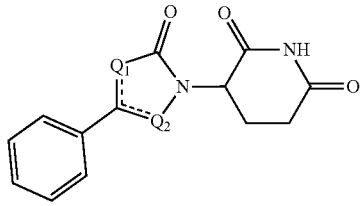

(ak)
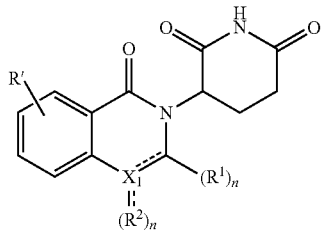

(al)
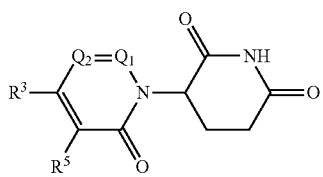

(am)
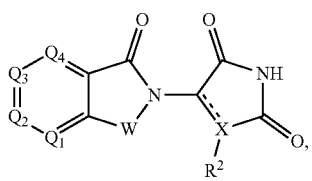

wherein:
W is selected from the group consisting of $CH_2$, O, CHR, C=O, $SO_2$, NH, N, optionally substituted cyclopropyl group, optionally substituted cyclobutyl group, and N-alkyl;
$Q_1$, $Q_2$, $Q_3$, $Q_4$, $Q_5$ each independently represent a carbon C or N substituted with a group independently selected from R', N or N-oxide;

$R^1$ is selected from absent (i.e., a bond), H, OH, CN, C1-C3 alkyl, C=O;
$R^2$ is selected from the group absent (i.e., a bond), H, OH, CN, C1-C3 alkyl, $CHF_2$, $CF_3$, CHO, $C(=O)NH_2$;
$R^3$ is selected from a bond, H, alkyl (e.g., C1-C6 or C1-C3 alkyl), substituted alkyl (e.g., substituted C1-C6 or C1-C3 alkyl), alkoxy (e.g., C1-C6 or C1-C3 alkoxyl), substituted alkoxy (e.g., substituted C1-C6 or C1-C3 alkoxyl);
$R^4$ is selected from a bond, H, alkyl, substituted alkyl;
$R^5$ and $R^6$ are each independently a bond, H, halogen, C(=O)R', CN, OH, $CF_3$;
X is C, CH, C=O, or N;
$X_1$ is C=O, N, CH, or $CH_2$;
R' is selected from a bond, H, halogen, amine, alkyl (e.g., C1-C3 alkyl), substituted alkyl (e.g., substituted C1-C3 alkyl), alkoxy (e.g., C1-C3 alkoxyl), substituted alkoxy (e.g., substituted C1-C3 alkoxyl), $NR^2R^3$, $C(=O)OR^2$, optionally substituted phenyl;
n is 0-4;
⫽ is a single or double bond; and
the CLM is covalently joined to a PTM, a chemical linker group (L), a ULM, or CLM);

(b) the PTM is a small molecule Leucine-rich repeat kinase 2 (LRRK2) targeting moiety that binds to the human LRRK2 or mutant thereof represented by the chemical structure:

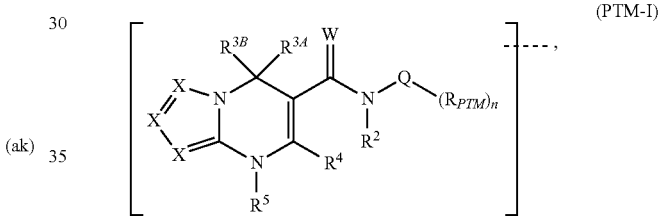
(PTM-I)

wherein:
X is CH or N;
W is O or S;
Q is selected from one of the following:

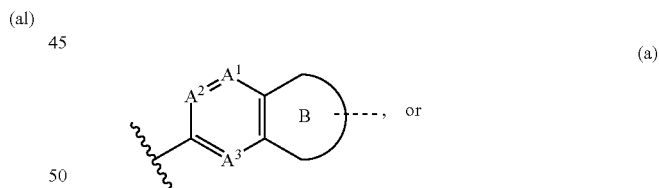
(a)

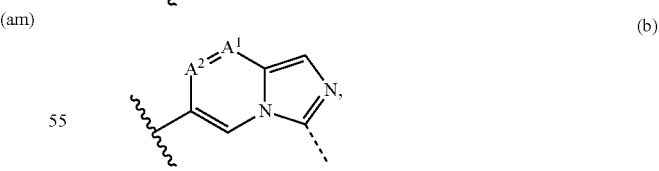
(b)

wherein:
$A^1$, $A^2$, and $A^3$ are each independently selected from N and $CR^6$, wherein for (a) no more than two of $A^1$, $A^2$, and $A^3$ are simultaneously N,
ring B is an optionally substituted C3-C8 aryl, optionally substituted C3-C8 heteroaryl, optionally substituted C3-C8 cycloalkyl, optionally substituted C3-C8 heterocycloalkyl, optionally substituted C3-C8 aryl, optionally substituted C3-C8 aryl, the  of Q indicates the point of attachment with the nitrogen, and the  of Q indicates an optional covalent attachment to $R_{PTM}$;

$R^2$ is H or $C_{1-4}$ alkyl;

$R^{3A}$ and $R^{3B}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^dR^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^1$ are each optionally substituted with 1, 2, 3, 4, or 5 substituents independently selected from $Cy^2$, $Cy^2$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

or $R^{3A}$ and $R^{3B}$ together form a $C_{3-7}$ cycloalkyl or 4-10 membered heterocycloalkyl ring, each optionally substituted with 1, 2, 3, 4, or 5 substituents independently selected from $Cy^2$, $Cy^2$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^4$ is H, $C_{1-4}$ alkyl, halo, $C_{1-4}$ haloalkyl, or CN;

$R^5$ is H, $C_{1-6}$ alkyl, $C_{2-6}$ alkenyl, $C_{2-6}$ alkynyl, $C_{6-10}$ aryl, $C_{3-10}$ cycloalkyl, 5-14 membered heteroaryl, 4-14 membered heterocycloalkyl, $C_{6-10}$ aryl —$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$ $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^1$ are each optionally substituted with 1, 2, 3, 4, or 5 substituents independently selected from $Cy^3$, $Cy^3$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, or $S(O)_2NR^{c2}R^{d2}$;

each $R^6$ is independently selected from H, halo, $C_{1-6}$ alkyl, $C_{1-6}$ haloalkyl, $C_{6-10}$ aryl, $C_{3-7}$ cycloalkyl, 5-6 membered heteroaryl, 4-7 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$, wherein said $C_{1-6}$ alkyl, $C_{1-6}$ haloalkyl, $C_{6-10}$ aryl, $C_{3-7}$ cycloalkyl, 5-6 membered heteroaryl, 4-7 membered heterocycloalkyl of $R^6$ are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $Cy^1$ is independently selected from $C_{6-10}$ aryl, $C_{3-10}$ cycloalkyl, 5-14 membered heteroaryl, and 4-14 membered heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;

each $Cy^2$ is independently selected from $C_{6-10}$ aryl, $C_{3-10}$ cycloalkyl, 5-14 membered heteroaryl, and 4-14 membered heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $Cy^3$ is independently selected from $C_{6-10}$ aryl, $C_{3-10}$ cycloalkyl, 5-14 membered heteroaryl, and 4-14 membered heterocycloalkyl, each optionally substituted by 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-14 membered heteroaryl, 4-14 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)

$NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^a$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, and $R^{d3}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R''$, $R^b$, $R^c$, $R^d$, $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, or $R^{d3}$ is optionally substituted with 1, 2, 3, 4, or 5 substituents independently selected from halo, $C_{1-4}$ alkyl, C 1-4 haloalkyl, $C_{1-6}$ haloalkyl, C2-6 alkenyl, C2-6 alkynyl, CN, $OR^{a4}$, $SR^{a4}$, $C(O)R^m$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^m$, $NR^{c4}C(O)NR^{c4}R^{d4}$, $NR^{c4}C(O)OR^{a4}$, $C(=NR^{e4})NR^{c4}R^{d4}$, $NR^{c4}C(=NR^{e4})NR^{c4}R^{d4}$, $S(O)R^{b4}$, $S(O)NR^{c4}R^{d4}$, $S(O)_2R^{b4}$, $NR^{c4}S(O)_2R^{b4}$, $NR^{c4}S(O)_2NR^{c4}R^{d4}$, and $S(O)_2NR^{c4}R^{d4}$;

each $R^{a4}$, $R^{b4}$, $R^{c4}$, and $R^{d4}$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-6 membered heteroaryl, 4-7 membered heterocycloalkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-6 membered heteroaryl, and 4-7 membered heterocycloalkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

each $R^e$, $R^{e1}$, $R^{e2}$, $R^{e3}$, and $R^{e4}$ is independently selected from H, $C_{1-4}$ alkyl, and CN;

$R_{PTM}$ is H; halogen (e.g., Cl or F); —CN; —OH; —NO$_2$; —NH$_2$; optionally substituted linear or branched alkyl (e.g., optionally substituted linear or branched C1-C6 alkyl or optionally substituted linear or branched C1-C4 alkyl or C1-C8 alkyl optionally substituted with OH); optionally substituted cycloalkyl (e.g., cyclopropyl, cyclobutyl, cyclopentyl, cyclohexyl); O-optionally substituted linear or branched C1-C4 alkyl; an optionally substituted C1-C4 alkynyl; an optionally substituted C1-C4 alkyne; optionally substituted linear or branched hydroxyalkyl (e.g., optionally substituted linear or branched C1-C7 hydroxyalkyl); optionally substituted alkylcycloalkyl (e.g., includes optionally substituted C1-C6 alkyl, optionally substituted C3-C10 cycloalkyl; or both); optionally substituted alkyl-aryl (e.g., includes an optionally substituted linear or branched C1-C6 alkyl, an optionally substituted 5-10 member heteroaryl, or both); optionally substituted alkyl-heteroaryl (e.g., includes an optionally substituted linear or branched C1-C6 alkyl, an optionally substituted 5-10 member heteroaryl, or both); optionally substituted alky 1-heteroaryl (e.g., includes a C1-C6 alkyl, an optionally substituted 5 or 6 member heteroaryl, optionally substituted with a C1-C4 alkyl; the heteroaryl is selected from oxazol-4-yl, 1,3,4-triazol-2-yl, and imidazole-1-yl; or combination thereof);

optionally substituted —NH— alkyl-heteroaryl (e.g., an optionally substituted linear or branched C1-C5 alkyl, an optionally substituted 5-8 member heteroaryl, optionally substituted with a C1-C4 alkyl, N—CH$_2$-pyrazol-4-yl, or a combination thereof); optionally substituted alkoxy (e.g., an optionally substituted linear or branched C1-C6 alkyl or —OCH$_3$); optionally substituted O-heterocyclyl (e.g., includes an optionally substituted 3-12 or 4-7 member heterocyclyl; an optionally substituted heterocycloalkyl; an optionally substituted $C_{3-12}$ monocyclic or bicyclic heterocycloalkyl; optionally substituted with at least one OH, C1-C5 alkyl (such as a methyl), =O, NH$_2$, or a combination thereof; or a combination thereof); optionally substituted S-heterocyclyl (e.g., includes an optionally substituted 4-7 member heterocyclyl; an optionally substituted heterocycloalkyl; optionally substituted with at least one C1-C4 alkyl (such as a methyl), =O, or a combination thereof; or a combination thereof); optionally substituted

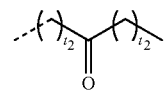

(e.g., optionally substituted with a linear or branched C1-C4 alkyl; —(CH$_2$)$_u$CO(CH$_2$)$_v$CH$_3$, —COCH$_3$, or —CH$_2$CH$_2$COCH$_3$, wherein each u and v is independently selected from 1, 2, 3, 4 or 5); optionally substituted

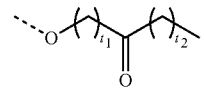

(e.g., optionally substituted with a linear or branched C1-C4 alkyl; —O(CH$_2$)$_u$CO(CH$_2$)$_v$CH$_3$, —O(CH$_2$)$_u$CH((CH$_2$)$_x$CH$_3$)(CH$_2$)$_w$CO(CH$_2$)$_v$CH$_3$, —O—CH$_2$COCH$_3$, —O—CH$_2$COCH$_2$CH$_3$, —O—CH(CH$_3$)COCH$_3$, —OCH$_2$COCH$_3$, or —OCH$_2$(CH$_3$)COCH$_3$, wherein each u, v, w, and x is independently selected from 1, 2, 3, 4 or 5); optionally substituted

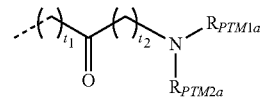

(e.g., optionally substituted with a linear or branched C1-C4 alkyl; —(CH$_2$)$_u$CO(CH$_2$)$_v$NR$_{PTM1a}$R$_{PTM2a}$, —CONR$_{PTM1a}$R$_{PTM2a}$, —CH$_2$CONR$_{PTM1a}$R$_{PTM2a}$, —CH$_2$CH$_2$CONR$_{PTM1a}$R$_{PTM2a}$, —CONHCH$_3$, or —CH$_2$CONHCH$_3$, wherein each u and v is independently selected from 1, 2, 3, 4 or 5); optionally substituted

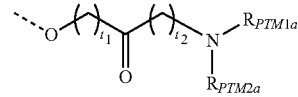

(e.g., optionally substituted with a linear or branched C1-C4 alkyl; —O(CH$_2$)$_u$CO(CH$_2$)$_v$NR$_{PTM1a}$R$_{PTM2a}$, —O(CH$_2$)$_u$CH((CH$_2$)$_x$CH$_3$)(CH$_2$)$_w$CO(CH$_2$)$_v$ NR$_{PTM1a}$R$_{PTM2a}$, —O—CH(CH$_3$) CONR$_{PTM1a}$R$_{PTM2a}$, —O—CH$_2$CONR$_{PTM1a}$R$_{PTM2a}$, Or —OCH$_2$C(O)NHOCH$_3$, wherein each u, v, w, and x is independently selected from 1, 2, 3, 4 or 5); optionally substituted

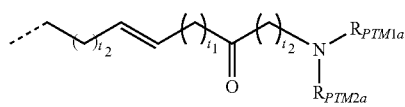

(e.g., optionally substituted with a linear or branched C1-C4 alkyl; —(CH$_2$)$_u$CHCH(CH$_2$)$_w$CO(CH$_2$)$_v$ NR$_{PTM1a}$R$_{PTM2a}$ or —CHCHCONR$_{PTM1a}$R$_{PTM2a}$; wherein each u, v, and w is independently selected from 1, 2, 3, 4 or 5); optionally substituted

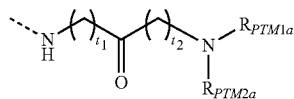

(e.g., optionally substituted with a linear or branched C1-C4 alkyl; —NH—(CH$_2$)$_u$CO(CH$_2$)$_v$ NR$_{PTM1a}$R$_{PTM2a}$ or —NH—CH$_2$CONR$_{PTM1a}$R$_{PTM2a}$, wherein each u and v is independently selected from 1, 2, 3, 4 or 5); fluoroalkoxy (e.g., a mono-, bi- and/or tri-fluoroalkoxy); optionally substituted monocyclic or bicyclic cycloalkyl (e.g., an optionally substituted 3-12 member cycloalkyl; optionally substituted with at least one of OH, =O, linear or branched C1-C6 alkyl (such as a methyl, ethyl, or butyl), or NH$_2$; or a combination thereof); optionally substituted hydroxycycloalkyl; optionally substituted aryl (e.g., an optionally substitute C5-C10 aryl, an optionally substituted 5-7 member aryl; optionally substituted with at least one halogen or C1-C3 alkyl (e.g., methyl or ethyl); or a combination thereof), optionally substituted heteroaryl (e.g., an optionally substituted 5-10 or member heteroaryl, an optionally substituted 5-7 member heteroaryl; an optionally substituted 5-member heteroaryl; optionally substituted with at least one halogen or C1-C3 alkyl (e.g., methyl or ethyl); or a combination thereof) optionally linked to Q via a C or N-atom of the heteroaryl (e.g., at least one of optionally linked to Q, optionally linked via an optionally substituted —(CH$_2$)$_u$O(CH$_2$)$_v$O(CH$_2$)$_x$—, or a combination thereof); optionally substituted monocyclic or bicyclic heterocyclyl (e.g., an optionally substituted 3-12 member heterocyclyl; an C3-C12 monocyclic or bicyclic heterocycloalkyl, azetidine1-yl, pyrrolidin-1-yl, piperidin-1yl, piperazin-1-yl, or morpholin-4-yl, or homopiperazin-1-yl, each optionally substituted with OH, a linear or branched C1-C5 alkyl (a methyl, ethyl, or butyl group) or NH$_2$) optionally linked to Q via a C or N atom of the heterocyclyl (e.g., at least one of optionally linked to Q, optionally linked via an optionally substituted —(CH$_2$)$_u$O(CH$_2$)$_v$O(CH$_2$)$_x$—, or both);
t$_1$ is selected from 1, 2, 3, 4 or 5;
each t$_2$ is independently is independently selected from 0, 1, 2, 3, 4, or 5;

R$_{PTM1a}$ and R$_{PTM2a}$ are independently H, optionally substituted C1-C4 alkyl (e.g., a CH$_3$ or CH$_2$CH$_3$), optionally substituted C1-C4 alkoxy (e.g., —OCH$_2$ or —CH$_2$CH$_3$), optionally substituted CH$_2$OCH$_3$ or R$_{PTM1a}$ and R$_{PTM2a}$ are joined together form an optionally substituted 3-10 member ring;
n is an integer from 0 to 10; and
  ✓ of the PTM indicates the site of attachment with a chemical linking group or a CLM; and
(c) the L is a bond or a chemical linking group that covalently couples the CLM to the PTM.

Therapeutic Compositions

The present invention further provides pharmaceutical compositions comprising therapeutically effective amounts of at least one bifunctional compound as described herein, in combination with a pharmaceutically acceptable carrier, additive or excipient.

In an additional aspect, the description provides therapeutic compositions comprising an effective amount of a compound as described herein or salt form thereof, and a pharmaceutically acceptable carrier, additive or excipient, and optionally an additional bioactive agent. The therapeutic compositions effect targeted protein degradation in a patient or subject, for example, an animal such as a human, and can be used for treating or ameliorating disease states or conditions which are modulated by degrading the target protein. In certain embodiments, the therapeutic compositions as described herein may be used to effectuate the degradation of protein for the treatment or amelioration of LRRK2-mediated neurodegenerative disease, inflammatory diseases, autoimmune diseases or cancer. In certain additional embodiments, the disease is Parkinson's disease, Parkinson disease with dementia, Parkinson's disease at risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, and Shy-Drager syndrome.

In alternative aspects, the present disclosure relates to a method for treating a disease state or ameliorating one or more symptoms of a disease or condition in a subject in need thereof by degrading the LRRK2 protein comprising administering to said patient or subject an effective amount, e.g., a therapeutically effective amount, of at least one compound as described herein, optionally in combination with a pharmaceutically acceptable carrier, additive or excipient, and optionally coadministered with an additional bioactive agent, wherein the composition is effective for treating or ameliorating the disease or disorder or one or more symptoms thereof in the subject. The method according to the present disclosure may be used to treat certain disease states or conditions including neurodegenerative diseases, by virtue of the administration of effective amounts of at least one compound described herein.

The present disclosure further includes pharmaceutical compositions comprising a pharmaceutically acceptable salt, in particular, acid or base addition salts of compounds as described herein. The acids which are used to prepare the pharmaceutically acceptable acid addition salts of the aforementioned compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

Pharmaceutically acceptable base addition salts may also be used to produce pharmaceutically acceptable salt forms of the compounds according to the present disclosure. The chemical bases that may be used as reagents to prepare pharmaceutically acceptable base salts of the present compounds are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium, zinc and magnesium), ammonium or water-soluble amine addition salts such as N-methylglucamine-(meglumine), and the lower alkanolammonium and other base salts of pharmaceutically acceptable organic amines, among others.

The compounds as described herein may, in accordance with the disclosure, be administered in single or divided doses by the oral, parenteral or topical routes. Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual, intra nasal, intra ocular, intrathecal, and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used. The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form or in depot formulation may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions as described herein may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient may be combined with emulsifying and suspending agents. If desired, certain sweetening, flavoring or coloring agents may also be added.

Alternatively, the pharmaceutical compositions as described herein may be administered in the form of suppositories for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered topically. Suitable topical formulations are readily prepared for each of these areas or organs. For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax and water. In certain preferred aspects of the disclosure, the compounds may be coated onto a stent which is to be surgically implanted into a patient in order to inhibit or reduce the likelihood of occlusion occurring in the stent in the patient.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions as described herein may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of active pharmaceutical ingredient in a pharmaceutical composition as described herein that may be combined with the carrier materials to produce a single dosage form will vary depending upon the condition of the subject and disease treated, as well as the particular mode of administration. Preferably, the compositions should be formulated to contain between about 0.05 milligram and about 750 milligrams or more, more preferably about 1 milligram to about 600 milligrams, and even more preferably about 10 milligrams to about 500 milligrams of active ingredient, alone or in combination with another compound according to the present disclosure.

It should also be understood that a specific dosage and treatment regimen for any particular patient will depend upon a variety of factors, including the activity and bioavailability of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure depending upon the pharmaceutically acceptable salt, solvate or polymorph, thereof optionally in a pharmaceutically acceptable carrier or diluent, either alone, or in combination with another known therapeutic agent.

The active compound is combined with the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 nanograms per kilograms (ng/kg) to 300 milligrams per kilograms (mg/kg), preferably 0.1 to 100 mg/kg per day, more generally 0.5 to about 25 mg per kilogram body weight of the recipient/patient per day. A typical topical dosage will range from 0.01-5% wt/wt in a suitable carrier.

The compound is conveniently administered in any suitable unit dosage form, including but not limited to a dosage form containing less than 1 milligrams (mg), 1 mg to 3000 mg, or 5 mg to 500 mg of active ingredient per unit dosage form. An oral dosage of about 25 mg-250 mg is often convenient.

The active ingredient is preferably administered to achieve peak plasma concentrations of the active compound of about 0.00001-30 millimole (mM), preferably about 0.1-30 micromole (µM). This may be achieved, for example, by the intravenous injection of a solution or formulation of the active ingredient, optionally in saline, or an aqueous medium or administered as a bolus of the active ingredient. Oral administration may also be appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, as described herein among others. In certain preferred aspects of the disclosure, one or more compounds according to the present disclosure are coadministered with another bioactive agent, such as an anti-cancer agent or a wound healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In any aspect or embodiment described herein, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, poly anhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

Therapeutic Methods

In an additional aspect, the description provides therapeutic methods comprising administration of an effective amount of a compound as described herein or salt form thereof, and a pharmaceutically acceptable carrier. The therapeutic methods are useful to effect protein degradation in a patient or subject in need thereof, for example, an animal such as a human, for treating or ameliorating a disease state, condition or related symptom that me be treated through targeted protein degradation.

The terms "treat", "treating", and "treatment", etc., as used herein, refer to any action providing a benefit to a patient for which the present compounds may be administered, including the treatment of any disease state, condition, or symptom which is related to the protein to which the present compounds bind. Disease states or conditions, including cancer, which may be treated using compounds according to the present disclosure are set forth hereinabove.

The description provides therapeutic methods for effectuating the degradation of proteins of interest for the treatment or amelioration of a disease, e.g., cancer. In any aspect or embodiment described herein, the disease is multiple myeloma. As such, in another aspect, the description provides a method of ubiquitinating/degrading a target protein in a cell. In certain embodiments, the method comprises administering a bifunctional compound of the invention. The control or reduction of specific protein levels in cells of a subject as afforded by the present disclosure provides treatment of a disease state, condition, or symptom. In any aspect or embodiment described herein, the method comprises administering an effective amount of a compound as described herein, optionally including a pharmaceutically acceptable excipient, carrier, adjuvant, another bioactive agent or combination thereof.

In additional embodiments, the description provides methods for treating or ameliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In another aspect, the description provides methods for identifying the effects of the degradation of proteins of interest in a biological system using compounds according to the present disclosure.

In another aspect, the description provides a process for making a molecule that can cause degradation of LRRK2 in a cell, comprising the steps of: i. providing a small molecule that binds LRRK2; ii. providing and E3 ubiquitin ligase binding moiety (ULM), preferably a CLM such as thalidomide, pomalidomide, lenalidomide or an analog thereof; and iii. covalently coupling the small molecule of step (i) to the ULM of step (ii) via a chemical linking group (L) to form a compound which binds to both a cereblon E3 ubiquitin ligase and LRRK2 protein in the cell, such that the cereblon E3 ubiquitin ligase is in proximity to, and ubiquitinates LRRK2 protein bound thereto, such that the ubiquitinated LRRK2 is then degraded.

In another aspect, the description provides a method for detecting whether a molecule can trigger degradation of a LRRK2 protein in a cell, the method comprising the steps of: (i) providing a molecule for which the ability to trigger degradation of LRRK2 protein in a cell is to be detected, said molecule comprising the structure: CLM-L-PTM, wherein CLM is a cereblon E3 ubiquitin ligase binding moiety capable of binding a cereblon E3 ubiquitin ligase in a cell, which CLM is thalidomide, pomalidomide, lenalidomide, or an analog thereof; PTM is a protein targeting moiety, which is a small molecule that binds to LRRK2, said LRRK2 having at least one lysine residue available to be ubiquitinated by a cereblon E3 ubiquitin ligase bound to the CLM of the molecule; and L is a chemical linking group that covalently links the CLM to the PTM to form the molecule; (ii) incubating a LRRK2 protein-expressing cell in the presence of the molecule of step (i); and (iii) detecting whether the LRRK2 protein in the cell has been degraded.

In any of the aspects or embodiments described herein, the small molecule capable of binding LRRK2, is a small molecule as described herein.

In another aspect of said treatment, the present disclosure provides a method of treating a human patient in need of said treatment of a disease state, condition, or symptom causally related to LRRK2 expression, over-expression, mutation, misfolding or dysregulation where the degradation of the LRRK2 protein will produce a therapeutic effect in the patient, the method comprising administering to the patient an effective amount of a compound according to the present disclosure, optionally in combination with another bioactive agent. The disease state, condition, or symptom may be caused by a microbial agent or other exogenous agent such as a vims, bacteria, fungus, protozoa or other microbe, or may be a disease state, which is caused by expression, overexpression, mutation, misfolding, or dysregulation of the protein, which leads to a disease state, condition, or symptom.

In another aspect, the present disclosure provides a method of treating or ameliorating at least one symptom of a disease or condition in a subject, comprising the steps of: providing a subject identified as having a symptom of a disease or condition causally related to expression, overexpression, mutation, misfolding, or dysregulation of LRRK2 protein in the subject, and the symptom of the disease or condition is treated or ameliorated by degrading LRRK2 protein in cells of the subject; and administering to the subject therapeutically effective amount of a compound comprising a small molecule of the present invention such that the LRRK2 protein is degraded, thereby treating or ameliorating at least one symptom of a disease or condition in the subject.

The term "disease state or condition" is used to describe any disease state or condition wherein protein expression overexpression, mutation, misfolding, or dysregulation (e.g., the amount of protein expressed in a patient is elevated) occurs and where degradation of the LRRK2 protein to reduce or stabilize the level of LRRK2 protein (whether mutated or not) in a patient provides beneficial therapy or relief of symptoms to a patient in need thereof. In certain instances, the disease state, condition, or symptom may be cured.

Disease state, condition, or symptom which may be treated using compounds according to the present disclosure include, for example, inflammatory conditions, and immunological conditions, asthma, autoimmune diseases such as multiple sclerosis, neurodegenerative disease such as Parkinson's disease, various cancers, ciliopathies, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, and Turner syndrome.

The term "neurodegenerative disease" (or Degenerative nerve diseases) is used throughout the specification to refer to the pathological process that affect many of body's activities, such as balance, movement, talking, breathing, and heart function. Many of these diseases are genetic, sometimes the cause is a medical condition such as alcoholism, a tumor, or a stroke. Other causes may include toxins, chemicals, and viruses, and sometimes the cause is unknown. Exemplary neurodegenerative disease which may be treated by the present compounds either alone or in combination with at least one additional anti-neurodegenerative disease therapeutic agent include therapeutic agents to treat Parkinson's disease, Parkinson disease with dementia, Parkinson's disease at risk syndrome, dementia with Lewy bodies, Lewy body variant of Alzheimer's disease, combined Parkinson's disease and Alzheimer's disease, multiple system atrophy, striatonigral degeneration, olivopontocerebellar atrophy, Huntington's disease, multiple sclerosis, amyotrophic lateral sclerosis and Shy-Drager syndrome. For example, Carmustine, Bexarotene, Tamibarotene, Imatinib, Paclitaxel, azithromycin, erythromycin, Doxycycline, Rifampicin, acyclovir, penciclovir and foscamet.

The term "bioactive agent" is used to describe an agent, other than a compound according to the present disclosure, which is used in combination with a present compound as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The term "additional anti-neurodegenerative disease agent" is used to describe an anti-neurodegenerative disease therapeutic agent, which may be combined with a compound according to the present disclosure to treat neurodegenerative disease. These agents include, for example, Carmustine, Bexarotene, Tamibarotene, Imatinib, Paclitaxel, azithromycin, erythromycin, Doxycycline, Rifampicin, acyclovir, penciclovir and foscamet.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

EXAMPLES

Abbreviations

ACN Acetonitrile
AcOH Acetic acid
DCM Dichloromethane
DMF Dimethylformamide
DMSO Dimethyl Sulfoxide
DIPEA N, N-Diisopropylethylamine
EtOAc/EA Ethyl Acetate
EtOH Ethanol
HATU Hexafluorophosphate Azabenzotriazole Tetramethyl Uronium
HPLC High pressure liquid chromatography
Hz Hertz
KOAc Potassium acetate
LCMS Liquid Chromatography/Mass Spectrometry
MHz Megahertz
NMR Nuclear Magnetic Resonance
MeOH Methanol
MS Mass Spectrometry
PE Petroleum ether
Psi Pound-force per square inch
RT or r.t. Room temperature
TEA Triethylamine
THF Tetrahydrofuran
TFA Trifluoracetic acid
TLC Thin layer chromatography
TMS Trimethylsilyl
General Synthetic Approach The synthetic realization and optimization of the bifunctional molecules as described herein may be approached in a stepwise or modular fashion. For example, identification of compounds that bind to the target protein, i.e., LRRK2 can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the chemical linking group previously referred to herein. Where crystallographic or NMR structural data are available, these can be used to focus such a synthetic effort.

In a very analogous way one can identify and optimize ligands for an E3 Ligase.

With PTMs and ULMs (e.g. CLMs) in hand, one skilled in the art can use known synthetic methods for their combination with or without a chemical linking group(s). Chemical linking group(s) can be synthesized with a range of compositions, lengths and flexibility and functionalized such that the PTM and ULM groups can be attached sequentially to distal ends of the linker. Thus, a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Synthetic Procedures

Synthesis of Intermediate 1: 4,5-Dimethyl-7H-tetrazolo[1,5-a]pyrimidine-6-carboxylic acid

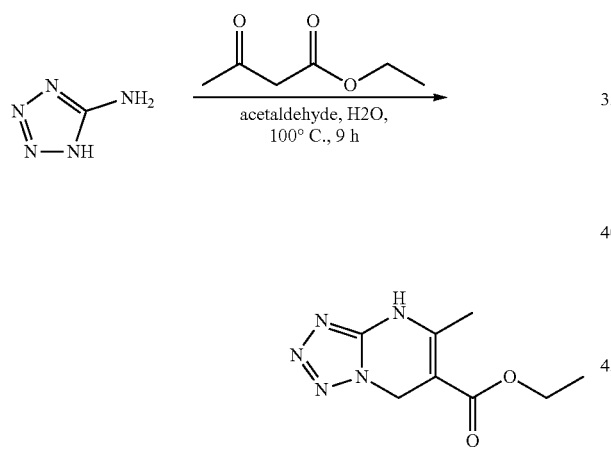

Step 1: Ethyl 5-methyl-4,7-dihydrotetrazolo[1,5-a]pyrimidine-6-carboxylate

To a solution of 1H-tetrazol-5-amine (5 gram (g), 48.50 millimole (mmol), 1 equivalent (eq), $H_2O$) in water (100 milliliters (mL)) was added formaldehyde (5.46 g, 72.75 mmol, 5.01 mL, 1.5 eq) and ethyl acetoacetate (6.31 g, 48.50 mmol, 6.13 mL, 1 eq). The mixture was stirred at 100° C. for 9 hours (hr) to give white solution. Then the solution became suspension. LCMS (EB16-543-P1A1) showed the reaction was completed. The mixture was cooled to 20° C. and concentrated in reduced pressure at 20° C. The suspension was filtered and the filter cake was concentrated in vacuum to give ethyl 5-methyl-4,7-dihydrotetrazolo[1,5-a]pyrimidine-6-carboxylate (7.2 g, 34.42 mmol, 70.96% yield) as a white solid.

Step 2: Ethyl 4,5-dimethyl-7H-tetrazolo[1,5-a]pyrimidine-6-carboxylate

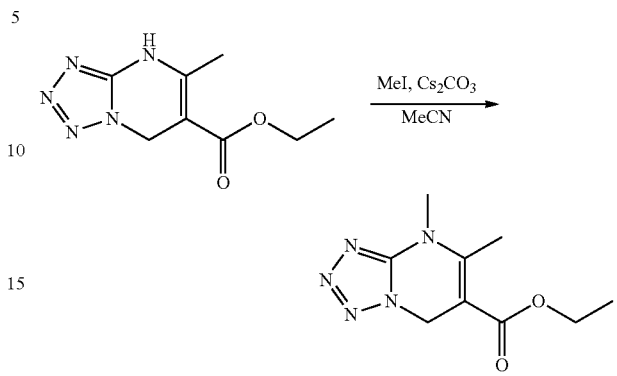

To a mixture of ethyl 5-methyl-4,7-dihydrotetrazolo[1,5-a]pyrimidine-6-carboxylate (7.2 g, 34.42 mmol, 1 eq) and $Cs_2CO_3$ (12.33 g, 37.86 mmol, 1.1 eq) in MeCN (70 mL) was added MeI (6.06 g, 42.68 mmol, 2.66 mL, 1.24 eq) in one portion at 20° C. under $N_2$. The mixture was stirred at 50° C. for 1 hour (h). LCMS (EB16-545-P1A1) showed the reaction was completed. The aqueous phase was extracted with ethyl acetate (50 mL*3). The combined organic phase was washed with brine (50 mL*2), dried with anhydrous $Na_2SO_4$, filtered and concentrated in vacuum to give ethyl 4,5-dimethyl-7H-tetrazolo[1,5-a]pyrimidine-6-carboxylate (7.5 g, 33.60 mmol, 97.61% yield) as a yellow solid.

Step 3: 4,5-Dimethyl-7H-tetrazolo[1,5-a]pyrimidine-6-carboxylic acid

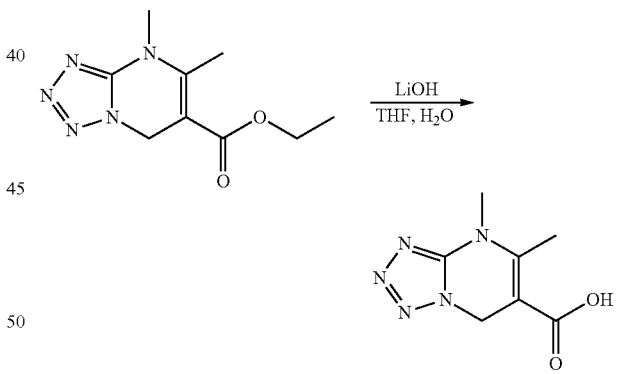

To a mixture of ethyl 4,5-dimethyl-7H-tetrazolo[1,5-a]pyrimidine-6-carboxylate (4 g, 17.92 mmol, 1 eq) in THF (30 mL) was added LiOH (1.29 g, 53.76 mmol, 3 eq) and $H_2O$ (5 mL) in one portion at 20° C. under $N_2$. The mixture was stirred at 60° C. for 16 hours. LCMS (EB16-548-P1A1) showed the reaction was completed. The mixture was cooled to 20° C. and concentrated in reduced pressure at 20° C. The residue was acidified to pH=1 with HCl. The solid formed and collected by filtration. The filter cake was filtered under vacuum to give 4,5-dimethyl-7H-tetrazolo[1,5-a]pyrimidine-6-carboxylic acid (2.9 g, 14.86 mmol, 82.92% yield) as a white solid.

Synthesis of Intermediate 2: 4,5,7-Trimethyl-7H-tetrazolo[1,5-a]pyrimidine-6-carboxylic acid. Synthesis of Intermediate 2 was made in a manner analogous to intermediate 1 using acetaldehyde in place of formaldehyde in step 1.

Synthesis of Intermediate 3: 4,5,7,7-Tetramethyltetrazolo[1,5-a]pyrimidine-6-carboxylic acid. Synthesis of Intermediate 3 was made in a manner analogous to intermediate 1 using ethyl 2-acetyl-3-methyl-but-2-enoate, prepared by the condensation of acetone and ethyl acetoacetate, in step 1.

Exemplary Synthesis of Exemplary Compound 1: N-[3-[2-[(3R,5S)-4-[[1-[[1-[2-(2,6-dioxo-3-piperidyl)-1,3-dioxo-isoindolin-5-yl]-4-piperidyl]methyl]-4-piperidyl]methyl]-3,5-dimethyl-piperazin-1-yl]-4-pyridyl]-1H-indazol-5-yl]-4,5-dimethyl-7H-tetrazolo[1,5-a]pyrimidine-6-carboxamide Step 1: Tert-butyl (3R,5S)-4-[(1-benzyloxycarbonyl-4-piperidyl)methyl]-3,5-dimethyl-piperazine-1-carboxylate

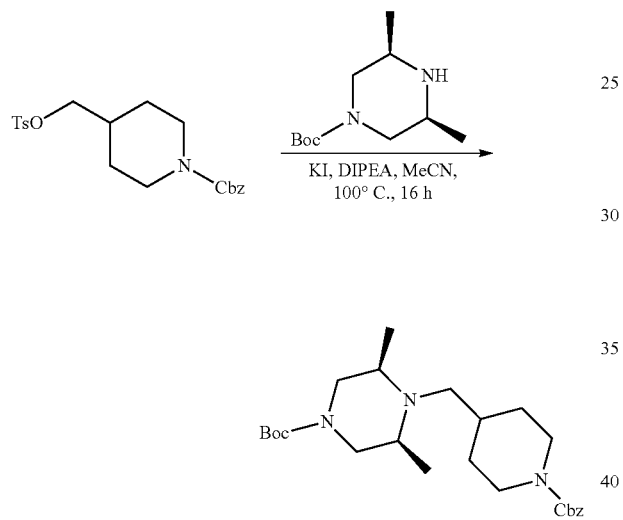

To a mixture of tert-butyl (3R,5S)-3,5-dimethylpiperazine-1-carboxylate (1 g, 4.67 mmol, 1 eq) and benzyl 4-(p-tolylsulfonyloxymethyl)piperidine-1-carboxylate (1.88 g, 4.67 mmol, 1 eq) in MeCN (5 mL) was added KI (2.32 g, 14.00 mmol, 3 eq) and DIPEA (1.81 g, 14.00 mmol, 2.44 mL, 3 eq) in one portion at 20° C. under $N_2$. The mixture was stirred at 100° C. for 16 hours. LCMS (EB16-606-P1A6) showed desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous $Na_2SO_4$, filtered and concentrated in vacuum. The residue was purified by silica gel chromatography (DCM:MeOH=10:1, Rf=0.59, 20 g, 0-14% (10 min) of Ethyl acetate in Petroleum ether, 14% (20 min) of Ethyl acetate in Petroleum ether) to give tert-butyl (3R,5S)-4-[(1-benzyloxycarbonyl-4-piperidyl)methyl]-3,5-dimethyl-piperazine-1-carboxylate (1.22 g, 2.74 mmol, 58.67% yield) as a yellow gum.

Step 2: Benzyl 4-[[(2R,6S)-2,6-dimethylpiperazin-1-yl]methyl]piperidine-1-carboxylate

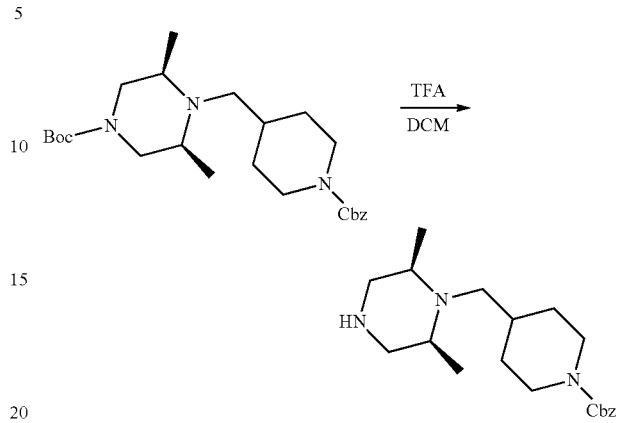

To a solution of tert-butyl (3R,5S)-4-[(1-benzyloxycarbonyl-4-piperidyl)methyl]-3,5-dimethyl-piperazine-1-carboxylate (1.22 g, 2.74 mmol, 1 eq) in DCM (5 mL) was added TFA (312.18 mg, 2.74 mmol, 202.71 microliter (uL), 1 eq) in one portion at 20° C. under $N_2$. The mixture was stirred at 20° C. for 30 min. LCMS (EB16-610-P1A1) showed the reaction was completed. The residue was basified to pH=7-8 with saturated $NaHCO_3$. The aqueous phase was extracted with DCM (5 mL*3). The combined organic phase was washed with brine (5 mL*2), dried with anhydrous $Na_2SO_4$, filtered and concentrated in vacuum to give benzyl 4-[[(2R,6S)-2,6-dimethylpiperazin-1-yl]methyl]piperidine-1-carboxylate (930 mg, 2.69 mmol, 98.32% yield) as a yellow gum.

Step 3: Benzyl 4-[[(2R,6S)-4-(4-bromo-2-pyridyl)-2,6-dimethyl-piperazin-1-yl]methyl]piperidine-1-carboxylate

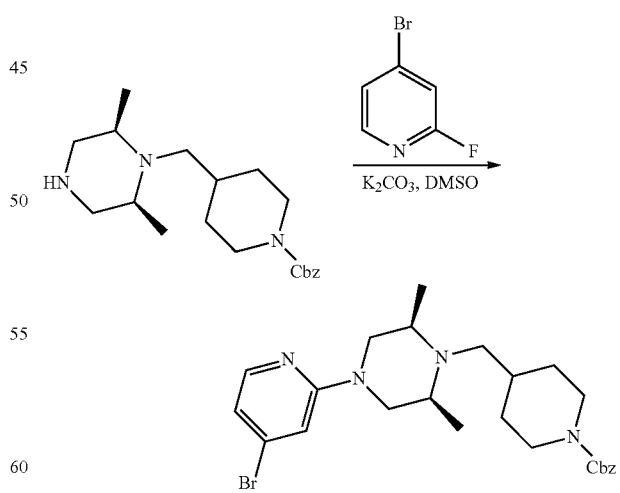

To a mixture of benzyl 4-[[(2R,6S)-2,6-dimethylpiperazin-1-yl]methyl]piperidine-1-carboxylate (930 mg, 2.69 mmol, 1 eq) and 4-bromo-2-fluoro-pyridine (473.74 mg, 2.69 mmol, 1 eq) in DMF (5 mL) was added $Cs_2CO_3$ (1.75 g, 5.38 mmol, 2 eq) in one portion at 25° C. The mixture was stirred at 100° C. for 12 hours. LCMS (EB16-612-P1A1) showed the reaction was completed. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous $Na_2SO_4$, filtered and concentrated in vacuum. The residue was purified by silica gel chromatography (12 g, 0-50%(10 min) of Ethyl acetate in Petroleum ether, 50%(10 min) of Ethyl acetate in Petroleum ether) to give benzyl 4-[[(2R,6S)-4-(4-bromo-2-pyridyl)-2,6-dimethyl-piperazin-1-yl]methyl]piperidine-1-carboxylate (580 mg, 1.16 mmol, 42.97% yield) as a yellow gum.

Step 4: [2-[(3R,5S)-4-[(1-benzyloxycarbonyl-4-piperidyl)methyl]-3,5-dimethyl-piperazin-1-yl]-4-pyridyl]boronic acid

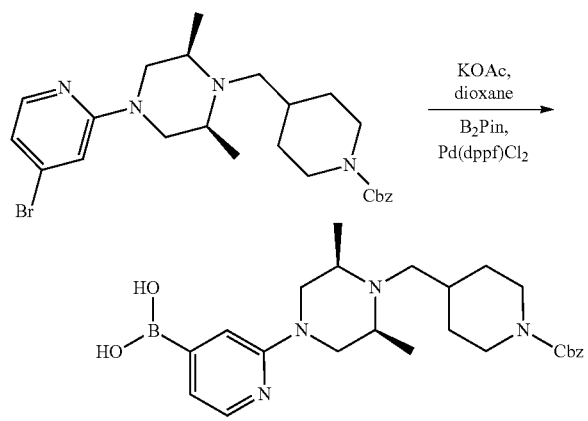

To a mixture of benzyl 4-[[(2R,6S)-4-(4-bromo-2-pyridyl)-2,6-dimethyl-piperazin-1-yl]methyl]piperidine-1-carboxylate (580 mg, 1.16 mmol, 1 eq) 4,4,5,5-tetramethyl-2-(4,4,5,5-tetramethyl-1,3,2-dioxaborolan-2-yl)-1,3,2-dioxaborolane (440.57 mg, 1.73 mmol, 1.5 eq) and KOAc (340.53 mg, 3.47 mmol, 3 eq) in dioxane (2 mL) was added Pd(dppf)Cl$_2$ (42.32 mg, 57.83 umol, 0.05 eq) one portion at 25° C. under N$_2$. The mixture was stirred at 100° C. for 2 hours. LCMS (EB16-615-P1A1) showed the reaction was completed. The mixture was cooled to 25° C., filtered and concentrated in vacuum to give [2-[(3R,5S)-4-[(1-benzyloxycarbonyl-4-piperidyl)methyl]-3,5-dimethyl-piperazin-1-yl]-4-pyridyl]boronic acid (669 mg, crude) as a black brown solid. The crude product was used into the next step without further purification.

Step 5: Benzyl 4-[[(2R,6S)-2,6-dimethyl-4-[4-(5-nitro-1H-indazol-3-yl)-2-pyridyl]piperazin-1-yl]methyl]piperidine-1-carboxylate

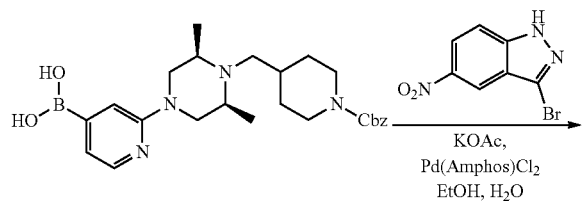

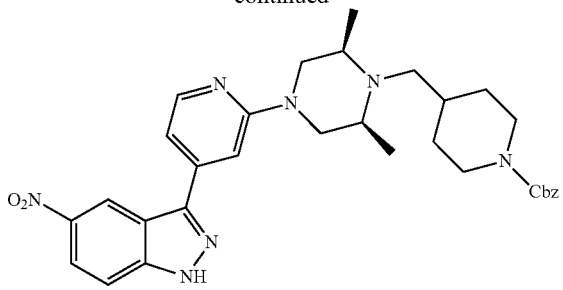

To a mixture of [2-[(3R,5S)-4-[(1-benzyloxycarbonyl-4-piperidyl)methyl]-3,5-dimethyl-piperazin-1-yl]-4-pyridyl]boronic acid (669 mg, 1.43 mmol, 1 eq), 3-bromo-5-nitro-1H-indazole (381.90 mg, 1.58 mmol, 1.1 eq) and KOAc (422.34 mg, 4.30 mmol, 3 eq) in EtOH (10 mL) and H$_2$O (2 mL) was added 4-ditert-butylphosphanyl-N,N-dimethyl-aniline; dichloropalladium (101.57 mg, 143.45 umol, 101.57 uL, 0.1 eq) in one portion at 25° C. under N$_2$. The mixture was stirred at 100° C. for 12 hours. LCMS (EB16-616-P1A2) showed the reaction was completed. The mixture was cooled to 20° C. and concentrated in reduced pressure. The residue was poured into water (10 mL). The aqueous phase was extracted with ethyl acetate (10 mL*3). The combined organic phase was washed with brine (10 mL*2), dried with anhydrous Na$_2$SO$_4$, filtered and concentrated in vacuum. The residue was purified by silica gel chromatography (12 g, 100-200 mesh silica gel, 0-100% (15 min) of Ethyl acetate in Petroleum ether, 100% (15 min) of Ethyl acetate in Petroleum ether) to give benzyl 4-[[(2R,6S)-2,6-dimethyl-4-[4-(5-nitro-1H-indazol-3-yl)-2-pyridyl]piperazin-1-yl]methyl]piperidine-1-carboxylate (609 mg, 980.78 umol, 68.37% yield, 94% purity) as a yellow gum.

Step 6: Benzyl 4-[[(2R,6S)-4-[4-(5-amino-1H-indazol-3-yl)-2-pyridyl]-2,6-dimethyl-piperazin-1-yl]methyl]piperidine-1-carboxylate

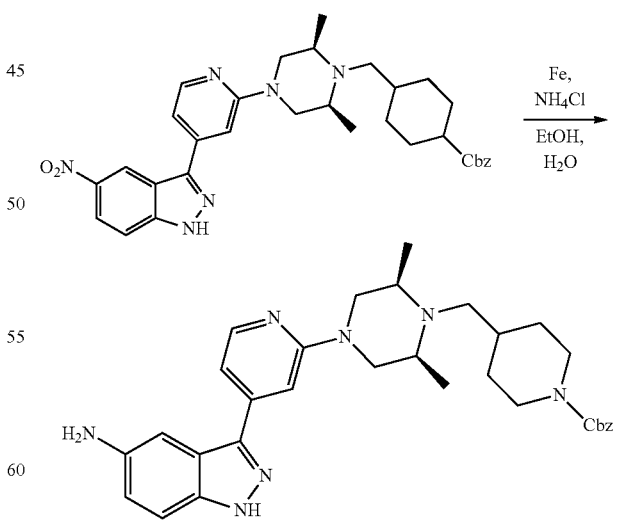

To a mixture of benzyl 4-[[(2R,6S)-2,6-dimethyl-4-[4-(5-nitro-1H-indazol-3-yl)-2-pyridyl]piperazin-1-yl]methyl]piperidine-1-carboxylate (609 mg, 1.04 mmol, 1 eq) and Fe (291.34 mg, 5.22 mmol, 5 eq) in H$_2$O (1 mL) and EtOH (5 mL) was added NH$_4$Cl (279.06 mg, 5.22 mmol, 5 eq) in one portion at 20° C. under N$_2$. The mixture was stirred at 80° C. for 1.5 hours. LCMS (EB16-620-P1A1) showed the reaction was completed. The residue was filtered and solution was concentrated in vacuum to give benzyl 4-[[(2R,6S)-4-[4-(5-amino-1H-indazol-3-yl)-2-pyridyl]-2,6-dimethyl-piperazin-1-yl]methyl]piperidine-1-carboxylate (550 mg, 814.53 umol, 78.07% yield, 82% purity) as a brown solid.

Step 7: Benzyl 4-[[(2R,6S)-4-[4-[5-(tert-butoxycarbonylamino)-1H-indazol-3-yl]-2-pyridyl]-2,6-dimethyl-piperazin-1-yl]methyl]piperidine-1-carboxylate

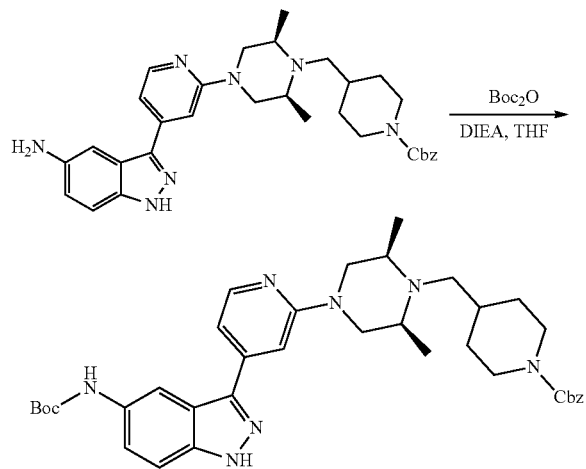

To a mixture of benzyl 4-[[(2R,6S)-4-[4-(5-amino-1H-indazol-3-yl)-2-pyridyl]-2,6-dimethyl-piperazin-1-yl]methyl]piperidine-1-carboxylate (400 mg, 722.42 umol, 1 eq) and Boc$_2$O (173.43 mg, 794.66 umol, 182.56 uL, 1.1 eq) in THF (5 mL) was added DIPEA (140.05 mg, 1.08 mmol, 188.75 uL, 1.5 eq) in one portion at 20° C. under N$_2$. The mixture was stirred at 20° C. for 16 hours. TLC showed the reaction was completed. The residue was poured into water (5 mL). The aqueous phase was extracted with ethyl acetate (5 mL*3). The combined organic phase was washed with brine (5 mL*2), dried with anhydrous Na$_2$SO$_4$, filtered and concentrated in vacuum. The residue was purified by silica gel chromatography (12 g, 0-50% (10 min) of Ethyl acetate in Petroleum ether, 50% (10 min) of Ethyl acetate in Petroleum ether) to give benzyl 4-[[(2R,6S)-4-[4-[5-(tert-butoxycarbonylamino)-1H-indazol-3-yl]-2-pyridyl]-2,6-dimethyl-piperazin-1-yl]methyl]piperidine-1-carboxylate (274 mg, 410.70 umol, 56.85% yield, 98% purity) as an off-white solid.

Step 8: Tert-butyl N-[3-[2-[(3R,5S)-3,5-dimethyl-4-(4-piperidylmethyl)piperazin-1-yl]-4-pyridyl]-1H-indazol-5-yl]carbamate

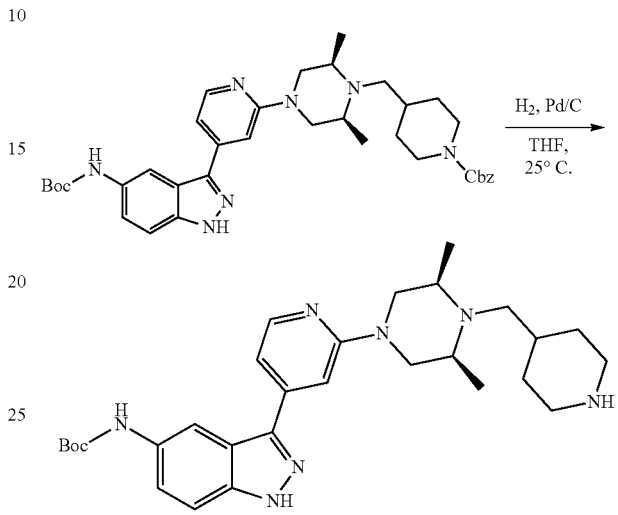

To a mixture of benzyl 4-[[(2R,6S)-4-[4-[5-(tert-butoxycarbonylamino)-1H-indazol-3-yl]-2-pyridyl]-2,6-dimethyl-piperazin-1-yl]methyl]piperidine-1-carboxylate (274 mg, 419.08 umol, 1 eq) in THF (5 mL) was added Pd/C (50 mg, 419.08 umol, 10% purity, 1 eq) under N$_2$. The suspension was degassed under vacuum and purged with H$_2$ several times. The mixture was stirred under H$_2$ (15 psi) at 25° C. for 16 hours. TLC showed the reaction was completed. The reaction mixture was filtered with MeOH (20 mL*3) and the filter was concentrated to give tert-butyl N-[3-[2-[(3R,5S)-3,5-dimethyl-4-(4-piperidylmethyl)piperazin-1-yl]-4-pyridyl]-1H-indazol-5-yl]carbamate (160 mg, 252.16 umol, 60.17% yield, 81.9% purity) as a white solid.

Step 9: Tert-butyl N-[3-[2-[(3R,5S)-4-[[1-[[1-[2-(2,6-dioxo-3-piperidyl)-1,3-dioxo-isoindolin-5-yl]-4-piperidyl]methyl]-4-piperidyl]methyl]-3,5-dimethyl-piperazin-1-yl]-4-pyridyl]-1H-indazol-5-yl]carbamate

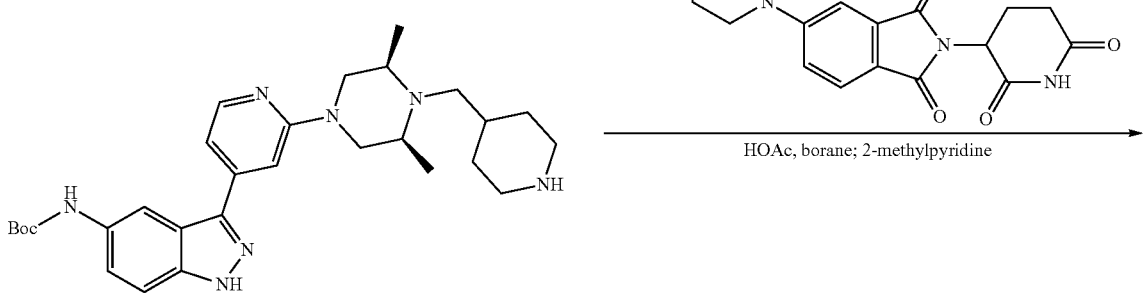

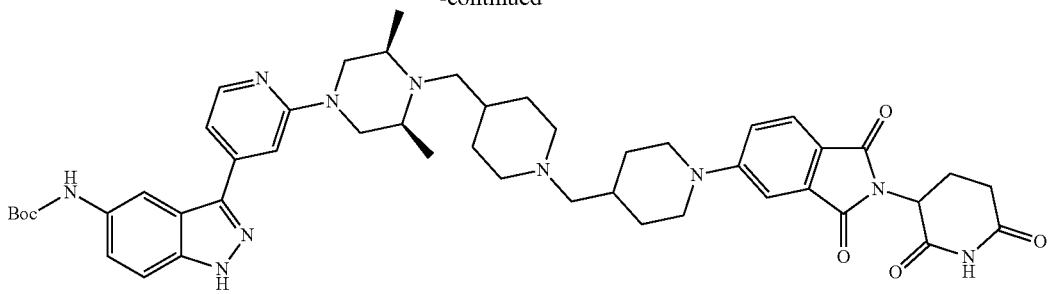

To a mixture of tert-butyl N-[3-[2-[(3R,5S)-3,5-dimethyl-4-(4-piperidylmethyl)piperazin-1-yl]-4-pyridyl]-1H-indazol-5-yl]carbamate (160 mg, 307.88 umol, 1 eq) and 1-[2-(2,6-dioxo-3-piperidyl)-1,3-dioxo-isoindolin-5-yl]piperidine-4-carbaldehyde (170.58 mg, 461.82 umol, 1.5 eq) in MeOH (5 mL) was added AcOH (18.49 mg, 307.88 umol, 17.61 uL, 1 eq) and borane; 2-methylpyridine (65.86 mg, 615.76 umol, 2 eq) in one portion at 20° C. under N₂. The mixture was stirred at 20° C. for 4 h. LCMS (EB16-636-P1A2) showed there was desired MS. The residue was poured into water (10 mL). The aqueous phase was extracted with ethyl acetate (10 mL*3). The combined organic phase was washed with brine (10 mL*2), dried with anhydrous Na₂SO₄, filtered and concentrated in vacuum. The residue was purified by silica gel chromatography (Dichloromethane:Methanol=10:1, Rf=0.09, 0-20% (15 min) of Methanol in Dichloromethane, 20% (5 min) of Methanol in Dichloromethane) to give tert-butyl N-[3-[2-[(3R,5S)-4-[[1-[[1-[2-(2,6-dioxo-3-piperidyl)-1,3-dioxo-isoindolin-5-yl]-4-piperidyl]methyl]-4-piperidyl]methyl]-3,5-dimethyl-piperazin-1-yl]-4-pyridyl]-1H-indazol-5-yl]carbamate (220 mg, 231.83 umol, 75.30% yield, 92% purity) as a yellow gum.

Step 10: 5-[4-[[4-[[(2R,6S)-4-[4-(5-Amino-1H-indazol-3-yl)-2-pyridyl]-2,6-dimethyl-piperazin-1-yl]methyl]-1-piperidyl]methyl]-1-piperidyl]-2-(2,6-dioxo-3-piperidyl)isoindoline-1,3-dione

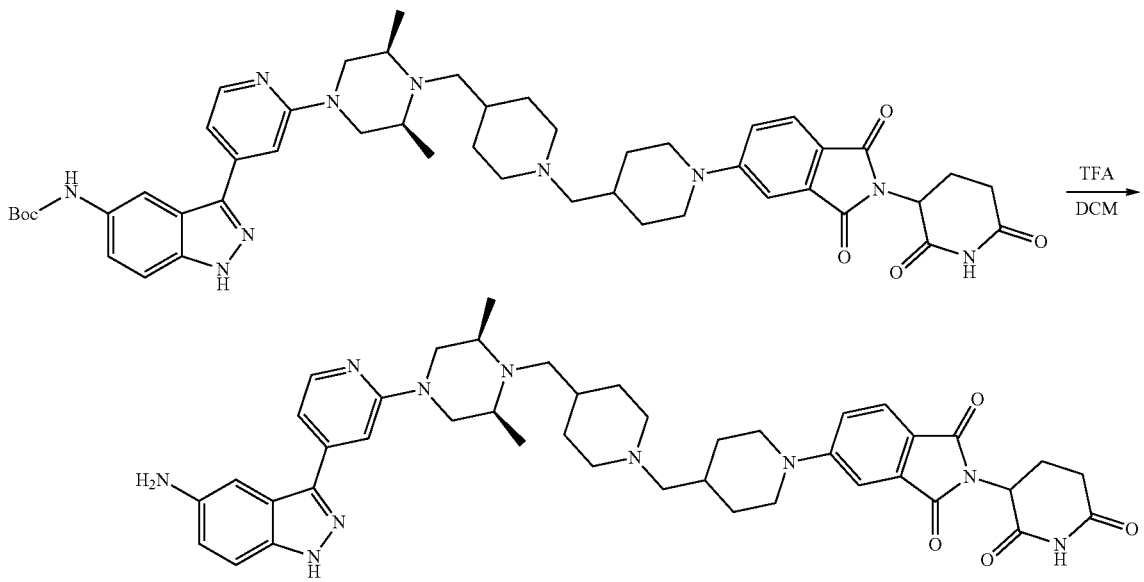

To a mixture of tert-butyl N-[3-[2-[(3R,5S)-4-[[1-[[1-[2-(2,6-dioxo-3-piperidyl)-1,3-dioxo-isoindolin-5-yl]-4-piperidyl]methyl]-4-piperidyl]methyl]-3,5-dimethyl-piperazin-1-yl]-4-pyridyl]-1H-indazol-5-yl]carbamate (220 mg, 251.99 umol, 1 eq) in DCM (3 mL) was added TFA (86.20 mg, 755.97 umol, 55.97 uL, 3 eq) in one portion at 20° C. under N₂. The mixture was stirred at 20° C. for 30 min. TLC (DCM:MeOH=3:1, Rf=0.14) showed the reaction was completed. The mixture was concentrated under reduced pressure to give 5-[4-[[4-[[(2R,6S)-4-[4-(5-amino-1H-indazol-3-yl)-2-pyridyl]-2,6-dimethyl-piperazin-1-yl]methyl]-1-piperidyl]methyl]-1-piperidyl]-2-(2,6-dioxo-3-piperidyl)isoindoline-1,3-dione (300 mg, crude, TFA) as a yellow gum.

Step 11: N-[3-[2-[(3R,5S)-4-[[1-[[1-[2-(2,6-dioxo-3-piperidyl)-1,3-dioxo-isoindolin-5-yl]-4-piperidyl]methyl]-4-piperidyl]methyl]-3,5-dimethyl-piperazin-1-yl]-4-pyridyl]-1H-indazol-5-yl]-4,5-dimethyl-7H-tetrazolo[1,5-a]pyrimidine-6-carboxamide
(Compound 1)

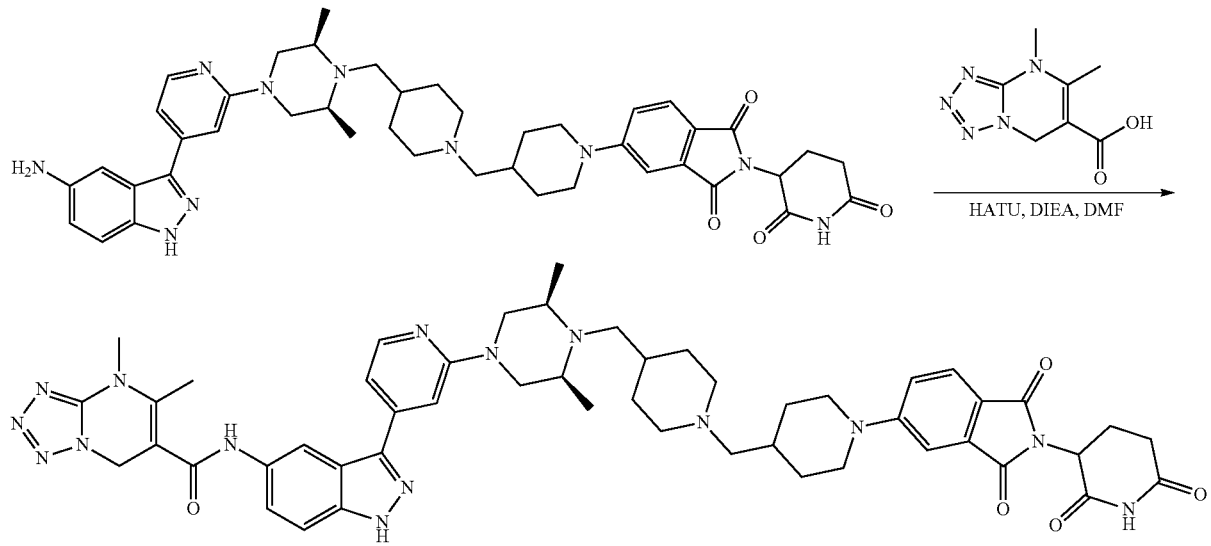

To a solution of 4,5-dimethyl-7H-tetrazolo[1,5-a]pyrimidine-6-carboxylic acid (Intermediate 1, 30.30 mg, 155.25 umol, 1.2 eq) and 5-[4-[[4-[[(2R,6S)-4-[4-(5-amino-1H-indazol-3-yl)-2-pyridyl]-2,6-dimethyl-piperazin-1-yl]methyl]-1-piperidyl]methyl]-1-piperidyl]-2-(2,6-dioxo-3-piperidyl)isoindoline-1,3-dione (100 mg, 129.38 umol, 1 eq) in DMF (2 mL) was stirred at 0° C. for 10 min, then was added DIPEA (83.61 mg, 646.88 umol, 112.68 uL, 5 eq) and HATU (49.19 mg, 129.38 umol, 1 eq). Then the mixture was stirred at 25° C. for 16 h under $N_2$. LCMS (EB16-642-P1A8) showed the reaction was completed. The residue was poured into water (10 mL). The aqueous phase was extracted with ethyl acetate (10 mL*3). The combined organic phase was washed with brine (10 mL*3), dried with anhydrous $Na_2SO_4$, filtered and concentrated in vacuum. The crude product was purified by reversed-phase HPLC (Column: Phenomenex luna C18 150*25 mm*10 um; Condition: water (0.2% FA)-ACN; Begin B: 0; End B: 40; FlowRate: 35 mL/min; Gradient Time: 35 min; 100% B Hold Time: 4 min) to give N-[3-[2-[(3R,5S)-4-[[1-[[1-[2-(2,6-dioxo-3-piperidyl)-1,3-dioxo-isoindolin-5-yl]-4-piperidyl]methyl]-4-piperidyl]methyl]-3,5-dimethyl-piperazin-1-yl]-4-pyridyl]-1H-indazol-5-yl]-4,5-dimethyl-7H-tetrazolo[1,5-a]pyrimidine-6-carboxamide (29.3 mg, 30.53 umol, 23.60% yield, 99% purity) as a yellow solid.

$^1$H NMR: (400 MHz, DMSO-$d_6$) δ: 13.42 (s, 1H), 11.08 (s, 1H), 10.07 (s, 1H), 8.67 (s, 1H), 8.22 (d, J=5.1 Hz, 1H), 7.67-7.51 (m, 3H), 7.28 (d, J=13.8 Hz, 2H), 7.23 (d, J=8.8 Hz, 1H), 7.16 (d, J=5.3 Hz, 1H), 5.30 (s, 2H), 5.11-5.02 (m, 1H), 4.12 (d, J=11.1 Hz, 2H), 4.03 (d, J=12.9 Hz, 2H), 3.44 (s, 3H), 3.00-2.80 (m, 5H), 2.72-2.53 (m, 6H), 2.39-2.30 (m, 2H), 2.27 (s, 3H), 2.16 (d, J=5.8 Hz, 2H), 2.05-1.97 (m, 1H), 1.95-1.71 (m, 7H), 1.37 (s, 1H), 1.12 (d, J=5.8 Hz, 10H).

Exemplary Synthesis of Exemplary Compound 2: N-[3-[2-[(3R,5S)-4-[[1-[[1-[2-(2,6-dioxo-3-piperidyl)-1,3-dioxo-isoindolin-5-yl]-4-piperidyl]methyl]-4-piperidyl]methyl]-3,5-dimethyl-piperazin-1-yl]-4-pyridyl]-1H-indazol-5-yl]-4,5,7-trimethyl-7H-tetrazolo[1,5-a]pyrimidine-6-carboxamide

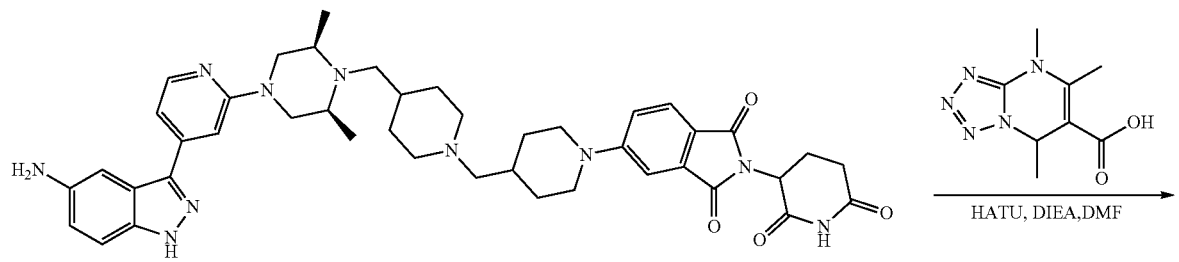

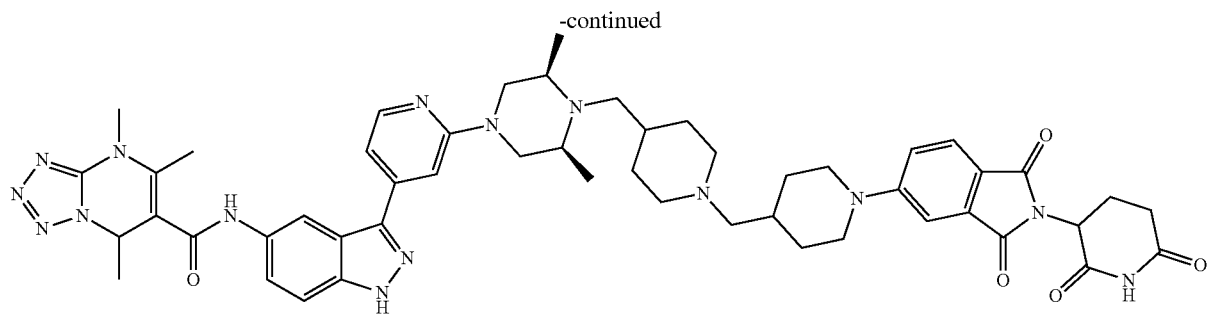
-continued

To a solution of 4,5,7-trimethyl-7H-tetrazolo[1,5-a]pyrimidine-6-carboxylic acid (32.48 mg, 155.25 umol, 1.2 eq) and 5-[4-[[(2R,6S)-4-[4-(5-amino-1H-indazol-3-yl)-2-pyridyl]-2,6-dimethyl-piperazin-1-yl]methyl]-1-piperidyl]methyl]-1-piperidyl]-2-(2,6-dioxo-3-piperidyl)isoindoline-1,3-dione (100 mg, 129.38 umol, 1 eq) in DMF (2 mL) was stirred at 0° C. for 10 min, then was added DIPEA (83.60 mg, 646.88 umol, 112.67 uL, 5 eq) and HATU (49.19 mg, 129.38 umol, 1 eq). Then the mixture was stirred at 25° C. for 16 h under N₂. LCMS (EB16-643-P1A1) showed the reaction was completed. The residue was poured into water (10 mL). The aqueous phase was extracted with ethyl acetate (10 mL*3). The combined organic phase was washed with brine (10 mL*3), dried with anhydrous Na₂SO₄, filtered and concentrated in vacuum. The crude product was purified by reversed-phase HPLC (Column: Phenomenex luna C18 150*25 mm*10 um; Condition: water (0.2% FA)-ACN; Begin B: 0; End B: 40; FlowRate: 35 mL/min; Gradient Time: 35 min; 100% B Hold Time: 4 min) to give N-[3-[2-[(3R,5S)-4-[[1-[[1-[2-(2,6-dioxo-3-piperidyl)-1,3-dioxo-isoindolin-5-yl]-4-piperidyl]methyl]-4-piperidyl]methyl]-3,5-dimethyl-piperazin-1-yl]-4-pyridyl]-1H-indazol-5-yl]-4,5,7-trimethyl-7H-tetrazolo[1,5-a]pyrimidine-6-carboxamide (34.9 mg, 35.84 umol, 27.70% yield, 99% purity) as a yellow solid.

¹H NMR: (400 MHz, DMSO) δ: 13.42 (s, 1H), 11.08 (s, 1H), 10.28 (s, 1H), 8.67 (s, 1H), 8.23 (d, J=5.3 Hz, 1H), 8.15 (s, 1H), 7.67-7.58 (m, 2H), 7.56-7.50 (m, 1H), 7.28 (d, J=13.6 Hz, 2H), 7.23 (d, J=8.8 Hz, 1H), 7.16 (d, J=5.4 Hz, 1H), 5.83-5.71 (m, 1H), 5.06 (dd, J=5.4, 12.9 Hz, 1H), 4.12 (d, J=12.0 Hz, 2H), 4.03 (d, J=12.9 Hz, 2H), 3.44 (s, 3H), 3.01-2.82 (m, 5H), 2.72-2.55 (m, 5H), 2.40-2.33 (m, 2H), 2.20 (s, 3H), 2.17 (s, 2H), 2.06-1.97 (m, 1H), 1.94-1.71 (m, 7H), 1.56 (d, J=6.4 Hz, 3H), 1.38 (s, 1H), 1.11 (d, J=5.8 Hz, 10H).

Exemplary Synthesis of Exemplary Compound 3: N-[3-[2-[(3S,5R)-4-[2-[2-[4-[2-(2,6-dioxo-3-piperidyl)-1,3-dioxo-isoindolin-5-yl]piperazin-1-yl]ethoxy]ethyl]-3,5-dimethyl-piperazin-1-yl]-4-pyridyl]-1H-indazol-5-yl]-4,5,7-trimethyl-7H-tetrazolo[1,5-a]pyrimidine-6-carboxamide Step 1: (2R,6S)-4-(4-bromo-2-pyridyl)-1-[2-(2,2-dimethoxyethoxy)ethyl]-2,6-dimethyl-piperazine

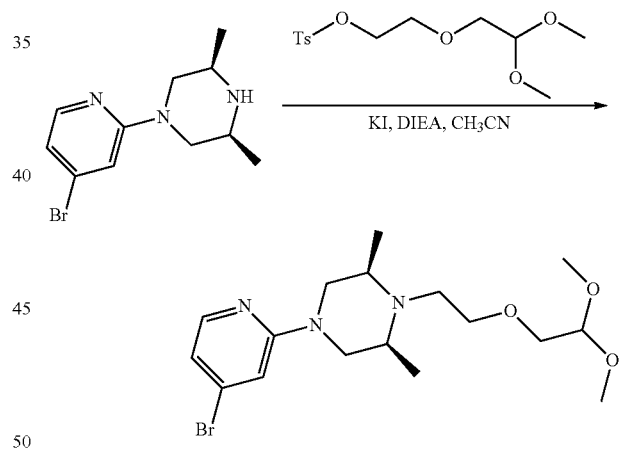

To a solution of (3R,5S)-1-(4-bromo-2-pyridyl)-3,5-dimethyl-piperazine (2 g, 7.40 mmol, 1 eq) and 2-(2,2-dimethoxyethoxy)ethyl 4-methylbenzenesulfonate (2.3 g, 7.56 mmol, 1.02 eq) in CH₃CN (20 mL) was added DIEA (1.91 g, 14.81 mmol, 2.58 mL, 2 eq) and KI (2.46 g, 14.81 mmol, 2 eq). After addition, the reaction mixture was stirred at 120° C. for 16 h. LCMS (EB12-469-P1B) showed desired MS. TLC (dichloromethane:methanol=10:1) showed several new spots. After cooling, the reaction mixture was filtered and concentrated under reduced pressure. The residue was purified by silica gel column chromatography (0 to 100% ethyl acetate in petroleum ether) to afford (2R,6S)-4-(4-bromo-2-pyridyl)-1-[2-(2,2-dimethoxyethoxy)ethyl]-2,6-dimethyl-piperazine (2.1 g, 4.79 mmol, 64.73% yield, 91.8% purity) as a yellow oil.

Step 2: (2R,6S)-1-[2-(2,2-dimethoxyethoxy)ethyl]-2,6-dimethyl-4-[4-(4,4,5,5-tetramethyl-1,3,2-dioxaborolan-2-yl)-2-pyridyl]piperazine

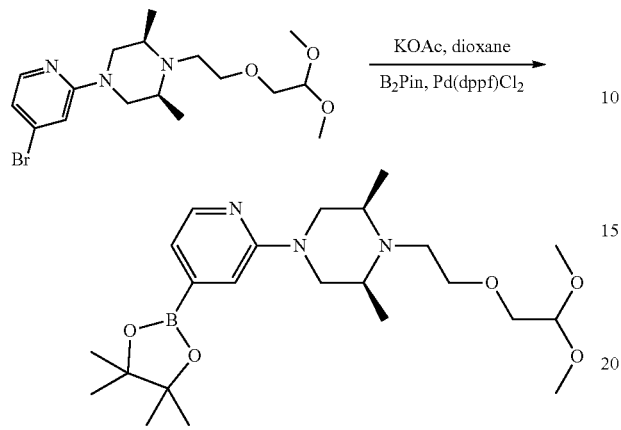

To a solution of (2R,6S)-4-(4-bromo-2-pyridyl)-1-[2-(2,2-dimethoxyethoxy)ethyl]-2,6-dimethyl-piperazine (2.1 g, 5.22 mmol, 1 eq) and 4,4,5,5-tetramethyl-2-(4,4,5,5-tetramethyl-1,3,2-dioxaborolan-2-yl)-1,3,2-dioxaborolane (1.72 g, 6.79 mmol, 1.3 eq) in dioxane (40 mL) was added KOAc (1.54 g, 15.66 mmol, 3 eq) and Pd(dppf)Cl$_2$ (381.93 mg, 521.97 umol, 0.1 eq). After addition, the reaction mixture was stirred at 100° C. for 1 h under N$_2$. LCMS (EB12-470-P1B1) showed desired MS. The reaction mixture was filtered and concentrated under reduced pressure to afford (2R,6S)-1-[2-(2,2-dimethoxyethoxy)ethyl]-2,6-dimethyl-4-[4-(4,4,5,5-tetramethyl-1,3,2-dioxaborolan-2-yl)-2-pyridyl]piperazine (3.8 g, 4.98 mmol, 95.40% yield) as a brown oil.

Step 3: 3-[2-[(3R,5S)-4-[2-(2,2-dimethoxyethoxy)ethyl]-3,5-dimethyl-piperazin-1-yl]-4-pyridyl]-5-nitro-1H-indazole

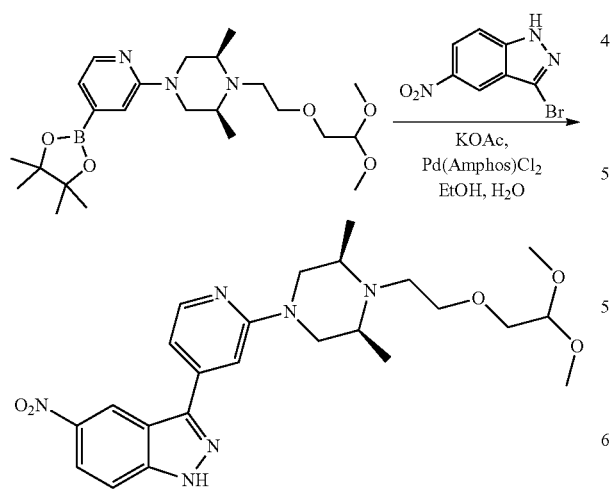

A mixture of (2R,6S)-1-[2-(2,2-dimethoxyethoxy)ethyl]-2,6-dimethyl-4-[4-(4,4,5,5-tetramethyl-1,3,2-dioxaborolan-2-yl)-2-pyridyl]piperazine (3.8 g, 4.98 mmol, 1 eq), 3-bromo-5-nitro-1H-indazole (1.81 g, 7.47 mmol, 1.5 eq), 4-ditert-butylphosphanyl-N,N-dimethyl-aniline; dichloropalladium (352.66 mg, 498.05 umol, 352.66 uL, 0.1 eq) and KOAc (1.47 g, 14.94 mmol, 3 eq) in EtOH (30 mL) and H$_2$O (6 mL) was stirred at 100° C. for 12 h under N$_2$. LCMS (EB12-473-P1B) showed desired MS. The reaction mixture was filtered and the filtrate was concentrated under reduced pressure. The residue was purified by silica gel column chromatography (0 to 15% methanol in dichloromethane) to afford 3-[2-[(3R,5S)-4-[2-(2,2-dimethoxyethoxy)ethyl]-3,5-dimethyl-piperazin-1-yl]-4-pyridyl]-5-nitro-1H-indazole (2 g, 3.80 mmol, 76.24% yield, 92% purity) as a brown gum.

Step 4: 2-[2-[(2R,6S)-2,6-dimethyl-4-[4-(5-nitro-1H-indazol-3-yl)-2-pyridyl]piperazin-1-yl]ethoxy]acetaldehyde

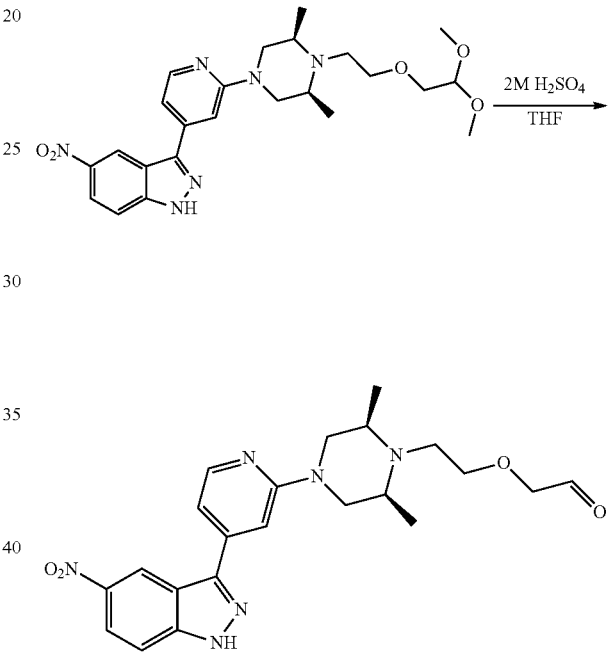

To a solution of 3-[2-[(3R,5S)-4-[2-(2,2-dimethoxyethoxy)ethyl]-3,5-dimethyl-piperazin-1-yl]-4-pyridyl]-5-nitro-1H-indazole (700 mg, 1.44 mmol, 1 eq) in THF (5 mL) was added H$_2$SO$_4$ (2 M, 4 mL) After addition, the reaction solution was stirred at 70° C. for 1 h. TLC (dichloromethane:methanol=10:1) showed starting material consumed and a new spot formed. After cooling, the reaction was diluted with water (10 mL) and washed with ethyl acetate (2×10 mL). The aqueous phase was raised to pH=14 with NaOH. The solid was collected by filtration. The solid was dried under reduced pressure to afford 2-[2-[(2R,6S)-2,6-dimethyl-4-[4-(5-nitro-1H-indazol-3-yl)-2-pyridyl]piperazin-1-yl]ethoxy]acetaldehyde (500 mg, 1.04 mmol, 71.83% yield, 91% purity) as a yellow solid. The crude product was used for next step directly.

Step 5: 5-[4-[2-[2-[(2R,6S)-2,6-dimethyl-4-[4-(5-nitro-1H-indazol-3-yl)-2-pyridyl]piperazin-1-yl]ethoxy]ethyl]piperazin-1-yl]-2-(2,6-dioxo-3-piperidyl)isoindoline-1,3-dione

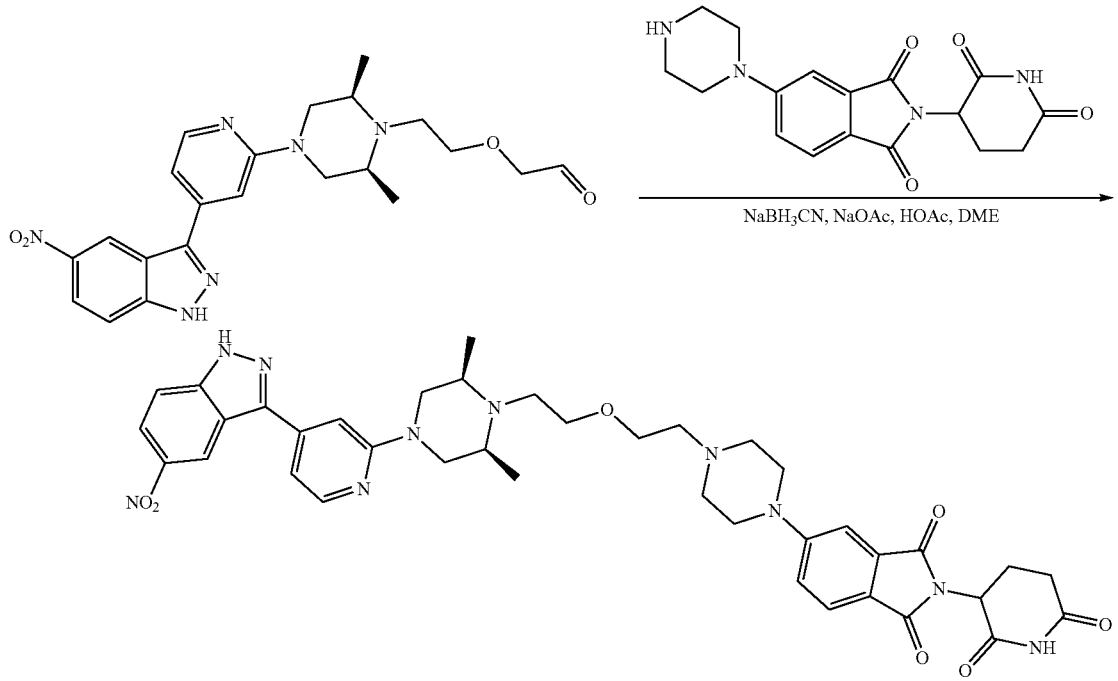

To a solution of 2-[2-[(2R,6S)-2,6-dimethyl-4-[4-(5-nitro-1H-indazol-3-yl)-2-pyridyl]piperazin-1-yl]ethoxy]acetaldehyde (250 mg, 570.15 umol, 1 eq) and AcOH (525.00 mg, 8.74 mmol, 0.5 mL, 15.33 eq) in DCE (10 mL) MeOH (10 mL) and DMSO (2 mL) was added 2-(2,6-dioxo-3-piperidyl)-5-piperazin-1-yl-isoindoline-1,3-dione (390.30 mg, 1.14 mmol, 2.00 eq) and NaOAc (140.32 mg, 1.71 mmol, 3 eq). The reaction solution was stirred at 25° C. for 30 min. Then NaBH₃CN (107.49 mg, 1.71 mmol, 3 eq) was added and the reaction was stirred at 25° C. for 12 h. LCMS (EB12-480-P1D2) showed desired MS. TLC (dichloromethane:methanol=10:1) showed several new spots. The reaction solution was diluted with water (20 mL) and extracted with ethyl acetate (3×20 mL). The organic layer was dried over sodium sulfate and concentrated under reduced pressure. The residue was purified by silica gel column chromatography (0 to 15% methanol in chloromethane) to afford 5-[4-[2-[2-[(2R,6S)-2,6-dimethyl-4-[4-(5-nitro-1H-indazol-3-yl)-2-pyridyl]piperazin-1-yl]ethoxy]ethyl]piperazin-1-yl]-2-(2,6-dioxo-3-piperidyl)isoindoline-1,3-dione (250 mg, 294.18 umol, 51.60% yield, 90% purity) as a yellow solid.

Step 6: 5-[4-[2-[2-[(2R,6S)-4-[4-(5-amino-1H-indazol-3-yl)-2-pyridyl]-2,6-dimethyl-piperazin-1-yl]ethoxy]ethyl]piperazin-1-yl]-2-(2,6-dioxo-3-piperidyl)isoindoline-1,3-dione

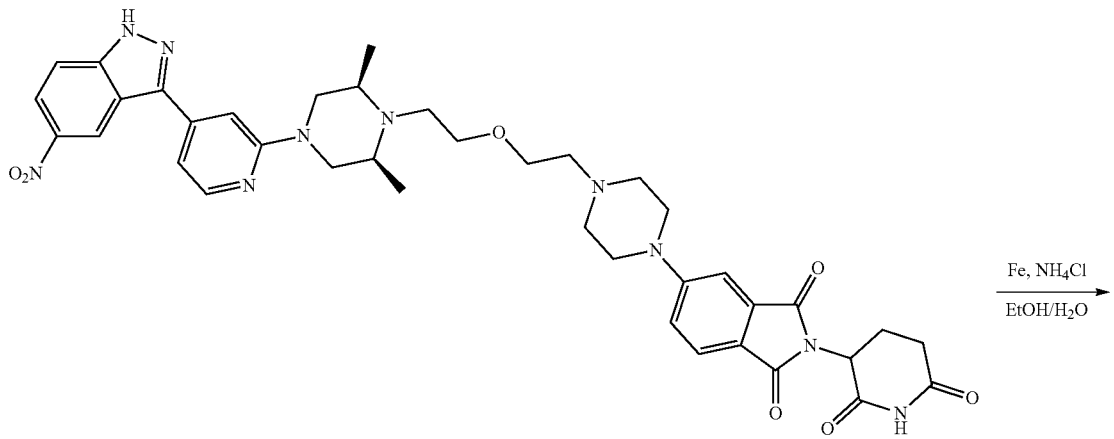

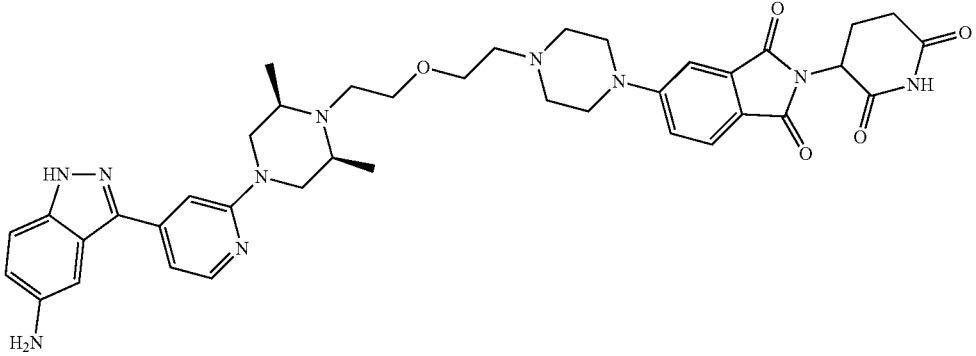

To a mixture of 5-[4-[2-[2-[(2R,6S)-2,6-dimethyl-4-[4-(5-nitro-1H-indazol-3-yl)-2-pyridyl]piperazin-1-yl]ethoxy]ethyl]piperazin-1-yl]-2-(2,6-dioxo-3-piperidyl)isoindoline-1,3-dione (250 mg, 326.87 umol, 1 eq) in EtOH (3 mL) and H$_2$O (0.5 mL) was added Fe (91.27 mg, 1.63 mmol, 5 eq) and NH$_4$Cl (87.42 mg, 1.63 mmol, 5 eq). After addition, the reaction mixture was stirred at 80° C. for 1 h. LCMS (EB12-481-P1C1) showed desired MS. The reaction mixture was filtered and filtrate was concentrated under reduced pressure. The resulting was dissolved with 10% methanol in dichloromethane (10 mL). The mixture was filtered and filtrate was concentrated under reduced pressure to afford 5-[4-[2-[2-[(2R,6S)-4-[4-(5-amino-1H-indazol-3-yl)-2-pyridyl]-2,6-dimethyl-piperazin-1-yl]ethoxy]ethyl]piperazin-1-yl]-2-(2,6-dioxo-3-piperidyl)isoindoline-1,3-dione (140 mg, 188.23 umol, 57.59% yield, 98.8% purity) as a yellow solid.

Step 7: N-[3-[2-[(3S,5R)-4-[2-[2-[4-[2-(2,6-dioxo-3-piperidyl)-1,3-dioxo-isoindolin-5-yl]piperazin-1-yl]ethoxy]ethyl]-3,5-dimethyl-piperazin-1-yl]-4-pyridyl]-1H-indazol-5-yl]-4,5-dimethyl-7H-tetrazolo[1,5-a]pyrimidine-6-carboxamide (Compound 3)

To a solution of 5-[4-[2-[2-[(2S,6R)-4-[4-(5-amino-1H-indazol-3-yl)-2-pyridyl]-2,6-dimethyl-piperazin-1-yl]ethoxy]ethyl]piperazin-1-yl]-2-(2,6-dioxo-3-piperidyl)isoindoline-1,3-dione (140 mg, 190.52 umol, 1 eq) and 4,5-dimethyl-7H-tetrazolo[1,5-a]pyrimidine-6-carboxylic acid (74.37 mg, 381.03 umol, 2 eq) in DMF (2 mL) was added DIEA (123.11 mg, 952.58 umol, 165.92 uL, 5 eq) and HATU (72.44 mg, 190.52 umol, 1 eq). After addition, the reaction solution was stirred at 25° C. for 12 h. LCMS (EB12-482-P1D) showed desired MS. The reaction solution was diluted with water (10 mL) and extracted with dichloromethane (3×10 mL). The organic layer was dried over sodium sulfate and concentrated under reduced pressure. The residue was purified by prep.HPLC (column: Phenomenex luna C18 150*25 mm*10 um; mobile phase: [water (0.225% FA)-ACN]; B %: 0%-40%; 35 min) to afford N-[3-[2-[(3S,5R)-4-[2-[2-[4-[2-(2,6-dioxo-3-piperidyl)-1,3-dioxo-isoindolin-5-yl]piperazin-1-yl]ethoxy]ethyl]-3,5-dimethyl-piperazin-1-yl]-4-pyridyl]-1H-indazol-5-yl]-4,5-dimethyl-7H-tetrazolo[1,5-a]pyrimidine-6-carboxamide (5.6 mg, 5.83 umol, 3.06% yield, 95% purity) as a yellow solid.

$^1$H NMR: (400 MHz, CD$_3$OD) δ: 8.65 (s, 1H), 8.40 (s, 1H), 8.17 (d, J=5.3 Hz, 1H), 7.52 (d, J=8.9 Hz, 1H),

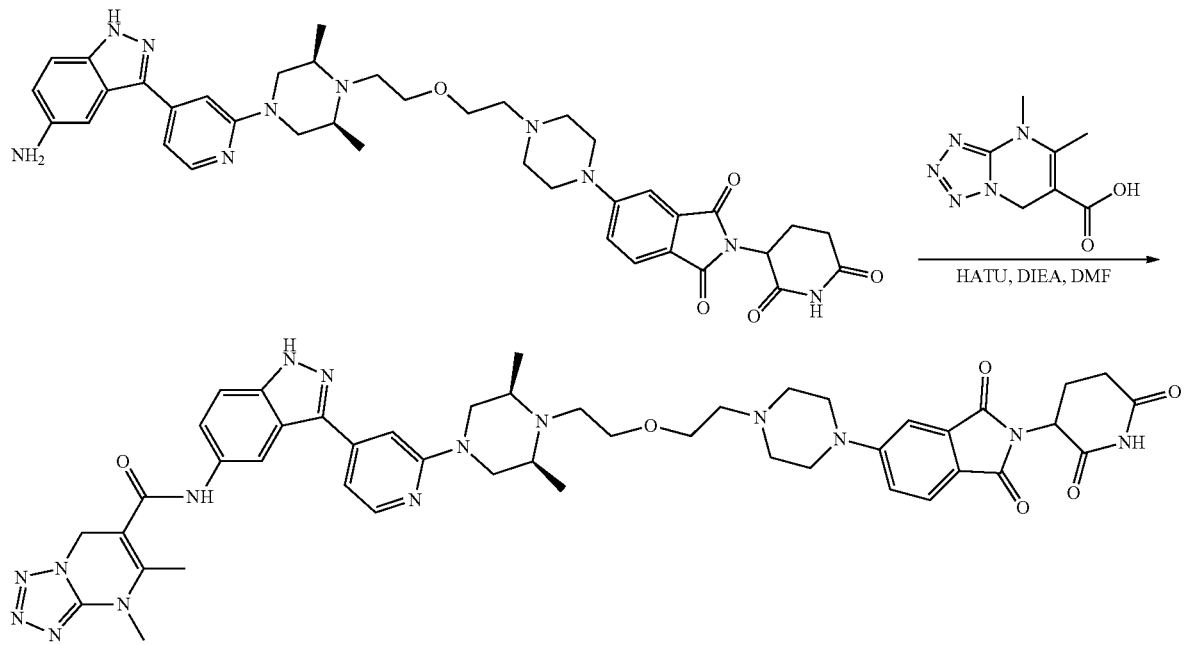

7.38-7.32 (m, 2H), 7.24 (d, J=5.3 Hz, 1H), 7.19 (d, J=8.5 Hz, 1H), 6.93 (d, J=2.1 Hz, 1H), 6.75 (dd, J=2.1, 8.5 Hz, 1H), 5.30 (s, 2H), 5.02 (br dd, J=5.5, 12.8 Hz, 1H), 4.53 (br t, J=11.4 Hz, 2H), 3.92-3.81 (m, 4H), 3.67 (br t, J=4.8 Hz, 2H), 3.55 (br s, 2H), 3.51 (s, 3H), 3.26-3.20 (m, 4H), 3.04-2.94 (m, 2H), 2.92-2.81 (m, 1H), 2.76 (br d, J=2.8 Hz, 1H), 2.68-2.56 (m, 7H), 2.36 (s, 3H), 2.14-2.05 (m, 1H), 1.48 (br d, J=5.4 Hz, 6H)

Exemplary Synthesis of Exemplary Compound 4:
N-[3-[2-[(3S,5R)-4-[2-[2-[2-[4-[2-(2,6-dioxo-3-piperidyl)-1,3-dioxo-isoindolin-5-yl]piperazin-1-yl]ethoxy]ethoxy]ethyl]-3,5-dimethyl-piperazin-1-yl]-4-pyridyl]-1H-indazol-5-yl]-4,5-dimethyl-7H-tetrazolo[1,5-a]pyrimidine-6-carboxamide Compound 4 was prepared in a manner analogous to example 3.

¹H NMR: (400 MHz, MeOD) δ: 8.71 (s, 1H), 8.27 (d, J=5.4 Hz, 1H), 7.55-7.48 (m, 2H), 7.41 (d, J=8.5 Hz, 1H), 7.38-7.31 (m, 2H), 6.99 (d, J=1.8 Hz, 1H), 6.87 (d, J=8.5 Hz, 1H), 5.29 (s, 2H), 5.05 (dd, J=5.4, 12.7 Hz, 1H), 4.55 (d, J=13.9 Hz, 2H), 3.85 (d, J=4.5 Hz, 2H), 3.79-3.53 (m, 10H), 3.51 (s, 3H), 3.22 (s, 4H), 3.05-2.93 (m, 2H), 2.91-2.51 (m, 9H), 2.34 (s, 3H), 2.16-2.07 (m, 1H), 1.49 (d, J=6.3 Hz, 6H).

Exemplary Synthesis of Exemplary Compound 5:
N-[3-[2-[(3S,5R)-4-[2-[4-[2-(2,6-dioxo-3-piperidyl)-1,3-dioxo-isoindolin-5-yl]piperazin-1-yl]ethyl]-3,5-dimethyl-piperazin-1-yl]-4-pyridyl]-1H-indazol-5-yl]-4,5-dimethyl-7H-tetrazolo[1,5-a]pyrimidine-6-carboxamide Step 1: Tert-butyl 4-[2-[(2R,6S)-4-(4-bromo-2-pyridyl)-2,6-dimethyl-piperazin-1-yl]ethyl]piperazine-1-carboxylate

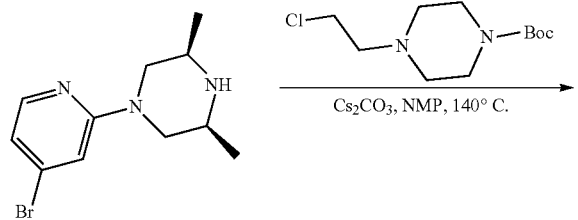

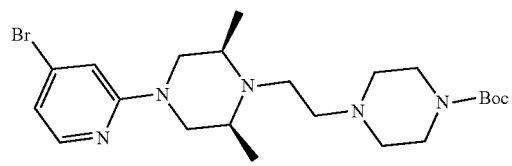

To a solution of (3R,5S)-1-(4-bromo-2-pyridyl)-3,5-dimethyl-piperazine (1.5 g, 5.55 mmol, 1 eq) and tert-butyl 4-(2-chloroethyl)piperazine-1-carboxylate (2.07 g, 8.33 mmol, 3.58 mL, 1.5 eq) in NMP (20 mL) then was added Cs₂CO₃ (5.43 g, 16.66 mmol, 3 eq) and KI (4.61 g, 27.76 mmol, 5.0 eq). Then the mixture was stirred at 140° C. for 16 h. TLC (Dichloromethane:Methanol=10:1, Rf=0.5) showed the reaction a new spot. The residue was diluted with H₂O (50 mL) extracted with ethyl acetate (50 mL×3). The combined organic layers were washed with brine (50 mL×2), dried over anhydrous sodium sulfate, filtered and concentrated under reduced pressure to give a residue. The residue was purified by silica gel column chromatography (0 to 10% Methanol in Dichloromethane) to give tert-butyl 4-[2-[(2R,6S)-4-(4-bromo-2-pyridyl)-2,6-dimethyl-piperazin-1-yl]ethyl]piperazine-1-carboxylate (1.2 g, 2.26 mmol, 40.77% yield, 91% purity) as a yellow gum.

Step 2: afford tert-butyl 4-[2-[(2R,6S)-2,6-dimethyl-4-[4-(4,4,5,5-tetramethyl-1,3,2-dioxaborolan-2-yl)-2-pyridyl]piperazin-1-yl]ethyl]piperazine-1-carboxylate

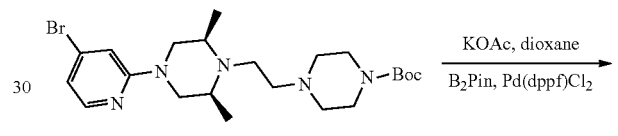

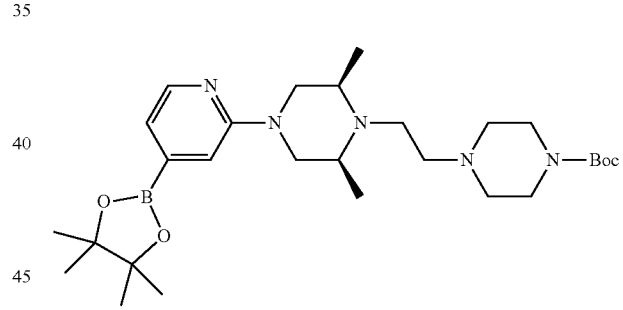

To a solution of tert-butyl 4-[2-[(2R,6S)-4-(4-bromo-2-pyridyl)-2,6-dimethyl-piperazin-1-yl]ethyl]piperazine-1-carboxylate (1.2 g, 2.49 mmol, 1 eq) and 4,4,5,5-tetramethyl-2-(4,4,5,5-tetramethyl-1,3,2-dioxaborolan-2-yl)-1,3,2-dioxaborolane (1.26 g, 4.97 mmol, 2. eq) in dioxane (10 mL) was added KOAc (732.30 mg, 7.46 mmol, 3 eq), Pd(dppf)Cl₂ (182.00 mg, 248.73 umol, 0.1 eq). Then the mixture was stirred at 100° C. for 1 hr under N₂. TLC (Dichloromethane:Methanol=10:1, Rf=0.3) showed the reaction a new spot. The reaction mixture was filtered and concentrated under reduced pressure to afford tert-butyl 4-[2-[(2R,6S)-2,6-dimethyl-4-[4-(4,4,5,5-tetramethyl-1,3,2-dioxaborolan-2-yl)-2-pyridyl]piperazin-1-yl]ethyl]piperazine-1-carboxylate (1.3 g, crude) as a brown gum.

Step 3: Tert-butyl 4-(2-((2R,6S)-2,6-dimethyl-4-(4-(5-nitro-1H-indazol-3-yl)pyridin-2-yl)piperazin-1-yl)ethyl)piperazine-1-carboxylate

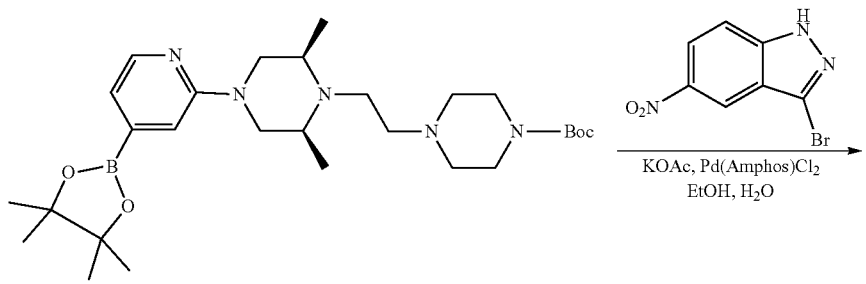

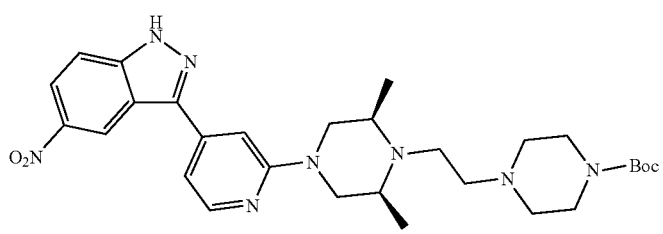

To a solution of tert-butyl 4-(2-((2R,6S)-2,6-dimethyl-4-(4-(4,4,5,5-tetramethyl-1,3,2-dioxaborolan-2-yl)pyridin-2-yl)piperazin-1-yl)ethyl)piperazine-1-carboxylate (1.3 g, 2.46 mmol, 1 eq) and 3-bromo-5-nitro-1H-indazole (713.03 mg, 2.95 mmol, 1.2 eq) in EtOH (10 mL) and H₂O (2 mL) was added KOAc (722.83 mg, 7.37 mmol, 3 eq), 4-ditert-butylphosphanyl-N,N-dimethyl-aniline; dichloropalladium (173.84 mg, 245.50 umol, 173.84 uL, 0.1 eq). Then the mixture was stirred at 100° C. for 2 hr under N₂. TLC (Dichloromethane:Methanol=10:1, Rf=0.4) showed the reaction a new spot. The reaction mixture was poured into H₂O (10 mL). The mixture was extracted with ethyl acetate (15 mL*3). The organic phase was washed with brine (10 mL), dried over anhydrous Na₂SO₄, concentrated in vacuum to give a residue. The residue was purified by silica gel column chromatography (0 to 15% Methanol in Dichloromethane) to give tert-butyl 4-(2-((2R,6S)-2,6-dimethyl-4-(4-(5-nitro-1H-indazol-3-yl)pyridin-2-yl)piperazin-1-yl)ethyl)piperazine-1-carboxylate (750 mg, 1.01 mmol, 41.12% yield, 76% purity) as a yellow solid.

Step 4: 3-[2-[(3S,5R)-3,5-dimethyl-4-(2-piperazin-1-ylethyl)piperazin-1-yl]-4-pyridyl]-5-nitro-1H-indazole

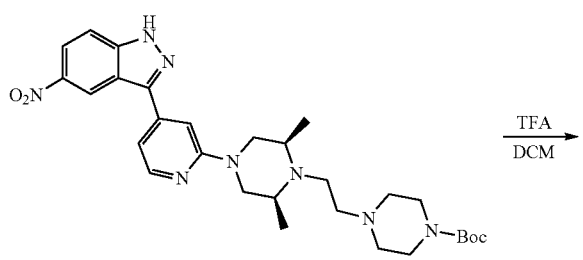

-continued

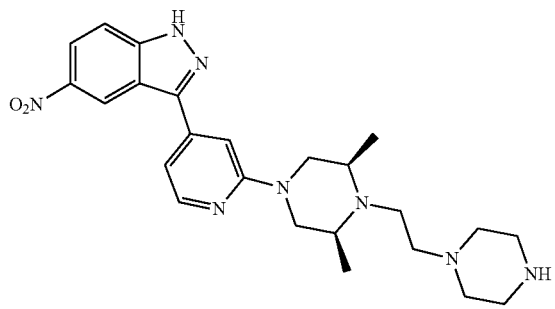

To a solution of tert-butyl4-[2-[(2S,6R)-2,6-dimethyl-4-[4-(5-nitro-1H-indazol-3-yl)-2-pyridyl]piperazin-1-yl]ethyl]piperazine-1-carboxylate (750 mg, 1.33 mmol, 1 eq) in DCM (10 mL) was added TFA (12.32 g, 108.05 mmol, 8 mL, 81.35 eq). After addition, the reaction solution was stirred at 20° C. for 1 h. LCMS (EB12-483-P1B) showed desired MS. The reaction solution was diluted with water (50 mL) and washed with dichloromethane (2×30 mL). The aqueous phase was basified to pH~14 with NaOH and extracted with ethyl acetate (3×50 mL). The organic layer was dried over sodium sulfate and concentrated under reduced pressure to afford 3-[2-[(3S,5R)-3,5-dimethyl-4-(2-piperazin-1-ylethyl)piperazin-1-yl]-4-pyridyl]-5-nitro-1H-indazole (450 mg, 852.42 umol, 64.18% yield, 88% purity) as a yellow solid.

Step 5: 5-[4-[2-[(2S,6R)-2,6-dimethyl-4-[4-(5-nitro-1H-indazol-3-yl)-2-pyridyl]piperazin-1-yl]ethyl]piperazin-1-yl]-2-(2,6-dioxo-3-piperidyl)isoindoline-1,3-dione

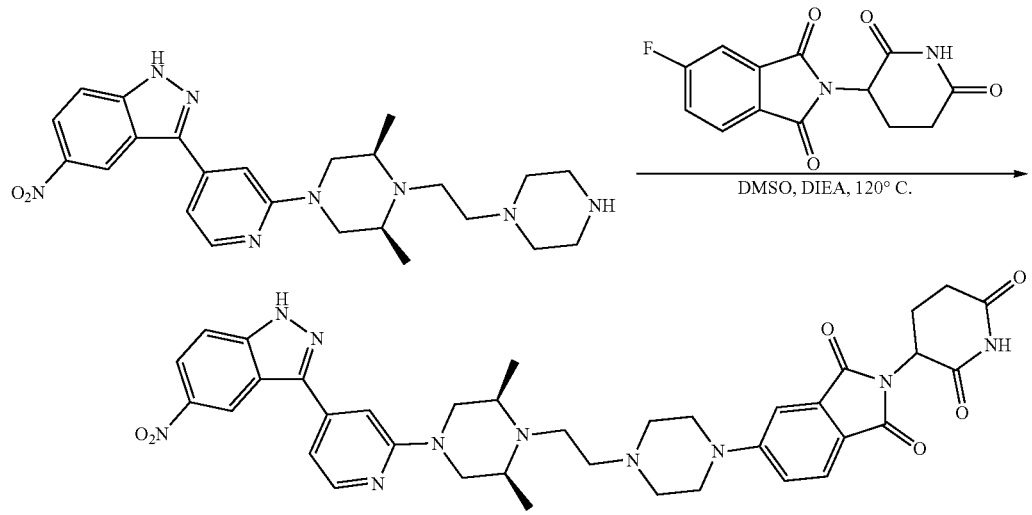

To a solution of 3-[2-[(3S,5R)-3,5-dimethyl-4-(2-piperazin-1-ylethyl)piperazin-1-yl]-4-pyridyl]-5-nitro-1H-indazole (250 mg, 538.14 umol, 1 eq) and 2-(2,6-dioxo-3-piperidyl)-5-fluoro-isoindoline-1,3-dione (222.97 mg, 807.21 umol, 1.5 eq) in DMSO (3 mL) was added DIEA (208.65 mg, 1.61 mmol, 281.20 uL, 3 eq). After addition, the reaction was stirred at 100° C. for 12 h. LCMS (EB12-486-P1B1) showed desired MS. TLC (dichloromethane:methanol=10:1) showed several new spots. After cooling, the reaction solution was diluted with water (10 mL) and extracted with dichloromethane (3×10 mL). The organic layer was washed with brine (2×15 mL), dried over sodium sulfate and concentrated under reduced pressure. The residue was purified by silica gel column chromatography (0 to 10% methanol in dichloromethane) to afford 5-[4-[2-[(2S,6R)-2,6-dimethyl-4-[4-(5-nitro-1H-indazol-3-yl)-2-pyridyl]piperazin-1-yl]ethyl]piperazin-1-yl]-2-(2,6-dioxo-3-piperidyl)isoindoline-1,3-dione (150 mg, 168.57 umol, 31.32% yield, 81% purity) as a yellow solid.

Step 6: 5-[4-[2-[(2S,6R)-4-[4-(5-amino-1H-indazol-3-yl)-2-pyridyl]-2,6-dimethyl-piperazin-1-yl]ethyl]piperazin-1-yl]-2-(2,6-dioxo-3-piperidyl)isoindoline-1,3-dione

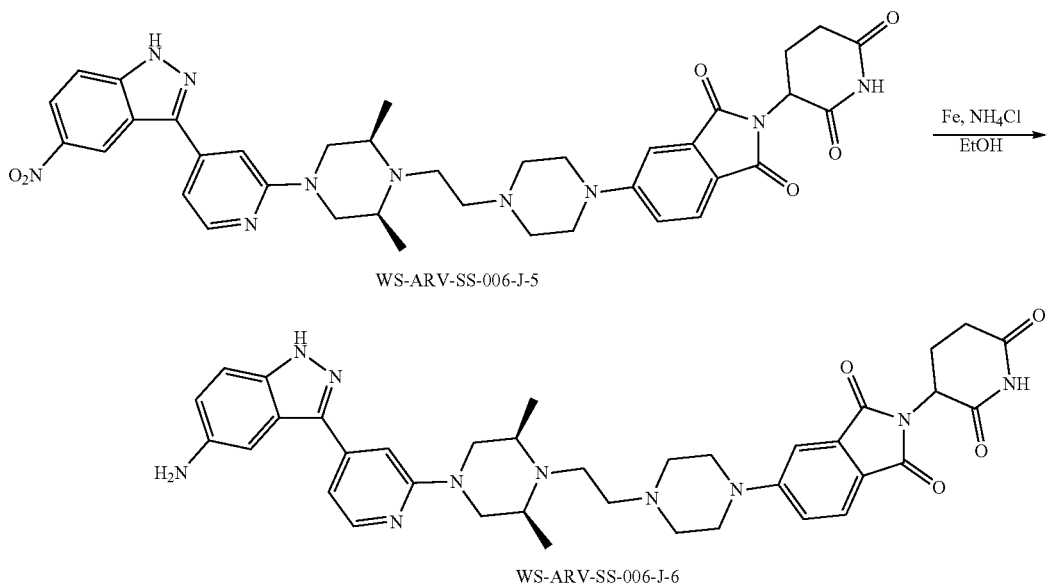

To a mixture of 5-[4-[2-[(2S,6R)-2,6-dimethyl-4-[4-(5-nitro-1H-indazol-3-yl)-2-pyridyl]piperazin-1-yl]ethyl]piperazin-1-yl]-2-(2,6-dioxo-3-piperidyl)isoindoline-1,3-dione (150 mg, 208.11 umol, 1 eq) in EtOH (3 mL) and H₂O (0.5 mL) was added Fe (58.11 mg, 1.04 mmol, 5 eq) and NH₄Cl (55.66 mg, 1.04 mmol, 5 eq). After addition, the reaction was stirred at 80° C. for 1 h. LCMS (EB12-487-P1B1) showed the reaction was completed. After cooling, the reaction mixture was filtered and filtrate was concentrated under reduced pressure. The residue was triturated with 10% methanol in chloromethane at 20° C. for 15 min. The solid was removed by filtration and filtrate was concentrated under reduced pressure to afford 5-[4-[2-[(2S,6R)-4-[4-(5-amino-1H-indazol-3-yl)-2-pyridyl]-2,6-dimethyl-piperazin-1-yl]ethyl]piperazin-1-yl]-2-(2,6-dioxo-3-piperidyl)isoindoline-1,3-dione (70 mg, 89.17 umol, 42.85% yield, 88% purity) as a yellow solid.

Step 7: N-[3-[2-[(3S,5R)-4-[2-[4-[2-(2,6-dioxo-3-piperidyl)-1,3-dioxo-isoindolin-5-yl]piperazin-1-yl]ethyl]-3,5-dimethyl-piperazin-1-yl]-4-pyridyl]-1H-indazol-5-yl]-4,5-dimethyl-7H-tetrazolo[1,5-a]pyrimidine-6-carboxamide (Compound 5)

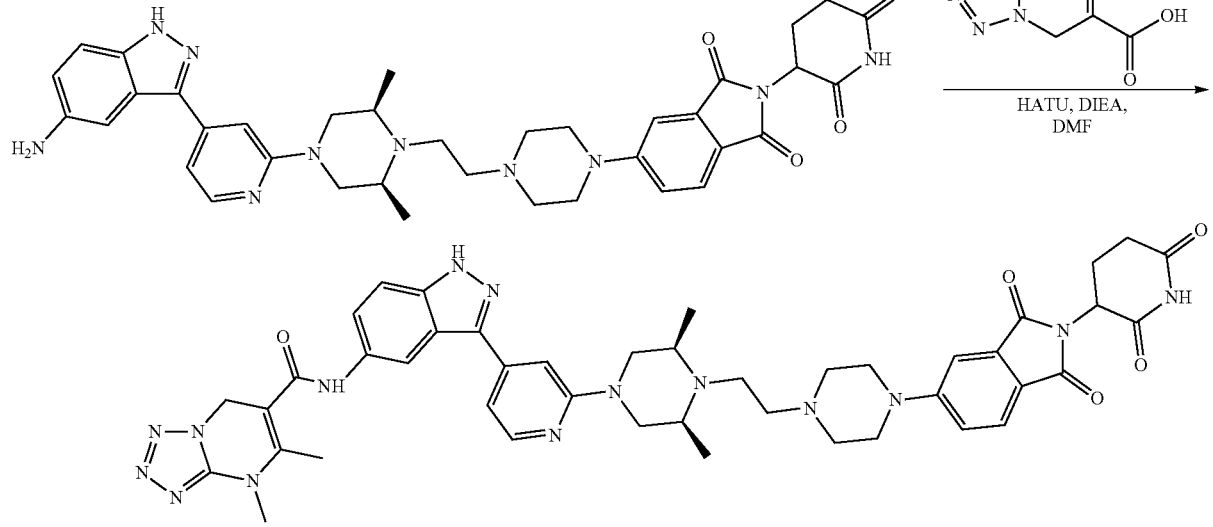

To a solution of 5-[4-[2-[(2S,6R)-4-[4-(5-amino-1H-indazol-3-yl)-2-pyridyl]-2,6-dimethyl-piperazin-1-yl]ethyl]piperazin-1-yl]-2-(2,6-dioxo-3-piperidyl)isoindoline-1,3-dione (130 mg, 188.19 umol, 1 eq) and 4,5-dimethyl-7H-tetrazolo[1,5-a]pyrimidine-6-carboxylicacid (37.14 mg, 190.30 umol, 1.01 eq) in DMF (2 mL) was added DIEA (72.97 mg, 564.57 umol, 98.34 uL, 3 eq) and HATU (71.56 mg, 188.19 umol, 1 eq). After addition, the reaction solution was stirred at 25° C. for 18 h. LCMS (EB12-489-P1B72) showed desired MS. The reaction was diluted with water (5 mL) and extracted with ethyl acetate (3×5 mL). The organic layer was dried over sodium sulfate and concentrated under reduced pressure. The residue was purified by prep.HPLC (column: PhenomenexLunaC18150*25 mm*10 um; mobile phase: [water (0.225% FA)-ACN]; B %: 0-30%; 35 min) to afford N-[3-[2-[(3S,5R)-4-[2-[4-[2-(2,6-dioxo-3-piperidyl)-1,3-di oxo-isoindolin-5-yl]piperazin-1-yl]ethyl]-3,5-dimethyl-piperazin-1-yl]-4-pyridyl]-1H-indazol-5-yl]-4,5-dimethyl-7H-tetrazolo[1,5-a]pyrimidine-6-carboxamide (10.7 mg, 12.26 umol, 6.51% yield, 99.42% purity) as a yellow solid.

¹H NMR: (400 MHz, METHANOL-d₄) δ: 8.69 (s, 1H), 8.41 (br s, 1H), 8.28 (d, J=5.3 Hz, 1H), 7.54-7.47 (m, 2H), 7.45 (s, 1H), 7.36 (d, J=6.6 Hz, 2H), 7.15 (s, 1H), 7.01 (br d, J=6.9 Hz, 1H), 5.29 (s, 2H), 5.08 (dd, J=5.5, 12.4 Hz, 1H), 4.59 (s, 3H), 4.43 (br s, 2H), 3.51 (s, 4H), 3.27 (br s, 4H), 3.02 (br t, J=12.6 Hz, 2H), 2.93-2.82 (m, 1H), 2.80-2.75 (m, 1H), 2.75-2.69 (m, 3H), 2.66 (br t, J=4.7 Hz, 4H), 2.35 (s, 3H), 2.19-2.05 (m, 1H), 1.44 (br d, J=4.9 Hz, 6H)

Exemplary Synthesis of Exemplary Compound 6: N-(3-{2-[(3R,5S)-4-{[1-({1-[2-(2,6-dioxopiperidin-3-yl)-1,3-dioxo-2,3-dihydro-1H-isoindol-5-yl]piperidin-4-yl}methyl)piperidin-4-yl]methyl}-3,5-dimethylpiperazin-1-yl]pyridin-4-yl}-1H-indazol-5-yl)-4,5,7,7-tetramethyl-4H,7H-[1,2,3,4]tetrazolo[1,5-a]pyrimidine-6-carboxamide Exemplary Compound 6 was prepared in a manner analogous to Exemplary Compound 1 using Intermediate 3.

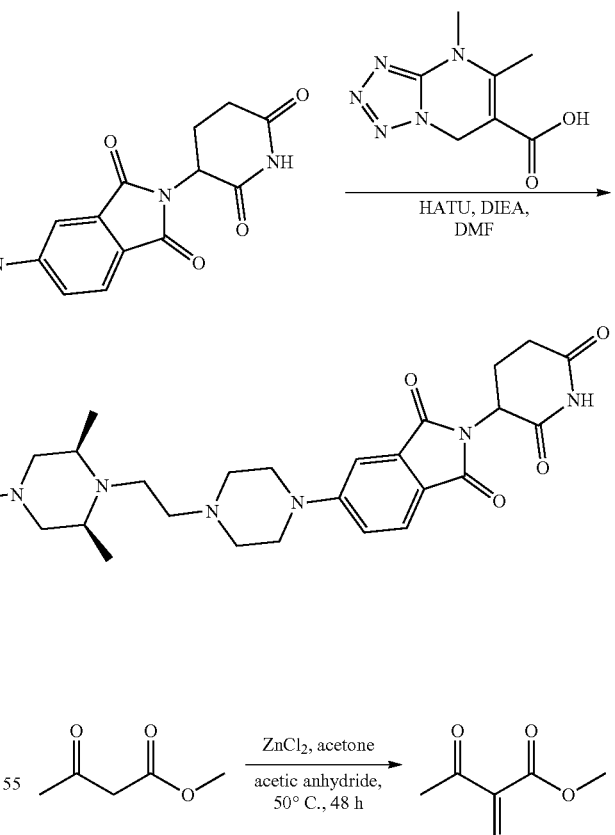

Step 1

To a mixture of methyl 3-oxobutanoate (29 g, 249.75 mmol, 26.85 mL, 1 eq), ZnCl2 (5.11 g, 37.46 mmol, 1.75 mL, 0.15 eq) and acetone (21.76 g, 374.63 mmol, 27.54 mL, 1.5 eq) was added AC₂O (33.15 g, 324.68 mmol, 30.41 mL, 1.3 eq) in one portion. The mixture was stirred at 50° C. for 48 hours to give yellow solution. TLC (Petroleum ether: Ethyl acetate=10:1, Rf=0.4) showed no start material and a new spot. The residue was diluted with H₂O (200 mL) extracted with ethyl acetate (200 mL×3). The combined organic layers were washed with brine (75 mL), dried over anhydrous sodium sulfate, filtered and concentrated under reduced pressure to give a residue. The residue was purified by silica gel column chromatography (0 to 10% Ethyl acetate in Petroleum ether) to give methyl 2-acetyl-3-methyl-but-2-enoate (18 g, 73.76 mmol, 29.53% yield, 64% purity) as a colorless oil.

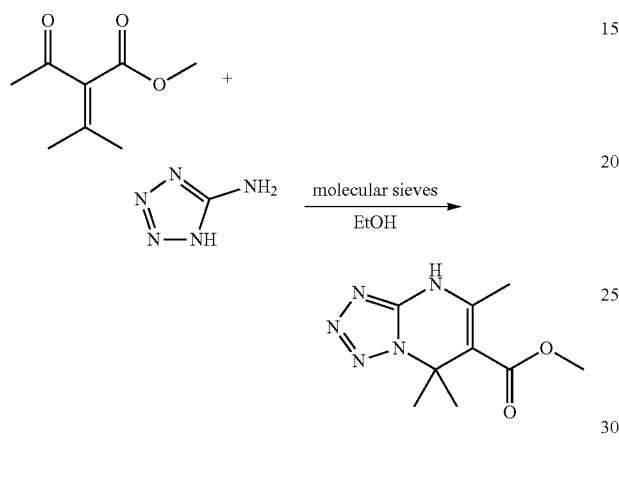

Step 2

To a mixture of methyl 2-acetyl-3-methyl-but-2-enoate (18 g, 115.25 mmol, 1 eq) and 1H-tetrazol-5-amine (9.80 g, 115.25 mmol, 1 eq) in EtOH (50 mL) and was added molecular sieves (10 g, 115.25 mmol, 1 eq) at 20° C. under N₂. The mixture was stirred at 50° C. for 16 hours to give yellow solution. TLC (Petroleum ether: Ethyl acetate=10:1, Rf=0.1) showed no start material and a new spot. The reaction mixture was filtered and concentrated under reduced pressure. The crude product was poured into H₂O (100 mL). The mixture was extracted with ethyl acetate (150 mL*3). The organic phase was washed with brine (80 mL), dried over anhydrous Na₂SO₄, concentrated in vacuum to give a residue. The residue was purified by silica gel column chromatography (0 to 30% Ethyl acetate in Petroleum ether) to give methyl 5,7,7-trimethyl-4H-tetrazolo[1,5-a]pyrimidine-6-carboxylate (11 g, 48.29 mmol, 41.90% yield, 98% purity) as a white solid.

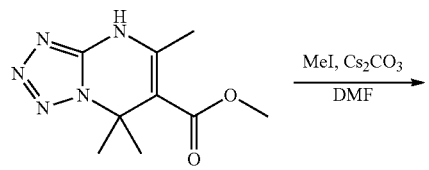

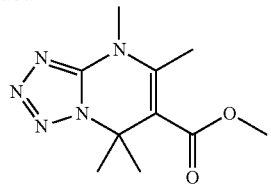

Step 3

To a mixture of methyl 5,7,7-trimethyl-4H-tetrazolo[1,5-a]pyrimidine-6-carboxylate (11 g, 49.28 mmol, 1 eq) in MeCN (100 mL) was added MeI (11.71 g, 82.50 mmol, 5.14 mL, 1.67 eq) in one portion and Cs₂CO₃ (19.27 g, 59.13 mmol, 1.2 eq) at 20° C. under N₂. The mixture was stirred at 50° C. for 1 hours to give yellow solution. The residue was diluted with H₂O (200 mL) extracted with ethyl acetate (100 mL×3). The combined organic layers were washed with brine (85 mL), dried over anhydrous sodium sulfate, filtered and concentrated under reduced pressure to give methyl 4,5,7,7-tetramethyltetrazolo[1,5-a]pyrimidine-6-carboxylate (11 g, crude) as a yellow solid.

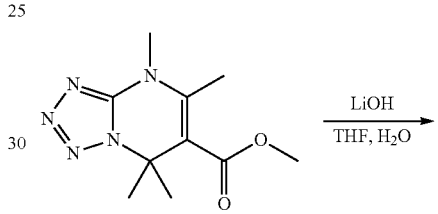

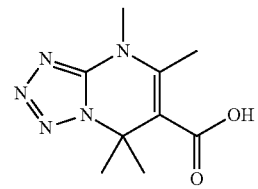

Step 4

To a mixture of methyl 4,5,7,7-tetramethyltetrazolo[1,5-a]pyrimidine-6-carboxylate (640 mg, 2.70 mmol, 1 eq) in THF (5 mL) was added LiOH (129.33 mg, 5.40 mmol, 2 eq) in H₂O (5 mL) at 20° C. The mixture was stirred at 50° C. for 16 hours to give yellow solution. TLC (Petroleum ether: Ethyl acetate=0:1, Rf=0.04) showed no start material. The THF was evaporated and the H₂O solution was acidified for pH=3 with 1M HCl, extracted with EtOAc, dried over Na₂SO₄, filtered and concentrated under reduced pressure to give 4,5,7,7-tetramethyltetrazolo[1,5-a]pyrimidine-6-carboxylic acid (424 mg, crude) as a white solid.

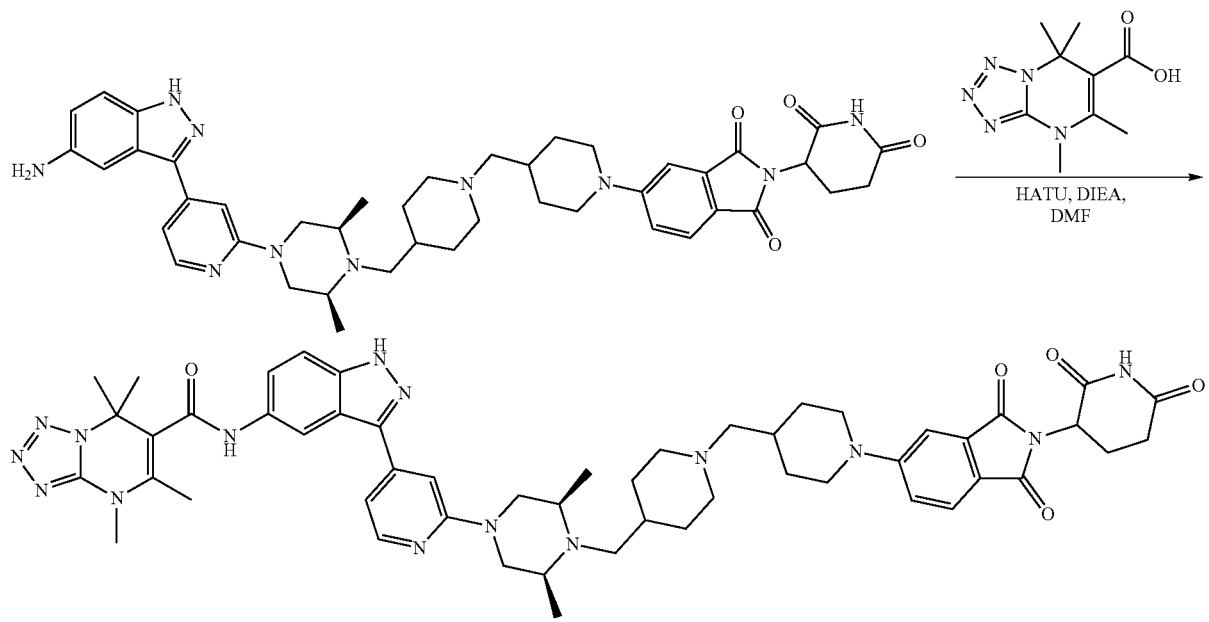

Step 5

To a mixture of 5-[4-[[4-[[(2R,6S)-4-[4-(5-amino-1H-indazol-3-yl)-2-pyridyl]-2,6-dimethyl-piperazin-1-yl]methyl]-1-piperidyl]methyl]-1-piperidyl]-2-(2,6-dioxo-3-piperidyl)isoindoline-1,3-dione (97 mg, 125.50 umol, 1 eq) and 4,5,7,7-tetramethyltetrazolo[1,5-a]pyrimidine-6-carboxylic acid (45.68 mg, 188.24 umol, 92% purity, 1.5 eq) in DMF (5 mL) was added DIEA (48.66 mg, 376.49 umol, 65.58 uL, 3 eq) in one portion and HATU (47.72 mg, 125.50 umol, 1 eq) at 25° C. under $N_2$. The mixture was stirred at 25° C. for 16 hours to give yellow solution. LCMS showed desired product. The residue was concentrated under reduced pressure to give a residue. The residue was purified by prep-HPLC (column: 3_Phenomenex Luna C18 75*30 mm*3 um; mobile phase: [water (0.1M FANH4)-ACN]; B %: 0%-30%, 40 min) to afford N-[3-[2-[(3R,5S)-4-[[1-[[1-[2-(2,6-dioxo-3-piperidyl)-1,3-dioxo-isoindolin-5-yl]-4-piperidyl]methyl]-4-piperidyl]methyl]-3,5-dimethyl-piperazin-1-yl]-4-pyridyl]-1H-indazol-5-yl]-4,5,7,7-tetramethyl-tetrazolo[1,5-a]pyrimidine-6-carboxamide (36.1 mg, 36.18 umol, 28.83% yield, 98.04% purity) as a yellow solid.

Exemplary Synthesis of Exemplary Compound 8: (7R)—N-(3-{2-[(3S)-4-{[1-({1-[2-(2,6-dioxopiperidin-3-yl)-1,3-dioxo-2,3-dihydro-1H-isoindol-5-yl]piperidin-4-yl}methyl)piperidin-4-yl]methyl}-3-methylpiperazin-1-yl]pyridin-4-yl}-1H-indazol-5-yl)-4,5,7-trimethyl-4H,7H-[1,2,3,4]tetrazolo[1,5-a]pyrimidine-6-carboxamide Exemplary Compound 8 was prepared in a manner analogous to Exemplary Compound 1 using enantiomer 2 of 4,5,7-trimethyl-7H-tetrazolo[1,5-a]pyrimidine-6-carboxylic acid.

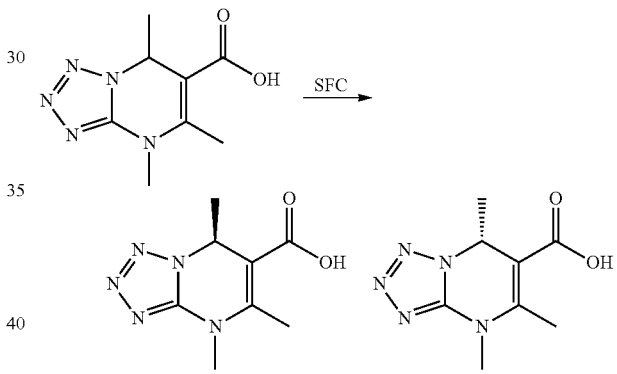

Step 1

The product 4,5,7-trimethyl-7H-tetrazolo[1,5-a]pyrimidine-6-carboxylic acid (9.5 g, 45.41 mmol, 1 eq) was separated by SFC (Column: DAICEL CHIRALPAK IC (250 mm*30 mm, 10 um); Condition: 0.1% $NH_3H_2O$ ETOH; Begin B: 20; End B: 20; FlowRate: 100 mL/min) to give enantiomer 1 designated as (7S)-4,5,7-trimethyl-7H-tetrazolo[1,5-a]pyrimidine-6-carboxylic acid (4.68 g, 22.15 mmol, 48.77% yield, 99% purity) (Rt=3.080 min, 4.68 g) and enantiomer 2 designated as (7R)-4,5,7-trimethyl-7H-tetrazolo[1,5-a]pyrimidine-6-carboxylic acid (4.1 g, 19.40 mmol, 42.73% yield, 99% purity) (Rt=3.258 min, 4.1 g) both as an off-white solid.

Enantiomer 1: Randomly assigned as (7S)-4,5,7-trimethyl-7H-tetrazolo[1,5-a]pyrimidine-6-carboxylic acid (4.68 g, 22.15 mmol, 48.77% yield, 99% purity) was obtained as an off-white solid (analytical chiral HPLC: ee %=100%, 4.11 min, α=−211).

Enantiomer 2: Randomly assigned as (7R)-4,5,7-trimethyl-7H-tetrazolo[1,5-a]pyrimidine-6-carboxylic acid (4.1 g, 19.40 mmol, 42.73% yield, 99% purity) was obtained as a off-white solid (analytical chiral HPLC: ee %=100%, 4.68 min, α=266).

Exemplary Synthesis of Exemplary Compound 9: (7S)—N-(3-{2-[(3S)-4-{[1-({1-[2-(2,6-dioxopiperidin-3-yl)-1,3-dioxo-2,3-dihydro-1H-isoindol-5-yl]piperidin-4-yl}methyl)piperidin-4-yl]methyl}-3-methylpiperazin-1-yl]pyridin-4-yl}-1H-indazol-5-yl)-4,5,7-trimethyl-4H,7H-[1,2,3,4]tetrazolo[1,5-a]pyrimidine-6-carboxamide Exemplary Compound 9 was prepared in a manner analogous to Exemplary Compound 8 using Enantiomer 1 of 4,5,7-trimethyl-7H-tetrazolo[1,5-a]pyrimidine-6-carboxylic acid.

Exemplary Synthesis of Exemplary Compound 10: N-(3-{2-[(3S)-4-{[1-({1-[2-(2,6-dioxopiperidin-3-yl)-1,3-dioxo-2,3-dihydro-1H-isoindol-5-yl]piperidin-4-yl}methyl)piperidin-4-yl]methyl}-3-methylpiperazin-1-yl]pyridin-4-yl}-1H-indazol-5-yl)-4,5-dimethyl-4H,7H-[1,2,3,4]tetrazolo[1,5-a]pyrimidine-6-carboxamide Exemplary Compound 10 was prepared in a manner analogous to Exemplary Compound 1 using Intermediate 1.

Exemplary Synthesis of Exemplary Compound 11: (7R)—N-{3-[2-(4-{[1-({1-[2-(2,6-dioxopiperidin-3-yl)-1,3-dioxo-2,3-dihydro-1H-isoindol-5-yl]piperidin-4-yl}methyl)piperidin-4-yl]methyl}piperazin-1-yl)pyridin-4-yl]-1H-indazol-5-yl}-4,5,7-trimethyl-4H,7H-[1,2,3,4]tetrazolo[1,5-a]pyrimidine-6-carboxamide Exemplary Compound 11 was prepared in a manner analogous to Exemplary Compound 1 using Enantiomer 2 of 4,5,7-trimethyl-7H-tetrazolo[1,5-a]pyrimidine-6-carboxylic acid.

Exemplary Synthesis of Exemplary Compound 12: (7S)—N-{3-[2-(4-{[1-({1-[2-(2,6-dioxopiperidin-3-yl)-1,3-dioxo-2,3-dihydro-1H-isoindol-5-yl]piperidin-4-yl}methyl)piperidin-4-yl]methyl}piperazin-1-yl)pyridin-4-yl]-1H-indazol-5-yl}-4,5,7-trimethyl-4H,7H-[1,2,3,4]tetrazolo[1,5-a]pyrimidine-6-carboxamide Exemplary Compound 12 was prepared in a manner analogous to Exemplary Compound 1 using Enantiomer 1 of 4,5,7-trimethyl-7H-tetrazolo[1,5-a]pyrimidine-6-carboxylic acid.

Exemplary Synthesis of Exemplary Compound 13: N-{3-[2-(4-{[1-({1-[2-(2,6-dioxopiperidin-3-yl)-1,3-dioxo-2,3-dihydro-1H-isoindol-5-yl]piperidin-4-yl}methyl)piperidin-4-yl]methyl}piperazin-1-yl)pyridin-4-yl]-1H-indazol-5-yl}-4,5-dimethyl-4H,7H-[1,2,3,4]tetrazolo[1,5-a]pyrimidine-6-carboxamide Exemplary Compound 13 was prepared in a manner analogous to Exemplary Compound 1 using Intermediate 1.

Exemplary Synthesis of Exemplary Compound 14: (7R)—N-{3-[2-(4-{2-[1-({1-[2-(2,6-dioxopiperidin-3-yl)-1,3-dioxo-2,3-dihydro-1H-isoindol-5-yl]piperidin-4-yl}methyl)piperidin-4-yl]ethyl}piperazin-1-yl)pyridin-4-yl]-1H-indazol-5-yl}-4,5,7-trimethyl-4H,7H-[1,2,3,4]tetrazolo[1,5-a]pyrimidine-6-carboxamide

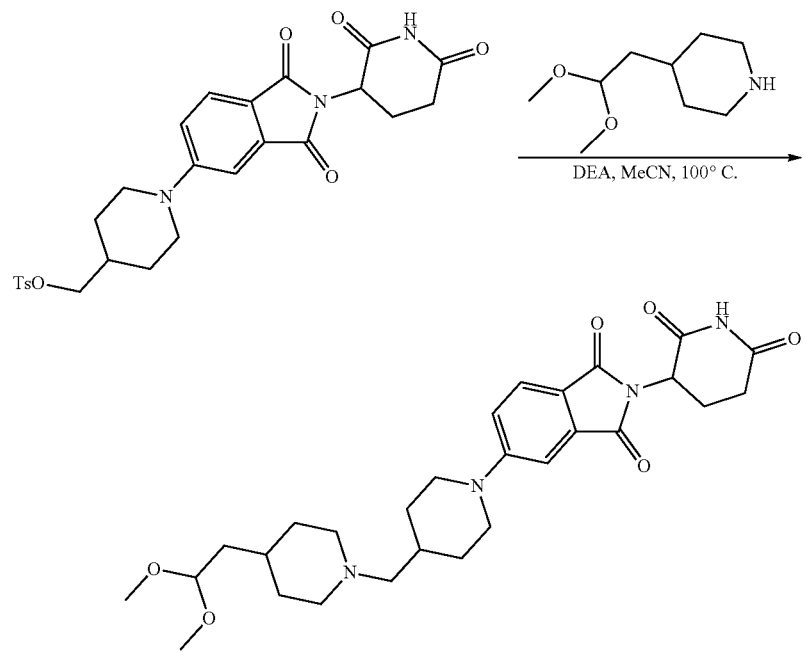

Step 1

To a solution of 4-(2,2-dimethoxyethyl)piperidine (118.67 mg, 684.97 umol, 1.2 eq) and [1-[2-(2,6-dioxo-3-piperidyl)-1,3-dioxo-isoindolin-5-yl]-4-piperidyl]methyl 4-methylbenzenesulfonate (300 mg, 570.81 umol, 1 eq) and DIEA (737.71 mg, 5.71 mmol, 994.22 uL, 10 eq) KI (947.54 mg, 5.71 mmol, 10 eq) in MeCN (10 mL). Then the mixture was stirred at 100° C. for 2 hours under N₂. The residue was diluted with H₂O 20 mL extracted with ethyl acetate (20 mL×3). The combined organic layers were washed with brine 15 mL, dried over anhydrous sodium sulfate, filtered and concentrated under reduced pressure to give a residue. The residue was purified by silica gel column chromatography (0 to 10% Methanol in Dichloromethane) to give 5-[4-[[4-(2,2-dimethoxyethyl)-1-piperidyl]methyl]-1-piperidyl]-2-(2,6-dioxo-3-piperidyl)isoindoline-1,3-dione (280 mg, 515.74 umol, 90.35% yield, 97% purity) as a yellow solid.

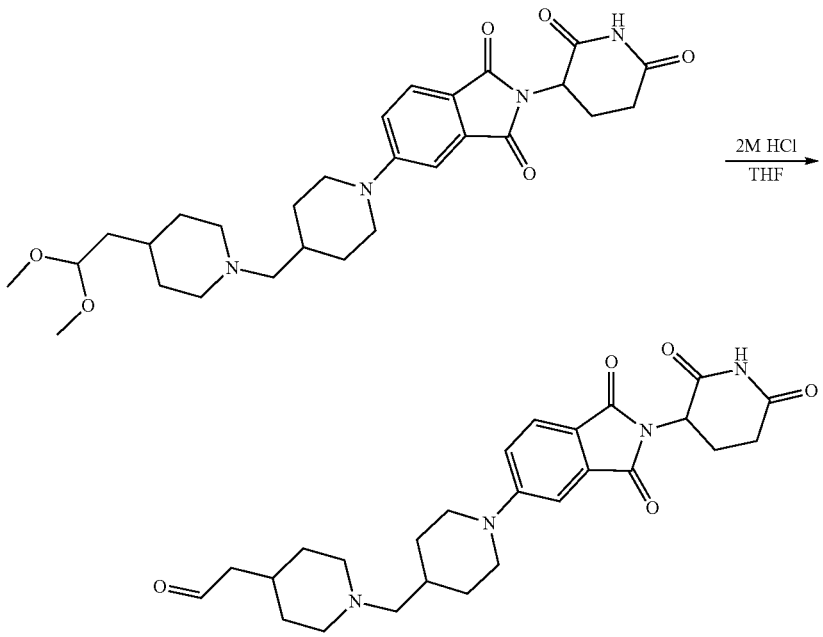

Step 2

To a solution of 5-[4-[[4-(2,2-dimethoxyethyl)-1-piperidyl]methyl]-1-piperidyl]-2-(2,6-dioxo-3-piperidyl)isoindoline-1,3-dione (280 mg, 531.69 umol, 1 eq) in THF (2 mL) was added HCl (2 M, 1.51 mL, 5.69 eq) and stirred at 25° C. for 1 hour. The reaction mixture was poured into H₂O (20 mL) and basified with aqueous NaHCO₃ till pH=8. The mixture was extracted with ethyl acetate (20 mL*5) and dried over anhydrous Na₂SO₄, concentrated in vacuum to give 2-[1-[[1-[2-(2,6-dioxo-3-piperidyl)-1,3-dioxo-isoindolin-5-yl]-4-piperidyl]methyl]-4-piperidyl]acetaldehyde (250 mg, crude) as a yellow solid.

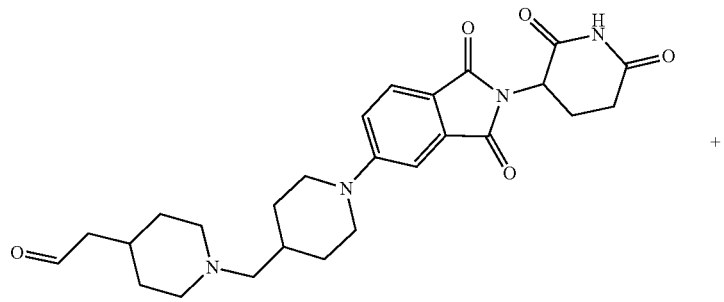

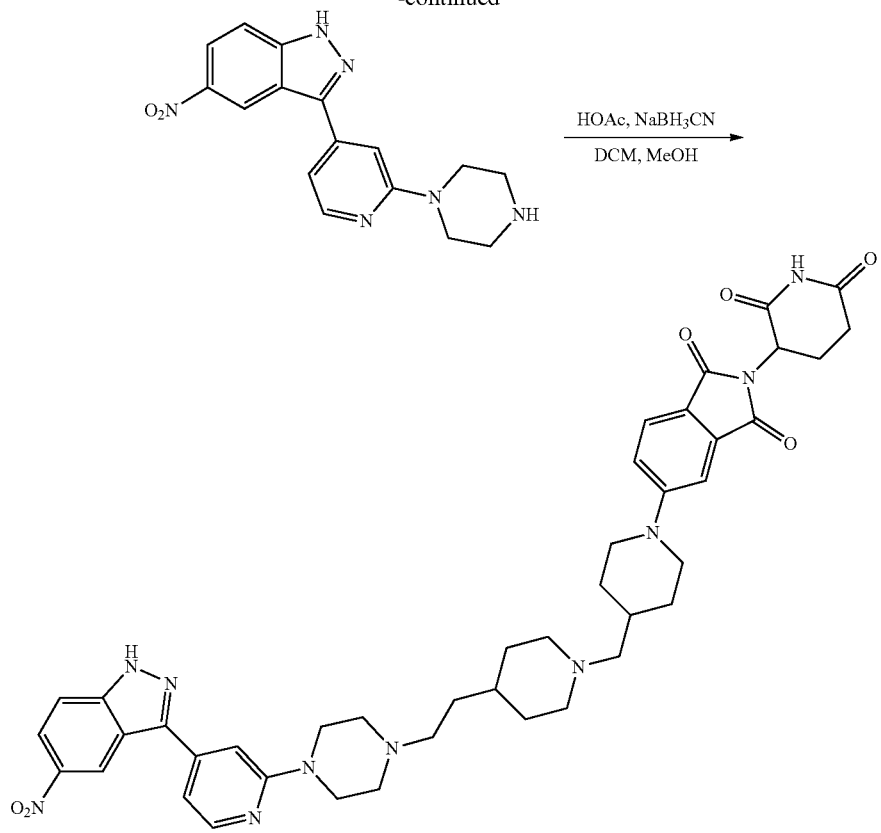

Step 3

To a solution of 2-[1-[[1-[2-(2,6-dioxo-3-piperidyl)-1,3-dioxo-isoindolin-5-yl]-4-piperidyl]methyl]-4-piperidyl]acetaldehyde (250 mg, 520.23 umol, 1 eq) and 5-nitro-3-(2-piperazin-1-yl-4-pyridyl)-1H-indazole (178.57 mg, 550.57 umol, 1.06 eq) in DCM (20 mL) and MeOH (30 mL) was added AcOH (3.12 mg, 52.02 umol, 2.98 uL, 0.1 eq) and the mixture was stirred at 20° C. for 20 minutes. Then the NaBH$_3$CN (98.07 mg, 1.56 mmol, 3 eq) was added of the solution and was stirred at 20° C. for 16 hours. TLC (Dichloromethane:Methanol=5:1, Rf=0.2) showed no start material and a new spot. The residue was concentrated under reduced pressure to give a residue. The residue was purified by silica gel column chromatography (0 to 50% Methanol in Dichloromethane) to 2-(2,6-dioxo-3-piperidyl)-5-[4-[[4-[2-[4-[4-(5-nitro-1H-indazol-3-yl)-2-pyridyl]piperazin-1-yl]ethyl]-1-piperidyl]methyl]-1-piperidyl]isoindoline-1,3-dione (400 mg, 344.79 umol, 66.28% yield, 68% purity) as a yellow solid.

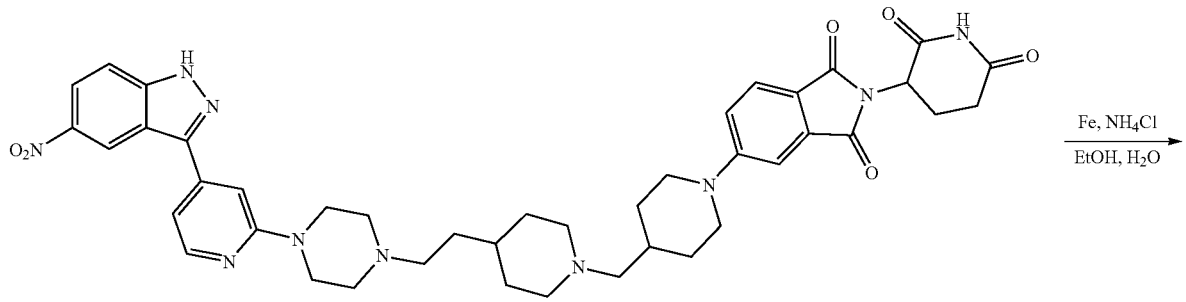

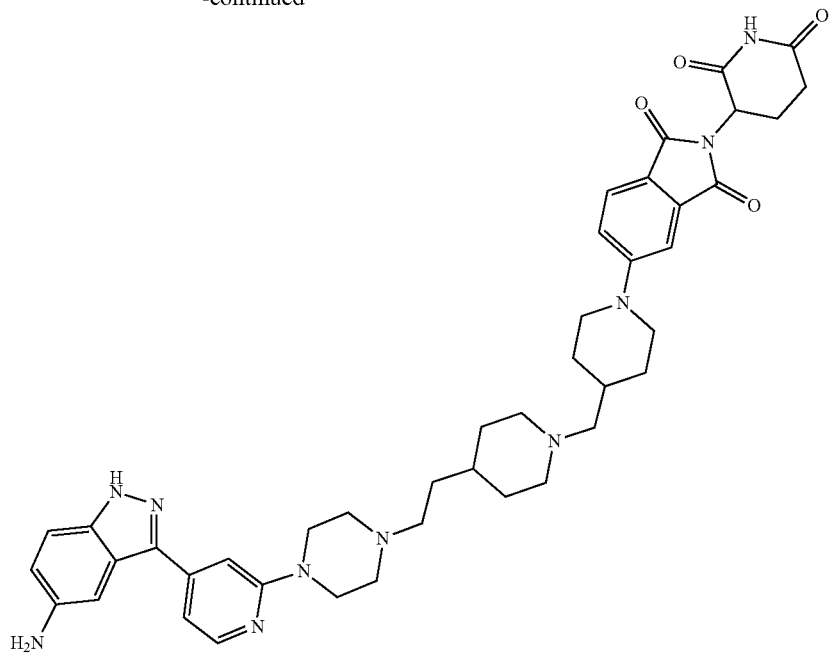

Step 4

To a solution of 2-(2,6-dioxo-3-piperidyl)-5-[4-[[4-[2-[4-[4-(5-nitro-1H-indazol-3-yl)-2-pyridyl]piperazin-1-yl]ethyl]-1-piperidyl]methyl]-1-piperidyl]isoindoline-1,3-dione (400 mg, 507.04 umol, 1 eq) in EtOH (10. mL) and $H_2O$ (5 mL) was added $NH_4Cl$ (135.61 mg, 2.54 mmol, 5 eq), Fe (141.58 mg, 2.54 mmol, 5 eq). Then the mixture was stirred at 90° C. for 1 hour under $N_2$. The reaction mixture was filtered and concentrated under reduced pressure. The residue was purified by prep-HPLC (Phenomenex luna C18 100*40 mm*3 um: water (0.05% NH3H2O+10 mM NH4HCO3)-ACN; B %: 18%-48%, 10 min) to afford 5-[4-[[4-[2-[4-[4-(5-amino-1H-indazol-3-yl)-2-pyridyl]piperazin-1-yl]ethyl]-1-piperidyl]methyl]-1-piperidyl]-2-(2,6-dioxo-3-piperidyl)isoindoline-1,3-dione (76 mg, 96.74 umol, 19.08% yield, 96.6% purity) as a yellow solid.

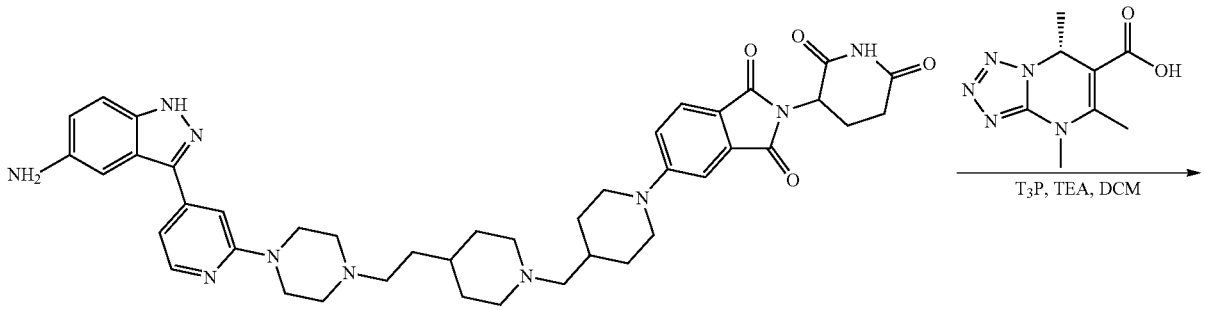

-continued

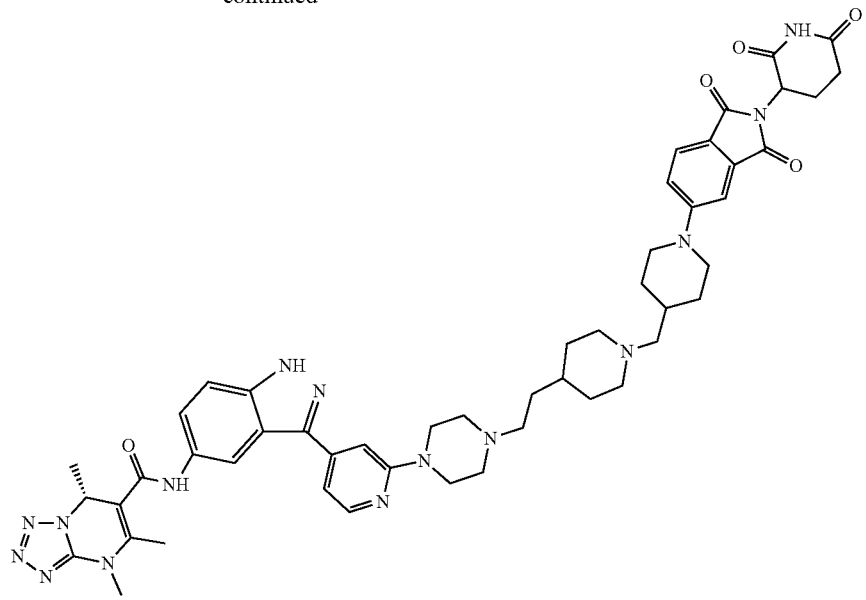

Step 5

To a solution of 5-[4-[[4-[2-[4-[4-(5-amino-1H-indazol-3-yl)-2-pyridyl]piperazin-1-yl]ethyl]-1-piperidyl]methyl]-1-piperidyl]-2-(2,6-dioxo-3-piperidyl)isoindoline-1,3-dione (45 mg, 59.30 umol, 1 eq) and (7R)-4,5,7-trimethyl-7H-tetrazolo[1,5-a]pyrimidine-6-carboxylic acid (12.40 mg, 59.30 umol, 1 eq) in DMF (2 mL) was stirred at 20° C. for 10 minutes, then was added DIEA (38.32 mg, 296.48 umol, 51.64 uL, 5 eq) and HATU (27.06 mg, 71.15 umol, 1.2 eq). Then the mixture was stirred at 70° C. for 3 hours under $N_2$. LCMS showed desired product MS. The residue was purified by prep-HPLC (column: 3_Phenomenex Luna C18 75*30 mm*3 um; mobile phase: water (0.225% FA)-ACN; B %: 0%-30%, 35 min) to afford (7R)—N-[3-[2-[4-[2-[1-[[1-[2-(2,6-dioxo-3-piperidyl)-1,3-dioxo-isoindolin-5-yl]-4-piperidyl]methyl]-4-piperidyl]ethyl]piperazin-1-yl]-4-pyridyl]-1H-indazol-5-yl]-4,5,7-trimethyl-7H-tetrazolo[1,5-a]pyrimidine-6-carboxamide (14.9 mg, 15.52 umol, 26.18% yield, 98.98% purity) as a yellow solid.

Exemplary Synthesis of Exemplary Compound 15: (7R)—N-(3-{2-[4-(3-{4-[2-(2,6-dioxopiperidin-3-yl)-1,3-dioxo-2,3-dihydro-1H-isoindol-5-yl]piperazin-1-yl}propyl)piperazin-1-yl]pyridin-4-yl}-1H-indazol-5-yl)-4,5,7-trimethyl-4H,7H-[1,2,3,4]tetrazolo[1,5-a]pyrimidine-6-carboxamide

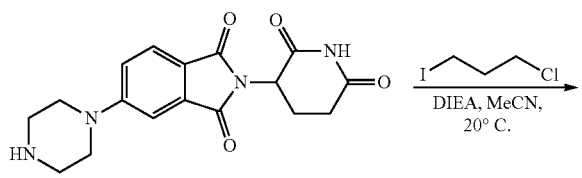

Step 1

To a solution of 2-(2,6-dioxo-3-piperidyl)-5-piperazin-1-yl-isoindoline-1,3-dione (500 mg, 1.10 mmol, 1 eq, TFA) and 1-chloro-3-iodo-propane (1.12 g, 5.48 mmol, 589.42 uL, 5 eq) in $CH_3CN$ (5 mL) was added $K_2CO_3$ (151.42 mg, 1.10 mmol, 1 eq). After addition, the reaction was stirred at 20° C. for 1 hour. TLC showed there was a new spot. The residue was poured into water (5 mL) and stirred for 5 minutes. The aqueous phase was extracted with ethyl acetate (5 mL*3). The combined organic phase was washed with brine (5 mL*2), dried with anhydrous $Na_2SO_4$, filtered and concentrated in vacuum. The residue was purified by silica gel chromatography (4 g, Rf=0.43, 100-200 mesh silica gel, 0-70% (10 min) of Ethyl acetate in Petroleum ether, 70% (10 min) Ethyl acetate in Petroleum ether) to give 5-[4-(3-chloropropyl)piperazin-1-yl]-2-(2,6-dioxo-3-piperidyl)isoindoline-1,3-dione (260 mg, 564.85 umol, 51.56% yield, 91% purity) as a yellow gum.

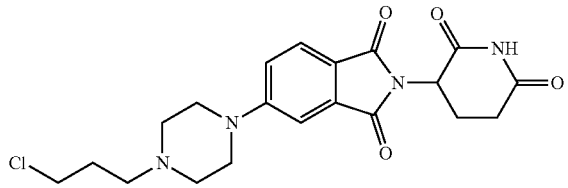

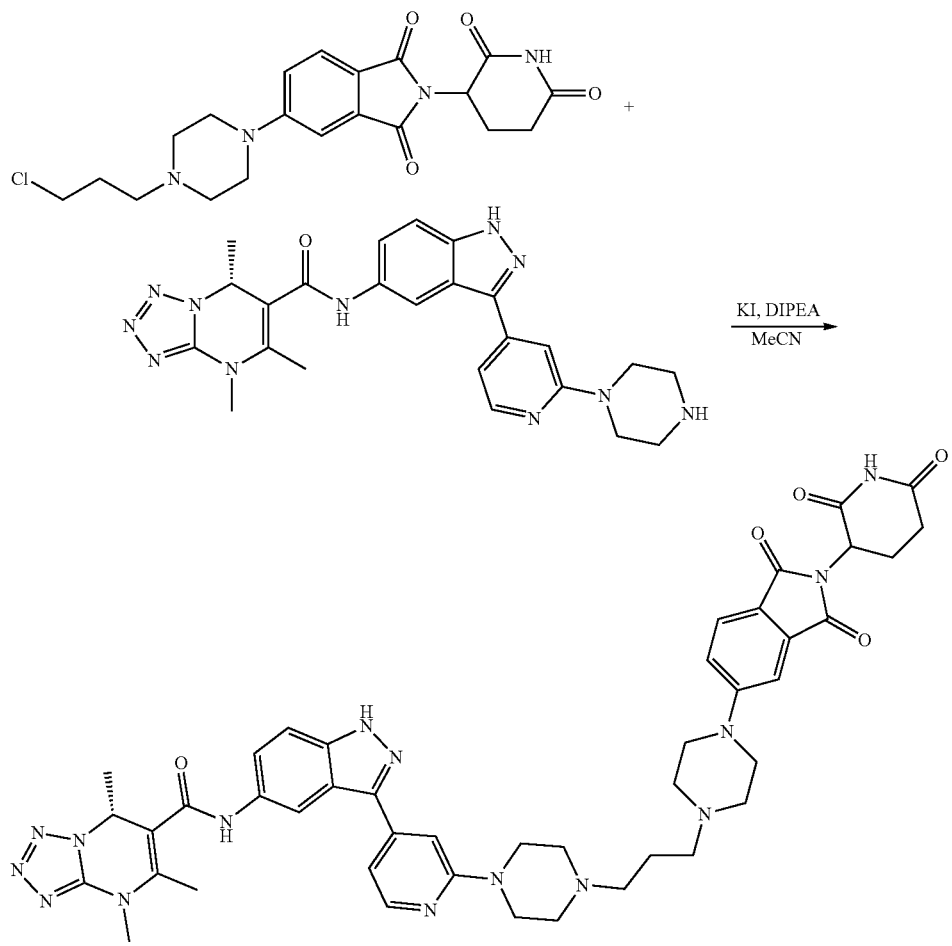

Step 2

To a mixture of (7R)-4,5,7-trimethyl-N-[3-(2-piperazin-1-yl-4-pyridyl)-1H-indazol-5-yl]-7H-tetrazolo[1,5-a]pyrimidine-6-carboxamide (55 mg, 113.28 umol, 1 eq) and 5-[4-(3-chloropropyl)piperazin-1-yl]-2-(2,6-dioxo-3-piperidyl)isoindoline-1,3-dione (47.45 mg, 113.28 umol, 1 eq) in MeCN (5 mL) was added KI (37.61 mg, 226.55 umol, 2 eq) and DIPEA (29.28 mg, 226.55 umol, 39.46 uL, 2 eq) in one portion at 20° C. under $N_2$. The mixture was stirred at 80° C. for 10 hours. LCMS showed there was ~78% of desired MS. The mixture was cooled to 20° C. and concentrated in reduced pressure at 20° C. The residue was poured into water (5 mL). The aqueous phase was extracted with ethyl acetate (5 mL*3). The combined organic phase was washed with brine (5 mL*2), dried with anhydrous $Na_2SO_4$, filtered and concentrated in vacuum. The crude product was purified by reversed-phase HPLC (Column: 3_Phenomenex Luna C18 75*30 mm*3 um; Condition: water (0.2% LA)-ACN; Begin B: 0; End B: 30; FlowRate: 25 mL/min; Gradient Time: 35 minutes; 100% B Hold Time: 3 minutes) to give (7R)—N-[3-[2-[4-[3-[4-[2-(2,6-dioxo-3-piperidyl)-1,3-dioxo-isoindolin-5-yl]piperazin-1-yl]propyl]piperazin-1-yl]-4-pyridyl]-1H-indazol-5-yl]-4,5,7-trimethyl-7H-tetrazolo[1,5-a]pyrimidine-6-carboxamide (19.5 mg, 21.34 umol, 18.84% yield, 95% purity) as a yellow solid.

Exemplary Synthesis of Exemplary Compound 17: (7R)—N-[3-(2-{4-[(1-{1-[2-(2,6-dioxopiperidin-3-yl)-1,3-dioxo-2,3-dihydro-1H-isoindol-5-yl]piperidin-4-yl}azetidin-3-yl)methyl]piperazin-1-yl}pyridin-4-yl)-1H-indazol-5-yl]-4,5,7-trimethyl-4H,7H-[1,2,3,4]tetrazolo[1,5-a]pyrimidine-6-carboxamide

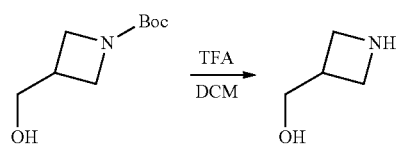

Step 1

To a solution of tert-butyl 3-(hydroxymethyl)azetidine-1-carboxylate (7.6 g, 40.59 mmol, 1 eq) in DCM (80 mL) was added HCl/MeOH (4 M, 38.00 mL, 3.74 eq), the mixture was stirred at 25° C. for 2 hours. TLC (Petroleum ether: Ethyl acetate=1:2, KMnO4, Plate1) showed a new spot formed and the starting materials consumed completely. The reaction mixture was concentrated under reduced pressure to remove DCM and HCl/MeOH to give a residue. The crude product was used into the next step without further purification. Compound azetidin-3-ylmethanol (5.7 g, crude, HCl) was obtained as a light yellow liquid.

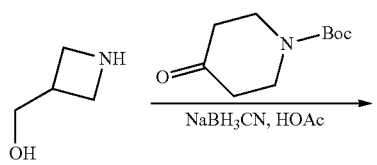

Step 2

To a solution of azetidin-3-ylmethanol (2 g, 16.18 mmol, 1 eq, HCl) and tert-butyl 4-oxopiperidine-1-carboxylate (4.84 g, 24.28 mmol, 1.5 eq) in DCM (10 mL) and MeOH (2 mL) was added AcONa (6.64 g, 80.92 mmol, 5 eq) and HOAc (1.94 g, 32.37 mmol, 1.85 mL, 2 eq) for 30 minutes, after the mixture was added NaBH$_3$CN (3.05 g, 48.55 mmol, 3 eq). Then the mixture was stirred 25° C. for 16 hours. TLC (Methanol:Dichloromethane=1:10, I$_2$, Plate1) showed a new spot formed and the starting materials was remained. The reaction mixture was concentrated under reduced pressure to remove DCM. The residue was diluted with water 40 mL and extracted with EA (30 mL*4). The combined organic layers were washed with brine (60 mL), dried over Na$_2$SO$_4$ filtered and concentrated under reduced pressure to give a residue. The residue was purified by flash silica gel chromatography (ISCO®; 40 g SepaFlash® Silica Flash Column, Eluent of 0-10% Methanol/Dichloromethane ether gradient @60 mL/min) to afford tert-butyl 4-[3-(hydroxymethyl)azetidin-1-yl]piperidine-1-carboxylate (2.2 g, 8.14 mmol, 50.28% yield) was obtained as a colorless gum.

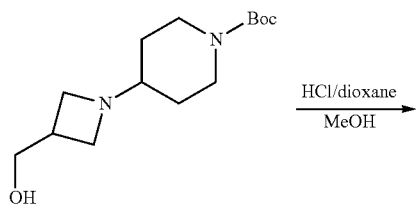

Step 3

To a solution of tert-butyl 4-[3-(hydroxymethyl)azetidin-1-yl]piperidine-1-carboxylate (2.2 g, 8.14 mmol, 1 eq) in MeOH (10 mL) was added HCl/dioxane (4 M, 10 mL). After addition, the reaction was stirred at 20° C. for 2 hours. LCMS showed desired mass (Rt=0.220 min). The reaction was concentrated under reduced pressure to afford [1-(4-piperidyl)azetidin-3-yl]methanol (1.8 g, crude, HCl) as a white solid. The crude product was used for next step directly.

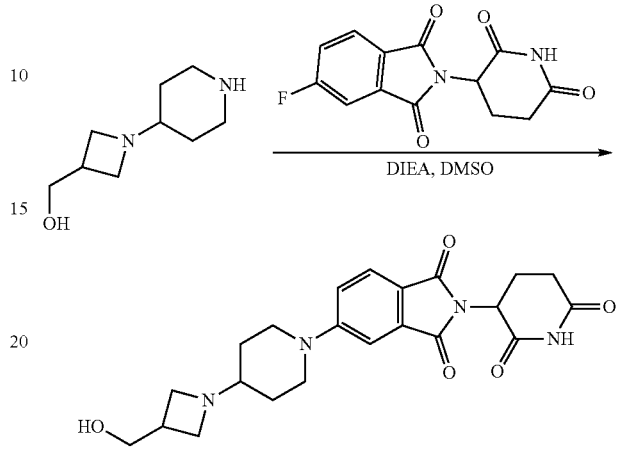

Step 4

To a solution of [1-(4-piperidyl)azetidin-3-yl]methanol (1.7 g, 8.22 mmol, 1 eq, HCl) in DMSO (20 mL) was added 2-(2,6-dioxo-3-piperidyl)-5-fluoro-isoindoline-1,3-dione (2.27 g, 8.22 mmol, 1 eq) and DIEA (3.19 g, 24.67 mmol, 4.30 mL, 3 eq). After addition, the reaction solution was stirred at 100° C. for 2 hours. LCMS showed desired mass. After cooling, the reaction was diluted with water (100 mL) and extracted with 10% methanol in dichloromethane (5×150 mL). The organic layer was dried over Na$_2$SO$_4$ and concentrated under reduced pressure. The residue was purified by silica gel column chromatography (0 to 20% methanol in dichloromethane) to afford 2-(2,6-dioxo-3-piperidyl)-5-[4-[3-(hydroxymethyl)azetidin-1-yl]-1-piperidyl]isoindoline-1,3-dione (1.4 g, 3.05 mmol, 37.12% yield, 93% purity) as a yellow solid.

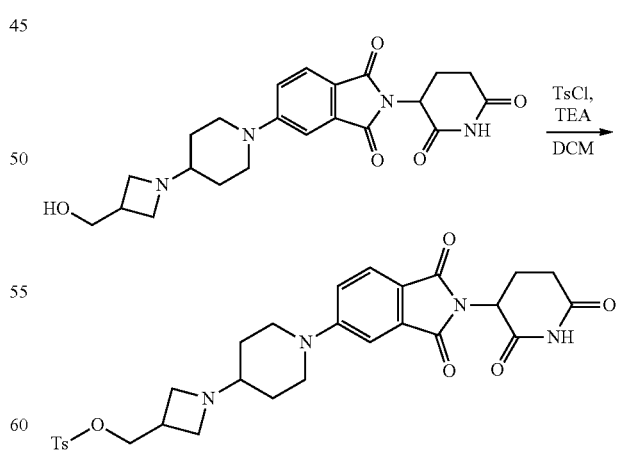

Step 5

To a solution of 2-(2,6-dioxo-3-piperidyl)-5-[4-[3-(hydroxymethyl)azetidin-1-yl]-1-piperidyl]isoindoline-1,3-dione (1.2 g, 2.81 mmol, 1 eq) in DCM (15 mL) was added TosCl (1.07 g, 5.63 mmol, 2 eq), DMAP (34.38 mg, 281.38 umol, 0.1 eq) and TEA (854.19 mg, 8.44 mmol, 1.17 mL, 3 eq). After addition, the reaction was stirred at 20° C. for 16 hours. LCMS showed desired MS. The reaction was diluted with water (30 mL) and extracted with dichloromethane (3×20 mL). The organic layer was dried over sodium sulfate and concentrated under reduced pressure. The residue was purified by silica gel column chromatography (0 to 6% methanol in dichloromethane) to afford [1-[1-[2-(2,6-dioxo-3-piperidyl)-1,3-dioxo-isoindolin-5-yl]-4-piperidyl]azetidin-3-yl]methyl 4-methylbenzenesulfonate (460 mg, 741.51 umol, 26.35% yield, 93.6% purity) as a yellow solid.

4-methylbenzenesulfonate (77 mg, 132.61 umol, 1.07 eq) and (7R)-4,5,7-trimethyl-N-[3-(2-piperazin-1-yl-4-pyridyl)-1H-indazol-5-yl]-7H-tetrazolo[1,5-a]pyrimidine-6-carboxamide (60 mg, 123.57 umol, 1 eq) in CH$_3$CN (2 mL) was added KI (41.03 mg, 247.15 umol, 2 eq) and DIEA (31.94 mg, 247.15 umol, 43.05 uL, 2 eq). After addition, the reaction was stirred at 80° C. for 16 hours. LCMS showed desired mass. After cooling, the reaction mixture was filtered and the filter cake was washed with DMSO (2 mL). The filtrate was purified by prep.HPLC (column: 3_Phenomenex Luna C18 75*30 mm*3 um; mobile phase: [water (10 mM NH$_4$HCO$_3$)-ACN]; B %: 30%-60%; 35 min) to afford (7R)—N-[3-[2-[4-[[1-[1-[2-(2,6-dioxo-3-piperidyl)-1,3-di-

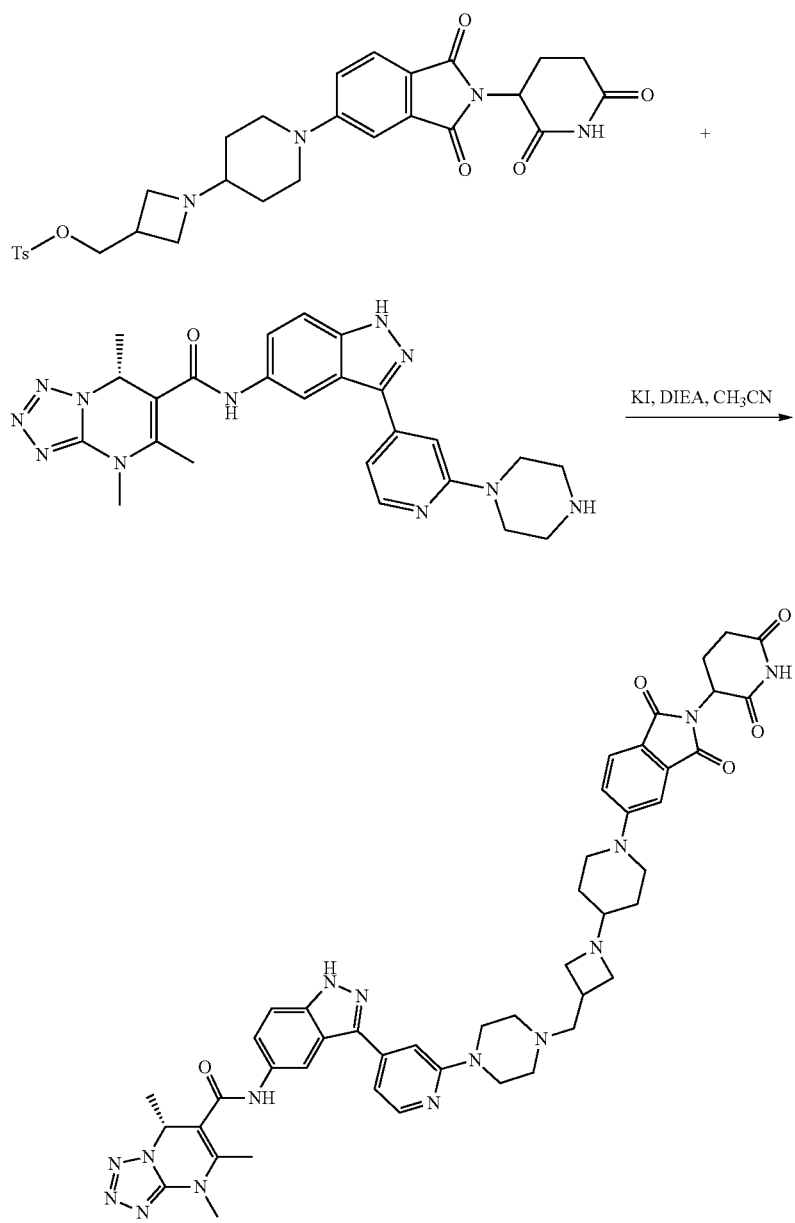

Step 6

To a solution of [1-[1-[2-(2,6-dioxo-3-piperidyl)-1,3-dioxo-isoindolin-5-yl]-4-piperidyl]azetidin-3-yl]methyl oxo-isoindolin-5-yl]-4-piperidyl]azetidin-3-yl]methyl]piperazin-1-yl]-4-pyridyl]-1H-indazol-5-yl]-4,5,7-trimethyl-7H-tetrazolo[1,5-a]pyrimidine-6-carboxamide (9.5 mg, 10.50 umol, 8.50% yield, 98.81% purity) as a yellow solid.

Exemplary Synthesis of Exemplary Compound 18: (7R)—N-(3-{2-[4-({1'-[2-(2,6-dioxopiperidin-3-yl)-1,3-dioxo-2,3-dihydro-1H-isoindol-5-yl]-[1,4'-bipiperidin]-4-yl}methyl)piperazin-1-yl]pyridin-4-yl}-1H-indazol-5-yl)-4,5,7-trimethyl-4H,7H-[1,2,3,4]tetrazolo[1,5-a]pyrimidine-6-carboxamide

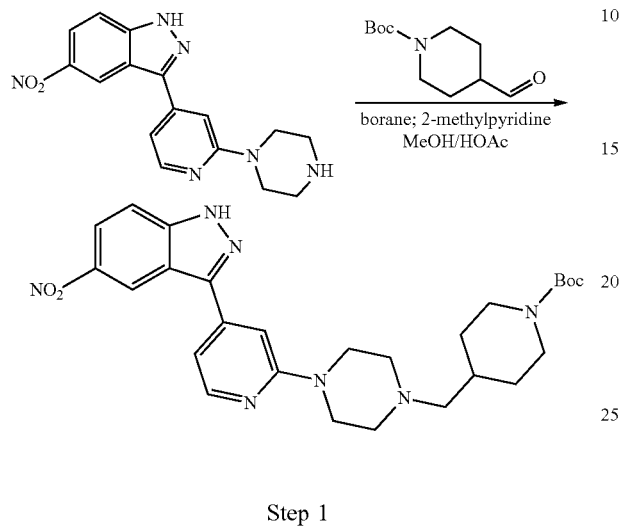

Step 1

To a solution of 5-nitro-3-(2-piperazin-1-yl-4-pyridyl)-1H-indazole (1 g, 3.08 mmol, 1 eq) and tert-butyl 4-formylpiperidine-1-carboxylate (723.32 mg, 3.39 mmol, 1.1 eq) in MeOH (10 mL) and HOAc (1 mL) was added borane; 2-methylpyridine (659.57 mg, 6.17 mmol, 2 eq). After addition, the reaction mixture was stirred at 30° C. for 2 hours. LCMS showed desired mass. The reaction mixture was diluted with water (30 mL) and basified to pH 12 with solid NaOH. Then the mixture was filtered to afford filtrate cake. The residue was purified by silica gel column chromatography (0 to 10% methanol in dichloromethane) to afford tert-butyl 4-[[4-[4-(5-nitro-1H-indazol-3-yl)-2-pyridyl]piperazin-1-yl]methyl]piperidine-1-carboxylate (1.6 g, 2.99 mmol, 97.04% yield, 97.54% purity) as a yellow solid.

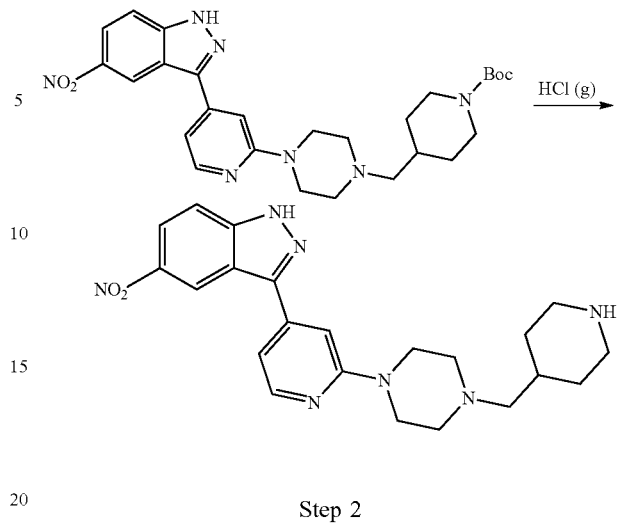

Step 2

To a solution of tert-butyl 4-[[4-[4-(5-nitro-1H-indazol-3-yl)-2-pyridyl]piperazin-1-yl]methyl]piperidine-1-carboxylate (1.6 g, 3.07 mmol, 1 eq) in MeOH (10 mL) was added HCl/dioxane (4 M, 10 mL, 13.04 eq). After addition, the reaction solution was stirred at 20° C. for 16 hours. LCMS showed desired mass. The reaction was concentrated under reduced pressure. The resulting was dissolved in water (50 mL) and neutralized to pH 7 with solid NaOH. The solid was collected by filtration to afford 5-nitro-3-[2-[4-(4-piperidylmethyl)piperazin-1-yl]-4-pyridyl]-1H-indazole (860 mg, crude) as a yellow solid. The crude product was used for next step directly.

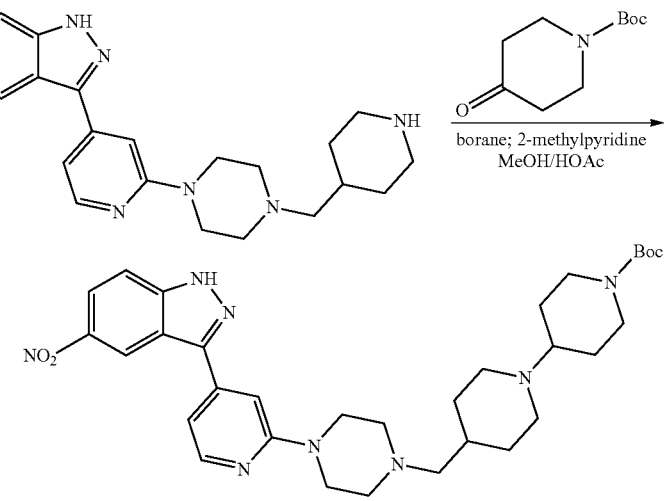

Step 3

To a solution of 5-nitro-3-[2-[4-(4-piperidylmethyl)piperazin-1-yl]-4-pyridyl]-1H-indazole (860 mg, 2.04 mmol, 1 eq) and tert-butyl 4-oxopiperidine-1-carboxylate (2.03 g, 10.20 mmol, 5 eq) in MeOH (50 mL) and HOAc (5 mL) was added borane; 2-methylpyridine (654.72 mg, 6.12 mmol, 3 eq). After addition, the reaction solution was stirred at 35° C. for 12 hours. LCMS desired MS. The reaction was diluted with water (100 mL) and washed with ethyl acetate (100 mL). The aqueous phase was basified to pH 14 with solid KOH and extracted with ethyl acetate (3×50 mL). The aqueous phase was filtered to collect the solid. The organic layer was dried over sodium sulfate and concentrated under reduced pressure. The residue was purified by silica gel column chromatography (0 to 50% methanol in dichloromethane) to afford tert-butyl 4-[4-[[4-[4-(5-nitro-1H-indazol-3-yl)-2-pyridyl]piperazin-1-yl]methyl]-1-piperidyl]piperidine-1-carboxylate (750 mg, 1.14 mmol, 55.88% yield, 91.94% purity) as a yellow solid.

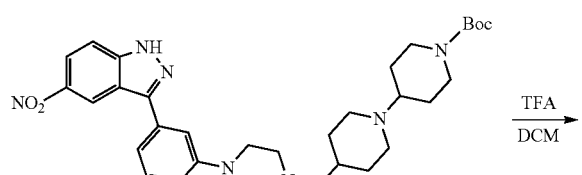

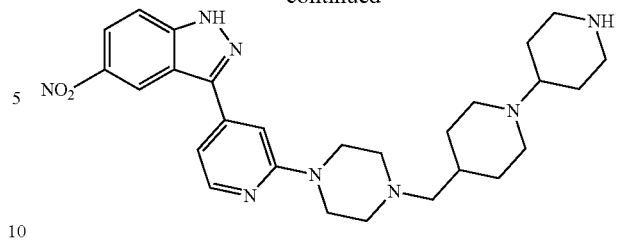

Step 4

To a solution of tert-butyl 4-[4-[[4-[4-(5-nitro-1H-indazol-3-yl)-2-pyridyl]piperazin-1-yl]methyl]-1-piperidyl]piperidine-1-carboxylate (750 mg, 1.24 mmol, 1 eq) in DCM (5 mL) was added TFA (3.08 g, 27.01 mmol, 2 mL, 21.78 eq). After addition, the reaction was stirred at 20° C. for 1 hour. LCMS showed desired MS. The reaction mixture was concentrated under reduced pressure to afford 5-nitro-3-[2-[4-[[1-(4-piperidyl)-4-piperidyl]methyl]piperazin-1-yl]-4-pyridyl]-1H-indazole (900 mg, crude, TFA) as a yellow gum. The crude product was used for next step directly.

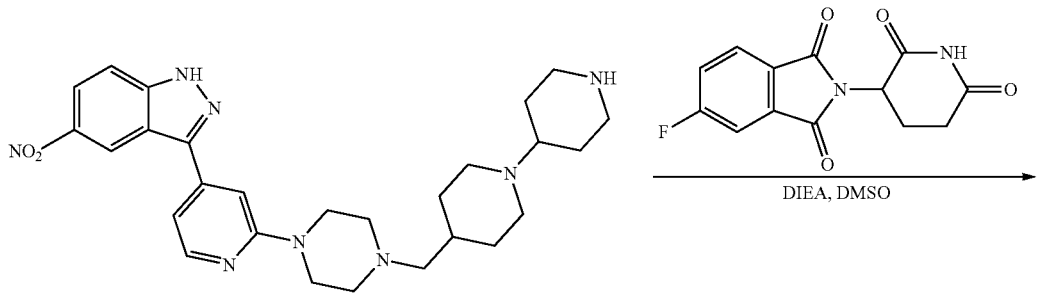

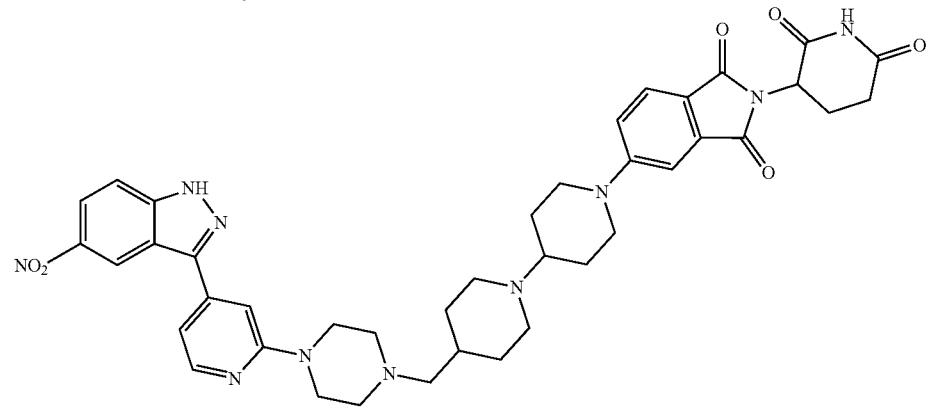

Step 5

To a solution of 5-nitro-3-[2-[4-[[1-(4-piperidyl)-4-piperidyl]methyl]piperazin-1-yl]-4-pyridyl]-1H-indazole (900 mg, 1.45 mmol, 1 eq, TFA) and 2-(2,6-dioxo-3-piperidyl)-5-fluoro-isoindoline-1,3-dione (602.76 mg, 2.18 mmol, 1.5 eq) in DMSO (10 mL) was added DIEA (940.08 mg, 7.27 mmol, 1.27 mL, 5 eq). After addition, the reaction was stirred at 100° C. for 12 hours. LCMS showed desired MS. After cooling, the reaction solution was diluted with water (100 mL). The solid was collected by filtration and dried under reduced pressure to afford 2-(2,6-dioxo-3-piperidyl)-5-[4-[4-[[4-[4-(5-nitro-1H-indazol-3-yl)-2-pyridyl]piperazin-1-yl]methyl]-1-piperidyl]-1-piperidyl]isoindoline-1,3-dione (800 mg, 862.21 umol, 59.27% yield, 82% purity) as a yellow solid. The crude product was used for next step directly.

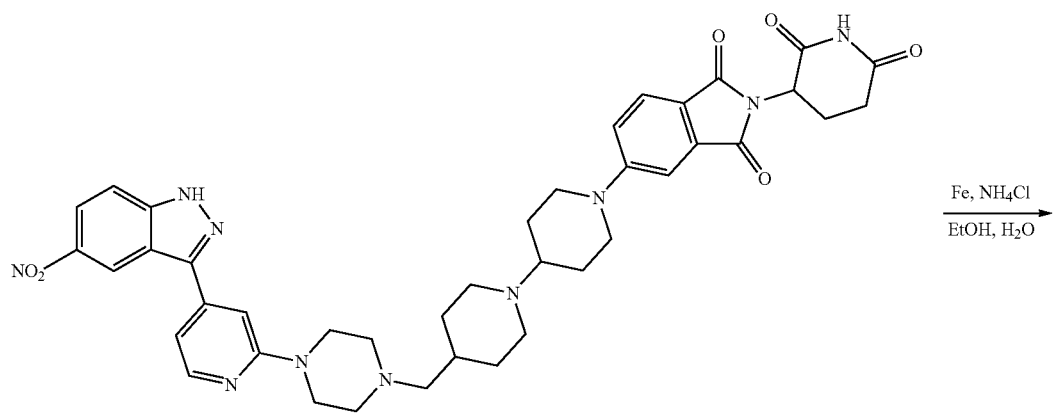

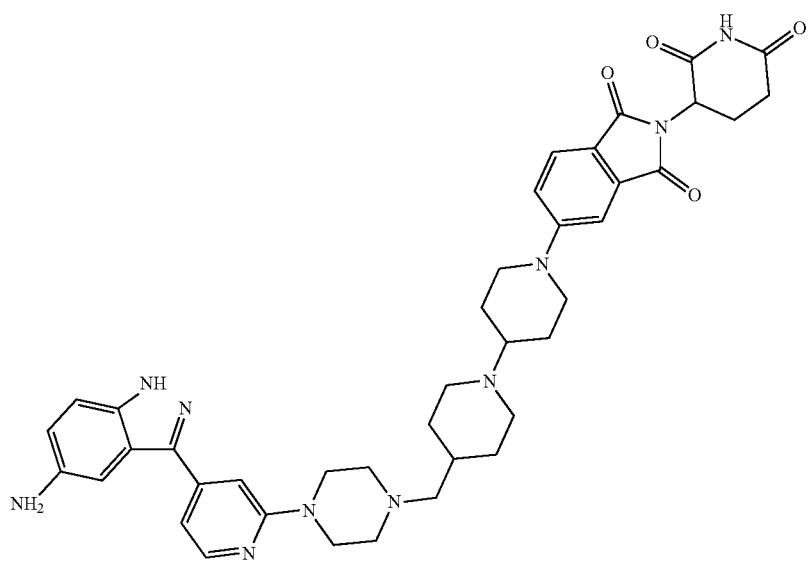

Step 6

To a mixture of 2-(2,6-dioxo-3-piperidyl)-5-[4-[4-[[4-[4-(5-nitro-1H-indazol-3-yl)-2-pyridyl]piperazin-1-yl]methyl]-1-piperidyl]-1-piperidyl]isoindoline-1,3-dione (400 mg, 525.74 umol, 1 eq) in EtOH (3 mL) and H₂O (0.5 mL) was added Fe (146.80 mg, 2.63 mmol, 5 eq) and NH₄Cl (140.61 mg, 2.63 mmol, 5 eq). After addition, the reaction was stirred at 80° C. for 2 hours. LCMS showed desired MS. After cooling, the reaction was filtered and filtrate was concentrated in vacuo. The resulting was dissolved in DMSO (10 mL) and then water (80 mL) was added. The solid was collected by filtration. The solid was dried under reduced pressure to afford 5-[4-[4-[[4-[4-(5-amino-1H-indazol-3-yl)-2-pyridyl]piperazin-1-yl]methyl]-1-piperidyl]-1-piperidyl]-2-(2,6-dioxo-3-piperidyl)isoindoline-1,3-dione (130 mg, 125.40 umol, 23.85% yield, 70.5% purity) as a yellow solid.

Step 7

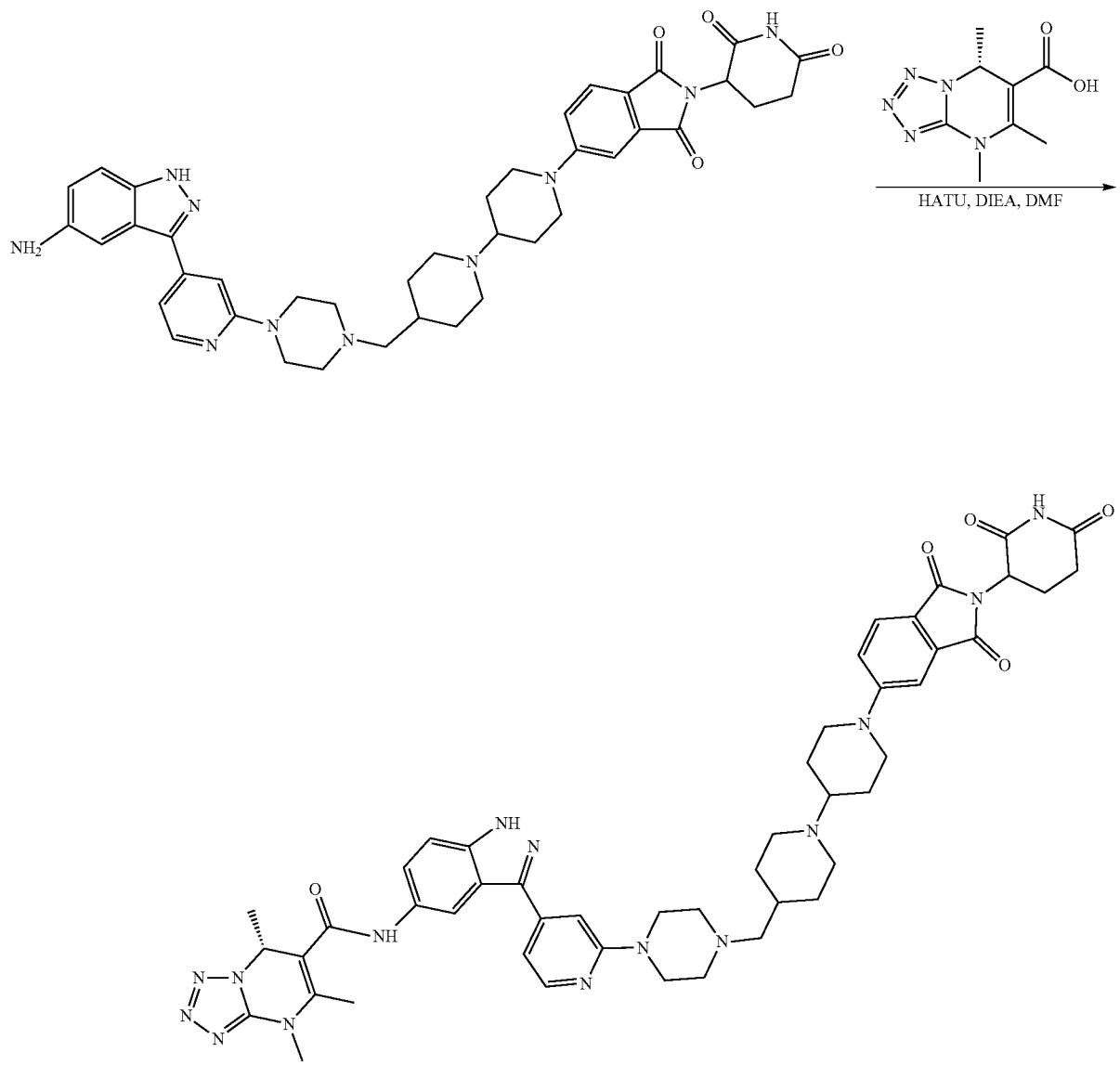 [SMILES: Nc1ccc2[nH]nc(-c3ccnc(N4CCN(CC5CCN(C6CCN(c7ccc8c(c7)C(=O)N(C7CCC(=O)NC7=O)C8=O)CC6)CC5)CC4)c3)c2c1 ; CC1=C(C(=O)O)[C@@H](C)n2nnnc2N1C ; CC1=C(C(=O)Nc2ccc(N)c(C(=N)c3ccnc(N4CCN(CC5CCN(C6CCN(c7ccc8c(c7)C(=O)N(C7CCC(=O)NC7=O)C8=O)CC6)CC5)CC4)c3)c2)[C@@H](C)n2nnnc2N1C]

To a solution of (7R)-4,5,7-trimethyl-7H-tetrazolo[1,5-a]pyrimidine-6-carboxylic acid (37.21 mg, 177.87 umol, 1 eq) and 5-[4-[4-[[4-[4-(5-amino-1H-indazol-3-yl)-2-pyridyl]piperazin-1-yl]methyl]-1-piperidyl]-1-piperidyl]-2-(2,6-dioxo-3-piperidyl)isoindoline-1,3-dione (130 mg, 177.87 umol, 1 eq) in DMF (2 mL) was added DIEA (68.97 mg, 533.62 umol, 92.94 uL, 3 eq) and HATU (67.63 mg, 177.87 umol, 1 eq). After addition, the reaction solution was stirred at 25° C. for 16 hours. LCMS showed desired MS. The reaction was filtered and filtrate cake was washed with DMSO (1 mL). The filtrate was purified by prep.HPLC (column: 3_Phenomenex Luna C18 75*30 mm*3 um; mobile phase: [water (0.225% FA)-ACN]; B %: 0-30%; 35 min) to afford (7R)—N-[3-[2-[4-[[1-[1-[2-(2,6-dioxo-3-piperidyl)-1,3-dioxo-isoindolin-5-yl]-4-piperidyl]-4-piperidyl]methyl]piperazin-1-yl]-4-pyridyl]-1H-indazol-5-yl]-4,5,7-trimethyl-7H-tetrazolo[1,5-a]pyrimidine-6-carboxamide (10.7 mg, 11.45 umol, 6.44% yield, 98.66% purity) as a yellow solid.

Exemplary Synthesis of Exemplary Compound 20:
(7R)—N-[3-(2-{4-[2-(2-{6-[2-(2,6-dioxopiperidin-3-yl)-1,3-dioxo-2,3-dihydro-1H-isoindol-5-yl]-2,6-diazaspiro[3.3]heptan-2-yl}ethoxy)ethyl]piperazin-1-yl}pyridin-4-yl)-1H-indazol-5-yl]-4,5,7-trimethyl-4H,7H-[1,2,3,4]tetrazolo[1,5-a]pyrimidine-6-carboxamide Exemplary Compound 20 was prepared in a manner analogous to Exemplary Compound 3.

Exemplary Synthesis of Exemplary Compound 21: (7S)—N-{3-[2-(4-{2-[4-({1-[2-(2,6-dioxopiperidin-3-yl)-1,3-dioxo-2,3-dihydro-1H-isoindol-5-yl]piperidin-4-yl}methyl)piperazin-1-yl]ethyl}piperazin-1-yl)pyridin-4-yl]-1H-indazol-5-yl}-4,5,7-trimethyl-4H,7H-[1,2,3,4]tetrazolo[1,5-a]pyrimidine-6-carboxamide

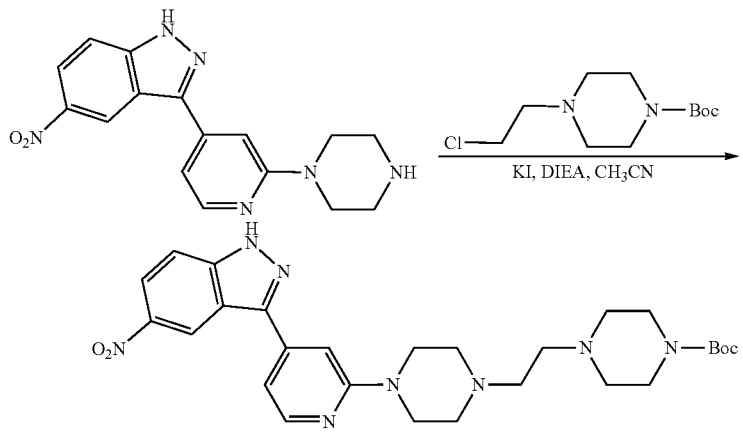

Step 1

To a solution of 5-nitro-3-(2-piperazin-1-yl-4-pyridyl)-1H-indazole (500 mg, 1.54 mmol, 1 eq) and tert-butyl 4-(2-chloroethyl)piperazine-1-carboxylate (500 mg, 2.01 mmol, 1.3 eq) in $CH_3CN$ (10 mL) was added KI (511.82 mg, 3.08 mmol, 2 eq) and DIEA (398.48 mg, 3.08 mmol, 537.04 uL, 2 eq). After addition, the reaction was stirred at 80° C. for 3 hours. LCMS showed desired MS. After cooling, the reaction mixture was diluted with water (10 mL) and extracted with dichloromethane (3×10 mL). The organic layer was dried over sodium sulfate and concentrated under reduced pressure. The residue was purified by silica gel column chromatography (0 to 10% methanol in dichloromethane) to afford tert-butyl 4-[2-[4-[4-(5-nitro-1H-indazol-3-yl)-2-pyridyl]piperazin-1-yl]ethyl]piperazine-1-carboxylate (303 mg, 558.99 umol, 36.26% yield, 99% purity) as a yellow solid.

Step 2

To a solution of tert-butyl 4-[2-[4-[4-(5-nitro-1H-indazol-3-yl)-2-pyridyl]piperazin-1-yl]ethyl]piperazine-1-carboxylate (303 mg, 564.64 umol, 1 eq) in DCM (3 mL) was added TFA (770.00 mg, 6.75 mmol, 0.5 mL, 11.96 eq). After addition, the reaction was stirred at 20° C. for 1 hour. LCMS showed reactant consumed and desired MS was detected. The reaction mixture was concentrated in vacuo. The resulting was dissolved in DCM (2 mL) and treated with DIEA (1 mL). The mixture was concentrated under reduced pressure to afford 5-nitro-3-[2-[4-(2-piperazin-1-ylethyl)piperazin-1-yl]-4-pyridyl]-1H-indazole (240 mg, crude) as a yellow solid. The crude product was used for next step directly.

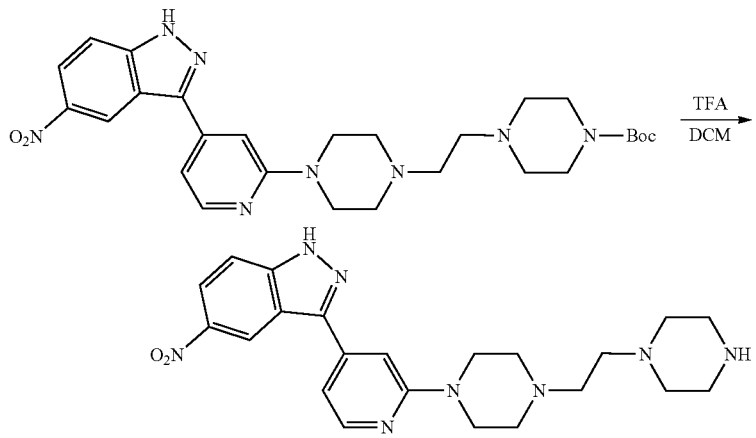

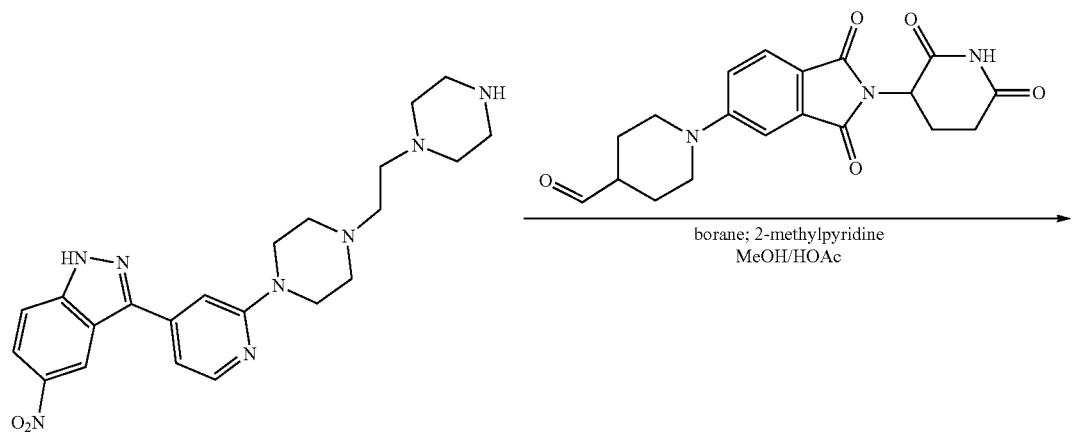

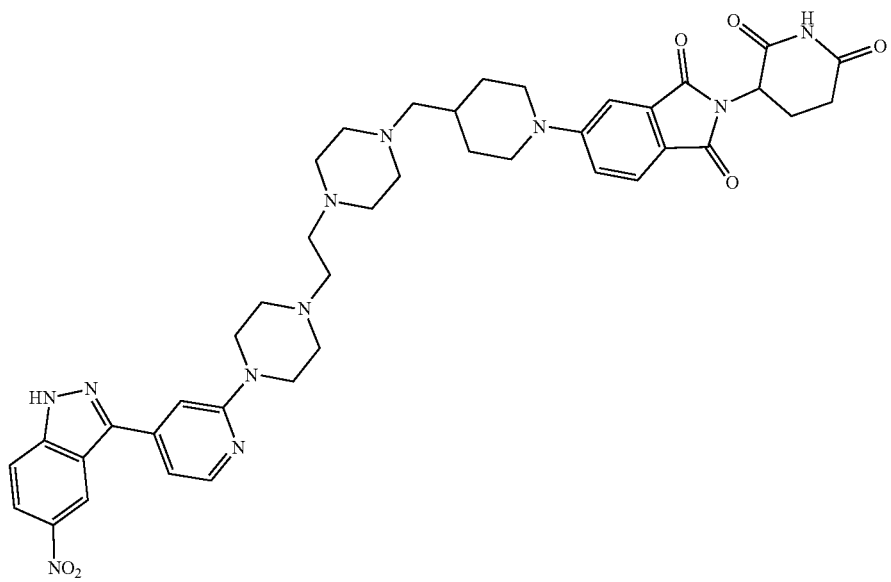

Step 3

To a solution of 5-nitro-3-[2-[4-(2-piperazin-1-ylethyl)piperazin-1-yl]-4-pyridyl]-1H-indazole (240 mg, 549.82 umol, 1 eq) and 1-[2-(2,6-dioxo-3-piperidyl)-1,3-dioxo-isoindolin-5-yl]piperidine-4-carbaldehyde (203.09 mg, 549.82 umol, 1 eq) in MeOH (10 mL) and HOAc (1 mL) was added borane; 2-methylpyridine (117.62 mg, 1.10 mmol, 2 eq). After addition, the reaction solution was stirred at 20° C. for 2 hour. LCMS showed starting material consumed and desired MS was detected. The reaction was diluted with water (20 mL) and extracted with dichloromethane (3×15 mL). The organic layer was dried over sodium sulfate and concentrated under reduced pressure. The residue was purified by silica gel column chromatography (0 to 40% methanol in dichloromethane) to afford 2-(2,6-dioxo-3-piperidyl)-5-[4-[[4-[2-[4-[4-(5-nitro-1H-indazol-3-yl)-2-pyridyl]piperazin-1-yl]ethyl]piperazin-1-yl]methyl]-1-piperidyl]isoindoline-1,3-dione (445 mg, 523.38 umol, 95.19% yield, 92.9% purity) as a yellow solid.

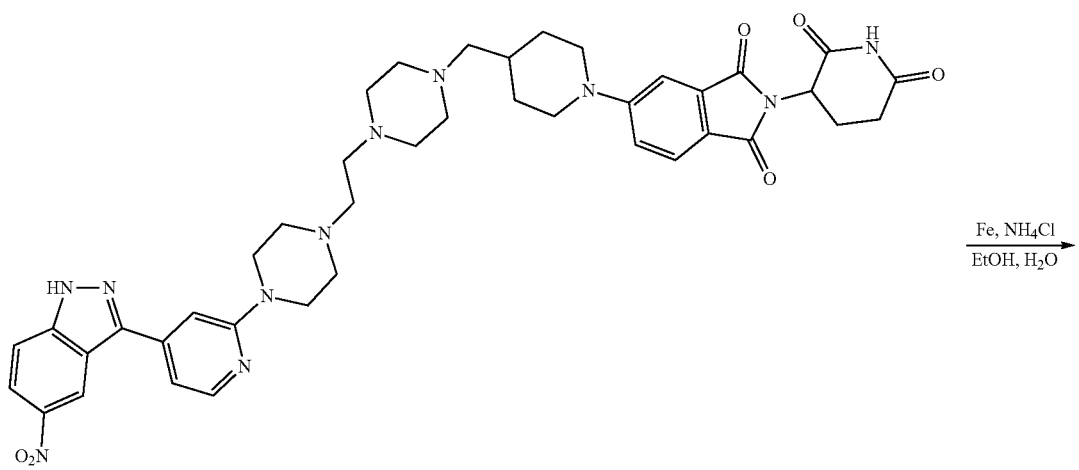

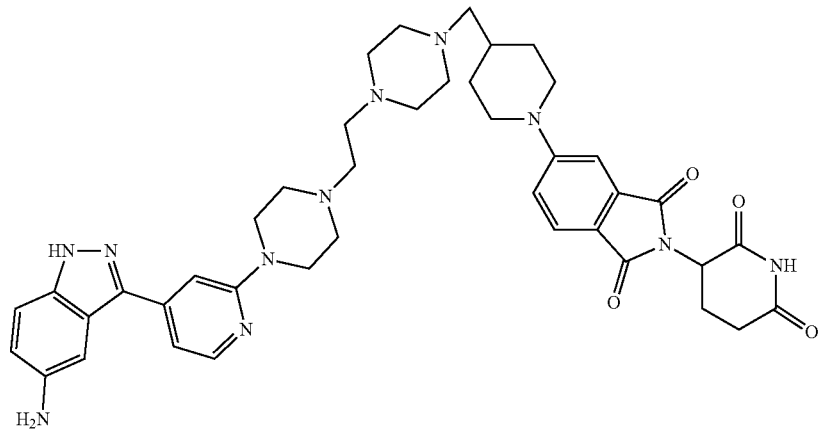

Step 4

To a solution of 2-(2,6-dioxo-3-piperidyl)-5-[4-[[4-[2-[4-[4-(5-nitro-1H-indazol-3-yl)-2-pyridyl]piperazin-1-yl]ethyl]piperazin-1-yl]methyl]-1-piperidyl]isoindoline-1,3-dione (445 mg, 563.38 umol, 1 eq) in EtOH (5 mL) and H2O (1 mL) was added Fe (157.31 mg, 2.82 mmol, 5 eq) and NH4Cl (150.68 mg, 2.82 mmol, 5 eq). After addition, the reaction was stirred at 80° C. for 1 hour. LCMS showed desired MS. After cooling, the reaction mixture was filtered and filtrate was concentrated in vacuo. The residue was triturated with 10% methanol in dichloromethane at 20° C. for 10 minutes. The resulting mixture was filtered and the filtrate was concentrated under reduced pressure to afford 5-[4-[[4-[2-[4-[4-(5-amino-1H-indazol-3-yl)-2-pyridyl]piperazin-1-yl]ethyl]piperazin-1-yl]methyl]-1-piperidyl]-2-(2,6-dioxo-3-piperidyl)isoindoline-1,3-dione (120 mg, 138.97 umol, 24.67% yield, 88% purity) as a yellow solid.

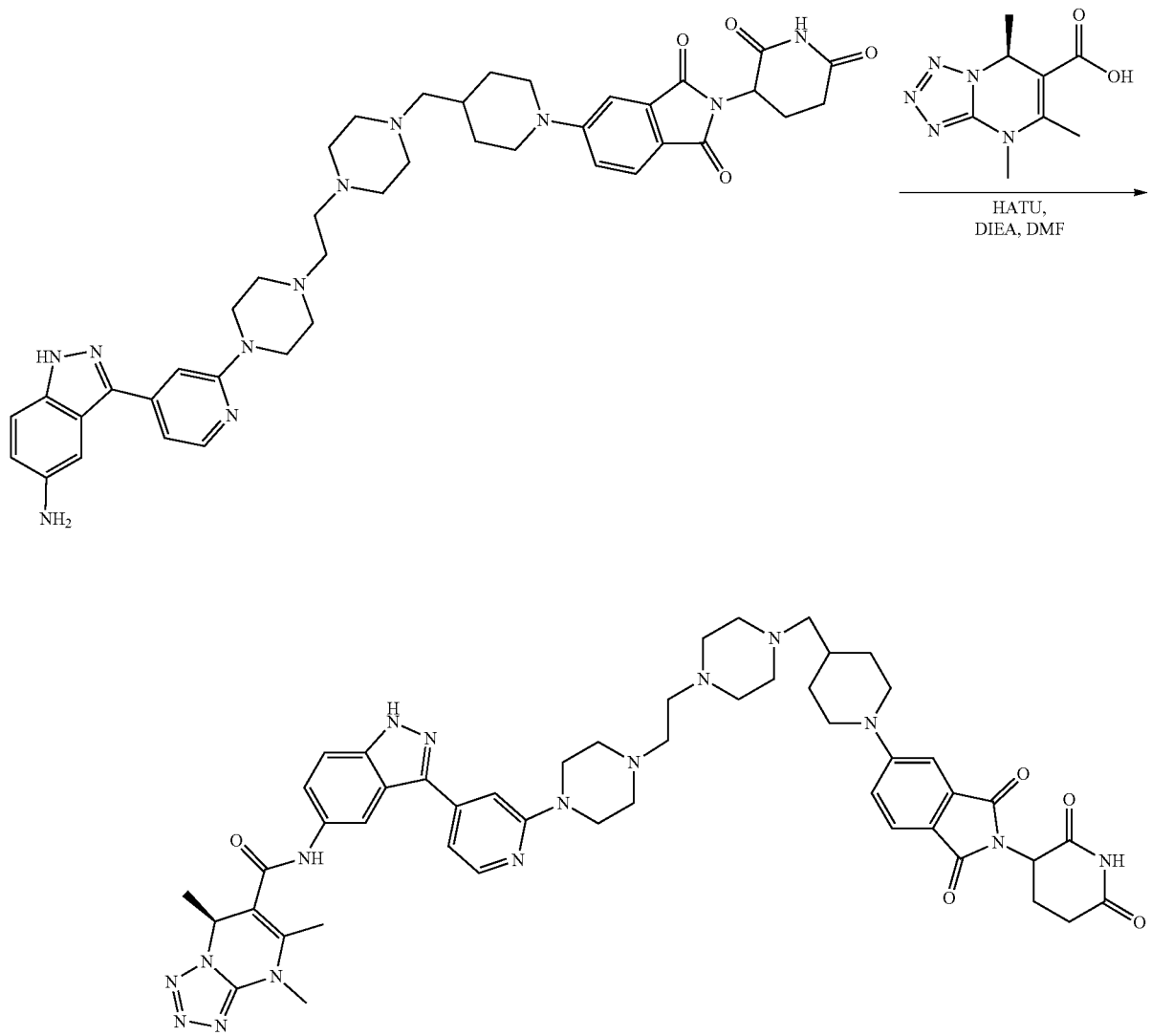

Step 5

To a solution of 5-[4-[[4-[2-[4-[4-(5-amino-1H-indazol-3-yl)-2-pyridyl]piperazin-1-yl]ethyl]piperazin-1-yl]methyl]-1-piperidyl]-2-(2,6-dioxo-3-piperidyl)isoindoline-1,3-dione (55 mg, 72.38 umol, 1 eq) and (7S)-4,5,7-trimethyl-7H-tetrazolo[1,5-a]pyrimidine-6-carboxylic acid (17 mg, 81.26 umol, 1.12 eq) in DMF (2 mF) was added DIEA (46.77 mg, 361.89 umol, 63.03 uL, 5 eq) and HATU (27.52 mg, 72.38 umol, 1 eq). After addition, the reaction was stirred at 25° C. for 12 hours. LCMS showed desired MS. The reaction was diluted with water (10 mF) and extracted with dichloromethane (3×15 mF). The organic layer was dried over sodium sulfate and concentrated under reduced pressure. The residue was purified by prep.HPLC (column: 3_Phenomenex Luna C18 75*30 mm*3 um; mobile phase: [water (0.225% FA)-ACN]; B %: 0-35%; 35 min) to afford (7S)—N-[3-[2-[4-[2-[4-[[1-[2-(2,6-dioxo-3-piperidyl)-1,3-dioxo-isoindolin-5-yl]-4-piperidyl]methyl]piperazin-1-yl]ethyl]piperazin-1-yl]-4-pyridyl]-1H-indazol-5-yl]-4,5,7-trimethyl-7H-tetrazolo[1,5-a]pyrimidine-6-carboxamide (12.8 mg, 13.11 umol, 18.11% yield, 97.40% purity) as a yellow solid.

Exemplary Synthesis of Exemplary Compound 22: (7R)—N-{3-[2-(4-{2-[1-({1-[2-(2,6-dioxopiperidin-3-yl)-1,3-dioxo-2,3-dihydro-1H-isoindol-5-yl]piperidin-4-yl}methyl)piperidin-4-yl]-2,2-difluoroethyl}piperazin-1-yl)pyridin-4-yl]-1H-indazol-5-yl}-4,5,7-trimethyl-4H,7H-[1,2,3,4]tetrazolo[1,5-a]pyrimidine-6-carboxamide Exemplary Compound 22 was prepared in a manner analogous to Exemplary Compound 1 using tert-butyl 4-[2-[4-(4-bromo-2-pyridyl)piperazin-1-yl]-1,1-difluoro-ethyl]piperidine-1-carboxylate.

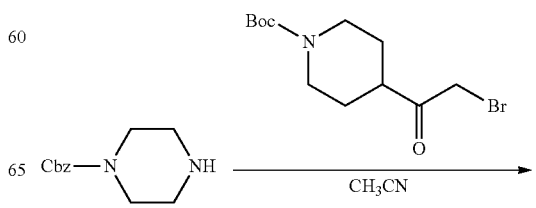

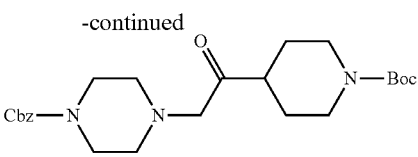

Step 1

To a solution of tert-butyl 4-(2-bromoacetyl)piperidine-1-carboxylate (2.78 g, 9.08 mmol, 1 eq) in MeCN (10 mL) was stirred at 20° C. Then the mixture was added benzyl piperazine-1-carboxylate (2 g, 9.08 mmol, 1.75 mL, 1 eq) and stirred at 20° C. for 16 hr under $N_2$. TLC (Dichloromethane:Methanol=10:1, Rf=0.6) showed no start material and a new spot. The residue was diluted with $H_2O$ (200 mL) extracted with ethyl acetate (70 mL×3). The combined organic layers were washed with brine (80 mL), dried over anhydrous sodium sulfate, filtered and concentrated under reduced pressure to give a residue. The residue was purified by silica gel column chromatography (0 to 10% Dichloromethane in Methanol) to give benzyl 4-[2-(1-tert-butoxycarbonyl-4-piperidyl)-2-oxo-ethyl]piperazine-1-carboxylate (1.9 g, 3.84 mmol, 42.27% yield, 90% purity) as a yellow gum.

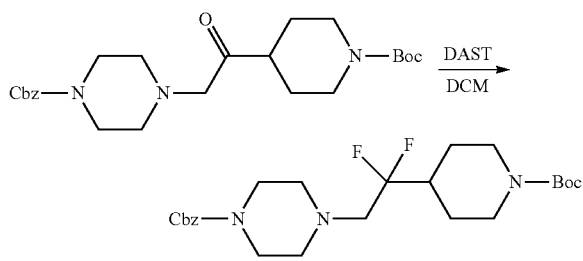

Step 2

To a solution of benzyl 4-[2-(1-tert-butoxycarbonyl-4-piperidyl)-2-oxo-ethyl]piperazine-1-carboxylate (1.9 g, 4.26 mmol, 1 eq) in DCM (30 mL) was stirred at 0° C. for 20 min. Then the mixture was added DAST (24.06 g, 149.25 mmol, 19.72 mL, 35 eq) and stirred at 20° C. for 16 hours under $N_2$. TLC (Petroleum ether: Ethyl acetate=1:1, Rf=0.5) showed no start material and a new spot. The reaction was cooled to 0° C. and quenched with aqueous $NaHCO_3$ (200 mL) extracted with ethyl acetate (100 mL×2). The combined organic layers were washed with brine (45 mL), dried over anhydrous sodium sulfate, filtered and concentrated under reduced pressure to give a residue. The residue was purified by silica gel column chromatography (0 to 50% Ethyl acetate in Petroleum ether) to give benzyl 4-[2-(1-tert-butoxycarbonyl-4-piperidyl)-2,2-difluoro-ethyl]piperazine-1-carboxylate (1.4 g, 2.55 mmol, 59.68% yield, 85% purity) as a Colorless gum.

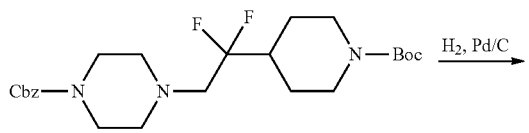

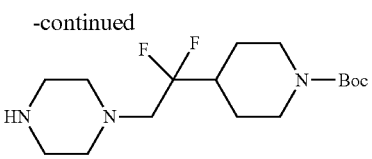

Step 3

To a solution of benzyl 4-[2-(1-tert-butoxycarbonyl-4-piperidyl)-2,2-difluoro-ethyl]piperazine-1-carboxylate (1.4 g, 2.99 mmol, 1 eq) in EtOH (10 mL) and EtOAc (10 mL). Then the mixture was added Pd/C (0.2 g, 299.43 umol, 10% purity, 0.1 eq) and stirred at 25° C. for 16 hours under $H_2$ (15 PSI). TLC (Petroleum ether: Ethyl acetate=1:1, Rf=0.01) showed no start material and a new spot. The reaction was filtered and concentrated under reduced pressure to give tert-butyl 4-(1,1-difluoro-2-piperazin-1-yl-ethyl)piperidine-1-carboxylate (900 mg, crude) as a colorless gum.

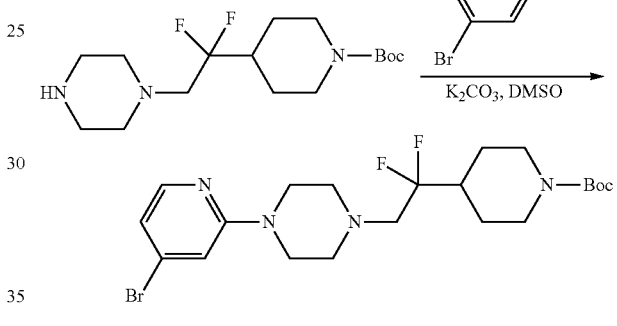

Step 4

To a solution of tert-butyl 4-(1,1-difluoro-2-piperazin-1-yl-ethyl)piperidine-1-carboxylate (900 mg, 2.70 mmol, 1 eq) and 4-bromo-2-fluoro-pyridine (500 mg, 2.84 mmol, 1.05 eq) and $K_2CO_3$ (746.15 mg, 5.40 mmol, 2 eq) in DMSO (15 mL). Then the mixture was stirred at 100° C. for 4 hours under $N_2$. TLC (Petroleum ether: Ethyl acetate=3:1, Rf=0.5) showed no start material and a new spot. The residue was diluted with $H_2O$ (50 mL) extracted with ethyl acetate (60 mL×3). The combined organic layers were washed with brine 40 mL, dried over anhydrous sodium sulfate, filtered and concentrated under reduced pressure to give a residue. The residue was purified by silica gel column chromatography (0 to 30% Ethyl acetate in Petroleum ether) to give tert-butyl 4-[2-[4-(4-bromo-2-pyridyl)piperazin-1-yl]-1,1-difluoro-ethyl]piperidine-1-carboxylate (1 g, 1.94 mmol, 71.91% yield, 95% purity) as a white solid.

Exemplary Synthesis of Exemplary Compound 23:
(7R)—N-{3-[2-(4-{2-[4-({1-[2-(2,6-dioxopiperidin-3-yl)-1,3-dioxo-2,3-dihydro-1H-isoindol-5-yl]piperidin-4-yl}methyl)piperidin-1-yl]ethyl}piperazin-1-yl)pyridin-4-yl]-1H-indazol-5-yl}-4,5,7-trimethyl-4H,7H-[1,2,3,4]tetrazolo[1,5-a]pyrimidine-6-carboxamide Exemplary Compound 23 was prepared in a manner analogous to Exemplary Compound 21 using enantiomer 2 of 4,5,7-trimethyl-7H-tetrazolo[1,5-a]pyrimidine-6-carboxylic acid.

315

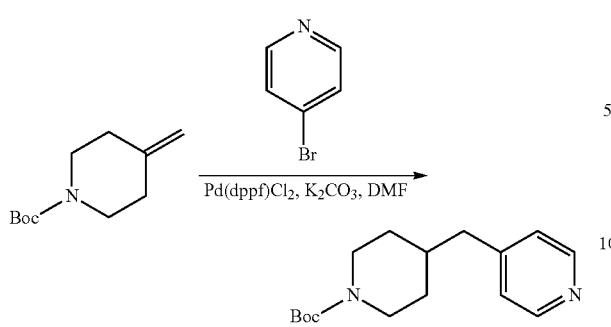

Step 1

To a solution of tert-butyl 4-methylenepiperidine-1-carboxylate (6.24 g, 31.65 mmol, 1 eq) was added 9-BBN (0.5 M, 63.29 mL, 1 eq) at 25° C. The reaction mixture was stirred at 80° C. for 1 hour under $N_2$. After cooling, 4-bromopyridine (5 g, 31.65 mmol, 1 eq), Pd(dppf)Cl2 (1.39 g, 1.90 mmol, 0.06 eq), K2CO3 (6.56 g, 47.47 mmol, 1.5 eq), DMF (50 mL) and H2O (5 mL) were added to the reaction. The resultant mixture was heated to 60° C. for 12 hours. LCMS showed desired MS. After cooling, the reaction mixture was diluted with water (100 mL) and extracted with ethyl acetate (3×100 mL). The organic layer was washed with brine (2×100 mL), dried over sodium sulfate and concentrated under reduced pressure. The residue was purified by silica gel column chromatography (0 to 40% ethyl acetate in petroleum ether) to afford tert-butyl 4-(4-pyridylmethyl)piperidine-1-carboxylate (3.49 g, 11.66 mmol, 36.83% yield, 92.3% purity) as a pale yellow oil.

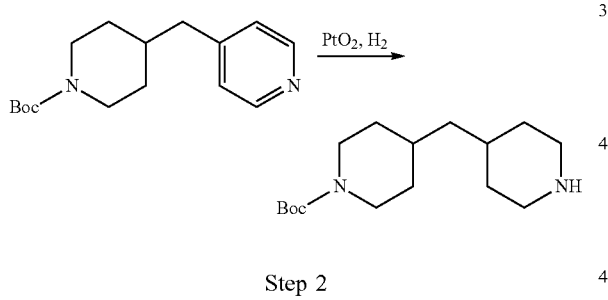

Step 2

To a solution of tert-butyl 4-(4-pyridylmethyl)piperidine-1-carboxylate (3.49 g, 12.63 mmol, 1 eq) in EtOH (50 mL) and HOAc (758.33 mg, 12.63 mmol, 722.21 uL, 1 eq) was added $PtO_2$ (430.12 mg, 1.89 mmol, 0.15 eq) at 25° C. Then the mixture was stirred at 70° C. for 24 hours under $H_2$ (50 psi). TLC (PE:EA=1:1) showed starting material consumed and a new spot formed. After cooling, the reaction was filtered and filtrate was concentrated under reduced pressure to afford tert-butyl 4-(4-piperidylmethyl)piperidine-1-carboxylate (3.9 g, crude) as a brown oil.

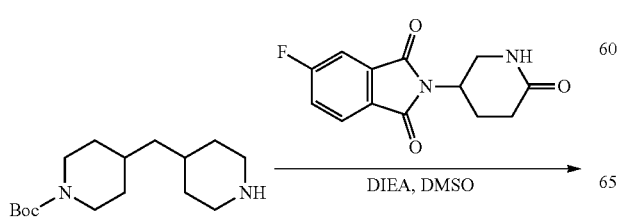

-continued

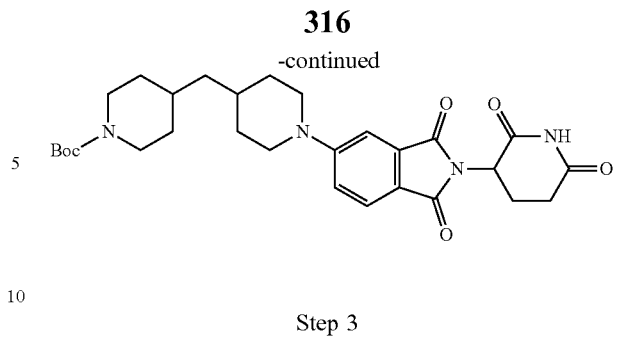

Step 3

To a solution of tert-butyl 4-(4-piperidylmethyl)piperidine-1-carboxylate (3.7 g, 13.10 mmol, 1.21 eq) and 2-(2,6-dioxo-3-piperidyl)-5-fluoro-isoindoline-1,3-dione (3 g, 10.86 mmol, 1 eq) in DMSO (40 mL) was added DIEA (5.61 g, 43.44 mmol, 7.57 mL, 4 eq). After addition, the reaction mixture was stirred at 100° C. for 2 hours. TLC (petroleum ether: ethyl acetate=1:1) showed a new spot. After cooling, the reaction was diluted with ethyl acetate (200 mL) and washed with brine (3×100 mL). The organic layer was dried over sodium sulfate and concentrated under reduced pressure. The residue was purified by silica gel column chromatography (0 to 50% ethyl acetate in petroleum ether) to afford tert-butyl 4-[[1-[2-(2,6-dioxo-3-piperidyl)-1,3-dioxo-isoindolin-5-yl]-4-piperidyl]methyl]piperidine-1-carboxylate (2.86 g, 4.41 mmol, 40.58% yield, 83% purity) as a yellow solid.

Exemplary Synthesis of Exemplary Compound 24: (7R)—N-[3-(2-{4-[1-({1-[2-(2,6-dioxopiperidin-3-yl)-1,3-dioxo-2,3-dihydro-1H-isoindol-5-yl]piperidin-4-yl}methyl)azetidin-3-yl]piperazin-1-yl}pyridin-4-yl)-1H-indazol-5-yl]-4,5,7-trimethyl-4H,7H-[1,2,3,4]tetrazolo[1,5-a]pyrimidine-6-carboxamide

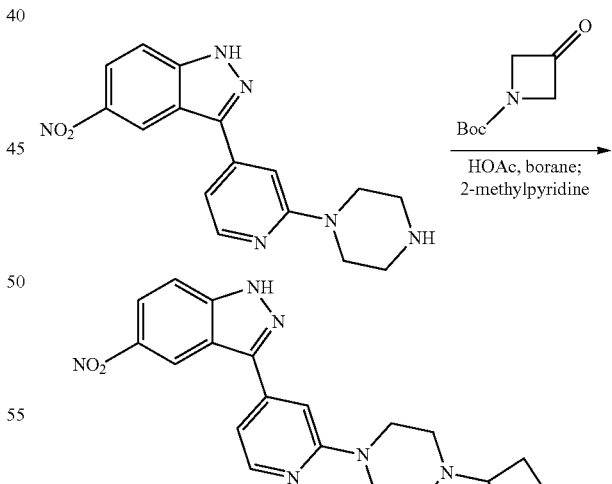

Step 1

To a solution of tert-butyl 3-oxoazetidine-1-carboxylate (170 mg, 993.03 umol, 1 eq) and 5-nitro-3-(2-piperazin-1-yl-4-pyridyl)-1H-indazole (305.97 mg, 943.38 umol, 0.95 eq) in HOAc (1 mL) and MeOH (10 mL) was stirred at 20°

317

C. for 20 minutes, then was added borane; 2-methylpyridine (212.43 mg, 1.99 mmol, 2 eq). Then the mixture was stirred at 30° C. for 16 hours under N$_2$. TLC (Dichloromethane:Methanol=10:1, Rf=0.3) showed no start material and a new spot. The residue was concentrated under reduced pressure to give a residue. The residue was purified by silica gel column chromatography (0 to 20% Dichloromethane in Methanol) to give tert-butyl 3-[4-[4-(5-nitro-1H-indazol-3-yl)-2-pyridyl]piperazin-1-yl]azetidine-1-carboxylate (460 mg, 774.13 umol, 77.96% yield, 80.7% purity) as a yellow solid.

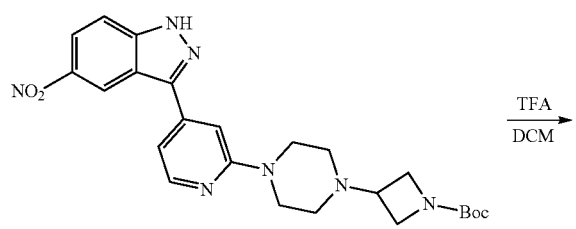

318

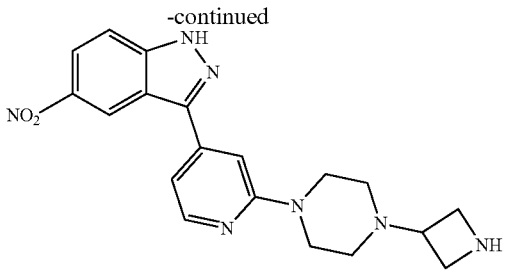

Step 2

To a solution of tert-butyl 3-[4-[4-(5-nitro-1H-indazol-3-yl)-2-pyridyl]piperazin-1-yl]azetidine-1-carboxylate (460 mg, 959.27 umol, 1 eq) in DCM (3 mL) was added TFA (4.25 g, 37.28 mmol, 2.76 mL, 38.86 eq) and then stirred at 20° C. for 1 hr. TLC (Dichloromethane:Methanol=5:1, Rf=0.01) showed no start material and a new spot. The residue was concentrated under reduced pressure to give 3-[2-[4-(azetidin-3-yl)piperazin-1-yl]-4-pyridyl]-5-nitro-1H-indazole (360 mg, crude, TFA) as a yellow solid.

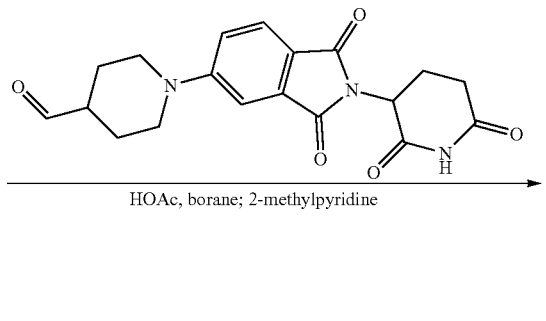

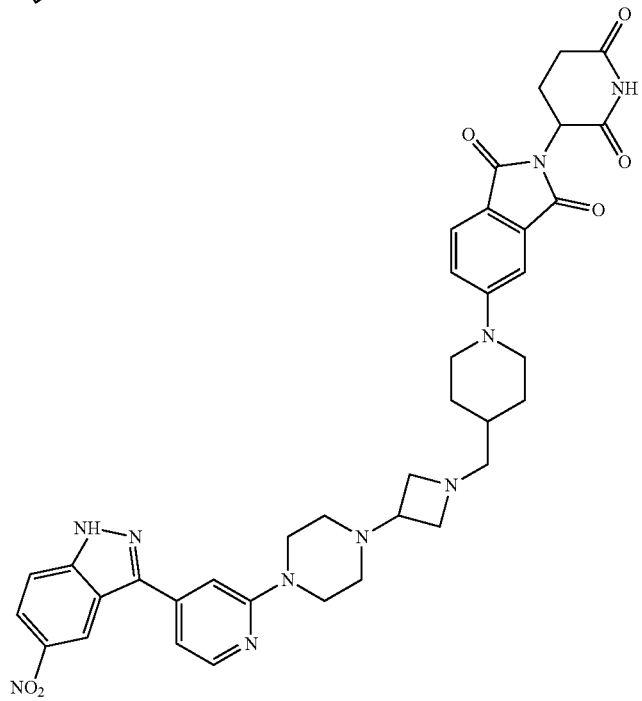

Step 3

To a solution of 1-(2-(2,6-dioxopiperidin-3-yl)-1,3-dioxoisoindolin-5-yl)piperidine-4-carbaldehyde (292.06 mg, 790.69 umol, 1 eq) and 3-(2-(4-(azetidin-3-yl)piperazin-1-yl)pyridin-4-yl)-5-nitro-1H-indazole (300.00 mg, 790.69 umol, 1 eq) in HOAc (1 mL) and MeOH (20 mL) was stirred at 20° C. for 20 minutes, then was added borane; 2-methylpyridine (169.15 mg, 1.58 mmol, 2 eq). Then the mixture was stirred at 30° C. for 16 hours under $N_2$. TLC (Dichloromethane:Methanol=5:1, Rf=0.1) showed no start material and a new spot. The residue was concentrated under reduced pressure to give a residue. The residue was purified by silica gel column chromatography (0 to 50% Dichloromethane in Methanol) to give 2-(2,6-dioxopiperidin-3-yl)-5-(4-((3-(4-(4-(5-nitro-1H-indazol-3-yl)pyridin-2-yl)piperazin-1-yl)azetidin-1-yl)methyl)piperidin-1-yl)isoindoline-1,3-dione (360 mg, 412.67 umol, 52.19% yield, 84% purity) as a yellow solid.

Step 4

To a solution of 2-(2,6-dioxo-3-piperidyl)-5-[4-[[3-[4-[4-(5-nitro-1H-indazol-3-yl)-2-pyridyl]piperazin-1-yl]azetidin-1-yl]methyl]-1-piperidyl]isoindoline-1,3-dione (360 mg, 491.28 umol, 1 eq) in EtOH (10 mL) and $H_2O$ (5 mL) was added Fe (137.18 mg, 2.46 mmol, 5 eq), $NH_4Cl$ (131.39 mg, 2.46 mmol, 5 eq). Then the mixture was stirred at 90° C. for 1 hour under $N_2$. LCMS showed desired product. The residue was concentrated under reduced pressure to give a residue. The residue was purified by prep-HPLC (Phenomenex Gemini-NX 150*30 mm*5 um: water (0.05% HCl)-ACN; B %: 10%-40%, 10 min) to afford 5-[4-[[3-[4-[4-(5-amino-1H-indazol-3-yl)-2-pyridyl]piperazin-1-yl]azetidin-1-yl]methyl]-1-piperidyl]-2-(2,6-dioxo-3-piperidyl)isoindoline-1,3-dione (177 mg, 231.70 umol, 47.16% yield, 92% purity) as a yellow solid.

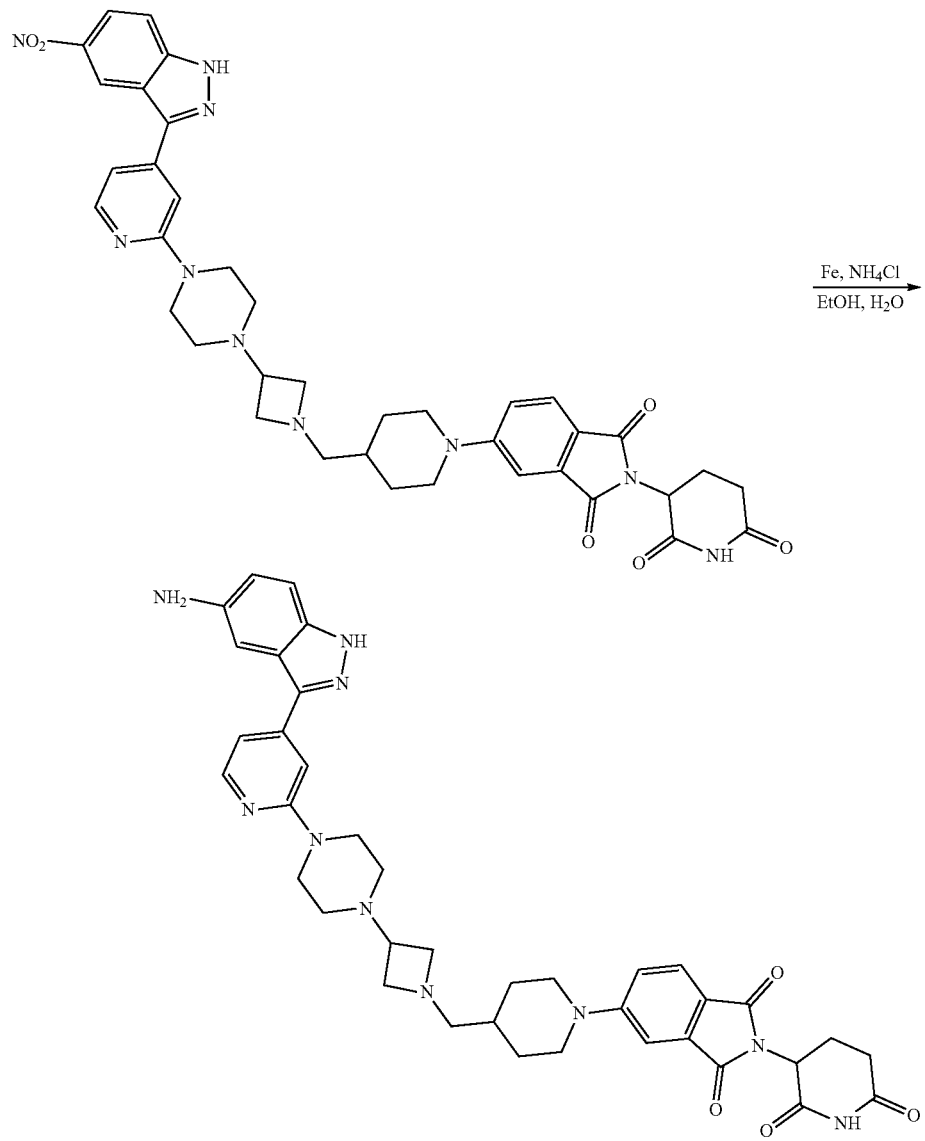

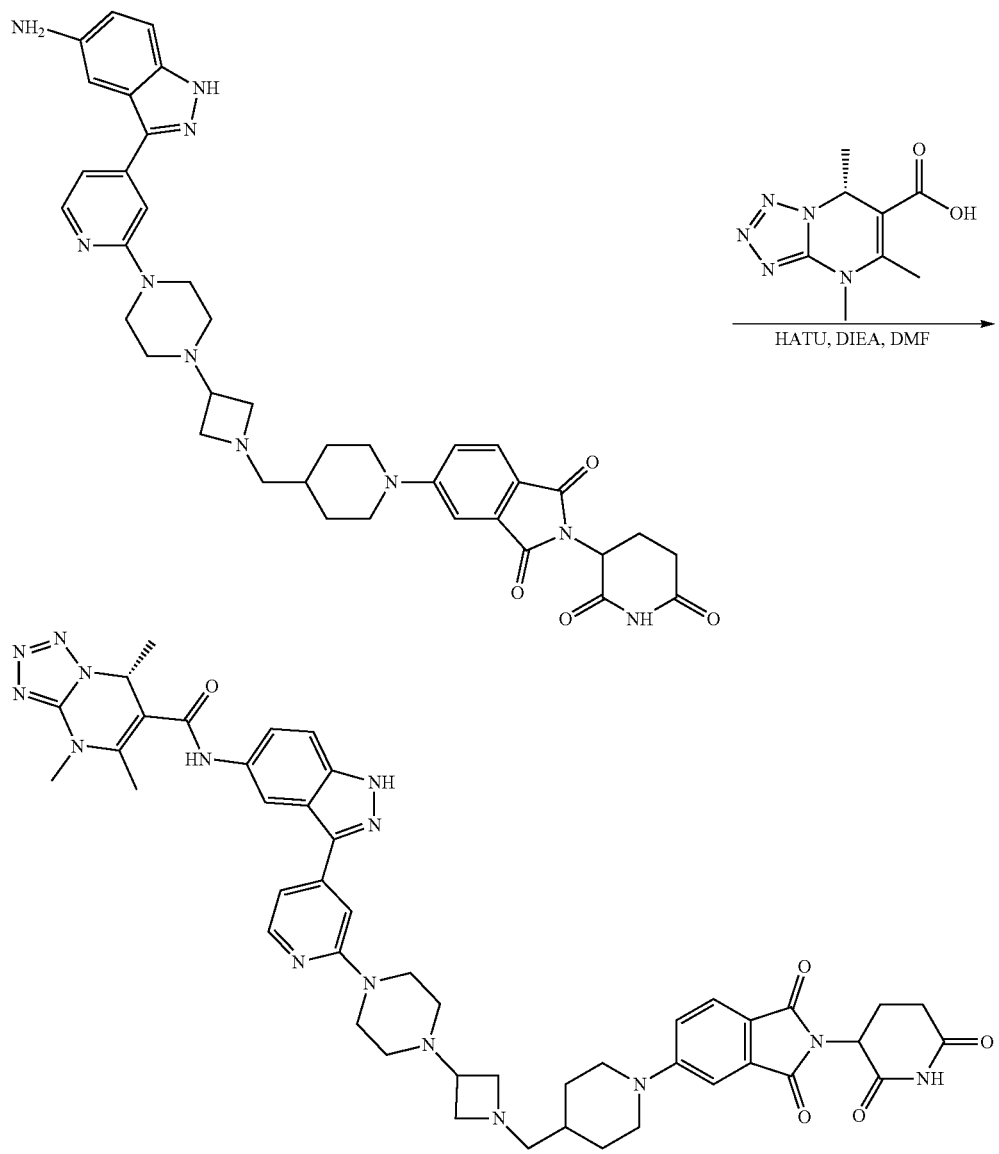

Step 5

To a solution of 5-[4-[[3-[4-[4-(5-amino-1H-indazol-3-yl)-2-pyridyl]piperazin-1-yl]azetidin-1-yl]methyl]-1-piperidyl]-2-(2,6-dioxo-3-piperidyl)isoindoline-1,3-dione (78 mg, 110.98 umol, 1 eq) and (7R)-4,5,7-trimethyl-7H-tetrazolo[1,5-a]pyrimidine-6-carboxylic acid (23.22 mg, 110.98 umol, 1 eq) in DMF (4 mL) was stirred at 20° C. for 10 minutes, then was added DIEA (71.72 mg, 554.92 umol, 96.65 uL, 5 eq) and HATU (42.20 mg, 110.98 umol, 1 eq). Then the mixture was stirred at 30° C. for 16 hours under $N_2$. LCMS showed desired product. The residue was concentrated under reduced pressure to give a residue. The residue was purified by prep-HPLC (column: 3_Phenomenex Luna C18 75*30 mm*3 um; mobile phase: [water (0.225% FA)-ACN]; B %: 0%-30%, 35 min) to give (7R)—N-[3-[2-[4-[1-[[1-[2-(2,6-dioxo-3-piperidyl)-1,3-dioxo-isoindolin-5-yl]-4-piperidyl]methyl]azetidin-3-yl]piperazin-1-yl]-4-pyridyl]-1H-indazol-5-yl]-4,5,7-trimethyl-7H-tetrazolo[1,5-a]pyrimidine-6-carboxamide (19.1 mg, 21.21 umol, 19.11% yield, 99.27% purity) as a yellow solid.

Exemplary Synthesis of Exemplary Compound 25: (7R)—N-{3-[2-(4-{2-[4-({1-[2-(2,6-dioxopiperidin-3-yl)-1,3-dioxo-2,3-dihydro-1H-isoindol-5-yl]piperidin-4-yl}methyl)piperazin-1-yl]ethyl}piperazin-1-yl)pyridin-4-yl]-1H-indazol-5-yl}-4,5,7-trimethyl-4H,7H-[1,2,3,4]tetrazolo[1,5-a]pyrimidine-6-carboxamide

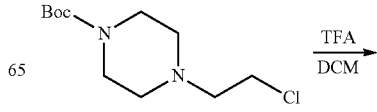

-continued

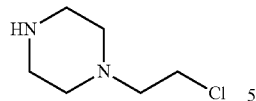

Step 1

To a solution of tert-butyl 4-(2-chloroethyl)piperazine-1-carboxylate (200 mg, 804.02 umol, 1 eq) in DCM (2 mL) added TFA (3.08 g, 27.01 mmol, 2 mL, 33.60 eq) and then the mixture was stirred at 20° C. for 1 hour. TLC (Dichloromethane:Methanol=10:1, Rf=0.02) showed no start material and a new spot. The residue was concentrated under reduced pressure to give 1-(2-chloroethyl)piperazine (119 mg, crude, TFA) as a Colorless oil.

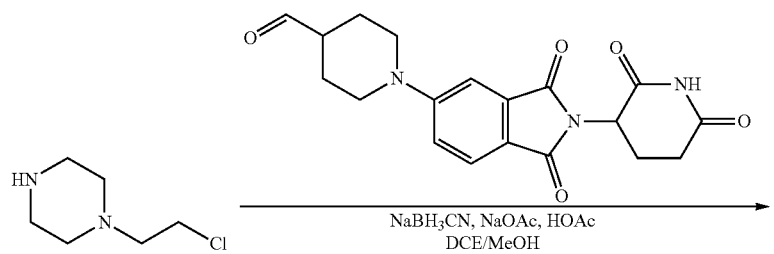

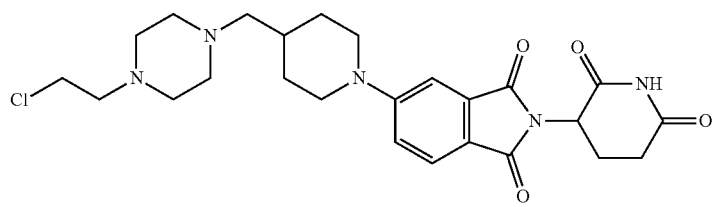

Step 2

To a solution of 1-(2-chloroethyl)piperazine (119 mg, 800.63 umol, 1 eq) and 1-[2-(2,6-dioxo-3-piperidyl)-1,3-dioxo-isoindolin-5-yl]piperidine-4-carbaldehyde (295.73 mg, 800.63 umol, 1 eq) in HOAC (1 mL) and MeOH (10 mL) was stirred at 20° C. for 20 min, then was added borane; 2-methylpyridine (171.27 mg, 1.60 mmol, 2 eq). Then the mixture was stirred at 30° C. for 16 hours under $N_2$. TLC (Dichloromethane:Methanol=10:1, Rf=0.3) showed no start material and a new spot. The residue was concentrated under reduced pressure to give a residue. The residue was purified by silica gel column chromatography (0 to 25% Dichloromethane in Methanol) to give 5-[4-[[4-(2-chloroethyl)piperazin-1-yl]methyl]-1-piperidyl]-2-(2,6-dioxo-3-piperidyl)isoindoline-1,3-dione (390 mg, 769.12 umol, 96.06% yield, 99% purity) as a yellow solid.

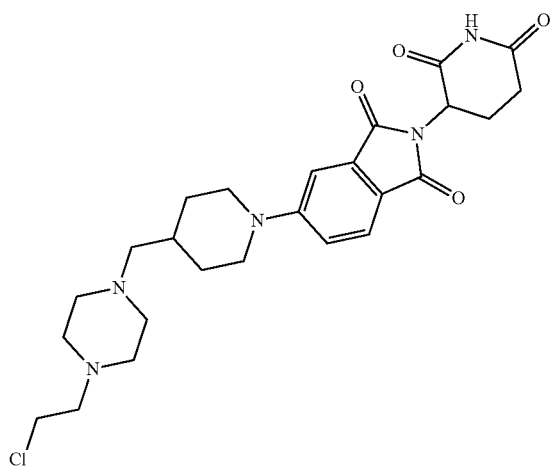

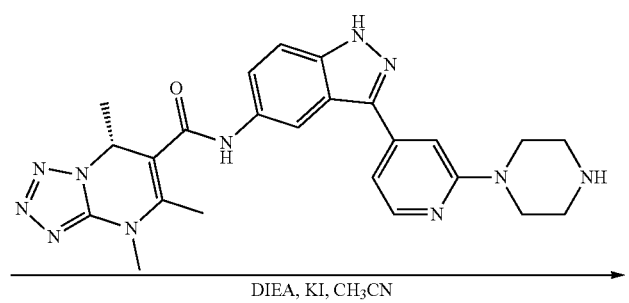

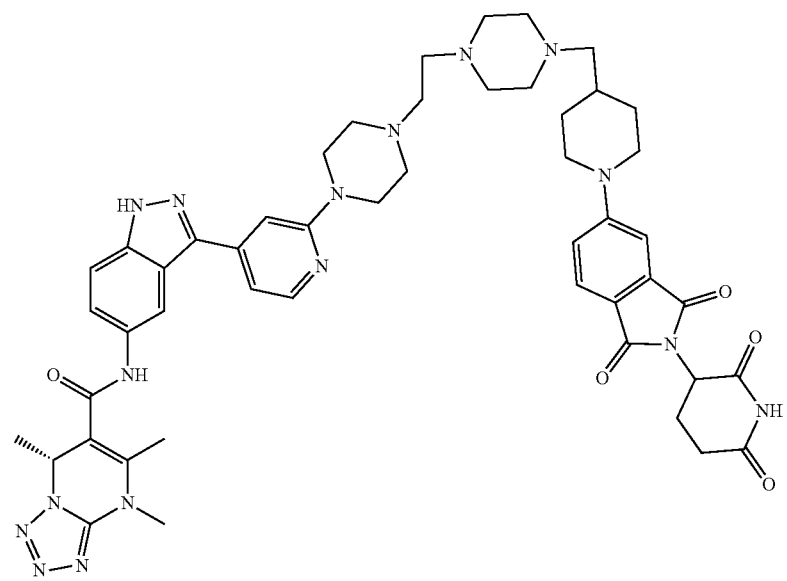

Step 3

To a solution of (7R)-4,5,7-trimethyl-N-[3-(2-piperazin-1-yl-4-pyridyl)-1H-indazol-5-yl]-7H-tetrazolo[1,5-a]pyrimidine-6-carboxamide (40 mg, 82.38 umol, 1 eq) and 5-[4-[[4-(2-chloroethyl)piperazin-1-yl]methyl]-1-piperidyl]-2-(2,6-dioxo-3-piperidyl)isoindoline-1,3-dione (45 mg, 89.64 umol, 1.09 eq) and DIEA (106.47 mg, 823.82 umol, 143.49 uL, 10 eq) and KI (136.75 mg, 823.82 umol, 10 eq) in MeCN (10 mL). Then the mixture was stirred at 80° C. for 4 hours under $N_2$. LCMS showed desired product. The residue was diluted with $H_2O$ (20 mL) and extracted with ethyl acetate (20 mL×3). The combined organic layers were washed with brine (15 mL), dried over anhydrous sodium sulfate, filtered and concentrated under reduced pressure to give a residue. The residue was purified by prep-HPLC (column: 3_Phenomenex Luna C18 75*30 mm*3 um; mobile phase: [water (0.225% LA)-ACN]; B %: 0%-30%, 35 min) to afford (7R)—N-[3-[2-[4-[2-[4-[[1-[2-(2,6-dioxo-3-piperidyl)-1,3-dioxo-isoindolin-5-yl]-4-piperidyl]methyl]piperazin-1-yl]ethyl]piperazin-1-yl]-4-pyridyl]-1H-indazol-5-yl]-4,5,7-trimethyl-7H-tetrazolo[1,5-a]pyrimidine-6-carboxamide (8.8 mg, 9.04 umol, 10.97% yield, 97.66% purity) as a yellow solid.

Exemplary Synthesis of Exemplary Compound 26: (7R)—N-(3-{2-[6-({1-[2-(2,6-dioxopiperidin-3-yl)-1,3-dioxo-2,3-dihydro-1H-isoindol-5-yl]piperidin-4-yl}methyl)-2,6-diazaspiro[3.3]heptan-2-yl]pyridin-4-yl}-1H-indazol-5-yl)-4,5,7-trimethyl-4H,7H-[1,2,3,4]tetrazolo[1,5-a]pyrimidine-6-carboxamide

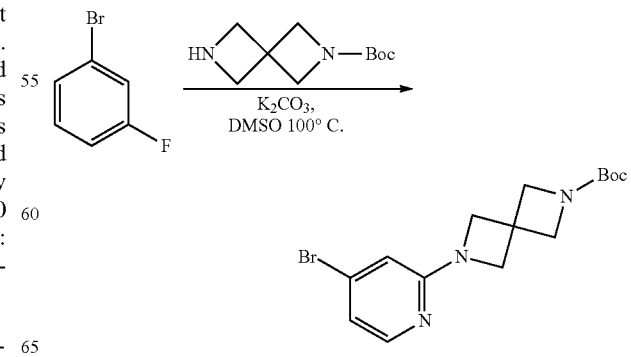

Step 1

To a mixture of 4-bromo-2-fluoro-pyridine (1 g, 5.68 mmol, 1 eq) and tert-butyl 2,6-diazaspiro[3.3]heptane-2-carboxylate; oxalic acid (1.38 g, 2.84 mmol, 0.5 eq) in DMSO (10 mL) was added K₂CO₃ (2.36 g, 17.04 mmol, 70.14 mL, 3 eq) in one portion at 100° C. under N₂. The mixture was stirred at 100° C. for 2 hours to give yellow solution. TLC and LCMS showed the reaction was completed. The mixture was cooled to 20° C. and concentrated in reduced pressure at 20° C. The residue was poured into water (10 mL). The aqueous phase was extracted with ethyl acetate (10 mL*4). The combined organic phase was washed with brine (10 mL*2), dried with anhydrous Na₂SO₄, filtered and concentrated in vacuum. The residue was purified by silica gel chromatography (Petroleum ether: Ethyl acetate=10:1, Rf=0.56, 12 g, 0-50% (10 min) of Ethyl acetate in Petroleum ether, 50% (5 min) of Ethyl acetate in Petroleum ether) to give tert-butyl 6-(4-bromo-2-pyridyl)-2,6-diazaspiro[3.3]heptane-2-carboxylate (1.3 g, 3.67 mmol, 64.61% yield) as a white solid.

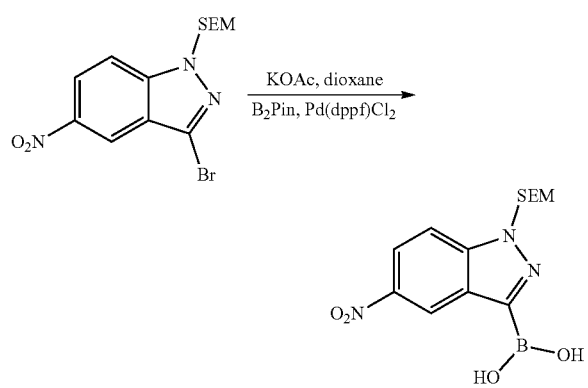

Step 2

To a mixture of 2-[(3-bromo-5-nitro-indazol-1-yl)methoxy]ethyl-trimethyl-silane (2 g, 5.37 mmol, 1 eq), 4,4,5,5-tetramethyl-2-(4,4,5,5-tetramethyl-1,3,2-dioxaborolan-2-yl)-1,3,2-dioxaborolane (2.05 g, 8.06 mmol, 1.5 eq) and Pd(dppf)Cl₂ (196.54 mg, 268.61 umol, 0.05 eq) in dioxane (20 mL) was added KOAc (1.58 g, 16.12 mmol, 3 eq) in one portion at 25° C. under N₂. The mixture was stirred at 100° C. for 1 hour. TLC showed the reaction was completed. The mixture was cooled to 25° C., filtered and concentrated in vacuum to give [5-nitro-1-(2-trimethylsilylethoxymethyl)indazol-3-yl]boronic acid (1.8 g, crude) as a black brown solid. The crude product was used into the next step without purification.

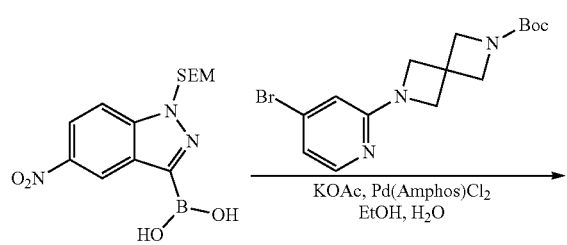

Step 3

To a mixture of tert-butyl 6-(4-bromo-2-pyridyl)-2,6-diazaspiro[3.3]heptane-2-carboxylate (1.3 g, 3.67 mmol, 1 eq), [5-nitro-1-(2-trimethylsilylethoxymethyl)indazol-3-yl]boronic acid (1.73 g, 5.14 mmol, 1.4 eq) and 4-ditert-butylphosphanyl-N,N-dimethyl-aniline; dichloropalladium (259.85 mg, 366.98 umol, 259.85 uL, 0.1 eq) in EtOH (10 mL) and H₂O (4 mL) was added KOAc (1.08 g, 11.01 mmol, 3 eq) in one portion at 25° C. under N₂. The mixture was stirred at 100° C. for 2 hours. LCMS showed the reaction was completed. The mixture was cooled to 20° C. and concentrated in reduced pressure. The residue was poured into water (10 mL). The aqueous phase was extracted with ethyl acetate (10 mL*3). The combined organic phase was washed with brine (10 mL*2), dried with anhydrous Na₂SO₄, filtered and concentrated in vacuum. The residue was purified by silica gel chromatography (20 g, 0-40% (10 min) of Ethyl acetate in Petroleum ether, 40% (10 min) of Ethyl acetate in Petroleum ether) to give tert-butyl 6-[4-[5-nitro-1-(2-trimethylsilylethoxymethyl)indazol-3-yl]-2-pyridyl]-2,6-diazaspiro[3.3]heptane-2-carboxylate (1.2 g, 2.12 mmol, 57.70% yield) as a yellow solid.

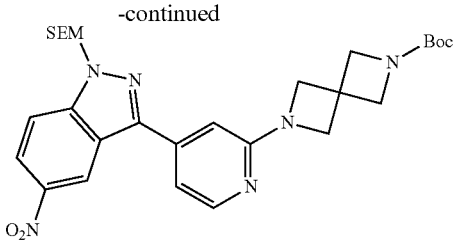

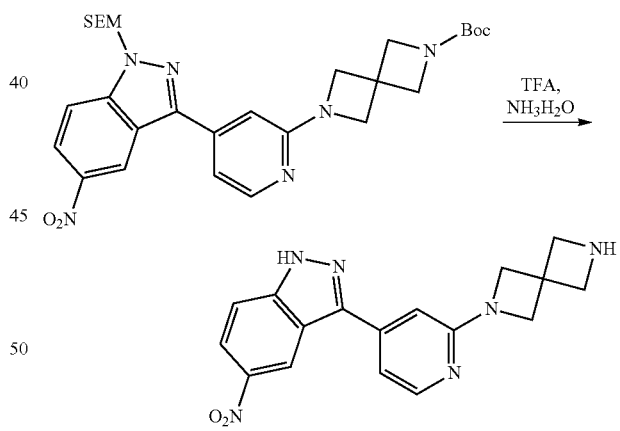

Step 4

To a mixture of tert-butyl 6-[4-[5-nitro-1-(2-trimethylsilylethoxymethyl)indazol-3-yl]-2-pyridyl]-2,6-diazaspiro[3.3]heptane-2-carboxylate (600 mg, 1.06 mmol, 1 eq) in DCM (5 mL) was added TFA (362.16 mg, 3.18 mmol, 235.17 uL, 3 eq) in one portion at 20° C. The mixture was stirred at 20° C. for 2 hours. The mixture added dioxane (10 mL) and NH₃.H₂O (556.55 mg, 6.35 mmol, 611.60 uL, 40% purity, 6 eq) in one portion at 20° C., The mixture was stirred at 20° C. for 2 hours. LCMS showed the reaction was completed. The residue was poured into water (5 mL), the aqueous phase was extracted with DCM (5 mL*3). The combined organic phase was washed with brine (5 mL*2), dried with anhydrous Na₂SO₄, filtered and concentrated in vacuum to give 3-[2-(2,6-diazaspiro[3.3]heptan-2-yl)-4-pyridyl]-5-nitro-1H-indazole (300 mg, 561.92 umol, 53.08% yield, 63% purity) as a yellow solid.

mg, 1.78 mmol, 2 eq) in one portion at 20° C. under N₂. The mixture was stirred at 30° C. for 16 hours. LCMS showed there was desired MS. The residue was poured into water (10 mL). The aqueous phase was extracted with ethyl acetate (10 mL*3). The combined organic phase was washed with brine (10 mL*2), dried with anhydrous Na₂SO₄, filtered and

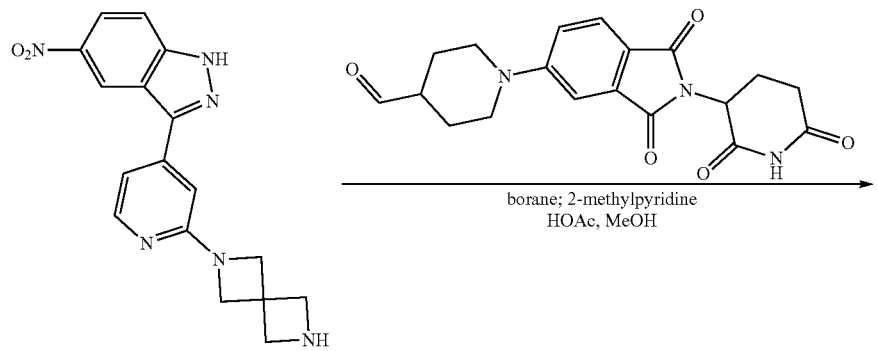

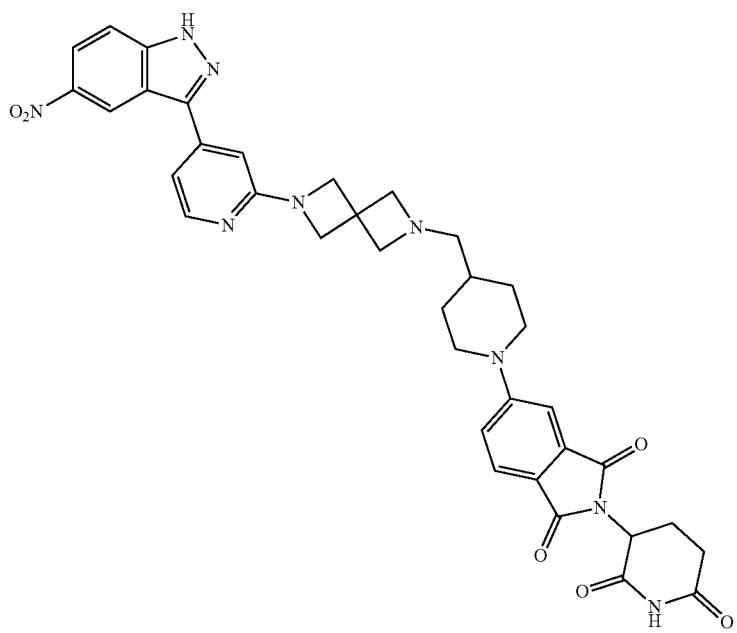

Step 5

To a mixture of 3-[2-(2,6-diazaspiro[3.3]heptan-2-yl)-4-pyridyl]-5-nitro-1H-indazole (300 mg, 891.94 umol, 1 eq) and 1-[2-(2,6-dioxo-3-piperidyl)-1,3-dioxo-isoindolin-5-yl]piperidine-4-carbaldehyde (329.45 mg, 891.94 umol, 1 eq) in MeOH (10 mL) was added CH₃COOH (53.56 mg, 891.94 umol, 51.01 uL, 1 eq) and borane; 2-methylpyridine (190.80 concentrated in vacuum. The residue was purified by silica gel chromatography (Dichloromethane:Methanol=10:1, Rf=0.32, 0-10% (10 min) of Methanol in Dichloromethane, 10% (5 min) of Methanol in Dichloromethane) to give 2-(2,6-dioxo-3-piperidyl)-5-[4-[[2-[4-(5-nitro-1H-indazol-3-yl)-2-pyridyl]-2,6-diazaspiro[3.3]heptan-6-yl]methyl]-1-piperidyl]isoindoline-1,3-dione (600 mg, 565.45 umol, 63.40% yield, 65% purity) as a yellow gum.

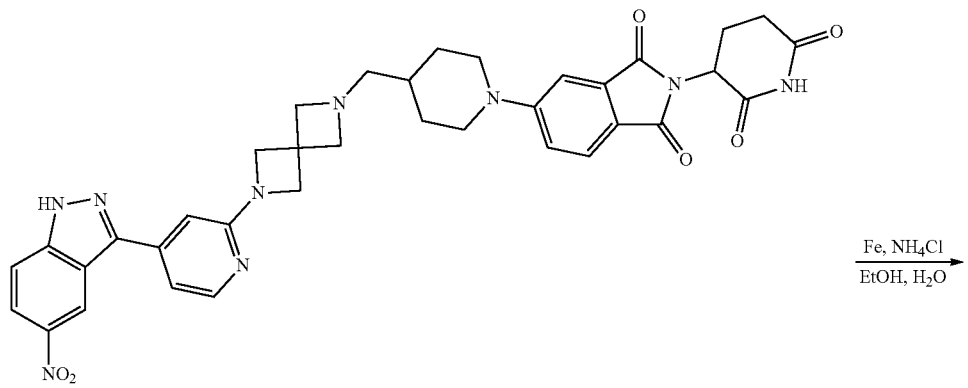

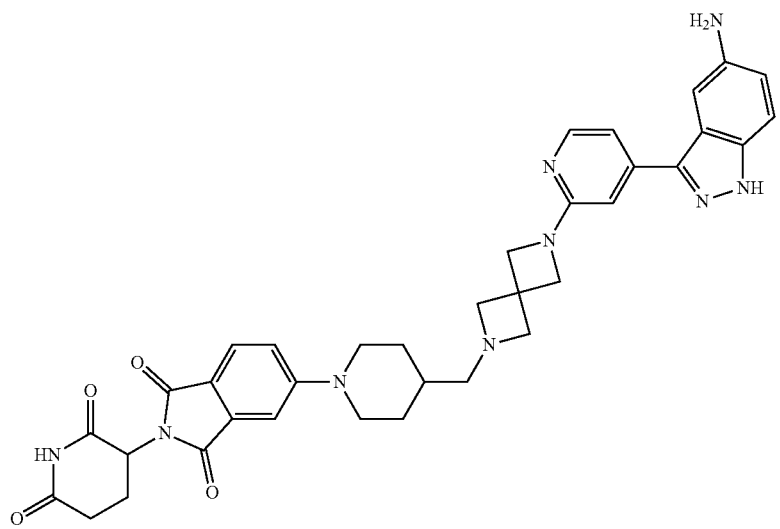

Step 6

To a mixture of 2-(2,6-dioxo-3-piperidyl)-5-[4-[[2-[4-(5-nitro-1H-indazol-3-yl)-2-pyridyl]-2,6-diazaspiro[3.3]heptan-6-yl]methyl]-1-piperidyl]isoindoline-1,3-dione (600 mg, 869.92 umol, 1 eq) and Fe (242.90 mg, 4.35 mmol, 5 eq) in EtOH (10 mL), $H_2O$ (5 mL) and DCM (5 mL) was added $NH_4Cl$ (232.67 mg, 4.35 mmol, 5 eq) in one portion at 20° C. under $N_2$. The mixture was stirred at 80° C. for 30 minutes. LCMS showed the reaction was completed. The residue was filtered with ethyl acetate (10 mL*5), and solution was concentrated in vacuum. The crude product was purified by reversed-phase HPLC (Column: YMC-Triart Prep C18 150*40 mm*7 um; Condition: water (0.05% HCl)-ACN; Begin B: 5; End B: 35; FlowRate: 60 mL/min; Gradient Time: 25 min; 100% B Hold Time: 2 min) to give 5-(4-((6-(4-(5-amino-1H-indazol-3-yl)pyridin-2-yl)-2,6-diazaspiro[3.3]heptan-2-yl)methyl)piperidin-1-yl)-2-(2,6-dioxopiperidin-3-yl)isoindoline-1,3-dione (110 mg, 166.07 umol, 19.09% yield, 99.6% purity) as a yellow solid.

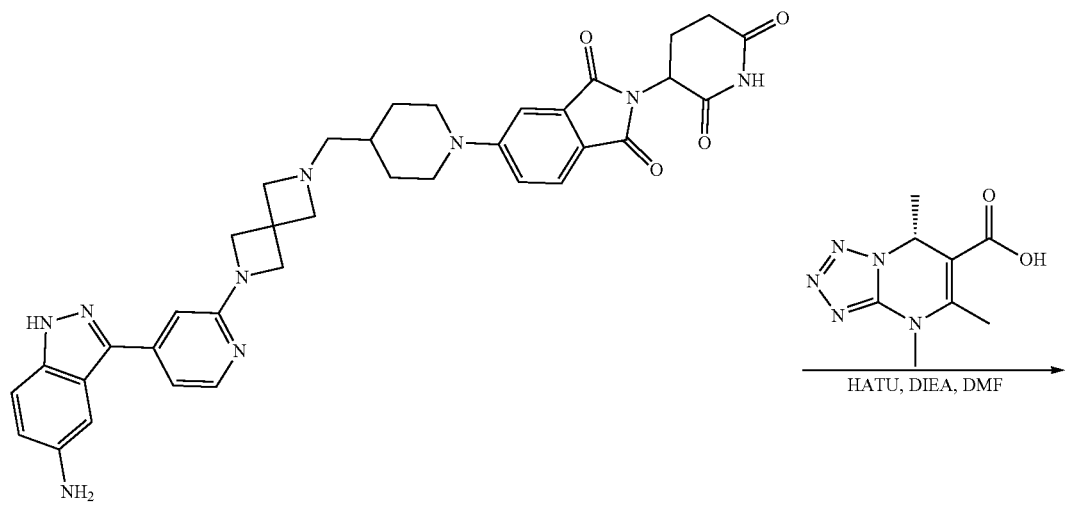

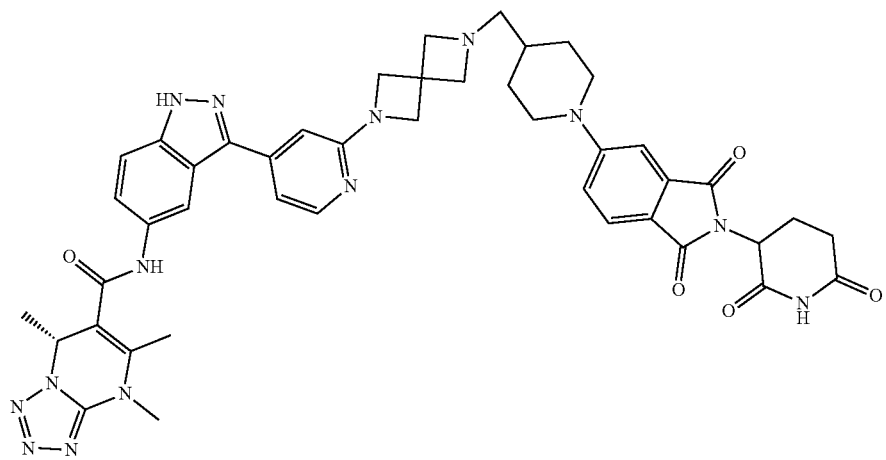

Step 7

To a solution of (7R)-4,5,7-trimethyl-7H-tetrazolo[1,5-a]pyrimidine-6-carboxylic acid (34.88 mg, 166.73 umol, 1 eq) and 5-[4-[[2-[4-(5-amino-1H-indazol-3-yl)-2-pyridyl]-2,6-diazaspiro[3.3]heptan-6-yl]methyl]-1-piperidyl]-2-(2,6-dioxo-3-piperidyl)isoindoline-1,3-dione (110 mg, 166.73 umol, 1 eq) in DMF (2 mL) was stirred at 0° C. for 10 minutes, then was added DIPEA (107.74 mg, 833.67 umol, 145.21 uL, 5 eq) and HATU (63.40 mg, 166.73 umol, 1 eq), Then the mixture was stirred at 25° C. for 16 hours under N$_2$. LCMS showed desired MS. The residue was poured into water (2 mL). The aqueous phase was extracted with ethyl acetate (2 mL*3). The combined organic phase was washed with brine (2 mL*2), dried with anhydrous Na$_2$SO$_4$, filtered and concentrated in vacuum. The crude product was purified by reversed-phase HPLC (Column: 3_Phenomenex Luna C18 75*30 mm*3 um; Condition: water (0.225% FA)-ACN; Begin B: 0; End B: 30; FlowRate: 25 mL/min; Gradient Time: 35 minutes; 100% B Hold Time: 3 minutes) to give (7R)—N-[3-[2-[6-[[1-[2-(2,6-dioxo-3-piperidyl)-1,3-dioxo-isoindolin-5-yl]-4-piperidyl]methyl]-2,6-diazaspiro[3.3]heptan-2-yl]-4-pyridyl]-1H-indazol-5-yl]-4,5,7-trimethyl-7H-tetrazolo[1,5-a]pyrimidine-6-carboxamide (29 mg, 34.01 umol, 20.40% yield, 99.78% purity) as a yellow solid.

Exemplary Synthesis of Exemplary Compound 27: (7S)—N-{3-[2-(4-{2-[4-({4-[2-(2,6-dioxopiperidin-3-yl)-1,3-dioxo-2,3-dihydro-1H-isoindol-5-yl]piperazin-1-yl}methyl)piperidin-1-yl]ethyl}piperazin-1-yl)pyridin-4-yl]-1H-indazol-5-yl}-4,5,7-trimethyl-4H,7H-[1,2,3,4]tetrazolo[1,5-a]pyrimidine-6-carboxamideuors

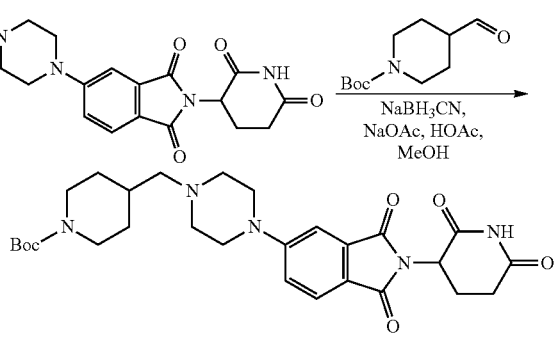

Step 1

To a solution of 2-(2,6-dioxo-3-piperidyl)-5-piperazin-1-yl-isoindoline-1,3-dione (2 g, 4.38 mmol, 1 eq, TFA) and tert-butyl 4-formylpiperidine-1-carboxylate (1.40 g, 6.57 mmol, 1.5 eq) in MeOH (20 mL) was added NaOAc (1.08 g, 13.15 mmol, 3 eq), HOAc (131.59 mg, 2.19 mmol, 125.32 uL, 0.5 eq) and NaBH₃CN (826.20 mg, 13.15 mmol, 3 eq) in one portion at 20° C. under N₂. The solution was stirred at 20° C. for 1 hour. TLC (DCM:MeOH=10:1, Rf=0.43) showed the reaction was completed, and a main spot (Rf=0.43) was showed on TLC. The residue was poured into water (20 mL). The aqueous phase was extracted with ethyl acetate (3×20 mL). The combined organic phase was washed with brine (2×20 mL), dried with anhydrous Na₂SO₄, filtered and concentrated in vacuum. The residue was purified by silica gel chromatography (column: 40 g, 100-200 mesh silica gel, 0-50% (5 min) of Ethyl acetate in Petroleum ether, 50-100% (10 min) of Ethyl acetate in Petroleum ether) to give tert-butyl 4-[[4-[2-(2,6-dioxo-3-piperidyl)-1,3-dioxo-isoindolin-5-yl]piperazin-1-yl]methyl]piperidine-1-carboxylate (2.2 g, 3.99 mmol, 90.98% yield, 97.8% purity) as a yellow gum.

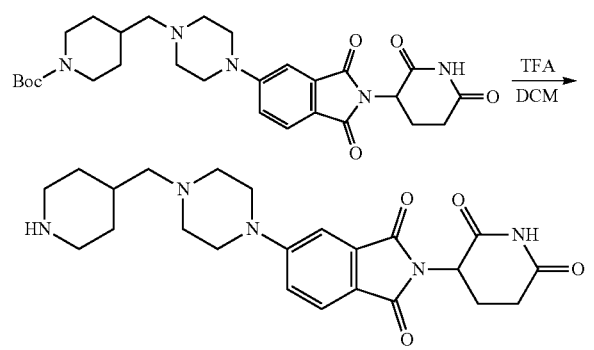

Step 2

To a solution of tert-butyl 4-[[4-[2-(2,6-dioxo-3-piperidyl)-1,3-dioxo-isoindolin-5-yl]piperazin-1-yl]methyl]piperidine-1-carboxylate (2.2 g, 4.08 mmol, 1 eq) in DCM (2 mL) was added TFA (1.39 g, 12.23 mmol, 905.58 uL, 3 eq) in one portion at 20° C. under N₂. The mixture was stirred at 20° C. for 30 minutes to give yellow solution. TLC (DCM:MeOH=10:1, Rf=0.43) showed the starting material was completed. The solution was concentrated in vacuum to give 2-(2,6-dioxo-3-piperidyl)-5-[4-(4-piperidylmethyl)piperazin-1-yl]isoindoline-1,3-dione (3 g, 3.73 mmol, 91.61% yield, 97.3% purity, 3TFA) as a yellow gum.

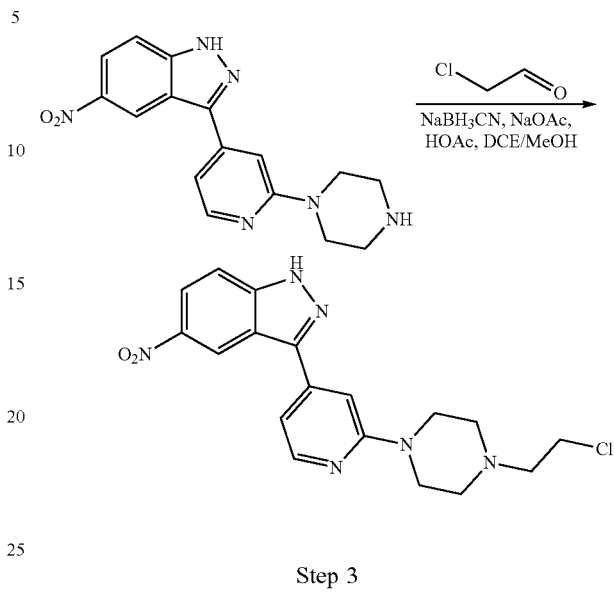

Step 3

To a mixture of 5-nitro-3-(2-piperazin-1-yl-4-pyridyl)-1H-indazole (500 mg, 1.54 mmol, 1 eq) and 2-chloroacetaldehyde (520 mg, 2.65 mmol, 426.23 uL, 40% purity, 1.72 eq) in DCE (20 mL) and MeOH (20 mL) was added CH₃COOH (0.1 mL) and NaBH₃CN (290.63 mg, 4.62 mmol, 3 eq) in one portion at 20° C. under N₂. The mixture was stirred at 20° C. for 2 hours. LCMS showed there was desired MS. The residue was poured into water (10 mL). The aqueous phase was extracted with ethyl acetate (10 mL*3). The combined organic phase was washed with brine (10 mL*2), dried with anhydrous Na₂SO₄, filtered and concentrated in vacuum. The residue was purified by silica gel chromatography (Dichloromethane:Methanol=10:1, Rf=0.27, 0-50% (15 min) of Ethyl acetate in Petroleum ether, 10% (5 min) of Ethyl acetate in Petroleum ether) to give 3-[2-[4-(2-chloroethyl)piperazin-1-yl]-4-pyridyl]-5-nitro-1H-indazole (350 mg, 904.78 umol, 58.69% yield) as a yellow solid.

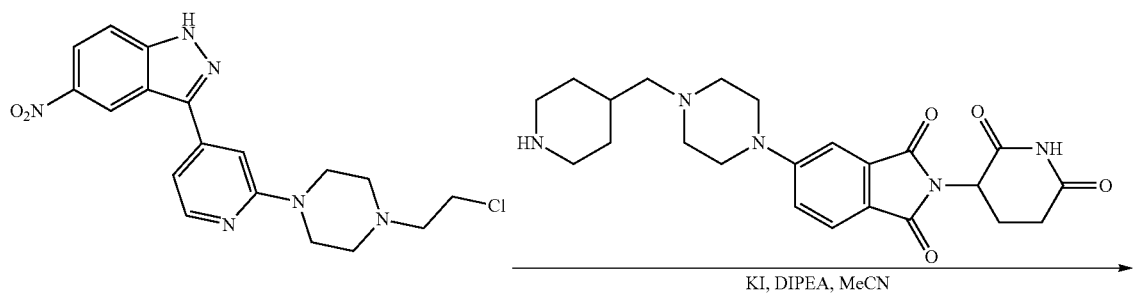

-continued

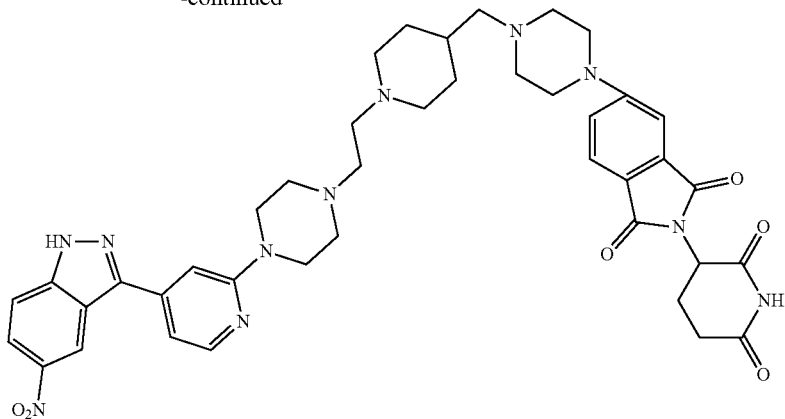

Step 4

To a mixture of 3-[2-[4-(2-chloroethyl)piperazin-1-yl]-4-pyridyl]-5-nitro-1H-indazole (350 mg, 904.78 umol, 1 eq) and 2-(2,6-dioxo-3-piperidyl)-5-[4-(4-piperidylmethyl)piperazin-1-yl]isoindoline-1,3-dione (397.66 mg, 508.79 umol, 5.62e-1 eq, 3TFA) in MeCN (10 mL) was added KI (300.39 mg, 1.81 mmol, 2 eq) and DIPEA (233.87 mg, 1.81 mmol, 315.19 uL, 2 eq) in one portion at 20° C. under $N_2$. The mixture was stirred at 80° C. for 16 hours. LCMS showed there was no starting material. The residue was added $H_2O$ (10 mL) and the solid formed was filtered under vacuum to give 2-(2,6-dioxo-3-piperidyl)-5-[4-[[1-[2-[4-[4-(5-nitro-1H-indazol-3-yl)-2-pyridyl]piperazin-1-yl]ethyl]-4-piperidyl]methyl]piperazin-1-yl]isoindoline-1,3-dione (600 mg, crude) as a yellow solid.

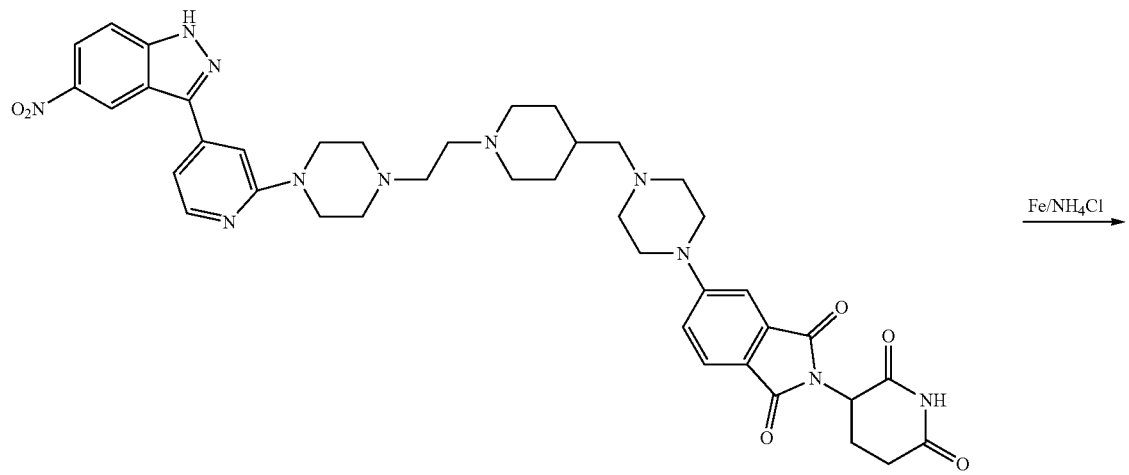

-continued

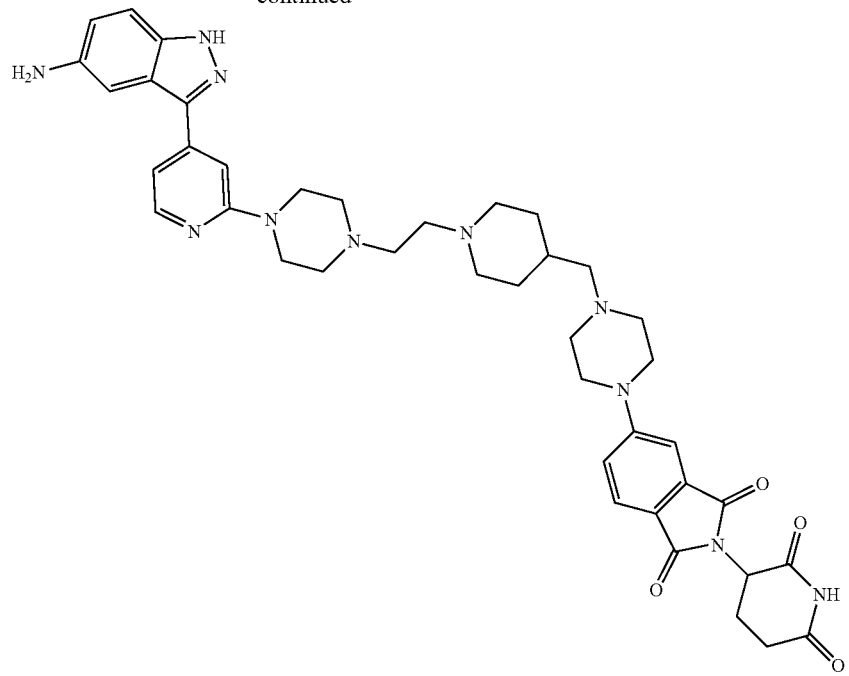

Step 5

To a mixture of 2-(2,6-dioxo-3-piperidyl)-5-[4-[[1-[2-[4-[4-(5-nitro-1H-indazol-3-yl)-2-pyridyl]piperazin-1-yl]ethyl]-4-piperidyl]methyl]piperazin-1-yl]isoindoline-1,3-dione (600 mg, 759.61 umol, 1 eq) and $NH_4Cl$ (203.16 mg, 3.80 mmol, 5 eq) in EtOH (10 mL), $H_2O$ (2 mL) and DCM (2 mL) was added Fe (212.10 mg, 3.80 mmol, 5 eq) in one portion at 20° C. under $N_2$. The mixture was stirred at 80° C. for 1 hour. LCMS showed the reaction was completed. The residue was filtered with ethyl acetate (10 mL*5) and solution was concentrated in vacuum. The crude product was purified by reversed-phase HPLC (Column: 3_Phenomenex Luna C18 75*30 mm*3 um; Condition: water (0.05% HCl)-ACN; Begin B: 10.End B: 80; FlowRate: 25 mL/min; Gradient Time: 35 min; 100% B Hold Time: 1 minute) to give 5-[4-[[1-[2-[4-[4-(5-amino-1H-indazol-3-yl)-2-pyridyl]piperazin-1-yl]ethyl]-4-piperidyl]methyl]piperazin-1-yl]-2-(2,6-dioxo-3-piperidyl)isoindoline-1,3-dione (180 mg, 232.14 umol, 30.56% yield, 98% purity) as a yellow solid.

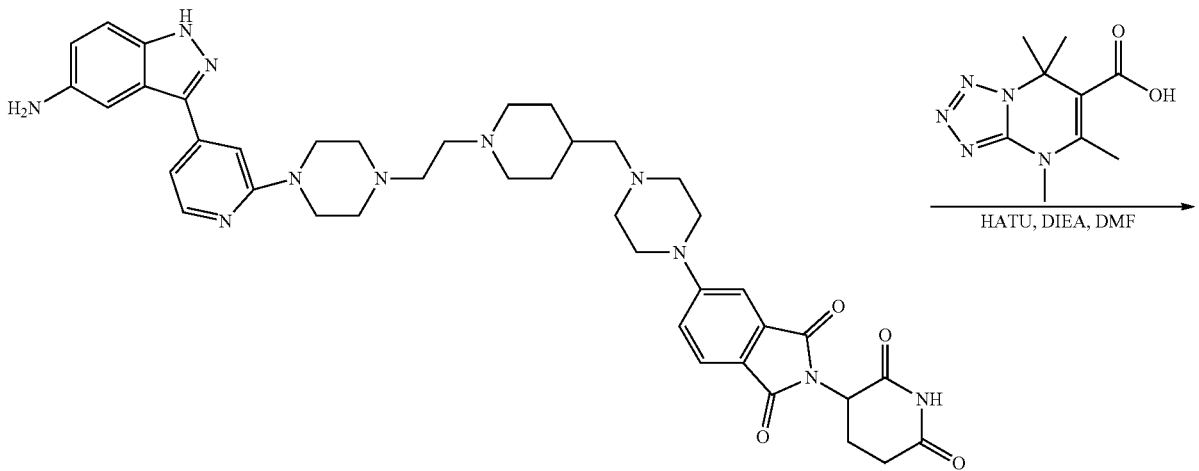

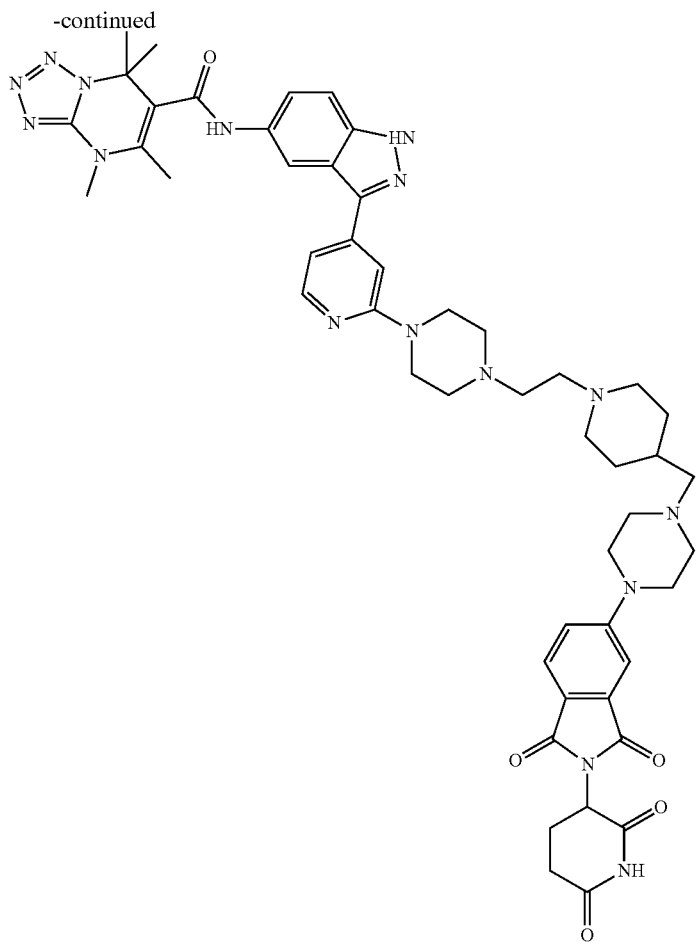

Step 6

To a mixture of 5-[4-[[1-[2-[4-[4-(5-amino-1H-indazol-3-yl)-2-pyridyl]piperazin-1-yl]ethyl]-4-piperidyl]methyl]piperazin-1-yl]-2-(2,6-dioxo-3-piperidyl)isoindoline-1,3-dione (90 mg, 118.44 umol, 1 eq) and 4,5,7,7-tetramethyltetrazolo[1,5-a]pyrimidine-6-carboxylic acid (43.11 mg, 177.66 umol, 92% purity, 1.5 eq) in DMF (5 mL) was added DIEA (45.92 mg, 355.31 umol, 61.89 uL, 3 eq) in one portion and HATU (45.03 mg, 118.44 umol, 1 eq) at 25° C. under $N_2$. The mixture was stirred at 25° C. for 16 hours to give yellow solution. LCMS showed desired product. The residue was concentrated under reduced pressure to give a residue. The residue was purified by prep-HPLC (column: 3_Phenomenex Luna C18 75*30 mm*3 um; mobile phase: [water (0.1M FANH4)-ACN]; B %: 0%-30%, 40 min) to afford N-[3-[2-[4-[2-[4-[[4-[2-(2,6-dioxo-3-piperidyl)-1,3-dioxo-isoindolin-5-yl]piperazin-1-yl]methyl]-1-piperidyl]ethyl]piperazin-1-yl]-4-pyridyl]-1H-indazol-5-yl]-4,5,7,7-tetramethyl-tetrazolo[1,5-a]pyrimidine-6-carboxamide (18.9 mg, 19.17 umol, 16.18% yield, 97.88% purity) as a yellow solid.

Exemplary Synthesis of Exemplary Compound 28: (7S)—N-(3-{2-[(3S)-4-{2-[4-({1-[2-(2,6-dioxopiperidin-3-yl)-1,3-dioxo-2,3-dihydro-1H-isoindol-5-yl]piperidin-4-yl}methyl)piperazin-1-yl]ethyl}-3-methylpiperazin-1-yl]pyridin-4-yl}-1H-indazol-5-yl)-4,5,7-trimethyl-4H,7H-[1,2,3,4]tetrazolo[1,5-a]pyrimidine-6-carboxamide Exemplary Compound 28 was prepared in a manner analogous to Exemplary Compound 27.

Exemplary Synthesis of Exemplary Compound 29: N-{3-[2-(4-{[1-({1-[2-(2,6-dioxopiperidin-3-yl)-1,3-dioxo-2,3-dihydro-1H-isoindol-5-yl]piperidin-4-yl}methyl)piperidin-4-yl]methyl}piperazin-1-yl)pyridin-4-yl]-1H-indazol-5-yl}-4,5,7,7-tetramethyl-4H,7H-[1,2,3,4]tetrazolo[1,5-a]pyrimidine-6-carboxamide

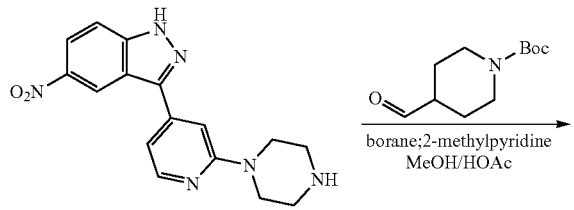

343
-continued

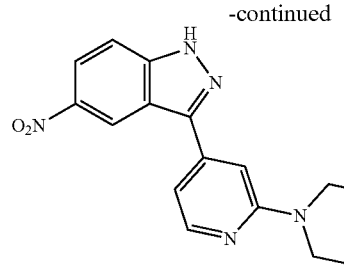

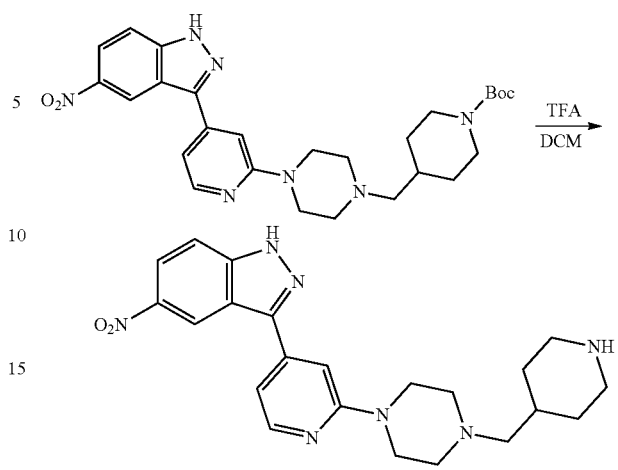

Step 1

To a solution of 5-nitro-3-(2-piperazin-1-yl-4-pyridyl)-1H-indazole (500 mg, 1.54 mmol, 1 eq) and tert-butyl 4-formylpiperidine-1-carboxylate (450 mg, 2.11 mmol, 1.37 eq) in HOAc (1 mL) and MeOH (10 mL) was added borane; 2-methylpyridine (329.78 mg, 3.08 mmol, 2 eq). After addition, the reaction solution was stirred at 20° C. for 2 hours. LCMS showed desired MS. The reaction was diluted with brine (100 mL). The solid was collected by filtration and dried under reduced pressure to afford tert-butyl 4-[[4-[4-(5-nitro-1H-indazol-3-yl)-2-pyridyl]piperazin-1-yl]methyl]piperidine-1-carboxylate (730 mg, 1.20 mmol, 78.07% yield, 86% purity) as a yellow solid.

Step 2

To a solution of tert-butyl 4-[[4-[4-(5-nitro-1H-indazol-3-yl)-2-pyridyl]piperazin-1-yl]methyl]piperidine-1-carboxylate (730 mg, 1.40 mmol, 1 eq) in DCM (10 mL) was added TFA (7.70 g, 67.53 mmol, 5 mL, 48.25 eq). After addition, the reaction solution was stirred at 20° C. for 3 hours. LCMS showed starting material consumed and desired MS was detected. The reaction was concentrated under reduced pressure to afford 5-nitro-3-[2-[4-(4-piperidylmethyl)piperazin-1-yl]-4-pyridyl]-1H-indazole (589 mg, crude) as a yellow gum. The crude product was used for next step directly.

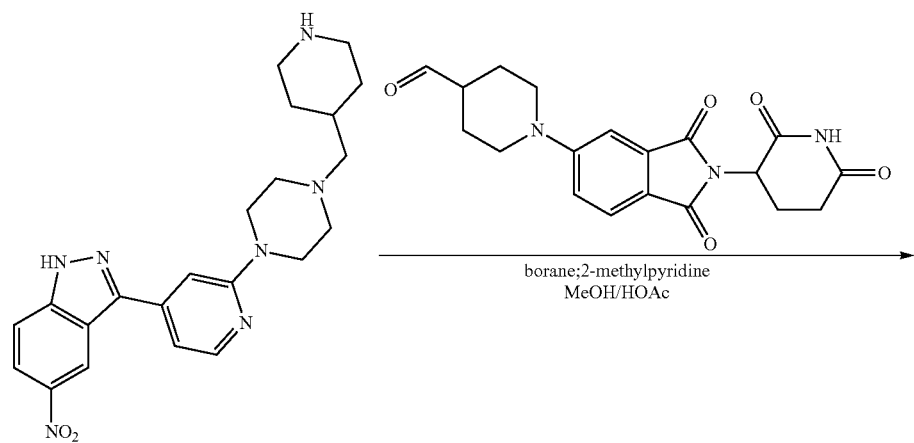

-continued

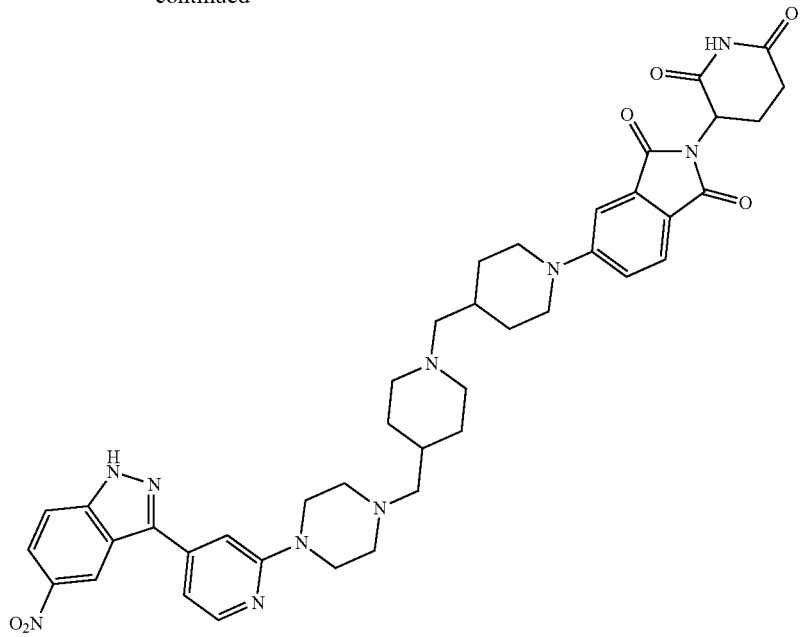

Step 3

To a solution of 5-nitro-3-[2-[4-(4-piperidylmethyl)piperazin-1-yl]-4-pyridyl]-1H-indazole (589 mg, 1.40 mmol, 1 eq) and 1-[2-(2,6-dioxo-3-piperidyl)-1,3-dioxo-isoindolin-5-yl]piperidine-4-carbaldehyde (619.39 mg, 1.68 mmol, 1.2 eq) in HOAc (5 mL) and MeOH (50 mL) was added borane; 2-methylpyridine (298.94 mg, 2.79 mmol, 2 eq). After addition, the reaction mixture was stirred at 20° C. for 12 hours. LCMS showed starting material consumed and desired MS detected. The reaction mixture was dilute with water (50 mL) and extracted with 10% methanol in dichloromethane (3×50 mL). The organic layer was dried over sodium sulfate and concentrated under reduced pressure. The residue was purified by silica gel column chromatography (0 to 40% methanol in dichloromethane) to afford 2-(2,6-dioxo-3-piperidyl)-5-[4-[[4-[[4-[4-(5-nitro-1H-indazol-3-yl)-2-pyridyl]piperazin-1-yl]methyl]-1-piperidyl]methyl]-1-piperidyl]isoindoline-1,3-dione (1 g, 1.25 mmol, 89.35% yield, 96.75% purity) as a yellow solid.

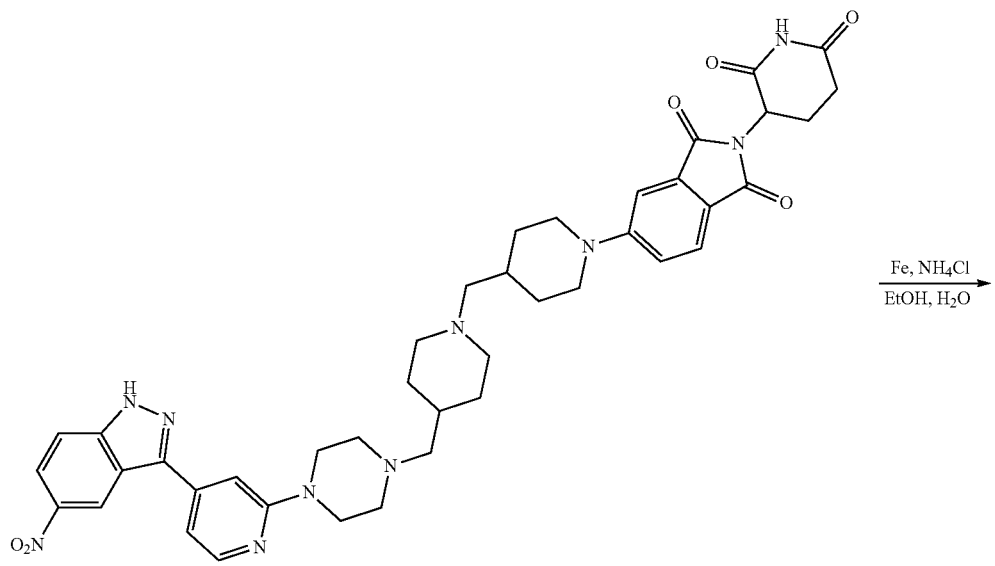

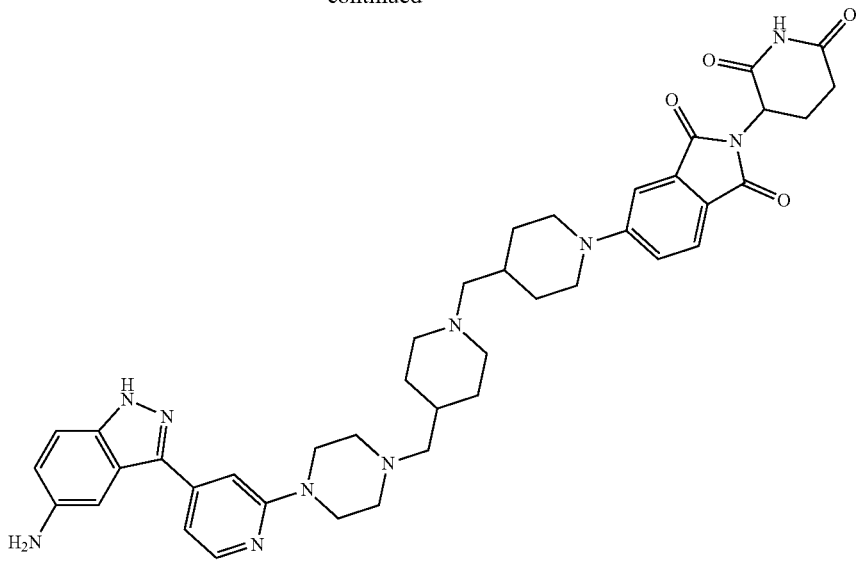

Step 4

To a solution of 2-(2,6-dioxo-3-piperidyl)-5-[4-[[4-[[4-[4-(5-nitro-1H-indazol-3-yl)-2-pyridyl]piperazin-1-yl]methyl]-1-piperidyl]methyl]-1-piperidyl]isoindoline-1,3-dione (500 mg, 645.27 umol, 1 eq) in EtOH (5 mL) and H₂O (2 mL) was added Le (180.18 mg, 3.23 mmol, 5 eq) and NH4Cl (172.58 mg, 3.23 mmol, 5 eq). After addition, the reaction mixture was stirred at 80° C. for 1 hour. LCMS showed desired MS. After cooling, the reaction mixture was filtered and filtrate was concentrated under reduced pressure. The residue was triturated with 10% methanol in dichloromethane (20 mL) and filtered. The filtrate was concentrated under reduced pressure to afford 5-[4-[[4-[[4-[4-(5-amino-1H-indazol-3-yl)-2-pyridyl]piperazin-1-yl]methyl]-1-piperidyl]methyl]-1-piperidyl]-2-(2,6-dioxo-3-piperidyl)isoindoline-1,3-dione (110 mg, 143.24 umol, 22.20% yield, 97% purity) as a yellow solid.

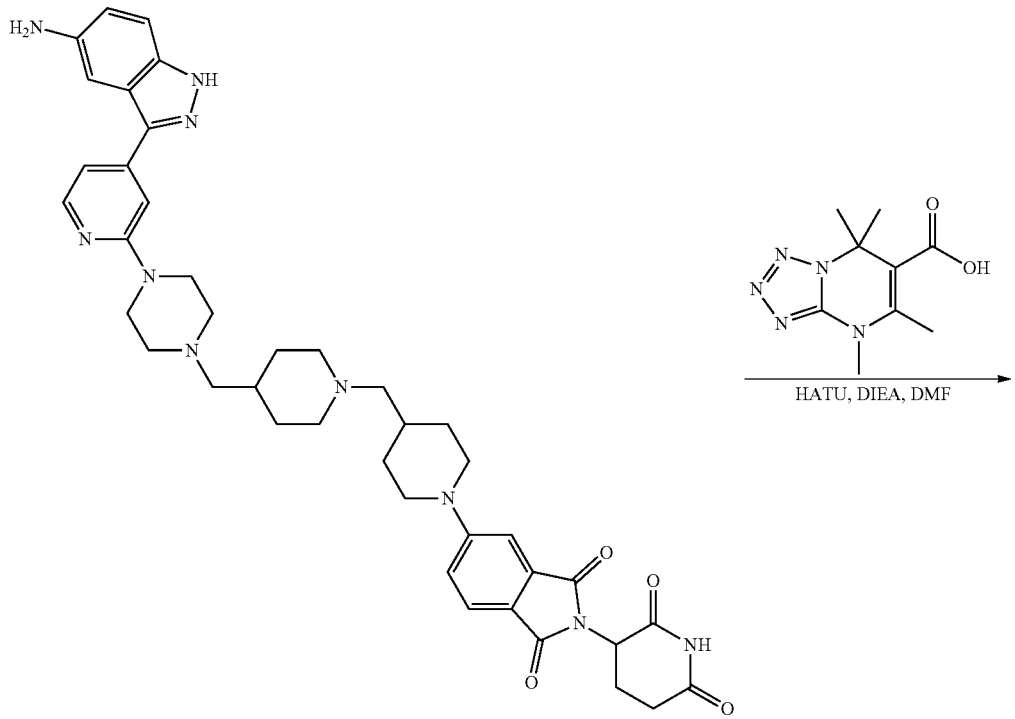

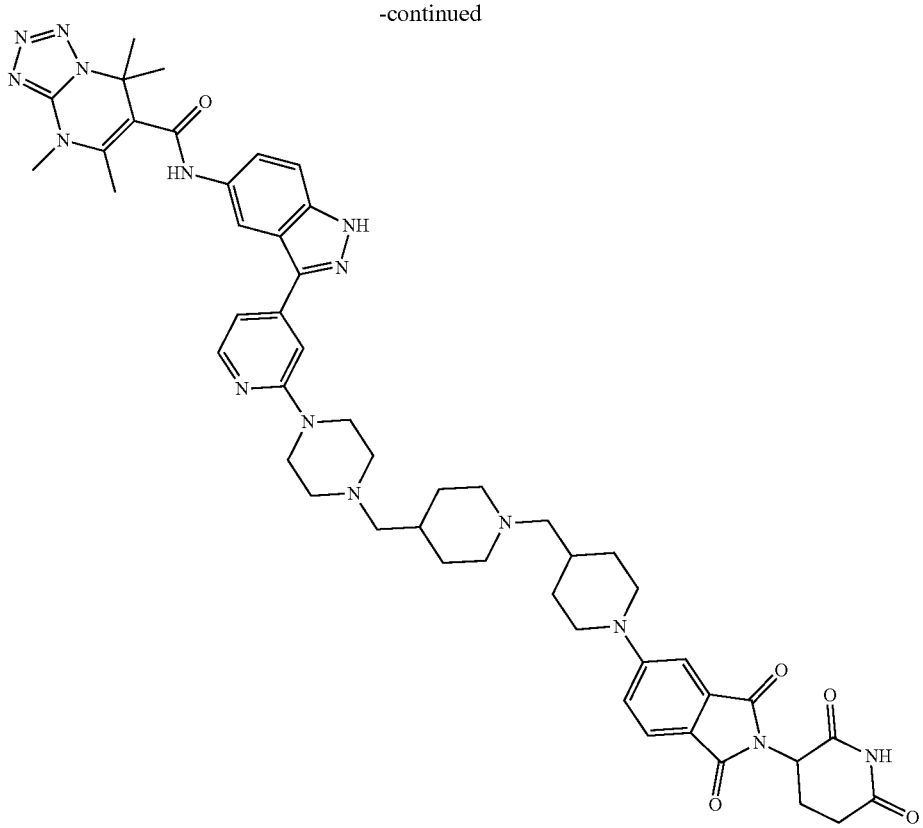

Step 5

To a mixture of 5-[4-[[4-[[4-[4-(5-amino-1H-indazol-3-yl)-2-pyridyl]piperazin-1-yl]methyl]-1-piperidyl]methyl]-1-piperidyl]-2-(2,6-dioxo-3-piperidyl)isoindoline-1,3-dione (100 mg, 134.25 umol, 1 eq) and 4,5,7,7-tetramethyltetrazolo[1,5-a]pyrimidine-6-carboxylic acid (56.19 mg, 201.37 umol, 80% purity, 1.5 eq) in DMF (5 mL) was added DIEA (52.05 mg, 402.75 umol, 70.15 uL, 3 eq) in one portion and HATU (51.05 mg, 134.25 umol, 1 eq) at 25° C. under N$_2$. The mixture was stirred at 25° C. for 16 hours to give yellow solution. LCMS showed desired product. The residue was concentrated under reduced pressure to give a residue. The residue was purified by prep-HPLC (column: 3_Phenomenex Luna C18 75*30 mm*3 um; mobile phase: [water (0.1M FANH4)-ACN]; B %: 0%-30%, 40 min) to afford N-[3-[2-[4-[[1-[[1-[2-(2,6-dioxo-3-piperidyl)-1,3-dioxo-isoindolin-5-yl]-4-piperidyl]methyl]-4-piperidyl]methyl]piperazin-1-yl]-4-pyridyl]-1H-indazol-5-yl]-4,5,7,7-tetramethyl-tetrazolo[1,5-a]pyrimidine-6-carboxamide (12 mg, 12.25 umol, 9.13% yield, 97% purity) as a yellow solid.

Exemplary Synthesis of Exemplary Compound 30: N-(3-{2-[(3S)-4-{2-[4-({1-[2-(2,6-dioxopiperidin-3-yl)-1,3-dioxo-2,3-dihydro-1H-isoindol-5-yl]piperidin-4-yl}methyl)piperazin-1-yl]ethyl}-3-methylpiperazin-1-yl]pyridin-4-yl}-1H-indazol-5-yl)-4,5,7,7-tetramethyl-4H,7H-[1,2,3,4]tetrazolo[1,5-a]pyrimidine-6-carboxamide Exemplary Compound 30 was prepared in a manner analogous to Exemplary Compound 29.

Exemplary Synthesis of Exemplary Compound 31: (7S)—N-(3-{2-[(3S)-4-{2-[4-({4-[2-(2,6-dioxopiperidin-3-yl)-1,3-dioxo-2,3-dihydro-1H-isoindol-5-yl]piperazin-1-yl}methyl)piperidin-1-yl]ethyl}-3-methylpiperazin-1-yl]pyridin-4-yl}-1H-indazol-5-yl)-4,5,7,7-trimethyl-4H,7H-[1,2,3,4]tetrazolo[1,5-a]pyrimidine-6-carboxamide Exemplary Compound 30 was prepared in a manner analogous to Exemplary Compound 29.

Exemplary Synthesis of Exemplary Compound 32: N-(3-{2-[(2S)-2-{[4-({1-[2-(2,6-dioxopiperidin-3-yl)-1,3-dioxo-2,3-dihydro-1H-isoindol-5-yl]piperidin-4-yl}methyl)piperazin-1-yl]methyl}morpholin-4-yl]pyridin-4-yl}-1H-indazol-5-yl)-4,5,7,7-tetramethyl-4H,7H-[1,2,3,4]tetrazolo[1,5-a]pyrimidine-6-carboxamide Exemplary Compound 30 was prepared in a manner analogous to Exemplary Compound 29.

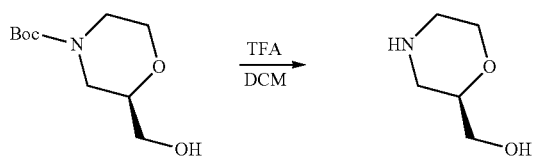 [SMILES: CC(C)(C)OC(=O)N1CCO[C@@H](CO)C1 ; OC[C@H]1CNCCO1]

Step 1

To a mixture of tert-butyl (2R)-2-(hydroxymethyl)morpholine-4-carboxylate (2 g, 9.21 mmol, 1 eq) in DCM (20 mL) was added TFA (4.62 g, 40.52 mmol, 3 mL, 4.40 eq) in one portion at 20° C. under N₂. The mixture was stirred at 20° C. for 30 minutes. TLC showed the reaction was completed. The solution was concentrated in vacuum to give [(2R)-morpholin-2-yl]methanol (2 g, 8.65 mmol, 93.98% yield, TFA) as a colourless oil.

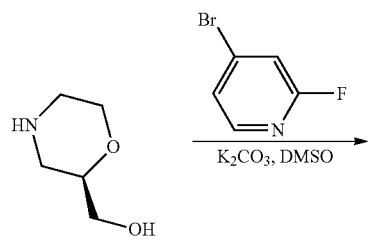

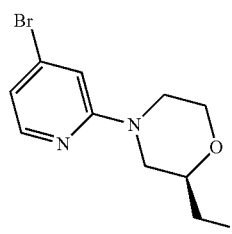

Step 2

To a mixture of 4-bromo-2-fluoro-pyridine (1.52 g, 8.65 mmol, 1 eq) and [(2R)-morpholin-2-yl]methanol (2 g, 8.65 mmol, 1 eq, TFA) in DMSO (10 mL) was added K₂CO₃ (11.96 g, 86.52 mmol, 70.14 mL, 10 eq) in one portion at 100° C. under N₂. The mixture was stirred at 100° C. for 2 hours to give yellow solution. TLC (Petroleum ether: Ethyl acetate=1:1, Rf=0.56) showed the reaction was completed. The mixture was cooled to 20° C. and concentrated in reduced pressure at 20° C. The residue was poured into water (50 mL). The aqueous phase was extracted with ethyl acetate (50 mL*4). The combined organic phase was washed with brine (50 mL*2), dried with anhydrous Na₂SO₄, filtered and concentrated in vacuum. The residue was purified by silica gel chromatography (Petroleum ether: Ethyl acetate=1:1, Rf=0.56, 20 g, 0-50% (10 min) of Ethyl acetate in Petroleum ether, 50% (10 min) of Ethyl acetate in Petroleum ether) to give [(2R)-4-(4-bromo-2-pyridyl)morpholin-2-yl]methanol (1.5 g, 5.49 mmol, 63.48% yield) as a yellow oil.

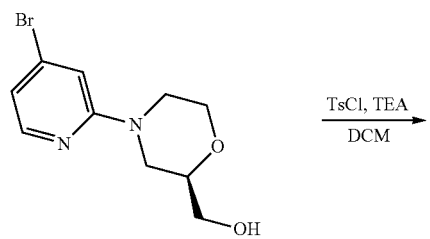

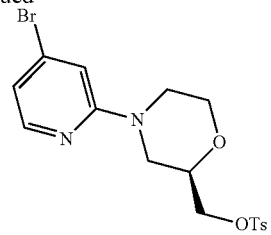

Step 3

To a mixture of [(2R)-4-(4-bromo-2-pyridyl)morpholin-2-yl]methanol (1.5 g, 5.49 mmol, 1 eq) in DCM (15 mL) was added TEA (1.11 g, 10.98 mmol, 1.53 mL, 2 eq) and 4-methylbenzenesulfonyl chloride (1.57 g, 8.24 mmol, 1.5 eq) in one portion at 0° C. under N₂. The mixture was stirred at 20° C. for 16 hours. LCMS showed the reaction was completed. The residue was poured into water (10 mL). The aqueous phase was extracted with DCM (20 mL*2). The combined organic phase was washed with brine (20 mL*2), dried with anhydrous Na₂SO₄, filtered and concentrated in vacuum. The residue was purified by silica gel chromatography (12 g, 0-100% (20 min) of Ethyl acetate in Petroleum ether) to give [(2R)-4-(4-bromo-2-pyridyl)morpholin-2-yl] methyl 4-methylbenzenesulfonate (2.1 g, 4.91 mmol, 89.52% yield) as a colourless oil

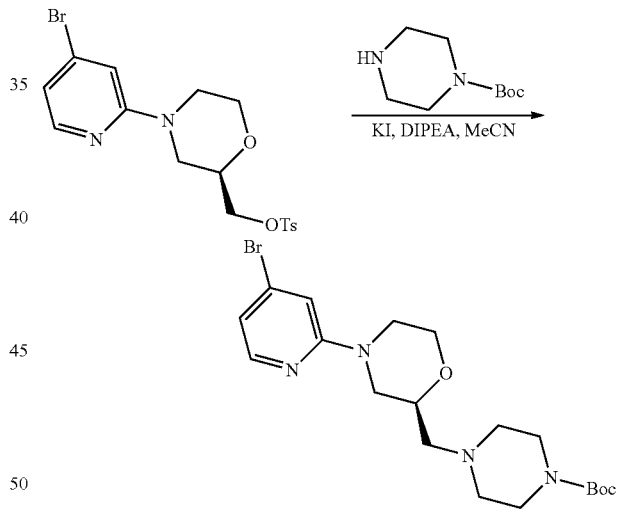

Step 4

To a mixture of [(2R)-4-(4-bromo-2-pyridyl)morpholin-2-yl]methyl 4-methylbenzenesulfonate (2.1 g, 4.91 mmol, 1 eq) and tert-butyl piperazine-1-carboxylate (1.83 g, 9.83 mmol, 2 eq) in MeCN (20 mL) was added KI (1.63 g, 9.83 mmol, 2 eq) and DIPEA (1.27 g, 9.83 mmol, 1.71 mL, 2 eq) in one portion at 20° C. under N₂. The mixture was stirred at 100° C. for 2 hours. TLC showed the reaction was completed. The mixture was cooled to 20° C. and concentrated in reduced pressure at 20° C. The residue was poured into water (20 mL). The aqueous phase was extracted with ethyl acetate (20 mL*3). The combined organic phase was washed with brine (20 mL*2), dried with anhydrous Na₂SO₄, filtered and concentrated in vacuum. The residue was purified by silica gel chromatography (12 g, 0-20% (5 min) of Ethyl acetate in Petroleum ether, 20% (15 minutes) of Ethyl acetate in Petroleum ether) to give tert-butyl 4-[[(2S)-4-(4-bromo-2-pyridyl)morpholin-2-yl]methyl]piperazine-1-carboxylate (1.1 g, 2.22 mmol, 45.14% yield, 89% purity) as a yellow gum.

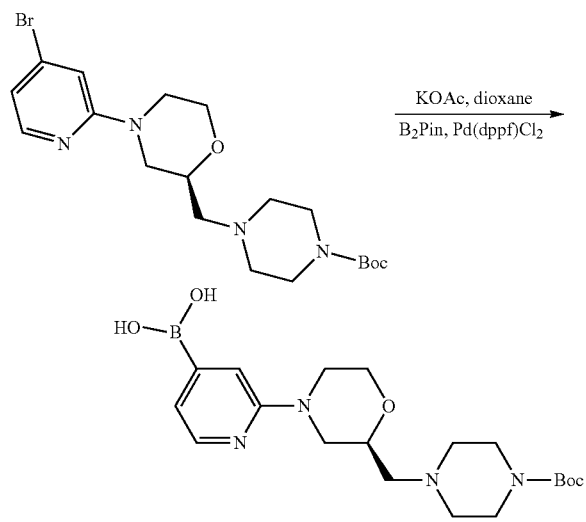

Step 5

To a mixture of tert-butyl 4-[[(2S)-4-(4-bromo-2-pyridyl)morpholin-2-yl]methyl]piperazine-1-carboxylate (1.1 g, 2.22 mmol, 89% purity, 1 eq), Pin₂B₂ (1.13 g, 4.44 mmol, 2 eq) and KOAc (653.06 mg, 6.65 mmol, 3 eq) in dioxane (300 mL) was added Pd(dppf)Cl₂ (81.15 mg, 110.91 umol, 0.05 eq) in one portion at 25° C. under N₂. The mixture was stirred at 100° C. for 1 hour. TLC showed the reaction was completed. The mixture was cooled to 25° C., filtered and concentrated in vacuum to give [2-[(2S)-2-[(4-tert-butoxycarbonylpiperazin-1-yl)methyl]morpholin-4-yl]-4-pyridyl] boronic acid (1 g, 1.75 mmol, 78.78% yield, 71% purity) as a black brown solid.

Exemplary Synthesis of Exemplary Compound 33:
N-{3-[2-(4-{2-[4-({4-[2-(2,6-dioxopiperidin-3-yl)-1,3-dioxo-2,3-dihydro-1H-isoindol-5-yl]piperazin-1-yl}methyl)piperidin-1-yl]ethyl}piperazin-1-yl)pyridin-4-yl]-1H-indazol-5-yl}-4,5,7,7-tetramethyl-4H,7H-[1,2,3,4]tetrazolo[1,5-a]pyrimidine-6-carboxamide Exemplary Compound 33 was prepared in a manner analogous to Exemplary Compound 27.

Exemplary Synthesis of Exemplary Compound 34:
N-(3-{2-[(3S)-4-{[1-({1-[2-(2,6-dioxopiperidin-3-yl)-1,3-dioxo-2,3-dihydro-1H-isoindol-5-yl]piperidin-4-yl}methyl)piperidin-4-yl]methyl}-3-methylpiperazin-1-yl]pyridin-4-yl}-1H-indazol-5-yl)-4,5,7,7-tetramethyl-4H,7H-[1,2,3,4]tetrazolo[1,5-a]pyrimidine-6-carboxamide Exemplary Compound 34 was prepared in a manner analogous to Exemplary Compound 1.

Exemplary Synthesis of Exemplary Compound 35:
N-{3-[2-(4-{2-[4-({1-[2-(2,6-dioxopiperidin-3-yl)-1,3-dioxo-2,3-dihydro-1H-isoindol-5-yl]piperidin-4-yl}methyl)piperazin-1-yl]ethyl}piperazin-1-yl)pyridin-4-yl]-1H-indazol-5-yl}-4,5,7,7-tetramethyl-4H,7H-[1,2,3,4]tetrazolo[1,5-a]pyrimidine-6-carboxamide Exemplary Compound 35 was prepared in a manner analogous to Exemplary Compound 27.

Exemplary Synthesis of Exemplary Compound 36:
N-(3-{2-[(3S)-4-{2-[4-({4-[2-(2,6-dioxopiperidin-3-yl)-1,3-dioxo-2,3-dihydro-1H-isoindol-5-yl]piperazin-1-yl}methyl)piperidin-1-yl]ethyl}-3-methylpiperazin-1-yl]pyridin-4-yl}-1H-indazol-5-yl)-4,5,7,7-tetramethyl-4H,7H-[1,2,3,4]tetrazolo[1,5-a]pyrimidine-6-carboxamide Exemplary Compound 35 was prepared in a manner analogous to Exemplary Compound 25.

Protein Level Control

This description also provides methods for the control of protein levels within a cell. The method is based on the use of compounds as described herein such that degradation of the target protein LRRK2 in vivo will result in the reducing the amount of the target protein in a biological system, preferably to provide a particular therapeutic benefit.

The following examples are used to assist in describing the present disclosure, but should not be seen as limiting the present disclosure in any way.

In certain embodiments, the description provides the following exemplary LRRK2-degrading bifunctional molecules (compounds of Table 1 or Compounds 1-36), including salts, polymorphs, analogs, derivatives, and deuterated forms thereof.

Assay for Testing LRRK2 Degradation Driven by Compounds as Described Herein,

The assay measures the degradation of wildtype and G2019S LRRK2 tagged with a HiBit tag on the C-terminus of the protein that was expressed from a mammalian expression vector, driven by the ubiquitin promoter in HEK293 cells. Each compound dose-response was repeated on three separate days, on three separate plates each day.

Plasmid Preparation. Transfection mixes were assembled as follows and incubated for 30 minutes at room temperature. In a 15 mL tube, 5.25 mL Opti-MEM (no additions) was mixed with 17 μL Firefly Luciferase plasmid at 1 μg/μL and 158 μL WT plasmid DNA at 1 μg/μL (175 μg total DNA) were mixed by flicking. In a new 15 mL tube, 5.25 mL OptiMEM was mixed with 17 μL Firefly Luciferase plasmid at 1 μg/μL and 158 μL G2019S plasmid DNA at 1 μg/μL (175 μg total DNA) were mixed by flicking. X-tremeGene HP was mixed thoroughly using a vortex. Next, 175 μL was added to each tube and flicked to mix. Both tubes were left to incubate for 30 minutes at room temperature.

While the transfection mixes were incubating, HEK293 cells acquired from ATCC (ATCC CRL-1573) were harvested with trypsin. Once cells are detached, the cells were resuspended in 12 mL OptiMEM+5% FBS and transferred to a 50 mL tube. The cells were mixed well and counted. Using OptiMEM+5% FBS, the cells were diluted in two 250 mL conical tubes at 0.71×10⁶ cells/mL in 70 mL. One tube was labeled "WT" and the other "G2019S". The WT and G2019S transfection mixes were added dropwise to the corresponding 250 mL tubes. The tubes were mixed first by pipetting then by swirling. The tubes were incubated at room temperature for at least 5 minutes.

Each tube was swirled before dispensing and after every three plates. Seventy microliters of cells were dispensed with WT or G2019S DNA to seven plates each. Three plates of each were tested with compound plate one (preparation described below) and three plates of each were tested with compound plate two (preparation described below). The first plate from each set served as a "prime" plate and was not used to test compounds. Each plate was incubated in the hood for 10 minutes before placing in the 37° C. incubator for 24 hours.

Preparation of Compound and Assay Plates. Two compound plates were made using 96 well polypropylene plates. Compounds were made up at 10 mM and were diluted to 1 mM in 30 µL. Each dose response curve included a well of DMSO, as a negative control and for normalization, and a well of 0.5 µM of Exemplary Compound 4 as a positive control. In addition to seven test compounds, each plate also included a dose response of Exemplary Compound 4. The compound plates were spun down along at 1200 rpm for 2 minutes.

The two compound plates were then mixed and 2 µL was diluted in intermediate plates having 248 µL of Opti-Mem in each well. Next, 10 µL diluted compounds from the intermediate plates were added to each test plate (three WT and three G2019S plates per compound plate for a total of 12 assay plates). The plates were incubated for 24 hours at 37° C.

All assay plates and all Nano-Glo Dual-Luciferase Reporter Assay System components (except for the DLR substrate) were equilibrated to room temperature. Next, the luciferase buffer was mixed with the lyophilized amber bottle until fully dissolved, and 75 µL of the luciferase mixture was added to each well of each assay plate. The assay plates were incubated for 10 minutes at room temperature with shaking for at least 5 minutes, and then read on a plate reader.

Developing Plates and Analyzing Data. One milliliter of DLR substrate and 1 mL LgBiT Protein were added to the Stop and Glo buffer, and 75 µL of the mixture was added to each well of each plate. Optically clear seals were added to each plate and each plate was incubated for 20 minutes with shaking for at least 10 minutes, and then read on a plate reader.

As mentioned above, plates were fun in triplicate and assay repeated twice (total of 6 replicates per exemplary compound. Each cell was examined for firefly luciferase for cell number and viability and Nanoluc for the LRRK2-HiBit quantification.

Ratio of (HiBit/luciferase)*1000 was determined and the data was_normalized to % of DMSO median value. Curve fitting was performed on each individual plate. The data for some of exemplary compounds of Table 1 below is shown below in Table 2 in the columns labeled *G2019S DC50 (nM) and **G2019S Dmax (%).

Exemplary Assay for Testing LRRK2 Degradation Driven by Exemplary Hetero-Bifunctional Compounds Designed to Target LRRK2

The assay measures the degradation of wildtype and G2019S LRRK2 tagged with a HiBit tag on the C-terminus of the protein that was expressed from a mammalian expression vector, driven by the ubiquitin promoter in HEK293 cells. Each compound dose-response was repeated on two separate days, on three separate plates each day.

Plasmid Preparation. Transfection mixes were assembled as follows and incubated for 30 minutes at room temperature. In a 15 mL tube, 5.25 mL Opti-MEM (no additions) was mixed with 17 µL Firefly Luciferase plasmid at 1 µg/µL and 158 µL WT plasmid DNA at 1 µg/µL (175 µg total DNA) were mixed by flicking. In a new 15 mL tube, 5.25 mL OptiMEM was mixed with 17 µL Firefly Luciferase plasmid at 1 µg/µL and 158 µL G2019S plasmid DNA at 1 µg/µL (175 µg total DNA) were mixed by flicking. X-tremeGene HP was mixed thoroughly using a vortex. Next, 175 µL was added to each tube and flicked to mix. Both tubes were left to incubate for 30 minutes at room temperature.

While the transfection mixes were incubating, HEK293 cells (acquired from ATCC; ATCC CRL-1573) were harvested with trypsin. Once cells are detached, the cells were resuspended in 12 mL OptiMEM+5% FBS and transferred to a 50 mL tube. The cells were mixed well and counted. Using OptiMEM+5% FBS, the cells were diluted in two 250 mL conical tubes at $0.71 \times 10^6$ cells/mL in 70 mL. One tube was labeled "WT" and the other "G2019S". The WT and G2019S transfection mixes were added dropwise to the corresponding 250 mL tubes. The tubes were mixed first by pipetting then by swirling. The tubes were incubated at room temperature for at least 5 minutes.

Each tube was swirled before dispensing and after every three plates. Seventy microliters of cells were dispensed with WT or G2019S DNA to seven plates each. Three plates of each were tested with compound plate one (preparation described below) and three plates of each were tested with compound plate two (preparation described below). The first plate from each set served as a "prime" plate and was not used to test compounds. Each plate was incubated in the hood for 10 minutes before placing in the 37° C. incubator for 24 hours.

Preparation of Compound and Assay Plates. Two compound plates were made using 96 well polypropylene plates. Compounds were made up at 10 mM and were diluted to 1 mM in 30 µL. Each dose response curve included a well of DMSO, as a negative control and for normalization, and a well of 0.5 µM of Exemplary Compound 4 as a positive control. In addition to seven test compounds, each plate also included a dose response of Exemplary Compound 4. The compound plates were spun down along at 1200 rpm for 2 minutes.

The two compound plates were then mixed and 2 µL was diluted in intermediate plates having 248 µL of Opti-Mem in each well. Next, 10 µL diluted compounds from the intermediate plates were added to each test plate (three WT and three G2019S plates per compound plate for a total of 12 assay plates). The plates were incubated for 24 hours at 37° C.

All assay plates and all Nano-Glo Dual-Luciferase Reporter Assay System components (except for the DLR substrate) were equilibrated to room temperature. Next, the luciferase buffer was mixed with the lyophilized amber bottle until fully dissolved, and 75 µL of the luciferase mixture was added to each well of each assay plate. The assay plates were incubated for 10 minutes at room temperature with shaking for at least 5 minutes, and then read on a plate reader.

Developing Plates and Analyzing Data. One milliliter of DLR substrate and 1 mL LgBiT Protein were added to the Stop and Glo buffer, and 75 µL of the mixture was added to each well of each plate. Optically clear seals were added to each plate and each plate was incubated for 20 minutes with shaking for at least 10 minutes, and then read on a plate reader.

As mentioned above, plates were run in triplicate and assay repeated twice (total of 6 replicates per exemplary compound. Each cell was examined for firefly luciferase for cell number and viability and Nanoluc for the LRRK2-HiBit quantification.

Ratio of (HiBit/luciferase)*1000 was determined and the data was normalized to % of DMSO median value. Curve fitting was performed on each individual plate. The data for exemplary compounds of Table 1 below is shown below in Table 2 in the G2019S DC50, G2019S Dmax, WT DC50 and WT Dmax columns.

Exemplary Assay for Testing LRRK2 Degradation Driven by Exemplary Hetero-Bifunctional Compounds Designed to Target LRRK2

The assay measures the degradation of LRRK2 in cells where the C-terminus (3') of the endogenous gene has been tagged with a HiBit sequence in HEK293 cells. The cells also express firefly luciferase, expressed from a Cytomegalovirus promoter and introduced into the HiBit tagged cells and stably expressed. The Nano-Glo® Dual Luciferase Reporter Assay System (Promega™, Madison, Wis.) was utilized.

Day 1—Preparation of Compound and Assay Plates. Two sets of plates were prepared: a triplicate set for the HiBit assay in white 384-well plates and a triplicate set of plate in black 384-well plates for the Alamar Blue cell viability assay. Briefly, the growth media (DMEM+Glutamax-10% fetal bovine serum-1% Penicillin-Streptomicin) from two T128 flasks was aspirated from the flasks. Cells were washed with Dulbecco's Phosphate Buffered Saline (dPBS) and aspirated. Trypsin (3 mL per flask) was added and the flasks were incubated for 2-3 minutes.

Ten mL of OptiMEM-10% fetal bovine-1% penicillin-streptomycin (hereinafter, "OptiMEM media") was added to the flask and the cells and transferred to a 50 mL conical tube. A cell count (25 ul of cell into Effendorf vial +25 ul of Trypan Blue Stain) was performed and the cell density adjusted to 15,000 cell/45 µl/well (3.33×10^5/mL) in OptiMEM media.

Forty-five microliters of the cell suspension (15,000 cells) was aliquoted to each well of the white 384-well plate. The plates incubated at room temperature for 10 minutes before being placed in the 37° C.+5% $CO_2$ incubator overnight Day 2—Compound Treatment. Exemplary compounds were prepared at a 1 mM starting concentration and 1:3 serial dilution for 11 points CRC prepared and stored in the freezer. The Master Compound Plate was thawed overnight at room temperature. DMSO (20 µL) was added into column 24 of the Master Compound Plate for negative control and 20 µL of 300 µM of Exemplary Compound 4 in column 23 as positive control.

Intermediate Compound Plate with 4% DMSO in OptiMEM Media. DMSO was added to warm OptiMEM media to achieve a 4% DMSO solution (approximately 50 mL/plate). One-hundred microliters of the OptiMEM-4% DMSO was aliquoted to each well of 384-Well Deep Well Microplates.

The Master Compound Plate and the Intermediate Compound Plate were spun down.

One microliter of compound from the Master Compound Plate was transferred into the Intermediate plate (a 1:100 dilution). The diluted mixture was mixed and 5 µL transferred into the assay plate (a 1:10 dilution) for the final starting concentration of 1 µM. The Treated Assay plates were incubated for 24 hours at 37° C.+5% $CO_2$. The Master Compound Plate was sealed and store at room temperature for a second run that was performed within a week.

Day 3—HiBit Assay. Five microliters of Alamar Blue was added to each well of the black 384-well plates. The plates were incubated for 2 hours in the incubator (37° C.+5% $CO_2$) and at room temperature for one hour. Fluorescence of each plate was read on a plated reader for the Alamar Blue viability assay.

One set of white assay plates was warmed to room temperature (45 minute).

The One Glo luciferase mixture was prepared. The media from white 384-well assay plates was aspirated. Twenty-five µL of the One Glo luciferase mixture was added to each well of the assay plates. The plates were incubated on the bench (room temperature) for 45 minutes, including 10 minutes of shaking at 700 rpm. The luminescence of each plate was read on a plate reader.

1:100 DLR substrate and 1:100 LgBiT Protein dilution were added to the Promega Stop and Glo buffer and mixed just before addition to assay plates. Twenty-five microliters of Stop and Glo mixture was added to each well. Assay plates incubated for at least 45 minutes, including 10 minutes of shaking at 700 rpm. The luminescence of each plate was read on a plate reader.

Analysis of LRRK2 HiBit Screening assays. As mentioned above, plates were run in triplicate and the assay repeated twice (total of 6 replicate for exemplary compound). For each treatment, measurements were taken for firefly luciferase for cell number, cell viability (Alamar Blue), and Nanoluc for the LRRK2-HiBit quantification.

The LRRK2 HiBit and alamar blue signal was normalized to % DMSO median value for each plate. Curve fitting was performed on each compound for replicates across three plates. The date for exemplary compounds of Table 1 below is shown below in Table 2 in the columns labeled *WT DC50 (nM) and **WT Dmax (%).

TABLE 1

Exemplary bifunctional compounds of the present disclosure.

| Ex. | Structure | Mass | Name |
|---|---|---|---|
| 1 | 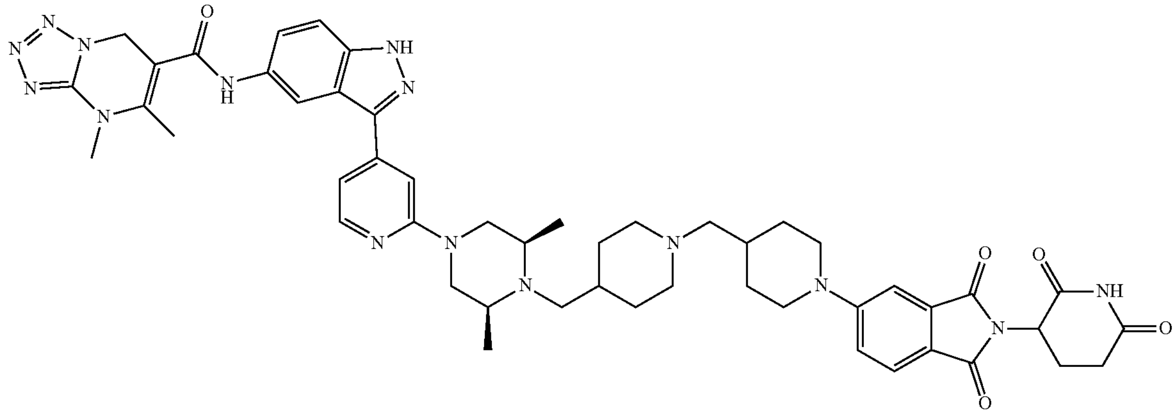 [SMILES: CC1=C(C(=O)Nc2ccc3[nH]nc(-c4ccnc(N5C[C@@H](C)N(CC6CCN(CC7CCN(c8ccc9c(c8)C(=O)N(C8CCC(=O)NC8=O)C9=O)CC7)CC6)[C@@H](C)C5)c4)c3c2)Cn2nnnc2N1C] | 949.48 | N-(3-(2-((3S,5R)-4-((1-(1-(2-(2,6-dioxopiperidin-3-yl)-1,3-dioxoisoindolin-5-yl)piperidin-4-yl)methyl)piperidin-4-yl)methyl)-3,5-dimethylpiperazin-1-yl)pyridin-4-yl)-1H-indazol-5-yl)-4,5-dimethyl-4,7-dihydrotetrazolo[1,5-a]pyrimidine-6-carboxamide |
| 2 | 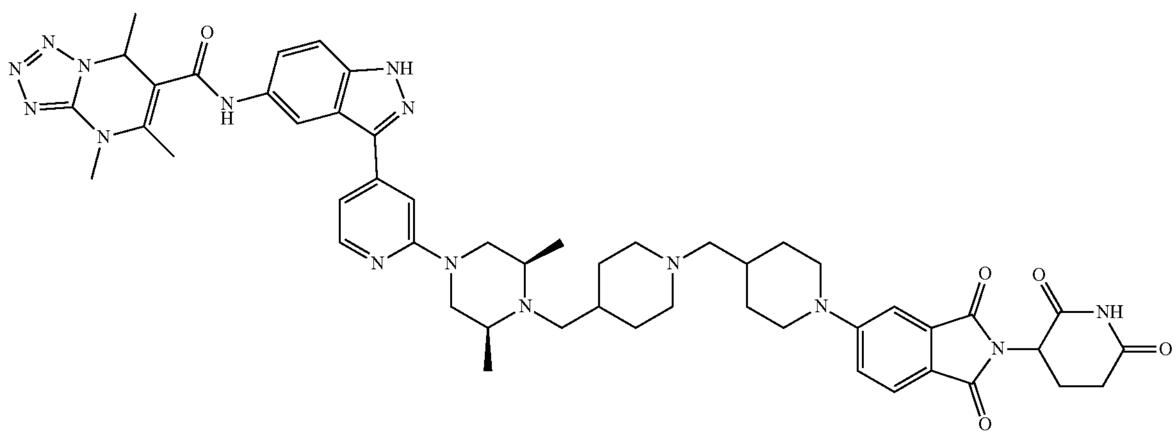 [SMILES: CC1=C(C(=O)Nc2ccc3[nH]nc(-c4ccnc(N5C[C@@H](C)N(CC6CCN(CC7CCN(c8ccc9c(c8)C(=O)N(C8CCC(=O)NC8=O)C9=O)CC7)CC6)[C@@H](C)C5)c4)c3c2)C(C)n2nnnc2N1C] | 963.50 | N-(3-(2-((3S,5R)-4-((1-(1-(2-(2,6-dioxopiperidin-3-yl)-1,3-dioxoisoindolin-5-yl)piperidin-4-yl)methyl)piperidin-4-yl)methyl)-3,5-dimethylpiperazin-1-yl)pyridin-4-yl)-1H-indazol-5-yl)-4,5,7-trimethyl-4,7-dihydrotetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 3 | 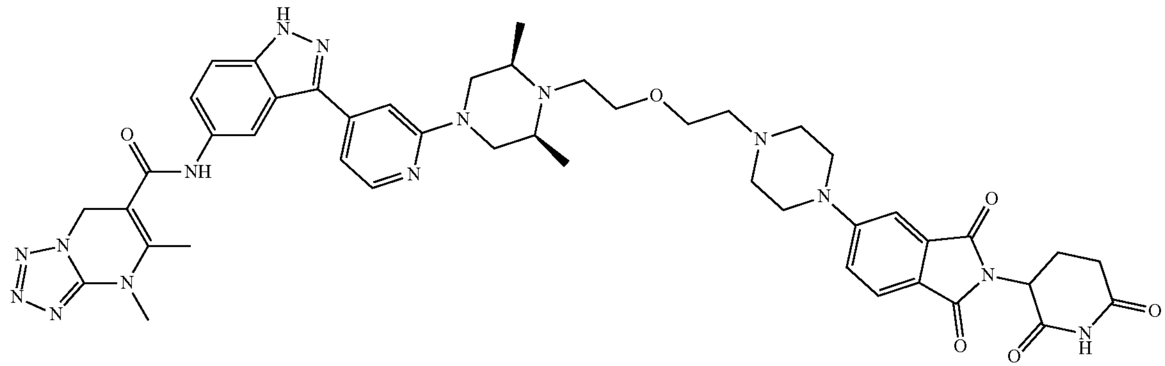 [SMILES: CC1=C(C(=O)Nc2ccc3[nH]nc(-c4ccnc(N5C[C@@H](C)N(CCOCCN6CCN(c7ccc8c(c7)C(=O)N(C7CCC(=O)NC7=O)C8=O)CC6)[C@@H](C)C5)c4)c3c2)Cn2nnnc2N1C] | 911.43 | N-(3-(2-((3R,5S)-4-(2-(2-(4-(2-(2,6-dioxopiperidin-3-yl)-1,3-dioxoisoindolin-5-yl)piperazin-1-yl)ethoxy)ethyl)-3,5-dimethylpiperazin-1-yl)pyridin-4-yl)-1H-indazol-5-yl)-4,5-dimethyl-4,7-dihydrotetrazolo[1,5-a]pyrimidine-6-carboxamide |
| 4 | 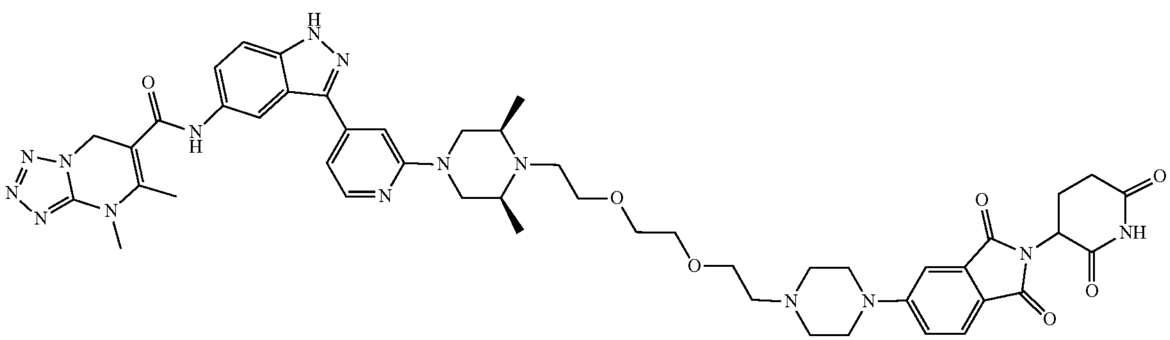 [SMILES: CC1=C(C(=O)Nc2ccc3[nH]nc(-c4ccnc(N5C[C@@H](C)N(CCOCCOCCN6CCN(c7ccc8c(c7)C(=O)N(C7CCC(=O)NC7=O)C8=O)CC6)[C@@H](C)C5)c4)c3c2)Cn2nnnc2N1C] | 955.46 | N-(3-(2-((3R,5S)-4-(2-(2-(2-(4-(2-(2,6-dioxoisoindolin-3-yl)piperazin-1-yl)ethoxy)ethoxy)ethyl)-3,5-dimethylpiperazin-1-yl)pyridin-4-yl)-1H-indazol-5-yl)-4,5-dimethyl-4,7-dihydrotetrazolo[1,5-a]pyrimidine-6-carboxamide |
| 5 | 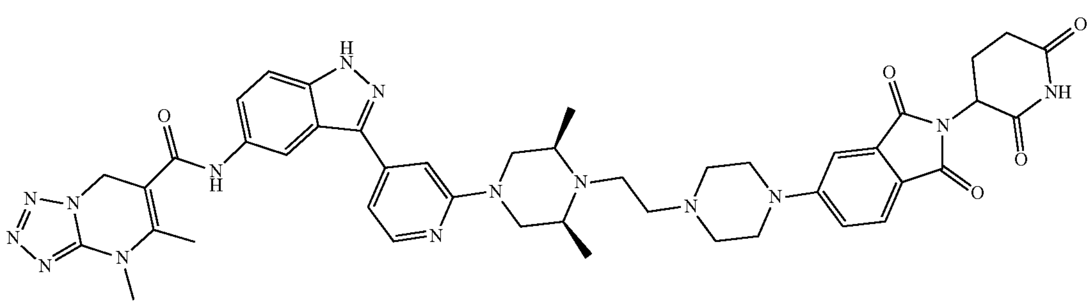 [SMILES: CC1=C(C(=O)Nc2ccc3[nH]nc(-c4ccnc(N5C[C@@H](C)N(CCN6CCN(c7ccc8c(c7)C(=O)N(C7CCC(=O)NC7=O)C8=O)CC6)[C@@H](C)C5)c4)c3c2)Cn2nnnc2N1C] | 867.40 | N-(3-(2-((3R,5S)-4-(2-(4-(2-(2,6-dioxopiperidin-3-yl)-1,3-dioxoisoindolin-5-yl)piperazin-1-yl)ethyl)-3,5-dimethylpiperazin-1-yl)pyridin-4-yl)-1H-indazol-5-yl)-4,5-dimethyl-4,7-dihydrotetrazolo[1,5-a]pyrimidine-6-carboxamide |

TABLE 1-continued

Exemplary bifunctional compounds of the present disclosure.

| Ex. | Structure | Mass | Name |
| --- | --- | --- | --- |
| 6 | 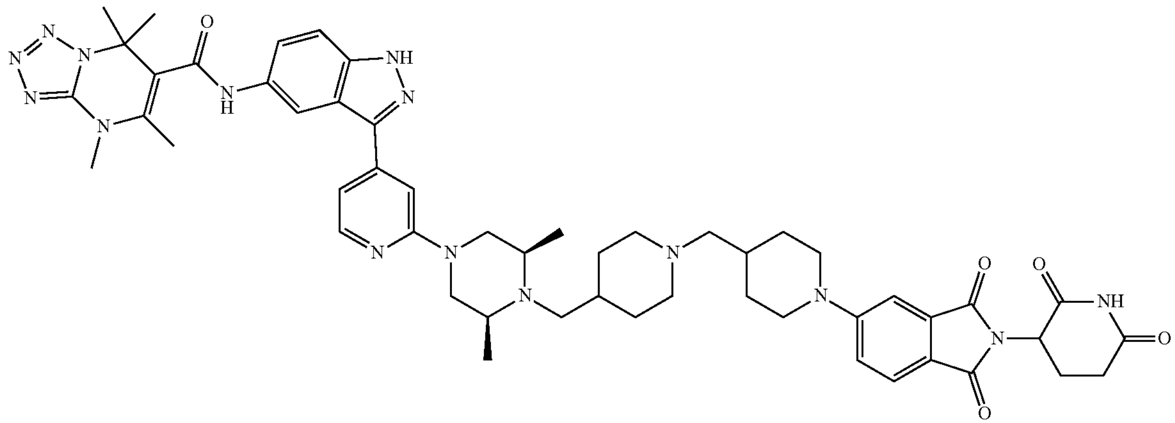 [SMILES: CC1=C(C(=O)Nc2ccc3[nH]nc(-c4ccnc(N5C[C@@H](C)N(CC6CCN(CC7CCN(c8ccc9c(c8)C(=O)N(C8CCC(=O)NC8=O)C9=O)CC7)CC6)[C@@H](C)C5)c4)c3c2)C(C)(C)n2nnnc2N1C] | 977.51 | N-(3-(2-((3S,5R)-4-(1-((1-(2-(2,6-dioxopiperidin-3-yl)-1,3-dioxoisoindolin-5-yl)piperidin-4-yl)methyl)piperidin-4-yl)methyl)-3,5-dimethylpiperazin-1-yl)pyridin-4-yl)-1H-indazol-5-yl)-4,5,7,7-tetramethyl-4,7-dihydrotetrazolo[1,5-a]pyrimidine-6-carboxamide |
| 7 | 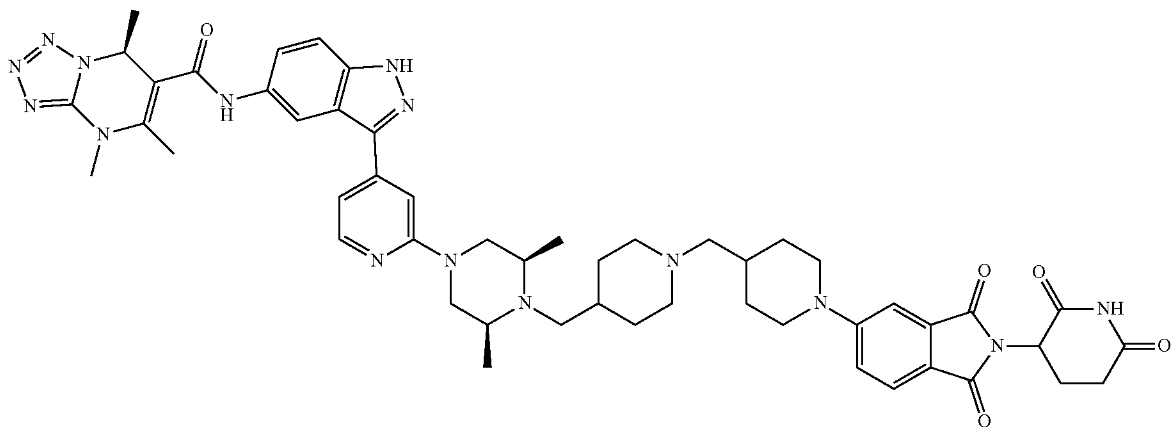 [SMILES: CC1=C(C(=O)Nc2ccc3[nH]nc(-c4ccnc(N5C[C@@H](C)N(CC6CCN(CC7CCN(c8ccc9c(c8)C(=O)N(C8CCC(=O)NC8=O)C9=O)CC7)CC6)[C@@H](C)C5)c4)c3c2)[C@H](C)n2nnnc2N1C] | 963.50 | (S)-N-(3-(2-((3S,5R)-4-(1-((1-(2-(2,6-dioxopiperidin-3-yl)-1,3-dioxoisoindolin-5-yl)piperidin-4-yl)methyl)piperidin-4-yl)methyl)-3,5-dimethylpiperazin-1-yl)pyridin-4-yl)-1H-indazol-5-yl)-4,5,7-trimethyl-4,7-dihydrotetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 8 | 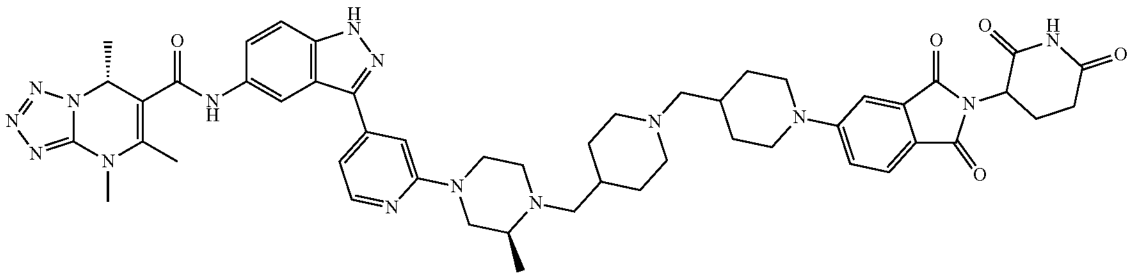 [SMILES: CC1=C(C(=O)Nc2ccc3[nH]nc(-c4ccnc(N5CCN(CC6CCN(CC7CCN(c8ccc9c(c8)C(=O)N(C8CCC(=O)NC8=O)C9=O)CC7)CC6)[C@@H](C)C5)c4)c3c2)[C@@H](C)n2nnnc2N1C] | 949.48 | (R)-N-(3-(2-((S)-4-((1-((1-(2-(2,6-dioxopiperidin-3-yl)-1,3-dioxoisoindolin-5-yl)piperidin-4-yl)methyl)piperidin-4-yl)methyl)-3-methylpiperazin-1-yl)pyridin-4-yl)-1H-indazol-5-yl)-4,5,7-trimethyl-4,7-dihydrotetrazolo[1,5-a]pyrimidine-6-carboxamide |
| 9 | 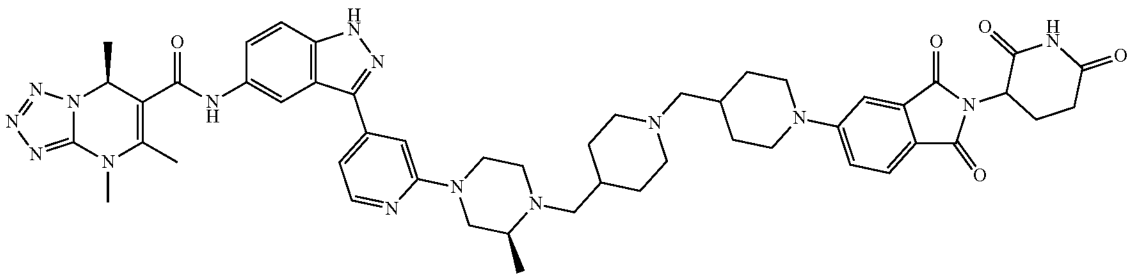 [SMILES: CC1=C(C(=O)Nc2ccc3[nH]nc(-c4ccnc(N5CCN(CC6CCN(CC7CCN(c8ccc9c(c8)C(=O)N(C8CCC(=O)NC8=O)C9=O)CC7)CC6)[C@@H](C)C5)c4)c3c2)[C@H](C)n2nnnc2N1C] | 949.48 | (S)-N-(3-(2-((S)-4-((1-((1-(2-(2,6-dioxopiperidin-3-yl)-1,3-dioxoisoindolin-5-yl)piperidin-4-yl)methyl)piperidin-4-yl)methyl)-3-methylpiperazin-1-yl)pyridin-4-yl)-1H-indazol-5-yl)-4,5,7-trimethyl-4,7-dihydrotetrazolo[1,5-a]pyrimidine-6-carboxamide |
| 10 | 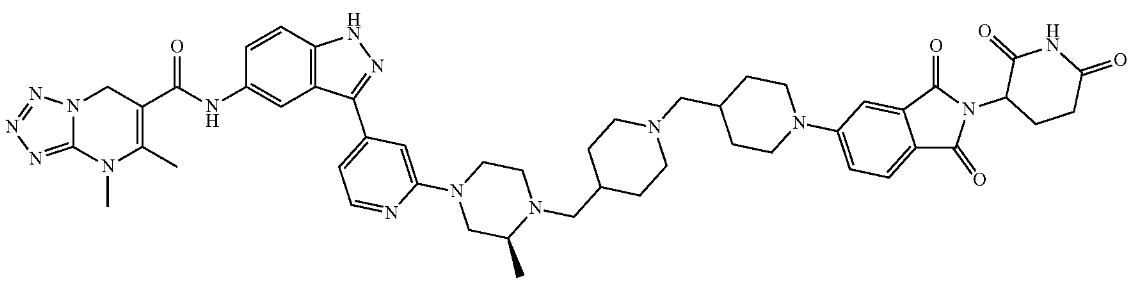 [SMILES: CC1=C(C(=O)Nc2ccc3[nH]nc(-c4ccnc(N5CCN(CC6CCN(CC7CCN(c8ccc9c(c8)C(=O)N(C8CCC(=O)NC8=O)C9=O)CC7)CC6)[C@@H](C)C5)c4)c3c2)Cn2nnnc2N1C] | 935.47 | N-(3-(2-((S)-4-((1-((1-(2-(2,6-dioxopiperidin-3-yl)-1,3-dioxoisoindolin-5-yl)piperidin-4-yl)methyl)piperidin-4-yl)methyl)-3-methylpiperazin-1-yl)pyridin-4-yl)-1H-indazol-5-yl)-4,5-dimethyl-4,7-dihydrotetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 11 | 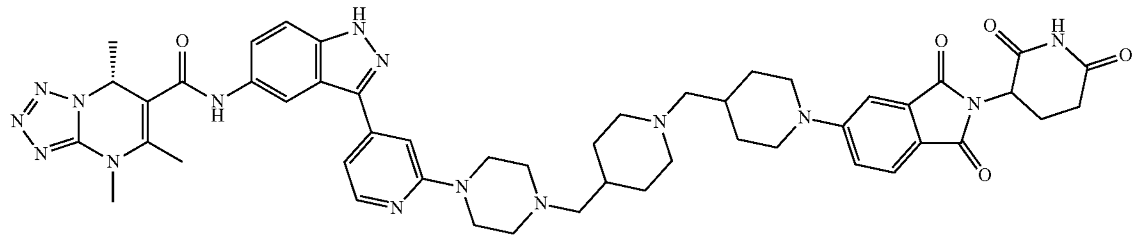 [SMILES: CC1=C(C(=O)Nc2ccc3[nH]nc(-c4ccnc(N5CCN(CC6CCN(CC7CCN(c8ccc9c(c8)C(=O)N(C8CCC(=O)NC8=O)C9=O)CC7)CC6)CC5)c4)c3c2)[C@@H](C)n2nnnc2N1C] | 935.47 | (7R)-N-(3-(2-(4-((1-((1-(2-(2,6-dioxopiperidin-3-yl)-1,3-dioxoisoindolin-5-yl)piperidin-4-yl)methyl)piperidin-4-yl)methyl)piperazin-1-yl)pyridin-4-yl)-1H-indazol-5-yl)-4,5,7-trimethyl-4,7-dihydrotetrazolo[1,5-a]pyrimidine-6-carboxamide |
| 12 | 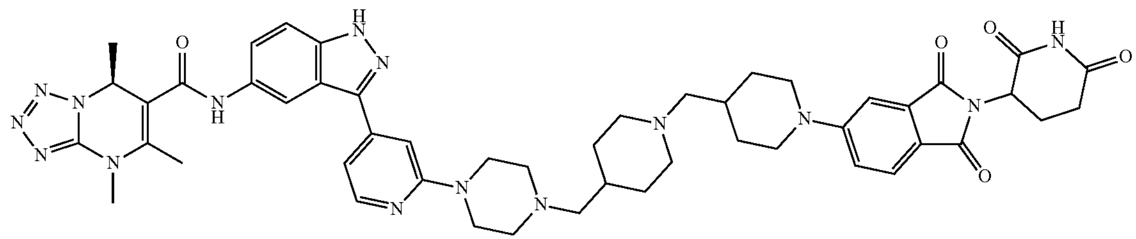 [SMILES: CC1=C(C(=O)Nc2ccc3[nH]nc(-c4ccnc(N5CCN(CC6CCN(CC7CCN(c8ccc9c(c8)C(=O)N(C8CCC(=O)NC8=O)C9=O)CC7)CC6)CC5)c4)c3c2)[C@H](C)n2nnnc2N1C] | 935.47 | (7S)-N-(3-(2-(4-((1-((1-(2-(2,6-dioxopiperidin-3-yl)-1,3-dioxoisoindolin-5-yl)piperidin-4-yl)methyl)piperidin-4-yl)methyl)piperazin-1-yl)pyridin-4-yl)-1H-indazol-5-yl)-4,5,7-trimethyl-4,7-dihydrotetrazolo[1,5-a]pyrimidine-6-carboxamide |
| 13 | 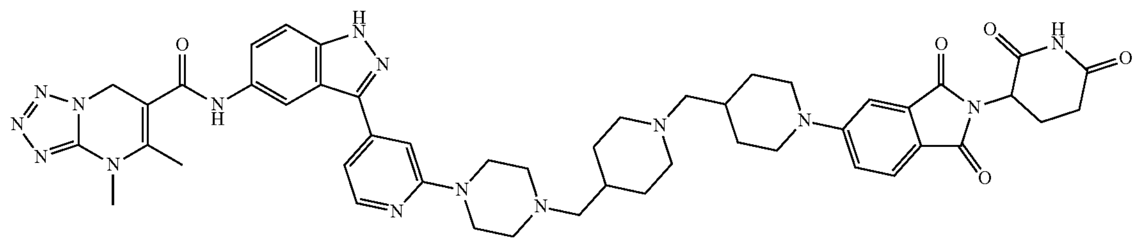 [SMILES: CC1=C(C(=O)Nc2ccc3[nH]nc(-c4ccnc(N5CCN(CC6CCN(CC7CCN(c8ccc9c(c8)C(=O)N(C8CCC(=O)NC8=O)C9=O)CC7)CC6)CC5)c4)c3c2)Cn2nnnc2N1C] | 921.45 | N-(3-(2-(4-((1-((1-(2-(2,6-dioxopiperidin-3-yl)-1,3-dioxoisoindolin-5-yl)piperidin-4-yl)methyl)piperidin-4-yl)methyl)piperazin-1-yl)pyridin-4-yl)-1H-indazol-5-yl)-4,5-dimethyl-4,7-dihydrotetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 14 | 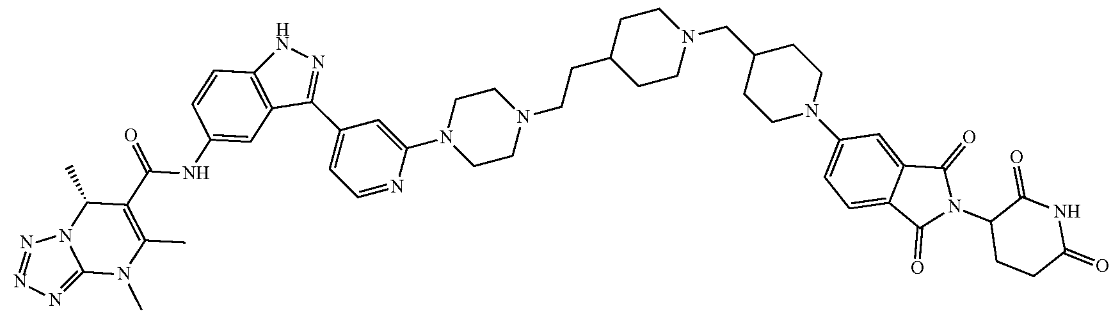 [SMILES: CC1=C(C(=O)Nc2ccc3[nH]nc(-c4ccnc(N5CCN(CCC6CCN(CC7CCN(c8ccc9c(c8)C(=O)N(C8CCC(=O)NC8=O)C9=O)CC7)CC6)CC5)c4)c3c2)[C@@H](C)n2nnnc2N1C] | 949.48 | (7R)-N-(3-(2-(4-(2-(1-((1-(2-(2,6-dioxopiperidin-3-yl)-1,3-dioxoisoindolin-5-yl)piperidin-4-yl)methyl)piperidin-4-yl)ethyl)piperazin-1-yl)pyridin-4-yl)-1H-indazol-5-yl)-4,5,7-trimethyl-4,7-dihydrotetrazolo[1,5-a]pyrimidine-6-carboxamide |
| 15 | 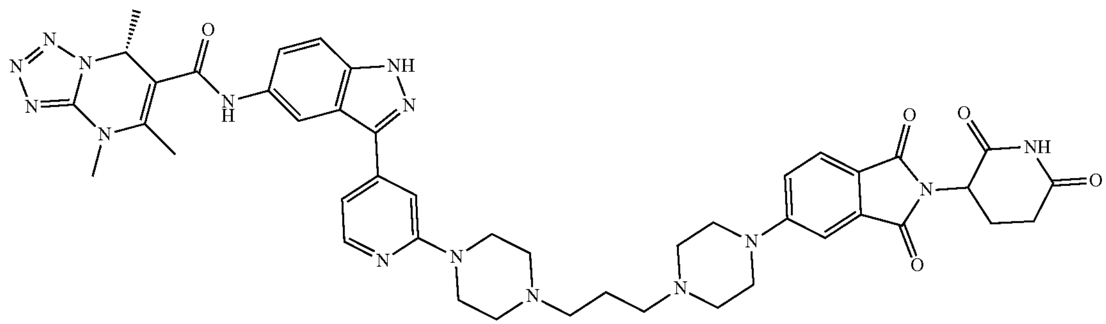 [SMILES: CC1=C(C(=O)Nc2ccc3[nH]nc(-c4ccnc(N5CCN(CCCN6CCN(c7ccc8c(c7)C(=O)N(C7CCC(=O)NC7=O)C8=O)CC6)CC5)c4)c3c2)[C@@H](C)n2nnnc2N1C] | 867.40 | (7R)-N-(3-(2-(4-(3-(4-(2-(2,6-dioxopiperidin-3-yl)-1,3-dioxoisoindolin-5-yl)piperazin-1-yl)propyl)piperazin-1-yl)pyridin-4-yl)-1H-indazol-5-yl)-4,5,7-trimethyl-4,7-dihydrotetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 16 | 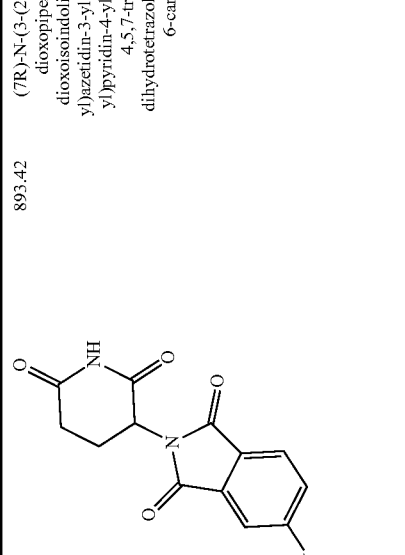 | 893.42 | (7R)-N-(3-(2-(4-((1-(1-(2-(2,6-dioxopiperidin-3-yl)-1,3-dioxoisoindolin-5-yl)piperidin-4-yl)azetidin-3-yl)methyl)piperazin-1-yl)pyridin-4-yl)-1H-indazol-5-yl)-4,5,7-trimethyl-4,7-dihydrotetrazolo[1,5-a]pyrimidine-6-carboxamide |
| 17 | 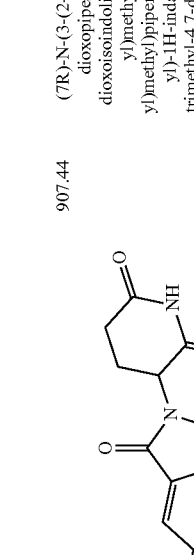 | 907.44 | (7R)-N-(3-(2-(4-((1-(1-(2-(2,6-dioxopiperidin-3-yl)-1,3-dioxoisoindolin-5-yl)piperidin-4-yl)methyl)azetidin-3-yl)methyl)piperazin-1-yl)pyridin-4-yl)-1H-indazol-5-yl)-4,5,7-trimethyl-4,7-dihydrotetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 18 | 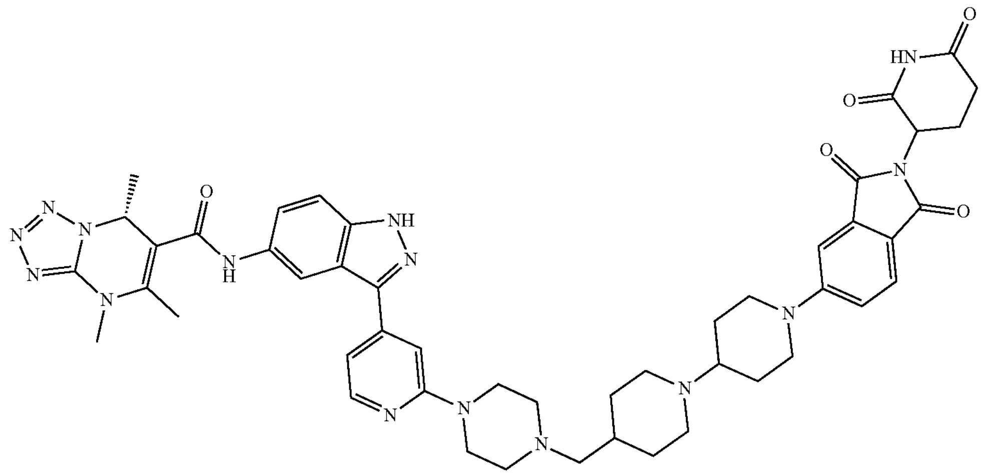 [SMILES: CC1=C(C(=O)Nc2ccc3[nH]nc(-c4ccnc(N5CCN(CC6CCN(C7CCN(c8ccc9c(c8)C(=O)N(C8CCC(=O)NC8=O)C9=O)CC7)CC6)CC5)c4)c3c2)[C@@H](C)n2nnnc2N1C] | 921.45 | (7R)-N-(3-(2-(4-(((1-(1-(2-(2,6-dioxopiperidin-3-yl)-1,3-dioxoisoindolin-5-yl)piperidin-4-yl)piperidin-4-yl)methyl)piperazin-1-yl)pyridin-4-yl)-1H-indazol-5-yl)-4,5,7-trimethyl-4,7-dihydrotetrazolo[1,5-a]pyrimidine-6-carboxamide |
| 19 | 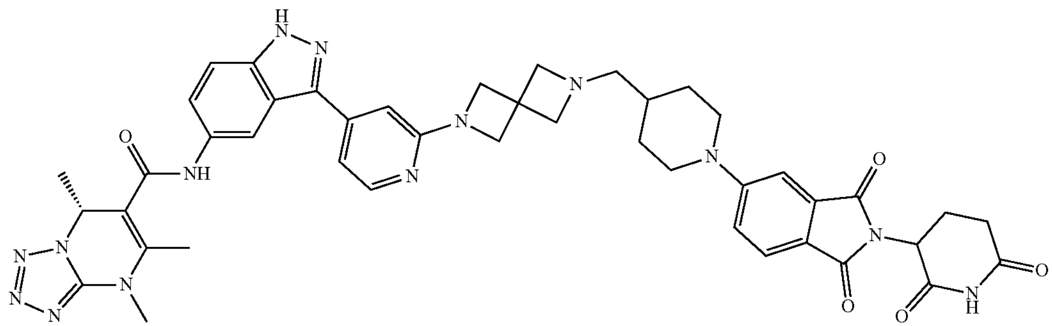 [SMILES: CC1=C(C(=O)Nc2ccc3[nH]nc(-c4ccnc(N5CC6(CN(CC7CCN(c8ccc9c(c8)C(=O)N(C8CCC(=O)NC8=O)C9=O)CC7)C6)C5)c4)c3c2)[C@@H](C)n2nnnc2N1C] | 850.38 | |

TABLE 1-continued

Exemplary bifunctional compounds of the present disclosure.

| Ex. | Structure | Mass | Name |
|---|---|---|---|
| 20 | 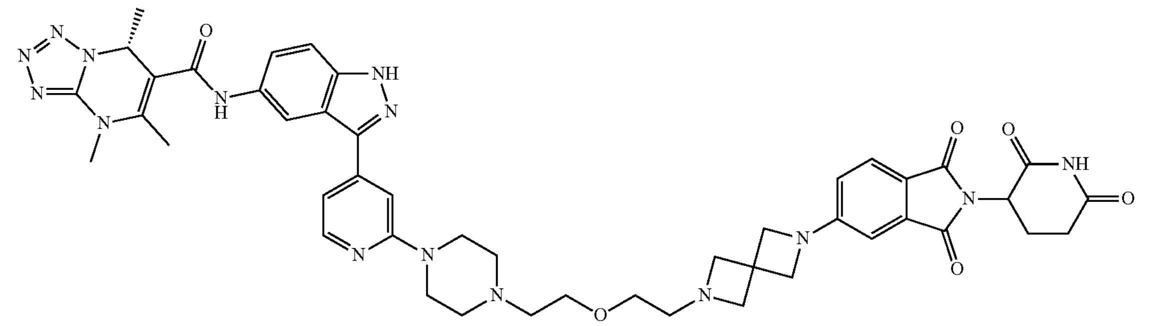 [SMILES: CC1=C(C(=O)Nc2ccc3[nH]nc(-c4ccnc(N5CCN(CCOCCN6CC7(C6)CN(c6ccc8c(c6)C(=O)N(C6CCC(=O)NC6=O)C8=O)C7)CC5)c4)c3c2)[C@@H](C)n2nnnc2N1C] | 909.41 | (7R)-N-[3-(2-{4-[2-(2-{6-[2-(2,6-dioxopiperidin-3-yl)-1,3-dioxo-2,3-dihydro-1H-isoindol-5-yl]-2,6-diazaspiro[3.3]heptan-2-yl}ethoxy)ethyl]piperazin-1-yl}pyridin-4-yl)-1H-indazol-5-yl]-4,5,7-trimethyl-4H,7H-[1,2,3,4]tetrazolo[1,5-a]pyrimidine-6-carboxamide |
| 21 | 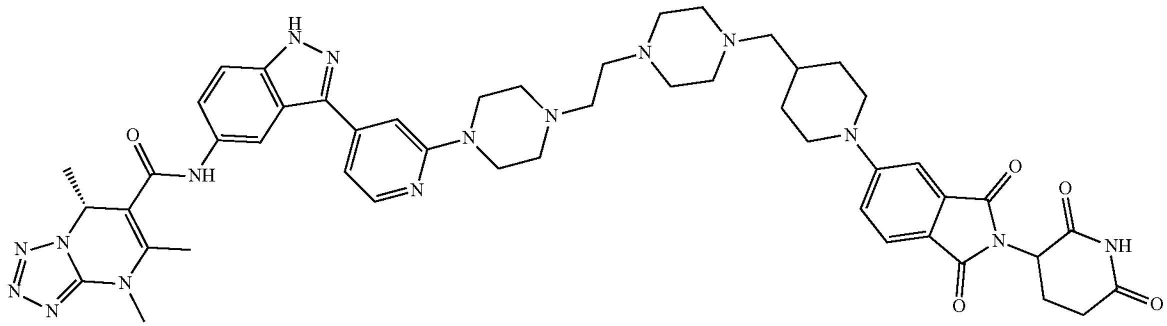 [SMILES: CC1=C(C(=O)Nc2ccc3[nH]nc(-c4ccnc(N5CCN(CCN6CCN(CC7CCN(c8ccc9c(c8)C(=O)N(C8CCC(=O)NC8=O)C9=O)CC7)CC6)CC5)c4)c3c2)[C@@H](C)n2nnnc2N1C] | 950.48 | (7R)-N-(3-(2-(4-(2-(4-((1-(2-(2,6-dioxopiperidin-3-yl)-1,3-dioxoisoindolin-5-yl)piperidin-4-yl)methyl)piperazin-1-yl)ethyl)piperazin-1-yl)pyridin-4-yl)-1H-indazol-5-yl)-4,5,7-trimethyl-4,7-dihydrotetrazolo[1,5-a]pyrimidine-6-carboxamide |
| 22 | 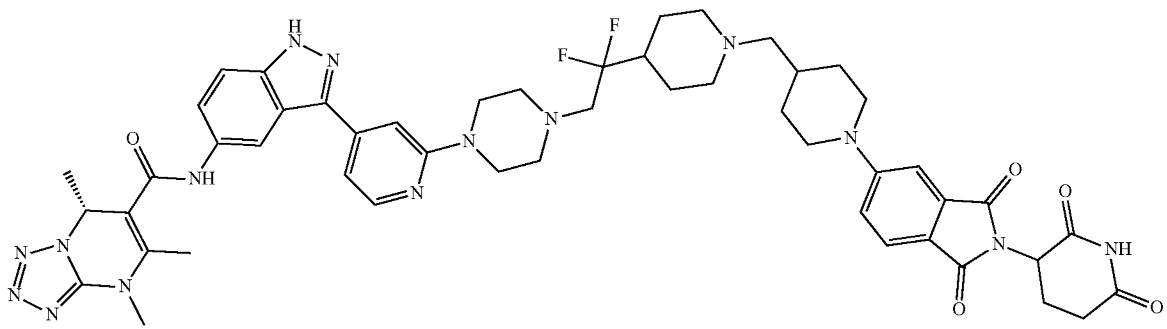 [SMILES: CC1=C(C(=O)Nc2ccc3[nH]nc(-c4ccnc(N5CCN(CC(F)(F)C6CCN(CC7CCN(c8ccc9c(c8)C(=O)N(C8CCC(=O)NC8=O)C9=O)CC7)CC6)CC5)c4)c3c2)[C@@H](C)n2nnnc2N1C] | 985.46 | (7R)-N-(3-(2-(4-(2-(1-(1-(2-(2,6-dioxopiperidin-3-yl)-1,3-dioxoisoindolin-5-yl)piperidin-4-yl)methyl)piperidin-4-yl)-2,2-difluoroethyl)piperazin-1-yl)pyridin-4-yl)-1H-indazol-5-yl)-4,5,7-trimethyl-4,7-dihydrotetrazolo[1,5-a]pyrimidine-6-carboxamide |

TABLE 1-continued

Exemplary bifunctional compounds of the present disclosure.

| Ex. | Mass | Name |
|---|---|---|
| 23 | 949.48 | (7R)-N-(3-(2-(4-(2-(4-((1-(2-(2,6-dioxopiperidin-3-yl)-1,3-dioxoisoindolin-5-yl)piperidin-4-yl)methyl)piperidin-1-yl)ethyl)piperazin-1-yl)pyridin-4-yl)-1H-indazol-5-yl)-4,5,7-trimethyl-4,7-dihydrotetrazolo[1,5-a]pyrimidine-6-carboxamide |
| 24 | 893.42 | (7R)-N-[3-(2-{4-[1-({1-[2-(2,6-dioxopiperidin-3-yl)-1,3-dioxo-2,3-dihydro-1H-isoindol-5-yl]piperidin-4-yl}methyl)azetidin-3-yl]piperazin-1-yl}pyridin-4-yl)-1H-indazol-5-yl]-4,5,7-trimethyl-4H,7H-[1,2,3,4]tetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 25 | 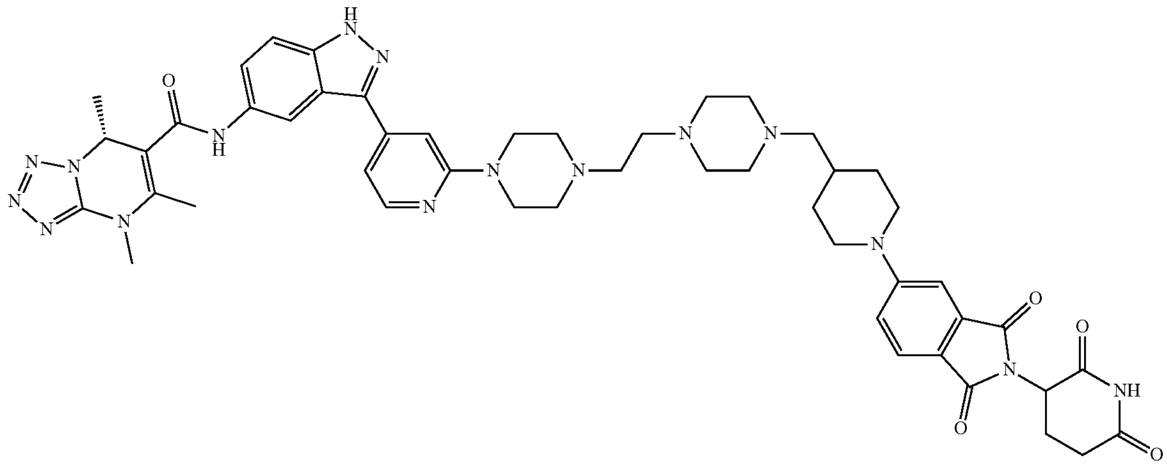 [SMILES: CC1=C(C(=O)Nc2ccc3[nH]nc(-c4ccnc(N5CCN(CCN6CCN(CC7CCN(c8ccc9c(c8)C(=O)N(C8CCC(=O)NC8=O)C9=O)CC7)CC6)CC5)c4)c3c2)[C@@H](C)n2nnnc2N1C] | 950.48 | (7R)-N-{3-[2-(4-{2-[4-({1-[2-(2,6-dioxopiperidin-3-yl)-1,3-dioxo-2,3-dihydro-1H-isoindol-5-yl]piperidin-4-yl}methyl)piperazin-1-yl]ethyl}piperazin-1-yl)pyridin-4-yl]-1H-indazol-5-yl}-4,5,7-trimethyl-4H,7H-[1,2,3,4]tetrazolo[1,5-a]pyrimidine-6-carboxamide |
| 26 | 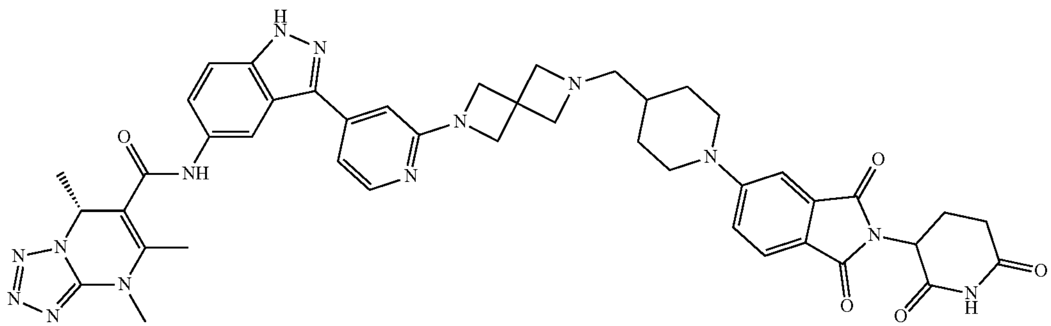 [SMILES: CC1=C(C(=O)Nc2ccc3[nH]nc(-c4ccnc(N5CC6(CN(CC7CCN(c8ccc9c(c8)C(=O)N(C8CCC(=O)NC8=O)C9=O)CC7)C6)C5)c4)c3c2)[C@@H](C)n2nnnc2N1C] | 850.38 | (7R)-N-(3-{2-[6-({1-[2-(2,6-dioxopiperidin-3-yl)-1,3-dioxo-2,3-dihydro-1H-isoindol-5-yl]piperidin-4-yl}methyl)-2,6-diazaspiro[3.3]heptan-2-yl]pyridin-4-yl}-1H-indazol-5-yl)-4,5,7-trimethyl-4H,7H-[1,2,3,4]tetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 27 | 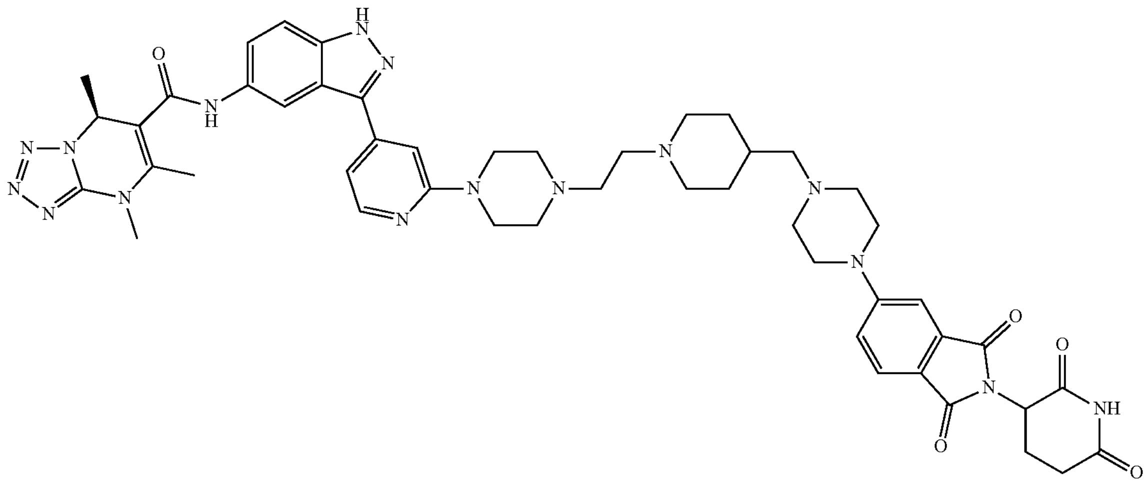 [SMILES: CC1=C(C(=O)Nc2ccc3[nH]nc(-c4ccnc(N5CCN(CCN6CCC(CN7CCN(c8ccc9c(c8)C(=O)N(C8CCC(=O)NC8=O)C9=O)CC7)CC6)CC5)c4)c3c2)[C@H](C)n2nnnc2N1C] | 950.48 | (7S)-N-{3-[2-(4-{2-[4-({4-[2-(2,6-dioxopiperidin-3-yl)-1,3-dioxo-2,3-dihydro-1H-isoindol-5-yl]piperazin-1-yl]methyl)piperidin-1-yl]ethyl}piperazin-1-yl)pyridin-4-yl]-1H-indazol-5-yl}-4,5,7-trimethyl-4H,7H-[1,2,3,4]tetrazolo[1,5-a]pyrimidine-6-carboxamide |
| 28 | 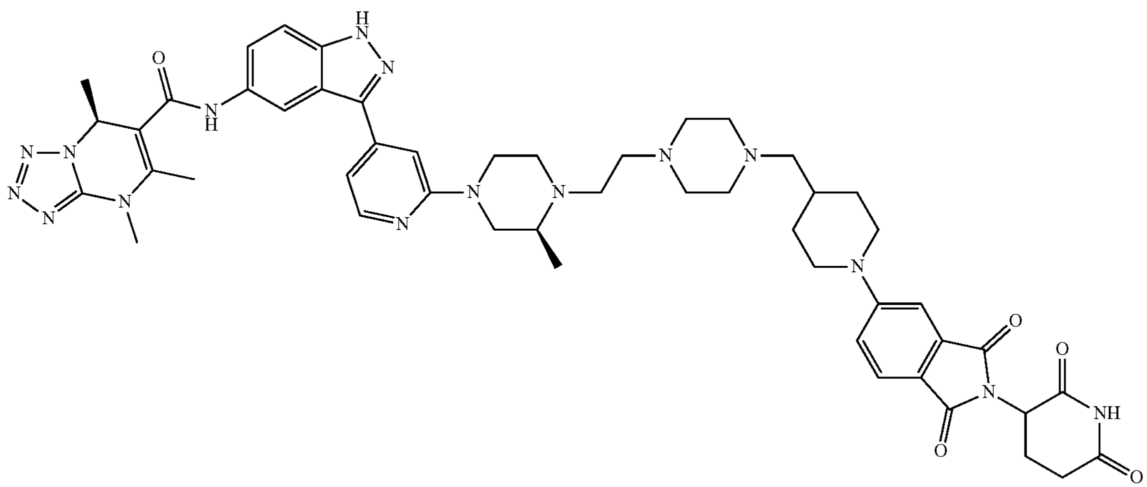 [SMILES: CC1=C(C(=O)Nc2ccc3[nH]nc(-c4ccnc(N5CCN(CCN6CCN(CC7CCN(c8ccc9c(c8)C(=O)N(C8CCC(=O)NC8=O)C9=O)CC7)CC6)[C@@H](C)C5)c4)c3c2)[C@H](C)n2nnnc2N1C] | 964.49 | (7S)-N-(3-{2-[(3S)-4-{2-[4-({1-[2-(2,6-dioxopiperidin-3-yl)-1,3-dioxo-2,3-dihydro-1H-isoindol-5-yl]piperidin-4-yl}methyl)piperazin-1-yl]ethyl}-3-methylpiperazin-1-yl]pyridin-4-yl}-1H-indazol-5-yl)-4,5,7-trimethyl-4H,7H-[1,2,3,4]tetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 29 | 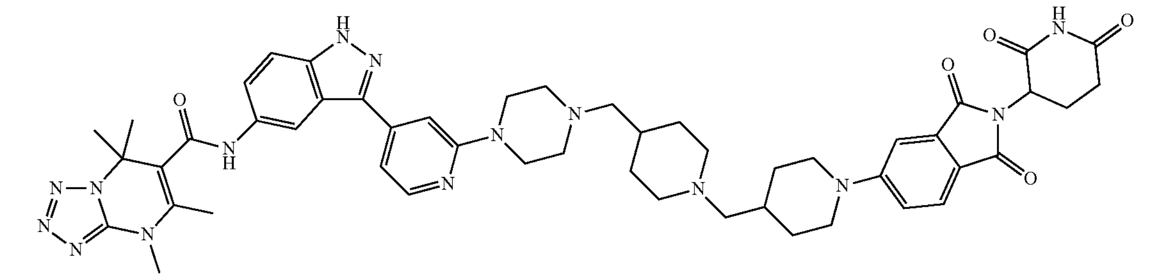 [SMILES: CC1=C(C(=O)Nc2ccc3[nH]nc(-c4ccnc(N5CCN(CC6CCN(CC7CCN(c8ccc9c(c8)C(=O)N(C8CCC(=O)NC8=O)C9=O)CC7)CC6)CC5)c4)c3c2)C(C)(C)n2nnnc2N1C] | 949.48 | N-{3-[2-(4-{[1-[2-(2,6-dioxopiperidin-3-yl)-1,3-dioxo-2,3-dihydro-1H-isoindol-5-yl]piperidin-4-yl]methyl)piperidin-4-yl]methyl]piperazin-1-yl]pyridin-4-yl}-1H-indazol-5-yl)-4,5,7,7-tetramethyl-4H,7H-[1,2,3,4]tetrazolo[1,5-a]pyrimidine-6-carboxamide |
| 30 | 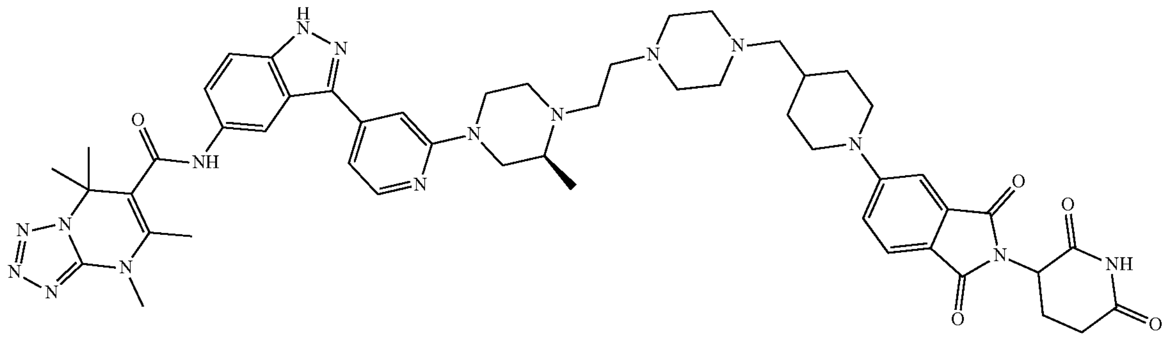 [SMILES: CC1=C(C(=O)Nc2ccc3[nH]nc(-c4ccnc(N5CCN(CCN6CCN(CC7CCN(c8ccc9c(c8)C(=O)N(C8CCC(=O)NC8=O)C9=O)CC7)CC6)[C@@H](C)C5)c4)c3c2)C(C)(C)n2nnnc2N1C] | 978.51 | N-(3-{2-[(3S)-4-{2-[4-({1-[2-(2,6-dioxopiperidin-3-yl)-1,3-dioxo-2,3-dihydro-1H-isoindol-5-yl]piperidin-4-yl}methyl)piperazin-1-yl]ethyl}-3-methylpiperazin-1-yl]pyridin-4-yl}-1H-indazol-5-yl)-4,5,7,7-tetramethyl-4H,7H-[1,2,3,4]tetrazolo[1,5-a]pyrimidine-6-carboxamide |
| 31 | 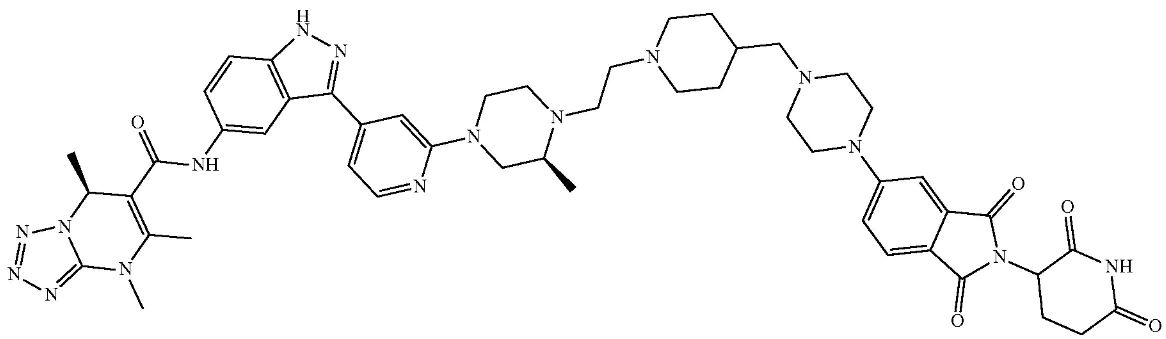 [SMILES: CC1=C(C(=O)Nc2ccc3[nH]nc(-c4ccnc(N5CCN(CCN6CCC(CN7CCN(c8ccc9c(c8)C(=O)N(C8CCC(=O)NC8=O)C9=O)CC7)CC6)[C@@H](C)C5)c4)c3c2)[C@H](C)n2nnnc2N1C] | 964.49 | (7S)-N-(3-{2-[(3S)-4-{2-[4-({4-[2-(2,6-dioxopiperidin-3-yl)-1,3-dioxo-2,3-dihydro-1H-isoindol-5-yl]piperazin-1-yl}methyl)piperidin-1-yl]ethyl}-3-methylpiperazin-1-yl]pyridin-4-yl}-1H-indazol-4-yl-5-yl)-4,5,7-trimethyl-4H,7H-[1,2,3,4]tetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 32 | 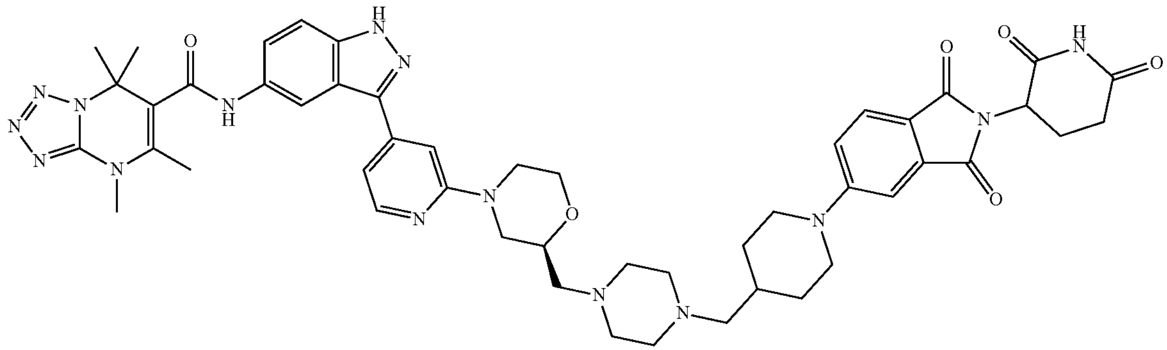 [SMILES: CC1=C(C(=O)Nc2ccc3[nH]nc(-c4ccnc(N5CCO[C@@H](CN6CCN(CC7CCN(c8ccc9c(c8)C(=O)N(C8CCC(=O)NC8=O)C9=O)CC7)CC6)C5)c4)c3c2)C(C)(C)n2nnnc2N1C] | 951.46 | N-(3-{2-[(2S)-2-{[4-({1-[2-(2,6-dioxopiperidin-3-yl)-1,3-dioxo-2,3-dihydro-1H-isoindol-5-yl]piperidin-4-yl}methyl)piperazin-1-yl]methyl}morpholin-4-yl]pyridin-4-yl)-1H-indazol-5-yl)-4,5,7,7-tetramethyl-4H,7H-[1,2,3,4]tetrazolo[1,5-a]pyrimidine-6-carboxamide |
| 33 | 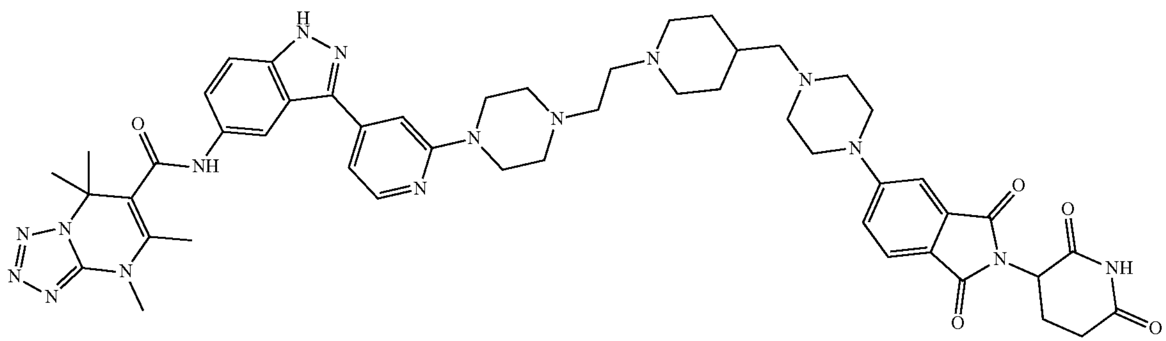 [SMILES: CC1=C(C(=O)Nc2ccc3[nH]nc(-c4ccnc(N5CCN(CCN6CCC(CN7CCN(c8ccc9c(c8)C(=O)N(C8CCC(=O)NC8=O)C9=O)CC7)CC6)CC5)c4)c3c2)C(C)(C)n2nnnc2N1C] | 964.49 | N-{3-[2-(4-{2-[4-({1-[2-(2,6-dioxopiperidin-3-yl)-1,3-dioxo-2,3-dihydro-1H-isoindol-5-yl]piperidin-1-yl}methyl)piperazin-1-yl]ethyl}piperazin-1-yl)pyridin-4-yl]-1H-indazol-5-yl}-4,5,7,7-tetramethyl-4H,7H-[1,2,3,4]tetrazolo[1,5-a]pyrimidine-6-carboxamide |
| 34 | 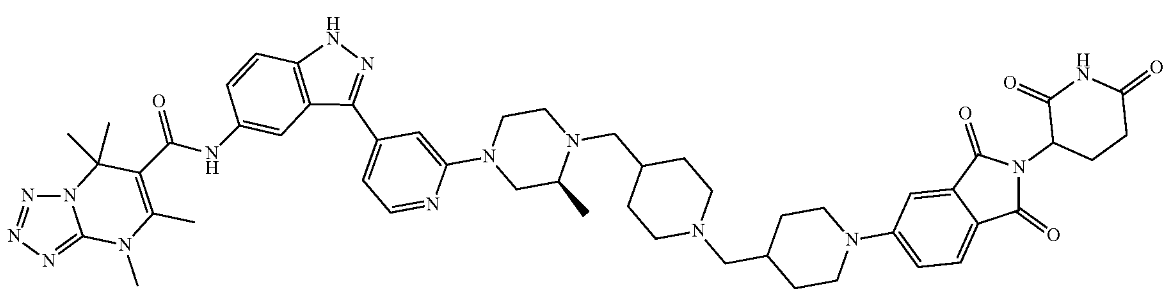 [SMILES: CC1=C(C(=O)Nc2ccc3[nH]nc(-c4ccnc(N5CCN(CC6CCN(CC7CCN(c8ccc9c(c8)C(=O)N(C8CCC(=O)NC8=O)C9=O)CC7)CC6)[C@@H](C)C5)c4)c3c2)C(C)(C)n2nnnc2N1C] | 963.50 | N-(3-{2-[(3S)-4-{[1-({1-[2-(2,6-dioxopiperidin-3-yl)-1,3-dioxo-2,3-dihydro-1H-isoindol-5-yl]piperidin-4-yl}methyl)piperidin-4-yl]methyl}-3-methylpiperazin-1-yl]pyridin-4-yl}-1H-indazol-5-yl)-4,5,7,7-tetramethyl-4H,7H-[1,2,3,4]tetrazolo[1,5-a]pyrimidine-6-carboxamide |

TABLE 1-continued

Exemplary bifunctional compounds of the present disclosure.

| Ex. | Structure | Mass | Name |
|---|---|---|---|
| 35 | 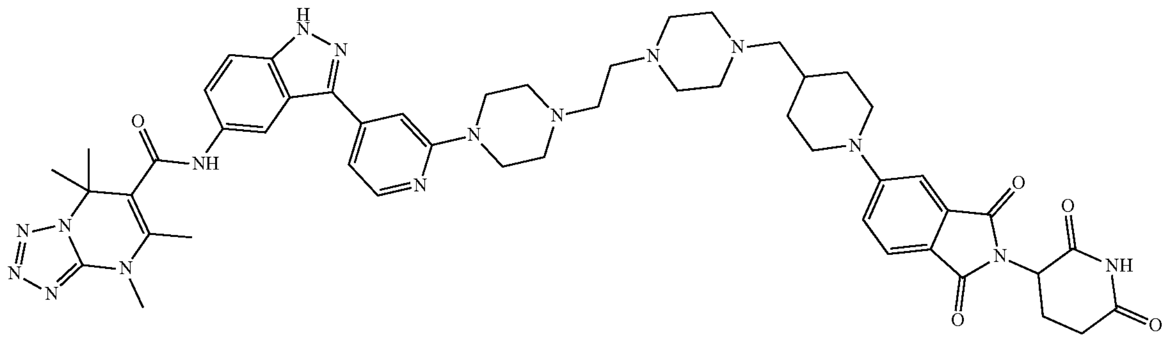 [SMILES: CC1=C(C(=O)Nc2ccc3[nH]nc(-c4ccnc(N5CCN(CCN6CCN(CC7CCN(c8ccc9c(c8)C(=O)N(C8CCC(=O)NC8=O)C9=O)CC7)CC6)CC5)c4)c3c2)C(C)(C)n2nnnc2N1C] | 964.49 | N-{3-[2-(4-{2-[4-({1-[2-(2,6-dioxopiperidin-3-yl)-1,3-dioxo-2,3-dihydro-1H-isoindol-5-yl]piperidin-4-yl}methyl)piperazin-1-yl]ethyl}piperazin-1-yl)pyridin-4-yl]-1H-indazol-5-yl}-4,5,7,7-tetramethyl-4H,7H-[1,2,3,4]tetrazolo[1,5-a]pyrimidine-6-carboxamide |
| 36 | 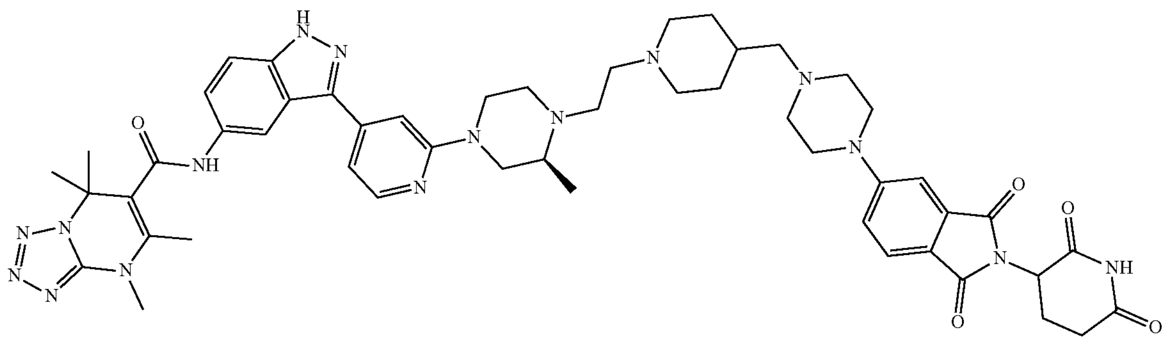 | 978.51 | N-(3-{2-[(3S)-4-{2-[4-({4-[2-(2,6-dioxopiperidin-3-yl)-1,3-dioxo-2,3-dihydro-1H-isoindol-5-yl]piperazin-1-yl]methyl)piperidin-1-yl]ethyl}-3-methylpiperazin-1-yl]pyridin-4-yl}-1H-indazol-5-yl)-4,5,7,7-tetramethyl-4H,7H-[1,2,3,4]tetrazolo[1,5-a]pyrimidine-6-carboxamide |

TABLE 2

Characterization of exemplary bifunctional compounds of the present disclosure.

| Ex. | NMR | Mean Observed Mass | *G2019S DC50 (nM) | **G2019S Dmax (%) | *WT DC50 (nM) | ** WT Dmax (%) |
|---|---|---|---|---|---|---|
| 1 | $^1$H NMR: (400 MHz, DMSO-d$_6$) δ: 13.42 (s, 1H), 11.08 (s, 1H), 10.07 (s, 1H), 8.67 (s, 1H), 8.22 (d, J = 5.1 Hz, 1H), 7.67-7.51 (m, 3H), 7.28 (d, J = 13.8 Hz, 2H), 7.23 (d, J = 8.8 Hz, 1H), 7.16 (d, J = 5.3 Hz, 1H), 5.30 (s, 2H), 5.11-5.02 (m, 1H), 4.12 (d, J = 11.1 Hz, 2H), 4.03 (d, J = 12.9 Hz, 2H), 3.44 (s, 3H), 3.00-2.80 (m, 5H), 2.72-2.53 (m, 6H), 2.39-2.30 (m, 2H), 2.27 (s, 3H), 2.16 (d, J = 5.8 Hz, 2H), 2.05-1.97 (m, 1H), 1.95-1.71 (m, 7H), 1.37 (s, 1H), 1.12 (d, J = 5.8 Hz, 10H). | 950.60 | A | B | B | B |
| 2 | $^1$H NMR: (400 MHz, DMSO) δ: 13.42 (s, 1H), 11.08 (s, 1H), 10.28 (s, 1H), 8.67 (s, 1H), 8.23 (d, J = 5.3 Hz, 1H), 8.15 (s, 1H), 7.67-7.58 (m, 2H), 7.56-7.50 (m, 1H), 7.28 (d, J = 13.6 Hz, 2H), 7.23 (d, J = 8.8 Hz, 1H), 7.16 (d, J = 5.4 Hz, 1H), 5.83-5.71 (m, 1H), 5.06 (dd, J = 5.4, 12.9 Hz, 1H), 4.12 (d, J = 12.0 Hz, 2H), 4.03 (d, J = 12.9 Hz, 2H), 3.44 (s, 3H), 3.01-2.82 (m, 5H), 2.72-2.55 (m, 5H), 2.40-2.33 (m, 2H), 2.20 (s, 3H), 2.17 (s, 2H), 2.06-1.97 (m, 1H), 1.94-1.71 (m, 7H), 1.56 (d, J = 6.4 Hz, 3H), 1.38 (s, 1H), 1.11 (d, J = 5.8 Hz, 10H). | 964.60 | A | B | B | B |
| 3 | $^1$H NMR: (400 MHz, CD$_3$OD) δ: 8.65 (s, 1H), 8.40 (s, 1H), 8.17 (d, J = 5.3 Hz, 1H), 7.52 (d, J = 8.9 Hz, 1H), 7.38-7.32 (m, 2H), 7.24 (d, J = 5.3 Hz, 1H), 7.19 (d, J = 8.5 Hz, 1H), 6.93 (d, J = 2.1 Hz, 1H), 6.75 (dd, J = 2.1, 8.5 Hz, 1H), 5.30 (s, 2H), 5.02 (br dd, J = 5.5, 12.8 Hz, 1H), 4.53 (br t, J = 11.4 Hz, 2H), 3.92-3.81 (m, 4H), 3.67 (br t, J = 4.8 Hz, 2H), 3.55 (br s, 2H), 3.51 (s, 3H), 3.26-3.20 (m, 4H), 3.04-2.94 (m, 2H), 2.92-2.81 (m, 1H), 2.76 (br d, J = 2.8 Hz, 1H), 2.68-2.56 (m, 7H), 2.36 (s, 3H), 2.14-2.05 (m, 1H), 1.48 (br d, J = 5.4 Hz, 6H) | 912.57 | D | — | D | — |
| 4 | $^1$H NMR: (400 MHz, MeOD) δ: 8.71 (s, 1H), 8.27 (d, J = 5.4 Hz, 1H), 7.55-7.48 (m, 2H), 7.41 (d, J = 8.5 Hz, 1H), 7.38-7.31 (m, 2H), 6.99 (d, J = 1.8 Hz, 1H), 6.87 (d, J = 8.5 Hz, 1H), 5.29 (s, 2H), 5.05 (dd, J = 5.4, 12.7 Hz, 1H), 4.55 (d, J = 13.9 Hz, 2H), 3.85 (d, J = 4.5 Hz, 2H), 3.79-3.53 (m, 10H), 3.51 (s, 3H), 3.22 (s, 4H), 3.05-2.93 (m, 2H), 2.91-2.51 (m, 9H), 2.34 (s, 3H), 2.16-2.07 (m, 1H), 1.49 (d, J = 6.3 Hz, 6H). | 956.59 | D | — | D | — |
| 5 | $^1$H NMR: (400 MHz, METHANOL-d$_4$) δ: 8.69 (s, 1H), 8.41 (br s, 1H), 8.28 (d, J = 5.3 Hz, 1H), 7.54-7.47 (m, 2H), 7.45 (s, 1H), 7.36 (d, J = 6.6 Hz, 2H), 7.15 (s, 1H), 7.01 (br d, J = 6.9 Hz, 1H), 5.29 (s, 2H), 5.08 (dd, J = 5.5, 12.4 Hz, 1H), 4.59 (s, 3H), 4.43 (br s, 2H), 3.51 (s, 4H), 3.27 (br s, 4H), 3.02 (br t, J = 12.6 Hz, 2H), 2.93-2.82 (m, 1H), 2.80-2.75 (m, 2H), 2.75-2.69 (m, 3H), 2.66 (br t, J = 4.7 Hz, 4H), 2.35 (s, 3H), 2.19-2.05 (m, 1H), 1.44 (br d, J = 4.9 Hz, 6H) | 868.54 | D | C | D | — |
| 6 | 1H NMR (400 MHz, MeOD-d4) δ: 8.74 (s, 1H), 8.46 (s, 1H), 8.15 (d, J = 5.4 Hz, 1H), 7.68 (d, J = 8.5 Hz, 1H), 7.58 (d, J = 8.9 Hz, 1H), 7.36 (d, J = 2.1 Hz, 1H), 7.31-7.20 (m, 4H), 5.07 (dd, J = 5.4, 12.3 Hz, 1H), 4.75 (br s, 1H), 4.71 (br s, 1H), 4.14-4.00 (m, 5H), 3.73 (s, 1H), 3.59 (br d, J = 11.0 Hz, 1H), 3.46 (s, 3H), 3.03 (br d, J = 14.3 Hz, 5H), 2.89-2.81 (m, 4H), 2.77 (br s, 2H), 2.74-2.67 (m, 2H), 2.63 (br d, J = 5.8 Hz, 2H), 2.20 (br d, J = 17.6 Hz, 2H), 2.14 (br s, 2H), 1.97-1.91 (m, 2H), 1.88 (s, 3H), 1.57 (br d, J = 14.9 Hz, 2H), 1.50 (s, 3H), 1.45-1.37 (m, 2H), 1.33-1.25 (m, 2H), 1.19-1.14 (m, 5H) | 978.8 | B | C | D | C |
| 8 | 1H NMR (400 MHz, MeOD-d4)δ: 8.68 (s, 1H), 8.47 (br s, 1H), 8.22 (d, J = 5.6 Hz, 1H), 7.68 (d, J = 8.5 Hz, 1H), 7.61 (d, J = 9.0 Hz, 1H), 7.50 (d, J = 8.6 Hz, 1H), 7.38 (br d, J = 5.9 Hz, 2H), 7.31-7.21 (m, 2H), 5.74 (br d, J = 5.8 Hz, 1H), 5.07 (dd, J = 5.4, 12.1 Hz, 1H), 4.12-4.07 (m, 2H), 4.01 (br d, J = 9.5 Hz, 2H), 3.50 (s, 5H), 3.11-2.99 (m, 5H), 2.95 (br s, 2H), 2.89-2.80 (m, 2H), 2.79-2.69 (m, 3H), 2.62 (br s, 1H), 2.43 (br s, 1H), 2.28 (s, 3H), 2.24-2.04 (m, 5H), 1.99-1.84 (m, 4H), 1.69 (d, J = 6.4 Hz, 3H), 1.51-1.37 (m, 4H), 1.22-1.17 (m, 3H) | 950.4 | A | B | B | B |
| 9 | 1H NMR (400 MHz, MeOD-d4) δ: 8.68 (s, 1H), 8.42 (br s, 1H), 8.22 (d, J = 5.3 Hz, 1H), 7.68 (d, J = 8.5 Hz, 1H), 7.61 (d, J = 9.0 Hz, 1H), 7.49 (dd, J = 1.6, 8.9 Hz, 1H), 7.41-7.34 (m, 2H), 7.30-7.21 (m, 2H), 5.74 (br d, J = 6.1 Hz, 1H), 5.07 (dd, J = 5.4, 12.4 Hz, 1H), 4.09 (br d, J = 12.9 Hz, 2H), 4.01 (br d, J = 12.3 Hz, 2H), 3.56 (br d, J = 9.0 Hz, 2H), 3.50 (s, 3H), 3.10-2.97 (m, 7H), 2.96-2.81 (m, 3H), 2.78-2.69 (m, 3H), 2.63 (br s, 1H), 2.44 (br t, J = 9.7 Hz, 1H), 2.28 (s, 3H), 2.25-2.15 (m, 3H), 2.13-2.06 (m, 1H), 1.99 (br d, J = 14.4 Hz, 1H), 1.92 (br d, J = 12.9 Hz, 3H), 1.68 (d, J = 6.4 Hz, 3H), 1.56-1.36 (m, 4H), 1.20 (d, J = 6.1 Hz, 3H) | 950.4 | C | B | D | C |
| 10 | 1H NMR (400 MHz, MeOD-d4) δ: 8.64 (s, 1H), 8.44 (s, 2H), 8.22 (d, J = 5.5 Hz, 1H), 7.68 (d, J = 8.5 Hz, 1H), 7.63-7.58 (m, 1H), 7.50 (d, J = 9.1 Hz, 1H), 7.40-7.34 (m, 2H), 7.31-7.22 (m, 2H), 5.29 (s, 2H), 5.07 (dd, J = 5.4, 12.6 Hz, 1H), 4.60 (br s, 2H), 4.09 (br d, J = 11.6 Hz, 2H), 4.01 (br d, J = 11.9 Hz, 2H), 3.55 (br s, 2H), 3.51 (s, 3H), 3.12-2.96 (m, 5H), 2.96-2.81 (m, 3H), 2.78-2.68 (m, 3H), 2.62 (br s, 1H), 2.43 (br t, J = 9.4 Hz, 1H), 2.34 (s, 3H), 2.20 (br s, 3H), 2.12-2.07 (m, 1H), 2.02-1.89 (m, 4H), 1.57-1.35 (m, 4H), 1.20 (d, J = 6.1 Hz, 3H) | 936.5 | A | B | B | B |
| 11 | 1H NMR (400 MHz, MeOD-d4) δ: 8.64 (s, 1H), 8.23 (d, J = 5.1 Hz, 1H), 7.63 (dd, J = 8.6, 15.1 Hz, 2H), 7.55-7.49 (m, 1H), 7.38 (s, 1H), 7.30 (d, J = 5.1 Hz, 1H), 6.99 (s, 1H), 6.83 (d, J = 7.4 Hz, 1H), 5.74 (d, J = 6.0 Hz, 1H), 5.06 (dd, J = 5.5, 12.8 Hz, 1H), 3.72-3.56 (m, 9H), 3.49 (s, 3H), 3.45 (s, 1H), 3.22-3.11 (m, 4H), 2.97 (s, 3H), 2.89-2.64 (m, 7H), 2.45-2.33 (m, 2H), 2.28 (s, 3H), 2.11 (d, J = 13.3 Hz, 3H), 1.94 (d, J = 7.4 Hz, 3H), 1.87-1.79 (m, 1H), 1.68 (d, J = 6.3 Hz, 3H), 1.52 (d, J = 6.9 Hz, 1H) | 936.3 | B | C | C | C |

TABLE 2-continued

Characterization of exemplary bifunctional compounds of the present disclosure.

| Ex. | NMR | Mean Observed Mass | *G2019S DC50 (nM) | **G2019S Dmax (%) | *WT DC50 (nM) | **WT Dmax (%) |
|---|---|---|---|---|---|---|
| 12 | 1H NMR (400 MHz, MeOD-d4) δ: 8.64 (s, 1H), 8.23 (d, J = 5.1 Hz, 1H), 7.63 (dd, J = 8.6, 15.1 Hz, 2H), 7.55-7.49 (m, 1H), 7.38 (s, 1H), 7.30 (d, J = 5.1 Hz, 1H), 6.99 (s, 1H), 6.83 (d, J = 7.4 Hz, 1H), 5.74 (d, J = 6.0 Hz, 1H), 5.06 (dd, J = 5.5, 12.8 Hz, 1H), 3.72-3.56 (m, 9H), 3.49 (s, 3H), 3.45 (s, 1H), 3.22-3.11 (m, 4H), 2.97 (s, 3H), 2.89-2.64 (m, 7H), 2.45-2.33 (m, 2H), 2.28 (s, 3H), 2.11 (d, J = 13.3 Hz, 3H), 1.94 (d, J = 7.4 Hz, 3H), 1.87-1.79 (m, 1H), 1.68 (d, J = 6.3 Hz, 3H), 1.52 (d, J = 6.9 Hz, 1H) | 936.4 | D | C | D | |
| 13 | 1H NMR (400 MHz, MeOD-d4) δ: 8.64 (s, 1H), 8.23 (d, J = 5.1 Hz, 1H), 7.63 (dd, J = 8.6, 15.1 Hz, 2H), 7.55-7.49 (m, 1H), 7.38 (s, 1H), 7.30 (d, J = 5.1 Hz, 1H), 6.99 (s, 1H), 6.83 (d, J = 7.4 Hz, 1H), 5.74 (d, J = 6.0 Hz, 1H), 5.06 (dd, J = 5.5, 12.8 Hz, 1H), 3.72-3.56 (m, 9H), 3.49 (s, 3H), 3.45 (s, 1H), 3.22-3.11 (m, 4H), 2.97 (s, 3H), 2.89-2.64 (m, 7H), 2.45-2.33 (m, 2H), 2.28 (s, 3H), 2.11 (d, J = 13.3 Hz, 3H), 1.94 (d, J = 7.4 Hz, 3H), 1.87-1.79 (m, 1H), 1.68 (d, J = 6.3 Hz, 3H), 1.52 (d, J = 6.9 Hz, 1H) | 922.4 | B | B | D | C |
| 14 | 1H NMR (400 MHz, MeOD-d4) δ: 8.75-8.61 (m, 1H), 8.38 (s, 2H), 8.28-8.18 (m, 1H), 7.63 (dd, J = 8.7, 13.6 Hz, 2H), 7.57-7.49 (m, 1H), 7.41 (s, 1H), 7.35-7.28 (m, 1H), 6.98 (s, 1H), 6.87-6.80 (m, 1H), 5.74 (br d, J = 6.0 Hz, 1H), 5.06 (dd, J = 5.6, 12.5 Hz, 1H), 4.62 (br s, 1H), 3.80-3.65 (m, 5H), 3.57 (br d, J = 9.0 Hz, 3H), 3.51-3.42 (m, 4H), 3.23-3.10 (m, 3H), 3.06-2.92 (m, 2H), 2.88-2.79 (m, 5H), 2.74 (br d, J = 15.9 Hz, 2H), 2.70-2.62 (m, 2H), 2.41 (br s, 1H), 2.28 (s, 3H), 2.15-2.01 (m, 3H), 1.93 (br d, J = 8.4 Hz, 2H), 1.87-1.73 (m, 2H), 1.70-1.61 (m, 5H), 1.52 (br d, J = 6.5 Hz, 2H) | 950.4 | C | C | D | B |
| 15 | 1H NMR (400 MHz, MeOD-d4) δ: 8.67 (s, 1H), 8.28 (d, J = 5.5 Hz, 1H), 7.69 (d, J = 8.5 Hz, 1H), 7.64-7.60 (m, 1H), 7.50 (dd, J = 1.8, 8.9 Hz, 1H), 7.45 (s, 1H), 7.39-7.33 (m, 2H), 7.26 (dd, J = 2.3, 8.4 Hz, 1H), 5.74 (d, J = 5.8 Hz, 1H), 5.07 (dd, J = 5.5, 12.4 Hz, 1H), 3.85 (s, 4H), 3.57-3.52 (m, 4H), 3.51-3.47 (m, 3H), 3.21-3.13 (m, 4H), 3.02 (t, J = 7.2 Hz, 2H), 2.88-2.80 (m, 5H), 2.78-2.69 (m, 4H), 2.28 (d, J = 0.9 Hz, 3H), 2.14-2.07 (m, 1H), 2.04-1.97 (m, 2H), 1.68 (d, J = 6.4 Hz, 3H) | 868.3 | B | B | D | B |
| 17 | 1H NMR (400 MHz, MeOD-d4) δ: 8.56 (d, J = 8.9 Hz, 1H), 8.23 (d, J = 5.3 Hz, 1H), 7.66 (d, J = 8.5 Hz, 1H), 7.63-7.54 (m, 2H), 7.37 (s, 1H), 7.35 (d, J = 2.1 Hz, 1H), 7.30 (d, J = 5.4 Hz, 1H), 7.22 (dd, J = 2.3, 8.6 Hz, 1H), 5.74 (q, J = 6.0 Hz, 1H), 5.06 (dd, J = 5.4, 12.6 Hz, 1H), 4.02 (br d, J = 13.3 Hz, 2H), 3.68-3.62 (m, 4H), 3.59 (br t, J = 7.6 Hz, 2H), 3.50 (s, 3H), 3.02-2.97 (m, 3H), 2.91-2.79 (m, 2H), 2.78-2.69 (m, 2H), 2.68-2.59 (m, 6H), 2.42 (br t, J = 10.4 Hz, 1H), 2.28 (d, J = 1.0 Hz, 3H), 2.15-2.07 (m, 1H), 1.88 (br d, J = 12.6 Hz, 2H), 1.69 (d, J = 6.4 Hz, 3H), 1.29 (br s, 3H) | 894.6 | C | B | D | B |
| 18 | 1H NMR (400 MHz, MeOD-d4) δ: 8.65 (s, 1H), 8.29 (br s, 2H), 8.23 (d, J = 5.4 Hz, 1H), 7.72 (d, J = 8.5 Hz, 1H), 7.64-7.59 (m, 1H), 7.51 (dd, J = 1.8, 9.0 Hz, 1H), 7.42 (d, J = 2.1 Hz, 1H), 7.39 (s, 1H), 7.33-7.27 (m, 2H), 5.82-5.69 (m, 1H), 5.15-5.02 (m, 1H), 4.24 (br d, J = 13.5 Hz, 2H), 3.66 (br s, 4H), 3.58 (br d, J = 11.6 Hz, 2H), 3.50 (s, 3H), 3.13-2.99 (m, 4H), 2.94-2.81 (m, 1H), 2.79-2.58 (m, 6H), 2.56 (s, 1H), 2.38 (br d, J = 7.1 Hz, 1H), 2.28 (s, 3H), 2.26-2.07 (m, 5H), 1.99 (br s, 1H), 1.90-1.76 (m, 2H), 1.68 (d, J = 6.4 Hz, 3H), 1.57-1.42 (m, 3H) | 922.6 | C | B | D | C |
| 20 | 1H NMR (400 MHz, MeOD-d4) δ: 8.67 (s, 1H), 8.34 (br s, 2H), 8.27 (d, J = 5.3 Hz, 1H), 7.57 (dd, J = 8.6, 18.2 Hz, 2H), 7.46 (dd, J = 1.6, 9.0 Hz, 1H), 7.42 (s, 1H), 7.34 (d, J = 5.3 Hz, 1H), 6.76 (d, J = 1.9 Hz, 1H), 6.60 (br d, J = 8.4 Hz, 1H), 5.74 (br d, J = 5.8 Hz, 1H), 5.04 (dd, J = 5.4, 12.7 Hz, 1H), 4.22 (br s, 8H), 3.82-3.71 (m, 6H), 3.67 (br t, J = 4.9 Hz, 2H), 3.48 (s, 3H), 3.28 (br s, 1H), 2.94-2.80 (m, 7H), 2.79-2.61 (m, 3H), 2.26 (s, 3H), 2.13-2.03 (m, 1H), 1.67 (d, J = 6.3 Hz, 3H) | 910.5 | D | | D | |
| 21 | 1H NMR (400 MHz, MeOD-d4) δ: 8.65 (s, 1H), 8.35 (s, 2H), 8.25 (d, J = 5.4 Hz, 1H), 7.64 (dd, J = 8.9, 18.9 Hz, 2H), 7.53-7.47 (m, 1H), 7.40 (s, 1H), 7.36-7.30 (m, 2H), 7.25-7.19 (m, 1H), 5.78-5.71 (m, 1H), 5.06 (dd, J = 5.7, 12.7 Hz, 1H), 4.05 (br d, J = 13.5 Hz, 2H), 3.72 (br s, 4H), 3.52-3.48 (m, 4H), 3.11-2.96 (m, 7H), 2.90-2.70 (m, 12H), 2.43 (br d, J = 4.4 Hz, 2H), 2.28 (d, J = 1.0 Hz, 3H), 2.11 (br d, J = 5.3 Hz, 1H), 1.91 (br d, J = 9.8 Hz, 3H), 1.69 (d, J = 6.4 Hz, 3H), 1.31 (br d, J = 14.6 Hz, 3H) | 951.6 | D | B | D | |
| 22 | 1H NMR (400 MHz, MeOD-d4) δ: 8.61 (s, 1H), 8.48 (br s, 1H), 8.23 (d, J = 5.3 Hz, 1H), 7.67 (d, J = 8.5 Hz, 1H), 7.63-7.59 (m, 1H), 7.55-7.50 (m, 1H), 7.39-7.34 (m, 2H), 7.30 (d, J = 5.1 Hz, 1H), 7.22 (dd, J = 2.3, 8.6 Hz, 1H), 5.74 (br d, J = 6.1 Hz, 1H), 5.19 (s, 1H), 4.11-4.03 (m, 2H), 3.65 (br s, 4H), 3.50 (s, 3H), 3.42-3.37 (m, 1H), 3.02 (br t, J = 11.8 Hz, 2H), 2.92-2.80 (m, 4H), 2.79-2.76 (m, 4H), 2.74-2.64 (m, 4H), 2.55 (br s, 1H), 2.33 (br d, J = 7.6 Hz, 1H), 2.28 (d, J = 1.0 Hz, 3H), 2.15-2.05 (m, 2H), 2.03-1.96 (m, 2H), 1.91 (br d, J = 11.5 Hz, 2H), 1.83-1.74 (m, 2H), 1.68 (d, J = 6.3 Hz, 3H), 1.44-1.27 (m, 3H) | 986.4 | A | B | A | B |
| 23 | 1H NMR (400 MHz, MeOD-d4) δ: 8.69 (s, 1H), 8.44 (s, 1H), 8.27 (d, J = 5.3 Hz, 1H), 7.72-7.58 (m, 2H), 7.52 (dd, J = 1.7, 8.9 Hz, 1H), 7.42 (s, 1H), 7.37-7.31 (m, 2H), 7.22 (dd, J = 2.3, 8.6 Hz, 1H), 5.76 (br d, J = 6.6 Hz, 1H), 5.08 (dd, J = 5.5, 12.5 Hz, 1H), 4.06 (br d, J = 13.1 Hz, 2H), 3.71 (br s, 4H), 3.64 (br d, J = 15.3 Hz, 2H), 3.52 (s, 3H), 3.11-2.95 (m, 5H), 2.87-2.69 (m, 11H), 2.30 (s, 3H), 2.17-2.09 (m, 1H), 2.01 (br d, J = 12.9 Hz, 2H), 1.86 (br d, J = 11.9 Hz, 2H), 1.70 (d, J = 6.4 Hz, 3H), 1.56-1.45 (m, 2H), 1.38-1.23 (m, 5H) | 950.6 | B | B | C | B |
| 24 | 1H NMR (400 MHz, MeOD-d4) δ: 8.65 (s, 1H), 8.47 (br s, 1H), 8.24 (d, J = 5.3 Hz, 1H), 7.67 (d, J = 8.5 Hz, 1H), 7.64-7.59 (m, 1H), 7.52 (d, J = 9.0 Hz, 1H), 7.41-7.34 (m, 2H), 7.32 (d, J = 5.3 Hz, 1H), 7.23 (dd, J = 2.1, 8.6 Hz, 1H), 5.78-5.70 (m, | 894.5 | B | B | B | C |

TABLE 2-continued

Characterization of exemplary bifunctional compounds of the present disclosure.

| Ex. | NMR | Mean Observed Mass | *G2019S DC50 (nM) | **G2019S Dmax (%) | *WT DC50 (nM) | **WT Dmax (%) |
|---|---|---|---|---|---|---|
| | 1H), 5.07 (dd, J = 5.4, 12.6 Hz, 1H), 4.08 (br d, J = 12.9 Hz, 4H), 3.82 (br s, 2H), 3.69 (br s, 4H), 3.50 (s, 3H), 3.27 (br s, 1H), 3.07-2.96 (m, 4H), 2.92-2.81 (m, 1H), 2.78-2.63 (m, 2H), 2.57 (br s, 4H), 2.28 (s, 3H), 2.15-2.06 (m, 1H), 1.95-1.81 (m, 3H), 1.68 (d, J = 6.3 Hz, 3H), 1.44-1.32 (m, 2H) | | | | | |
| 25 | 1H NMR (400 MHz, MeOD-d4) δ: 8.64 (s, 1H), 8.45 (s, 1H), 8.25 (d, J = 5.3 Hz, 1H), 7.66 (d, J = 8.6 Hz, 1H), 7.63-7.60 (m, 1H), 7.52 (dd, J = 1.7, 8.9 Hz, 1H), 7.40 (s, 1H), 7.35-7.30 (m, 2H), 7.21 (dd, J = 2.2, 8.6 Hz, 1H), 5.74 (br d, J = 5.9 Hz, 1H), 5.06 (br dd, J = 5.4, 12.5 Hz, 1H), 4.05 (br d, J = 13.5 Hz, 2H), 3.71 (br s, 4H), 3.50 (s, 3H), 3.00 (br t, J = 11.4 Hz, 7H), 2.88-2.67 (m, 13H), 2.40 (br d, J = 6.3 Hz, 2H), 2.28 (s, 3H), 2.15-2.06 (m, 1H), 1.90 (br d, J = 10.9 Hz, 3H), 1.68 (d, J = 6.4 Hz, 3H), 1.37-1.25 (m, 3H) | 951.6 | B | A | C | A |
| 26 | 1H NMR: (400 MHz, DMSO) δ: 13.45 (s, 1H), 11.07 (s, 1H), 10.29 (s, 1H), 8.53 (s, 1H), 8.21-8.18 (m, 1H), 7.66-7.58 (m, 3H), 7.29 (s, 1H), 7.24-7.17 (m, 2H), 6.86-6.79 (m, 1H), 5.80-5.68 (m, 1H), 5.06 (dd, J = 5.4, 12.9 Hz, 1H), 4.08 (s, 3H), 4.02 (d, J = 13.3 Hz, 2H), 3.35-3.27 (m, 8H), 2.99-2.79 (m, 4H), 2.69-2.53 (m, 3H), 2.33 (s, 1H), 2.20 (s, 3H), 2.07-1.97 (m, 1H), 1.75 (d, J = 11.5 Hz, 2H), 1.57 (d, J = 6.4 Hz, 3H), 1.23-1.11 (m, 2H) | 851.3 | D | A | D | |
| 27 | 1H NMR (400 MHz, MeOD-d4) δ: 8.67 (s, 1H), 8.26 (d, J = 5.3 Hz, 1H), 7.70 (d, J = 8.5 Hz, 1H), 7.62 (d, J = 8.9 Hz, 1H), 7.50 (d, J = 1.8 Hz, 1H), 7.40 (s, 1H), 7.37 (d, J = 2.1 Hz, 1H), 7.32 (d, J = 5.5 Hz, 1H), 7.24 (dd, J = 2.3, 8.6 Hz, 1H), 5.75 (d, J = 5.8 Hz, 1H), 5.08 (dd, J = 5.5, 12.5 Hz, 1H), 3.70 (d, J = 4.6 Hz, 4H), 3.67-3.59 (m, 3H), 3.51 (s, 3H), 3.48 (d, J = 3.8 Hz, 4H), 3.10-3.02 (m, 2H), 2.90-2.81 (m, 3H), 2.80-2.72 (m, 6H), 2.68-2.59 (m, 5H), 2.35 (d, J = 7.3 Hz, 2H), 2.29 (d, J = 0.9 Hz, 3H), 2.16-2.06 (m, 3H), 1.95 (s, 1H), 1.69 (d, J = 6.3 Hz, 3H), 1.59-1.48 (m, 2H) | 951.3 | D | B | D | |
| 28 | 1H NMR (400 MHz, MeOD-d4) δ: 8.72 (s, 1H), 8.31 (s, 2H), 8.25 (d, J = 5.4 Hz, 1H), 7.69-7.54 (m, 2H), 7.48 (dd, J = 1.8, 8.9 Hz, 1H), 7.43 (s, 1H), 7.37-7.29 (m, 2H), 7.21 (dd, J = 2.3, 8.7 Hz, 1H), 5.74 (br d, J = 5.9 Hz, 1H), 5.06 (dd, J = 5.4, 12.4 Hz, 1H), 4.06 (br t, J = 13.4 Hz, 4H), 3.52-3.49 (m, 3H), 3.27-3.15 (m, 4H), 3.11-2.90 (m, 9H), 2.87-2.66 (m, 9H), 2.42 (br d, J = 6.3 Hz, 2H), 2.28 (d, J = 0.9 Hz, 3H), 2.16-2.05 (m, 1H), 1.95-1.83 (m, 3H), 1.68 (d, J = 6.4 Hz, 3H), 1.34-1.24 (m, 5H) | 965.7 | D | B | D | |
| 29 | 1H NMR (400 MHz, MeOD-d4) δ: 8.78 (s, 1H), 8.47 (s, 2H), 8.17 (d, J = 5.3 Hz, 1H), 7.68 (d, J = 8.6 Hz, 1H), 7.58 (d, J = 9.0 Hz, 1H), 7.37-7.32 (m, 2H), 7.29-7.22 (m, 3H), 5.07 (dd, J = 5.4, 12.4 Hz, 1H), 4.75 (br s, 1H), 4.71 (s, 1H), 4.09 (br d, J = 13.3 Hz, 2H), 3.70 (s, 1H), 3.63 (br d, J = 11.6 Hz, 2H), 3.58 (br s, 4H), 3.48 (s, 3H), 3.16 (br s, 1H), 3.08-3.01 (m, 4H), 2.88-2.82 (m, 1H), 2.79-2.72 (m, 2H), 2.68 (br d, J = 13.1 Hz, 1H), 2.60 (br s, 3H), 2.43 (br d, J = 7.0 Hz, 2H), 2.23-2.17 (m, 3H), 2.13-2.07 (m, 1H), 1.98-1.86 (m, 6H), 1.61 (br d, J = 11.4 Hz, 2H), 1.51 (s, 3H), 1.46-1.39 (m, 2H), 1.33-1.28 (m, 1H) | 950.6 | B | C | D | C |
| 30 | 1H NMR (400 MHz, MeOD-d4) δ: 8.85 (s, 1H), 8.39 (s, 2H), 8.18 (d, J = 5.4 Hz, 1H), 7.65 (d, J = 8.6 Hz, 1H), 7.58 (d, J = 8.9 Hz, 1H), 7.37-7.30 (m, 2H), 7.29-7.22 (m, 2H), 7.19 (dd, J = 2.0, 8.6 Hz, 1H), 5.06 (dd, J = 5.4, 12.4 Hz, 1H), 4.75 (br s, 1H), 4.71 (s, 1H), 4.06-3.96 (m, 3H), 3.88-3.81 (m, 1H), 3.71 (s, 1H), 3.47 (d, J = 2.0 Hz, 4H), 3.25 (br d, J = 10.8 Hz, 1H), 3.22-3.14 (m, 5H), 3.12 (br d, J = 12.9 Hz, 1H), 3.01-2.93 (m, 3H), 2.90 (br d, J = 4.8 Hz, 1H), 2.88-2.85 (m, 1H), 2.84-2.74 (m, 6H), 2.74-2.64 (m, 2H), 2.39 (br d, J = 4.3 Hz, 2H), 2.28-2.04 (m, 2H), 1.91-1.83 (m, 6H), 1.51 (s, 3H), 1.33-1.19 (m, 6H) | 979.7 | B | C | D | C |
| 31 | 1H NMR (400 MHz, MeOD-d4) δ: 8.73-8.64 (m, 1H), 8.49 (br s, 1H), 8.23 (d, J = 5.5 Hz, 1H), 7.68 (d, J = 8.5 Hz, 1H), 7.64-7.56 (m, 1H), 7.49 (br d, J = 9.0 Hz, 1H), 7.41-7.31 (m, 2H), 7.30 (br d, J = 4.8 Hz, 1H), 7.26-7.19 (m, 1H), 5.73 (br d, J = 6.5 Hz, 1H), 5.07 (br dd, J = 5.5, 12.3 Hz, 1H), 3.98 (br d, J = 12.6 Hz, 2H), 3.57-3.37 (m, 9H), 3.23-3.04 (m, 2H), 2.96-2.68 (m, 12H), 2.61 (br s, 4H), 2.33 (br d, J = 7.4 Hz, 2H), 2.28 (s, 2H), 2.17-1.98 (m, 4H), 1.88 (br s, 1H), 1.68 (d, J = 6.4 Hz, 2H), 1.61-1.42 (m, 2H), 1.31-1.14 (m, 4H) | 965.8 | D | C | D | |
| 32 | 1H NMR (400 MHz, MeOD-d4) δ: 8.54 (dd, J = 1.3, 8.9 Hz, 1H), 8.51 (s, 1H), 8.22 (d, J = 5.4 Hz, 1H), 7.65 (d, J = 8.5 Hz, 1H), 7.57 (d, J = 8.9 Hz, 1H), 7.37-7.32 (m, 2H), 7.30 (s, 1H), 7.27 (d, J = 5.3 Hz, 1H), 7.20 (dd, J = 2.3, 8.6 Hz, 1H), 5.06 (dd, J = 5.4, 12.4 Hz, 1H), 4.75 (s, 1H), 4.70 (d, J = 1.5 Hz, 1H), 4.19 (br d, J = 12.5 Hz, 1H), 4.08-4.00 (m, 4H), 3.88 (br s, 1H), 3.77-3.71 (m, 1H), 3.70 (s, 1H), 3.47 (d, J = 0.8 Hz, 3H), 3.05-2.93 (m, 6H), 2.89-2.81 (m, 3H), 2.81-2.75 (m, 4H), 2.74-2.63 (m, 4H), 2.44 (br d, J = 6.0 Hz, 2H), 2.14-2.07 (m, 1H), 1.92-1.87 (m, 6H), 1.51 (s, 3H), 1.32 (br s, 2H) | 952.6 | B | C | D | |
| 33 | 1H NMR (400 MHz, MeOD-d4) δ: 8.88 (s, 1H), 8.39 (s, 1H), 8.16 (d, J = 5.4 Hz, 1H), 7.68 (d, J = 8.6 Hz, 1H), 7.58 (d, J = 8.9 Hz, 1H), 7.38-7.33 (m, 2H), 7.30-7.20 (m, 3H), 5.07 (br dd, J = 5.4, 12.4 Hz, 1H), 4.76 (br s, 1H), 4.72 (br s, 1H), 3.82 (br d, J = 9.6 Hz, 2H), 3.71 (s, 1H), 3.58 (br s, 3H), 3.54-3.51 (m, 1H), 3.50-3.46 (m, 6H), 3.21 (br t, J = 11.7 Hz, 2H), 2.88 (br t, J = 6.3 Hz, 2H), 2.83 (br d, J = 5.6 Hz, 1H), 2.78-2.75 (m, 1H), 2.73 (br s, 1H), 2.71-2.60 (m, 9H), 2.41-2.33 (m, 2H), 2.22-2.06 (m, 4H), 2.03 (br d, J = 7.1 Hz, 1H), 1.90-1.86 (m, 3H), 1.68-1.57 (m, 2H), 1.52 (s, 3H), 1.34-1.27 (m, 1H) | 965.7 | D | C | D | C |
| 34 | 1H NMR (400 MHz, MeOD-d4) δ: 8.76 (br s, 1H), 8.53 (s, 1H), 8.15 (d, J = 5.3 Hz, 1H), 7.68 (d, J = 8.5 Hz, 1H), 7.58 (d, J = 8.9 Hz, 1H), 7.36 (d, J = 2.1 Hz, 1H), 7.31 (s, 1H), 7.29-7.19 (m, 3H), 5.07 (dd, J = 5.5, 12.4 Hz, 1H), 4.75 (br s, 1H), 4.71 (br | 964.7 | B | C | D | |

TABLE 2-continued

Characterization of exemplary bifunctional compounds of the present disclosure.

| Ex. | NMR | Mean Observed Mass | *G2019S DC50 (nM) | **G2019S Dmax (%) | *WT DC50 (nM) | ** WT Dmax (%) |
|---|---|---|---|---|---|---|
| | s, 1H), 4.09 (br d, J = 12.8 Hz, 2H), 3.92 (br d, J = 11.5 Hz, 1H), 3.80 (br d, J = 12.0 Hz, 1H), 3.71 (s, 1H), 3.54 (br s, 2H), 3.47 (s, 3H), 3.07-2.97 (m, 6H), 2.91-2.81 (m, 2H), 2.75-2.65 (m, 3H), 2.57 (br s, 1H), 2.28-2.19 (m, 3H), 2.15-2.09 (m, 2H), 2.04 (br s, 1H), 1.93 (br d, J = 11.9 Hz, 2H), 1.88 (s, 3H), 1.58 (br d, J = 8.6 Hz, 2H), 1.50 (s, 3H), 1.42 (br d, J = 10.9 Hz, 2H), 1.35-1.27 (m, 4H), 1.11 (br t, J = 6.4 Hz, 3H) | | | | | |
| 35 | 1H NMR (400 MHz, MeOD-d4) δ: 8.83 (s, 1H), 8.45 (s, 1H), 8.18 (d, J = 5.3 Hz, 1H), 7.66 (d, J = 8.5 Hz, 1H), 7.58 (d, J = 8.9 Hz, 1H), 7.35-7.31 (m, 2H), 7.29-7.19 (m, 3H), 5.06 (br dd, J = 5.4, 12.3 Hz, 1H), 4.75-4.75 (m, 1H), 4.71 (br s, 1H), 4.06 (br s, 1H), 4.03 (br s, 1H), 3.70 (s, 1H), 3.62 (br s, 4H), 3.48 (s, 3H), 2.99 (br t, J = 12.0 Hz, 4H), 2.90 (br s, 2H), 2.86 (br d, J = 4.1 Hz, 1H), 2.87-2.85 (m, 1H), 2.82 (br s, 4H), 2.76 (br s, 2H), 2.73 (br s, 2H), 2.72-2.65 (m, 1H), 2.70-2.65 (m, 1H), 2.41 (br d, J = 5.5 Hz, 2H), 2.12-2.06 (m, 1H), 1.95-1.84 (m, 8H), 1.51 (s, 3H), 1.30 (br d, J = 11.4 Hz, 4H) | 965.6 | B | C | D | |
| 36 | 1H NMR (400 MHz, MeOD-d4) δ: 8.79 (br s, 1H), 8.55 (s, 1H), 8.16 (d, J = 5.4 Hz, 1H), 7.68 (d, J = 8.5 Hz, 1H), 7.57 (d, J = 9.0 Hz, 1H), 7.34 (br d, J = 12.4 Hz, 2H), 7.28-7.18 (m, 3H), 5.07 (br dd, J = 5.3, 12.3 Hz, 1H), 4.75 (br s, 1H), 4.70 (br s, 1H), 3.90 (br d, J = 11.4 Hz, 1H), 3.77 (br d, J = 11.6 Hz, 1H), 3.70 (s, 1H), 3.50-3.44 (m, 8H), 3.20 (br d, J = 12.9 Hz, 2H), 2.99 (br d, J = 3.1 Hz, 1H), 2.91-2.81 (m, 3H), 2.71 (br d, J = 10.9 Hz, 4H), 2.60 (br s, 4H), 2.49 (br t, J = 9.1 Hz, 1H), 2.33 (br d, J = 6.5 Hz, 2H), 2.24-2.13 (m, 1H), 2.13-2.08 (m, 1H), 2.03 (br d, J = 12.9 Hz, 2H), 1.90-1.86 (m, 4H), 1.51 (s, 4H), 1.36-1.23 (m, 4H), 1.16 (br t, J = 6.6 Hz, 3H) | 979.7 | D | C | D | |

*$DC_{50}$ Ranges: A < 10; 10 ≤ B < 50; 50 ≤ C < 100; D ≥ 100.
**$D_{Max}$ Ranges: A ≥ 70; 50 ≤ B < 70; C < 50

A novel bifunctional molecule, which contains a recruiting moiety that selectively or preferentially binds to a LRRK2 protein having at least one mutation that is G2019S and an E3 ubiquitin ligase recruiting moiety is described. The bifunctional molecules of the present disclosure actively ubiquitinate the mutated LRRK2, resulting in proteasomal degradation, leading to suppression of cellular proliferation and induction of apoptosis.

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the disclosure described herein. Such equivalents are intended to be encompassed by the following claims. It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

What is claimed is:

1. A compound having the chemical structure:

PTM-L-CLM, or a pharmaceutically acceptable salt thereof, wherein:

(a) the CLM is represented by the chemical structure:

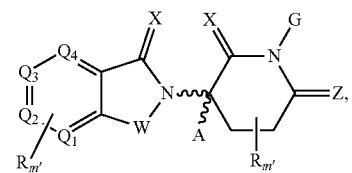

(a1)

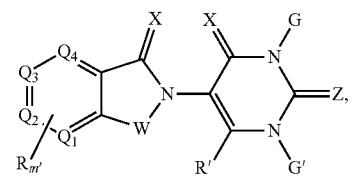

(b)

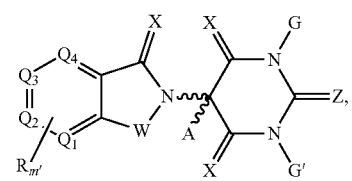

(c)

-continued

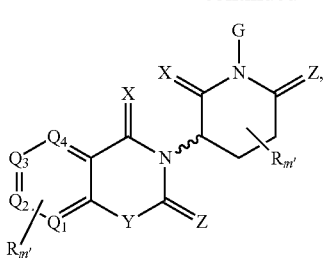

(d1)

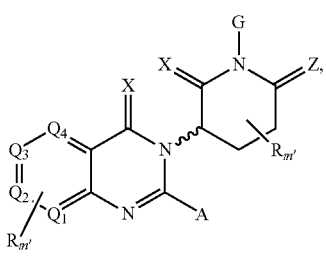

(e)

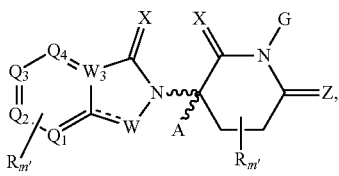

(a2)

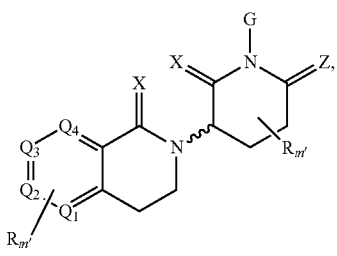

(d2)

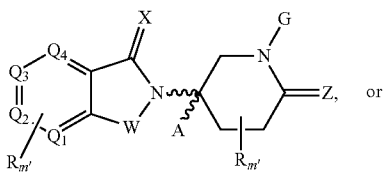

(a3)

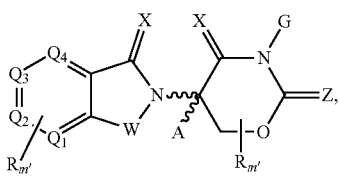

(a4)

wherein:
W is selected from $CH_2$, O, CHR, C=O, $SO_2$, NH, N, optionally substituted cyclopropyl group, optionally substituted cyclobutyl group, and N-alkyl;
$W_3$ is C or N;
each X is independently selected from absent, O, S, and $CH_2$,
Y is selected from $CH_2$, —C=CR', NH, N-alkyl, N-aryl, N-heteroaryl, N-cycloalkyl, N-heterocyclyl, O, and S;
Z is selected from absent, O, S, and $CH_2$;
G and G' are independently selected from H, unsubstituted or substituted linear or branched alkyl, OH, R'OCOOR, R'OCONRR", $CH_2$-heterocyclyl optionally substituted with R', and benzyl optionally substituted with R';
$Q_1$, $Q_2$, $Q_3$, and $Q_4$ represent C or N substituted with a group independently selected from H, R, N, and N-oxide;
A is independently selected from H, unsubstituted or substituted linear or branched alkyl, cycloalkyl, —Cl, and —F;
m' is 1, 2, 3, 4, 5, 6, 7, 8, 9, or 10;
R is a bond, H, —CONR'R", —C(=O)R', —OR', —NR'R", —SR', —$SO_2$R', —$SO_2$NR'R", —CR'R"—, —CR'NR'R"—, (—CR'O)$_n$R", optionally substituted heterocyclyl, aryl, optionally substituted alkyl-aryl, heteroaryl, unsubstituted or substituted linear or branched alkyl, optionally substituted alkoxyl group, optionally substituted heterocyclyl, —P(O)(OR')R", —P(O)R'R", —OP(O)(OR')R", —OP(O)R'R", —Cl, —F, —Br, —I, —$CF_3$, —CN, —NR'$SO_2$NR'R", —NR'CONR'R", —CONR-'COR", —NR'C(=N—CN)NR'R", —C(=N—CN)NR'R", —NR'C(=N—CN)R", —NR'C(=C—$NO_2$)NR'R", —$SO_2$NR'COR", —$NO_2$, —$CO_2$R', —C(C=N—OR')R", —CR'=CR'R", —CCR', —S(C=O)(C=N—R')R", —$SF_5$ and —$OCF_3$, wherein at least one R or W is modified to be covalently joined to the PTM, or the CLM;
R' and R" are independently selected from a bond, H, optionally substituted alkyl, optionally substituted cycloalkyl, optionally substituted aryl, optionally substituted heteroaryl, optionally substituted heterocyclic, and optionally substituted heterocyclyl;
n' is 1, 2, 3, 4, 5, 6, 7, 8, 9, or 10;
≡ represents a single bond or a double bond; and
∼ represents a bond that may be stereospecific or non-stereospecific;
(b) the PTM has a chemical structure selected from:

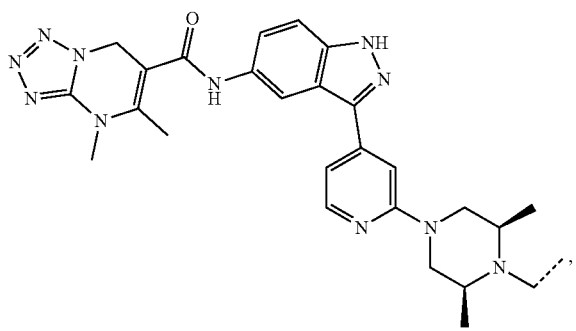

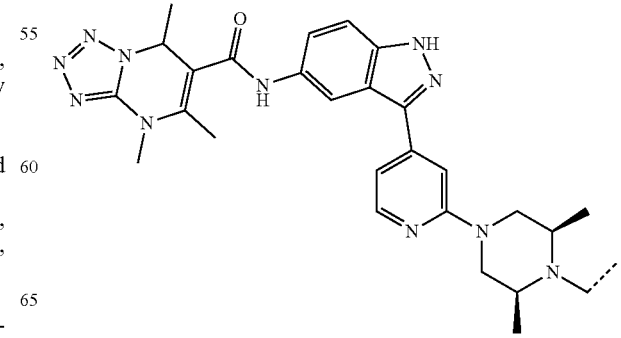

399
-continued
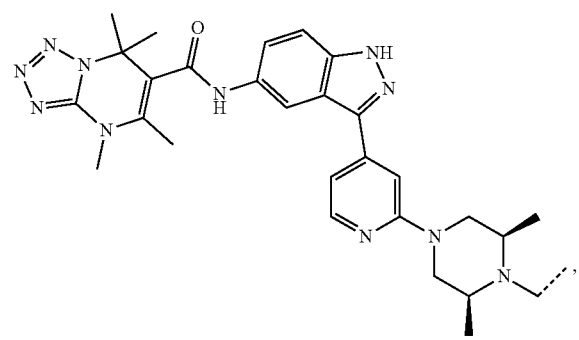
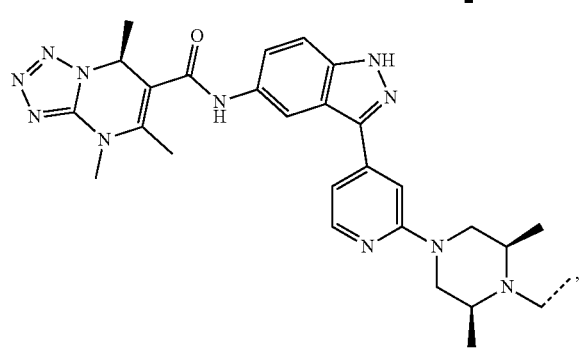
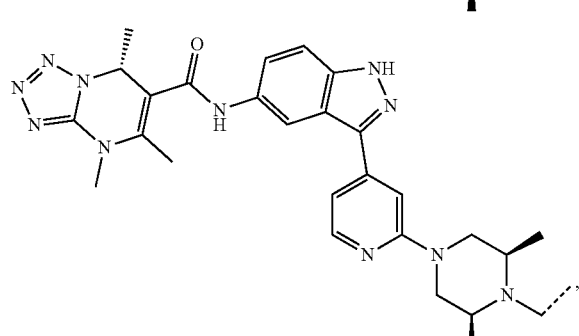
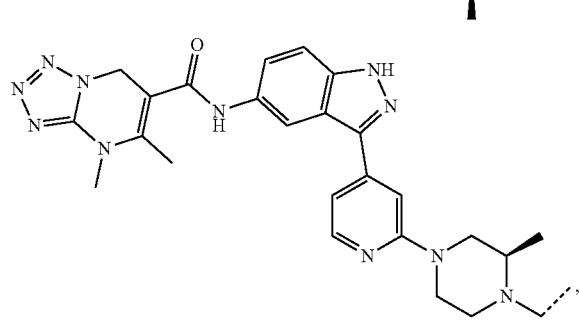
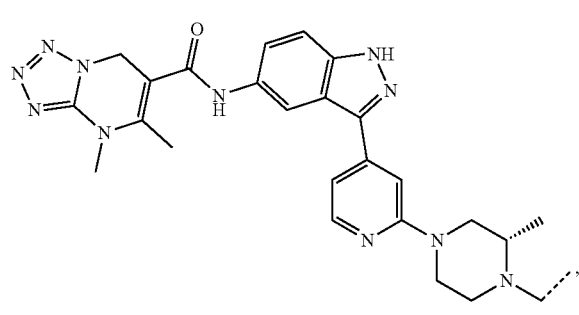
400
-continued
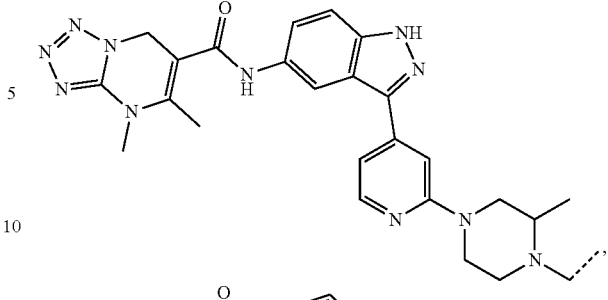
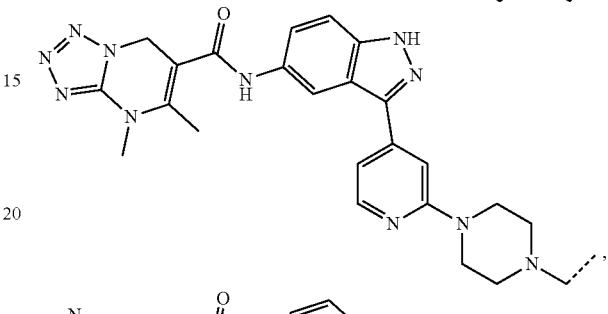
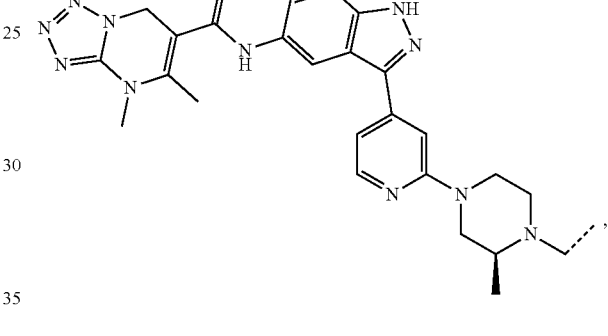
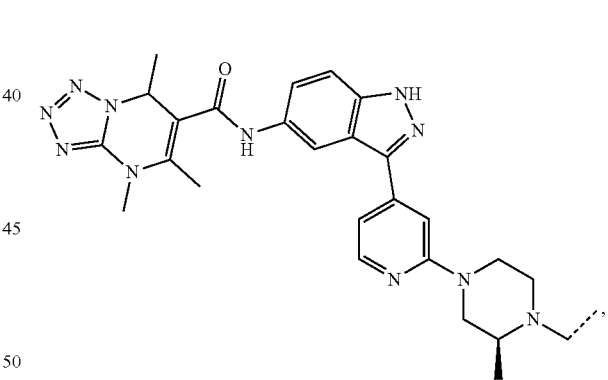
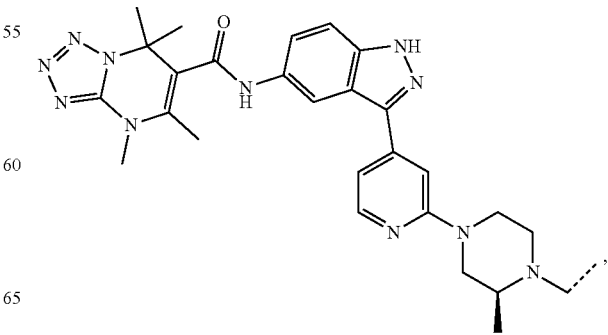

401
-continued
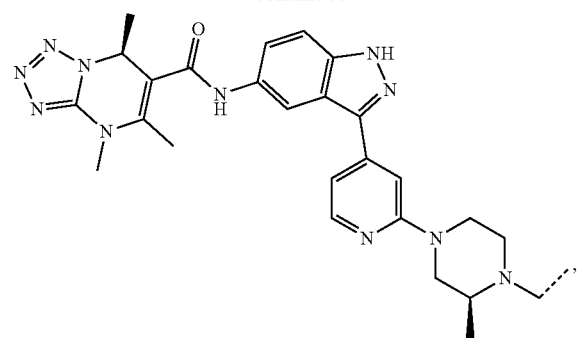
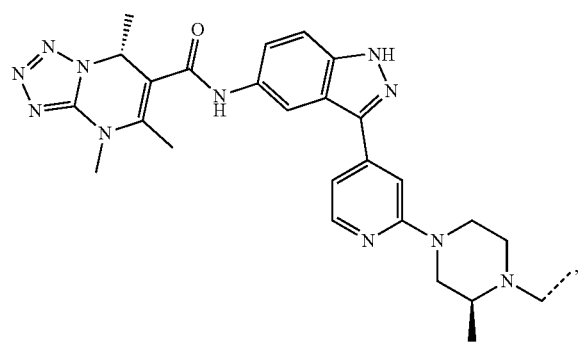
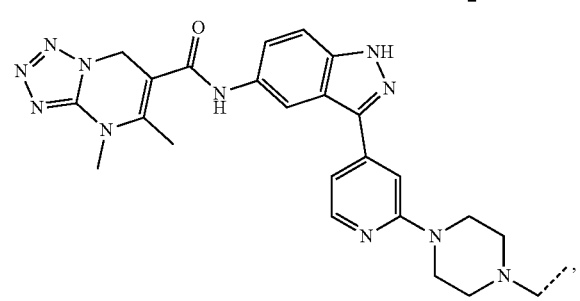
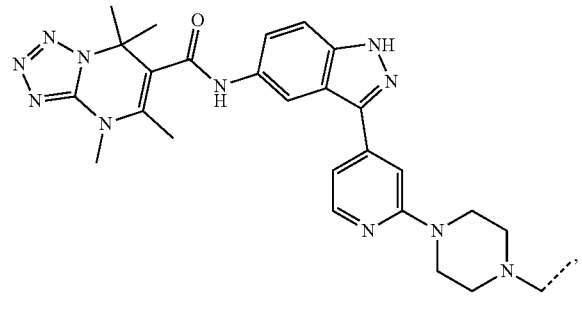
402
-continued
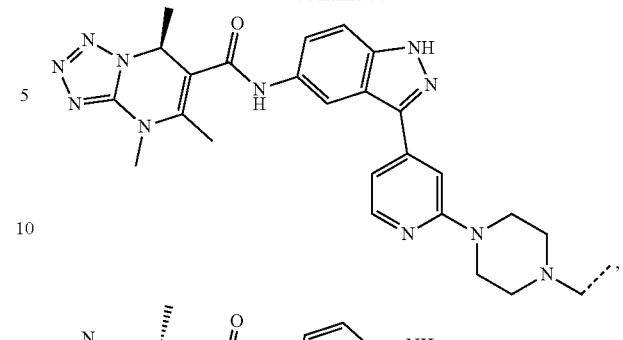
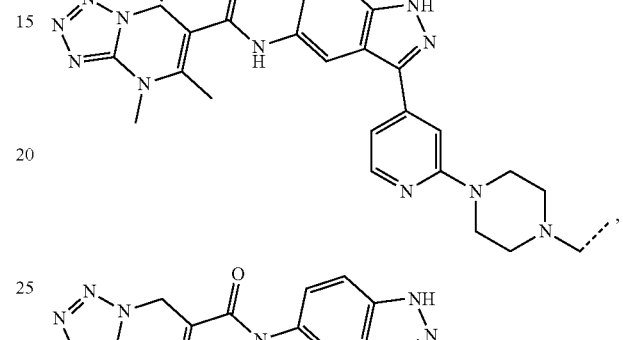
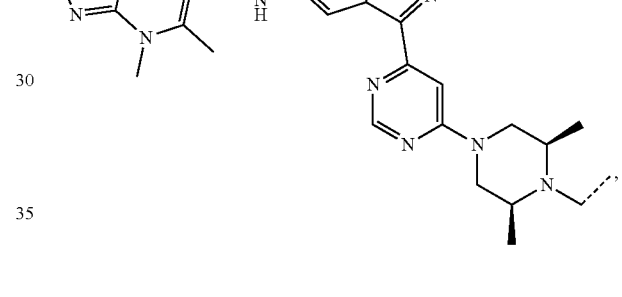
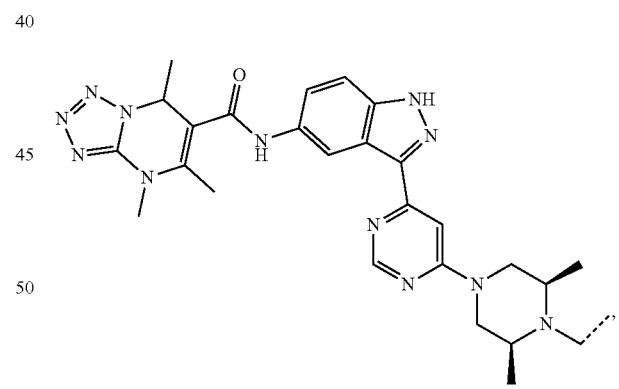
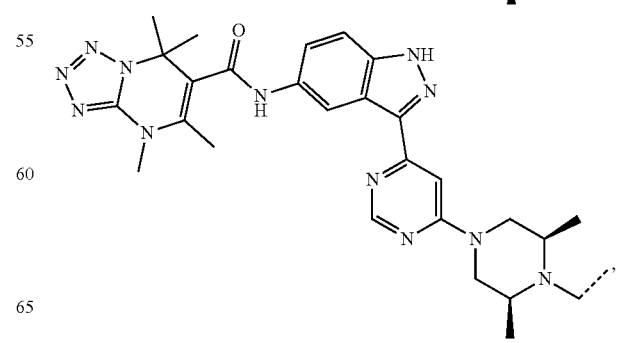

403
-continued
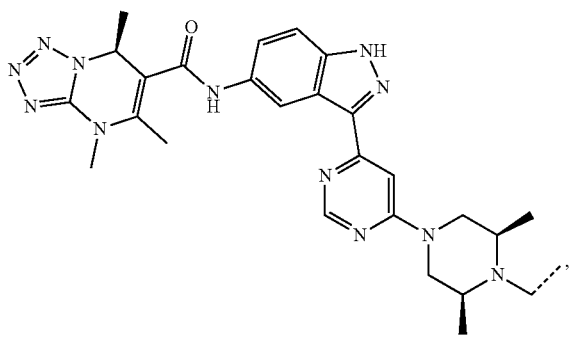
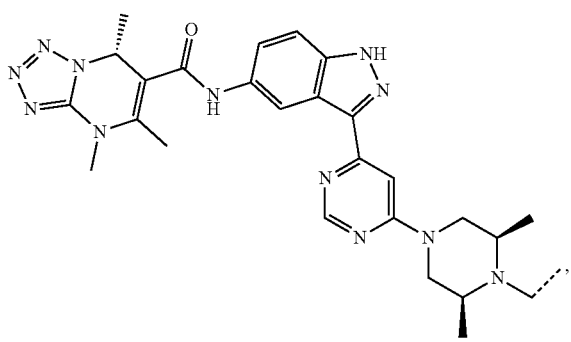
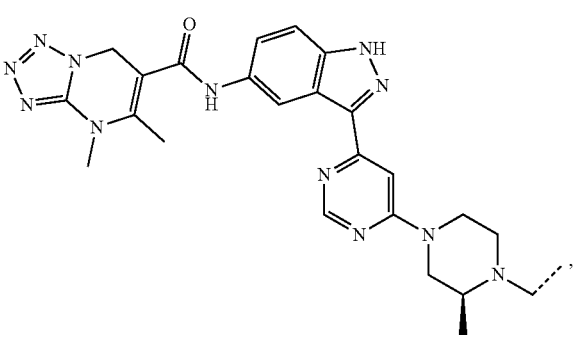
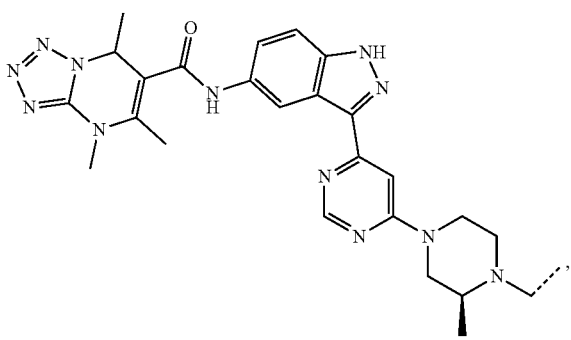
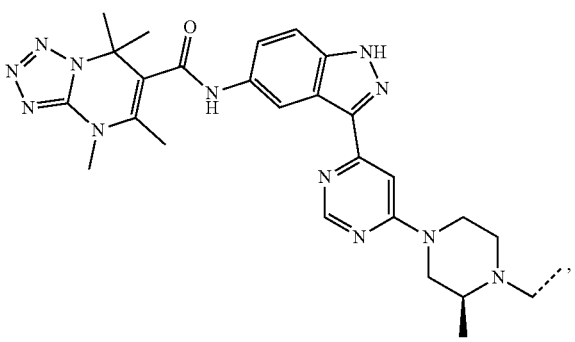
404
-continued
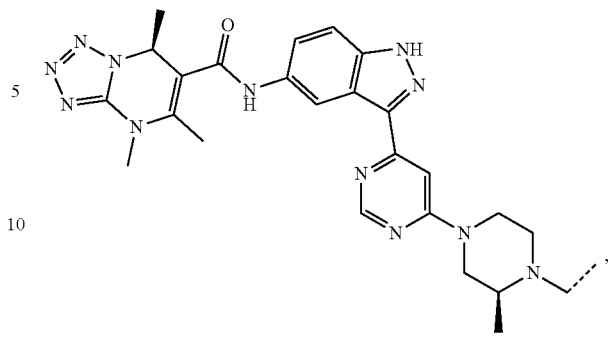
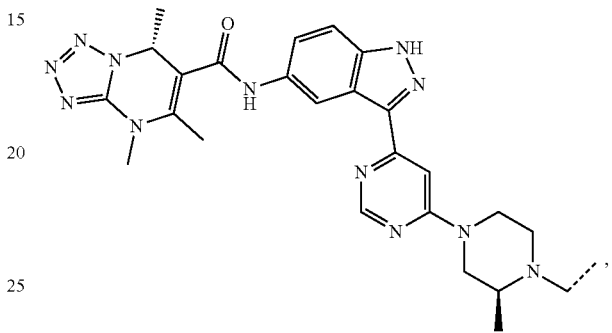
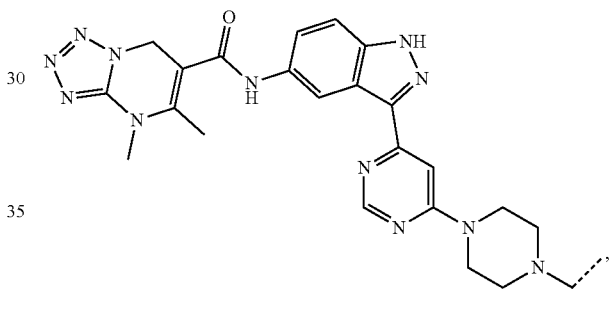
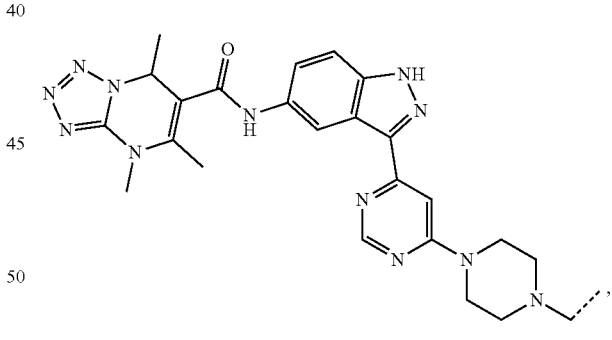
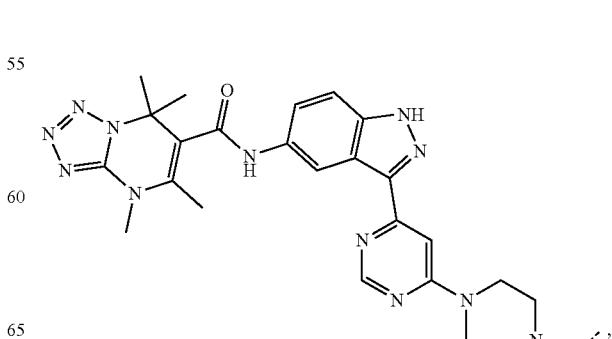

405
-continued
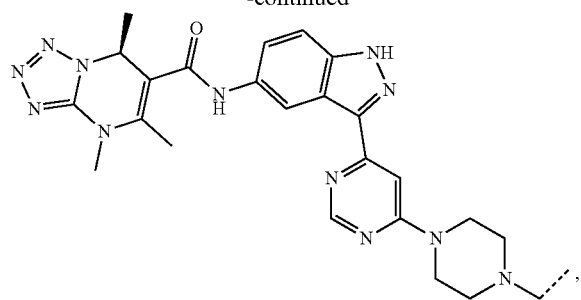
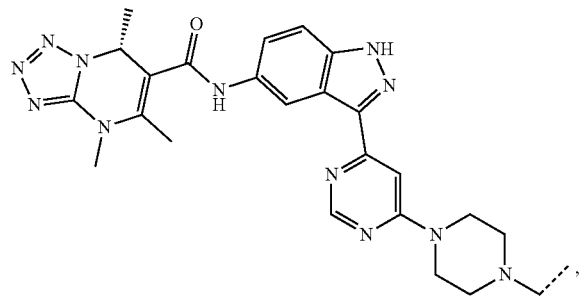
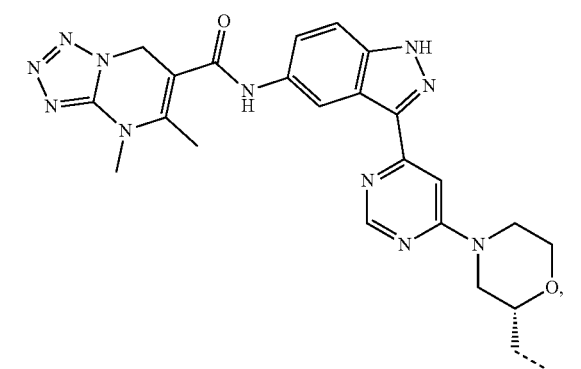
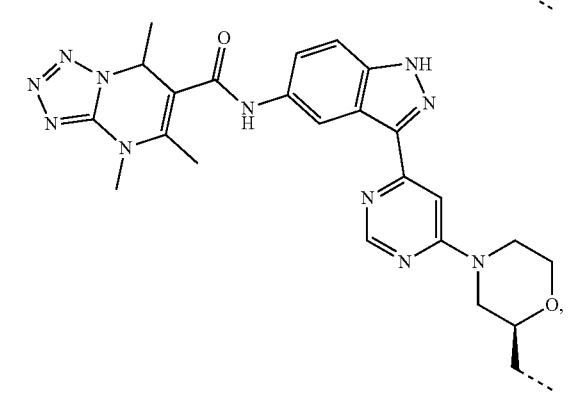
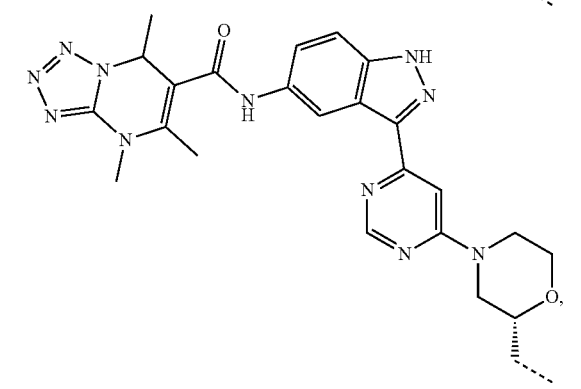
406
-continued
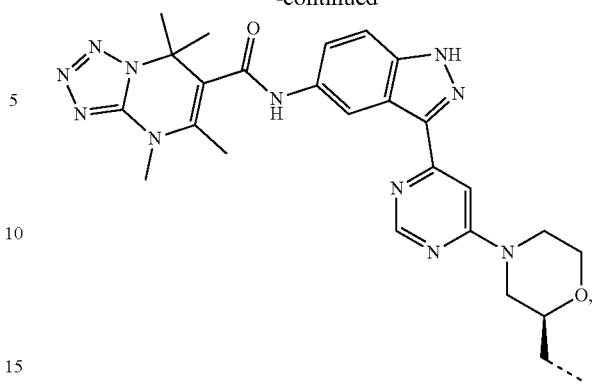
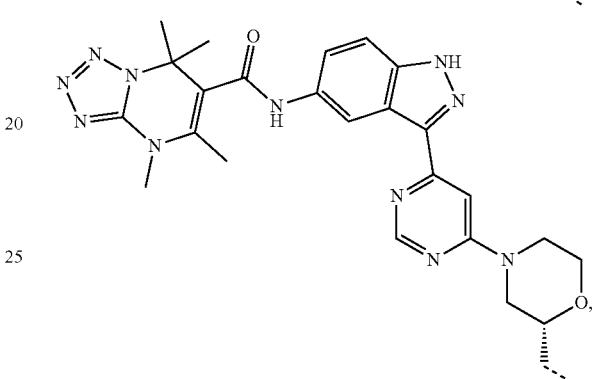
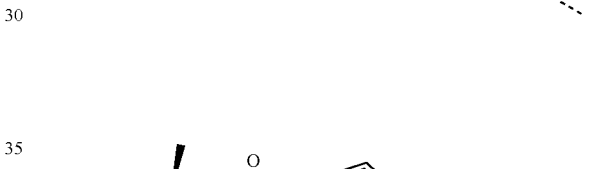
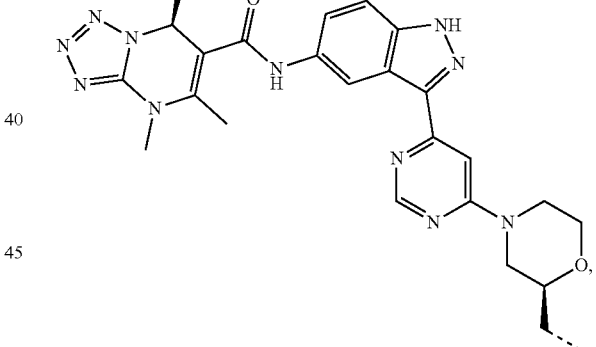
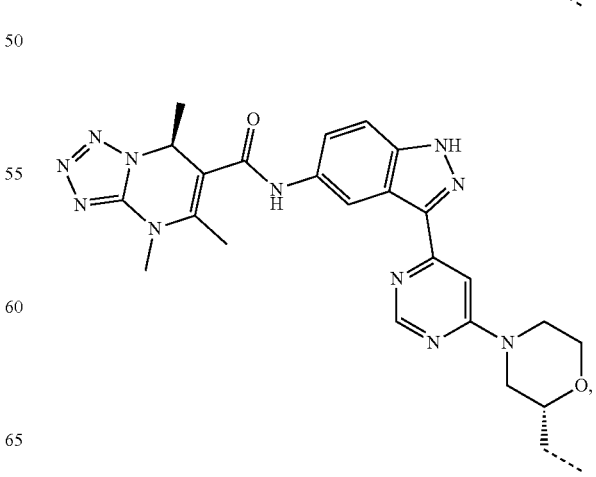

407
-continued
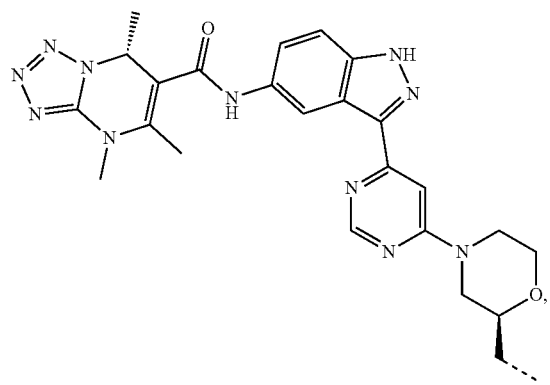
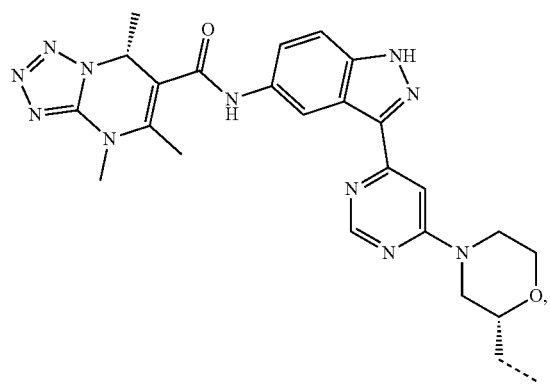
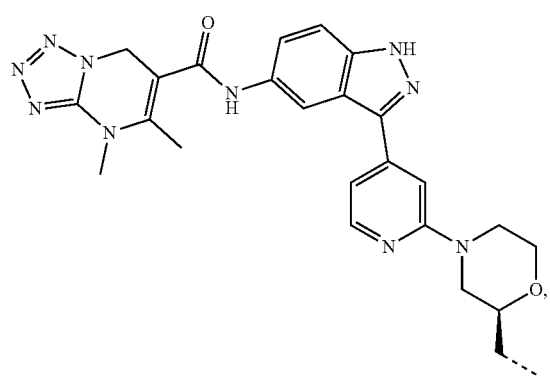
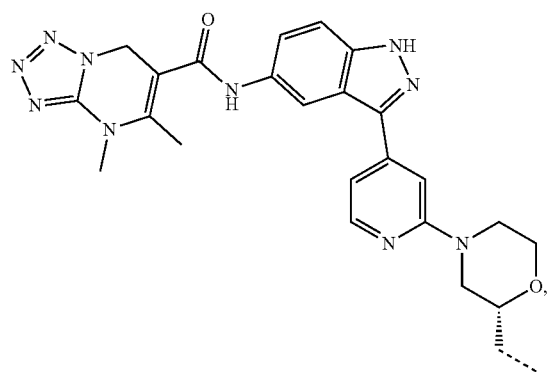
408
-continued
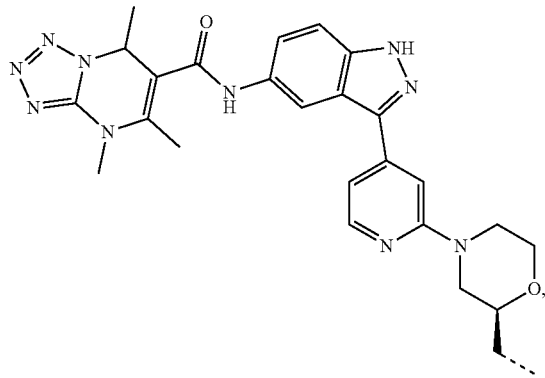
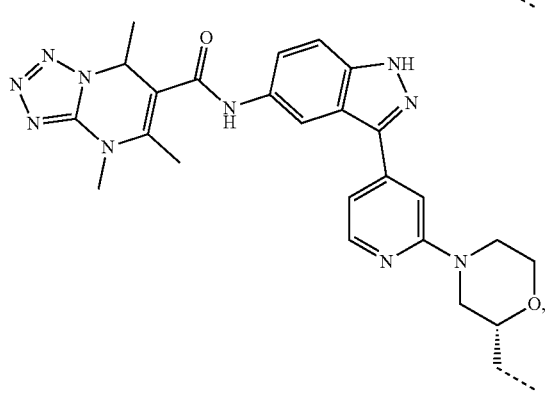
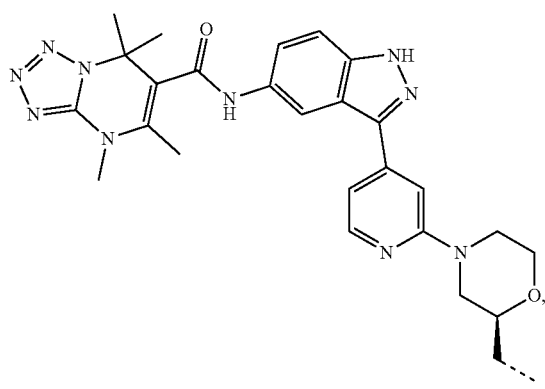
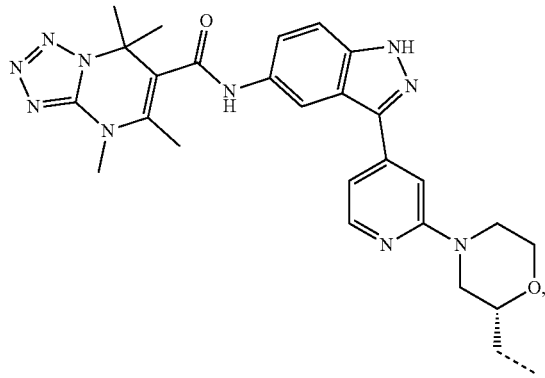

409
-continued
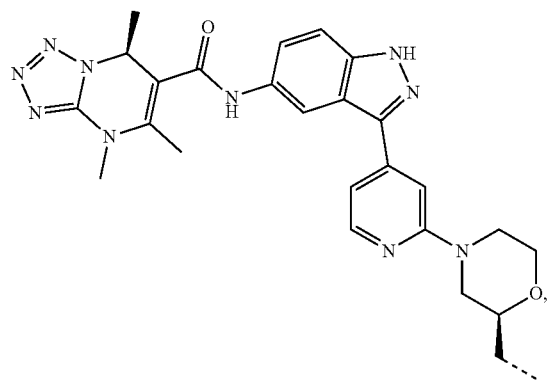
410
-continued
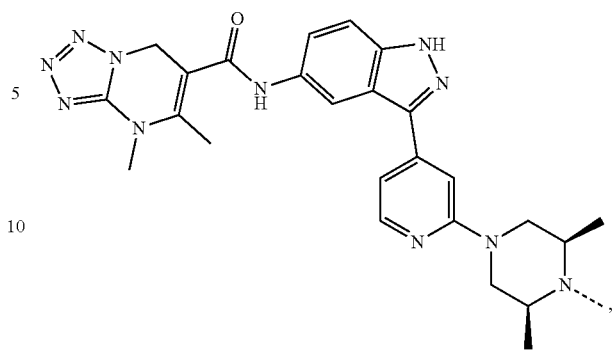
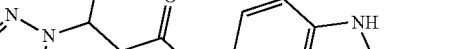

411
-continued
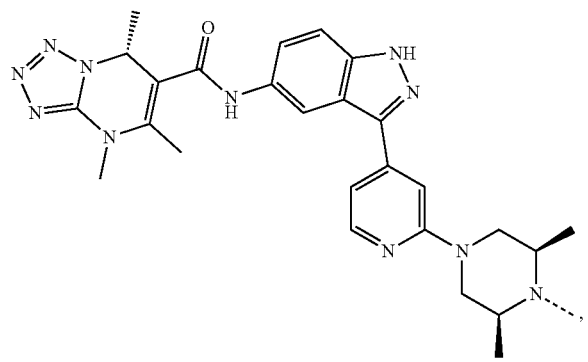
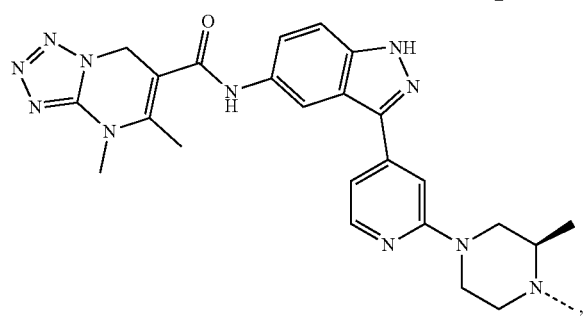
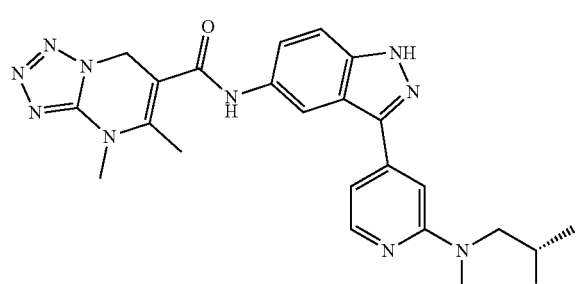
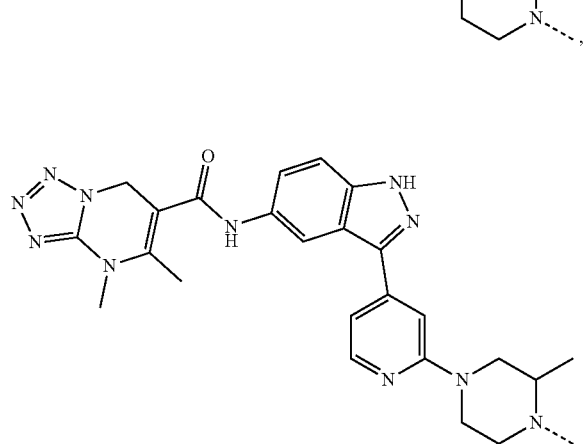
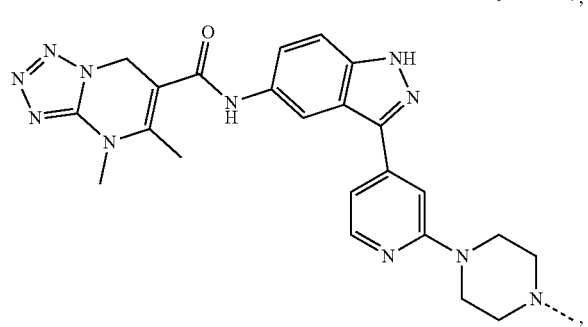
412
-continued
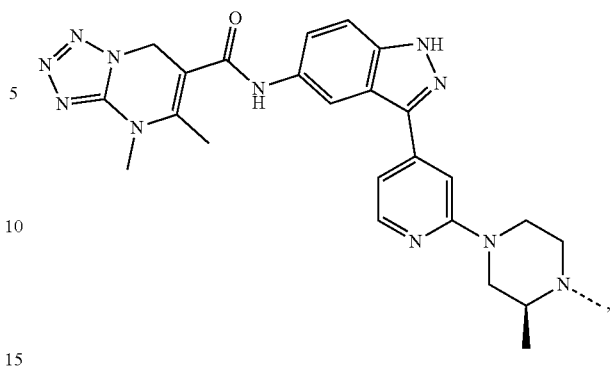
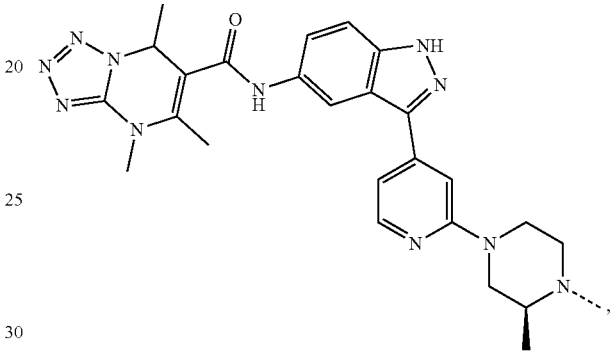
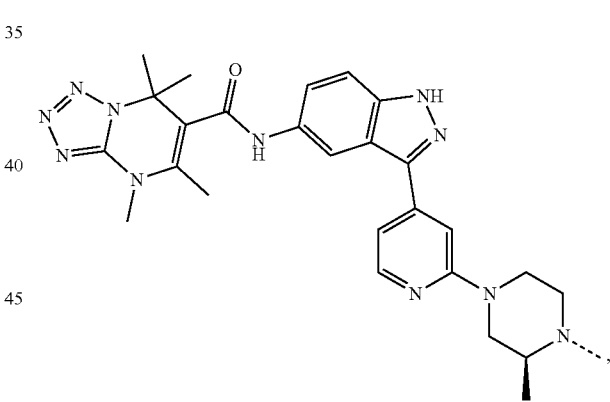
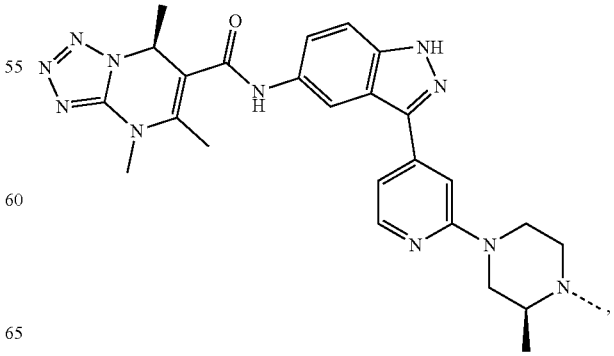

413
-continued
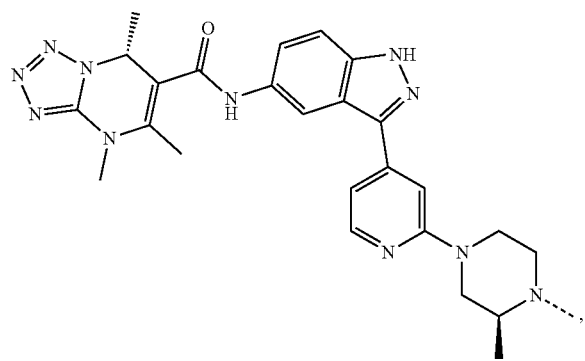
414
-continued
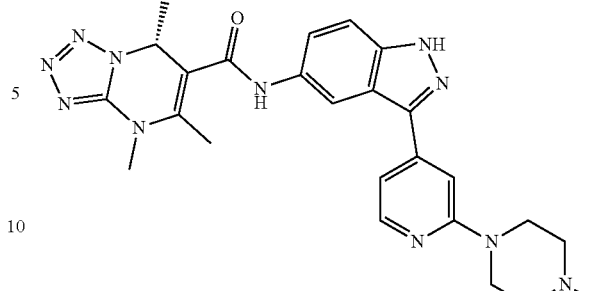

415
-continued
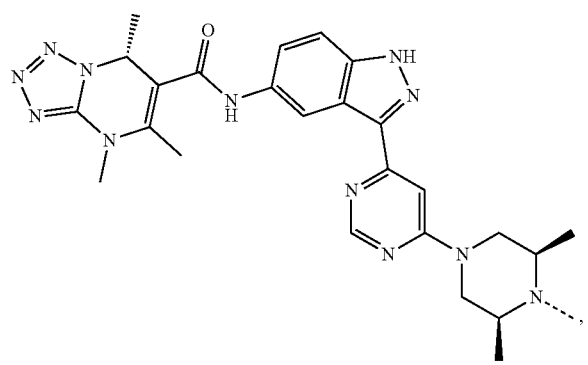
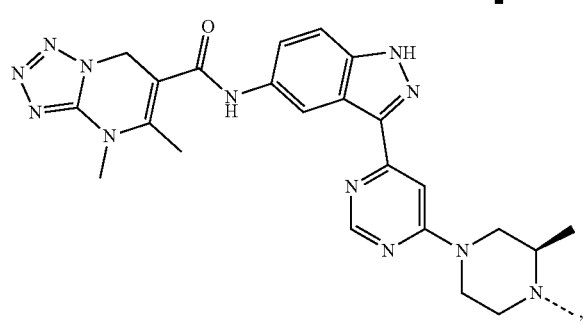
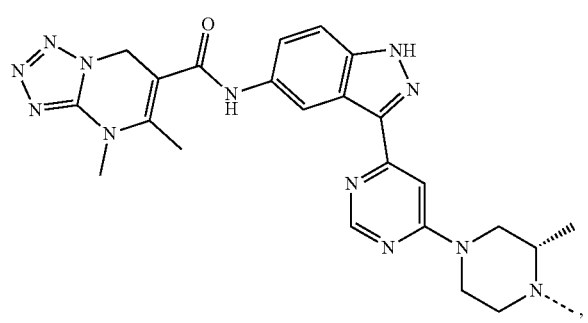
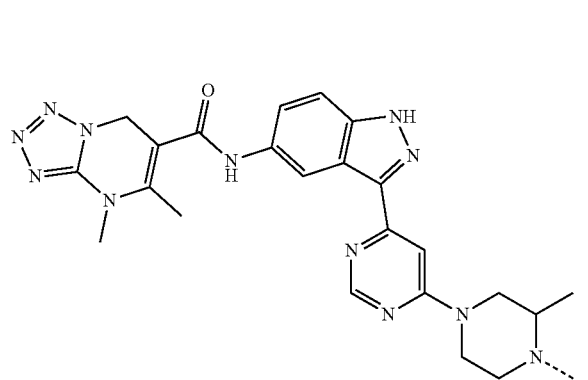
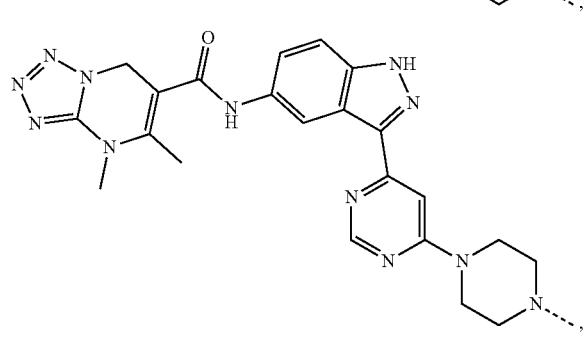
416
-continued
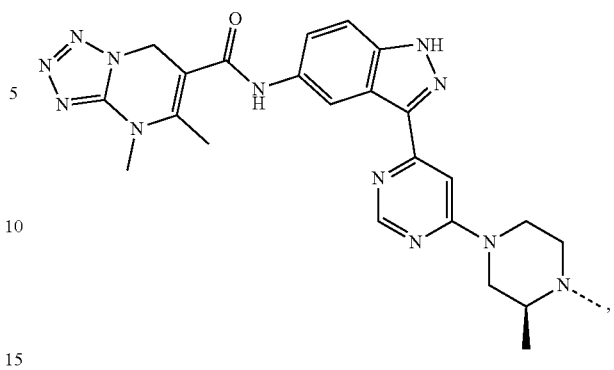
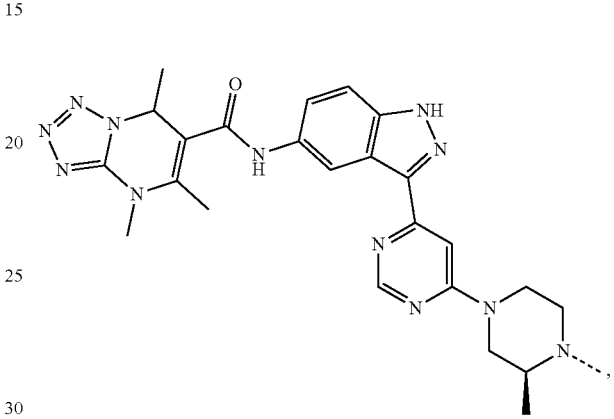
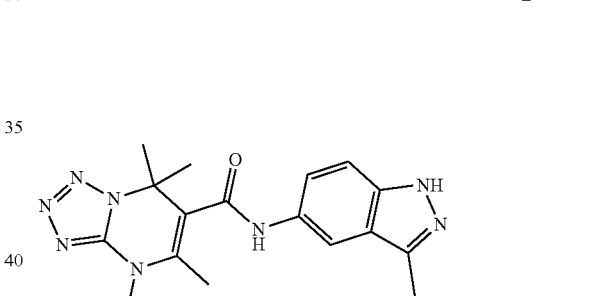
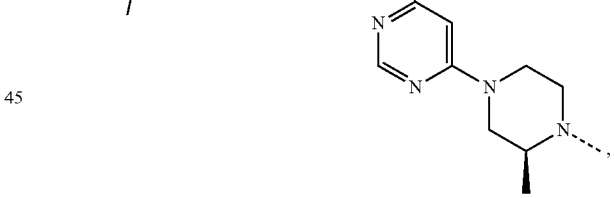
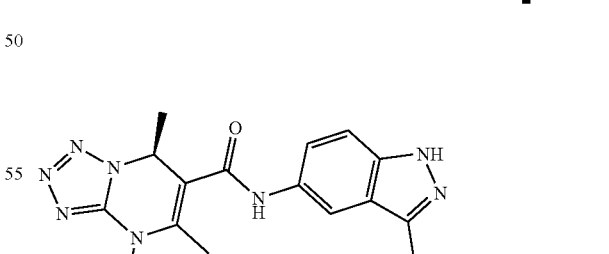
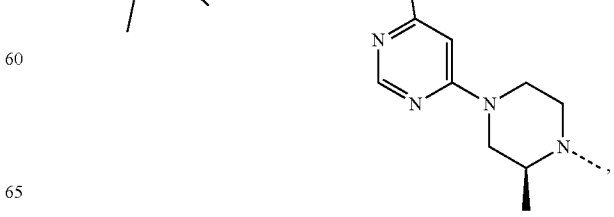

417
-continued
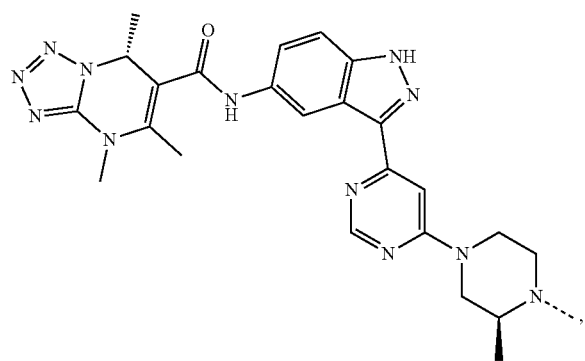
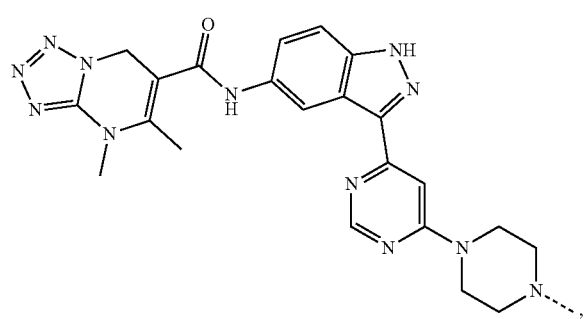
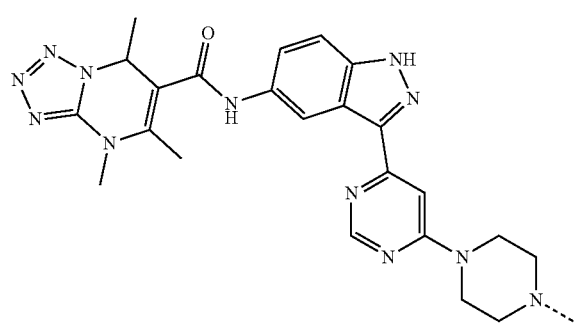
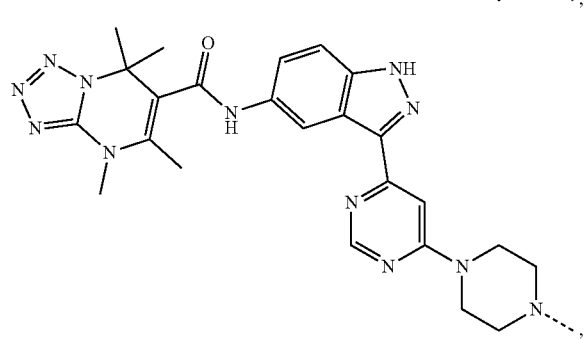
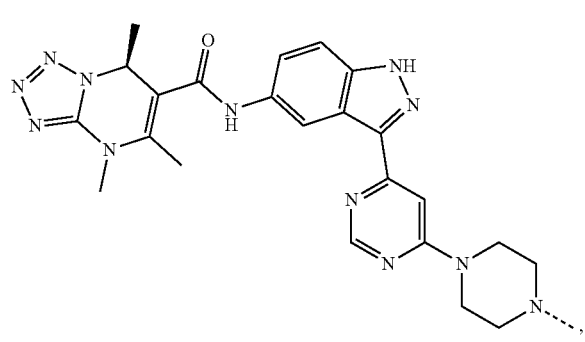
418
-continued
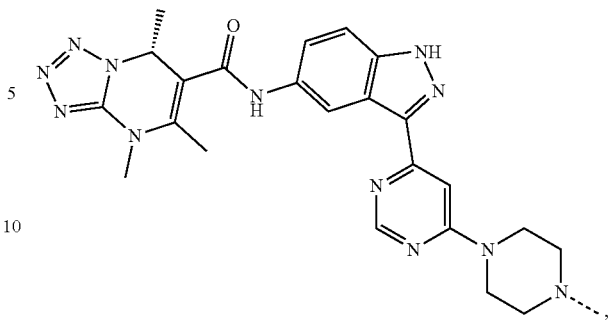
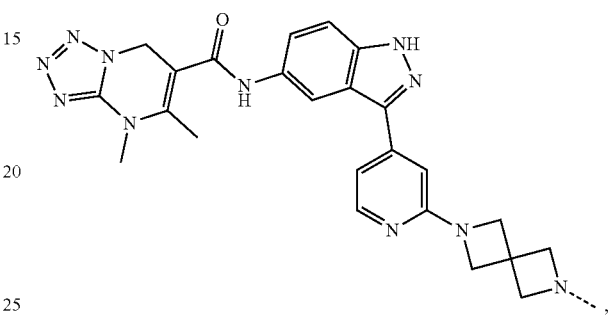
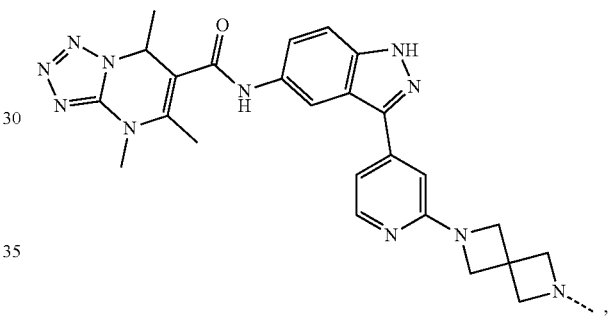
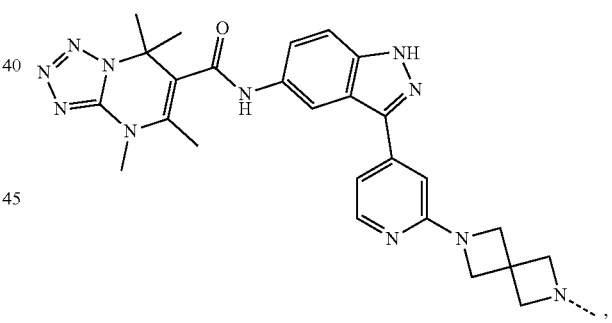
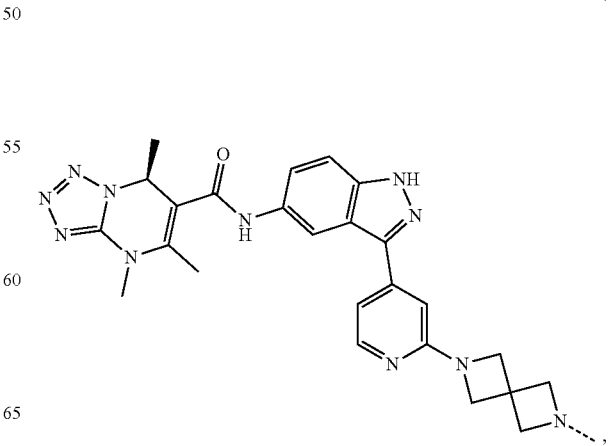

419
-continued
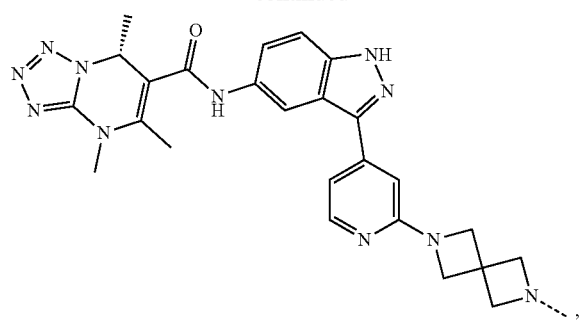
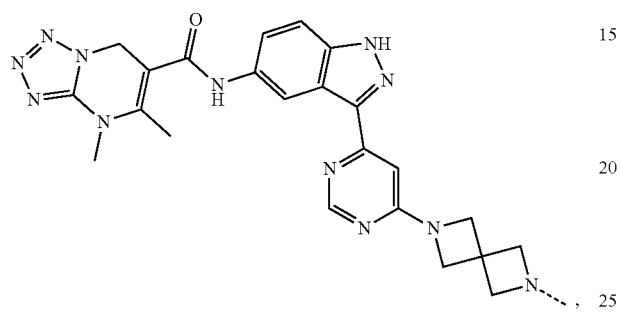
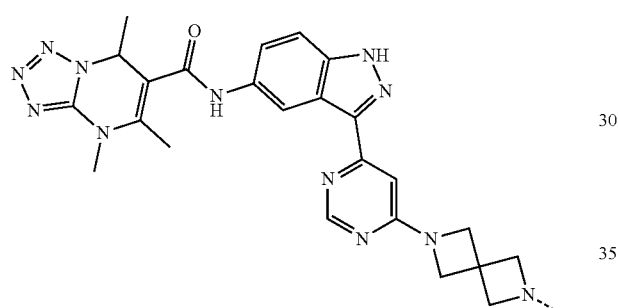
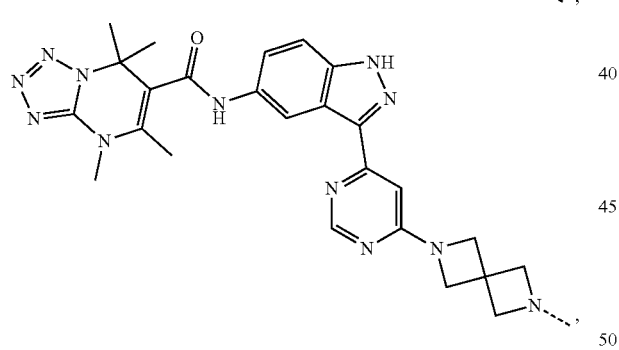
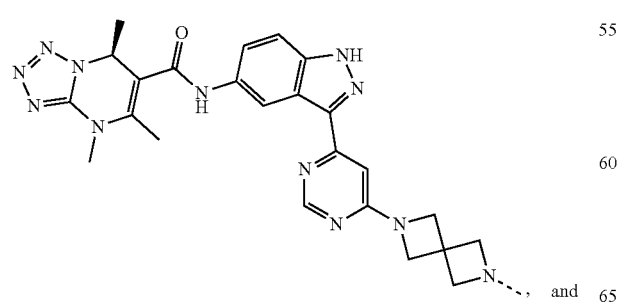
, and
420
-continued
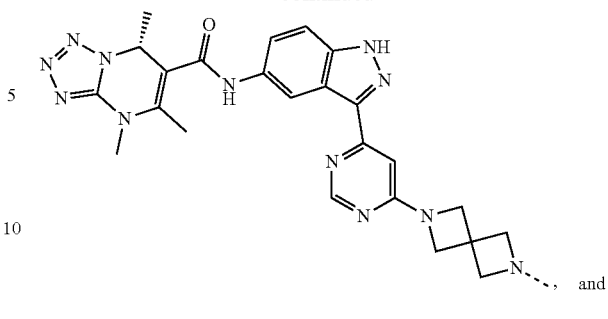
, and
wherein the ⟋ of the PTM indicates the site of attachment with a chemical linking group; and
(c) the L is a bond or is a chemical linking group that covalently couples the CLM to the PTM and is selected from:
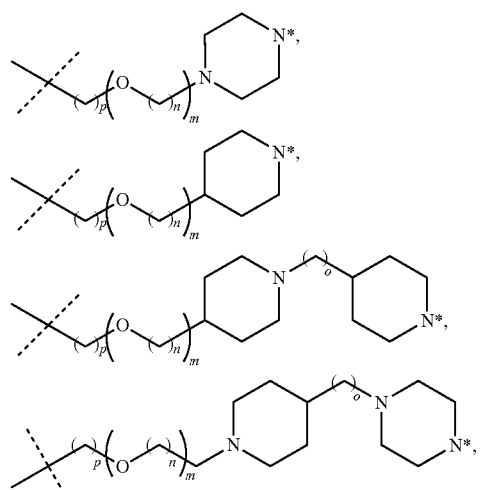
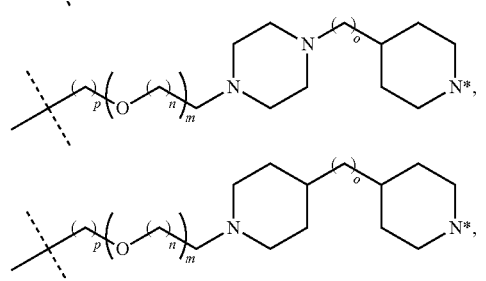
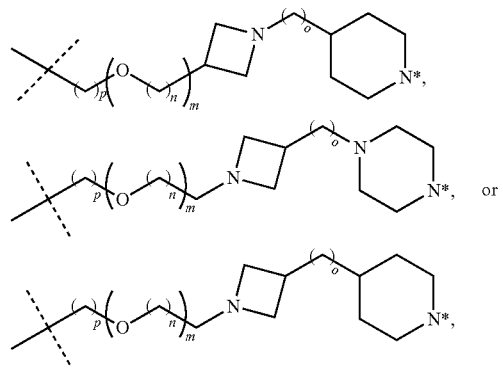

wherein:
    N* is a nitrogen atom that is covalently linked to the CLM or the PTM, or that is shared with the CLM or the PTM;
    each m, n, o, and p is independently 0, 1, 2, 3, 4, 5, 6, 7, 8, 9, 10, 11, 12, 13, 14, 15, 16, 17, 18, 19, or 20; and
    the chemical linker group is optionally substituted with 1, 2, 3, or 4 substitutions independently selected from halogen and $C_{1-4}$ alkyl.
2. The compound according to claim 1, wherein PTM is:
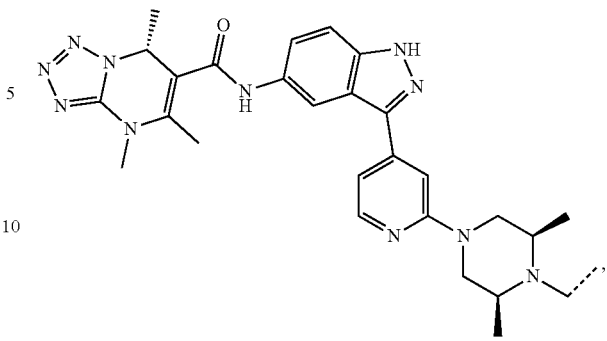
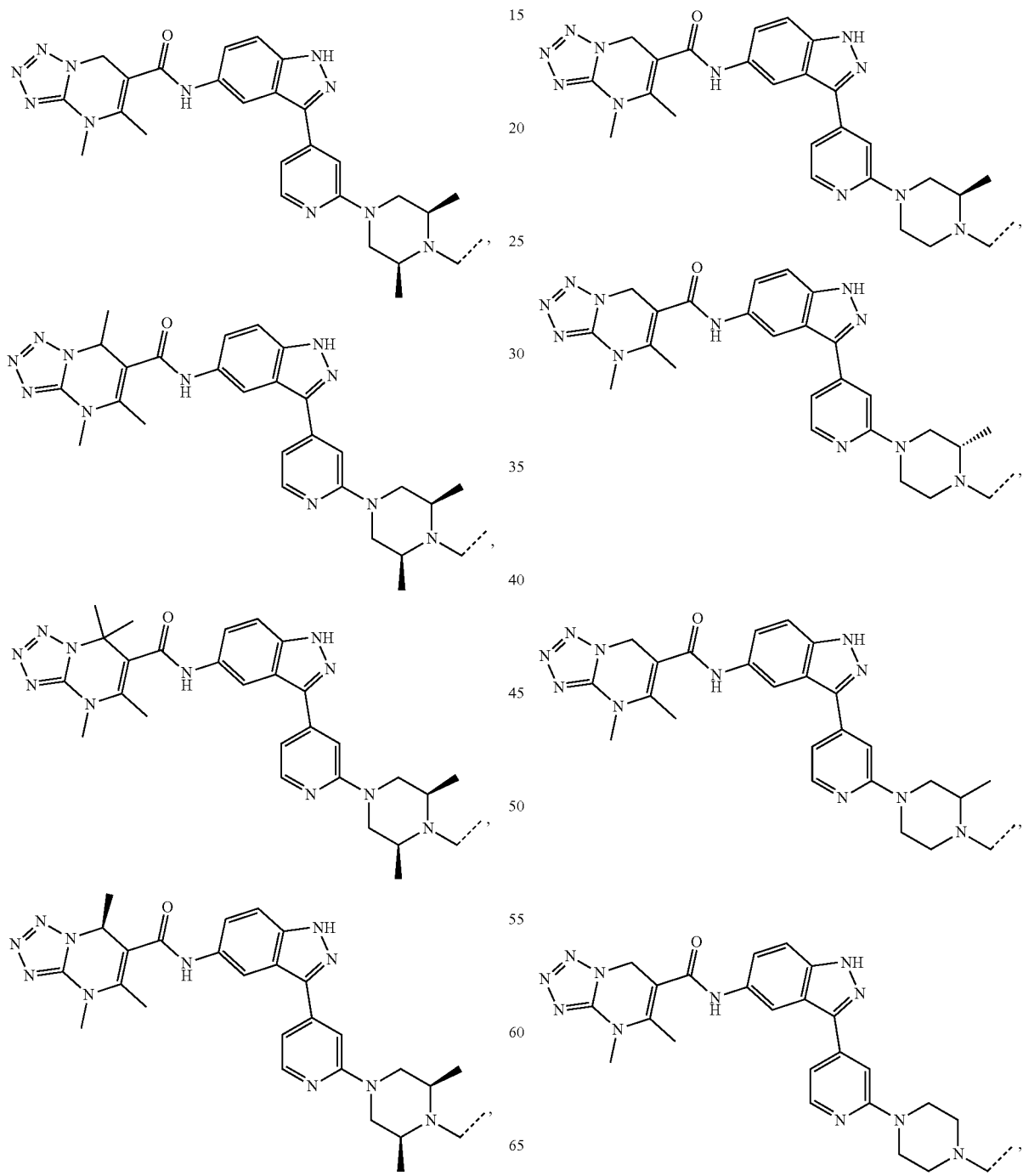

423
-continued
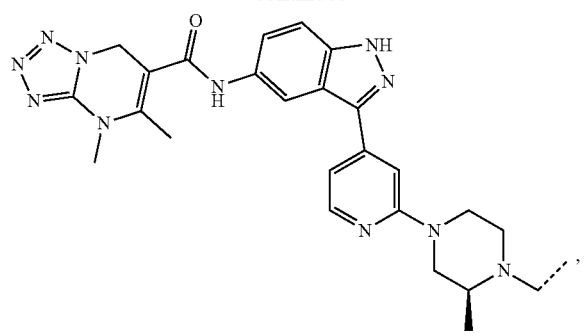
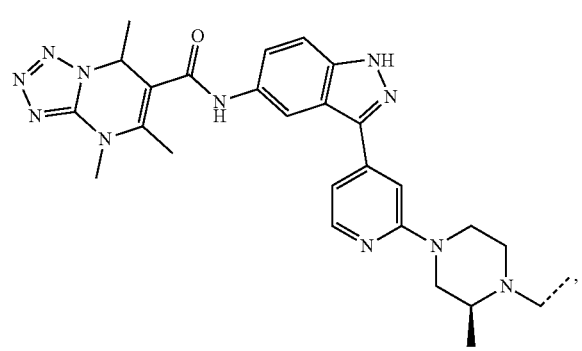
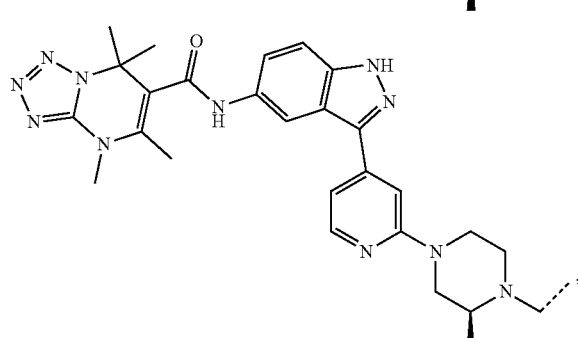
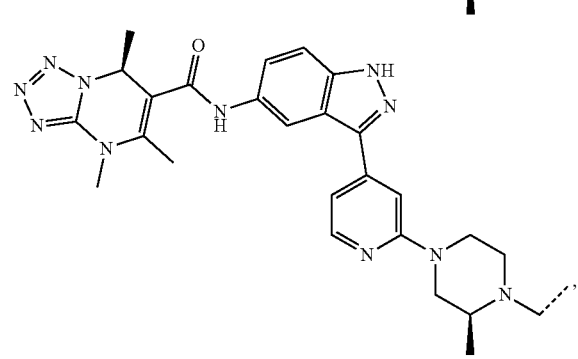
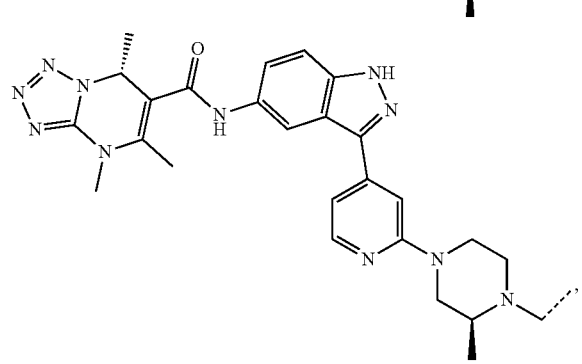
424
-continued
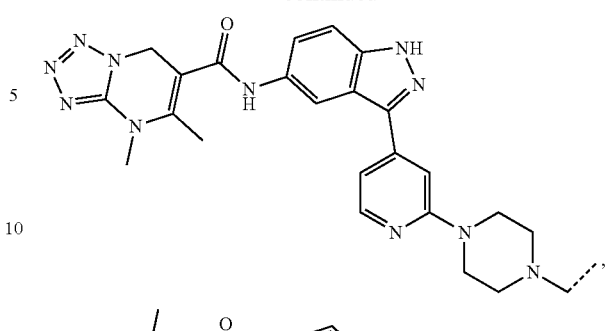
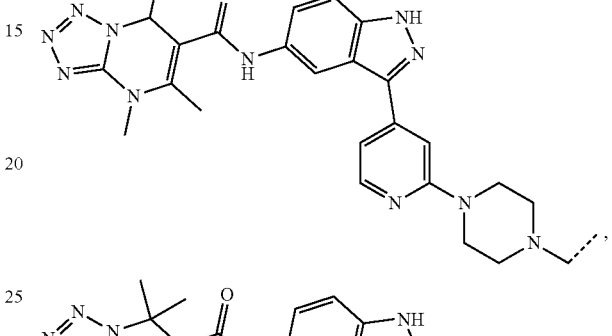
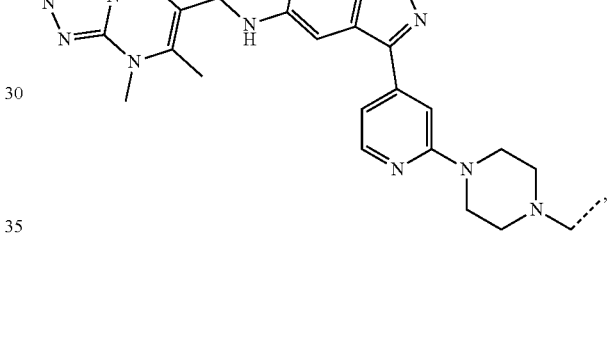
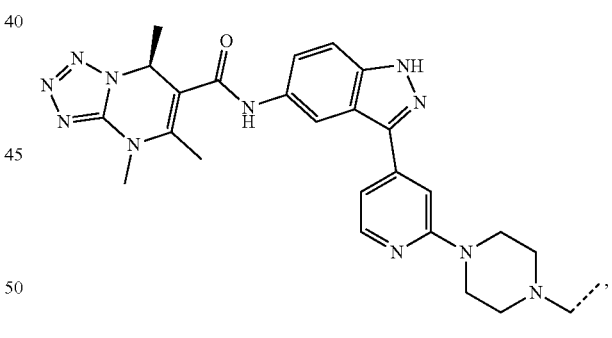
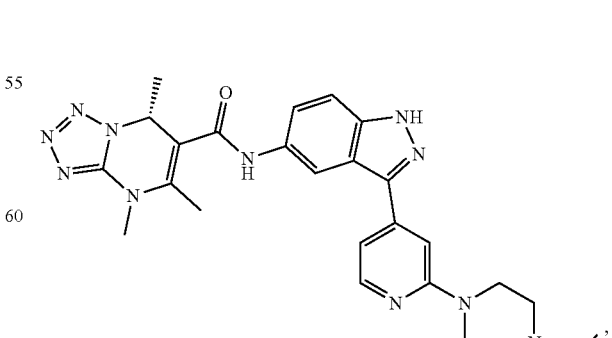

425
-continued
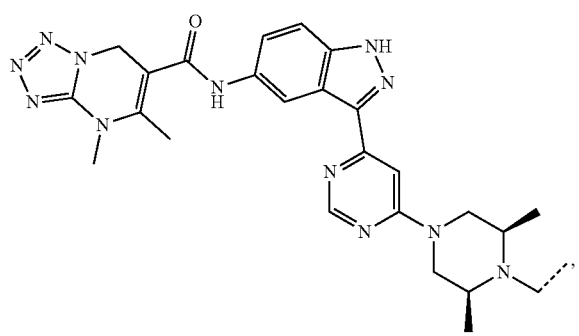
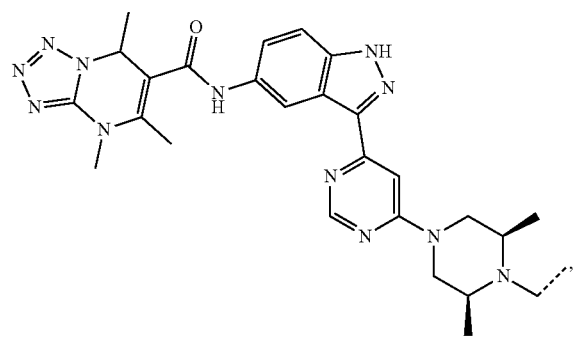
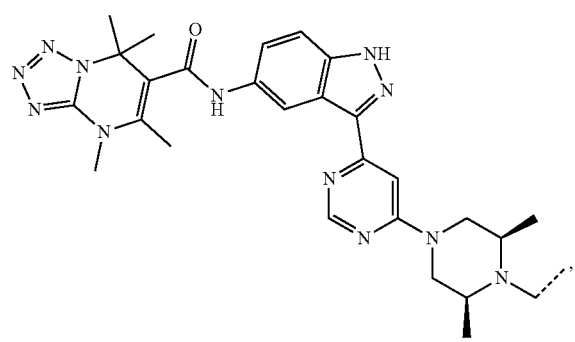
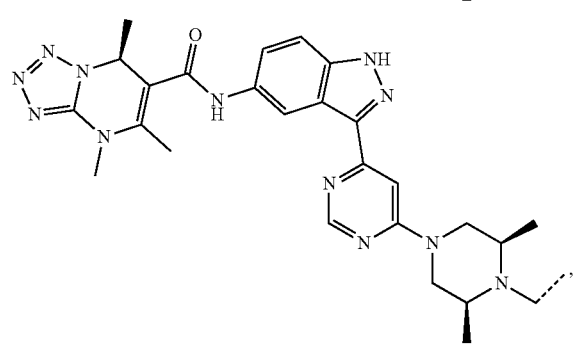
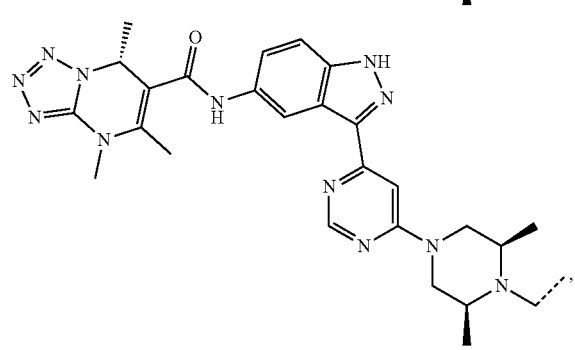
426
-continued
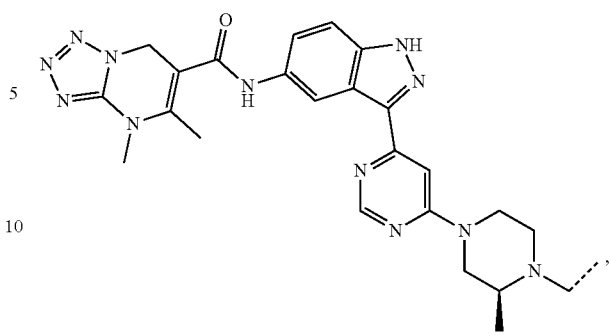
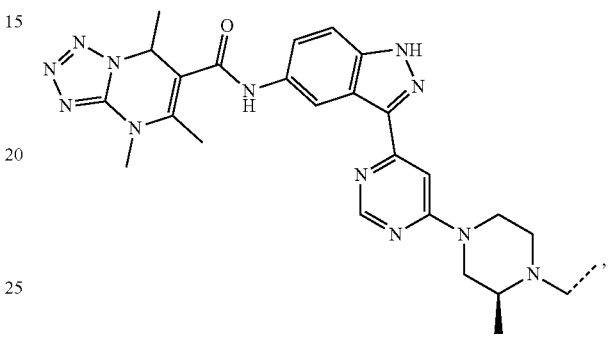
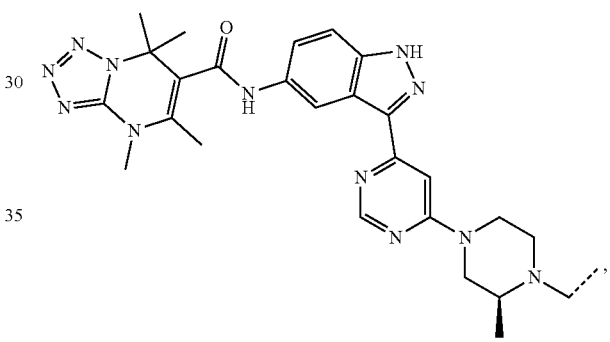
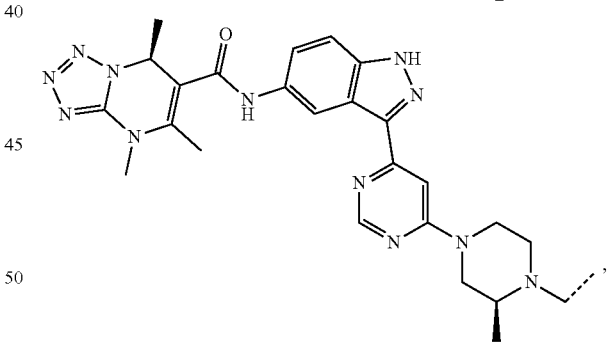
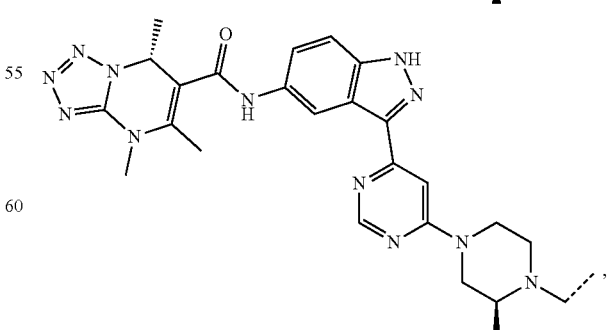

427
-continued
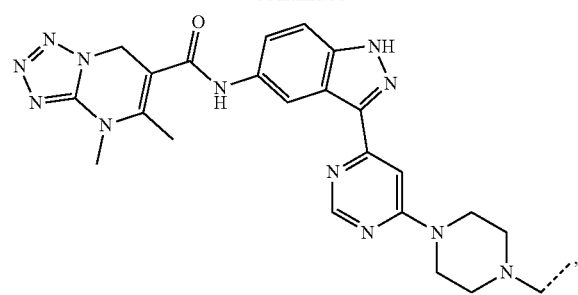
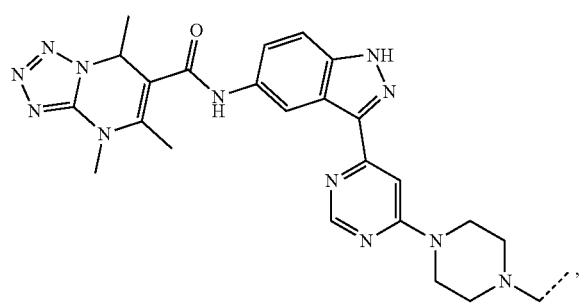
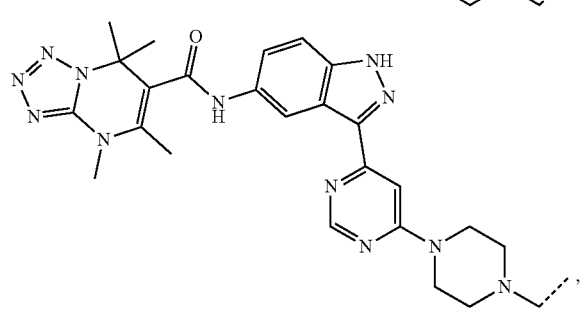
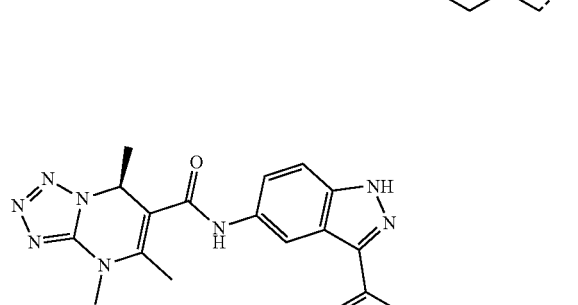
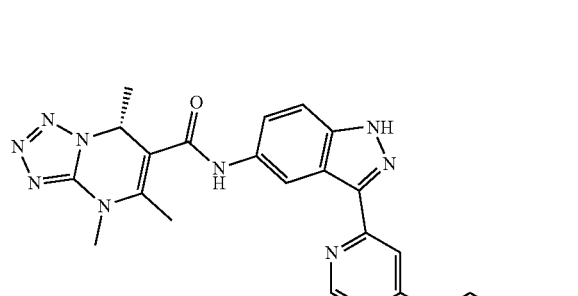,
428
-continued
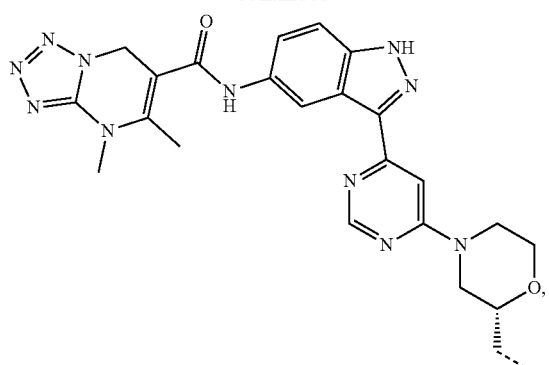
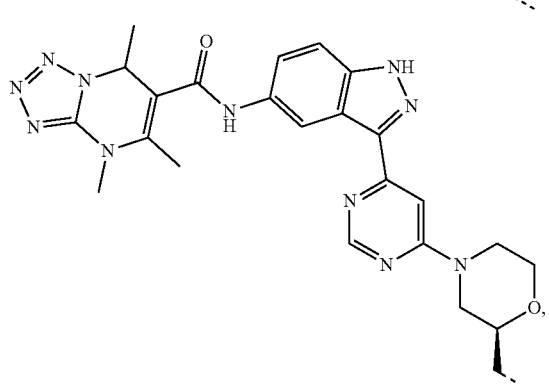
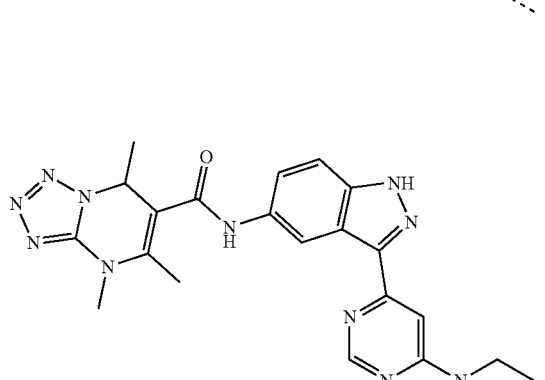
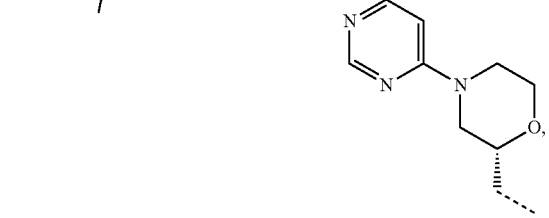
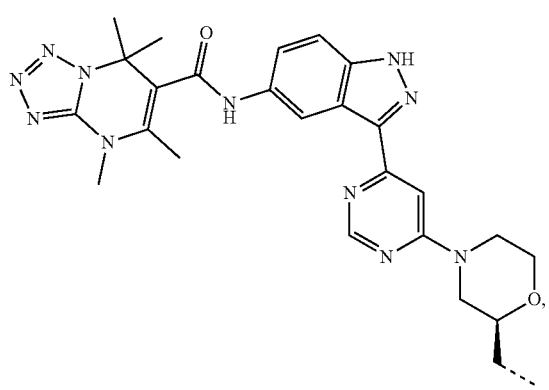

429
-continued
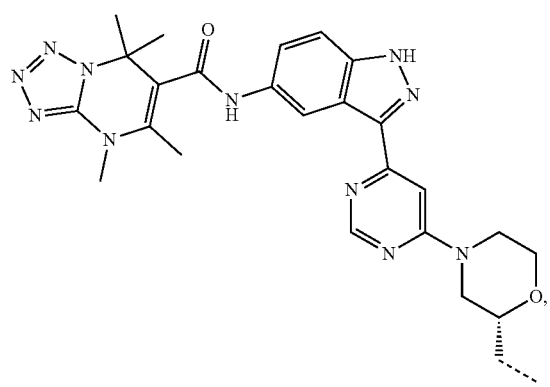
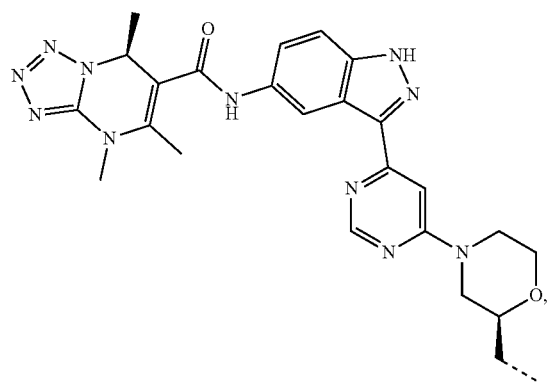
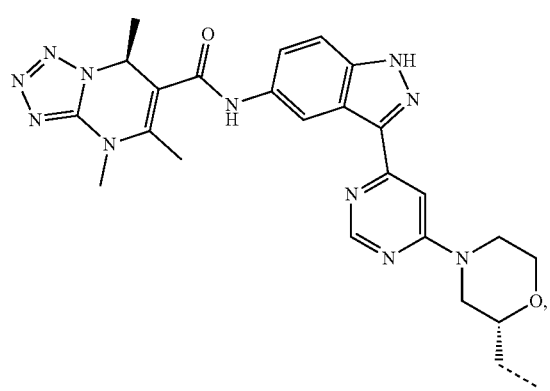
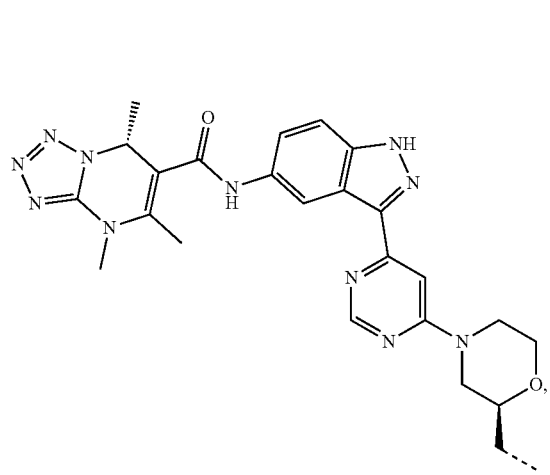
430
-continued
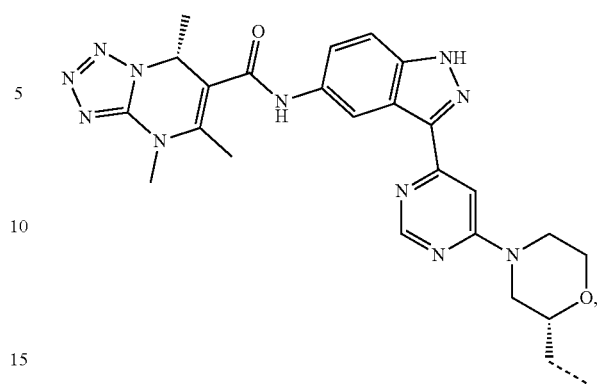
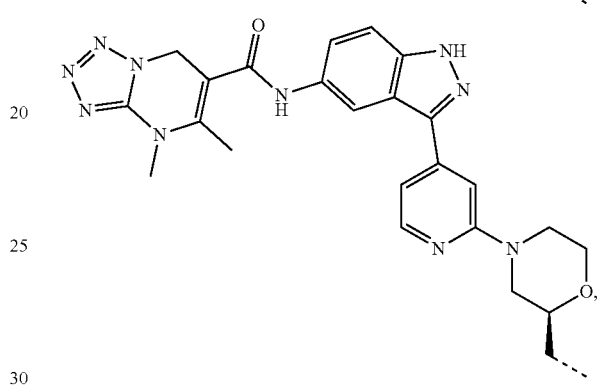
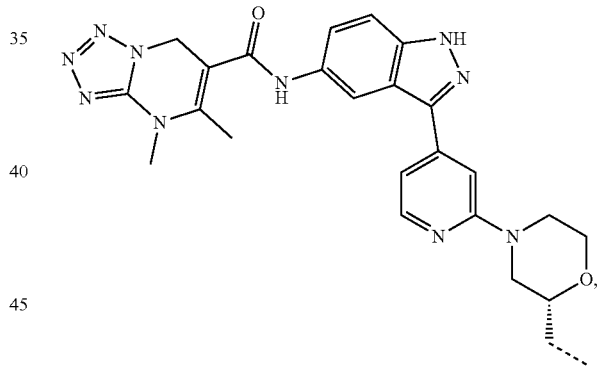
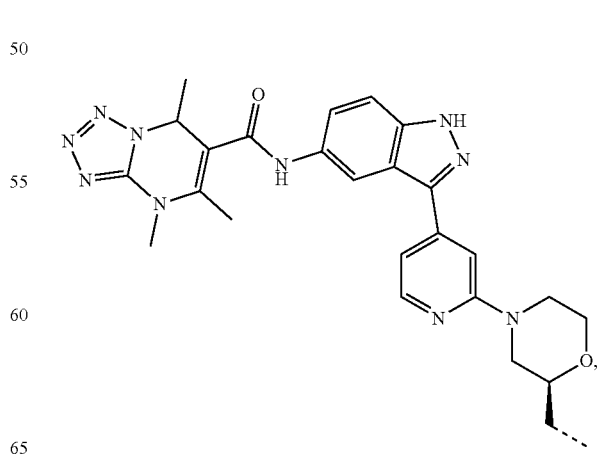

431
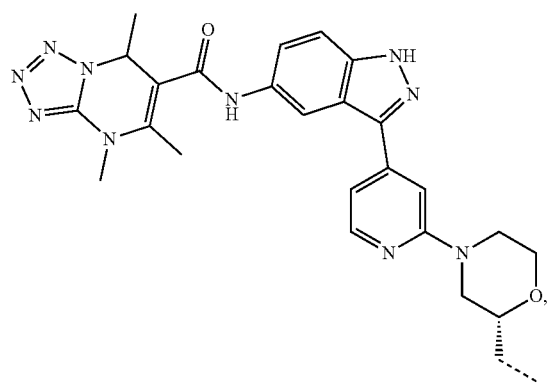
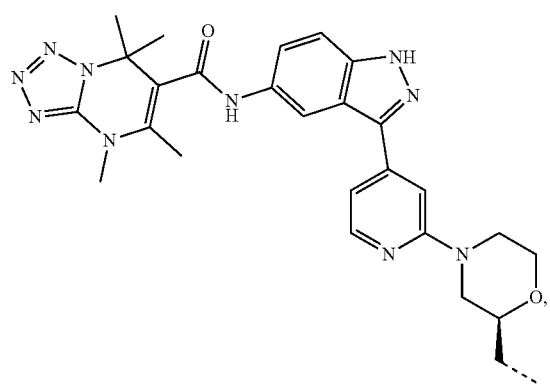
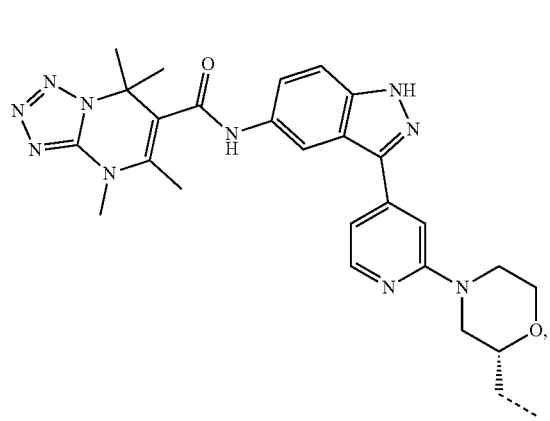
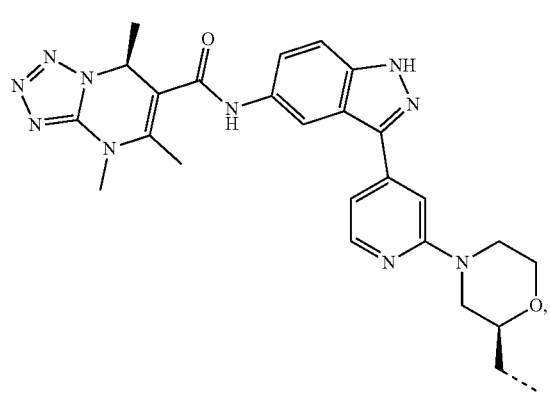
432
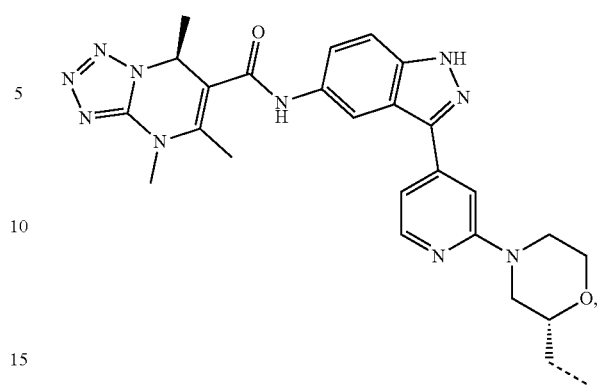
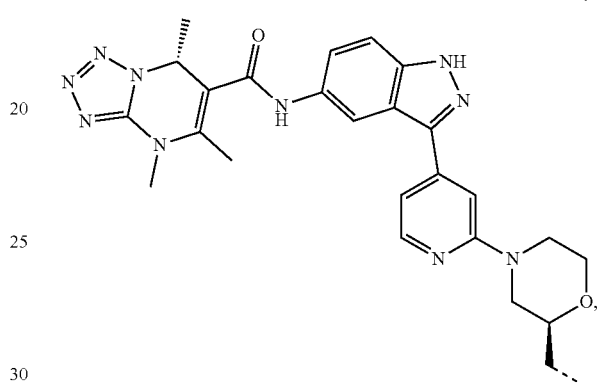
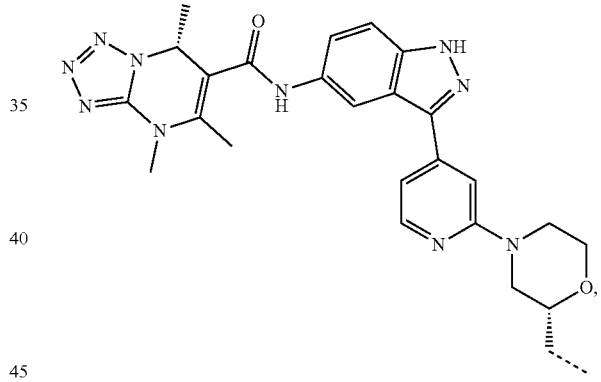
wherein ⸺ indicates a site of attachment of L or the CLM, and wherein each PTM is coupled to at least one L or the CLM.
3. The compound of claim 1, wherein the CLM is:
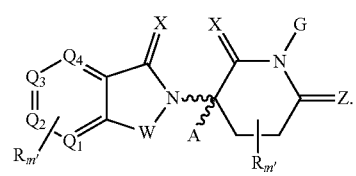

4. The compound of claim 1, wherein the CLM is:
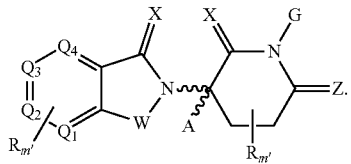
5. The compound of to claim 1, wherein PTM is:
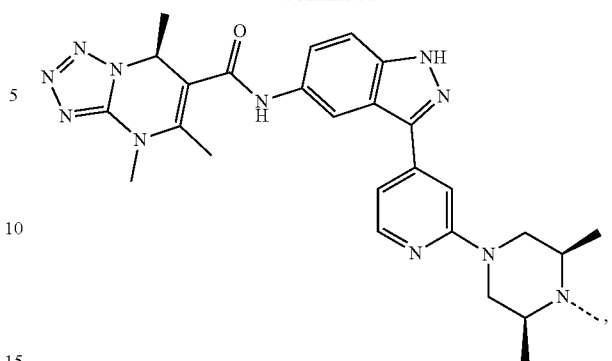
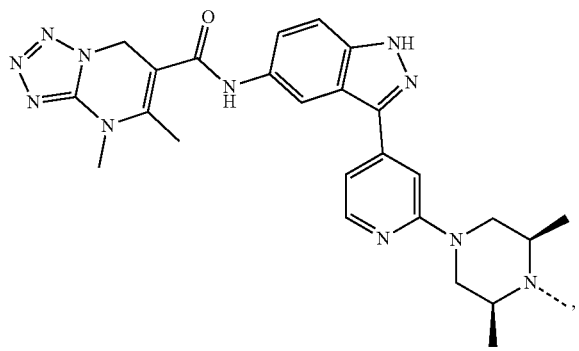
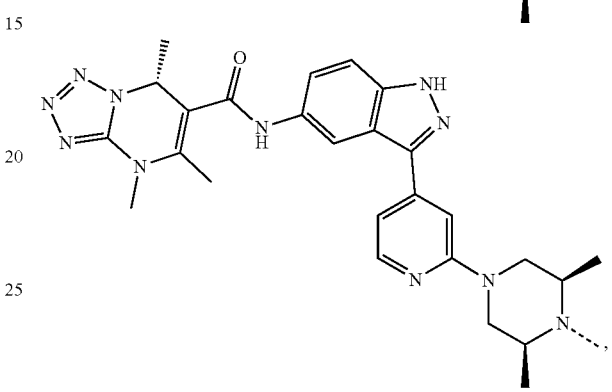
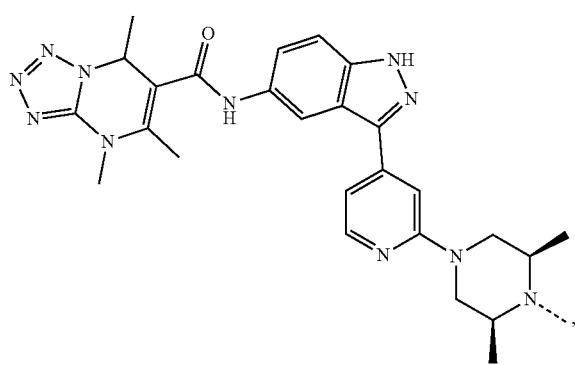
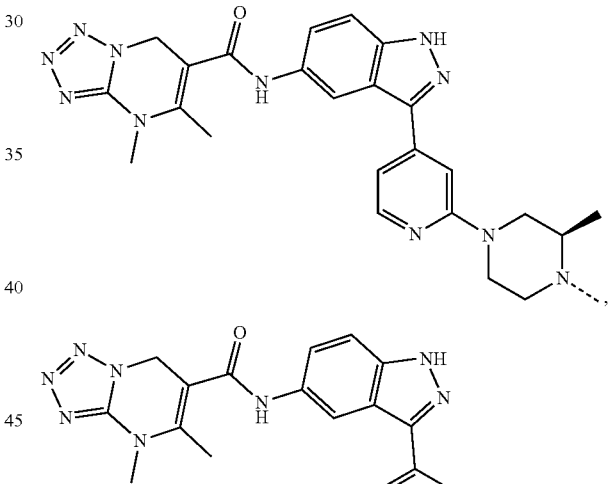
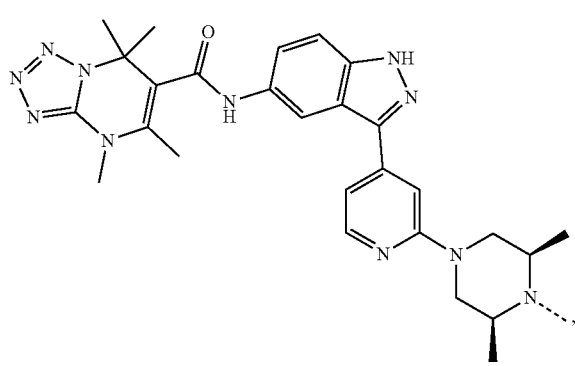
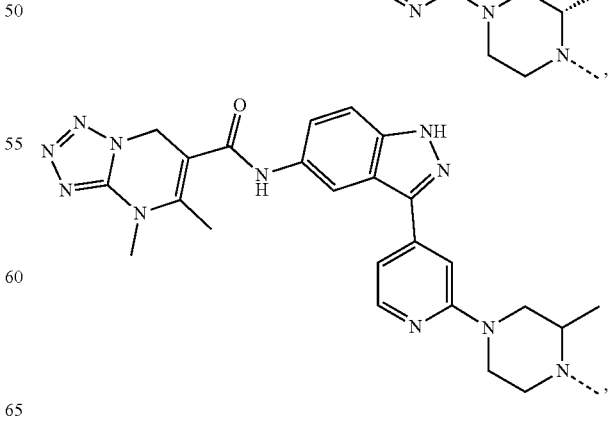

435
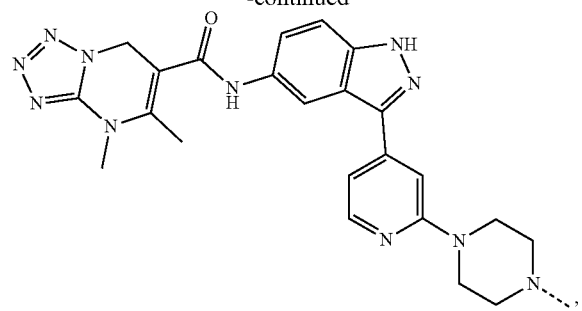
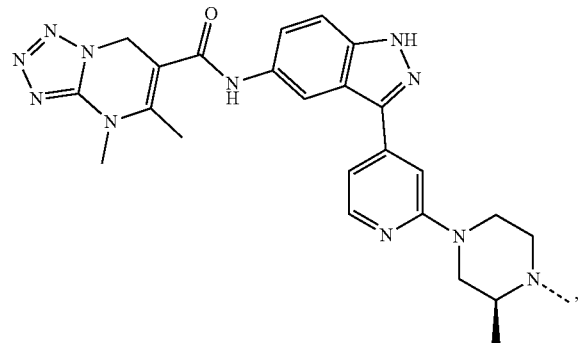
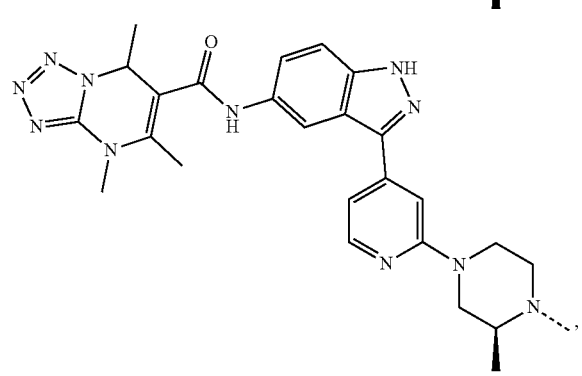
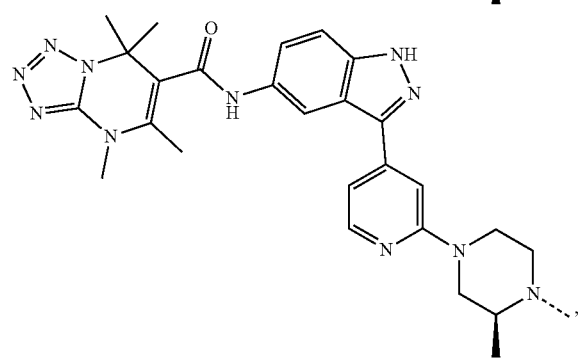
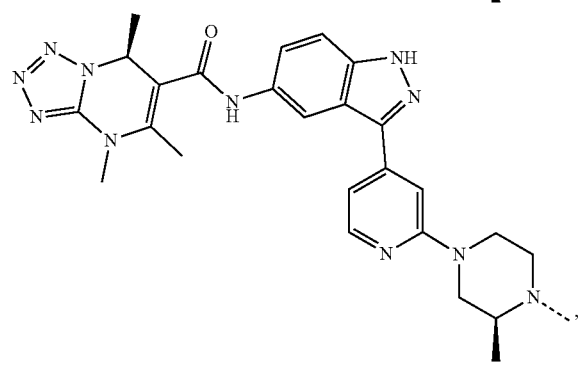
436
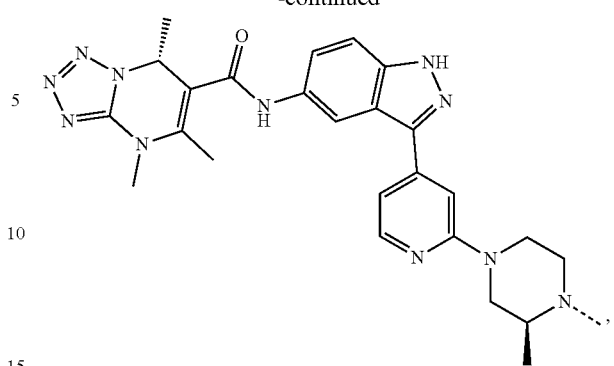
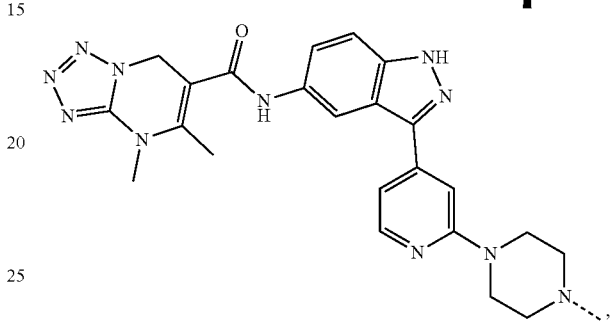
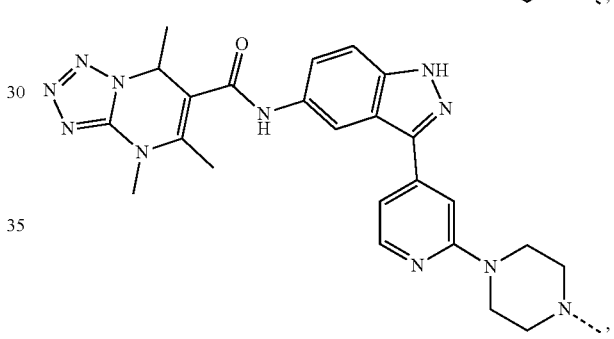
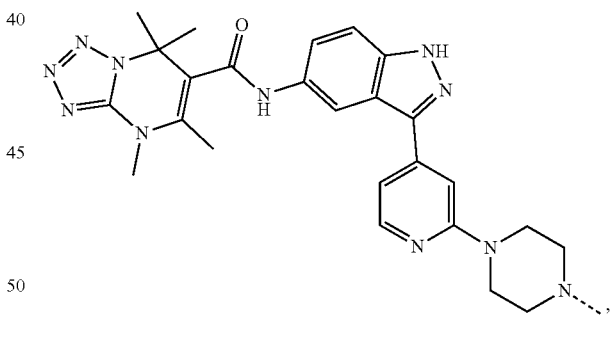
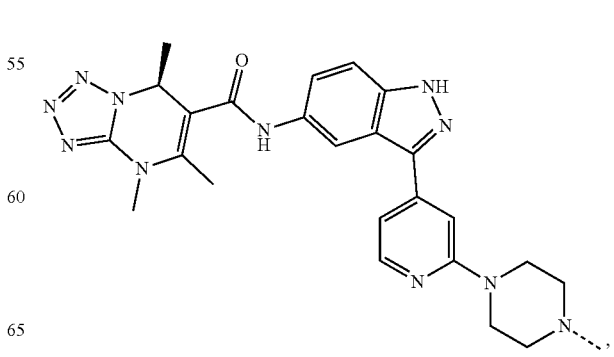

437
-continued
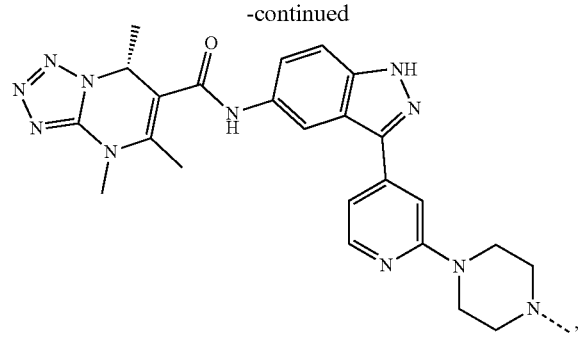
438
-continued
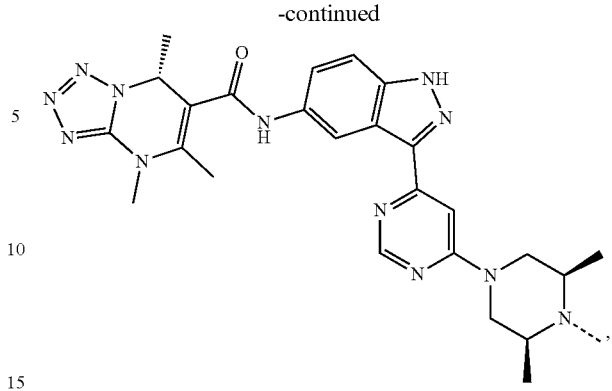
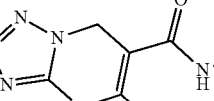
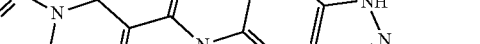

439
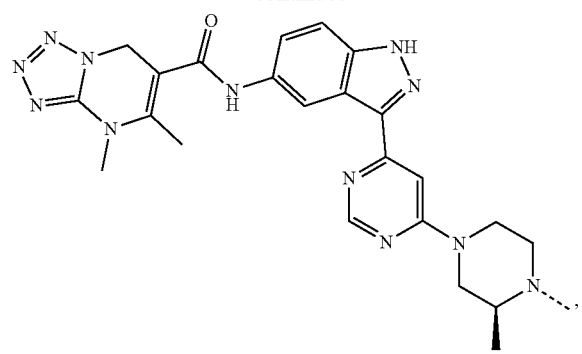
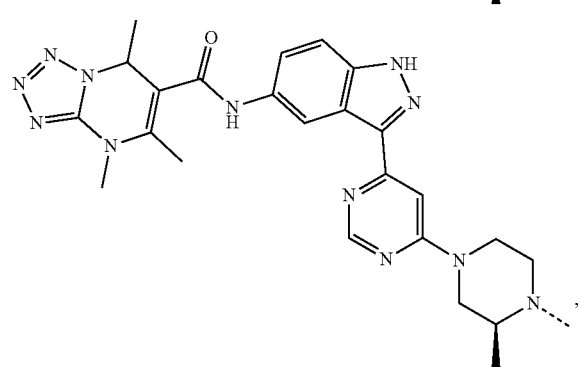
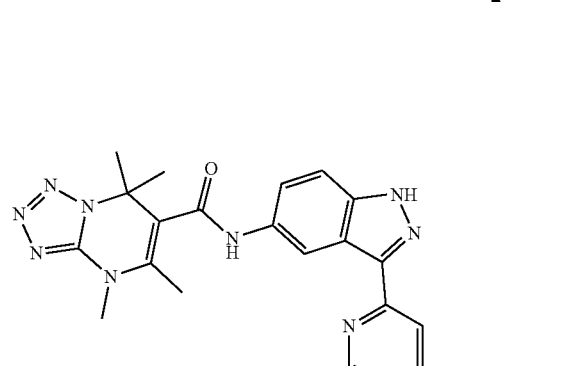
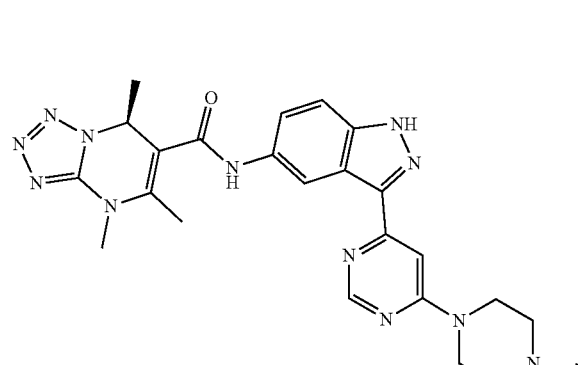
440
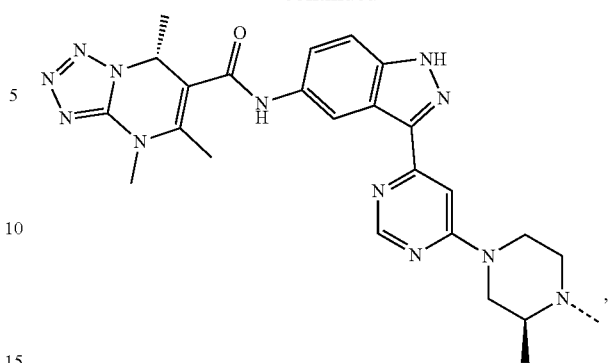
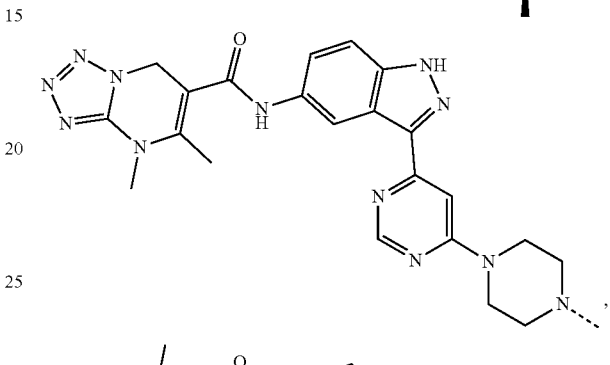
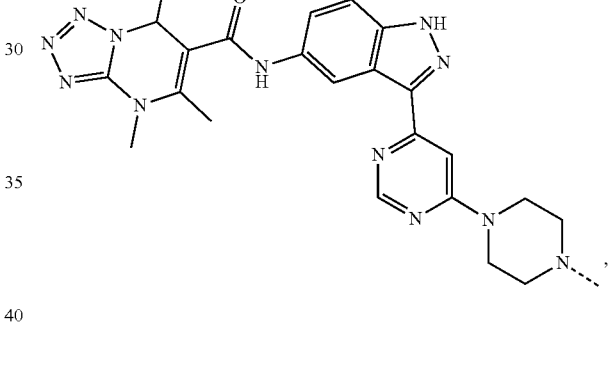
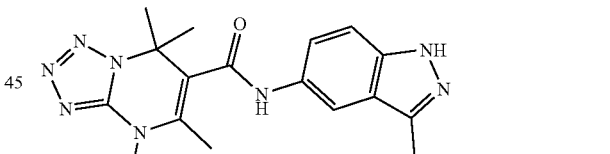
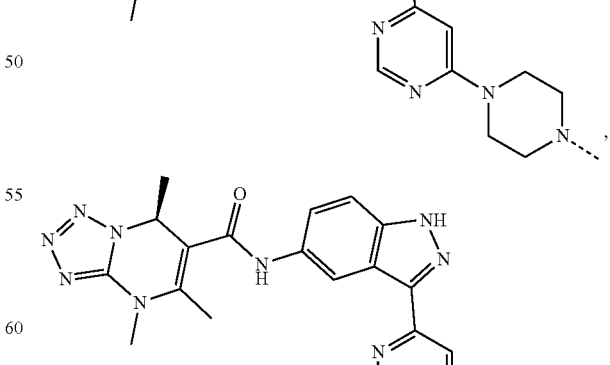

441
-continued
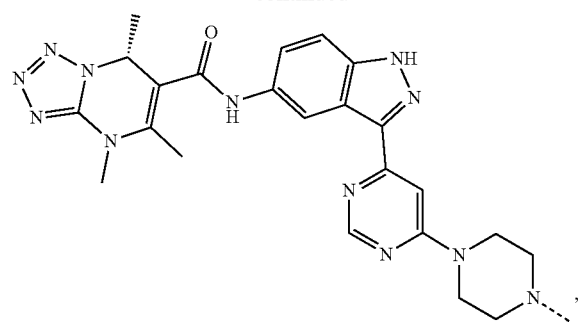
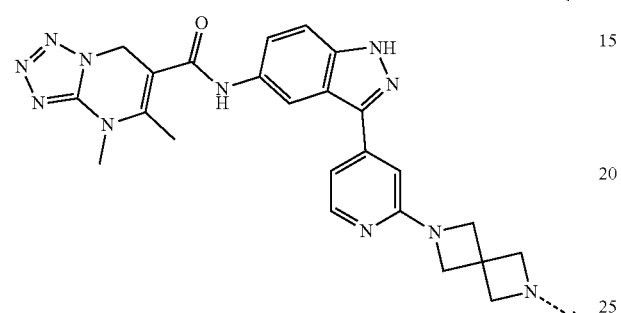
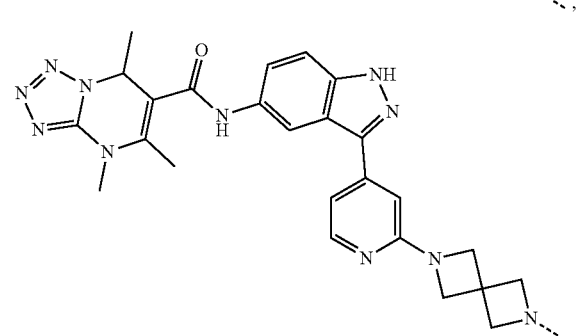
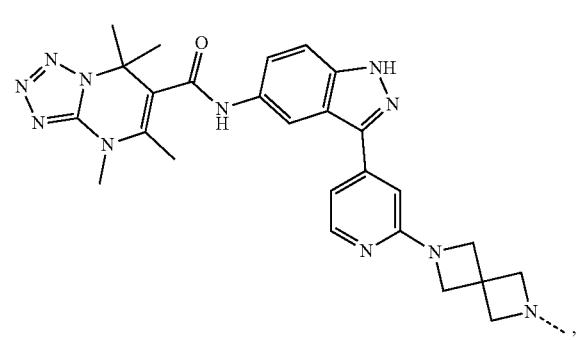
442
-continued
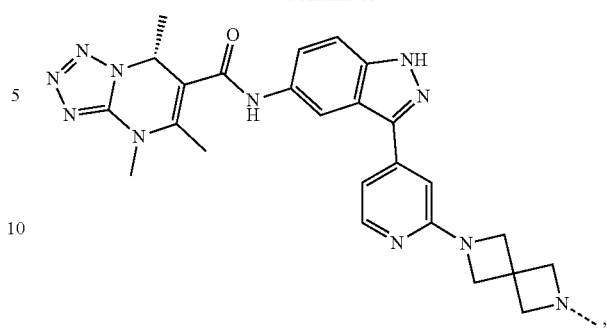
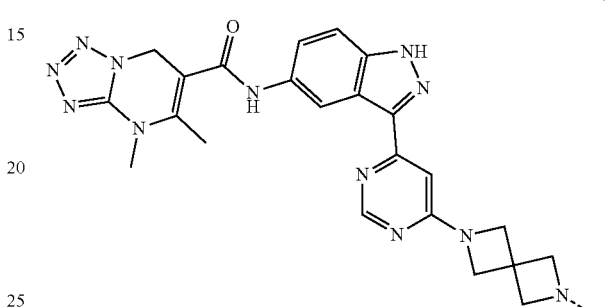
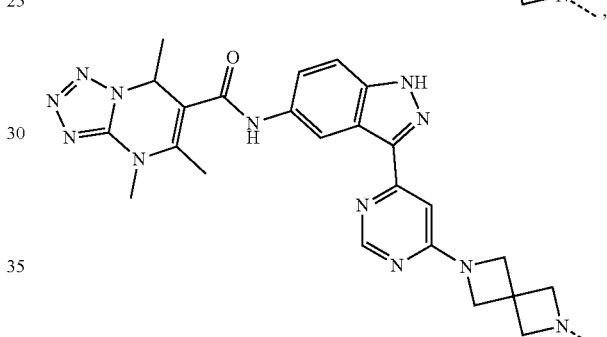
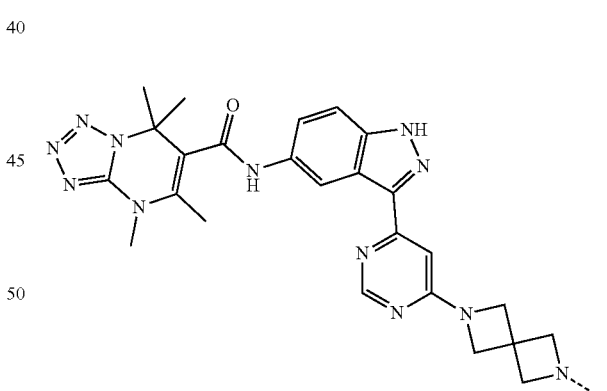
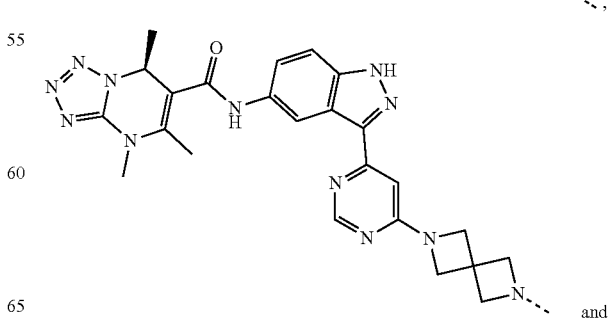
and 443
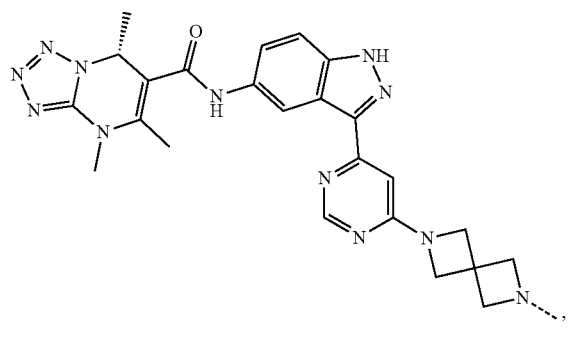
wherein ⌇ indicates a site of attachment of L or the CLM, and wherein each PTM is coupled to at least one or the CLM.
6. The compound claim 1, wherein:
(a) the CLM is:
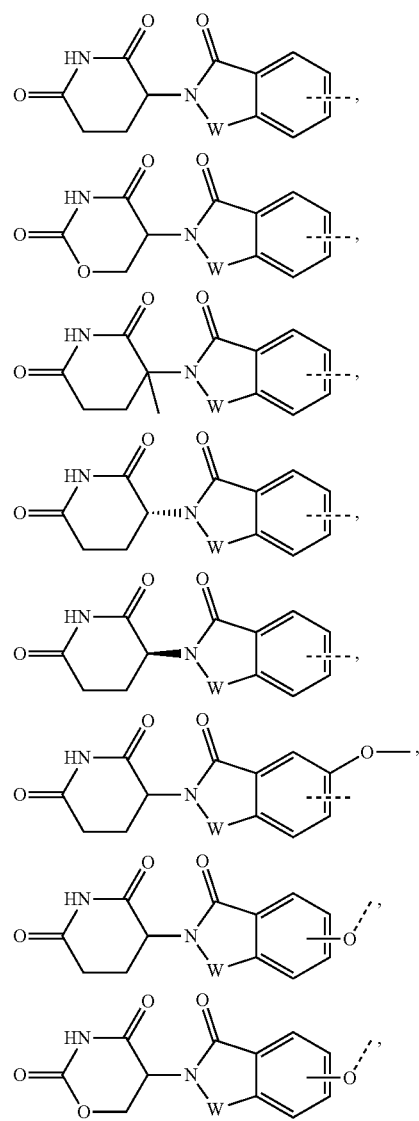
444
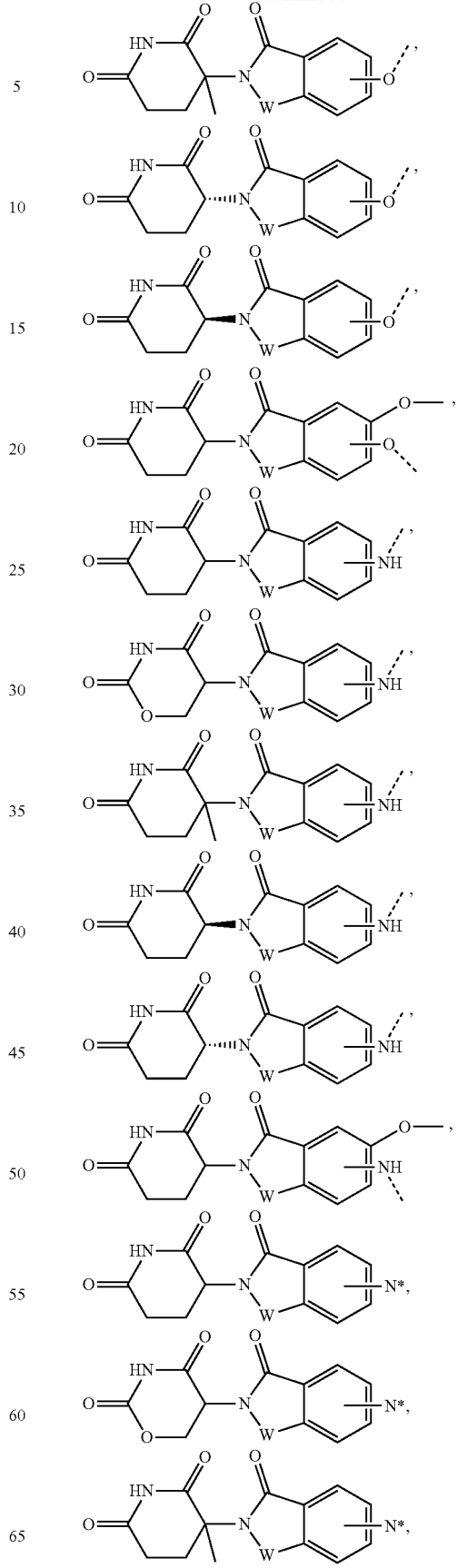

445
-continued
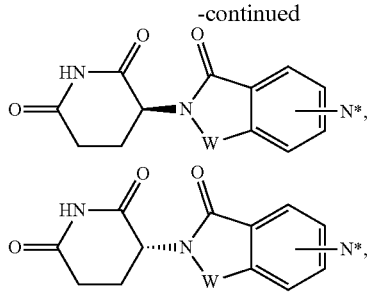
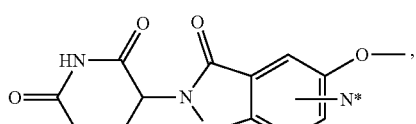
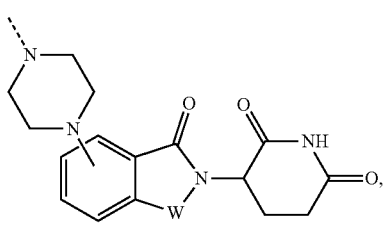
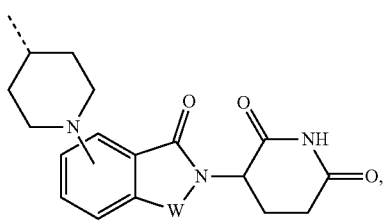
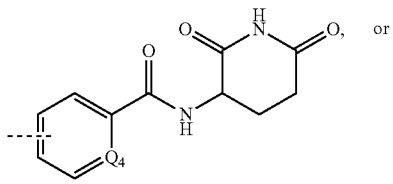
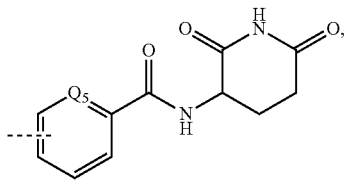
wherein:
- ⸺ of the CLM indicates the point of attachment with L or the PTM; and
- N* is a nitrogen atom that is shared with the L or the PTM;
446
(b) the PTM is:
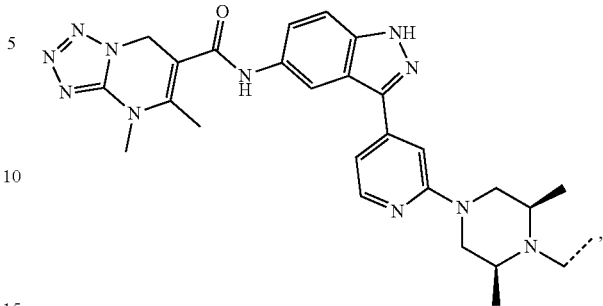
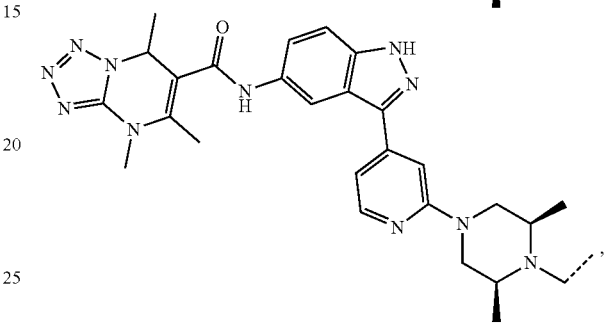
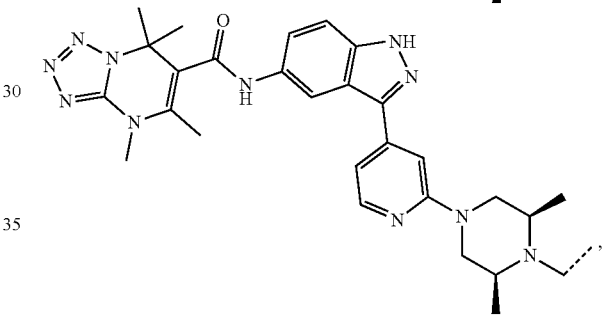
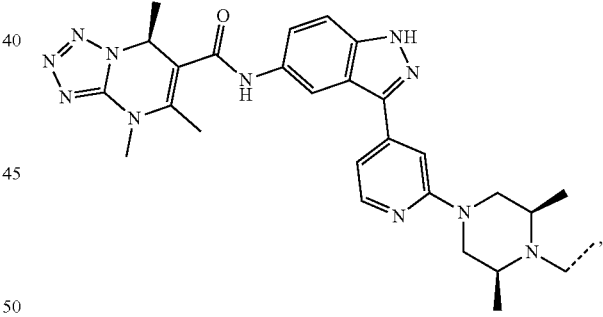
wherein
- ⸺ of the PTM indicates the point of attachment with L or the CLM;
(c) L is selected from:
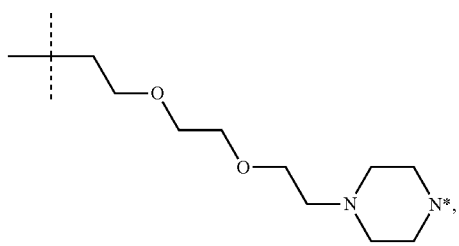

447
-continued
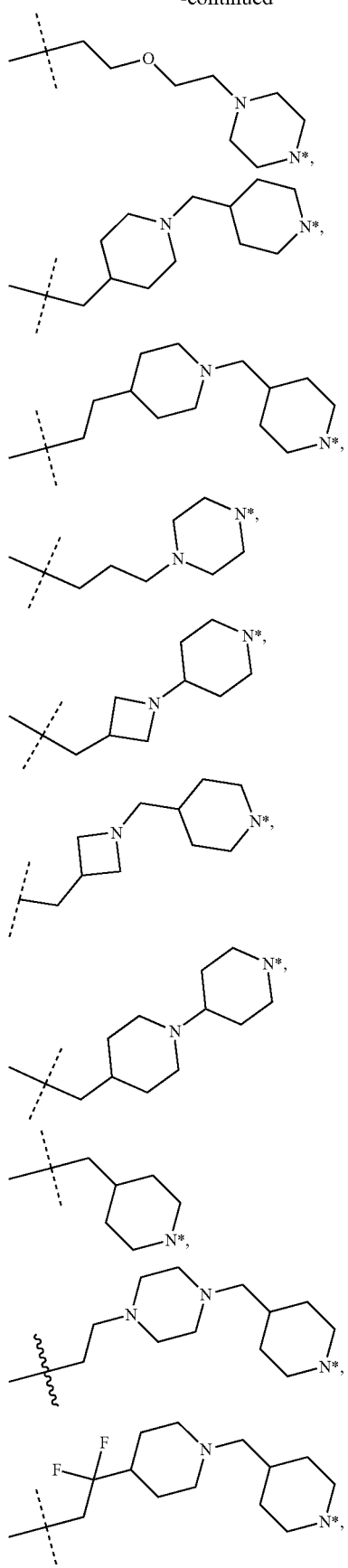
448
-continued
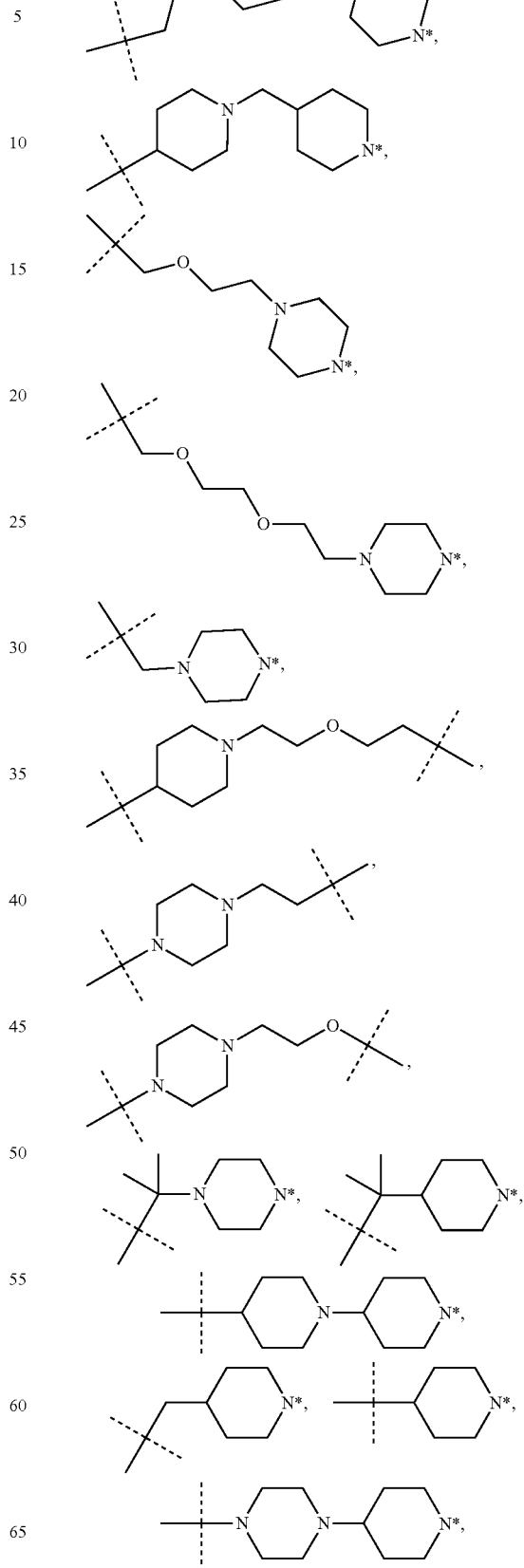

449
-continued
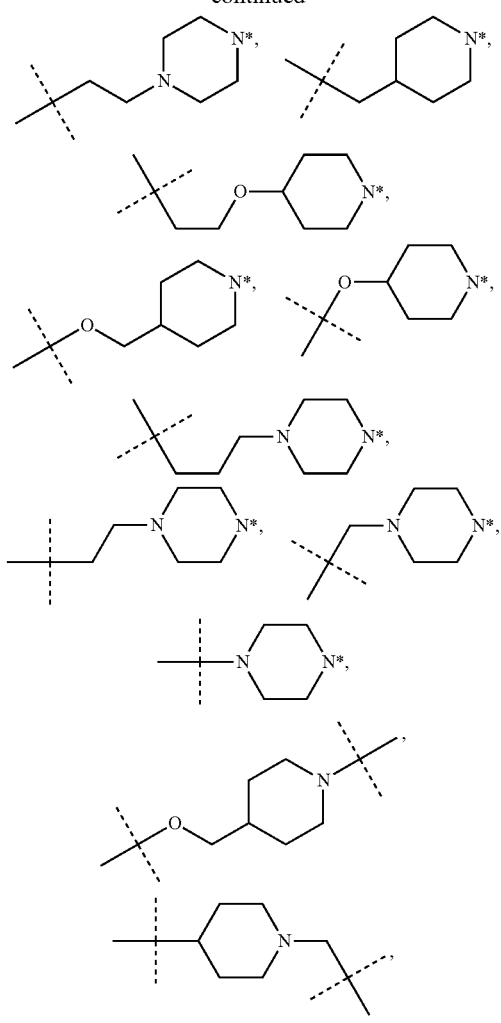
wherein ⌇ or * indicates the site that is covalently linked to the CLM or the PTM, or that is shared with the CLM or the PTM; or
(d) a combination thereof.
7. The compound of claim 1, wherein:
(a) the CLM is:
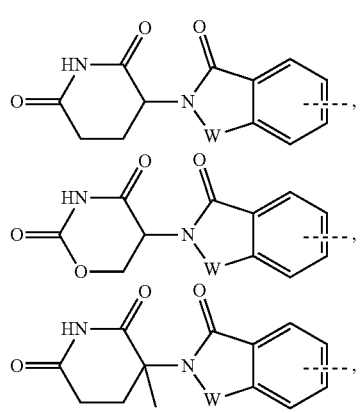
450
-continued
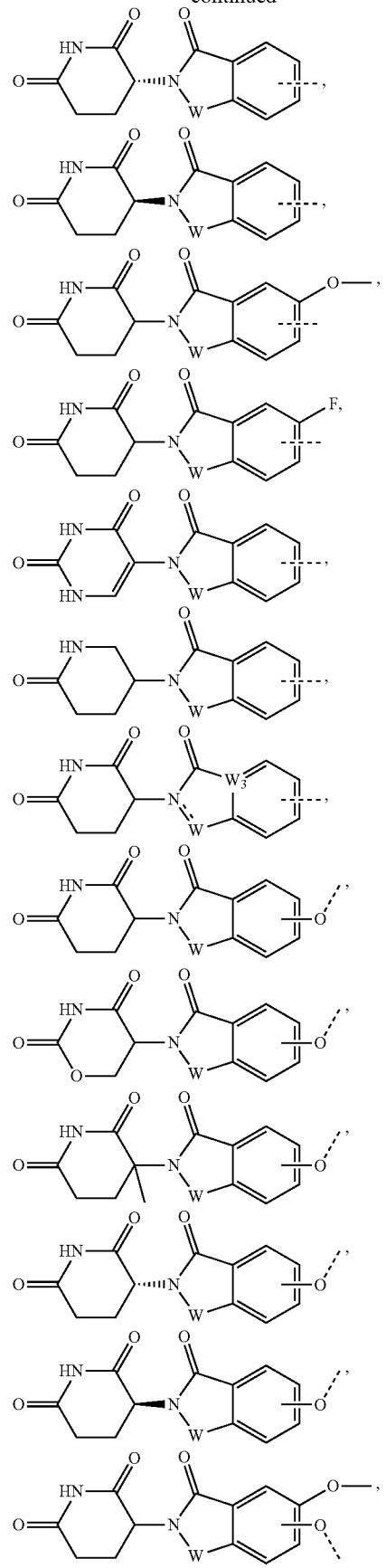

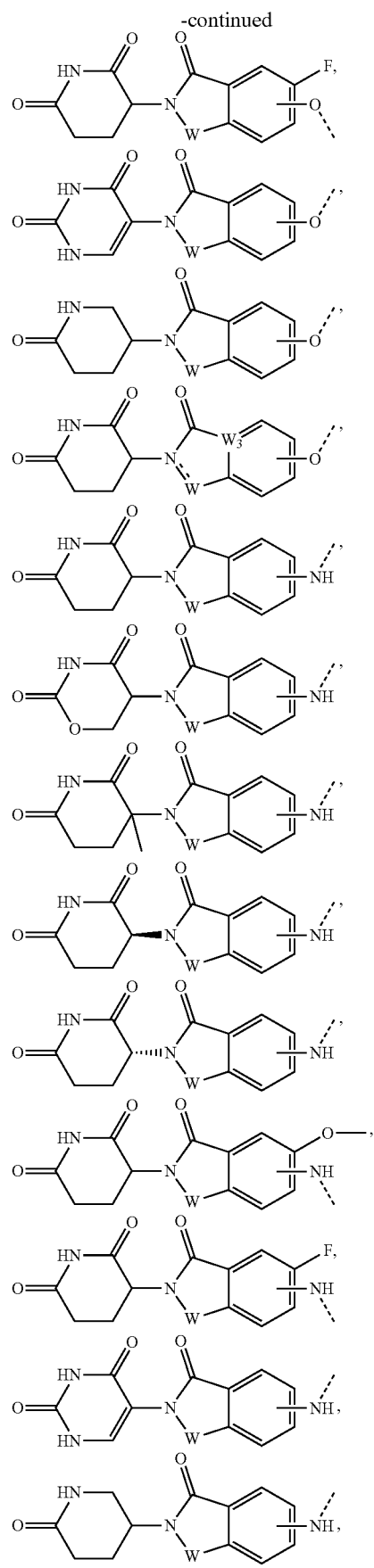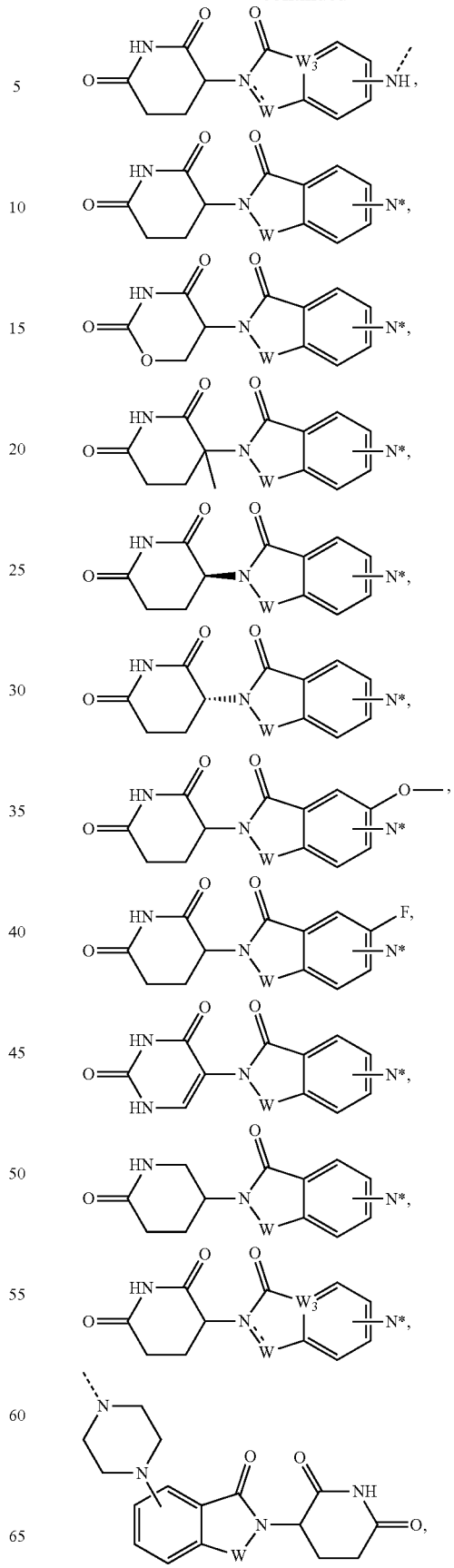

453
-continued
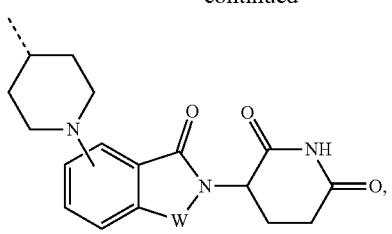
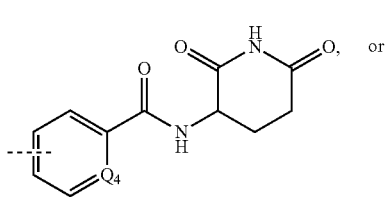  or
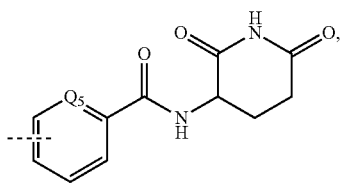
wherein:
- ⌐⌐ of the CLM indicates the point of attachment with L or the PTM; and
- N* is a nitrogen atom that is shared with L or the PTM;
(b) the PTM is:
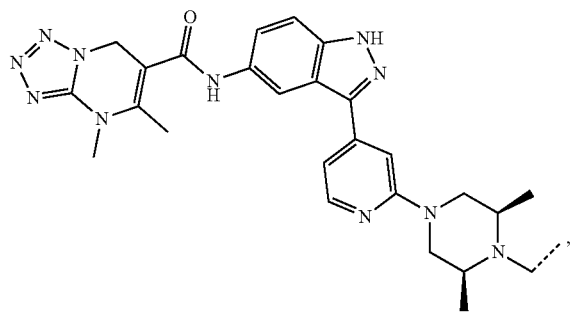
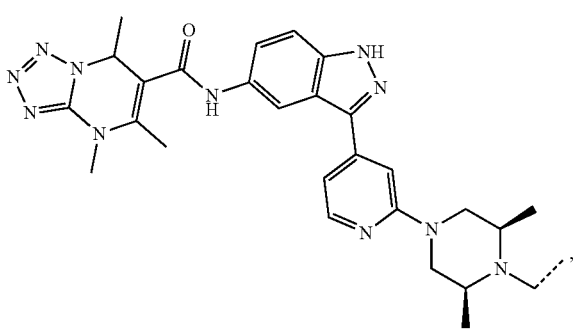
454
-continued
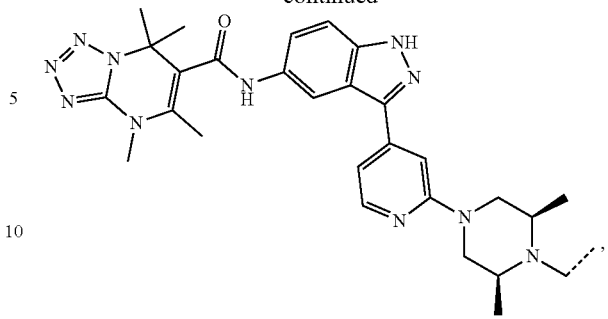
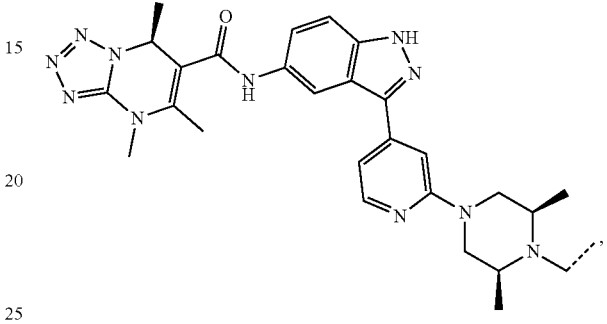
wherein
- ⌐⌐ of the PTM indicates the point of attachment with L or the CLM; and
(c) L is selected from:
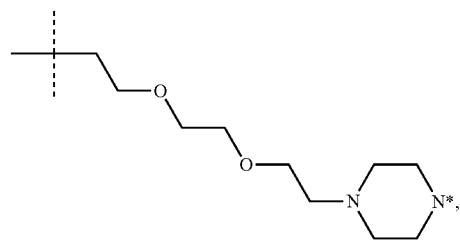
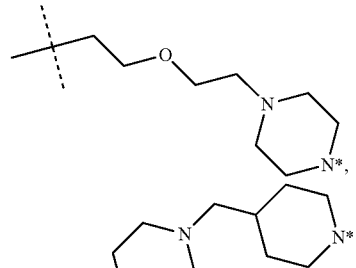
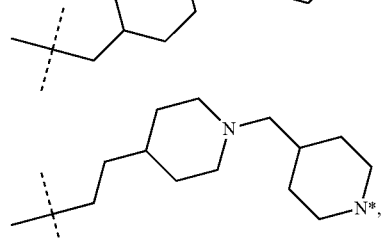
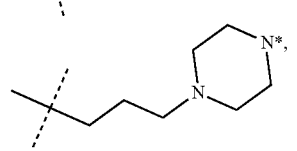

455
-continued
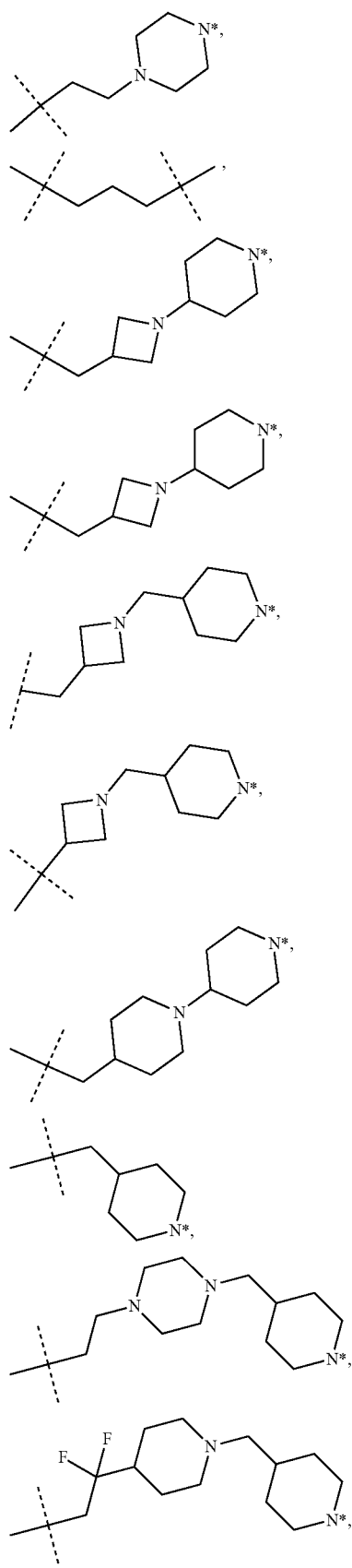
456
-continued
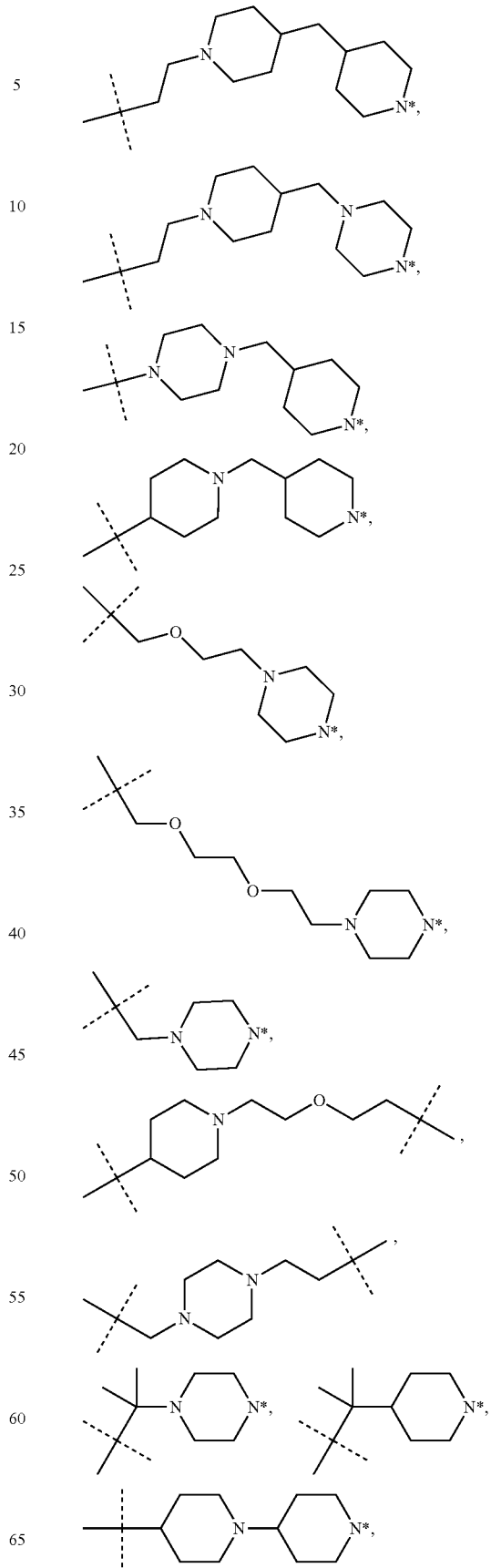

-continued
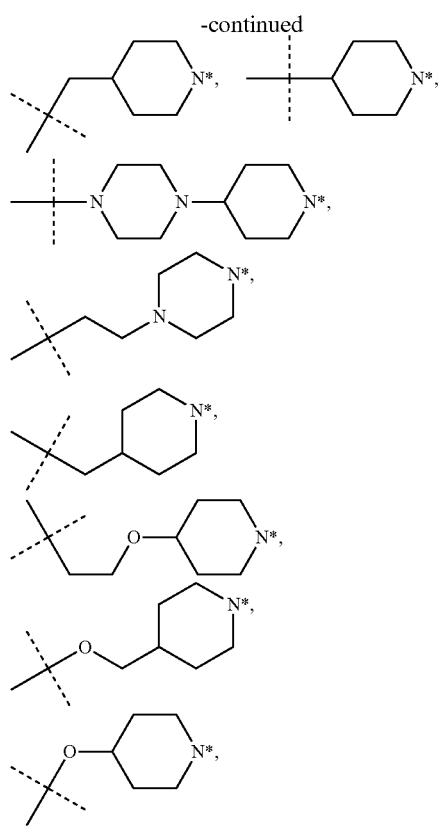
-continued
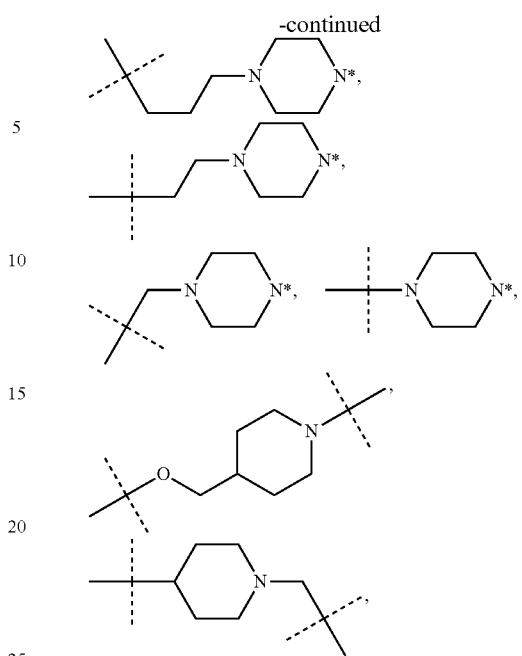
wherein ╱╱╱ or * indicates the site that is covalently linked to the CLM or the PTM, or that is shared with the CLM or the PTM.
8. The compound of claim 1, wherein the compound is selected from:
(1)
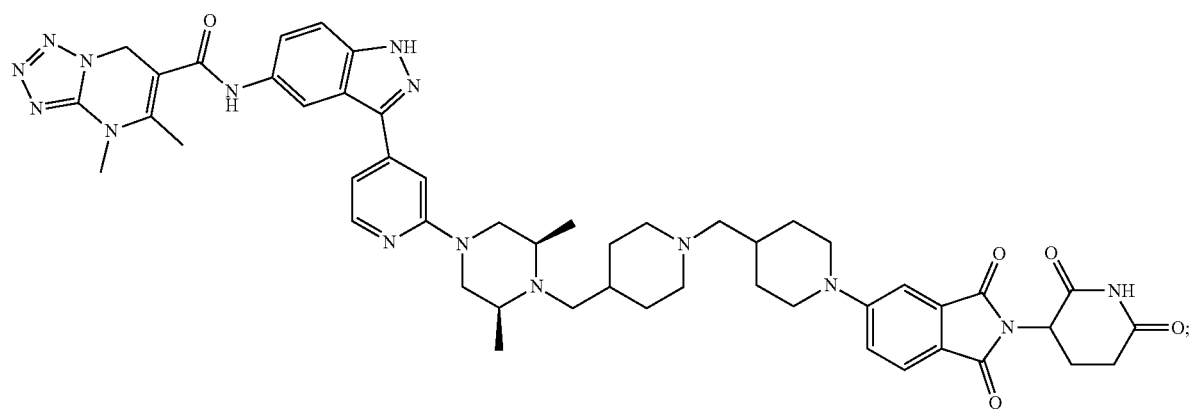

(2)
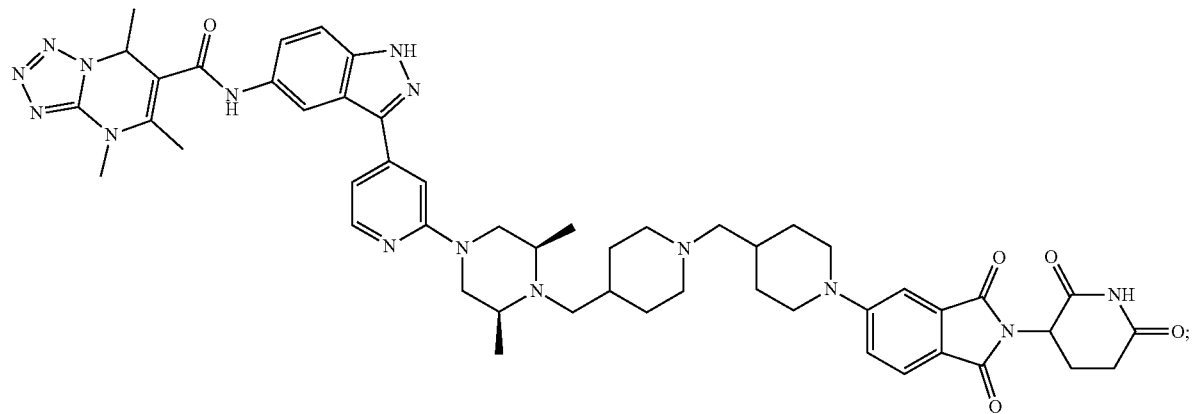
(3)
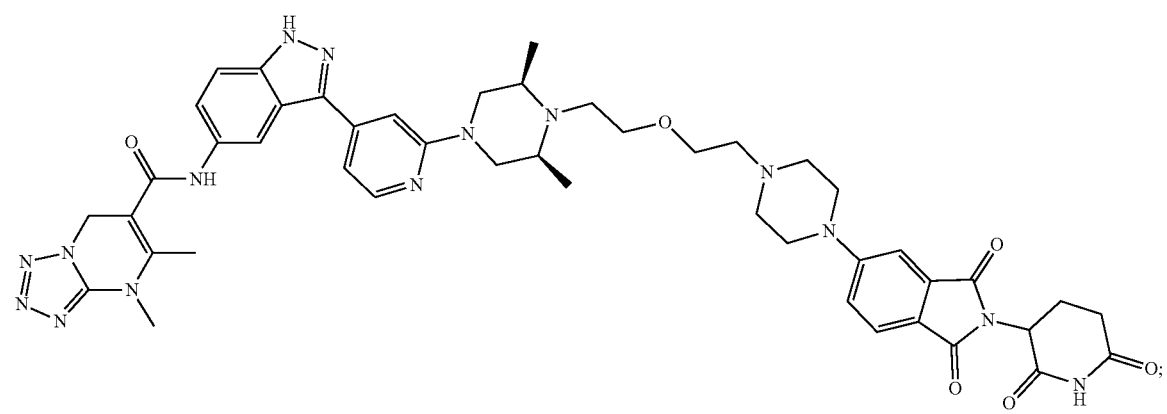
(4)
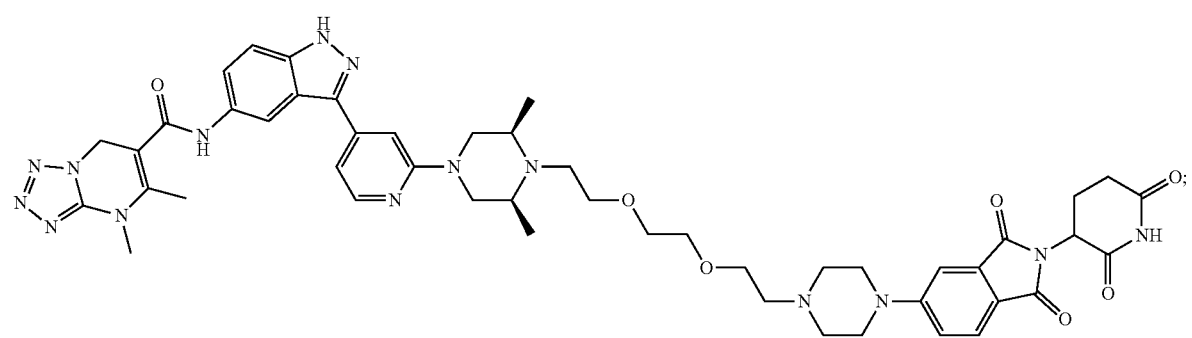
(5)
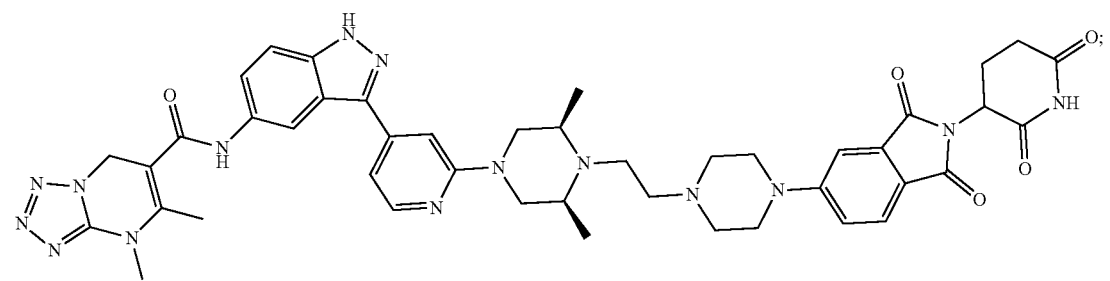

(6)
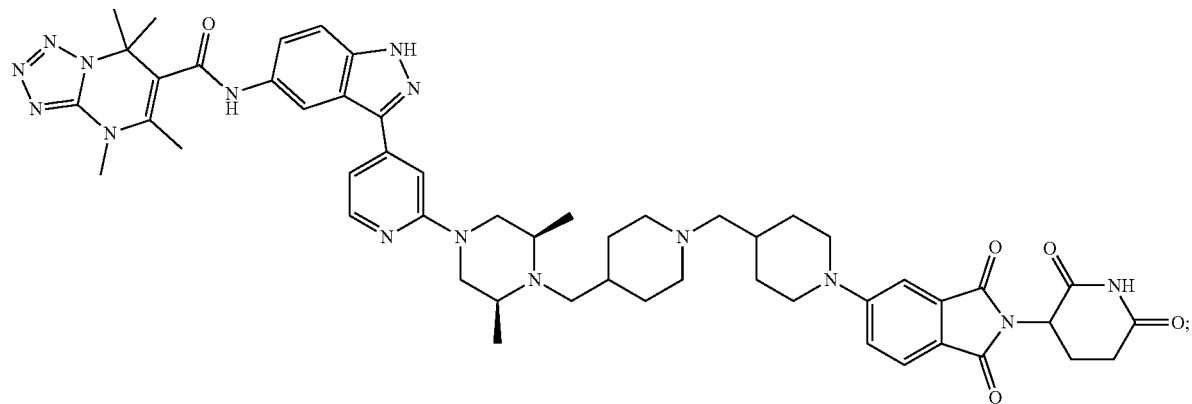
(7)
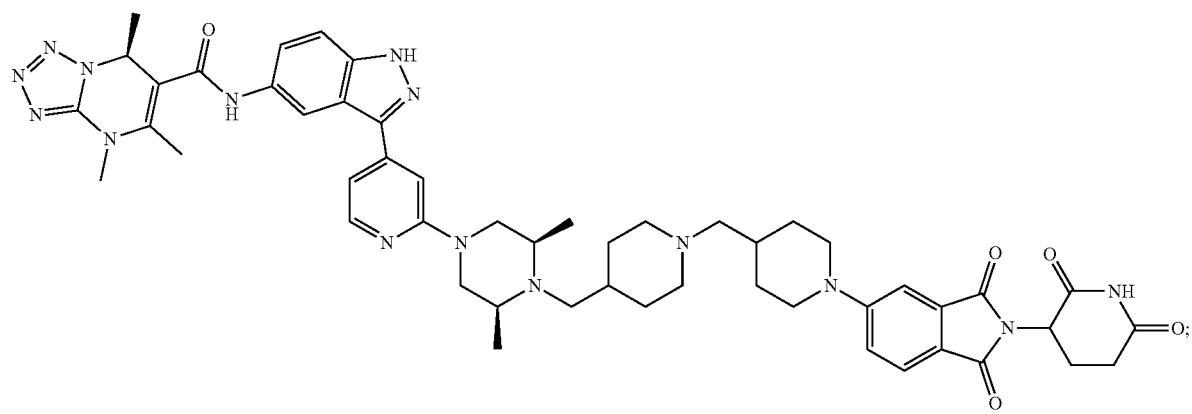
(8)
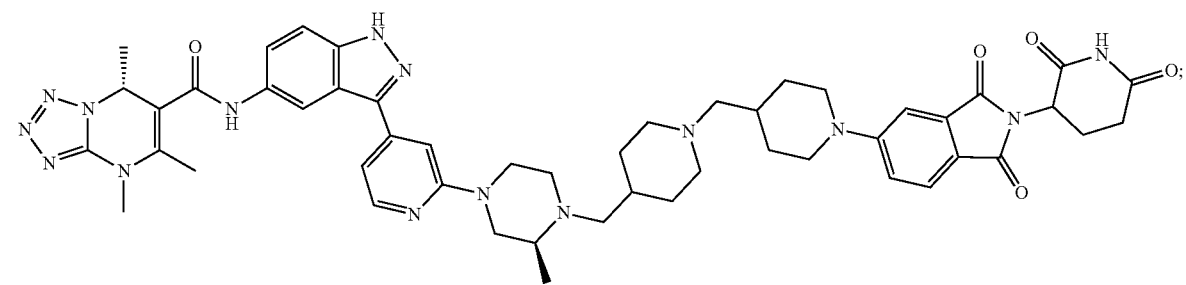
(9)
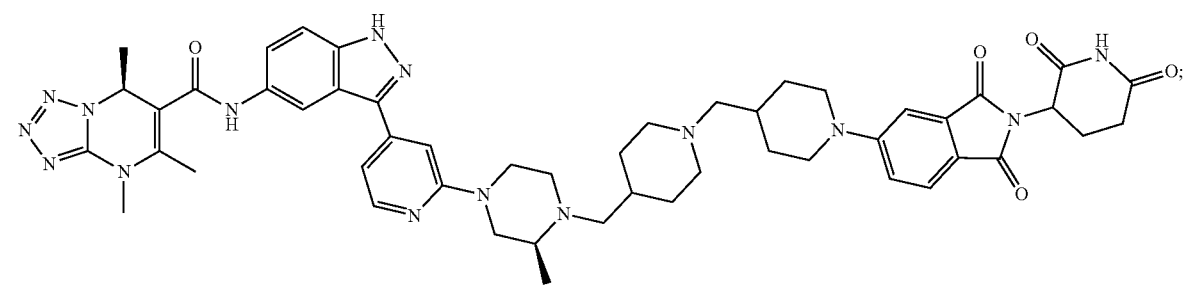

(10)
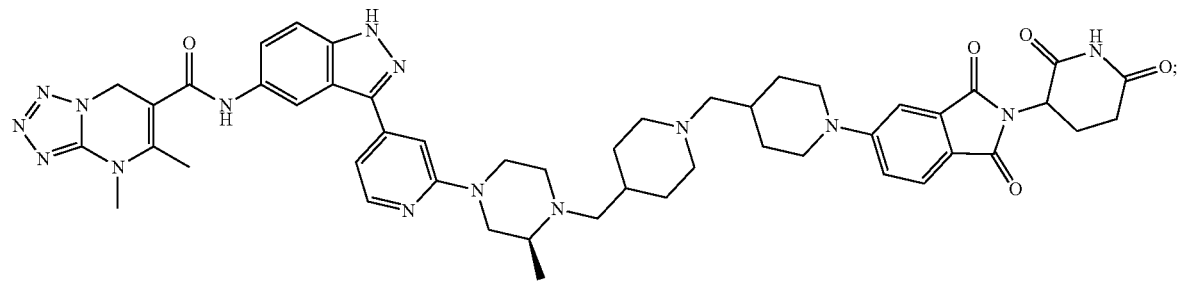
(11)
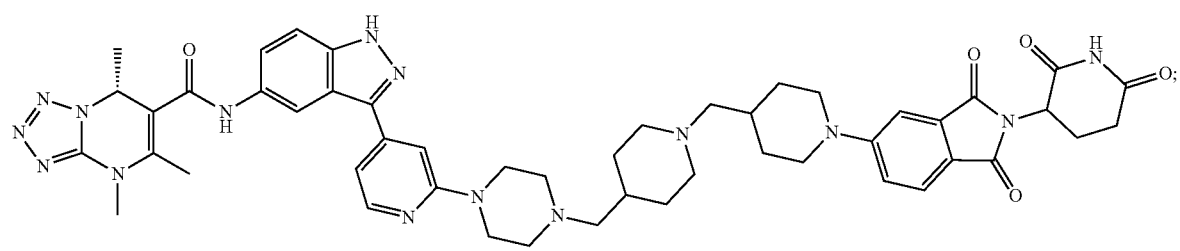
(12)
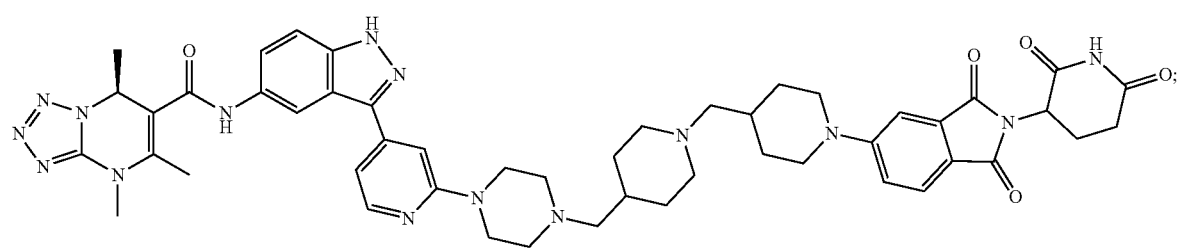
(13)
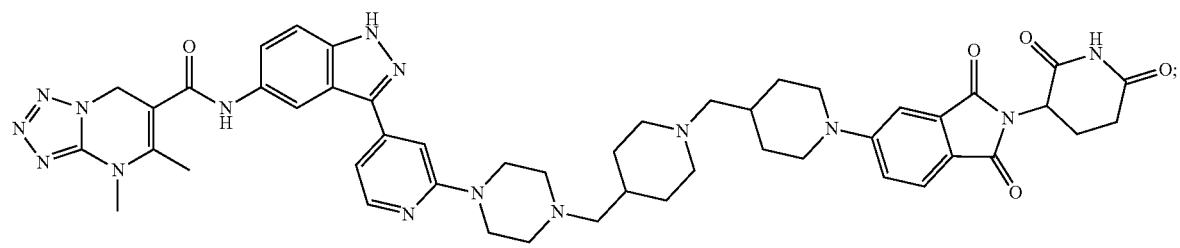
(14)
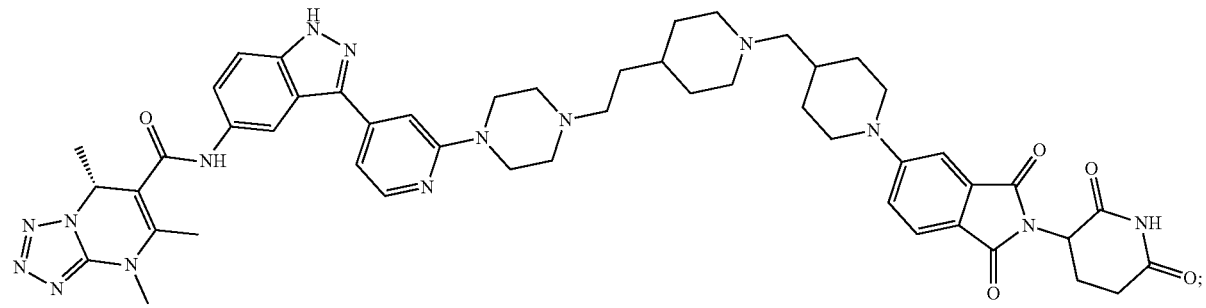

(15)
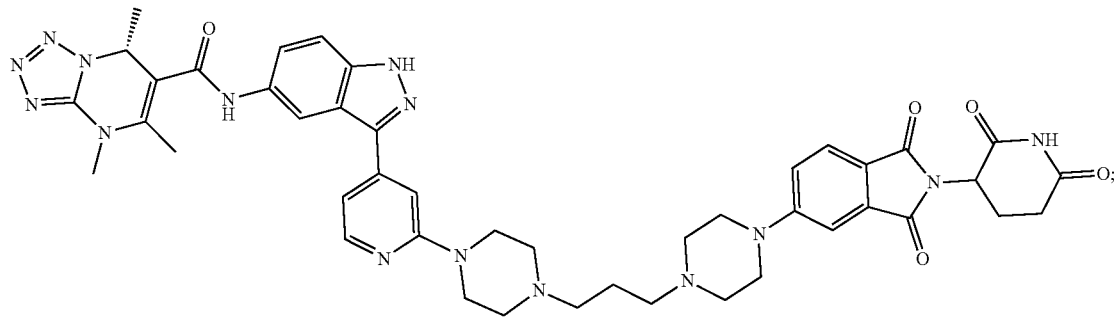
(16)
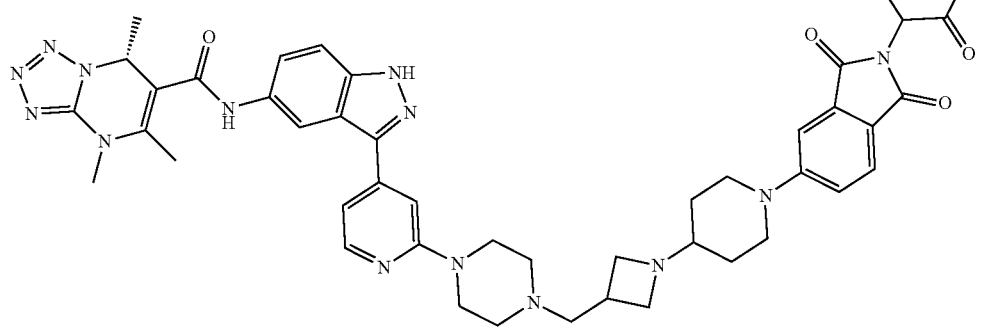
(17)
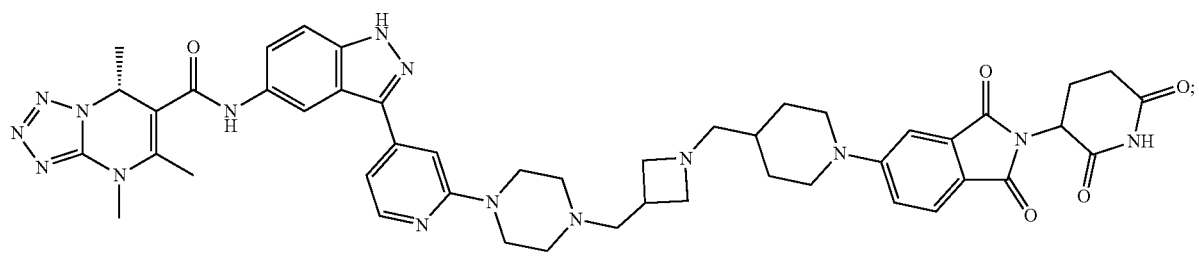
(18)
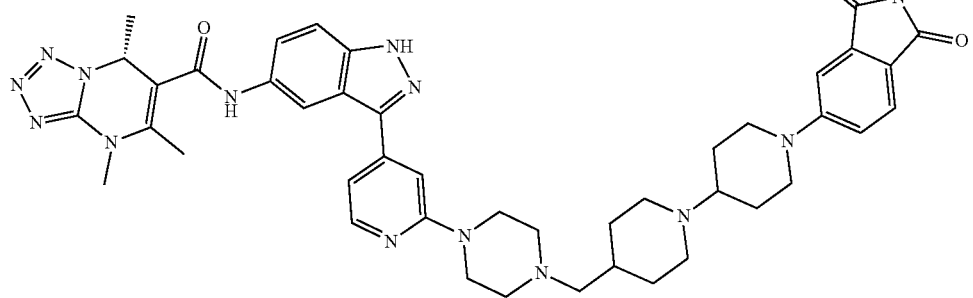

(19)
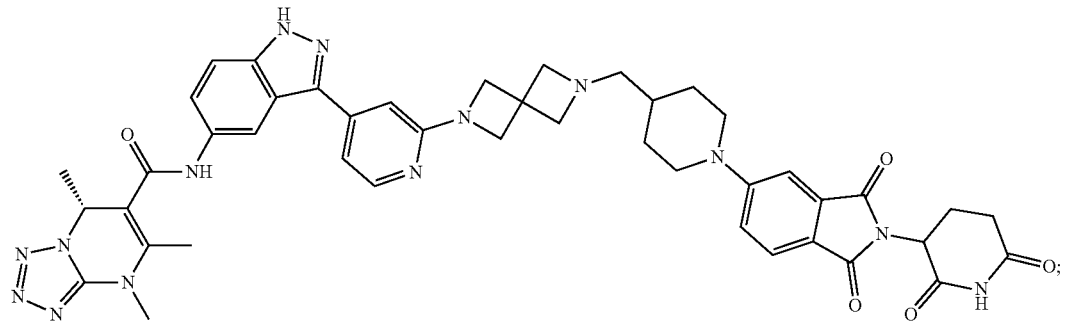
(20)
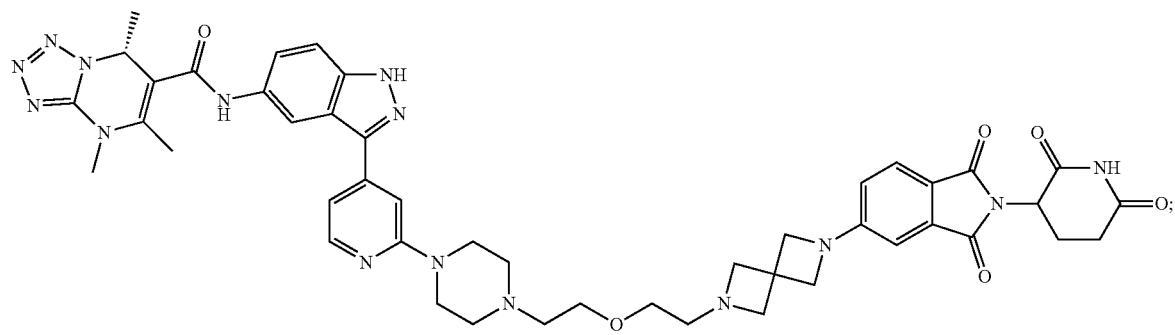
(21)
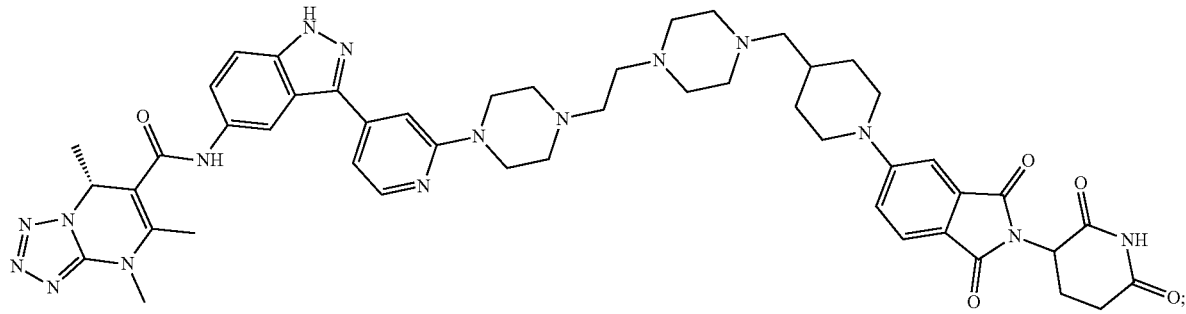
(22)
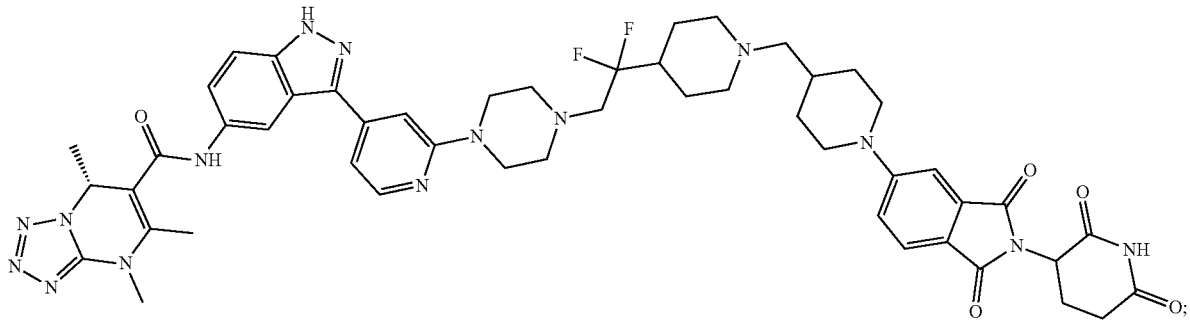

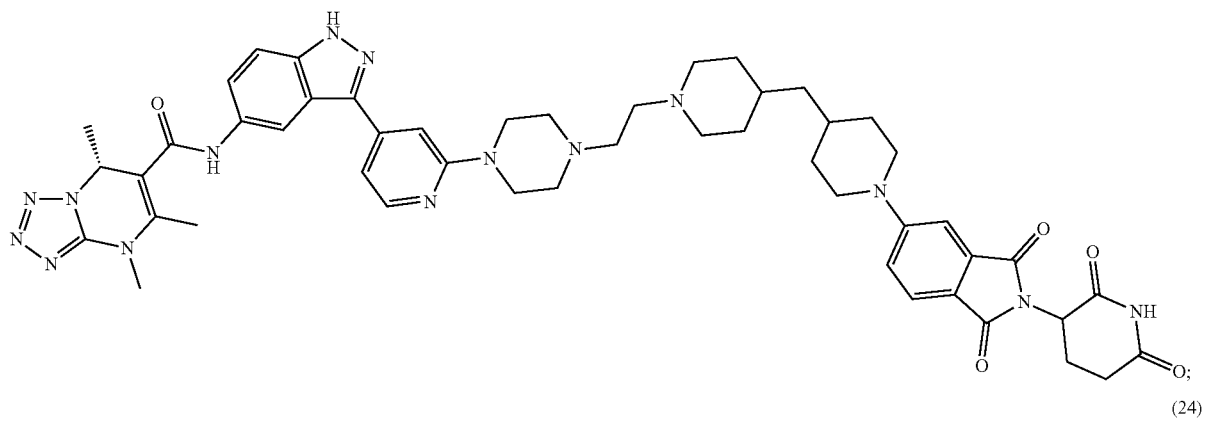
(23)
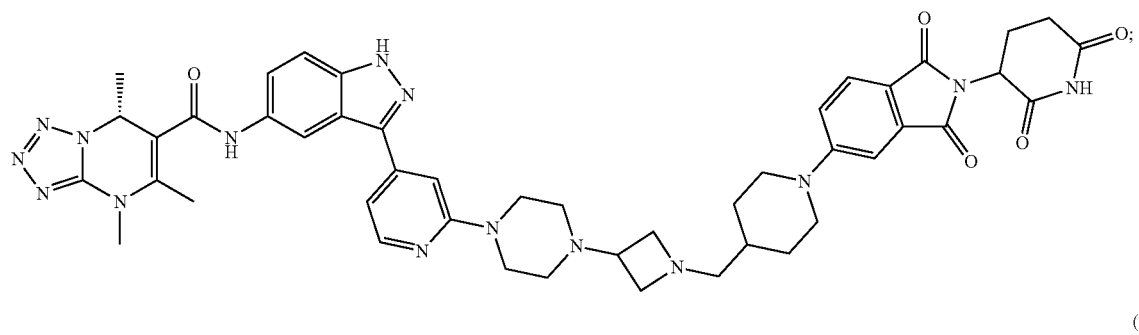
(24)
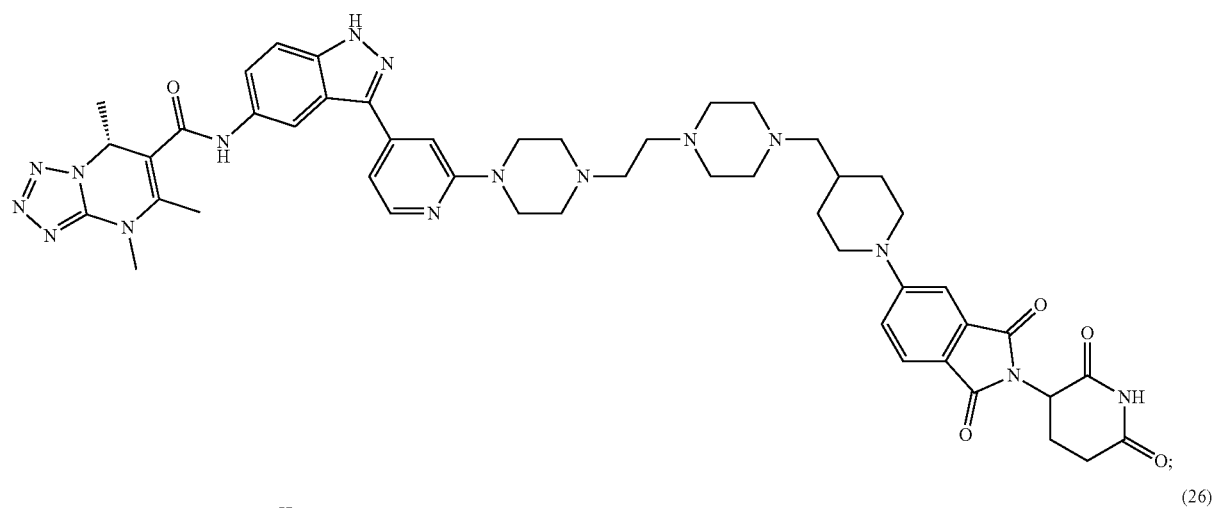
(25)
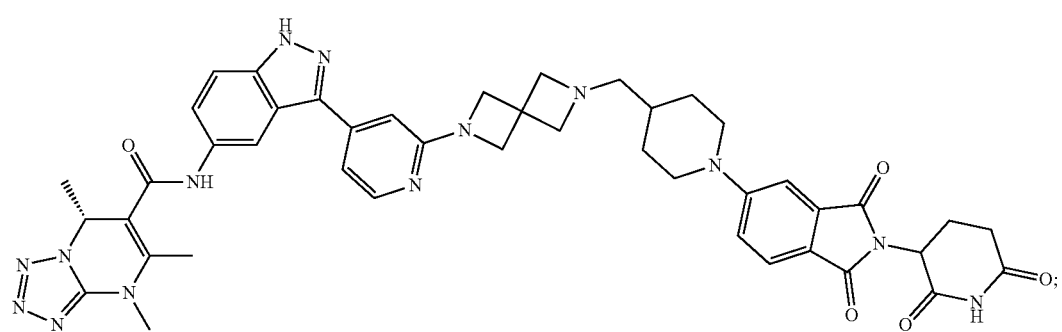
(26)

-continued
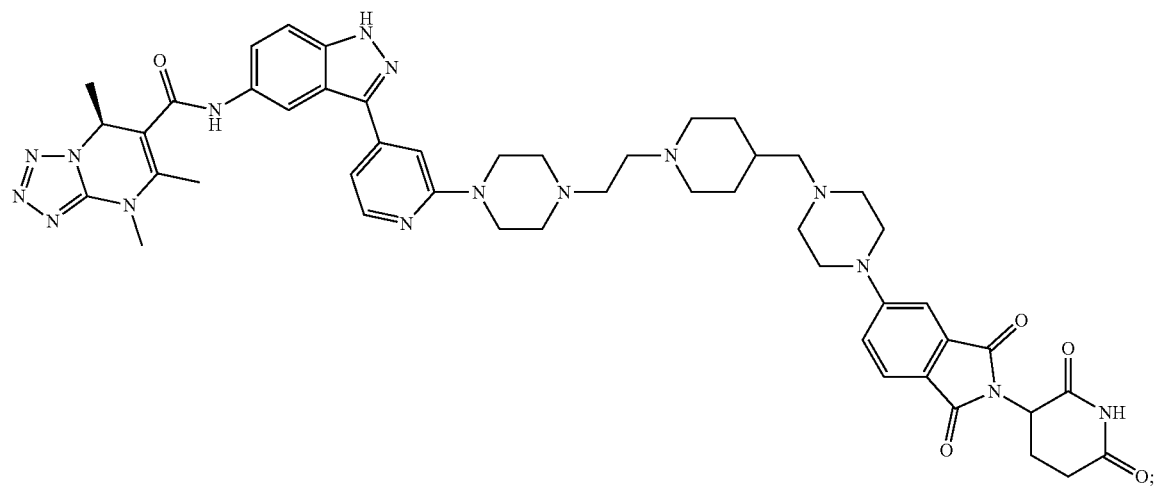
(27)
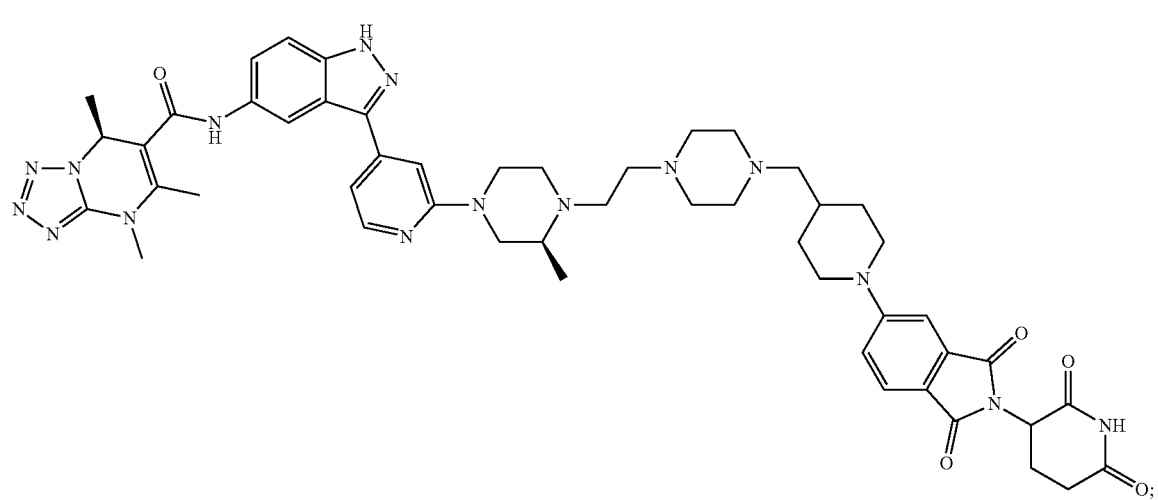
(28)
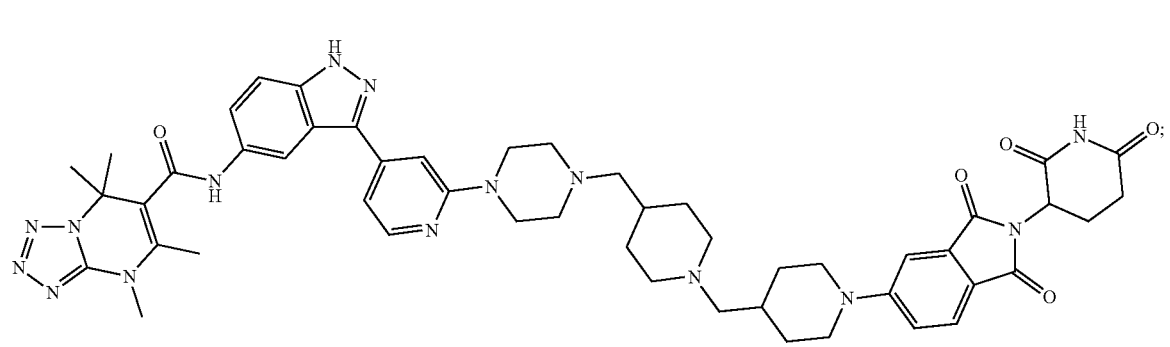
(29)
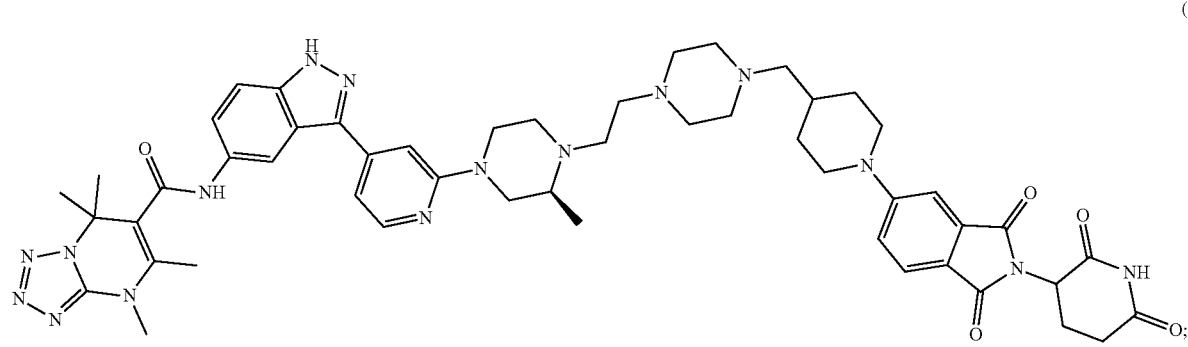
(30)

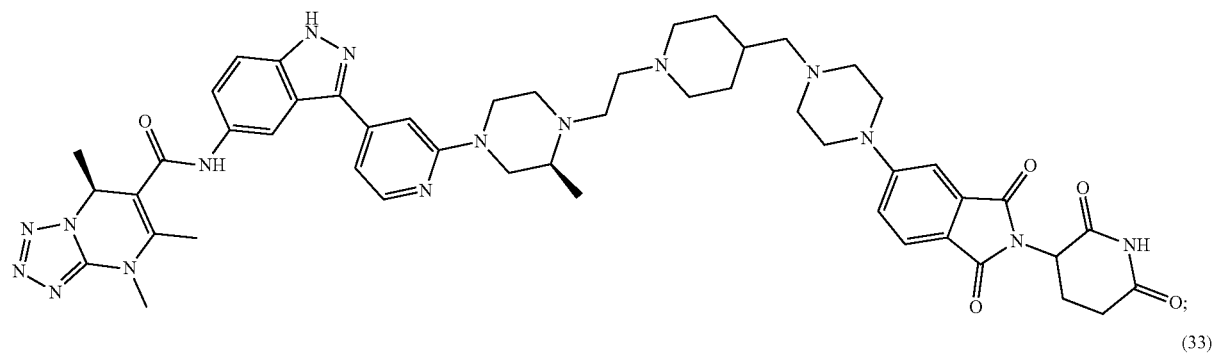
(31)
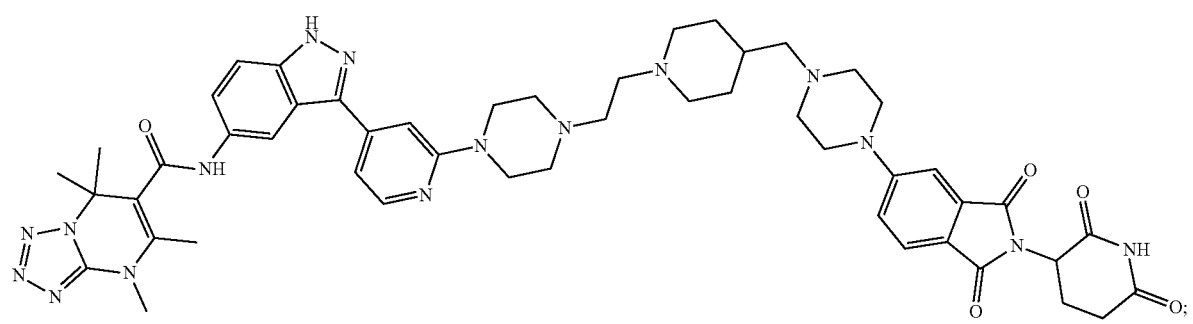
(33)
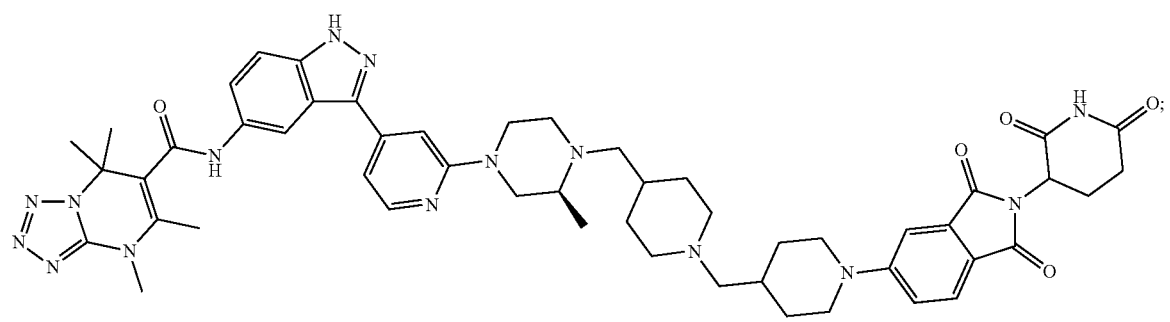
(34)
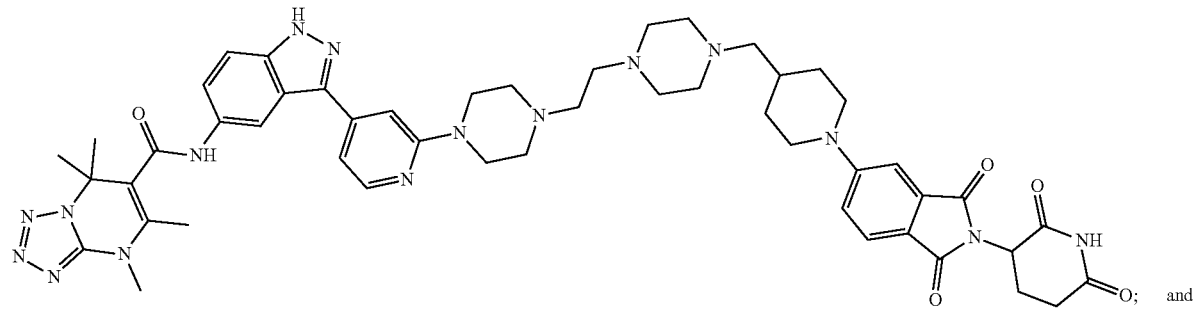
(35) and

-continued (36)

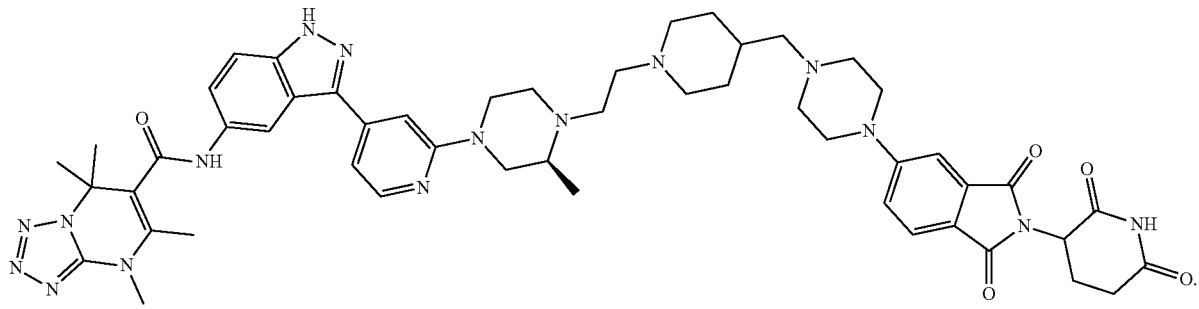

9. A pharmaceutical composition comprising an amount of a compound of claim 1, and a pharmaceutically acceptable carrier.

10. The pharmaceutical composition of claim 9, wherein the composition further comprises an additional bioactive agent.

11. The pharmaceutical composition of claim 10, wherein the additional bioactive agent is an anti-neurodegenerative, an anti-inflammatory, a chemotherapy agent, or an immunomodulatory agent.

12. The compound of claim 1, wherein the compound is:

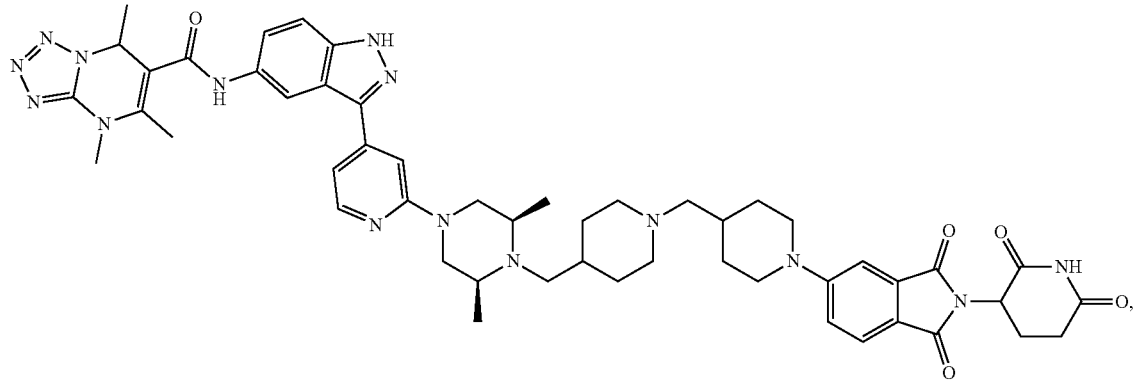 [SMILES: CC1=C(C(=O)Nc2ccc3[nH]nc(-c4ccnc(N5C[C@@H](C)N(CC6CCN(CC7CCN(c8ccc9c(c8)C(=O)N(C8CCC(=O)NC8=O)C9=O)CC7)CC6)[C@@H](C)C5)c4)c3c2)C(C)n2nnnc2N1C]

or a pharmaceutically acceptable salt thereof.

* * * * *